(12) United States Patent
Chen

(10) Patent No.: US 12,220,419 B2
(45) Date of Patent: Feb. 11, 2025

(54) BCL-2 INHIBITORS

(71) Applicant: Newave Pharmaceutical Inc., Pleasanton, CA (US)

(72) Inventor: Yi Chen, Pleasanton, CA (US)

(73) Assignee: Newave Pharmaceutical Inc., Pleasanton, CA (US)

( * ) Notice: Subject to any disclaimer, the term of this patent is extended or adjusted under 35 U.S.C. 154(b) by 779 days.

(21) Appl. No.: 17/269,004

(22) PCT Filed: Aug. 21, 2019

(86) PCT No.: PCT/US2019/047404
§ 371 (c)(1),
(2) Date: Feb. 17, 2021

(87) PCT Pub. No.: WO2020/041406
PCT Pub. Date: Feb. 27, 2020

(65) Prior Publication Data
US 2021/0315904 A1    Oct. 14, 2021

Related U.S. Application Data

(60) Provisional application No. 62/846,754, filed on May 13, 2019, provisional application No. 62/846,500, (Continued)

(51) Int. Cl.
| | | |
|---|---|---|
| *A61K 31/553* | (2006.01) | |
| *A61K 31/282* | (2006.01) | |
| *A61K 31/4184* | (2006.01) | |
| *A61K 31/4745* | (2006.01) | |
| *A61K 31/4985* | (2006.01) | |
| *A61K 31/519* | (2006.01) | |
| *A61K 31/52* | (2006.01) | |
| *A61K 31/635* | (2006.01) | |
| *A61K 31/7048* | (2006.01) | |
| *A61K 33/243* | (2019.01) | |
| *A61K 35/17* | (2015.01) | |
| *A61K 38/07* | (2006.01) | |

(Continued)

(52) U.S. Cl.
CPC .......... *A61K 31/553* (2013.01); *A61K 31/282* (2013.01); *A61K 31/4184* (2013.01); *A61K 31/4745* (2013.01); *A61K 31/4985* (2013.01); *A61K 31/519* (2013.01); *A61K 31/52* (2013.01); *A61K 31/635* (2013.01); *A61K 31/7048* (2013.01); *A61K 33/243* (2019.01); *A61K 35/17* (2013.01); *A61K 38/07* (2013.01); *A61K 39/3955* (2013.01); *A61K 47/6849* (2017.08); *A61P 35/02* (2018.01); *C07D 471/14* (2013.01); *C07D 491/147* (2013.01); *C07D 498/14* (2013.01); *C07D 498/22* (2013.01); *C07D 513/14* (2013.01); *C07D 515/14* (2013.01); *C07D 519/00* (2013.01)

(58) Field of Classification Search
None
See application file for complete search history.

(56) References Cited

U.S. PATENT DOCUMENTS

| | | |
|---|---|---|
| 7,642,260 B2 | 1/2010 | Bruncko et al. |
| 7,767,684 B2 | 8/2010 | Bruncko et al. |

(Continued)

FOREIGN PATENT DOCUMENTS

| | | |
|---|---|---|
| EP | 2376480 A2 | 10/2011 |
| WO | 2005/049593 A2 | 6/2005 |

(Continued)

OTHER PUBLICATIONS

Davis et al. "Amorphous solid dispersions of BCS class II drugs: A rational approach to solvent and polymer selection," Chemical Engineering Research and Design 110 (2016) 192-199. (Year: 2016).*
CNN.com./Health, FDA mulls drug to slow late-stage Alzheimer's. Retrieved online at: http://www.cnn.com/2003/Health/Conditions/09/24/alzheimers.drug.ap/index.html. 2 pages, Sep. 24, 2003.
Damaslo, Alzheimer's Disease and Related Dementias. Cecil Textbook of Medicine. 20th Edition, vol. 2. J. Claude Bennett (Ed.), W.B. Saunders Company, Philadelphia. pp. 1992-1996, (1996).
Golub et al., Molecular classification of cancer: class discovery and class prediction by gene expression monitoring. Science. Oct. 15, 1999;286(5439):531-537.
Lala et al., Role of nitric oxide in tumor progression: lessons from experimental tumors. Cancer Metastasis Rev. 1998;17(1):91-106.

(Continued)

*Primary Examiner* — Jeffrey S Lundgren
*Assistant Examiner* — Michael J Schmitt
(74) *Attorney, Agent, or Firm* — McCarter & English, LLP; Yu Lu; Zhongyu "Alex" Wang

(57) ABSTRACT

The disclosure includes compounds of Formula (A), wherein $R_1$, $R_2$, $R_3$, $R_4$, $R_5$, $R_6$, $R_7$, $R_8$, $R_9$, $R_{10}$, and $R_{11}$, h, j, m, n, k, v, s, g, V, W, L, $Z_1$, $Q_1$, $Q_2$, $Q_3$, $Q_4$, $Q_5$, $Q_6$, and $Q_7$, are defined herein. Also disclosed is a method for treating a neoplastic disease, an autoimmune disease, or a neurodegenerative disease with these compounds.

(A)

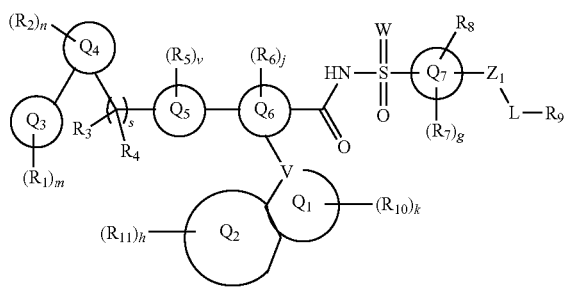

30 Claims, No Drawings

Related U.S. Application Data filed on May 10, 2019, provisional application No. 62/791,840, filed on Jan. 13, 2019, provisional application No. 62/771,055, filed on Nov. 24, 2018, provisional application No. 62/722,377, filed on Aug. 24, 2018, provisional application No. 62/722,326, filed on Aug. 24, 2018, provisional application No. 62/721,858, filed on Aug. 23, 2018, provisional application No. 62/721,769, filed on Aug. 23, 2018, provisional application No. 62/721,596, filed on Aug. 22, 2018, provisional application No. 62/721,203, filed on Aug. 22, 2018.

(51) Int. Cl.
  *A61K 39/395* (2006.01)
  *A61K 47/68* (2017.01)
  *A61P 35/02* (2006.01)
  *C07D 471/14* (2006.01)
  *C07D 491/147* (2006.01)
  *C07D 498/14* (2006.01)
  *C07D 498/22* (2006.01)
  *C07D 513/14* (2006.01)
  *C07D 515/14* (2006.01)
  *C07D 519/00* (2006.01)

(56) References Cited

U.S. PATENT DOCUMENTS

| | | |
|---|---|---|
| 7,973,161 B2 | 7/2011 | Bruncko et al. |
| 8,084,607 B2 | 12/2011 | Bruncko et al. |
| 8,173,811 B2 | 5/2012 | Bruncko et al. |
| 8,354,404 B2 | 1/2013 | Bruncko et al. |
| 8,546,399 B2 | 10/2013 | Bruncko et al. |
| 8,557,983 B2 | 10/2013 | Doherty et al. |
| 8,563,735 B2 | 10/2013 | Bruncko et al. |
| 8,580,794 B2 | 11/2013 | Doherty et al. |
| 8,586,754 B2 | 11/2013 | Bruncko et al. |
| 8,614,318 B2 | 12/2013 | Bruncko et al. |
| 8,686,136 B2 | 4/2014 | Bruncko et al. |
| 8,952,157 B2 | 2/2015 | Ding et al. |
| 9,006,247 B2 | 4/2015 | Tao et al. |
| 9,029,404 B2 | 5/2015 | Doherty et al. |
| 9,034,875 B2 | 5/2015 | Doherty et al. |
| 9,045,420 B2 | 6/2015 | Doherty et al. |
| 9,045,444 B2 | 6/2015 | Ding et al. |
| 9,045,475 B2 | 6/2015 | Elmore et al. |
| 9,045,920 B2 | 6/2015 | Minemura |
| 9,072,748 B2 | 7/2015 | Bruncko et al. |
| 9,073,855 B2 | 7/2015 | Doherty et al. |
| 9,125,913 B2 | 9/2015 | Bruncko et al. |
| 9,174,982 B2 | 11/2015 | Bruncko et al. |
| 9,303,025 B2 | 4/2016 | Bruncko et al. |
| 9,315,488 B2 | 4/2016 | Ding et al. |
| 9,403,822 B2 | 8/2016 | Tao et al. |
| 10,377,755 B2 | 8/2019 | Chen et al. |
| 2010/0152183 A1 | 6/2010 | Bruncko et al. |
| 2010/0298321 A1 | 11/2010 | Bruncko et al. |
| 2010/0298323 A1 | 11/2010 | Bruncko et al. |
| 2010/0305122 A1 | 12/2010 | Bruncko et al. |
| 2011/0124628 A1 | 5/2011 | Bruncko et al. |
| 2012/0108590 A1 | 5/2012 | Birtalan et al. |
| 2014/0057890 A1 | 2/2014 | Bruncko et al. |
| 2016/0304451 A1 | 10/2016 | Elmore et al. |
| 2017/0096424 A1 | 4/2017 | Tao et al. |
| 2017/0158666 A1 | 6/2017 | Bruncko et al. |
| 2018/0251426 A1 | 9/2018 | Bruncko et al. |
| 2020/0071329 A1 | 3/2020 | Chen et al. |
| 2020/0190109 A1 | 6/2020 | Chen et al. |
| 2020/0197406 A1 | 6/2020 | Chen et al. |
| 2021/0171523 A1 | 6/2021 | Chen et al. |

FOREIGN PATENT DOCUMENTS

| | | |
|---|---|---|
| WO | 2005/049594 A1 | 6/2005 |
| WO | 2009/036035 A1 | 3/2009 |
| WO | 2010/065824 A2 | 6/2010 |
| WO | 2010/065865 A2 | 6/2010 |
| WO | 2010/138588 A2 | 12/2010 |
| WO | 2011/068560 A1 | 6/2011 |
| WO | 2011/068561 A1 | 6/2011 |
| WO | 2011/149492 A1 | 12/2011 |
| WO | 2011/150016 A1 | 12/2011 |
| WO | 2012/058392 A1 | 5/2012 |
| WO | 2012/071336 A1 | 5/2012 |
| WO | 2012/121758 A1 | 9/2012 |
| WO | 2014/165044 A1 | 10/2014 |
| WO | 2017/132474 A1 | 8/2017 |
| WO | 2018/127130 A1 | 7/2018 |
| WO | 2018/192462 A1 | 10/2018 |
| WO | 2019/040550 A1 | 2/2019 |
| WO | 2019/040573 A1 | 2/2019 |
| WO | 2020/041405 A1 | 2/2020 |
| WO | 2020/041406 A1 | 2/2020 |

OTHER PUBLICATIONS

Layzer, Section Five—Degenerative Diseases of the Nervous System. Cecil Textbook of Medicine. 20th Edition, vol. 2. J. Claude Bennett (Ed.), W.B. Saunders Company, Philadelphia. pp. 2050-2057, (1996).

Pubchem, SCHEMBL 17897155, Compound Summary for CID 24729558. 14 pages. Retrieved online at: https://pubchem.ncbi.nlm.nih.gov/compound/24729558. Mar. 4, 2017.

Souers et al., ABT-199, a potent and selective BCL-2 inhibitor, achieves antitumor activity while sparing platelets. Nat Med. Feb. 2013;19(2):202-8.

International Search Report and Written Opinion for Application No. PCT/US2018/047411, dated Oct. 1, 2018, 8 pages.

International Search Report and Written Opinion for Application No. PCT/US2018/047444, dated Oct. 8, 2018, 9 pages.

International Search Report and Written Opinion for Application No. PCT/US2019/047403, dated Oct. 17, 2019, 12 pages.

International Search Report and Written Opinion for Application No. PCT/US2019/047404, dated Oct. 9, 2019, 10 pages.

International Search Report and Written Opinion for Application No. PCT/US2019/068685, dated Jun. 29, 2020, 19 pages.

International Search Report and Written Opinion for Application No. PCT/US2020/020010, dated Jun. 3, 2020, 10 pages.

International Search Report and Written Opinion for Application No. PCT/US2020/066650, dated Mar. 29, 2021, 18 pages.

\* cited by examiner

BCL-2 INHIBITORS

REFERENCE TO RELATED APPLICATIONS

This application is a U.S. national stage application, filed under 35 U.S.C. § 371 (c), of International Application No. PCT/US2019/047404, filed on Aug. 21, 2019, which claims the benefit of the filing dates of U.S. Provisional Application No. 62/721,203, filed on Aug. 22, 2018; 62/721,596, filed on Aug. 22, 2018; 62/721,769, filed on Aug. 23, 2018; 62/721,858, filed on Aug. 23, 2018; 62/722,326, filed on Aug. 24, 2018; 62/722,377, filed on Aug. 24, 2018; 62/771,055, filed on Nov. 24, 2018; 62/791,840, filed on Jan. 13, 2019; 62/846,500, filed on May 10, 2019; and 62/846,754, filed on May 13, 2019. The entire contents of each of the above-referenced applications are hereby incorporated herein by reference.

BACKGROUND OF THE INVENTION

Apoptosis, or programmed cell death, is a conserved and regulated process that is the primary mechanism for the removal of aged, damaged and unnecessary cells. The ability to block apoptotic signaling is a key hallmark of cancer and is thus important for oncogenesis, tumor maintenance and chemoresistance [Hanahan, D. & Weinberg, R. A. The hallmarks of cancer. Cell 100, 57-70 (2000).]. Dynamic binding interactions between prodeath (for example, BCL-2-associated X protein (BAX), BCL-2 antagonist/killer 1 (BAK), BCL-2-associated agonist of cell death (BAD), BCL-2-like 11 (BIM), NOXA and BCL-2 binding component 3 (PUMA)) and prosurvival (BCL-2, BCL-XL, BCL-2-like 2 (BCL-W), myeloid cell leukemia sequence 1 (MCL-1) and BCL-2-related protein A1 (BFL-1)) proteins in the BCL-2 family control commitment to programmed cell death. Altering the balance among these opposing factions provides one means by which cancer cells undermine normal apoptosis and gain a survival advantage [Youle, R. J. & Strasser, A. The BCL-2 protein family: opposing activities that mediate cell death. Nat. Rev. Mol. Cell Biol. 9, 47-59 (2008)].

BCL-2, the first identified apoptotic regulator, was originally cloned from the breakpoint of a t(14;18) translocation present in human B cell lymphomas [Tsujimoto, Y., et al. Science 228, 1440-1443 (1985); Cleary, M. L., et al Cell 47, 19-28 (1986); Boise, L. H. et al. Cell 74, 597-608 (1993)]. This protein has since been shown to have a dominant role in the survival of multiple lymphoid malignancies [Vaux, D. L., et al pre-B cells. Nature 335, 440-442 (1988)]. Overexpression of BCL-2 proteins correlates with resistance to chemotherapy, clinical outcome, disease progression, overall prognosis or a combination thereof in various cancers and disorders of the immune system. Involvement of BCL-2 proteins in bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer, spleen cancer, and the like is described in PCT/US2004/36770, published as WO 2005/049593, and PCT/US2004/37911, published as WO/2005/049594. Involvement of BCL-2 proteins in immune and autoimmune diseases is described in Current Allergy and Asthma Reports 2003, 3, 378-384; British Journal of Hematology 2000, 110(3), 584-90; Blood 2000, 95(4), 1283-92; and New England Journal of Medicine 2004, 351(14), 1409-1418. Involvement of BCL-2 proteins in arthritis is disclosed in WO 2009/064938. Involvement of BCL-2 proteins in bone marrow transplant rejection is disclosed in US 2008-0182845 A1. All incorporated herein by reference.

In the last decade, several BCL-2 inhibitors such as ABT-737, ABT-263, and ABT-199 as shown below have been identified and entered human clinical trials for cancers treatment.

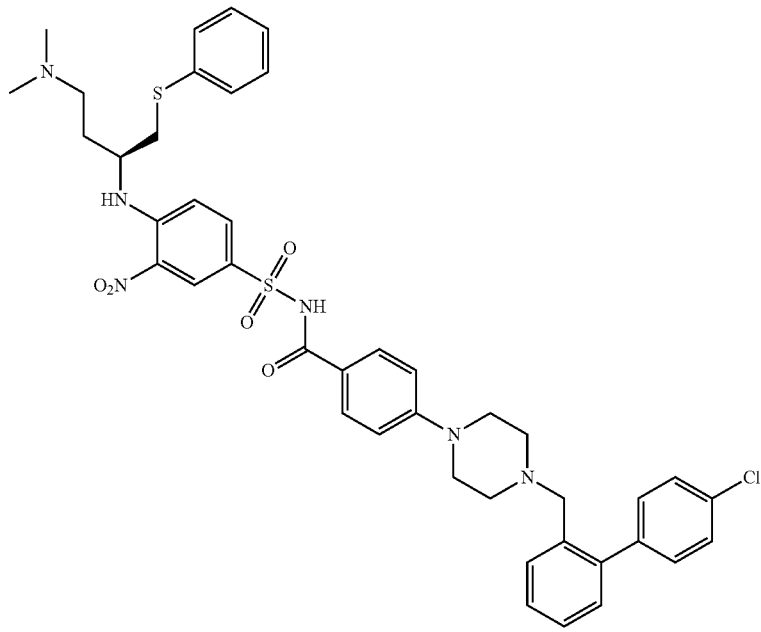

ABT-737

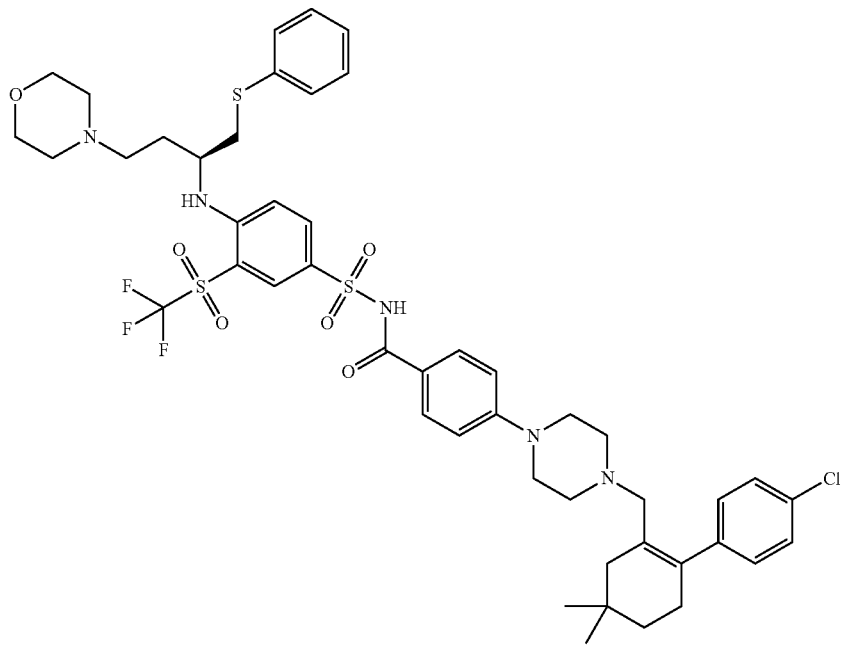

ABT-199

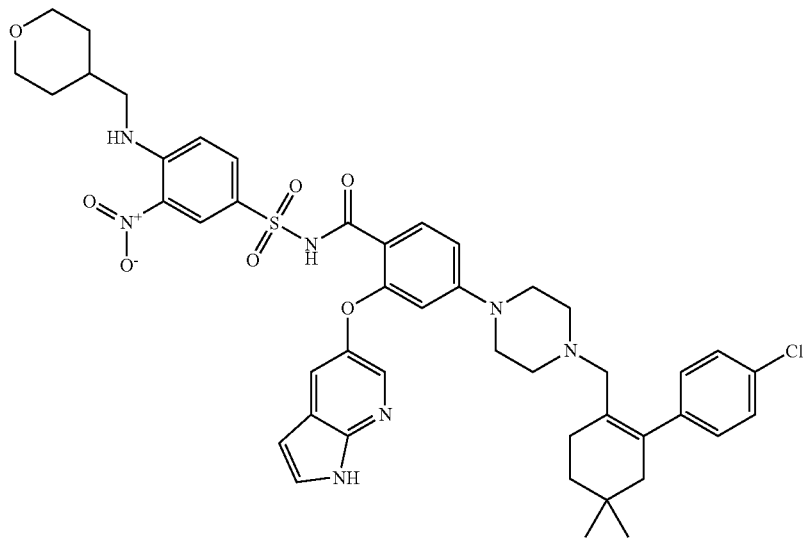

ABT-263

ABT-737 is discovered by nuclear magnetic resonance (NMR)-based screening, parallel synthesis and structure based fragment drug design [Tillman Oltersdorf, et al, Nature, Vol 435, 2005, p 677]. ABT-737 a small-molecule inhibitor of the anti-apoptotic proteins BCL-2, Bcl-XL and Bcl-w, with an affinity two to three orders of magnitude more potent than previously reported compounds. Mechanistic studies reveal that ABT-737 does not directly initiate the apoptotic process, but enhances the effects of death signals, displaying synergistic cytotoxicity with chemotherapeutics and radiation. ABT-737 exhibits single-agent-mechanism-based killing of cells from lymphoma and small-cell lung carcinoma lines, as well as primary patient-derived cells, and in animal models, ABT-737 improves survival, causes regression of established tumors, and produces cures in a high percentage of the mice. Unfortunately, ABT-737 is not orally bioavailable, and its formulation for intravenous delivery is hampered by its low aqueous solubility.

After extensive MedChem effort, an orally bioavailable BCL-2 inhibitor ABT-263 (Navitoclax) has been developed [Cheol-Min Park, et al J. Med. Chem. 2008, 51, 6902-6915]. ABT-263 is a potent inhibitor of Bcl-xL, BCL-2 and Bcl-w with Ki of ≤0.5 nM, ≤1 nM and ≤1 nM. ABT-263 has an $IC_{50}$ of 110 nM against SCLC H146 cell line. When ABT-263 is administered at 100 mg/kg/day in the H345 xenograft model, significant antitumor efficacy is observed with 80% TGI and 20% of treated tumors indicating at least a 50% reduction in tumor volume. Oral administration of ABT-263 alone causes complete tumor regressions in xenograft models of small-cell lung cancer and acute lymphoblastic leukemia [Tse C, et al. Cancer Res. 2008, 68(9), 3421-3428]. In the clinical trial, however, the inhibition of BCL-XL by ABT-263 (navitoclax) induces a rapid, concentration-dependent decrease in the number of circulating platelets. This mechanism-based thrombocytopenia is the dose-limiting toxicity of single-agent navitoclax treatment in patients and limits the ability to drive drug concentrations into a highly efficacious range.

Thus, a BCL-2 selective (BCL-XL sparing) inhibitor would culminate in substantially reduced thrombocytopenia while maintaining efficacy in lymphoid malignancies. The resulting increase in the therapeutic window should allow for greater BCL-2 suppression and clinical efficacy in BCL-2-dependent tumor types. After extensive MedChem, ABT-199 (GDC-0199) has been successfully developed [Andrew J Souers, et al, Nature Medicine, Volume 19,22, p202, 2013]. ABT-199 is a BCL-2-selective inhibitor with Ki of <0.01 nM, >4800-fold more selective versus Bcl-xL and Bcl-w, and no activity to Mcl-1. ABT-199 potently inhibits RS4;11 cells with $EC_{50}$ of 8 nM. In addition, ABT-199 induces a rapid apoptosis in RS4;11 cells with cytochrome c release, caspase activation, and the accumulation of sub-G0/G1 DNA. Quantitative immunoblotting reveals that sensitivity to ABT-199 correlated strongly with the expression of BCL-2, including NHL, DLBCL, MCL, AML and ALL cell lines. ABT-199 also induces apoptosis in CLL with an average $EC_{50}$ of 3.0 nM. A single dose of 100 mg/kg of ABT-199 causes a maximal tumor growth inhibition of 95% and tumor growth delay of 152% in RS4; 11 xenografts. ABT-199 also inhibits xenograft growth (DoHH2, Granta-519) as a single agent or in combination with Bendamustine and other agents. Human Phase I and II data showed that ABT-199 is highly efficacious for CLL who have 17p deletion, and was approved by FDA in 2016.

WO/2017/132474, WO/2019/040550, and WO/2019/040573 disclosed a novel class of BCL-2 inhibitors. However, there is still a strong need for continuing search in this field of art for more potent BCL-2 inhibitor.

SUMMARY OF THE INVENTION

Described herein are compounds of Formulae (A), (A-1), (A-2), (A-3), (A-4), (A-5), (AA), (AA-1), (AA-2), (AA-3), (AA-4), and (AA-5), and the compounds of the examples (collectively referred to herein as "the compounds of the invention"), that inhibit the activity of BCL-2 family proteins, such as Bcl-2, and pharmaceutically acceptable salts, solvates, polymorphs, tautomers, stereoisomers, isotopic forms, or prodrugs thereof.

In one aspect, the invention provides a compound represented by structural formula (A):

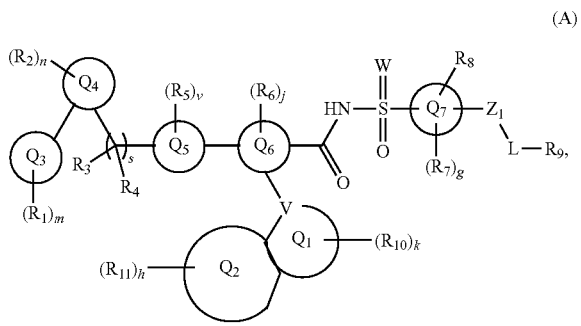

(A)

or an N-oxide thereof, or a pharmaceutically acceptable salt, solvate, polymorph, tautomer, stereoisomer, an isotopic form, or a prodrug of the compound of Formula (A) or N-oxide thereof. The definition of each variable is recited herein.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

Also within the scope of this invention is a pharmaceutical composition containing one or more of the compounds (such as any one of those in Formulae (A), (A-1), (A-2), (A-3), (A-4), (A-5), (AA), (AA-1), (AA-2), (AA-3), (AA-4), and (AA-5), or a pharmaceutically acceptable salt, solvate, polymorph, tautomer, stereoisomer, an isotopic form, or a prodrug thereof or an N-oxide thereof), modifications, and/or salts thereof described herein, and a pharmaceutically acceptable diluent or carrier, for use in treating a neoplastic disease, therapeutic uses thereof, and use of the compounds for the manufacture of a medicament for treating the disease/disorder.

This invention also relates to a method of treating a disease treatable by inhibiting the activity of one or more Bcl-2 family member proteins, such as a neoplastic disease, an autoimmune disease, or a neorodegenerative disease, comprising administering to a subject in need thereof an effective amount of one or more compounds of the invention, modifications, and/or salts thereof described herein, or a pharmaceutical composition comprising the compound(s) of the invention.

In certain embodiments, the neoplastic disease, autoimmune disease, or neorodegenerative disease is characterized by abnormal (e.g., enhanced or increased) BCL-2 family protein (such as Bcl-2) activity. For example, the neoplastic disease can be a hematological malignancy or cancer including solid tumor; the autoimmune disease can be type I diabetes; and the neorodegenerative disease can be schizophrenia.

In certain embodiments, the neoplastic disease is myeloma, multiple myeloma, lymphoma, follicular lymphoma (FL), non-Hodgkin's lymphoma, leukemia, acute leukemia, acute lymphoblastic leukemia (ALL) (such as BCL-2-dependent ALL and pediatric ALL), chronic lymphoblastic leukemia (CLL) (such as relapsed/refractory CLL, del(17p) CLL), chronic myeloid leukemia (CML) (such as blast-crisis CML), mantle cell lymphoma (MCL), diffuse large B-cell lymphoma, lung cancer such as small cell lung cancer (SCLC), melanoma, breast cancer, or prostate cancer, including drug-resistant cancer thereof.

In certain embodiments, the method further comprises administering one or more further treatment(s) effective to treat the neoplastic disease, such as surgery, radiation therapy, a chemotherapeutic agent (such as bendamustine, NL-101(7-(5-(bis(2-chloroethyl)amino)-1-methyl-1H-benzo[d]imidazol-2-yl)-N-hydroxyheptanamide), cisplatin, carboplatin, etoposide, topotecan), a target therapy (e.g., an anti-CD20 antibody such as rituximab, a Bruton's tyrosine kinase inhibitor such as ibrutinib and acalabrutinib (ACP-196), a PI3Kδ inhibitor such as idelalisib); an antibody-drug conjugate or ADC (such as anti-CD30 ADC brentuximab vedotin), an immunotherapy (such as an anti-PD-1 antibody including pembrolizumab and nivolumab, or an anti-PD-L1 antibody including atezolizumab, durvalumab, and avelumab), or a CAR-T therapy (such as tisagenlecleucel, axicabtagene ciloleucel).

Also provided herein is the use of one or more compounds of the invention, or a pharmaceutically acceptable salt thereof, or a pharmaceutical composition comprising one or more compounds of the invention, for the preparation of a medicament for the treatment of the above-referenced diseases or conditions.

In another embodiment, provided herein the compounds of the invention, or a pharmaceutically acceptable salt thereof, or a pharmaceutical composition comprising one or more of the disclosed compounds are for use in treating the above-referenced diseases or conditions.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

In a first embodiment, the invention provides compounds of the Formula (A) or an N-oxide thereof, or a pharmaceutically acceptable salt, solvate, polymorph, tautomer, stereoisomer, an isotopic form, or a prodrug of said compound of Formula (A) or N-oxide thereof:

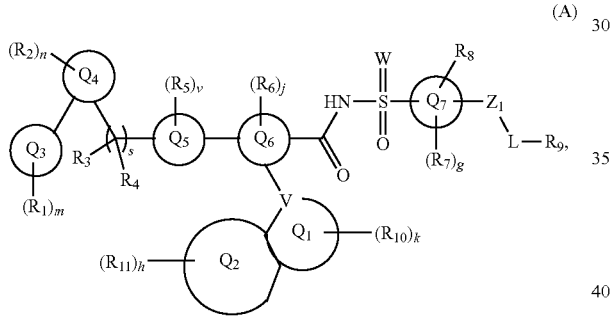

(A)

wherein
V is N or P(O);
$Q_1$ is 6-9 membered heterocycloalkyl, 6-9 membered heterocycloalkenyl, or 6-9 membered heteroaryl;
$Q_2$ is 6-membered heterocycloalkyl, 6-membered heterocycloalkenyl, 6-membered aryl, or 6-membered heteroaryl;
$Q_3$ is cycloalkyl, cycloalkenyl, bridged cycloalkyl, heterocycloalkyl, heterocycloalkenyl, aryl or heteroaryl;
$Q_4$ is cycloalkyl, cycloalkenyl, heterocycloalkyl, heterocycloalkenyl, aryl, or heteroaryl;
$Q_5$ is 6-membered heterocycloalkyl, or 6-membered heterocycloalkenyl;
$Q_6$ is 6-membered aryl, or 5-6 membered heteroaryl;
$Q_7$ is 6-membered aryl or 5-6 membered heteroaryl, each of which is optionally fused with a benzene, heteroarene, cycloalkane, cycloalkene, heterocycloalkene, or heterocycloalkene;
each of $R_1$, $R_2$, $R_3$, $R_4$, $R_5$, $R_6$, $R_7$, $R_8$, $R_{10}$, and $R_{11}$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_p R_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, —$P(O)R_bR_c$, -alkyl-$P(O)R_bR_c$, —$S(O)(=N(R_b))R_c$, —$B=S(O)R_bR_c$, =$NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;
$R_9$ is $R_{9A}$ or $R_{9B}$;
$R_{9A}$ is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_p R_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, —$P(O)R_bR_c$, -alkyl-$P(O)R_bR_c$, —$S(O)(=N(R_b))R_c$, —$N=S(O)R_bR_c$, =$NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;
$R_{9B}$ is a small molecule E3 ubiquitin ligase binding moiety that binds an E3 ubiquitin ligase;
each $R_d$, independently, is H, D, alkyl, spiroalkyl, alkenyl, alkynyl, halo, cyano, amine, nitro, hydroxy, =O, —$P(O)R_{bb}R_{cc}$, -alkyl-$P(O)R_{bb}R_{cc}$, —$S(O)(=N(R_{bb}))R_{cc}$, —$N=S(O)R_{bb}R_{cc}$, =$NR_{bb}$, $C(O)NHOH$, $C(O)OH$, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_c$;
$R_a$, $R_b$, $R_c$, $R_{bb}$ and $R_{cc}$, independently, is H, D, alkyl, spiroalkyl, alkenyl, alkynyl, alkoxy, alkoxyalkyl, haloalkyl, hydroxyalkyl, aminoalkyl, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_c$;
each $R_c$, independently, is H, D, alkyl, spiroalkyl, alkenyl, alkynyl, halo, cyano, amine, nitro, hydroxy, =O, $C(O)NHOH$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;
$Z_1$ is a bond, $(CH_2)_p$, $N(H)$, $O$, $S$, $C(O)$, $S(O_2)$, $OC(O)$, $C(O)O$, $OSO_2$, $S(O_2)O$, $C(O)S$, $SC(O)$, $C(O)C(O)$, $C(O)N(H)$, $N(H)C(O)$, $S(O_2)N(H)$, $N(H)S(O_2)$, $OC(O)O$, $OC(O)S$, $OC(O)N(H)$, $N(H)C(O)O$, $N(H)C(O)S$, $N(H)C(O)N(H)$, $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group;
L is $L_1$ or $L_2$;
$L_1$ is bond, alkenyl, alkynyl, cycloalkyl, cycloalkenyl, heterocycloalkyl, heterocycloalkenyl, aryl, or heteroaryl, in which said alkenyl, alkynyl, cycloalkyl, cycloalkenyl, heterocycloalkyl, heterocycloalkenyl, aryl, or heteroaryl is optionally substituted with one or more $R_d$;
$L_2$ is an alkyl in which one or more -$L_i$- are optionally inserted between any two adjacent carbon atoms;
-$L_i$- is —$N(R_a)$—, —O—, —S—, —$C(O)$—, —$S(O_2)$—, —$OC(O)$—, —$C(O)O$—, —$OSO_2$—, —$S(O_2)O$—, —$C(O)S$—, —$SC(O)$—, —$C(O)C(O)$—, —$C(O)N(R_a)$—, —$N(R_a)C(O)$—, —$S(O_2)N(R_a)$—, —$N(R_a)S$ (O₂)—, —OC(O)O—, —OC(O)S—, —OC(O)N(R$_a$)—, —N(R$_a$)C(O)O—, —N(R$_a$)C(O)S—, —N(R$_a$)C(O)N(R$_a$)—, a bivalent alkenyl group, a bivalent alkynyl group, a bivalent cycloalkyl group, a bivalent heterocycloalkyl group, a bivalent aryl group, a bivalent heteroaryl group;

W is O or N(R$_a$);

two of R$_1$ group, taken together with the atoms to which they are attached, may optionally form a cycloalkyl or heterocycloalkyl, in which said cycloalkyl or heterocycloalkyl of R$_1$, is optionally substituted with one or more R$_d$;

two of R$_2$ group, taken together with the atom(s) to which they are attached, may optionally form a cycloalkyl or heterocycloalkyl, in which said cycloalkyl or heterocycloalkyl of R$_2$, is optionally substituted with one or more R$_d$;

R$_3$ and R$_4$ group, taken together with the atom to which they are attached, may optionally form a cycloalkyl or heterocycloalkyl, in which said cycloalkyl or heterocycloalkyl of R$_3$ and R$_4$, is optionally substituted with one or more R$_d$;

two of R$_5$ group, taken together with the atom(s) to which they are attached, may optionally form a cycloalkyl or heterocycloalkyl, in which said cycloalkyl or heterocycloalkyl of R$_5$, is optionally substituted with one or more R$_d$;

two of R$_6$ group, taken together with the atoms to which they are attached, may optionally form a cycloalkyl or heterocycloalkyl, in which said cycloalkyl or heterocycloalkyl of R$_6$, is optionally substituted with one or more R$_d$;

two of R$_7$ group, taken together with the atoms to which they are attached, may optionally form a cycloalkyl or heterocycloalkyl, in which said cycloalkyl or heterocycloalkyl of R$_7$, is optionally substituted with one or more R$_d$;

two of R$_{10}$ group, taken together with the atom(s) to which they are attached, may optionally form a cycloalkyl or heterocycloalkyl, in which said cycloalkyl or heterocycloalkyl of R$_{10}$, is optionally substituted with one or more R$_d$;

two of R$_{11}$ group, taken together with the atom(s) to which they are attached, may optionally form a cycloalkyl, heterocycloalkyl, aryl, or heteroaryl, in which said cycloalkyl, heterocycloalkyl, aryl, or heteroaryl of R$_{11}$, is optionally substituted with one or more R$_d$;

R$_2$ and R$_5$ group, taken together with the atoms to which they are attached, may optionally form a cycloalkyl or heterocycloalkyl, in which said cycloalkyl or heterocycloalkyl of R$_2$ and R$_5$, is optionally substituted with one or more R$_d$;

R$_3$ and R$_5$ group, taken together with the atoms to which they are attached, may optionally form a cycloalkyl or heterocycloalkyl, in which said cycloalkyl or heterocycloalkyl of R$_3$ and R$_5$, is optionally substituted with one or more R$_d$;

R$_b$ and R$_c$ group, taken together with the atom to which they are attached, may optionally form a cycloalkyl, or heterocycloalkyl, in which said cycloalkyl or heterocycloalkyl of R$_b$ and R$_c$, is optionally substituted with one or more R$_c$;

two of R$_d$ group, taken together with the atom(s) to which they are attached, may optionally form a cycloalkyl or heterocycloalkyl, in which said cycloalkyl or heterocycloalkyl of R$_d$, is optionally substituted with one or more R$_c$;

two of R$_c$ group, taken together with the atom(s) to which they are attached, may optionally form a cycloalkyl or heterocycloalkyl, in which said cycloalkyl or heterocycloalkyl of R$_c$ is optionally substituted with one or more groups selected from H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

each of g and j is, independently, 0, 1, 2, or 3;

each of n, v and k is, independently, 0, 1, 2, 3, 4, 5, 6, 7, or 8;

s is 0 or 1; and each of h, m, p, and q is, independently, 0, 1, 2, 3, 4, or 5; optionally, the compound of Formula (A) is not 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydro-[1,4]oxazino[3,2-f]indol-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(6,7-dihydroimidazo[4',5':4,5]benzo[1,2-b][1,4]oxazin-8(3H)-yl)-N-((3-nitro-4-(((tetrahydro-2H-pyran-4-yl)methyl)amino)phenyl)sulfonyl)benzamide, and 4-(4-((4'-chloro-5,5-dimethyl-3,4,5,6-tetrahydro-[1,1'-biphenyl]-2-yl)methyl)piperazin-1-yl)-2-(6,7-dihydro-[1,4]oxazino[3,2-f]indazol-5(1H)-yl)-N-((3-nitro-4-(((tetrahydro-2H-pyran-4-yl)methyl)amino)phenyl)sulfonyl)benzamide.

In a second embodiment, the invention provides the compound of the first embodiment, or an N-oxide thereof, or a pharmaceutically acceptable salt, solvate, polymorph, tautomer, stereoisomer, an isotopic form, or a prodrug thereof, wherein Formula (A) does not include Formula (A'):

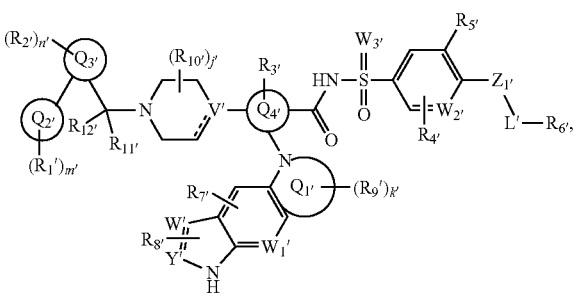

Formula (A')

wherein:

Q$_1$, is a 6- or 7-membered heterocycloalkyl, 6- or 7-membered heterocycloalkenyl, or 6- or 7-membered heteroaryl;

Q$_2$' is an aryl or heteroaryl;

Q$_3$, is a cycloalkyl, cycloalkenyl, heterocycloalkyl, heterocycloalkenyl, aryl, or heteroaryl;

$Q_{4'}$ is

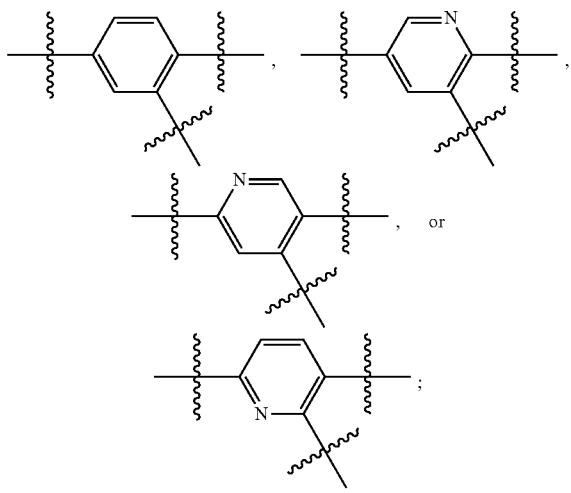

each of $R_1$, $R_2$, $R_3$, $R_4$, $R_5$, $R_6$, $R_7$, $R_8$, $R_9$, $R_{10}$, $R_{11}$, and $R_{12}$, independently, is H, D, alkyl, alkenyl, alkynyl, cycloalkyl, cycloalkenyl, heterocycloalkyl, heterocycloalkenyl, aryl, heteroaryl, halo, nitro, oxo, cyano, $OR_a$, $SR_a$, alkyl-$R_a$, $NH(CH_2)_p$, $R_a$, $C(O)R_a$, $S(O)R_a$, $SO_2R_a$, $C(O)OR_a$, $OC(O)R_a$, $NR_bR_cP(O)R_bR_c$, alkyl-$P(O)R_bR_c$, $C(O)N(ROR_c)$, $N(R_b)C(O)R_c$, $S(O)(=N(R_a))R_b$, —B=$S(O)R_bR_c$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_{d'}$;

$R_a$, $R_b$, $R_c$ and $R_{d'}$, independently, is H, D, alkyl, alkenyl, alkynyl, halo, cyano, amine, nitro, hydroxy, C(O)NHOH, C(O)OH, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, haloalkylamino, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_{c'}$;

$R_{c'}$ is H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

$Z_{1'}$ is a bond, $(CH_2)_p$, N(H), O, S, C(O), $S(O_2)$, OC(O), C(O)O, $OSO_2$, $S(O_2)O$, C(O)S, SC(O), C(O)C(O), C(O)N(H), N(H)C(O), $S(O_2)N(H)$, $N(H)S(O_2)$, OC(O)O, OC(O)S, OC(O)N(H), N(H)C(O)O, N(H)C(O)S, N(H)C(O)N(H), $(CH_2)_pN(H)(CH_2)_{q'}$, $(CH_2)_pN(H)C(O)(CH_2)_{q'}$, $(CH_2)_pC(O)N(H)(CH_2)_{q'}$, $OC(O)N(H)(CH_2)_{p'+1}N(H)(CH_2)_{q'}$, a bivalent alkenyl group, or a bivalent alkynyl group;

L' is a bond, alkyl, alkenyl, alkynyl, cycloalkyl, cycloalkenyl, heterocycloalkyl, heterocycloalkenyl, aryl, or heteroaryl, in which said alkyl, cycloalkyl, cycloalkenyl, heterocycloalkyl, heterocycloalkenyl, aryl, or heteroaryl is optionally substituted with one or more $R_{d'}$;

each of Y', W', $W_{1'}$, and $W_{2'}$, independently, is CH or N, except that $W_{1'}$ is N when $Q_{1'}$ is 6-membered;

$W_3$, is O or $N(R_{a'})$;

V' is N, C, or CH;

two of $R_9$, group, taken together with the atom to which they are attached, may optionally form a cycloalkyl or heterocycloalkyl, in which said cycloalkyl or heterocycloalkyl of $R_{9'}$ is optionally substituted with one or more $R_{d'}$;

two of $R_2$ group, taken together with the atom to which they are attached, may optionally form a cycloalkyl or heterocycloalkyl, in which said cycloalkyl or heterocycloalkyl of $R_2$ is optionally substituted with one or more $R_{d'}$;

two of $R_{10'}$ group, taken together with the atom to which they are attached, may optionally form a cycloalkyl or heterocycloalkyl, in which said cycloalkyl or heterocycloalkyl of $R_{10'}$ is optionally substituted with one or more $R_{d'}$;

$R_{11'}$ and $R_{12'}$ group, taken together with the atom to which they are attached, may optionally form a cycloalkyl or heterocycloalkyl, in which said cycloalkyl or heterocycloalkyl of $R_{11'}$ or $R_{12'}$ is optionally substituted with one or more $R_{d'}$;

$R_{10'}$ and $R_{2'}$ group, taken together with the atom to which they are attached, may optionally form a cycloalkyl or heterocycloalkyl, in which said cycloalkyl or heterocycloalkyl of $R_{10'}$ or $R_{2'}$ is optionally substituted with one or more $R_{d'}$;

$R_{4'}$ and —$Z_1$-L-$R_6$, group, taken together with the atom to which they are attached, may optionally form a cycloalkyl, cycloalkenyl, heterocycloalkyl, heterocycloalkenyl, aryl, or heteroaryl, in which said cycloalkyl, cycloalkenyl, heterocycloalkyl, heterocycloalkenyl, aryl, or heteroaryl of $R_4$' is optionally substituted with one or more $R_{d'}$;

$R_{b'}$ and $R_{c'}$ group, taken together with the atom to which they are attached, may optionally form a cycloalkyl, or heterocycloalkyl, in which said cycloalkyl or heterocycloalkyl of $R_{b'}$ and $R_{c'}$ is optionally substituted with one or more $R_{c'}$;

two of $R_{d'}$ group, taken together with the atom to which they are attached, may optionally form a cycloalkyl, or heterocycloalkyl, in which said cycloalkyl or heterocycloalkyl of $R_{d'}$ is optionally substituted with one or more $R_{c'}$;

two of $R_{c'}$ group, taken together with the atom to which they are attached, may optionally form a cycloalkyl, or heterocycloalkyl;

each of j' and k', independently, is 0, 1, 2, 3, 4, 5, 6, 7, or 8; and each of m', n', p', q', and r', independently, is 0, 1, 2, 3, or 4.

In an alternative second embodiment, the compounds of Formula (A) do not include the compounds explicitly/expressly disclosed in International Application Publication Nos. WO2019/040550 and WO2019/040573, both of which are incorporated herein by reference. Some of these previously disclosed compounds are listed below and are incorporated herein.

In a third embodiment, the invention provides a compound according to the first or second (hereinafter including the alternative second) embodiment, or an N-oxide thereof, or a pharmaceutically acceptable salt, solvate, polymorph, tautomer, stereoisomer, an isotopic form, or a prodrug of said compound or N-oxide thereof, wherein the compound is represented by Formula (A-1):

Formula (A-1)

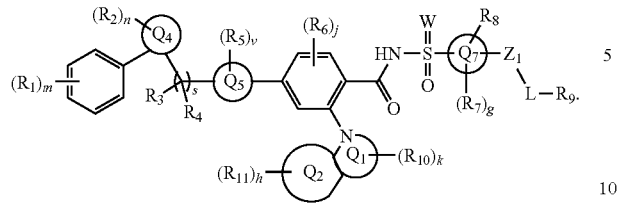

In a fourth embodiment, the invention provides a compound according to the first, second, or third embodiment, or an N-oxide thereof, or a pharmaceutically acceptable salt, solvate, polymorph, tautomer, stereoisomer, an isotopic form, or a prodrug of said compound or N-oxide thereof, wherein the compound is represented by Formula (A-2):

Formula (A-2)

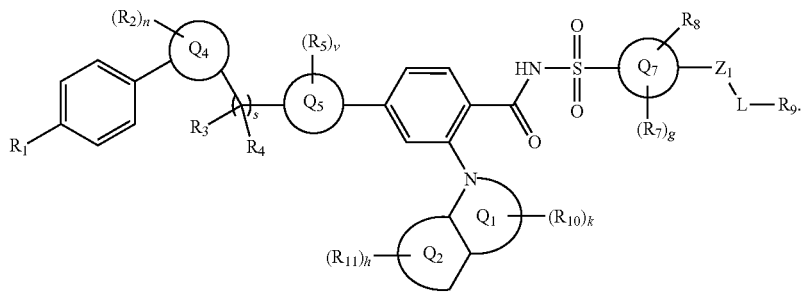

In a fifth embodiment, the invention provides a compound according to the first, second, third, or fourth embodiment, or an N-oxide thereof, or a pharmaceutically acceptable salt, solvate, polymorph, tautomer, stereoisomer, an isotopic form, or a prodrug of said compound or N-oxide thereof, wherein the compound is represented by Formula (A-3):

Formula (A-3)

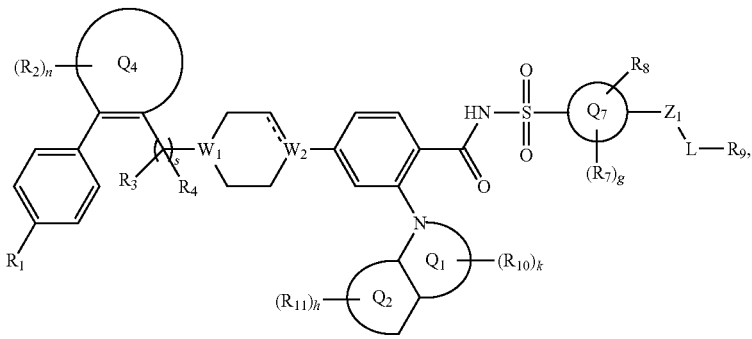

wherein "—" is absent or a bond; $W_1$ is N or CH; and $W_2$ is N or C or CH.

In a six embodiment, the invention provides a compound according to the first, second, third, fourth, or fifth embodiment, or an N-oxide thereof, or a pharmaceutically acceptable salt, solvate, polymorph, tautomer, stereoisomer, an isotopic form, or a prodrug of said compound or N-oxide thereof, wherein the compound is represented by Formula (A-4):

Formula (A-4)

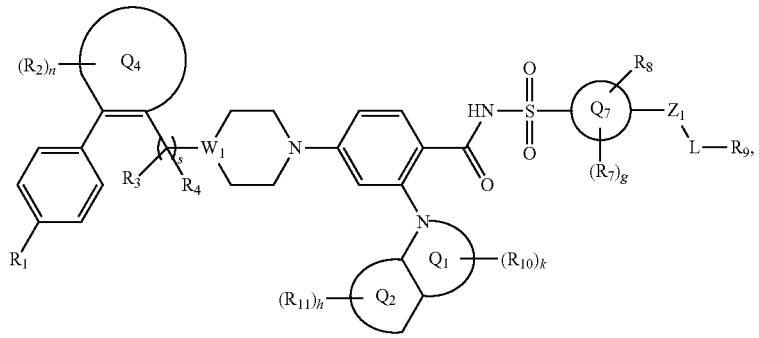

In a seventh embodiment, the invention provides a compound according to the first, second, third, fourth, fifth, or sixth embodiment, or an N-oxide thereof, or a pharmaceutically acceptable salt, solvate, polymorph, tautomer, stereoisomer, an isotopic form, or a prodrug of said compound or N-oxide thereof, wherein the compound is represented by Formula (A-5):

Formula (A-5)

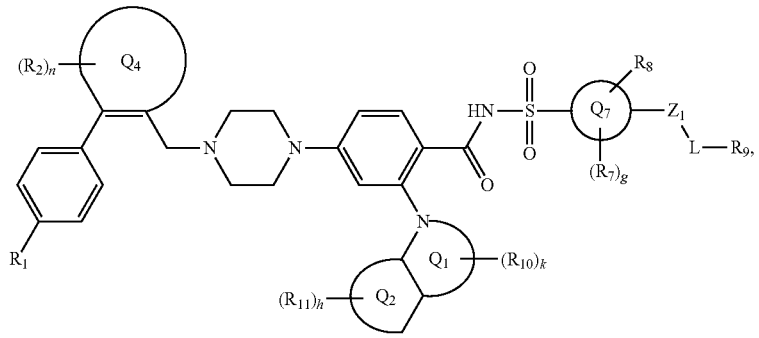

In an eighth embodiment, the invention provides a compound according to the first, second, third, fourth, fifth, sixth, or seventh embodiment, or an N-oxide thereof, or a pharmaceutically acceptable salt, solvate, polymorph, tautomer, stereoisomer, an isotopic form, or a prodrug of said compound or N-oxide thereof, wherein is

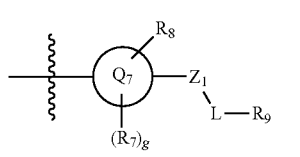

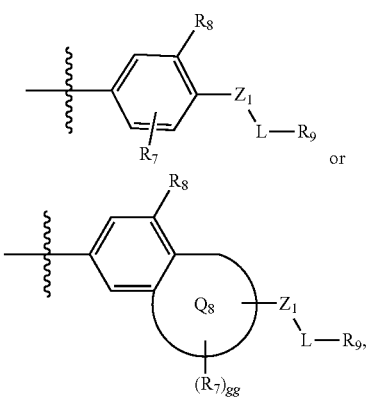

or in which $Q_8$ is 5-7 membered heterocycloalkyl, 5-7 membered heterocycloalkenyl, phenyl, or 5-7 membered heteroaryl; and gg is 0, 1, 2, 3, or 4.

In a ninth embodiment, the invention provides a compound according to the first, second, third, fourth, fifth, sixth, seventh, or eighth embodiment, or an N-oxide thereof, or a pharmaceutically acceptable salt, solvate, polymorph, tautomer, stereoisomer, an isotopic form, or a prodrug of said compound of Formula or N-oxide thereof, wherein

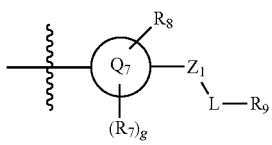

is

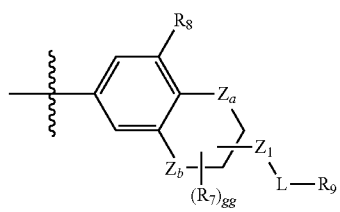

in which each $Z_a$ and $Z_b$ is independently —O—, —CH$_2$—, —C(O)—, —N(R$_a$)—, —S—, —S(O)—, —S(O$_2$)—, —S(O)(=N(R$_a$))—, —P(O)(R$_a$)—; wherein R$_a$ of $Z_a$ and $Z_b$, independently, is H, D, C$_1$-C$_6$alkyl, C$_2$-C$_6$alkenyl, C$_1$-C$_6$alkylcarbonyl, C$_1$-C$_6$alkoxycarbonyl, C$_3$-C$_6$cycloalkyl, 5-8 membered monocyclic heterocycloalkyl, C$_6$-C$_{14}$aryl, or 5-8 membered monocyclic heteroaryl, in which said C$_1$-C$_6$alkyl, C$_3$-C$_6$cycloalkyl, 5-8 membered monocyclic heterocycloalkyl, C$_6$-C$_{14}$aryl, 5-8 membered monocyclic heteroaryl is optionally substituted with one or more R$_c$.

In a tenth embodiment, the invention provides a compound according to the first, second, third, fourth, fifth, sixth, seventh, eighth, or ninth embodiment, or an N-oxide thereof, or a pharmaceutically acceptable salt, solvate, polymorph, tautomer, stereoisomer, an isotopic form, or a prodrug of said compound or N-oxide thereof, wherein

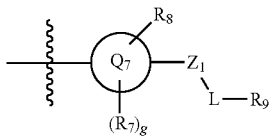

is

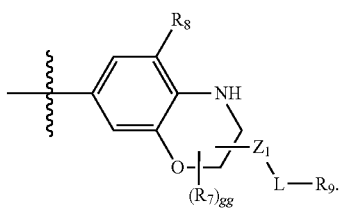

In an eleventh embodiment, the invention provides a compound according to the first, second, third, fourth, fifth, sixth, seventh, eighth, ninth, or tenth embodiment, or an N-oxide thereof, or a pharmaceutically acceptable salt, solvate, polymorph, tautomer, stereoisomer, an isotopic form, or a prodrug of said compound or N-oxide thereof, wherein $Z_1$ is absent or (CH$_2$)$_p$; L is L$_1$ and L$_1$ is bond, and R$_9$ is 5-7 membered heterocyclyl or 7-10 membered bridged heterocyclyl, each of which is optionally substituted with 1-3 groups selected from halo, —OH, —CN, —COOH, —NH$_2$, —N(CH$_3$)$_2$, —(C$_1$-C$_4$)alkyl, and —(C$_1$-C$_4$)alkoxy.

In a twelfth embodiment, the invention provides a compound according to the first, second, third, fourth, fifth, sixth, seventh, eighth, ninth, tenth, or eleventh embodiment, or an N-oxide thereof, or a pharmaceutically acceptable salt, solvate, polymorph, tautomer, stereoisomer, an isotopic form, or a prodrug of said compound or N-oxide thereof, wherein

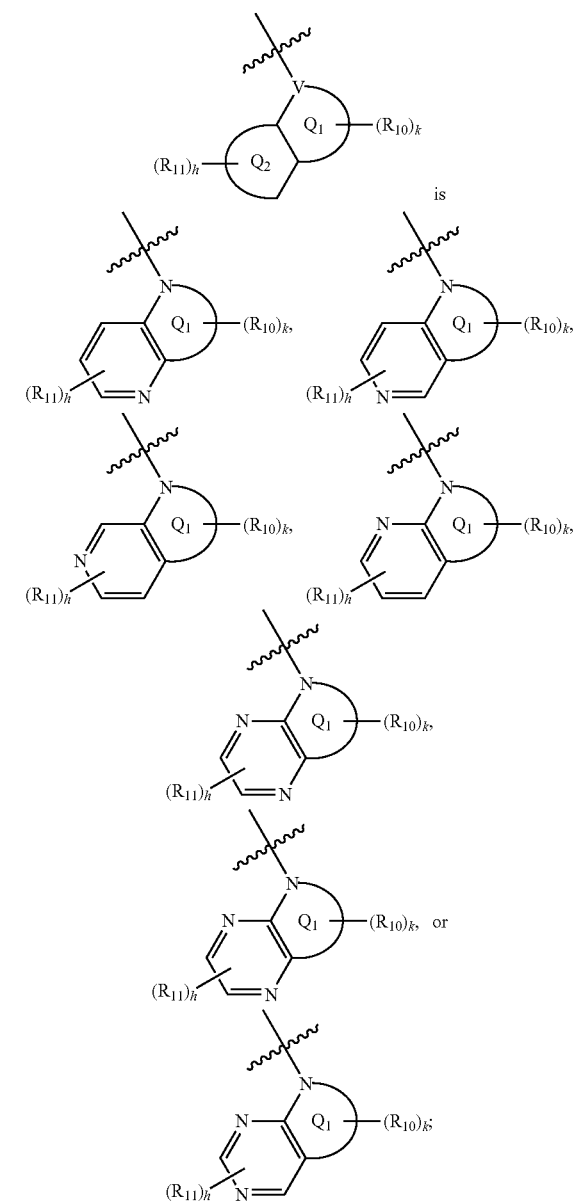

and h is 0, 1, or 2.

In a thirteenth embodiment, the invention provides a compound according to the first, second, third, fourth, fifth, sixth, seventh, eighth, ninth, tenth, or eleventh embodiment, or an N-oxide thereof, or a pharmaceutically acceptable salt, solvate, polymorph, tautomer, stereoisomer, an isotopic form, or a prodrug of said compound or N-oxide thereof, wherein
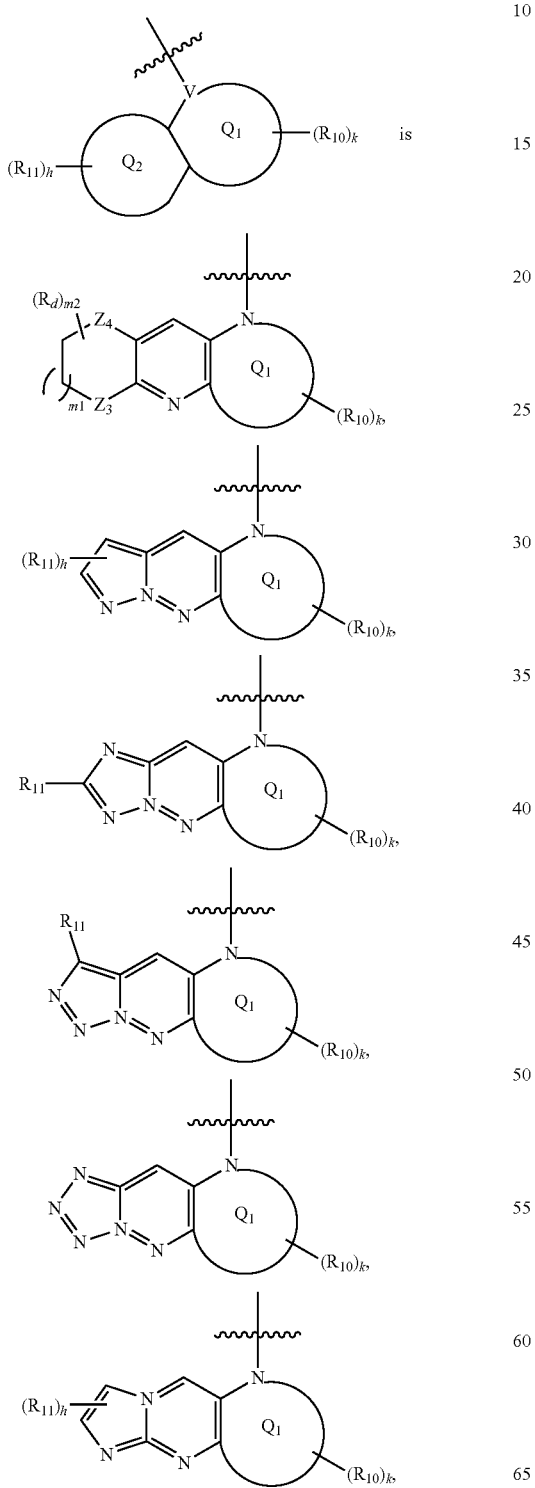
is
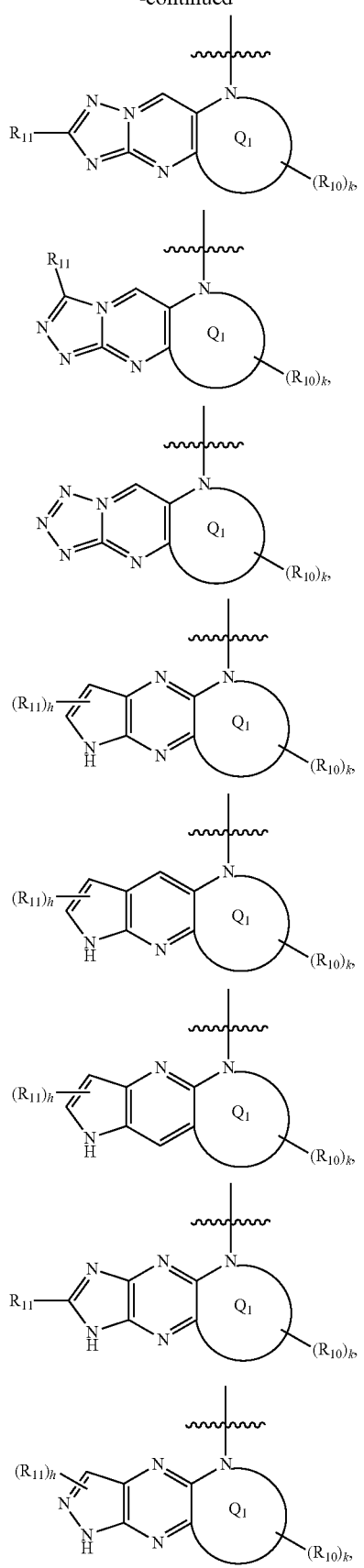

-continued

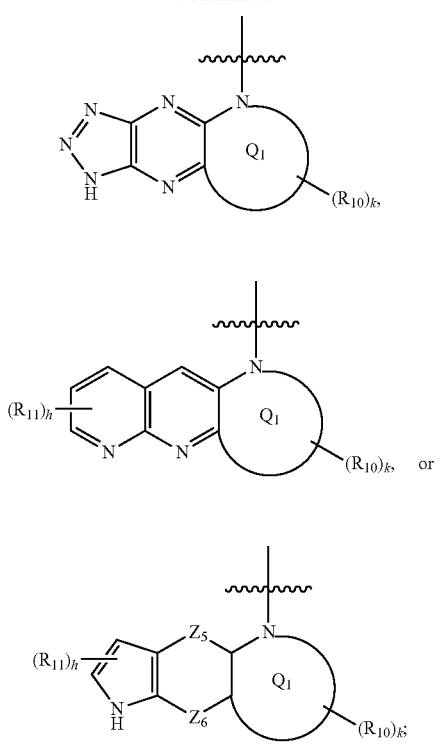

h is 0, 1, or 2;

each of $m_1$ and $m_2$, independently, is 0, 1, or 2; and each of $Z_3$, $Z_4$, $Z_5$ and $Z_6$, independently, is a bond, $(CH_2)_p$, N(H), O, S, C(O), $S(O_2)$, OC(O), C(O)O, $OSO_2$, $S(O_2)O$, C(O)S, SC(O), C(O)C(O), C(O)N(H), N(H)C(O), $S(O_2)N(H)$, $N(H)S(O_2)$, OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group. In one specific embodiment,

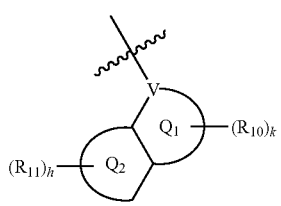

is

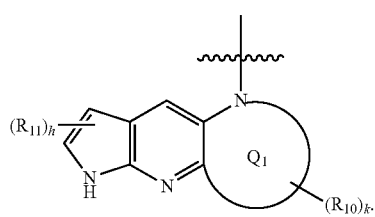

In a more specific embodiment,

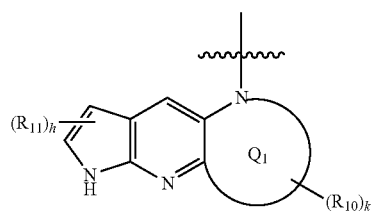

is

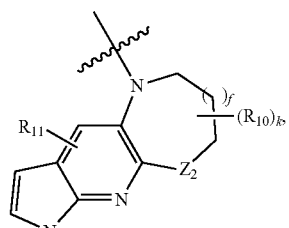

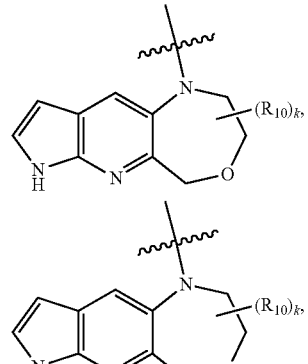

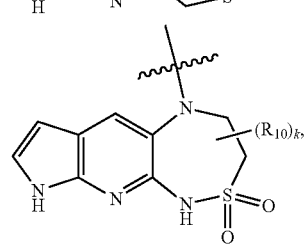

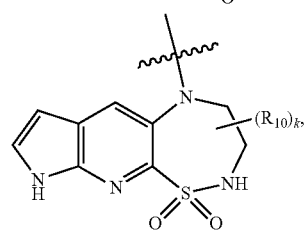

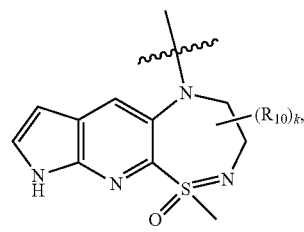

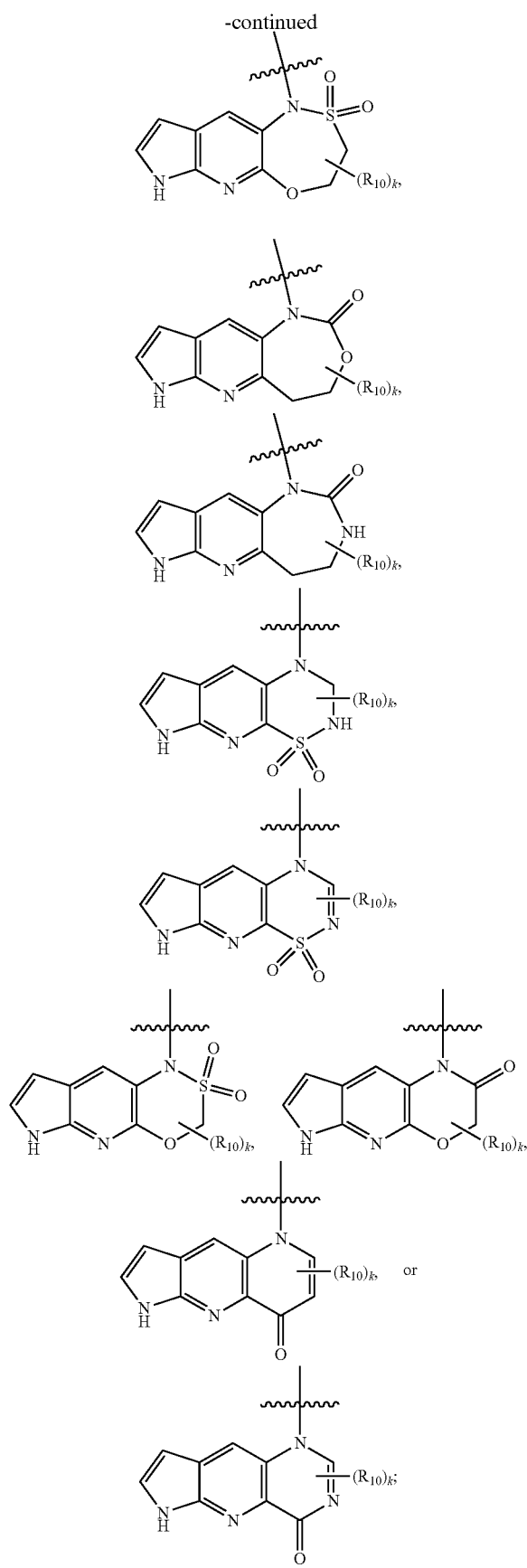

wherein $Z_2$ is —O—, —CH$_2$—, —C(O)—, —N(R$_a$)—, —S—, —S(O)—, —S(O$_2$)—, —S(O)(=N(R$_a$))—, —P(O)(R$_a$)—; wherein R$_a$ of $Z_2$, independently, is H, D, $C_1$-$C_6$alkyl, $C_2$-$C_6$alkenyl, $C_1$-$C_6$alkylcarbonyl, $C_1$-$C_6$alkoxycarbonyl, $C_3$-$C_6$cycloalkyl, 5-8 membered monocyclic heterocycloalkyl, $C_6$-$C_{14}$aryl, or 5-8 membered monocyclic heteroaryl, in which said $C_1$-$C_6$alkyl, $C_3$-$C_6$cycloalkyl, 5-8 membered monocyclic heterocycloalkyl, $C_6$-$C_{14}$aryl, 5-8 membered monocyclic heteroaryl is optionally substituted with one or more R$_c$;

k is 0, 1, 2, 3, or 4; and f is 0, 1, 2, or 3. In one specific embodiment,

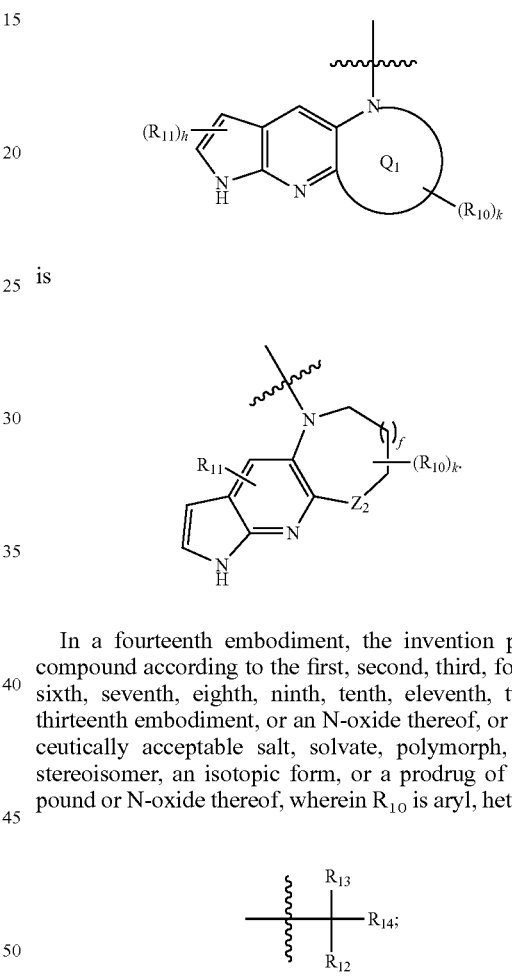

is

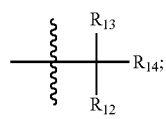

In a fourteenth embodiment, the invention provides a compound according to the first, second, third, fourth, fifth, sixth, seventh, eighth, ninth, tenth, eleventh, twelfth, or thirteenth embodiment, or an N-oxide thereof, or a pharmaceutically acceptable salt, solvate, polymorph, tautomer, stereoisomer, an isotopic form, or a prodrug of said compound or N-oxide thereof, wherein $R_{10}$ is aryl, heteroaryl, or $$\begin{array}{c} R_{13} \\ | \\ -\!\!\!-\!\!\!-\!\!\!-\!\!\!- R_{14}; \\ | \\ R_{12} \end{array}$$

$R_{12}$ is H, D, alkyl, alkenyl, alkynyl, cycloalkyl, cycloalkenyl, heterocycloalkyl, heterocycloalkenyl, aryl, heteroaryl, halo, nitro, oxo, cyano, OR$_a$, SR$_a$, alkyl-R$_a$, NH(CH$_2$)$_p$R$_a$, C(O)R$_a$, S(O)R$_a$, SO$_2$R$_a$, C(O)OR$_a$, OC(O)R$_a$, NR$_b$R$_c$, P(O)R$_b$R$_c$, alkyl-P(O)R$_b$R$_c$, C(O)N(R$_b$)R$_c$, N(R$_b$)C(O)R$_c$, S(O)(=N(ROR$_c$, —N=S(O)R$_b$R$_c$, SO$_2$N(R$_b$)R$_c$, or N(R$_b$)SO$_2$R$_c$, in which said cycloalkyl, cycloalkenyl, heterocycloalkyl, heterocycloalkenyl, aryl, heteroaryl is optionally substituted with one or more R$_d$; and each of $R_{13}$, and $R_{14}$, independently, is H, D, alkyl, halo-alkyl, or $R_{13}$ and $R_{14}$, taken together with the atom to which they are attached, may optionally form a cycloalkyl or heterocycloalkyl, in which said cycloalkyl or heterocycloalkyl is optionally substituted with one or more R$_d$; and the remaining variables are as defined ins.

In a fifteenth embodiment, the invention provides a compound according to the thirteenth embodiment, or an N-oxide thereof, or a pharmaceutically acceptable salt, solvate, polymorph, tautomer, stereoisomer, an isotopic form, or a prodrug of said compound or N-oxide thereof, wherein

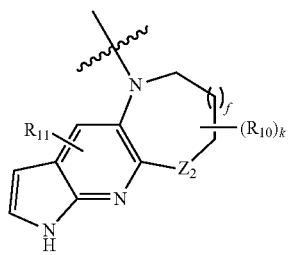

is

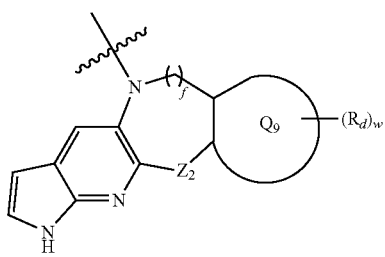

in which $Q_9$ is a $C_4$-$C_6$ cycloalkyl, 4-6 membered heterocycloalkyl, phenyl, or 5-6 membered heteroaryl; and w is 0, 1, 2, 3, or 4. In one specific embodiment, $Q_9$ is $C_5$-$C_6$ cycloalkyl, 5-6 membered heterocycloalkyl, or 5-6 membered heteroaryl; each of which is optionally substituted with 1 to 3 groups selected from halogen, $C_1$-$C_4$ alkyl, $C_1$-$C_4$ haloalkyl, $C_1$-$C_4$ alkoxy, —OH, CN, and $NH_2$.

In a sixteenth embodiment, the invention provides a compound according to the first, second, third, fourth, fifth, sixth, seventh, eighth, ninth, tenth, twelfth, thirteenth, fourteenth, or fifteenth embodiment, or an N-oxide thereof, or a pharmaceutically acceptable salt, solvate, polymorph, tautomer, stereoisomer, an isotopic form, or a prodrug of said compound or N-oxide thereof, wherein $R_9$ is $R_{9B}$. In one specific embodiment, wherein $R_{9B}$ is a small molecule E3 ubiquitin ligase binding moiety that binds an E3 ubiquitin ligase; said E3 ubiquitin ligase is Von Hippel-Lindau (VLM), cereblon (CLM), mouse double-minute homolog2 (MLM), and IAP (ILM).

In a seventeenth embodiment, the invention provides a compound according to the sixteenth embodiment, or an N-oxide thereof, or a pharmaceutically acceptable salt, solvate, polymorph, tautomer, stereoisomer, an isotopic form, or a prodrug of said compound or N-oxide thereof, wherein $R_9$ is

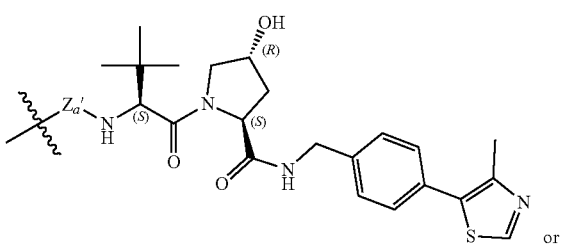

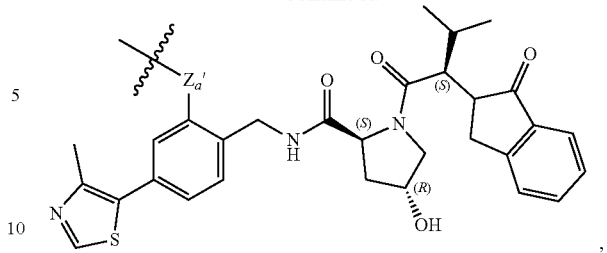

wherein $Z_a'$ is a bond, $(CH_2)_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O$_2$)N(H), N(H)S(O$_2$), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group.

In an eighteenth embodiment, the invention provides a compound according to the sixteenth embodiment, or an N-oxide thereof, or a pharmaceutically acceptable salt, solvate, polymorph, tautomer, stereoisomer, an isotopic form, or a prodrug of said compound or N-oxide thereof, wherein $R_9$ is

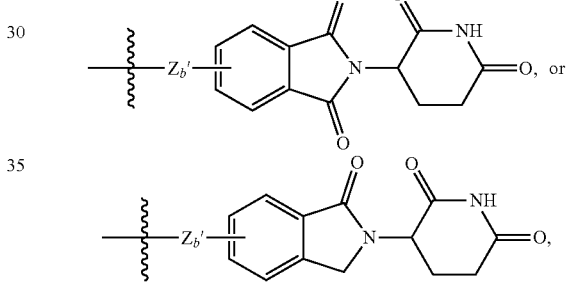

wherein $Z_b'$ is a bond, $(CH_2)_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O$_2$)N(H), N(H)S(O$_2$), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group.

In a nineteenth embodiment, the invention provides a compound according to the first, second, third, fourth, fifth, sixth, seventh, eighth, ninth, tenth, twelfth, thirteenth, fourteenth, fifteenth, sixteenth, seventeenth, or eighteenth embodiment, or an N-oxide thereof, or a pharmaceutically acceptable salt, solvate, polymorph, tautomer, stereoisomer, an isotopic form, or a prodrug thereof, wherein L is $L_2$, and $L_2$ is

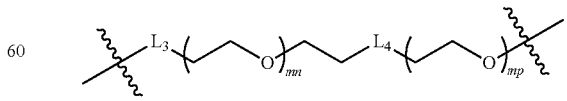

wherein each of mn and mp is independently an integer of 0 to 12; and each of $L_3$ and $L_4$ independently, is a bond, $(CH_2)_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O₂)N(H), N(H)S(O₂), OC(O)O, OC(O)S, OC(O)N(H), N(H)C(O)O, N(H)C(O)S, N(H)C(O)N(H), (CH₂)ₚN(H)(CH₂)q, (CH₂)ₚN(H)C(O)(CH₂)q, (CH₂)ₚC(O)N(H)(CH₂)q, OC(O)N(H)(CH₂)ₚ₊₁N(H)(CH₂)q, a bivalent alkenyl group, or a bivalent alkynyl group. In one specific embodiment, wherein said L₂ is

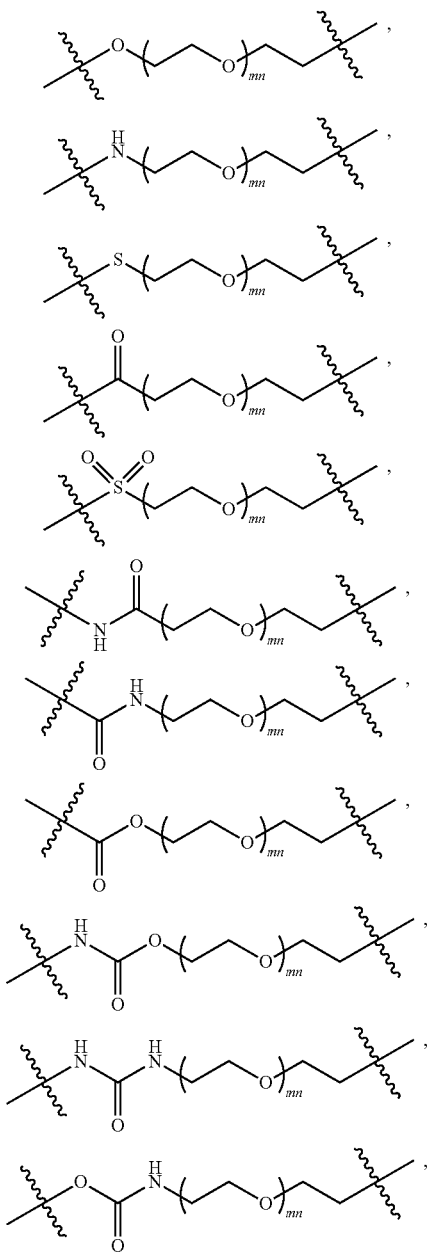

in which mn is 0 to 12.

In a twentieth embodiment, the invention provides a compound according to the first, second, third, fourth, fifth, sixth, seventh, eighth, ninth, tenth, eleventh, twelfth, thirteenth, fourteenth, fifteenth, sixteenth, seventeenth, eighteenth, or nineteenth embodiment, or an N-oxide thereof, or a pharmaceutically acceptable salt, solvate, polymorph, tautomer, stereoisomer, an isotopic form, or a prodrug thereof, wherein

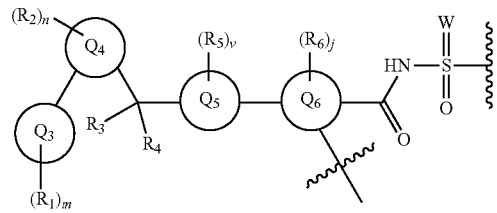

is

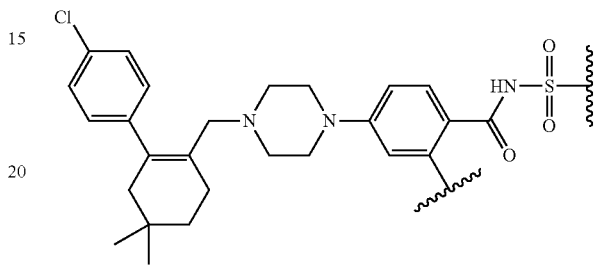

In a twenty first embodiment, the invention provides a compound according to the first, second, third, fourth, fifth, sixth, seventh, eighth, ninth, tenth, eleventh, twelfth, thirteenth, fourteenth, fifteenth, sixteenth, seventeenth, eighteenth, nineteenth, or twentieth embodiment, or an N-oxide thereof, or a pharmaceutically acceptable salt, solvate, polymorph, tautomer, stereoisomer, an isotopic form, or a prodrug thereof, wherein R₈ is NO₂.

The present invention also discloses a compound of Formula (AA), or an N-oxide thereof, or a pharmaceutically acceptable salt, solvate, polymorph, tautomer, stereoisomer, an isotopic form, or a prodrug of said compound of Formula (AA) or N-oxide thereof:

Formula (AA)

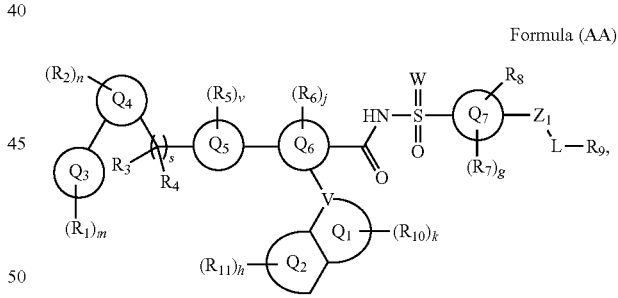

wherein
V is N or P(O);
Q₁ is 5-membered heterocycloalkyl, 5-membered heterocycloalkenyl, or 5-membered heteroaryl;
Q₂ is 6-membered heterocycloalkyl, 6-membered heterocycloalkenyl, 6-membered aryl, or 6-membered heteroaryl;
Q₃ is cycloalkyl, cycloalkenyl, bridged cycloalkyl, heterocycloalkyl, heterocycloalkenyl, aryl or heteroaryl;
Q₄ is cycloalkyl, cycloalkenyl, heterocycloalkyl, heterocycloalkenyl, aryl, or heteroaryl;
Q₅ is 6-membered heterocycloalkyl, or 6-membered heterocycloalkenyl;
Q₆ is 6-membered aryl, or 5-6 membered heteroaryl;

$Q_7$ is 6-membered aryl or 5-6 membered heteroaryl, each of which is optionally fused with a benzene, heteroarene, cycloalkane, cycloalkene, heterocycloalkene, or heterocycloalkene;

each of $R_1$, $R_2$, $R_3$, $R_4$, $R_5$, $R_6$, $R_7$, $R_8$, $R_{10}$, and $R_{11}$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $C(O)N(R_b)R_c$, $N(R_b)C(O)R_c$, —$P(O)R_bR_c$, -alkyl-$P(O)R_bR_c$, —$S(O)(=N(ROR_c$, —$N=S(O)R_bR_c$, =$NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_9$ is $R_{9A}$ or $R_{9B}$;

$R_{9A}$ is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, —$P(O)R_bR_c$, -alkyl-$P(O)R_bR_c$, —$S(O)(=N(R_b))R_c$, —$N=S(O)R_bR_c$, =$NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_{9B}$ is a small molecule E3 ubiquitin ligase binding moiety that binds an E3 ubiquitin ligase;

$R_a$, $R_b$, $R_c$, $R_{bb}$ and $R_{cc}$, independently, is H, D, alkyl, spiroalkyl, alkenyl, alkynyl, alkoxy, alkoxyalkyl, haloalkyl, hydroxyalkyl, aminoalkyl, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_c$;

$R_d$, independently, is H, D, alkyl, spiroalkyl, alkenyl, alkynyl, halo, cyano, amine, nitro, hydroxy, =O, —$P(O)R_{bb}R_{cc}$, -alkyl-$P(O)R_{bb}R_{cc}$, —$S(O)(=N(R_{bb}))R_{cc}$, —$N=S(O)R_{bb}R_{cc}$, =$NR_b$, $C(O)NHOH$, $C(O)OH$, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_c$;

$R_c$, independently, is H, D, alkyl, spiroalkyl, alkenyl, alkynyl, halo, cyano, amine, nitro, hydroxy, =O, $C(O)NHOH$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

$Z_1$ is a bond, $(CH_2)_p$, $N(H)$, O, S, $C(O)$, $S(O_2)$, $OC(O)$, $C(O)O$, $OSO_2$, $S(O_2)O$, $C(O)S$, $SC(O)$, $C(O)C(O)$, $C(O)N(H)$, $N(H)C(O)$, $S(O_2)N(H)$, $N(H)S(O_2)$, $OC(O)O$, $OC(O)S$, $OC(O)N(H)$, $N(H)C(O)O$, $N(H)C(O)S$, $N(H)C(O)N(H)$, $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group;

L is $L_1$ or $L_2$;

$L_1$ is bond, alkenyl, alkynyl, cycloalkyl, cycloalkenyl, heterocycloalkyl, heterocycloalkenyl, aryl, or heteroaryl, in which said alkenyl, alkynyl, cycloalkyl, cycloalkenyl, heterocycloalkyl, heterocycloalkenyl, aryl, or heteroaryl is optionally substituted with one or more $R_d$;

$L_2$ is an alkyl in which one or more -$L_i$- are optionally inserted between any two adjacent carbon atoms;

-$L_i$- is —$N(R_a)$—, —O—, —S—, —$C(O)$—, —$S(O_2)$—, —$OC(O)$—, —$C(O)O$—, —$OSO_2$—, —$S(O_2)O$—, —$C(O)S$—, —$SC(O)$—, —$C(O)C(O)$—, —$C(O)N(R_a)$—, —$N(R_a)C(O)$—, —$S(O_2)N(R_a)$—, —$N(R_a)S(O_2)$—, —$OC(O)O$—, —$OC(O)S$—, —$OC(O)N(R_a)$—, —$N(R_a)C(O)O$—, —$N(R_a)C(O)S$—, —$N(R_a)C(O)N(R_a)$—, a bivalent alkenyl group, a bivalent alkynyl group, a bivalent cycloalkyl group, a bivalent heterocycloalkyl group, a bivalent aryl group, a bivalent heteroaryl group;

W is O or $N(R_a)$;

two of $R_1$ group, taken together with the atoms to which they are attached, may optionally form a cycloalkyl or heterocycloalkyl, in which said cycloalkyl or heterocycloalkyl of $R_1$, is optionally substituted with one or more $R_d$;

two of $R_2$ group, taken together with the atom(s) to which they are attached, may optionally form a cycloalkyl or heterocycloalkyl, in which said cycloalkyl or heterocycloalkyl of $R_2$, is optionally substituted with one or more $R_d$;

$R_3$ and $R_4$ group, taken together with the atom to which they are attached, may optionally form a cycloalkyl or heterocycloalkyl, in which said cycloalkyl or heterocycloalkyl of $R_3$ and $R_4$, is optionally substituted with one or more $R_d$;

two of $R_5$ group, taken together with the atom(s) to which they are attached, may optionally form a cycloalkyl or heterocycloalkyl, in which said cycloalkyl or heterocycloalkyl of $R_5$, is optionally substituted with one or more $R_d$;

two of $R_6$ group, taken together with the atoms to which they are attached, may optionally form a cycloalkyl or heterocycloalkyl, in which said cycloalkyl or heterocycloalkyl of $R_6$, is optionally substituted with one or more $R_d$;

two of $R_7$ group, taken together with the atoms to which they are attached, may optionally form a cycloalkyl or heterocycloalkyl, in which said cycloalkyl or heterocycloalkyl of $R_7$, is optionally substituted with one or more $R_d$;

two of $R_{10}$ group, taken together with the atom(s) to which they are attached, may optionally form a cycloalkyl or heterocycloalkyl, in which said cycloalkyl or heterocycloalkyl of $R_{10}$, is optionally substituted with one or more $R_d$;

two of $R_{11}$ group, taken together with the atom(s) to which they are attached, may optionally form a cycloalkyl, heterocycloalkyl, aryl, or heteroaryl, in which said cycloalkyl, heterocycloalkyl, aryl, or heteroaryl of $R_{11}$, is optionally substituted with one or more $R_d$;

$R_2$ and $R_5$ group, taken together with the atoms to which they are attached, may optionally form a cycloalkyl or heterocycloalkyl, in which said cycloalkyl or heterocycloalkyl of $R_2$ and $R_5$, is optionally substituted with one or more $R_d$;

$R_3$ and $R_5$ group, taken together with the atoms to which they are attached, may optionally form a cycloalkyl or heterocycloalkyl, in which said cycloalkyl or heterocycloalkyl of $R_3$ and $R_5$, is optionally substituted with one or more $R_d$;

$R_b$ and $R_c$ group, taken together with the atom to which they are attached, may optionally form a cycloalkyl, or heterocycloalkyl, in which said cycloalkyl or heterocycloalkyl of $R_b$ and $R_c$, is optionally substituted with one or more $R_c$;

two of $R_d$ group, taken together with the atom(s) to which they are attached, may optionally form a cycloalkyl, or heterocycloalkyl, in which said cycloalkyl or heterocycloalkyl of $R_d$, is optionally substituted with one or more $R_c$;

two of $R_c$ group, taken together with the atom(s) to which they are attached, may optionally form a cycloalkyl or heterocycloalkyl, in which said cycloalkyl or heterocycloalkyl of $R_c$ is optionally substituted with one or more groups selected from H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

each of g and j is, independently, 0, 1, 2, or 3;

each of n, v and k is, independently, 0, 1, 2, 3, 4, 5, 6, 7, or 8;

s is 0 or 1; and each of h, m, p, and q is, independently, 0, 1, 2, 3, 4, or 5; with the proviso that Formula (AA) does not include Formula (I):

W" is CH or N, and the tricyclic

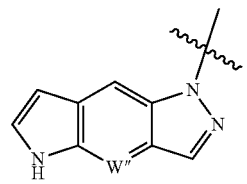

is optionally substituted with one or more $R_{7''}$;

each of $R_{1''}$, $R_{2''}$, $R_{3'}$, $R_{4''}$, $R_{5''}$, $R_{6''}$, and $R_{7''}$, independently, is H, alkyl, alkenyl, alkynyl, cycloalkyl, cycloalkenyl, heterocycloalkyl, heterocycloalkenyl, aryl, heteroaryl, halo, nitro, oxo, cyano, $OR_{a''}$, $SR_{a''}$, alkyl-$R_{a''}$, $NH(CH_2)_{p''}$—$R_{a''}$, $C(O)R_{a''}$, $S(O)R_{a''}$, $SO_2R_{a''}$, $C(O)OR_{a''}$, $OC(O)R_{a''}$, $NR_{b''}R_{c''}$, $P(O)R_{b''}R_{c''}$, $C(O)N(R_{b''})R_{c''}$, $N(R_{b''})C(O)R_{c''}$, $SO_2N(R_{b''})R_{c''}$, or $N(R_{b''})SO_2R_{c''}$, in which said cycloalkyl, cycloalkenyl, heterocycloalkyl, heterocycloalkenyl, aryl, heteroaryl is optionally substituted with one or more $R_{d''}$;

optionally, two of $R_{2''}$ group, taken together with the atom to which they are attached, may optionally form a cycloalkyl or heterocycloalkyl optionally substituted with one or more $R_{q''}$;

$R_{a''}$, $R_{b''}$, $R_{c''}$, and $R_{d''}$, independently, is H, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

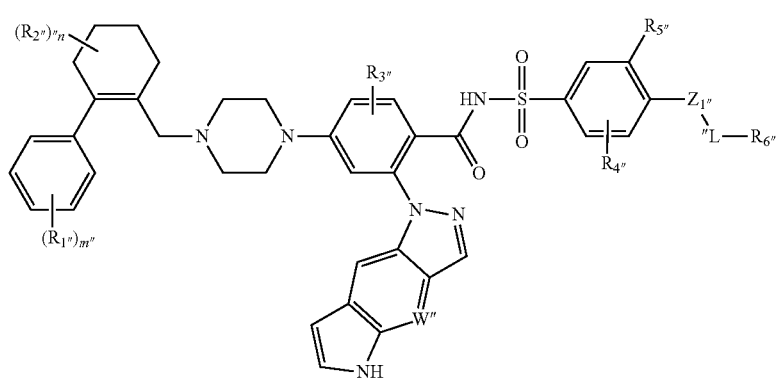

Formula (I)

wherein $Z_{1''}$, is absent, $(CH_2)_{p''}$, N(H), O, S, C(O), $S(O)_2$, OC(O), C(O)O, $OS(O)_2$, $S(O)_2O$, C(O)S, SC(O), C(O)C(O), C(O)N(H), N(H)C(O), $S(O)_2N(H)$, $N(H)S(O)_2$, OC(O)O, OC(O)S, OC(O)N(H), N(H)C(O)O, N(H)C(O)S, N(H)C(O)N(H), $(CH_2)_{p''}N(H)(CH_2)_{q''}$, $(CH_2)_pN(H)C(O)(CH_2)_{q''}$, $(CH_2)_{p''}C(O)N(H)(CH_2)_{q''}$, OC(O)N(H) $(CH_2)_{p''+1}N(H)(CH_2)_{q''}$, a bivalent alkenyl group, or a bivalent alkynyl group;

L" is absent, alkylene, alkenylene, alkynylene, cycloalkylene, cycloalkenylene, heterocycloalkylene, heterocycloalkenylene, wherein said alkylene, alkenylene, alkynylene, cycloalkylene, cycloalkenylene, heterocycloalkylene, or heterocycloalkenylene is optionally substituted with one or more $R_{d''}$; and each of m", n", p", and q", independently, is 0, 1, 2, 3, or 4.

In an alternative embodiment, the compounds of Formula (AA) do not include the compounds explicitly/specifically disclosed in International Application Publication No. WO 2017/132474, which is incorporated herein by reference. Some of these previously disclosed compounds are listed below and are incorporated herein In some embodiments, the compound of Formula (AA) or an N-oxide thereof, or a pharmaceutically acceptable salt, solvate, polymorph, tautomer, stereoisomer, an isotopic form, or a prodrug thereof, wherein the compound is further represented by Formula (AA-1):

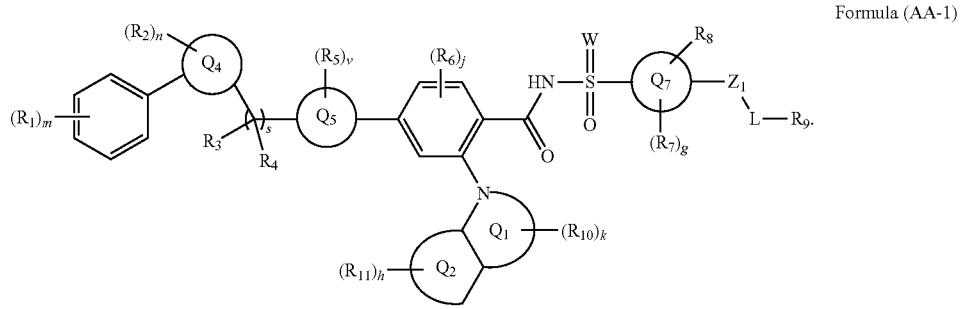

Formula (AA-1)

In some embodiments, the compound of Formula (AA) or an N-oxide thereof, or a pharmaceutically acceptable salt, solvate, polymorph, tautomer, stereoisomer, an isotopic form, or a prodrug thereof, wherein the compound is further represented by Formula (AA-2):

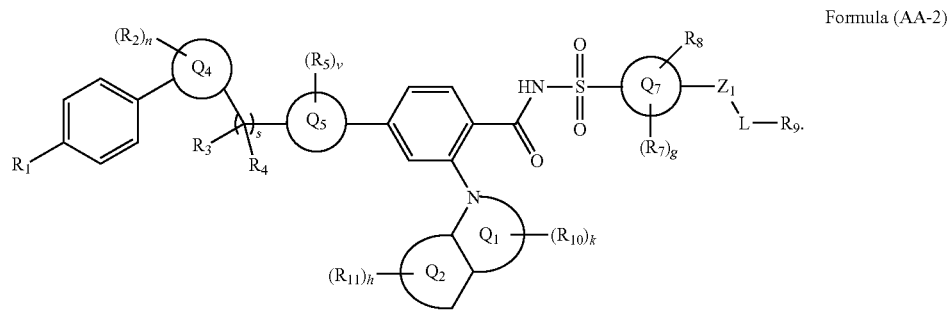

Formula (AA-2)

In some embodiments, the compound of Formula (AA) or an N-oxide thereof, or a pharmaceutically acceptable salt, solvate, polymorph, tautomer, stereoisomer, an isotopic form, or a prodrug thereof, wherein the compound is further represented by Formula (AA-3):

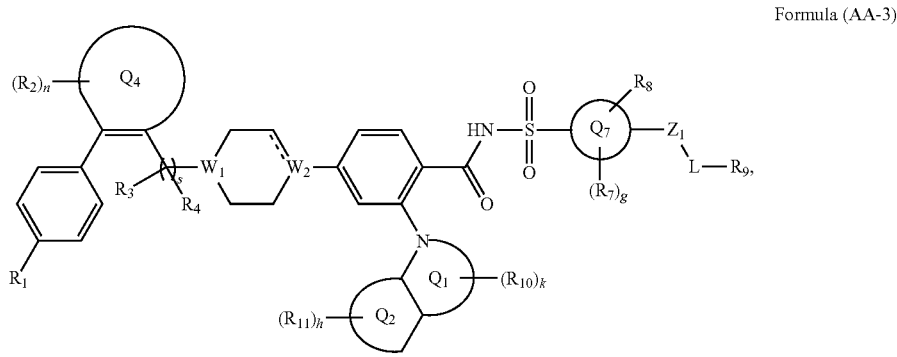

Formula (AA-3)

in which each of $W_1$ and $W_2$, independently is N or CH.

In some embodiments, the compound of Formula (AA) or an N-oxide thereof, or a pharmaceutically acceptable salt, solvate, polymorph, tautomer, stereoisomer, an isotopic form, or a prodrug thereof, wherein the compound is further represented by Formula (AA-4):

Formula (AA-4)

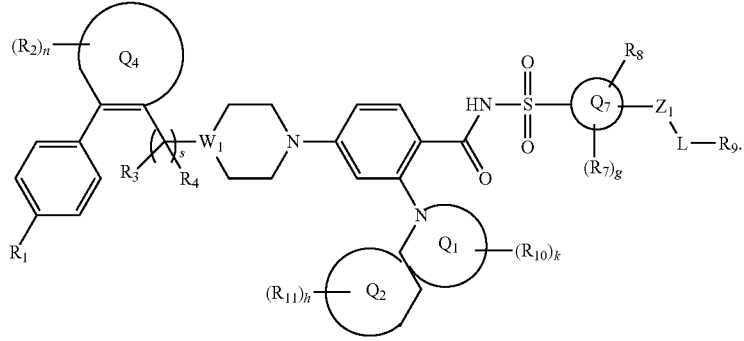

In some embodiments, the compound of Formula (AA) or an N-oxide thereof, or a pharmaceutically acceptable salt, solvate, polymorph, tautomer, stereoisomer, an isotopic form, or a prodrug thereof, wherein the compound is further represented by Formula (AA-5):

Formula (AA-5)

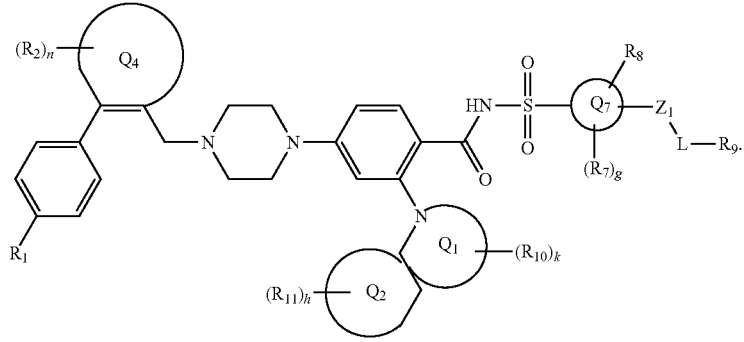

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein is

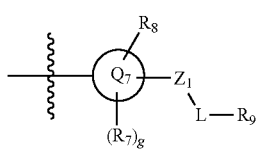

is

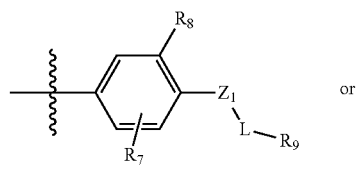

or

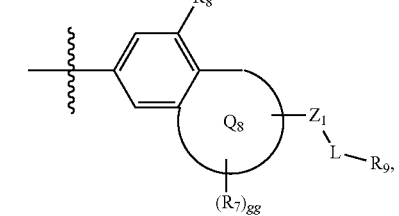

in which $Q_8$ is 5-7 membered heterocycloalkyl, 5-7 membered heterocycloalkenyl, phenyl, or 5-7 membered heteroaryl; and gg is 0, 1, 2, 3, or 4.

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein

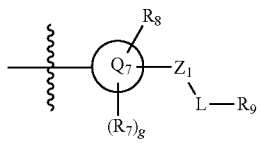

is

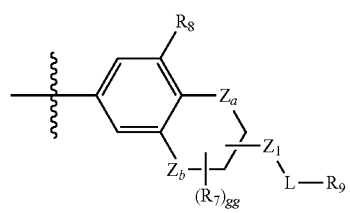

in which each $Z_a$ and $Z_b$ is independently —O—, —CH$_2$—, —C(O)—, —N(R$_a$)—, —S—, —S(O)—, —S(O$_2$)—, —S(O)(=N(R$_a$))—, —P(O)(R$_a$)—; wherein R$_a$ of $Z_a$ and $Z_b$, independently, is H, D, C$_1$-C$_6$alkyl, C$_2$-C$_6$alkenyl, C$_1$-C$_6$alkylcarbonyl, C$_1$-C$_6$alkoxycarbonyl, C$_3$-C$_6$cycloalkyl, 5-8 membered monocyclic heterocycloalkyl, C$_6$-C$_{14}$aryl, or 5-8 membered monocyclic heteroaryl, in which said C$_1$-C$_6$alkyl, C$_3$-C$_6$cycloalkyl, 5-8 membered monocyclic heterocycloalkyl, C$_6$-C$_{14}$aryl, 5-8 membered monocyclic heteroaryl is optionally substituted with one or more R$_c$.

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein

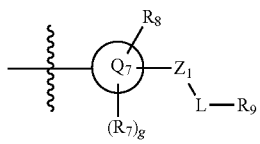

is

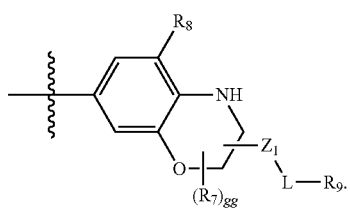

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein $Z_1$ is absent or (CH$_2$)$_p$; L is L$_1$ and L$_1$ is bond, and R$_9$ is 5-7 membered heterocyclyl or 7-10 membered bridged heterocyclyl, each of which is optionally substituted with 1-3 groups selected from halo, —OH, —CN, —COOH, —NH$_2$, —N(CH$_3$)$_2$, —(C$_1$-C$_4$)alkyl, and —(C$_1$-C$_4$)alkoxy.

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein

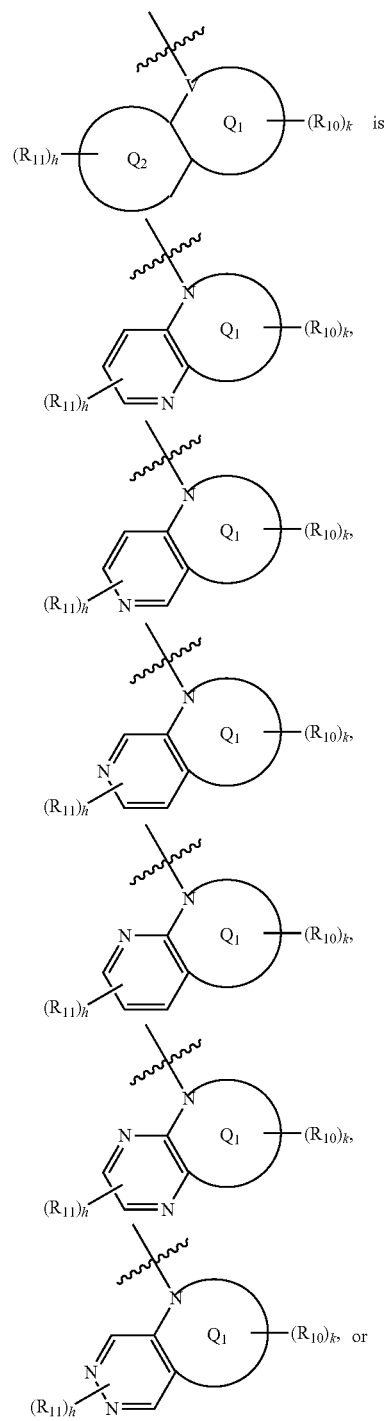

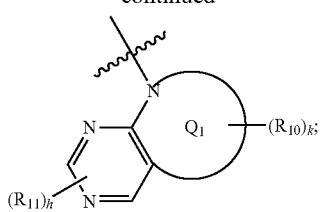
and h is 0, 1, or 2.
In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein
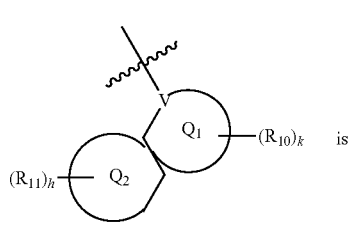 is
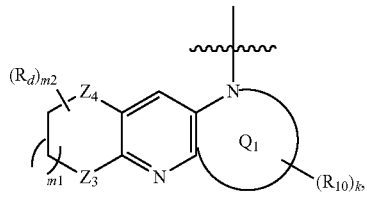
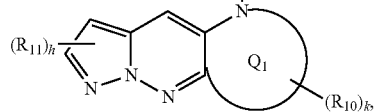
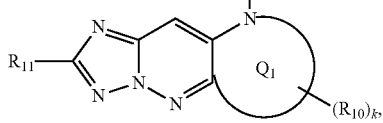
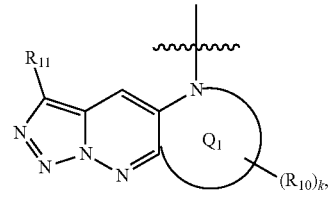
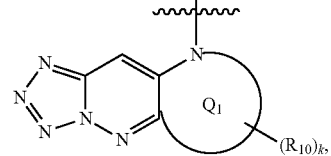
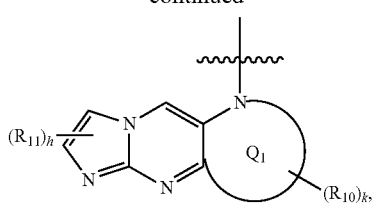
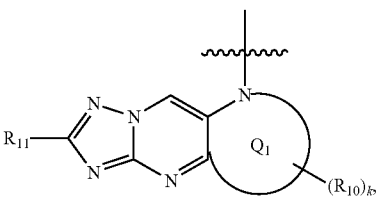
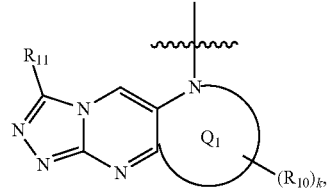
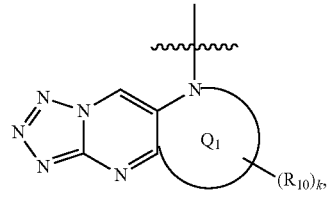
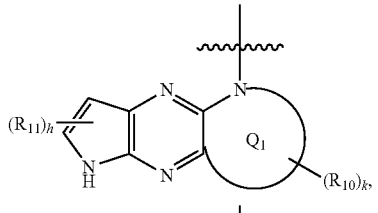
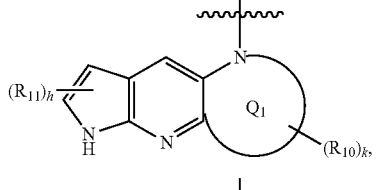
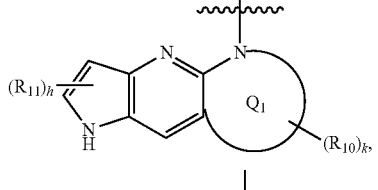
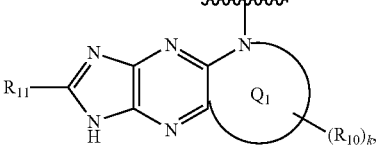

-continued

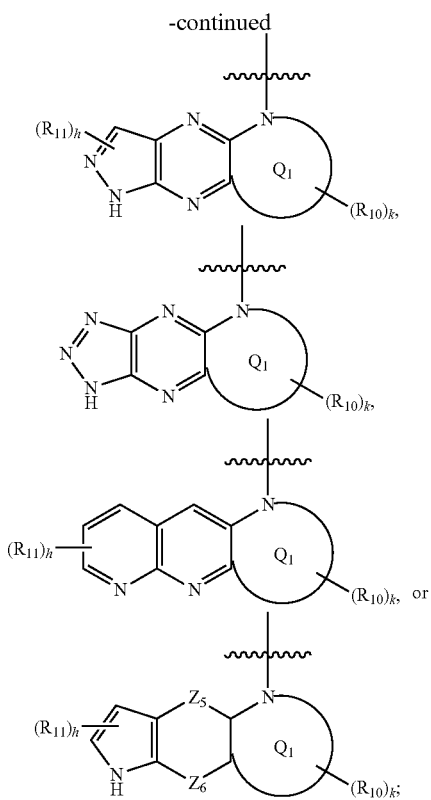

h is 0, 1, or 2;
each of $m_1$ and $m_2$, independently, is 0, 1, or 2; and
each of $Z_3$, $Z_4$, $Z_5$ and $Z_6$, independently, is a bond, $(CH_2)_p$, N(H), O, S, C(O), S(O_2), OC(O), C(O)O, OSO_2, S(O_2)O, C(O)S, SC(O), C(O)C(O), C(O)N(H), N(H)C(O), S(O_2)N(H), N(H)S(O_2), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group. In one specific embodiment,

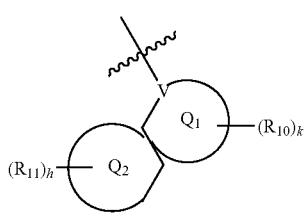

is

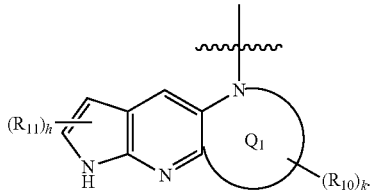

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein $R_{10}$ is aryl, heteroaryl, or

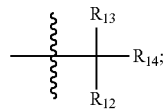

$R_{12}$ is H, D, alkyl, alkenyl, alkynyl, cycloalkyl, cycloalkenyl, heterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $P(O)R_bR_c$, alkyl-$P(O)R_bR_c$, $C(O)N(R_b)R_c$, $N(R_b)C(O)R_c$, S(O)(=N($R_b$))$R_c$, —B=S(O)$R_bR_c$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$; and each of $R_{13}$, and $R_{14}$, independently, is H, D, alkyl, halo-alkyl, or $R_{13}$ and $R_{14}$, taken together with the atom to which they are attached, may optionally form a cycloalkyl or heterocycloalkyl, in which said cycloalkyl or heterocycloalkyl is optionally substituted with one or more $R_d$.

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein $R_9$ is $R_{9B}$. In one specific embodiment, $R_{9B}$ is a small molecule E3 ubiquitin ligase binding moiety that binds an E3 ubiquitin ligase; and said E3 ubiquitin ligase is Von Hippel-Lindau (VLM), cereblon (CLM), mouse double-minute homolog2 (MLM), and IAP (ILM).

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein $R_9$ is

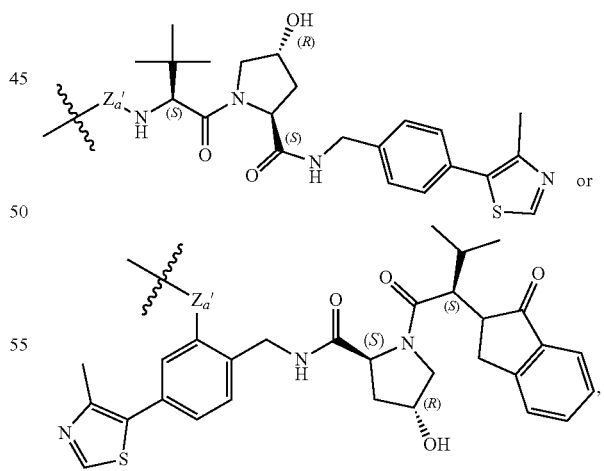

wherein
$Z_a'$ is a bond, $(CH_2)_p$, N(H), O, S, C(O), S(O_2), OC(O), C(O)O, OSO_2, S(O_2)O, C(O)S, SC(O), C(O)C(O), C(O)N(H), N(H)C(O), S(O_2)N(H), N(H)S(O_2), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)$ $(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group.

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein $R_9$ is

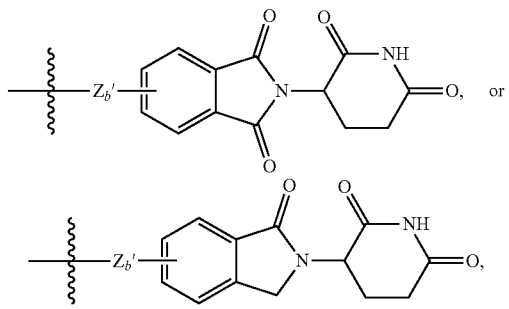

wherein
$Z_{b''}$ is a bond, $(CH_2)_p$, N(H), O, S, C(O), $S(O_2)$, OC(O), C(O)O, $OSO_2$, $S(O_2)O$, C(O)S, SC(O), C(O)C(O), C(O)N(H), N(H)C(O), $S(O_2)N(H)$, $N(H)S(O_2)$, OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group.

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein L is $L_2$, and $L_2$ is

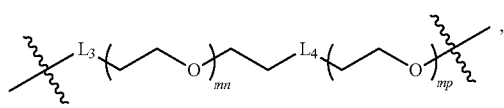

wherein
each of mn and mp is independently an integer of 0 to 12; and
each of $L_3$ and $L_4$ independently, is a bond, $(CH_2)_p$, N(H), O, S, C(O), $S(O_2)$, OC(O), C(O)O, $OSO_2$, $S(O_2)O$, C(O)S, SC(O), C(O)C(O), C(O)N(H), N(H)C(O), $S(O_2)N(H)$, $N(H)S(O_2)$, OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group. In one specific embodiment, said $L_2$ is

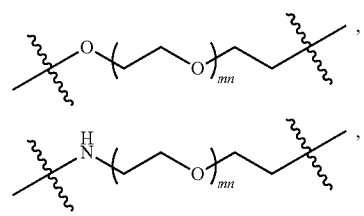

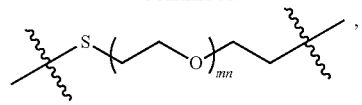

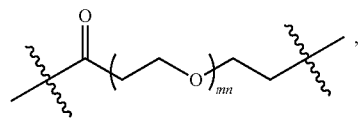

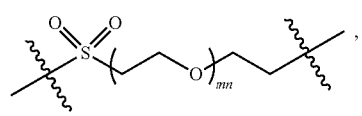

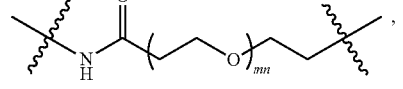

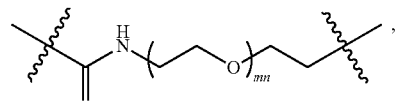

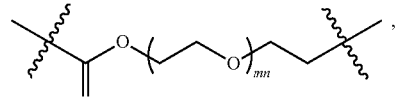

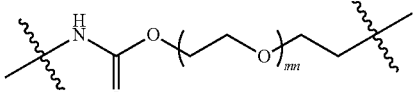

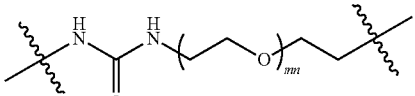

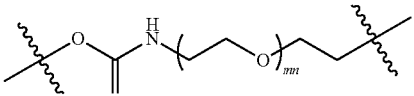

in which mn is 0 to 12.

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein

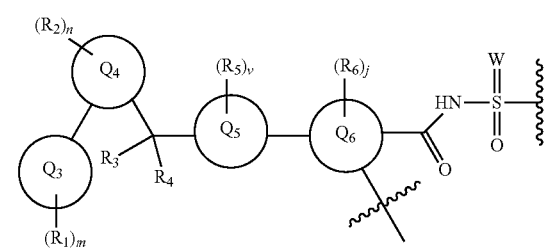

is

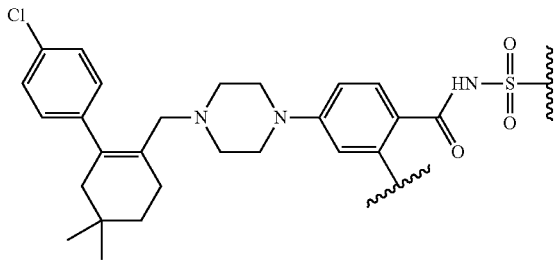

In some embodiments, the compound of Formula (AA), (AA-1), (AA-2), (AA-3), (AA-4), (AA-5), or an N-oxide thereof, or a pharmaceutically acceptable salt, solvate, polymorph, tautomer, stereoisomer, an isotopic form, or a prodrug thereof, wherein $R_8$ is $NO_2$.

Exemplary compounds described herein include, but are not limited to, the following:

4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((3-fluorotetrahydro-2H-pyran-3-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-3-yl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((piperidin-4-ylmethyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1-cyclopropylpiperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1-cyclopropyl-4-fluoropiperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluoro-1-(oxetan-3-yl)piperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((1-(oxetan-3-yl)piperidin-4-yl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((1-(tetrahydrofuran-3-yl)piperidin-4-yl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((1-(tetrahydro-2H-pyran-4-yl)piperidin-4-yl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluoro-1-(tetrahydrofuran-3-yl)piperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluoro-1-(tetrahydro-2H-pyran-4-yl)piperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluoro-1-(methylsulfonyl)piperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1-(methylsulfonyl)piperidin-4-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((2-morpholinoethyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((3-morpholinopropyl)amino)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-((morpholin-2-ylmethyl)amino)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-((morpholin-2-ylmethyl)amino)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-methylmorpholin-2-yl)methyl)amino)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-methylmorpholin-2-yl)methyl)amino)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-cyclopropylmorpholin-2-yl)methyl)amino)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-cyclopropylmorpholin-2-yl)methyl)amino)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((4-(oxetan-3-yl)morpholin-2-yl)methyl)amino)phenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((3-nitro-4-(((4-(oxetan-3-yl)morpholin-2-yl)methyl)amino)phenyl)sulfonyl)-2-(pyrazolo[4,3-b]pyrrolo[3,2-e]pyridin-1(5H)-yl)benzamide, (S)—N-((4-(((4-acetylmorpholin-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, (R)—N-((4-(((4-acetylmorpholin-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-(dimethylglycyl)morpholin-2-yl)methyl)amino)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-(dimethylglycyl)morpholin-2-yl)methyl)amino)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-(methylsulfonyl)morpholin-2-yl)methyl)amino)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-(methylsulfonyl)morpholin-2-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-hydroxycyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-hydroxy-4-methylcyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((((1r,4r)-4-hydroxycyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((((1s,4s)-4-hydroxycyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((((1r,4r)-4-methoxycyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((((1s,4s)-4-methoxycyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((((1s,4s)-4-hydroxy-4-methylcyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((((1r,4r)-4-hydroxy-4-methylcycloohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((((1s,4s)-4-ethyl-4-hydroxycyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((((1r,4r)-4-ethyl-4-hydroxycyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1-methylpyrrolidin-3-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1-isopropylpyrrolidin-3-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1-cyclopropylpyrrolidin-3-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((1-(oxetan-3-yl)pyrrolidin-3-yl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((1-(tetrahydrofuran-3-yl)pyrrolidin-3-yl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((1-(tetrahydro-2H-pyran-4-yl)pyrrolidin-3-yl)methyl)

amino)phenyl)sulfonyl-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((3-nitro-4-(((1-(tetrahydro-2H-pyran-4-yl)pyrrolidin-3-yl)methyl)amino)phenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((1-(tetrahydro-2H-pyran-4-yl)pyrrolidin-3-yl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-methylpiperidin-4-yl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-cyclopropylpiperidin-4-yl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)piperidin-4-yl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(oxetan-3-yl)piperidin-4-yl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1s,4s)-4-morpholinocycloohexyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-methylpyrrolidin-3-yl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1r,4r)-4-morpholinocyclohexyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-cyclopropylpyrrolidin-3-yl)amino)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-((1-(methylsulfonyl)pyrrolidin-3-yl)amino)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-((1-(methylsulfonyl)pyrrolidin-3-yl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)pyrrolidin-3-yl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(oxetan-3-yl)pyrrolidin-3-yl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-(cyclopropylamino)cyclohexyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((4-((tetrahydro-2H-pyran-4-yl)amino)cyclohexyl)amino)phenyl)sulfonyl)-2-(pyrazolo[4,3-b]pyrrolo[3,2-e]pyridin-1(5H)-yl)benzamide, N-((4-(((2-oxaspiro[3,5]nonan-7-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-cyanocyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((3-(cyclopropyl(oxetan-3-yl)amino)propyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-cyano-4-methylcyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-methylmorpholin-2-yl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-methylmorpholin-2-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4,4-difluorocyclohexyl)methyl)amino)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((1,4,4-trifluorocyclohexyl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((tetrahydro-2H-pyran-4-yl)methoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-fluorotetrahydro-2H-pyran-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-3-yl)methoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((3-fluorotetrahydro-2H-pyran-3-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(piperidin-4-ylmethoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-fluoropiperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-methylpiperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(oxetan-3-yl)piperidin-4-yl)methoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-fluoro-1-methylpiperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-cyclopropyl-4-fluoropiperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-cyclopropylpiperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-fluoro-1-(oxetan-3-yl)piperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydrofuran-3-yl)piperidin-4-yl)methoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-fluoro-1-(tetrahydrofuran-3-yl)piperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-fluoro-1-(tetrahydro-2H-pyran-4-yl)piperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-(methylsulfonyl)piperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-fluoro-1-(methylsulfonyl)piperidin-4-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)piperidin-4-yl)methoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(2-morpholinoethoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(3-morpholinopropoxy)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(morpholin-2-ylmethoxy)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-(morpholin-2-ylmethoxy)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-((4-methylmorpholin-2-yl)methoxy)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-((4-methylmorpholin-2-yl)methoxy)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-((4-cyclopropylmorpholin-2-yl)methoxy)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-((4-cyclopropylmorpholin-2-yl)methoxy)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-((4-(oxetan-3-yl)morpholin-2-yl)methoxy)phenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((3-nitro-4-((4-(oxetan-3-yl)morpholin-2-yl)methoxy)phenyl)sulfonyl)-2-(pyrazolo[4,3-b]pyrrolo[3,2-e]pyridin-1(5H)-yl)benzamide, (S)—N-((4-((4-acetylmorpholin-2-yl)methoxy)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, (R)—N-((4-((4-acetylmorpholin-2-yl)methoxy)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-((4-(methylsulfonyl)morpholin-2-yl)methoxy)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-((4-(methylsulfonyl)morpholin-2-yl)methoxy)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-((4-(dimethylglycyl)morpholin-2-yl)methoxy)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-((4-(dimethylglycyl)morpholin-2-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-hydroxy-4-methylcyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-hydroxycyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1r,4r)-4-methoxycyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1s,4s)-4-hydroxycyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1r,4r)-4-hydroxycyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1s,4s)-4-methoxycyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1s,4s)-4-hydroxy-4-methylcycloohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1s,4s)-4-ethyl-4-hydroxycyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1r,4r)-4-hydroxy-4-methylcycloohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1r,4r)-4-ethyl-4-hydroxycyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-methylpyrrolidin-3-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-isopropylpyrrolidin-3-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(oxetan-3-yl)pyrrolidin-3-yl)methoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-cyclopropylpyrrolidin-3-yl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydrofuran-3-yl)pyrrolidin-3-yl)methoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)pyrrolidin-3-yl)methoxy)phenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)pyrrolidin-3-yl)methoxy)phenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)pyrrolidin-3-yl)methoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-methylpiperidin-4-yl)oxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-cyclopropylpiperidin-4-yl)oxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)piperidin-4-yl)oxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(oxetan-3-yl)piperidin-4-yl)oxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1s,4s)-4-morpholinocyclohexyl)oxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((1r,4r)-4- morpholinocyclohexyl)oxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-methylpyrrolidin-3-yl)oxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((1-cyclopropylpyrrolidin-3-yl)oxy)-3-nitrophenyl)sulfonyl)-2-(pyrazolo[4,3-b]pyrrolo[3,2-e]pyridin-1(5H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-((1-(methylsulfonyl)pyrrolidin-3-yl)oxy)-3-nitrophenyl)sulfonyl)-2-(pyrazolo[4,3-b]pyrrolo[3,2-e]pyridin-1(5H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-((1-(methylsulfonyl)pyrrolidin-3-yl)oxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(oxetan-3-yl)pyrrolidin-3-yl)oxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)pyrrolidin-3-yl)oxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-(cyclopropylamino)cyclohexyl)oxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((4-((tetrahydro-2H-pyran-4-yl)amino)cyclohexyl)oxy)phenyl)sulfonyl)-2-(pyrazolo[4,3-b]pyrrolo[3,2-e]pyridin-1(5H)-yl)benzamide, N-((4-((2-oxaspiro[3.5]nonan-7-yl)methoxy)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(3-(cyclopropyl(oxetan-3-yl)amino)propoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-cyano-4-methylcyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4,4-difluorocyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((1,4,4-trifluorocyclohexyl)methoxy)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-cyanocyclohexyl)methoxy)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-morpholino-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(3-morpholino azetidin-1-yl)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(7-oxa-2-azaspiro[3.5]nonan-2-yl)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-methylpiperazin-1-yl)methyl)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-cyclopropylpiperazin-1-yl)methyl)-3-nitrophenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((4-(tetrahydro-2H-pyran-4-yl)piperazin-1-yl)methyl)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-((4-(oxetan-3-yl)piperazin-1-yl)methyl)phenyl)sulfonyl)-2-(pyrazolo[4,3-b]pyrrolo[3,2-e]pyridin-1(5H)-yl)benzamide, N-((3-chloro-4-((1-methylpiperidin-4-yl)methoxy)phenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, N-((3-chloro-4-((4-fluoro-1-methylpiperidin-4-yl)methoxy)phenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, N-((3-chloro-4-((1-cyclopropylpiperidin-4-yl)methoxy)phenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, N-((3-chloro-4-((1-cyclopropyl-4-fluoropiperidin-4-yl)methoxy)phenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, N-((3-chloro-4-((1-(oxetan-3-yl)piperidin-4-yl)methoxy)phenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, N-((3-chloro-4-((4-fluoro-1-(oxetan-3-yl)piperidin-4-yl)methoxy)phenyl)sulfonyl)-4-(4-((4'-chloro-5,5-dimethyl- 3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, N-((3-chloro-4-((1-(tetrahydro-2H-pyran-4-yl)piperidin-4-yl)methoxy)phenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, N-((3-chloro-4-((4-fluoro-1-(tetrahydro-2H-pyran-4-yl)piperidin-4-yl)methoxy)phenyl)sulfonyl)-4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-fluoro-1-methylpiperidin-4-yl)methoxy)-3-((trifluoromethyl)sulfonyl)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-(oxetan-3-yl)morpholin-2-yl)methyl)amino)-3-((trifluoromethyl)sulfonyl)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)-N-((4-(((tetrahydro-2H-pyran-4-yl)methyl)amino)-3-((trifluoromethyl)sulfonyl)phenyl)sulfonyl)benzamide, 4-(4-((4'-chloro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(pyrazolo[4,3-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4-fluoro-1-(oxetan-3-yl)piperidin-4-yl)methoxy)-3-((trifluoromethyl)sulfonyl)phenyl)sulfonyl)-2-(pyrazolo[4,3-b]pyrrolo[3,2-e]pyridin-1(5H)-yl)benzamide, 4-(4-((5-(4-chlorophenyl)spiro[2.5]oct-5-en-6-yl)methyl)piperazin-1-yl)-N-((3-nitro-4-(((tetrahydro-2H-pyran-4-yl)methyl)amino)phenyl)sulfonyl)-2-(pyrazolo[4,3-b]pyrrolo[3,2-e]pyridin-1(5H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2-methyl-3-oxo-3,5-dihydropyrazolo[4,3-b]pyrrolo[3,2-e]pyridin-1(2H)-yl)benzamide, 4-(4-((4'-chloro-5,5-dimethyl-3,4,5,6-tetrahydro-[1,1'-biphenyl]-2-yl)methyl)piperazin-1-yl)-2-(2-methyl-3-oxo-3,5-dihydropyrazolo[4,3-b]pyrrolo[3,2-e]pyridin-1(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-methyl-3-oxo-3,5-dihydropyrazolo[4,3-b]pyrrolo[3,2-e]pyridin-1(2H)-yl)benzamide, (S)—N-((4-(((1,4-dioxan-2-yl)methyl)amino)-3-nitrophenyl)sulfonyl)-2-(5-amino-2-methyl-3-oxo-2,3-dihydro-1H-pyrazolo[4,3-b]pyridin-1-yl)-4-(4-((4'-chloro-5,5-dimethyl-3,4,5,6-tetrahydro-[1,1'-biphenyl]-2-yl)methyl)piperazin-1-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2-methyl-3-oxo-3,5-dihydropyrrolo[2,3-f]indazol-1(2H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2-methyl-3-oxo-3,5-dihydropyrazolo[3,4-b]pyrrolo[2,3-e]pyridin-1(2H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2-methyl-3-oxo-3,5-dihydroimidazo[4,5-b]pyrazolo[3,4-e]pyridin-1(2H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-oxo-2H-oxazolo[5,4-b]pyrrolo[3,2-e]pyridin-1(5H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-2-oxo-3,5-dihydroimidazo[4,5-b]pyrrolo[3,2-e]pyridin-1(2H)-yl)benzamide, 4-(4-((4'-chloro-5,5-dimethyl-3,4,5,6-tetrahydro-[1,1'-biphenyl]-2-yl)methyl)piperazin-1-yl)-2-(3-cyclopropyl-2-oxo-3,5-dihydroimidazo[4,5-b]pyrrolo[3,2-e]pyridin-1(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-oxo-3-(pyridin-3-yl)-3,5-dihydroimidazo[4,5-b]pyrrolo[3,2-e]pyridin-1(2H)-yl)benzamide.

4-(4-((4'-chloro-5,5-dimethyl-3,4,5,6-tetrahydro-[1,1'-biphenyl]-2-yl)methyl)piperazin-1-yl)-2-(2,2-difluoro-3,5-dihydrodipyrrolo[2,3-b:2',3'-e]pyridin-1(2H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,3-dimethyl-3,5-dihydrodipyrrolo[2,3-b:2',3'-e]pyridin-1(2H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,2-dimethyl-3,5-dihydrodipyrrolo[2,3-b:2',3'-e]pyridin-1(2H)-yl)-N-((4-(((4-fluorotetrahydro-2H-pyran-4-yl)methyl)amino)-3-nitrophenyl)sulfonyl)benzamide, 4-(4-{[2-(4-chlorophenyl)-4,4-dimethylcyclohex-1-en-1-yl]methyl}piperazin-1-yl)-N-[4-({[(2S)-1,4-dioxan-2-yl]methyl}amino)-3-nitrobenzenesulfonyl]-2-{5-methyl-4-oxo-5,8,14,16-tetraazatetracyclo[7.7.0.0$^2$,$^{\omega}$,0$^{11}$,$^1$υ]hexadeca-1(16),9,11(15), 12-tetraen-8-yl}benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(6,7,9,9a-tetrahydro-1H-pyrano[3',4':4,5]pyrrolo[3,2-b]pyrrolo[3,2-e]pyridin-5(5aH)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5a,6,8,8a-tetrahydrofuro[3',4':4,5]pyrrolo[3,2-b]pyrrolo[3,2-e]pyridin-5(1H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(1,5a,6,8,9,9a-hexahydro-5H-pyrano[4',3':4,5]pyrrolo[3,2-b]pyrrolo[3,2-e]pyridin-5-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3,4,4a,9,10b-hexahydro-5H-pyrano[2',3:4,5]pyrrolo[3,2-b]pyrrolo[3,2-e]pyridin-5-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,3a,8,9b-tetrahydrofuro[2',3':4,5]pyrrolo[3,2-b]pyrrolo[3,2-e]pyridin-4(2H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(7,7-difluoro-1,5a,6,7,8,8a-hexahydro-5H-cyclopenta[4,5]pyrrolo[3,2-b]pyrrolo[3,2-e]pyridin-5-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(imidazo[2',1':2,3]imidazo[4,5-b]pyrrolo[3,2-e]pyridin-10(6H)-yl)benzamide, 4-(4-((4'-chloro-5,5-dimethyl-3,4,5,6-tetrahydro-[1,1'-biphenyl]-2-yl)methyl)piperazin-1-yl)-2-(dipyrrolo[2,3-b:2',3'-e]pyridin-1(5H)-yl)-N-((3-nitro-4-(((tetrahydro-2H-pyran-4-yl)methyl)amino)phenyl)sulfonyl)benzamide, 4-(4-{[2-(4-chlorophenyl)-4,4-dimethylcyclohex-1-en-1-yl]methyl}piperazin-1-yl)-N-[4-({[(2S)-1,4-dioxan-2-yl]methyl}amino)-3-nitrobenzenesulfonyl]-2-{4,8,14,16-tetraazatetracyclo[7.7.0.0$^2$, $^\omega$.0$^{11}$,$^1\upsilon$]hexadeca-1(16),2(7),3,5,9,11(15),12-heptaen-8-yl}benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(6,9-dihydro-1H-pyrano[3',4':4,5]pyrrolo[3,2-b]pyrrolo[3,2-e]pyridin-5(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(6,8-dihydrofuro[3',4':4,5]pyrrolo[3,2-b]pyrrolo[3,2-e]pyridin-5(1H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(1,6,8,9-tetrahydro-5H-pyrano[4',3':4,5]pyrrolo[3,2-b]pyrrolo[3,2-e]pyridin-5-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrano[3',2':4,5]pyrrolo[3,2-b]pyrrolo[3,2-e]pyridin-10(6H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,3-difluoro-3,4-dihydro-2H-pyrano[3',2':4,5]pyrrolo[3,2-b]pyrrolo[3,2-e]pyridin-10(6H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3,4,9-tetrahydro-5H-pyrano[2',3':4,5]pyrrolo[3,2-b]pyrrolo[3,2-e]pyridin-5-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydro-[1,4]dioxino[2',3':4,5]pyrrolo[3,2-b]pyrrolo[3,2-e]pyridin-10(6H)-yl)benzamide, 4-(4-{[2-(4-chlorophenyl)-4,4-dimethylcycloohex-1-en-1-yl]methyl}piperazin-1-yl)-N-[4-({[(2S)-1,4-dioxan-2-yl]methyl}amino)-3-nitrobenzenesulfonyl]-2-{4-methyl-5-oxo-4,8,14,16-tetraazatetracyclo[7.7.0.0$^2$, $^\omega$.0$^{11}$,$^1\upsilon$]hexadeca-1(16),2(7),9,11(15),12-pentaen-8-yl}benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(6,7,8,9-tetrahydropyrrolo[3',2':5,6]pyrido[3,2-b]indol-5(1H)-yl)benzamide, 4-(4-{[2-(4-chlorophenyl)-4,4-dimethylcycloohex-1-en-1-yl]methyl}piperazin-1-yl)-N-[4-({[(2S)-1,4-dioxan-2-yl]methyl}amino)-3-nitrobenzenesulfonyl]-2-{4-methyl-4-oxo-5,8,14,16-tetraazatetracyclo[7.7.0.0$^2$, $^\omega$.0$^{11}$,$^1\upsilon$]hexadeca-1(16),2(7),9,11(15),12-pentaen-8-yl}benzamide, 4-(4-{[2-(4-chlorophenyl)-4,4-dimethylcycloohex-1-en-1-yl]methyl}piperazin-1-yl)-N-[4-({[(2S)-1,4-dioxan-2-yl]methyl}amino)-3-nitrobenzenesulfonyl]-2-[4-(propan-2-yl)-4,8,14,16-tetraazatetracyclo[7.7.0.0$^2$, $^\omega$.0$^{11}$,$^1\upsilon$]hexadeca-1(16),2(7),9,11(15),12-pentaen-8-yl]benzamide, 4-(4-((4'-chloro-5,5-dimethyl-3,4,5,6-tetrahydro-[1,1'-biphenyl]-2-yl)methyl)piperazin-1-yl)-2-(imidazo[4,5-b]pyrrolo[3,2-e]pyridin-1(5H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(pyrrolo[2,3-b][1,2,3]triazolo[4,5-e]pyridin-1(5H)-yl)benzamide, (S)—N-((4-(((1,4-dioxan-2-yl)methyl)amino)-3-nitrophenyl)sulfonyl)-4-(4-((2-(4-chlorophenyl)cyclohept-1-en-1-yl)methyl)piperazin-1-yl)-2-(2-methyl-3-oxo-3,5-dihydropyrazolo[4,3-b]pyrrolo[3,2-e]pyridin-1(2H)-yl)benzamide, (S)—N-((4-(((1,4-dioxan-2-yl)methyl)amino)-3-nitrophenyl)sulfonyl)-4-(4-((4-(4-chlorophenyl)-6,6-dimethyl-5,6-dihydro-2H-pyran-3-yl)methyl)piperazin-1-yl)-2-(2-methyl-3-oxo-3,5-dihydropyrazolo[4,3-b]pyrrolo[3,2-e]pyridin-1(2H)-yl)benzamide, (S)—N-((4-(((1,4-dioxan-2-yl)methyl)amino)-3-nitrophenyl)sulfonyl)-4-(4-((4'-chloro-3,4,5,6-tetrahydro-[1,1'-biphenyl]-2-yl)methyl)piperazin-1-yl)-2-(2-methyl-3-oxo-3,5-dihydropyrazolo[4,3-b]pyrrolo[3,2-e]pyridin-1(2H)-yl)benzamide, (S)—N-((4-(((1,4-dioxan-2-yl)methyl)amino)-3-nitrophenyl)sulfonyl)-4-(4-((2-(4-chlorophenyl)cyclopent-1-en-1-yl)methyl)piperazin-1-yl)-2-(2-methyl-3-oxo-3,5-dihydropyrazolo[4,3-b]pyrrolo[3,2-e]pyridin-1(2H)-yl)benzamide, N-((4-(((((5r,8r)-1-oxaspiro[4.5]decan-8-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2-methyl-3-oxo-3,5-dihydropyrazolo[4,3-b]pyrrolo[3,2-e]pyridin-1(2H)-yl)benzamide, N-((4-((((R)-1,4-dioxan-2-yl)methyl)amino)-3-nitrophenyl)sulfonyl)-4-(4-((R)-(4'-chloro-[1,1'-biphenyl]-2-yl)(hydroxy)methyl)piperidin-1-yl)-2-(2-methyl-3-oxo-3,5-dihydropyrazolo[4,3-b]pyrrolo[3,2-e]pyridin-1(2H)-yl)benzamide, N-((4-((((R)-1,4-dioxan-2-yl)methyl)amino)-3-nitrophenyl)sulfonyl)-4-(4-((R)-(6-(4-chlorophenyl)spiro[3.5]non-6-en-7-yl)(hydroxy)methyl)piperidin-1-yl)-2-(2-methyl-3-oxo-3,5-dihydropyrazolo[4,3-b]pyrrolo[3,2-e]pyridin-1(2H)-yl)benzamide, N—(((S)-3-((S)-1,4-dioxan-2-yl)-5-nitro-3,4-dihydro-2H-benzo[b][1,4]oxazin-7-yl)sulfonyl)-4-(4-((4'-chloro-5,5- dimethyl-3,4,5,6-tetrahydro-[1,1'-biphenyl]-2-yl)methyl)
piperazin-1-yl)-2-(2-methyl-3-oxo-3,5-dihydropyrazolo
[4,3-b]pyrrolo[3,2-e]pyridin-1(2H)-yl)benzamide,
N—(((S)-3-((R)-1,4-dioxan-2-yl)-5-nitro-3,4-dihydro-2H-
benzo[b][1,4]oxazin-7-yl)sulfonyl)-4-(4-((4'-chloro-5,5-
dimethyl-3,4,5,6-tetrahydro-[1,1'-biphenyl]-2-yl)methyl)
piperazin-1-yl)-2-(2-methyl-3-oxo-3,5-dihydropyrazolo
[4,3-b]pyrrolo[3,2-e]pyridin-1(2H)-yl)benzamide,
N—(((R)-3-((S)-1,4-dioxan-2-yl)-5-nitro-3,4-dihydro-2H-
benzo[b][1,4]oxazin-7-yl)sulfonyl)-4-(4-((4'-chloro-5,5-
dimethyl-3,4,5,6-tetrahydro-[1,1'-biphenyl]-2-yl)methyl)
piperazin-1-yl)-2-(2-methyl-3-oxo-3,5-dihydropyrazolo
[4,3-b]pyrrolo[3,2-e]pyridin-1(2H)-yl)benzamide,
N—(((R)-3-((R)-1,4-dioxan-2-yl)-5-nitro-3,4-dihydro-2H-
benzo[b][1,4]oxazin-7-yl)sulfonyl)-4-(4-((4'-chloro-5,5-
dimethyl-3,4,5,6-tetrahydro-[1,1'-biphenyl]-2-yl)methyl)
piperazin-1-yl)-2-(2-methyl-3-oxo-3,5-dihydropyrazolo
[4,3-b]pyrrolo[3,2-e]pyridin-1(2H)-yl)benzamide,
(S)-4-(4-((4'-chloro-5,5-dimethyl-3,4,5,6-tetrahydro-[1,1'-
biphenyl]-2-yl)methyl)piperazin-1-yl)-2-(2-methyl-3-
oxo-3,5-dihydropyrazolo[4,3-b]pyrrolo[3,2-e]pyridin-1
(2H)-yl)-N-((3-((4-methylpiperazin-1-yl)methyl)-5-nitro-
3,4-dihydro-2H-benzo[b][1,4]oxazin-7-yl)sulfonyl)
benzamide,
(R)-4-(4-((4'-chloro-5,5-dimethyl-3,4,5,6-tetrahydro-[1,1'-
biphenyl]-2-yl)methyl)piperazin-1-yl)-2-(2-methyl-3-
oxo-3,5-dihydropyrazolo[4,3-b]pyrrolo[3,2-e]pyridin-1
(2H)-yl)-N-((3-(2-morpholinoethyl)-5-nitro-3,4-dihydro-
2H-benzo[b][1,4]oxazin-7-yl)sulfonyl)benzamide,
(R)-4-(4-((4'-chloro-5,5-dimethyl-3,4,5,6-tetrahydro-[1,1'-
biphenyl]-2-yl)methyl)piperazin-1-yl)-N-((3-(4-hydroxy-
4-methylcyclohexyl)-5-nitro-3,4-dihydro-2H-benzo[b][1,
4]oxazin-7-yl)sulfonyl)-2-(2-methyl-3-oxo-3,5-
dihydropyrazolo[4,3-b]pyrrolo[3,2-e]pyridin-1(2H)-yl)
benzamide,
(R)-4-(4-((4'-chloro-5,5-dimethyl-3,4,5,6-tetrahydro-[1,1'-
biphenyl]-2-yl)methyl)piperazin-1-yl)-2-(2-methyl-3-
oxo-3,5-dihydropyrazolo[4,3-b]pyrrolo[3,2-e]pyridin-1
(2H)-yl)-N-((3-(morpholinomethyl)-5-nitro-3,4-dihydro-
2H-benzo[b][1,4]oxazin-7-yl)sulfonyl)benzamide,
(R)-4-(4-((4'-chloro-5,5-dimethyl-3,4,5,6-tetrahydro-[1,1'-
biphenyl]-2-yl)methyl)piperazin-1-yl)-N-((3-((4-hy-
droxy-4-methylpiperidin-1-yl)methyl)-5-nitro-3,4-di-
hydro-2H-benzo[b][1,4]oxazin-7-yl)sulfonyl)-2-(2-
methyl-3-oxo-3,5-dihydropyrazolo[4,3-b]pyrrolo[3,2-e]
pyridin-1(2H)-yl)benzamide,
(S)-4-(4-((4'-chloro-5,5-dimethyl-3,4,5,6-tetrahydro-[1,1'-
biphenyl]-2-yl)methyl)piperazin-1-yl)-N-((3-cyclopro-
pyl-5-nitro-3,4-dihydro-2H-benzo[b][1,4]oxazin-7-yl)
sulfonyl)-2-(2-methyl-3-oxo-3,5-dihydropyrazolo[4,3-b]
pyrrolo[3,2-e]pyridin-1(2H)-yl)benzamide,
N—(((R)-3-(((1S,4S)-2-oxa-5-azabicyclo[2.2.1]heptan-5-
yl)methyl)-5-nitro-3,4-dihydro-2H-benzo[b][1,4]oxazin-
7-yl)sulfonyl)-4-(4-((4'-chloro-5,5-dimethyl-3,4,5,6-tet-
rahydro-[1,1'-biphenyl]-2-yl)methyl)piperazin-1-yl)-2-
(2-methyl-3-oxo-3,5-dihydropyrazolo[4,3-b]pyrrolo[3,2-
e]pyridin-1(2H)-yl)benzamide,
(S)-4-(4-((4'-chloro-5,5-dimethyl-3,4,5,6-tetrahydro-[1,1'-
biphenyl]-2-yl)methyl)piperazin-1-yl)-2-(2-methyl-3-
oxo-3,5-dihydropyrazolo[4,3-b]pyrrolo[3,2-e]pyridin-1
(2H)-yl)-N-((5-nitro-3-(pyridin-2-ylmethyl)-3,4-dihydro-
2H-benzo[b][1,4]oxazin-7-yl)sulfonyl)benzamide,
4-(4-((4'-chloro-5,5-dimethyl-3,4,5,6-tetrahydro-[1,1'-bi-
phenyl]-2-yl)methyl)piperazin-1-yl)-2-(2-methyl-3-oxo-
3,5-dihydropyrazolo[4,3-b]pyrrolo[3,2-e]pyridin-1(2H)-
yl)-N-((3-((4-methylpiperazin-1-yl)methyl)-5-nitro-3,4-
dihydro-2H-benzo[b][1,4]thiazin-7-yl)sulfonyl)
benzamide,
4-(4-((4'-chloro-5,5-dimethyl-3,4,5,6-tetrahydro-[1,1'-bi-
phenyl]-2-yl)methyl)piperazin-1-yl)-2-(2-methyl-3-oxo-
3,5-dihydropyrazolo[4,3-b]pyrrolo[3,2-e]pyridin-1(2H)-
yl)-N-((2-(morpholinomethyl)-8-nitro-2,3-dihydrobenzo
[b][1,4]dioxin-6-yl)sulfonyl)benzamide,
4-(4-(3-(2-(4-chlorophenyl)-1-isopropyl-5-methyl-4-(meth-
ylsulfonyl)-1H-pyrrol-3-yl)-5-fluorophenyl)piperazin-1-
yl)-2-(2-methyl-3-oxo-3,5-dihydropyrazolo[4,3-b]pyr-
rolo[3,2-e]pyridin-1(2H)-yl)-N-((3-nitro-4-(((tetrahydro-
2H-pyran-4-yl)methyl)amino)phenyl)sulfonyl)
benzamide, 5-(4-chlorophenyl)-1,2-dimethyl-4-(3-(4-(3-
(2-methyl-3-oxo-3,5-dihydropyrazolo[4,3-b]pyrrolo[3,2-
e]pyridin-1(2H)-yl)-4-(((3-nitro-4-(((tetrahydro-2H-
pyran-4-yl)methyl)amino)phenyl)sulfonyl)carbamoyl)
phenyl)piperazin-1-yl)phenyl)-1H-pyrrole-3-carboxylic
acid,
(2S,4R)-1-((S)-14-(tert-butyl)-1-(4-(2-((4-(N-(4-(4-((4'-
chloro-5,5-dimethyl-3,4,5,6-tetrahydro-[1,1'-biphenyl]-2-
yl)methyl)piperazin-1-yl)-2-(2-methyl-3-oxo-3,5-dihy-
dropyrazolo[4,3-b]pyrrolo[3,2-e]pyridin-1(2H)-yl)
benzoyl)sulfamoyl)-2-nitrophenyl)amino)ethyl)
piperazin-1-yl)-12-oxo-3,6,9-trioxa-13-azapentadecan-
15-oyl)-4-hydroxy-N-(4-(4-methylthiazol-5-yl)benzyl)
pyrrolidine-2-carboxamide,
(2S,4R)-1-((S)-2-(3-(2-(2-(4-(2-((4-(N-(4-(4-((4'-chloro-5,
5-dimethyl-3,4,5,6-tetrahydro-[1,1'-biphenyl]-2-yl)
methyl)piperazin-1-yl)-2-(2-methyl-3-oxo-3,5-dihydro-
pyrazolo[4,3-b]pyrrolo[3,2-e]pyridin-1(2H)-yl)benzoyl)
sulfamoyl)-2-nitrophenyl)amino)ethyl)piperazin-1-yl)
ethoxy)ethoxy)propanamido)-3,3-dimethylbutanoyl)-4-
hydroxy-N-(4-(4-methylthiazol-5-yl)benzyl)pyrrolidine-
2-carboxamide,
(2S,4R)-1-((S)-2-(3-(2-(4-(2-((4-(N-(4-(4-((4'-chloro-5,5-
dimethyl-3,4,5,6-tetrahydro-[1,1'-biphenyl]-2-yl)methyl)
piperazin-1-yl)-2-(2-methyl-3-oxo-3,5-dihydropyrazolo
[4,3-b]pyrrolo[3,2-e]pyridin-1(2H)-yl)benzoyl)
sulfamoyl)-2-nitrophenyl)amino)ethyl)piperazin-1-yl)
ethoxy)propanamido)-3,3-dimethylbutanoyl)-4-hydroxy-
N-(4-(4-methylthiazol-5-yl)benzyl)pyrrolidine-2-
carboxamide,
(2S,4R)-1-((S)-20-(tert-butyl)-1-((4-(N-(4-(4-((4'-chloro-5,
5-dimethyl-3,4,5,6-tetrahydro-[1,1'-biphenyl]-2-yl)
methyl)piperazin-1-yl)-2-(2-methyl-3-oxo-3,5-dihydro-
pyrazolo[4,3-b]pyrrolo[3,2-e]pyridin-1(2H)-yl)benzoyl)
sulfamoyl)-2-nitrophenyl)amino)-18-oxo-3,6,9,12,15-
pentaoxa-19-azahenicosan-21-oyl)-4-hydroxy-N-(4-(4-
methylthiazol-5-yl)benzyl)pyrrolidine-2-carboxamide,
(2S,4R)-1-((S)-17-(tert-butyl)-1-((4-(N-(4-(4-((4'-chloro-5,
5-dimethyl-3,4,5,6-tetrahydro-[1,1'-biphenyl]-2-yl)
methyl)piperazin-1-yl)-2-(2-methyl-3-oxo-3,5-dihydro-
pyrazolo[4,3-b]pyrrolo[3,2-e]pyridin-1(2H)-yl)benzoyl)
sulfamoyl)-2-nitrophenyl)amino)-15-oxo-3,6,9,12-
tetraoxa-16-azaoctadecan-18-oyl)-4-hydroxy-N-(4-(4-
methylthiazol-5-yl)benzyl)pyrrolidine-2-carboxamide,
(2S,4R)-1-((S)-14-(tert-butyl)-1-((4-(N-(4-(4-((4'-chloro-5,
5-dimethyl-3,4,5,6-tetrahydro-[1,1'-biphenyl]-2-yl)
methyl)piperazin-1-yl)-2-(2-methyl-3-oxo-3,5-dihydro-
pyrazolo[4,3-b]pyrrolo[3,2-e]pyridin-1(2H)-yl)benzoyl)
sulfamoyl)-2-nitrophenyl)amino)-12-oxo-3,6,9-trioxa-
13-azapentadecan-15-oyl)-4-hydroxy-N-(4-(4-
methylthiazol-5-yl)benzyl)pyrrolidine-2-carboxamide,
4-(4-((4'-chloro-5,5-dimethyl-3,4,5,6-tetrahydro-[1,1'-bi-
phenyl]-2-yl)methyl)piperazin-1-yl)-N-((4-((2-(4-(2-(2-
(2-(2-((2-(2,6-dioxopiperidin-3-yl)-1,3-dioxoisoindolin- 4-yl)amino)ethoxy)ethoxy)ethoxy)ethyl)piperazin-1-yl)ethyl)amino)-3-nitrophenyl)sulfonyl)-2-(2-methyl-3-oxo-3,5-dihydropyrazolo[4,3-b]pyrrolo[3,2-e]pyridin-1(2H)-yl)benzamide, 4-(4-((4'-chloro-5,5-dimethyl-3,4,5,6-tetrahydro-[1,1'-biphenyl]-2-yl)methyl)piperazin-1-yl)-N-((4-((2-(4-(2-(2-(2-((2-(2,6-dioxopiperidin-3-yl)-1,3-dioxoisoindolin-4-yl)amino)ethoxy)ethoxy)ethyl)piperazin-1-yl)ethyl)amino)-3-nitrophenyl)sulfonyl)-2-(2-methyl-3-oxo-3,5-dihydropyrazolo[4,3-b]pyrrolo[3,2-e]pyridin-1(2H)-yl)benzamide, 4-(4-((4'-chloro-5,5-dimethyl-3,4,5,6-tetrahydro-[1,1'-biphenyl]-2-yl)methyl)piperazin-1-yl)-N-((4-((2-(4-(2-(2-((2-(2,6-dioxopiperidin-3-yl)-1,3-dioxoisoindolin-4-yl)amino)ethoxy)ethyl)piperazin-1-yl)ethyl)amino)-3-nitrophenyl)sulfonyl)-2-(2-methyl-3-oxo-3,5-dihydropyrazolo[4,3-b]pyrrolo[3,2-e]pyridin-1(2H)-yl)benzamide, 4-(4-((4'-chloro-5,5-dimethyl-3,4,5,6-tetrahydro-[1,1'-biphenyl]-2-yl)methyl)piperazin-1-yl)-N-((4-((17-((2-(2,6-dioxopiperidin-3-yl)-1,3-dioxoisoindolin-4-yl)amino)-3,6,9,12,15-pentaoxaheptadecyl)amino)-3-nitrophenyl)sulfonyl)-2-(2-methyl-3-oxo-3,5-dihydropyrazolo[4,3-b]pyrrolo[3,2-e]pyridin-1(2H)-yl)benzamide, 4-(4-((4'-chloro-5,5-dimethyl-3,4,5,6-tetrahydro-[1,1'-biphenyl]-2-yl)methyl)piperazin-1-yl)-N-((4-((14-((2-(2,6-dioxopiperidin-3-yl)-1,3-dioxoisoindolin-4-yl)amino)-3,6,9,12-tetraoxatetradecyl)amino)-3-nitrophenyl)sulfonyl)-2-(2-methyl-3-oxo-3,5-dihydropyrazolo[4,3-b]pyrrolo[3,2-e]pyridin-1(2H)-yl)benzamide, 4-(4-((4'-chloro-5,5-dimethyl-3,4,5,6-tetrahydro-[1,1'-biphenyl]-2-yl)methyl)piperazin-1-yl)-N-((4-((2-(2-(2-(2-((2-(2,6-dioxopiperidin-3-yl)-1,3-dioxoisoindolin-4-yl)amino)ethoxy)ethoxy)ethoxy)ethyl)amino)-3-nitrophenyl)sulfonyl)-2-(2-methyl-3-oxo-3,5-dihydropyrazolo[4,3-b]pyrrolo[3,2-e]pyridin-1(2H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl-2,2,3,3-d4)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,3-dimethyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]thiazin-1(6H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]oxazin-1(6H)-yl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6]pyrido[2,3-b][1,4]thiazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-methyl-2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,2-dimethyl-2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2'H-spiro[cyclopropane-1,3'-pyrrolo[3',2':5,6]pyrido[2,3-b][1,4]oxazin]-1'(6'H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2,3,4,6-tetrahydro-1H-pyrrolo[2,3-b][1,5]naphthyridin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-oxo-2,3,4,6-tetrahydro-1H-pyrrolo[2,3-b][1,5]naphthyridin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-oxo-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(4-oxo-2,3,4,6-tetrahydro-1H-pyrrolo[2,3-b][1,5]naphthyridin-1-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2,3,4,6-tetrahydro-1H-pyrrolo[3',2':5,6]pyrido[2,3-b]pyrazin-1-yl)benzamide, 4-(4-((4'-chloro-5,5-dimethyl-3,4,5,6-tetrahydro-[1,1'-biphenyl]-2-yl)methyl)piperazin-1-yl)-2-(4,4-dioxido-2,3-dihydropyrrolo[3',2':5,6]pyrido[2,3-b][1,4]thiazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)
sulfonyl)-2-(4-(methylimino)-4-oxido-2,3,4,6-
tetrahydro-1H-4λ4-pyrrolo[3',2':5,6]pyrido[2,3-b][1,4]
thiazin-1-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-3-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((2-morpholinoethyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-methylmorpholin-2-yl)methyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((4-(oxetan-3-yl)morpholin-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-hydroxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((((1r,4r)-4-methoxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((((1s,4s)-4-hydroxy-4-methylcyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((((1s,4s)-4-ethyl-4-hydroxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(tetrahydro-2H-pyran-4-yl)piperidin-4-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1s,4s)-4-morpholinocyclohexyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((4-(cyclopropylamino)cyclohexyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4,4-difluorocyclohexyl)methyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((tetrahydro-2H-pyran-4-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((tetrahydro-2H-pyran-3-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(2-morpholinoethoxy)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-methylmorpholin-2-yl)methoxy)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((4-(oxetan-3-yl)morpholin-2-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-hydroxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4r)-4-methoxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1s,4s)-4-hydroxy-4-methylcyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1s,4s)-4-ethyl-4-hydroxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(tetrahydro-2H-pyran-4-yl)piperidin-4-yl)oxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1s,4s)-4-morpholinocyclohexyl)oxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((4-(cyclopropylamino)cyclohexyl)oxy)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4,4-difluorocyclohexyl)methoxy)-3-nitrophenyl)sulfonyl)-2-(2,3-dihydropyrrolo[3',2':5,6]pyrido[2,3-b][1,4]oxazin-1(6H)-yl)benzamide, 4-(4-((2-(4-chlorophenyl)cyclopent-1-en-1-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((2-(4-chlorophenyl)cyclohept-1-en-1-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4-(4-chlorophenyl)-6,6-dimethyl-5,6-dihydro-2H-pyran-3-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-4-(methoxymethyl)-4-methyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-5-fluoro-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((6-(((4-fluorotetrahydro-2H-pyran-4-yl)methyl)amino)-5-nitropyridin-3-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-((trifluoromethyl)sulfonyl)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(6,7-dihydroimidazo[4',5':5,6]pyrido[2,3-b][1,4]oxazin-8(3H)-yl)-N-((3-nitro-4-(((tetrahydro-2H-pyran-4-yl)methyl)amino)phenyl)sulfonyl)benzamide, 4-(4-((9-(4-chlorophenyl)-3-methyl-3-azaspiro[5.5]undec-8-en-8-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((9-(4-chlorophenyl)-3-(1,3-difluoropropan-2-yl)-3-azaspiro[5.5]undec-8-en-8-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-difluoro-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((5-(4-chlorophenyl)spiro[2.5]oct-5-en-6-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((7-(4-chlorophenyl)spiro[3.5]non-6-en-6-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-3'-fluoro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-3',5,5-trimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 2-(2,3-dihydropyrrolo[3',2':5,6]pyrido[2,3-b][1,4]oxazin-1(6H)-yl)-4-(4-((4,4-dimethyl-2-(pyridin-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide, 4-(4-((2-(1H-indol-5-yl)-4,4-dimethylcyclohex-1-en-1-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)—N-((4-(((1,4-dioxan-2-yl)methyl)amino)-3-fluoro-5-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (R)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (R)—N-((4-(((1,4-dioxan-2-yl)methyl)amino)-3-nitrophenyl)sulfonyl)-4-(4-((6-(4-chlorophenyl)-2-oxaspiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (R)—N-((4-(((1,4-dioxan-2-yl)methyl)amino)-3-fluoro-5-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((6-(4-chlorophenyl)-2-oxaspiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((6-(4-chlorophenyl)-2-oxaspiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-6-fluorobenzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-5-fluorobenzamide, 4-(4-((4'-chloro-5,5-bis(methyl-d3)-3,4,5,6-tetrahydro-[1,1'-biphenyl]-2-yl)methyl)-2-methylpiperazin-1-yl-2,3,3,5,5,6,6-d7)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, diethyl (2-(((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)methyl)morpholino)methyl)phosphonate, diethyl (((3-((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)propyl)(methyl)amino)methyl)phosphonate, 2-(((2-((4-(N-(4-(4-(((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)((pivaloyloxy)methoxy)phosphoryl)oxy)ethyl pivalate, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-methyl-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-hydroxy-1-oxidophosphinan-4-yl)methyl)amino)-3-nitrophenyl)sulfonyl)benzamide, ((4-(((4-(N-(4-(4-(((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)methyl)-1-oxidophosphinan-1-yl)oxy)methyl pivalate, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((2-methyl-2-oxido-1,3,2-oxazaphosphinan-5-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((2-(2-methyl-2-oxido-1,3,2-oxazaphosphinan-3-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-(dimethylphosphoryl)piperidin-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-(dimethylphosphoryl)-4-(((tetrahydro-2H-pyran-4-yl)methyl)amino)phenyl)sulfonyl)benzamide, N-((4-(((1,4-dioxaspiro[4.5]decan-8-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, N-((4-(((2-oxaspiro[3.5]nonan-7-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((2-(hexahydrofuro[3,4-c]pyridin-5(3H)-yl)ethyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(3-oxooctahydro-7H-imidazo[1,5-d][1,4]diazepin-7-yl)ethyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(3-oxooctahydro-5H-pyrrolo[3,4-c]pyridin-5-yl)ethyl)amino)phenyl)sulfonyl)benzamide, N-((4-((2-(2-oxa-5-azabicyclo[2.2.2]octan-5-yl)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((3-hydroxy-3-methylbicyclo[3.1.1]heptan-6-yl)methyl)amino)-3-nitrophenyl)sulfonyl)benzamide, N-((4-((2-(2-oxa-5-azabicyclo[2.2.1]heptan-5-yl)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 2-((3R)-8-(2-((4-(N-(4-(4-(((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)-6,6-difluoro-8-azabicyclo[3.2.1]octan-3-yl)acetic acid, 4-(4-((4'-chloro-5,5-dimethyl-3,4,5,6-tetrahydro-[1,1'-biphenyl]-2-yl)methyl)piperazin-1-yl)-N-((4-((2-(6,6-difluoro-8-azabicyclo[3.2.1]octan-8-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(tetrahydro-2H-pyran-4-yl)-2-azaspiro[3.3]heptan-6-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-thiopyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-imino-1-oxidohexahydro-1l6-thiopyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-(methylsulfonyl)morpholin-2-yl)methyl)amino)-3-nitrophenyl)sulfonyl)benzamide, N-((4-(((4-aminotetrahydro-2H-pyran-4-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(tetrahydro-2H-pyran-4-yl)cyclopropyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((2-(5,6-dihydroimidazo[1,2-a]pyrazin-7(8H)-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((5,6,7,8-tetrahydroimidazo[1,2-a]pyridin-6-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((3-(difluoromethoxy)benzyl)amino)-3-nitrophenyl)sulfonyl)-2-(2,
3-dihydropyrrolo[3',2':5,6]pyrido[2,3-b][1,4]oxazin-1
(6H)-yl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5-trihydroxytetrahydrofuran-2-yl)methyl) amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5,6-tetrahydroxytetrahydro-2H-pyran-2-yl) methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4,5-dihydroxy-6,6-dimethyltetrahydro-2H-pyran-2-yl) methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((2,3,5-trihydroxy-6-(hydroxymethyl)tetrahydro-2H-pyran-4-yl)methyl)amino)phenyl)sulfonyl) benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((2,3,4,5,6-pentahydroxycyclohexyl)methyl) amino)phenyl)sulfonyl)benzamide
(R)—N-((4-(((1,4-dioxan-2-yl)methyl)amino)-3-nitrophenyl)sulfonyl)-4-(1-((4'-chloro-5,5-dimethyl-3,4,5,6-tetrahydro-[1,1'-biphenyl]-2-yl)methyl)-1,2,3,6-tetrahydropyridin-4-yl)-2-(2,3-dihydropyrrolo[3',2':5,6]pyrido[2,3-b][1,4]oxazin-1(6H)-yl)benzamide,
4-(1-((6-(4-chlorophenyl)spiro[3.5]non-6-en-7-yl)methyl)-1,2,3,6-tetrahydropyridin-4-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl) sulfonyl)benzamide,
(R)—N-((4-(((1,4-dioxan-2-yl)methyl)amino)-3-nitrophenyl)sulfonyl)-4-(1-((4'-chloro-5,5-dimethyl-3,4,5,6-tetrahydro-[1,1'-biphenyl]-2-yl)methyl)piperidin-4-yl)-2-(2,3-dihydropyrrolo[3',2':5,6]pyrido[2,3-b][1,4]oxazin-1(6H)-yl)benzamide,
(S)—N-((4-(((1,4-dioxan-2-yl)methyl)amino)-3-nitrophenyl)sulfonyl)-5-(4-((6-(4-chlorophenyl)spiro[3.5]non-6-en-7-yl)methyl)piperazin-1-yl)-3-(2,3-dihydropyrrolo[3',2':5,6]pyrido[2,3-b][1,4]oxazin-1(6H)-yl)picolinamide,
(S)—N-((4-(((1,4-dioxan-2-yl)methyl)amino)-3-nitrophenyl)sulfonyl)-6-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)nicotinamide,
4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl) amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,2-dimethyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl) amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(3-(hydroxymethyl)-2,3-dihydropyrrolo[3',2':5,6]pyrido[2,3-b][1,4] oxazin-1(6H)-yl)-N-((3-nitro-4-(((tetrahydro-2H-pyran-4-yl)methyl)amino)phenyl)sulfonyl)benzamide,
(S)-4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl) amino)phenyl)sulfonyl)benzamide,
(R)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl) amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(4,4-dioxido-2,3-dihydropyrrolo[3',2':5,6]pyrido[2,3-b][1,4]thiazin-1(6H)-yl)-N-((3-nitro-4-(((tetrahydro-2H-pyran-4-yl)methyl) amino)phenyl)sulfonyl)benzamide,
(S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6] pyrido[2,3-b][1,4]oxazin-1(6H)-yl)benzamide,
(S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-2,3-dihydropyrrolo[3',2':5,6] pyrido[2,3-b][1,4]thiazin-1(6H)-yl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl-2,2,3,3-d4)-N-((4-(((4-fluorotetrahydro-2H-pyran-4-yl)methyl) amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(3-methyl-2,3-dihydropyrrolo[3',2':5,6] pyrido[2,3-b][1,4]oxazin-1(6H)-yl)benzamide,
(R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(3-methyl-2,3-dihydropyrrolo[3',2':5,6] pyrido[2,3-b][1,4]oxazin-1(6H)-yl)benzamide,
4-(4-((4'-chloro-5,5-dimethyl-3,4,5,6-tetrahydro-[1,1'-biphenyl]-2-yl)methyl)piperazin-1-yl)-2-(3,3-dimethyl-2,3-dihydropyrrolo[3',2':5,6]pyrido[2,3-b][1,4]oxazin-1(6H)-yl)-N-((4-(((4-fluorotetrahydro-2H-pyran-4-yl)methyl) amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(3'H-spiro[cyclopropane-1,2'-pyrrolo[3',2':5, 6]pyrido[2,3-b][1,4]oxazin]-1'(6'H)-yl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]thiazin-1(6H)-yl)-N-((4-(((4-fluorotetrahydro-2H-pyran-4-yl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(2-oxo-2,3-dihydropyrrolo[3',2':5,6]pyrido[2, 3-b][1,4]oxazin-1(6H)-yl)benzamide,
4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl) sulfonyl)-2-(3-oxo-2,3,4,6-tetrahydro-1H-pyrrolo[3',2':5, 6]pyrido[2,3-b]pyrazin-1-yl)benzamide,
4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)
sulfonyl)-2-(4-oxo-4,6-dihydro-1H-pyrrolo[2,3-b][1,5]
naphthyridin-1-yl)benzamide,
4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)
sulfonyl)-2-(4-methyl-2,3,4,6-tetrahydro-1H-pyrrolo[3',2':5,6]pyrido[2,3-b]pyrazin-1-yl)benzamide,
4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)
sulfonyl)-2-(4-imino-4-oxido-2,3,4,6-tetrahydro-1H-4λ4-pyrrolo[3',2':5,6]pyrido[2,3-b][1,4]thiazin-1-yl)
benzamide,
4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)
sulfonyl)-2-(4-methyl-4-oxido-2,3,6-trihydropyrrolo[3',2':5,6]pyrido[3,2-b][1,4]azaphosphinin-1-yl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((3-fluorotetrahydro-2H-pyran-3-yl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((3-morpholinopropyl)amino)-3-nitrophenyl)sulfonyl)
benzamide,
(S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-methylmorpholin-2-yl)methyl)amino)-3-nitrophenyl)sulfonyl)benzamide,
(S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((4-(oxetan-3-yl)morpholin-2-yl)methyl)amino)
phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-hydroxy-4-methylcyclohexyl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((((1s,4s)-4-methoxycyclohexyl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((((1r,4r)-4-hydroxy-4-methylcyclohexyl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((((1r,4r)-4-ethyl-4-hydroxycyclohexyl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(oxetan-3-yl)piperidin-4-yl)amino)phenyl)
sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4r)-4-morpholinocyclohexyl)amino)-3-nitrophenyl)
sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-(methyl(oxetan-3-yl)amino)cyclohexyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((1,4,4-trifluorocyclohexyl)methyl)amino)
phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-fluorotetrahydro-2H-pyran-4-yl)methoxy)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((3-fluorotetrahydro-2H-pyran-3-yl)methoxy)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(3-morpholinopropoxy)-3-nitrophenyl)sulfonyl)
benzamide,
(R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-methylmorpholin-2-yl)methoxy)-3-nitrophenyl)
sulfonyl)benzamide,
(R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((4-(oxetan-3-yl)morpholin-2-yl)methoxy)
phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((4-hydroxy-4-methylcyclohexyl)methoxy)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((((1s,4s)-4-methoxycyclohexyl)methoxy)-3-nitrophenyl)
sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4r)-4-hydroxy-4-methylcyclohexyl)methoxy)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4r)-4-ethyl-4-hydroxycyclohexyl)methoxy)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1-(oxetan-3-yl)piperidin-4-yl)oxy)phenyl)
sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1r,4r)-4-morpholinocyclohexyl)oxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((methyl(oxetan-3-yl)amino)cyclohexyl)oxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((1,4,4-trifluorocyclohexyl)methoxy)phenyl)sulfonyl)benzamide, 4-(4-((4-(4-chlorophenyl)-5,6-dihydro-2H-pyran-3-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, (Z)-4-(4-((2-(4-chlorophenyl)cyclooct-1-en-1-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-4-methoxy-4-methyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(5-((4'-chloro-5,5-dimethyl-3,4,5,6-tetrahydro-[1,1'-biphenyl]-2-yl)methyl)-2,5-diazabicyclo[2.2.2]octan-2-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-(4-(((4-fluorotetrahydro-2H-pyran-4-yl)methyl)amino)-3-nitrophenylsulfonimidoyl)benzamide, 4-(4-((4'-chloro-5,5-dimethyl-3,4,5,6-tetrahydro-[1,1'-biphenyl]-2-yl)methyl)piperazin-1-yl)-N-((5-chloro-6-((tetrahydro-2H-pyran-4-yl)methoxy)pyridin-3-yl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-(S-(trifluoromethyl)sulfonimidoyl)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydro-[1,4]oxazino[3,2-f]indol-1(6H)-yl)-N-((3-nitro-4-(((tetrahydro-2H-pyran-4-yl)methyl)amino)phenyl)sulfonyl)benzamide, 4-(4-((9-(4-chlorophenyl)-3-isopropyl-3-azaspiro[5.5]undec-8-en-8-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((9-(4-chlorophenyl)-3-(oxetan-3-yl)-3-azaspiro[5.5]undec-8-en-8-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-5,5-bis(fluoromethyl)-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-(1-(4'-chloro-5,5-dimethyl-3,4,5,6-tetrahydro-[1,1'-biphenyl]-2-yl)cyclopropyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((6-(4-chlorophenyl)spiro[2.5]oct-5-en-5-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, 4-(4-((4'-chloro-2'-fluoro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((4'-chloro-2',5,5-trimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 2-(2,3-dihydropyrrolo[3',2':5,6]pyrido[2,3-b][1,4]oxazin-1(6H)-yl)-4-(4-((4,4-dimethyl-2-(pyridin-2-yl)cyclohex-1-en-1-yl)methyl)piperazin-1-yl)-N-((3-nitro-4-(((tetrahydro-2H-pyran-4-yl)methyl)amino)phenyl)sulfonyl)benzamide, 2-(2,3-dihydropyrrolo[3',2':5,6]pyrido[2,3-b][1,4]oxazin-1(6H)-yl)-4-(4-((4,4-dimethyl-2-(1H-pyrrolo[2,3-b]pyridin-5-yl)cyclohex-1-en-1-yl)methyl)piperazin-1-yl)-N-((3-nitro-4-(((tetrahydro-2H-pyran-4-yl)methyl)amino)phenyl)sulfonyl)benzamide, (S)—N-((4-(((1,4-dioxan-2-yl)methyl)amino)-3-fluoro-5-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (S)—N-((4-(((1,4-dioxan-2-yl)methyl)amino)-3-nitrophenyl)sulfonyl)-4-(4-((6-(4-chlorophenyl)-2-oxaspiro[3.5]non-6-en-7-yl)methyl)piperazin-1-yl)-2-(2,3-dihydropyrrolo[3',2':5,6]pyrido[2,3-b][1,4]oxazin-1(6H)-yl)benzamide, (S)—N-((4-(((1,4-dioxan-2-yl)methyl)amino)-3-fluoro-5-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-3-fluorobenzamide, (S)—N-((4-(((1,4-dioxan-2-yl)methyl)amino)-3-fluoro-5-nitrophenyl)sulfonyl)-4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-6-fluorobenzamide, 4-(4-((4'-chloro-5,5-bis(methyl-d3)-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl-2,2,3,3-d4)-N-((3-nitro-4-(((tetrahydro-2H-pyran-4-yl)methyl)amino)phenyl)sulfonyl)benzamide, ((2-(((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)methyl)morpholino)methyl)phosphonic acid, diethyl (2-((2-((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)(methyl)amino)ethyl)phosphonate, ethyl P-(2-((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)-N,N-dimethylphosphonamidate, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-(dimethylamino)-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-ethoxy-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-isopropoxy-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((1,2,3-trimethyl-2-oxido-1,3,2-diazaphosphinan-5-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((2-(2-methyl-2-oxido-1,3,2-diazaphosphinan-1-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-(dimethylphosphoryl)morpholin-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(dimethylphosphoryl)-3-nitrophenyl)sulfonyl)benzamide, N-((4-(((1,4-dithiaspiro[4.5]decan-8-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, N-((4-((2-(6-azaspiro[2.5]octan-6-yl)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-((2-(2,2-difluoro-7-azaspiro[3.5]nonan-7-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(2-(oxetan-3-yl)octahydro-5H-pyrrolo[3,4-c]pyridin-5-yl)ethyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(1-oxooctahydro-5H-pyrrolo[3,4-c]pyridin-5-yl)ethyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((3-hydroxybicyclo[3.1.1]heptan-6-yl)methyl)amino)-3-nitrophenyl)sulfonyl)benzamide, N-((4-(((3-amino-3-methylbicyclo[3.1.1]heptan-6-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(5-(oxetan-3-yl)-2,5-diazabicyclo[2.2.1]heptan-2-yl)ethyl)amino)phenyl)sulfonyl)benzamide, 2-((3S)-8-(2-((4-(N-(4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzoyl)sulfamoyl)-2-nitrophenyl)amino)ethyl)-6,6-difluoro-8-azabicyclo[3',2']octan-3-yl)acetic acid, 4-(4-((4'-chloro-5,5-dimethyl-3,4,5,6-tetrahydro-[1,1'-biphenyl]-2-yl)methyl)piperazin-1-yl)-N-((4-((2-(6,6-difluoro-8-azabicyclo[3.2.1]octan-8-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, N-((4-((7-oxaspiro[3.5]nonan-2-yl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1,1-dioxidotetrahydro-2H-thiopyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((1-(isopropylimino)-1-oxidohexahydro-1l6-thiopyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-(S-methylsulfonimidoyl)morpholin-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-cyanotetrahydro-2H-pyran-4-yl)methyl)amino)-3-nitrophenyl)
sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-((2-(tetrahydro-2H-pyran-4-yl)propan-2-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((2-(5,6-dihydro-[1,2,4]triazolo[1,5-a]pyrazin-7(8H)-yl)ethyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((1-(thiazol-2-yl)piperidin-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((4-(difluoromethoxy)benzyl)amino)-3-nitrophenyl)sulfonyl)-2-(2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((3,5-dihydroxytetrahydrofuran-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5-trihydroxy-6,6-dimethyltetrahydro-2H-pyran-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((2,3,5-trihydroxytetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5-trihydroxy-6-(methylthio)tetrahydro-2H-pyran-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((3,4,5-trihydroxy-6-(((4,5,6-trihydroxy-2-(hydroxymethyl)tetrahydro-2H-pyran-3-yl)methoxy)methyl)tetrahydro-2H-pyran-2-yl)methyl)amino)phenyl)sulfonyl)benzamide, N-((4-(((1,4-dioxan-2-yl)methyl)amino)-3-nitrophenyl)sulfonyl)-4-(1-((6-(4-chlorophenyl)-2-oxaspiro[3.5]non-6-en-7-yl)methyl)-1,2,3,6-tetrahydropyridin-4-yl)-2-(2,3-dihydropyrrolo[3',2':5,6]pyrido[2,3-b][1,4]oxazin-1(6H)-yl)benzamide, 4-(14(6-(4-chlorophenyl)-2-oxaspiro[3.5]non-6-en-7-yl)methyl)-1,2,3,6-tetrahydropyridin-4-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(1-((4'-chloro-5,5-dimethyl-3,4,5,6-tetrahydro-[1,1'-biphenyl]-2-yl)methyl)piperidin-4-yl)-2-(2,3-dihydropyrrolo[3',2':5,6]pyrido[2,3-b][1,4]oxazin-1(6H)-yl)-N-((3-nitro-4-(((tetrahydro-2H-pyran-3-yl)methyl)amino)phenyl)sulfonyl)benzamide, (S)-6-(4-(((6-(4-chlorophenyl)-2-oxaspiro[3.5]non-6-en-7-yl)methyl)piperazin-1-yl)-4-(2,3-dihydropyrrolo[3',2':5,6]pyrido[2,3-b][1,4]oxazin-1(6H)-yl)-N-((3-nitro-4-(((tetrahydro-2H-pyran-3-yl)methyl)amino)phenyl)sulfonyl)nicotinamide, (S)—N-((4-(((1,4-dioxan-2-yl)methyl)amino)-3-nitrophenyl)sulfonyl)-6-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)nicotinamide, N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((((S)-2-fluoro-1,4-dioxan-2-yl)methyl)amino)-3-nitrophenyl)sulfonyl)-2-((S)-3-methyl-2,3-dihydropyrrolo[3',2':5,6]pyrido[2,3-b][1,4]oxazin-1(6H)-yl)benzamide, (R)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide, (R)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, N-((4-(((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((((R)-2-fluoro-1,4-dioxan-2-yl)methyl)amino)-3-nitrophenyl)sulfonyl)-2-((S)-3-methyl-2,3-dihydropyrrolo[3',2':5,6]pyrido[2,3-b][1,4]oxazin-1(6H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3, 3-difluoro-2,3-dihydropyrrolo[3',2':5,6]pyrido[2,3-b][1,4]oxazin-1(6H)-yl)benzamide,
(R)-4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((4-(((2-fluoro-1,4-dioxan-2-yl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(3,3-difluoro-2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-((dimethyl(oxo)-16-sulfaneylidene)amino)cyclohexyl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((2-(4-((dimethyl(oxo)-16-sulfaneylidene)amino)piperidin-1-yl)ethyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((4-((1-oxidotetrahydro-1l6-thiophen-1-ylidene)amino)cyclohexyl)methyl)amino)phenyl)sulfonyl)benzamide, or
(S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-((1-(4-((dimethyl(oxo)-16-sulfaneylidene)amino)piperidin-1-yl)propan-2-yl)amino)-3-nitrophenyl)sulfonyl)benzamide.
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide,
(R)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide,
(S)-4-(4-((4'-chloro-5,5-dimethyl-3,4,5,6-tetrahydro-[1,1'-biphenyl]-2-yl)methyl)piperazin-1-yl)-2-(4-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide,
N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-4-methyl-3,4-dihydro-2H-pyrrolo[3',2':5,6]pyrido[2,3-b][1,4]oxazepin-1(7H)-yl)benzamide,
N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-4-methyl-3,4-dihydro-2H-pyrrolo[3',2':5,6]pyrido[2,3-b][1,4]oxazepin-1(7H)-yl)benzamide,
(R)-4-(4-((4'-chloro-5,5-dimethyl-3,4,5,6-tetrahydro-[1,1'-biphenyl]-2-yl)methyl)piperazin-1-yl)-2-(4-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide,
N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-4-methyl-3,4-dihydro-2H-pyrrolo[3',2':5,6]pyrido[2,3-b][1,4]oxazepin-1(7H)-yl)benzamide,
N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-4-methyl-3,4-dihydro-2H-pyrrolo[3',2':5,6]pyrido[2,3-b][1,4]oxazepin-1(7H)-yl)benzamide,
(S)-4-(4-((4'-chloro-5,5-dimethyl-3,4,5,6-tetrahydro-[1,1'-biphenyl]-2-yl)methyl)piperazin-1-yl)-2-(4,4-difluoro-3,4-dihydro-2H-pyrrolo[3',2':5,6]pyrido[2,3-b][1,4]oxazepin-1(7H)-yl)-N-((4-(((2-fluoro-1,4-dioxan-2-yl)methyl)amino)-3-nitrophenyl)sulfonyl)benzamide,
(R)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(4,4-difluoro-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(4,4-difluoro-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(3,3-dimethyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide,
(S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide,
(R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-3,4-dihydro-2H-pyrrolo[3',2':5,6]pyrido[2,3-b][1,4]oxazepin-1(7H)-yl)benzamide,
(S)-4-(4-((4'-chloro-5,5-dimethyl-3,4,5,6-tetrahydro-[1,1'-biphenyl]-2-yl)methyl)piperazin-1-yl)-2-(3-cyano-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide,
(R)-2-(3-amino-3,4-dihydro-2H-pyrrolo[3',2':5,6]pyrido[2,3-b][1,4]oxazepin-1(7H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide,
(R)-4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3-hydroxy-3-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3-methyl-3-(trifluoromethyl)-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3-cyano-3-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-(trifluoromethyl)-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]thiazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,3-difluoro-3,4-dihydro-2H-pyrrolo[3',2':5,6]pyrido[2,3-b][1,4]thiazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3-hydroxy-3-methyl-3,4-dihydro-2H-pyrrolo[3',2':5,6]pyrido[2,3-b][1,4]thiazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3-cyano-3-methyl-3,4-dihydro-2H-pyrrolo[3',2':5,6]pyrido[2,3-b][1,4]thiazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,3-difluoro-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3-cyano-3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-hydroxy-3-methyl-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl-3,3-d2)-N-((4-(((4-fluorotetrahydro-2H-pyran-4-yl)methyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(4,4-dimethyl-3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-methyl-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2H,4H-spiro[pyrrolo[3',2':5,6]pyrido[2,3-b][1,4]oxazepine-3,2'-[1,3]dithiolan]-1(7H)-yl)benzamide, (R)-4-(4-((4'-chloro-5,5-dimethyl-3,4,5,6-tetrahydro-[1,1'-biphenyl]-2-yl)methyl)piperazin-1-yl)-2-(3,3-difluoro-4-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(6,7,8,9-tetrahydropyrrolo[3',2':5,6]pyrido[3,2-b]azepin-5(1H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl-3,3,4,4-d4)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3,4,5,7-tetrahydropyrrolo[3',2':5,6]pyrido[2,3-b][1,4]diazepin-1(2H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-oxo-3,4,5,7-tetrahydropyrrolo[3',2':5,6]pyrido[2,3-b][1,4]diazepin-1(2H)-yl)benzamide, 4-(4-((4'-chloro-5,5-dimethyl-3,4,5,6-tetrahydro-[1,1'-biphenyl]-2-yl)methyl)piperazin-1-yl)-2-(5-(methylimino)-5-oxido-3,4,5,7-tetrahydro-5l4-pyrrolo[3',2':5,6]pyrido[2,3-b][1,4]thiazepin-1(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2',3'-dihydrospiro[cyclopropane-1,4'-pyrrolo[3',2':5,6]pyrido[2,3-b][1,4]oxazepin]-1'(7'H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-3-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-morpholinoethyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4-methylmorpholin-2-yl)methyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((4-(oxetan-3-yl)morpholin-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4-hydroxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((((1r,4r)-4-methoxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((((1s,4s)-4-hydroxy-4-methylcyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((((1s,4s)-4-ethyl-4-hydroxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((1-(tetrahydro-2H-pyran-4-yl)piperidin-4-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1s,4s)-4-morpholinocyclohexyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((4-(cyclopropylamino)cyclohexyl)amino)-3-nitrophenyl)sulfonyl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4,4-difluorocyclohexyl)methyl)amino)-3-nitrophenyl)sulfonyl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((tetrahydro-2H-pyran-4-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((tetrahydro-2H-pyran-3-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(2-morpholinoethoxy)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((4-methylmorpholin-2-yl)methoxy)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((4-(oxetan-3-yl)morpholin-2-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((4-hydroxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1r,4r)-4-methoxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1s,4s)-4-hydroxy-4-methylcyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1s,4s)-4-ethyl-4-hydroxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((1-(tetrahydro-2H-pyran-4-yl)piperidin-4-yl)oxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1s,4s)-4-morpholinocyclohexyl)oxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((4-(cyclopropylamino)cyclohexyl)oxy)-3-nitrophenyl)sulfonyl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-N-((4-((4,4-difluorocyclohexyl)methoxy)-3-nitrophenyl)sulfonyl)-2-(3,4-dihydro-2H-pyrrolo[3',2':5,6]pyrido[2,3-b][1,4]oxazepin-1(7H)-yl)benzamide, 4-(4-((2-(4-chlorophenyl)cyclopent-1-en-1-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((2-(4-chlorophenyl)cyclohept-1-en-1-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4-(4-chlorophenyl)-6,6-dimethyl-5,6-dihydro-2H-pyran-3-yl)methyl)piperazin-1-yl)-2-(3,4-dihydro-2H-pyrrolo[3',2':5,6]pyrido[2,3-b][1,4]oxazepin-1(7H)-yl)-

N-((3-nitro-4-(((tetrahydro-2H-pyran-4-yl)methyl)amino)phenyl)sulfonyl)benzamide, 4-(4-((4'-chloro-4-(methoxymethyl)-4-methyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-5-fluoro-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((5-nitro-6-(((tetrahydro-2H-pyran-4-yl)methyl)amino)pyridin-3-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((tetrahydro-2H-pyran-4-yl)methyl)amino)-3-((trifluoromethyl)sulfonyl)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydro-3H-imidazo[4',5':5,6]pyrido[2,3-b][1,4]oxazepin-9(6H)-yl)-N-((3-nitro-4-(((tetrahydro-2H-pyran-4-yl)methyl)amino)phenyl)sulfonyl)benzamide, 4-(4-((9-(4-chlorophenyl)-3-methyl-3-azaspiro[5.5]undec-8-en-8-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((9-(4-chlorophenyl)-3-(1,3-difluoropropan-2-yl)-3-azaspiro[5.5]undec-8-en-8-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-5,5-difluoro-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((5-(4-chlorophenyl)spiro[2.5]oct-5-en-6-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((7-(4-chlorophenyl)spiro[3.5]non-6-en-6-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-3'-fluoro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 2-(3,4-dihydro-2H-pyrrolo[3',2':5,6]pyrido[2,3-b][1,4]oxazepin-1(7H)-yl)-4-(4-((4,4-dimethyl-2-(pyridin-3-yl)cyclohex-1-en-1-yl)methyl)piperazin-1-yl)-N-((3-nitro-4-(((tetrahydro-2H-pyran-4-yl)methyl)amino)phenyl)sulfonyl)benzamide, (R)—N-((4-(((1,4-dioxan-2-yl)methyl)amino)-3-fluoro-5-nitrophenyl)sulfonyl)-4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)benzamide, (R)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)benzamide, (R)—N-((4-(((1,4-dioxan-2-yl)methyl)amino)-3-nitrophenyl)sulfonyl)-4-(4-((6-(4-chlorophenyl)-2-oxaspiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)benzamide, (R)—N-((4-(((1,4-dioxan-2-yl)methyl)amino)-3-fluoro-5-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, 4-(4-((6-(4-chlorophenyl)-2-oxaspiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((6-(4-chlorophenyl)-2-oxaspiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-6-fluorobenzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-5-fluorobenzamide, 4-(4-((4'-chloro-5,5-bis(methyl-d3)-3,4,5,6-tetrahydro-[1,1'-biphenyl]-2-yl)methyl)-2-methylpiperazin-1-yl-2,3,3,5,5,6,6-d7)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, diethyl ((2-(((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)methyl)morpholino)methyl)phosphonate, diethyl (((3-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)propyl)(methyl)amino)methyl)phosphonate, 2-(((2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)ethyl)((pivaloyloxy)methoxy)phosphoryl)oxy)ethyl pivalate, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1-methyl-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1-hydroxy-1-oxidophosphinan-4-yl)methyl)amino)-3-nitrophenyl)sulfonyl)benzamide, ((4-(((4-(N-(4-(4-((4'-chloro-5,5-dimethyl-3,4,5,6-tetra-hydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)methyl)-1-oxidophosphinan-1-yl)oxy)methyl pivalate, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((2-methyl-2-oxido-1,3,2-oxazaphosphinan-5-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(2-methyl-2-oxido-1,3,2-oxazaphosphinan-3-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1-(dimethylphosphoryl)piperidin-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-(dimethylphosphoryl)-4-(((tetrahydro-2H-pyran-4-yl)methyl)amino)phenyl)sulfonyl)benzamide, N-((4-(((1,4-dioxaspiro[4.5]decan-8-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-(((2-oxaspiro[3.5]nonan-7-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(hexahydrofuro[3,4-c]pyridin-5(3H)-yl)ethyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((2-(3-oxooctahydro-7H-imidazo[1,5-d][1,4]diazepin-7-yl)ethyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((2-(3-oxooctahydro-5H-pyrrolo[3,4-c]pyridin-5-yl)ethyl)amino)phenyl)sulfonyl)benzamide, N-((4-((2-(2-oxa-5-azabicyclo[2.2.2]octan-5-yl)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((3-hydroxy-3-methylbicyclo[3.1.1]heptan-6-yl)methyl)amino)-3-nitrophenyl)sulfonyl)benzamide, N-((4-((2-(2-oxa-5-azabicyclo[2.2.1]heptan-5-yl)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, 2-((3R)-8-(2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)ethyl)-6,6-difluoro-8-azabicyclo[3.2.1]octan-3-yl)acetic acid, 4-(4-((4'-chloro-5,5-dimethyl-3,4,5,6-tetrahydro-[1,1'-biphenyl]-2-yl)methyl)piperazin-1-yl)-N-((4-((2-(6,6-difluoro-8-azabicyclo[3.2.1]octan-8-yl)ethyl)amino)-3-nitrophenyl)sulfonyl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((2-(tetrahydro-2H-pyran-4-yl)-2-azaspiro[3.3]heptan-6-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-thiopyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1-imino-1-oxidohexahydro-1l6-thiopyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4-(methylsulfonyl)morpholin-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((((dimethyl(oxo)-k6-sulfaneylidene)amino)cyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(4-((dimethyl(oxo)-k6-sulfaneylidene)amino)piperidin-1-yl)ethyl)amino)-3-nitrophenyl)sulfonyl)benzamide, N-((4-(((4-aminotetrahydro-2H-pyran-4-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-44(1-(tetrahydro-2H-pyran-4-yl)cyclopropyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(5,6-dihydroimidazo[1,2-a]pyrazin-7(8H)-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((5,6,7,8-tetrahydroimidazo[1,2-a]pyridin-6-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((3-(difluoromethoxy)benzyl)amino)-3-nitrophenyl)sulfonyl)-2-(3, 4-dihydro-2H-pyrrolo[3',2':5,6]pyrido[2,3-b][1,4]
oxazepin-1(7H)-yl)benzamide,
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((3,4,5-trihydroxytetrahydrofuran-2-yl)methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((3,4,5,6-tetrahydroxytetrahydro-2H-pyran-2-yl)methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4,5-dihydroxy-6,6-dimethyltetrahydro-2H-pyran-2-yl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((2,3,5-trihydroxy-6-(hydroxymethyl)tetrahydro-2H-pyran-4-yl)methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((2,3,4,5,6-pentahydroxycyclohexyl)methyl)amino)phenyl)sulfonyl)benzamide,
(R)—N-((4-(((1,4-dioxan-2-yl)methyl)amino)-3-nitrophenyl)sulfonyl)-4-(1-((4'-chloro-5,5-dimethyl-3,4,5,6-tetrahydro-[1,1'-biphenyl]-2-yl)methyl)-1,2,3,6-tetrahydropyridin-4-yl)-2-(3,4-dihydro-2H-pyrrolo[3',2':5,6]pyrido[2,3-b][1,4]oxazepin-1(7H)-yl)benzamide,
4-(1-((6-(4-chlorophenyl)spiro[3.5]non-6-en-7-yl)methyl)-1,2,3,6-tetrahydropyridin-4-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide,
(S)—N-((4-(((1,4-dioxan-2-yl)methyl)amino)-3-nitrophenyl)sulfonyl)-5-(4-((6-(4-chlorophenyl)spiro[3.5]non-6-en-7-yl)methyl)piperazin-1-yl)-3-(3,4-dihydro-2H-pyrrolo[3',2':5,6]pyrido[2,3-b][1,4]oxazepin-1(7H)-yl)picolinamide,
(S)—N-((4-(((1,4-dioxan-2-yl)methyl)amino)-3-nitrophenyl)sulfonyl)-6-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)nicotinamide,
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide,
(S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((2-fluoro-1,4-dioxan-2-yl)methyl)amino)-3-nitrophenyl)sulfonyl)benzamide,
(R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((2-fluoro-1,4-dioxan-2-yl)methyl)amino)-3-nitrophenyl)sulfonyl)benzamide,
(S)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(4-methyl-3,4-dihydro-2H-pyrrolo[3',2':5,6]pyrido[2,3-b][1,4]oxazepin-1(7H)-yl)benzamide,
4-(4-((4'-chloro-5,5-dimethyl-3,4,5,6-tetrahydro-[1,1'-biphenyl]-2-yl)methyl)piperazin-1-yl)-N-((4-((((R)-2-fluoro-1,4-dioxan-2-yl)methyl)amino)-3-nitrophenyl)sulfonyl)-2-((S)-4-methyl-3,4-dihydro-2H-pyrrolo[3',2':5,6]pyrido[2,3-b][1,4]oxazepin-1(7H)-yl)benzamide,
4-(4-((4'-chloro-5,5-dimethyl-3,4,5,6-tetrahydro-[1,1'-biphenyl]-2-yl)methyl)piperazin-1-yl)-N-((4-((((S)-2-fluoro-1,4-dioxan-2-yl)methyl)amino)-3-nitrophenyl)sulfonyl)-2-((S)-4-methyl-3,4-dihydro-2H-pyrrolo[3',2':5,6]pyrido[2,3-b][1,4]oxazepin-1(7H)-yl)benzamide,
(R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(4-methyl-3,4-dihydro-2H-pyrrolo[3',2':5,6]pyrido[2,3-b][1,4]oxazepin-1(7H)-yl)benzamide,
4-(4-((4'-chloro-5,5-dimethyl-3,4,5,6-tetrahydro-[1,1'-biphenyl]-2-yl)methyl)piperazin-1-yl)-N-((4-((((R)-2-fluoro-1,4-dioxan-2-yl)methyl)amino)-3-nitrophenyl)sulfonyl)-2-((R)-4-methyl-3,4-dihydro-2H-pyrrolo[3',2':5,6]pyrido[2,3-b][1,4]oxazepin-1(7H)-yl)benzamide,
4-(4-((4'-chloro-5,5-dimethyl-3,4,5,6-tetrahydro-[1,1'-biphenyl]-2-yl)methyl)piperazin-1-yl)-N-((4-((((S)-2-fluoro-1,4-dioxan-2-yl)methyl)amino)-3-nitrophenyl)sulfonyl)-2-((R)-4-methyl-3,4-dihydro-2H-pyrrolo[3',2':5,6]pyrido[2,3-b][1,4]oxazepin-1(7H)-yl)benzamide,
(R)-4-(4-((4'-chloro-5,5-dimethyl-3,4,5,6-tetrahydro-[1,1'-biphenyl]-2-yl)methyl)piperazin-1-yl)-2-(4,4-difluoro-3,4-dihydro-2H-pyrrolo[3',2':5,6]pyrido[2,3-b][1,4]oxazepin-1(7H)-yl)-N-((4-(((2-fluoro-1,4-dioxan-2-yl)methyl)amino)-3-nitrophenyl)sulfonyl)benzamide,
(S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(4,4-difluoro-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(4,4-difluoro-3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(4,4-dimethyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-3,4-dihydro-2H-pyrrolo[3',2':5,6]pyrido[2,3-b][1,4]oxazepin-1(7H)-yl)benzamide,
(R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide,
(S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(trifluoromethyl)-3,4-dihydro-2H-pyrrolo[3',2':5,6]pyrido[2,3-b][1,4]oxazepin-1(7H)-yl)benzamide,
(R)-4-(4-((4'-chloro-5,5-dimethyl-3,4,5,6-tetrahydro-[1,1'-biphenyl]-2-yl)methyl)piperazin-1-yl)-2-(3-cyano-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)-2-(3-amino-3,4-dihydro-2H-pyrrolo[3',2':5,6]pyrido[2,3-b][1,4]oxazepin-1(7H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3-hydroxy-3-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3-methyl-3-(trifluoromethyl)-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3-cyano-3-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(2-methyl-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-(trifluoromethyl)-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(5,5-dioxido-3,4-dihydro-2H-pyrrolo[3',2':5,6]pyrido[2,3-b][1,4]thiazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]thiazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3-methoxy-3-methyl-3,4-dihydro-2H-pyrrolo[3',2':5,6]pyrido[2,3-b][1,4]thiazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3-methyl-3-(trifluoromethyl)-3,4-dihydro-2H-pyrrolo[3',2':5,6]pyrido[2,3-b][1,4]thiazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,3-difluoro-3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3-cyano-3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-hydroxy-3-methyl-3,4-dihydro-2H-pyrrolo[3',2':5,6]pyrido[2,3-b][1,4]oxazepin-1(7H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,3-dimethyl-3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-methyl-3,4-dihydro-2H-pyrrolo[3',2':5,6]pyrido[2,3-b][1,4]oxazepin-1(7H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-(hydroxymethyl)-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2'H,4'H-spiro[cyclobutane-1,3'-pyrrolo[3',2':5,6]pyrido[2,3-b][1,4]oxazepin]-1'(7'H)-yl)benzamide, (S)-4-(4-((4'-chloro-5,5-dimethyl-3,4,5,6-tetrahydro-[1,1'-biphenyl]-2-yl)methyl)piperazin-1-yl)-2-(3,3-dimethyl-4-(trifluoromethyl)-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3-(hydroxymethyl)-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(9-oxo-6,7,8,9-tetrahydropyrrolo[3',2':5,6]pyrido[3,2-b]azepin-5(1H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(5-(oxetan-3-yl)-3,4,5,7-tetrahydropyrrolo[3',2':5,6]pyrido[2,3-b][1,4]diazepin-1(2H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-oxo-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(5-imino-5-oxido-3,4,5,7-tetrahydro-5l4-pyrrolo[3',2':5,6]pyrido[2,3-b][1, 4]thiazepin-1(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(5-methyl-5-oxido-3,4,7-trihydropyrrolo[3',2':5,6]pyrido[3,2-b][1,4]azaphosphepin-1(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((3-fluorotetrahydro-2H-pyran-3-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((3-morpholinopropyl)amino)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4-methylmorpholin-2-yl)methyl)amino)-3-nitrophenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((4-(oxetan-3-yl)morpholin-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4-hydroxy-4-methylcyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((((1s,4s)-4-methoxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((((1r,4r)-4-hydroxy-4-methylcyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((((1r,4r)-4-ethyl-4-hydroxycyclohexyl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((1-(oxetan-3-yl)piperidin-4-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1r,4r)-4-morpholinocyclohexyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((4-(methyl(oxetan-3-yl)amino)cyclohexyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((1,4,4-trifluorocyclohexyl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((4-fluorotetrahydro-2H-pyran-4-yl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((3-fluorotetrahydro-2H-pyran-3-yl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(3-morpholinopropoxy)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((4-methylmorpholin-2-yl)methoxy)-3-nitrophenyl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((4-(oxetan-3-yl)morpholin-2-yl)methoxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((4-hydroxy-4-methylcyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1s,4s)-4-methoxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1r,4r)-4-hydroxy-4-methylcyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1r,4r)-4-ethyl-4-hydroxycyclohexyl)methoxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((1-(oxetan-3-yl)piperidin-4-yl)oxy)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1r,4r)-4-morpholinocyclohexyl)oxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((4-(methyl(oxetan-3-yl)amino)cyclohexyl)oxy)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H- pyrrolo[3',2':5,6]pyrido[2,3-b][1,4]oxazepin-1(7H)-yl)-N-((3-nitro-4-((1,4,4-trifluorocyclohexyl)methoxy)phenyl)sulfonyl)benzamide, 4-(4-((4-(4-chlorophenyl)-5,6-dihydro-2H-pyran-3-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (Z)-4-(4-((2-(4-chlorophenyl)cyclooct-1-en-1-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-4-methoxy-4-methyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(5-((4'-chloro-5,5-dimethyl-3,4,5,6-tetrahydro-[1,1'-biphenyl]-2-yl)methyl)-2,5-diazabicyclo[2.2.2]octan-2-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-(3-nitro-4-(((tetrahydro-2H-pyran-4-yl)methyl)amino)phenylsulfonimidoyl)benzamide, 4-(4-((4'-chloro-5,5-dimethyl-3,4,5,6-tetrahydro-[1,1'-biphenyl]-2-yl)methyl)piperazin-1-yl)-N-((5-chloro-6-((tetrahydro-2H-pyran-4-yl)methoxy)pyridin-3-yl)sulfonyl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((tetrahydro-2H-pyran-4-yl)methyl)amino)-3-(S-(trifluoromethyl)sulfonimidoyl)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-[1,4]oxazepino[3,2-f]indol-1(7H)-yl)-N-((3-nitro-4-(((tetrahydro-2H-pyran-4-yl)methyl)amino)phenyl)sulfonyl)benzamide, 4-(4-((9-(4-chlorophenyl)-3-isopropyl-3-azaspiro[5.5]undec-8-en-8-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((9-(4-chlorophenyl)-3-(oxetan-3-yl)-3-azaspiro[5.5]undec-8-en-8-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-5,5-bis(fluoromethyl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-(1-(4'-chloro-5,5-dimethyl-3,4,5,6-tetrahydro-[1,1'-biphenyl]-2-yl)cyclopropyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((6-(4-chlorophenyl)spiro[2.5]oct-5-en-5-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-3',5,5-trimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((2-(1H-indol-5-yl)-4,4-dimethylcyclohex-1-en-1-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)—N-((4-(((1,4-dioxan-2-yl)methyl)amino)-3-fluoro-5-nitrophenyl)sulfonyl)-4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((6-(4-chlorophenyl)-2-oxaspiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-fluoro-5-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide, (S)—N-((4-(((1,4-dioxan-2-yl)methyl)amino)-3-nitrophenyl)sulfonyl)-4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-3-fluorobenzamide, (S)—N-((4-(((1,4-dioxan-2-yl)methyl)amino)-3-fluoro-5-nitrophenyl)sulfonyl)-4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-6-fluorobenzamide, 4-(4-((4'-chloro-5,5-bis(methyl-d3)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl-2,2,3,3,4,4-d6)-N-((3-nitro-4-(((tetrahydro-2H-pyran-4-yl)methyl)amino)phenyl)sulfonyl)benzamide, ((2-(((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)methyl)morpholino)methyl)phosphonic acid, diethyl (2-(((2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]

oxazepin-1(7H)-yl)benzoyl)sulfamoyl)-2-nitrophenyl)
amino)ethyl)(methyl)amino)ethyl)phosphonate, ethyl P-(2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)ethyl)-N,N-dimethylphosphonamidate, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1-(dimethylamino)-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1-ethoxy-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1-isopropoxy-1-oxidophosphinan-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((1,2,3-trimethyl-2-oxido-1,3,2-diazaphosphinan-5-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(2-methyl-2-oxido-1,3,2-diazaphosphinan-1-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4-(dimethylphosphoryl)morpholin-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(dimethylphosphoryl)-3-nitrophenyl)sulfonyl)benzamide, N-((4-(((1,4-dithiaspiro[4.5]decan-8-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-(((2-(6-azaspiro[2.5]octan-6-yl)ethyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-N-((4-((2-(2,2-difluoro-7-azaspiro[3.5]nonan-7-yl)ethyl)amino)-3-nitrophenyl)sulfonyl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((2-(2-(oxetan-3-yl)octahydro-5H-pyrrolo[3,4-c]pyridin-5-yl)ethyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-

N-((3-nitro-4-((2-(1-oxooctahydro-5H-pyrrolo[3,4-c]pyridin-5-yl)ethyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((3-hydroxybicyclo[3.1.1]heptan-6-yl)methyl)amino)-3-nitrophenyl)sulfonyl)benzamide, N-((4-(((3-amino-3-methylbicyclo[3.1.1]heptan-6-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((2-(5-(oxetan-3-yl)-2,5-diazabicyclo[2.2.1]heptan-2-yl)ethyl)amino)phenyl)sulfonyl)benzamide, 2-((3S)-8-(2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)ethyl)-6,6-difluoro-8-azabicyclo[3.2.1]octan-3-yl)acetic acid, 4-(4-((4'-chloro-5,5-dimethyl-3,4,5,6-tetrahydro-[1,1'-biphenyl]-2-yl)methyl)piperazin-1-yl)-N-((4-((2-(6,6-difluoro-8-azabicyclo[3.2.1]octan-8-yl)ethyl)amino)-3-nitrophenyl)sulfonyl)-2-(3,4-dihydro-2H-pyrrolo[3',2':5,6]pyrido[2,3-b][1,4]oxazepin-1(7H)-yl)benzamide, N-((4-((7-oxaspiro[3.5]nonan-2-yl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1,1-dioxidotetrahydro-2H-thiopyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((1-(isopropylimino)-1-oxidohexahydro-1λ6-thiopyran-4-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4-(S-methylsulfonimidoyl)morpholin-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((4-((1-oxidotetrahydro-1l6-thiophen-1-ylidene)amino)cyclohexyl)methyl)amino)phenyl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((1-(4-((dimethyl(oxo)-λ6-sulfaneylidene)amino)piperidin-1-yl)propan-2-yl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-cyanotetrahydro-2H-pyran-4-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-((2-(tetrahydro-2H-pyran-4-yl)propan-2-yl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(5,6-dihydro-[1,2,4]triazolo[1,5-a]pyrazin-7(8H)-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((1-(thiazol-2-yl)piperidin-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-((4-(difluoromethoxy)benzyl)amino)-3-nitrophenyl)sulfonyl)-2-(3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((3,5-dihydroxytetrahydrofuran-2-yl)methyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((3,4,5-trihydroxy-6,6-dimethyltetrahydro-2H-pyran-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((2,3,5-trihydroxytetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((3,4,5-trihydroxy-6-(methylthio)tetrahydro-2H-pyran-2-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((3,4,5-trihydroxy-6-(((4,5,6-trihydroxy-2-(hydroxymethyl)tetrahydro-2H-pyran-3-yl)methoxy)methyl)tetrahydro-2H-pyran-2-yl)methyl)amino)phenyl)sulfonyl)benzamide, N-((4-(((1,4-dioxan-2-yl)methyl)amino)-3-nitrophenyl)sulfonyl)-4-(1-((6-(4-chlorophenyl)-2-oxaspiro[3.5]non-6-en-7-yl)methyl)-1,2,3,6-tetrahydropyridin-4-yl)-2-(3,4-dihydro-2H-pyrrolo[3',2':5,6]pyrido[2,3-b][1,4]oxazepin-1(7H)-yl)benzamide, 4-(14(6-(4-chlorophenyl)-2-oxaspiro[3.5]non-6-en-7-yl)methyl)-1,2,3,6-tetrahydropyridin-4-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, (S)-6-(4-((6-(4-chlorophenyl)-2-oxaspiro[3.5]non-6-en-7-yl)methyl)piperazin-1-yl)-4-(3,4-dihydro-2H-pyrrolo[3',2':5,6]pyrido[2,3-b][1,4]oxazepin-1(7H)-yl)-N-((3-nitro-4-(((tetrahydro-2H-pyran-3-yl)methyl)amino)phenyl)sulfonyl)nicotinamide, (S)—N-((4-(((1,4-dioxan-2-yl)methyl)amino)-3-nitrophenyl)sulfonyl)-6-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)nicotinamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2-oxo-2,3-dihydropyrrolo[3',2':5,6]pyrido[2,3-b][1,4]oxazin-1(6H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,3-dimethyl-2-oxo-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2H,4H-spiro[pyrrolo[3',2':5,6]pyrido[2,3-b][1,4]oxazepine-3,2'-[1,3]dithiolan]-1(7H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(4-(trifluoromethyl)-3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-4-(trifluoromethyl)-3,4-dihydro-2H-pyrrolo[3',2':5,6]pyrido[2,3-b][1,4]oxazepin-1(7H)-yl)benzamide, N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-4-(trifluoromethyl)-3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-4-(trifluoromethyl)-3,4-dihydro-2H-pyrrolo[3',2':5,6]pyrido[2,3-b][1,4]oxazepin-1(7H)-yl)benzamide, N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-4-(trifluoromethyl)-3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]thiazin-1(6H)-yl)benzamide, (R)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]thiazin-1(6H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-3-methyl-2,3-dihydropyrrolo[3',2':5,6]pyrido[2,3-b][1,4]thiazin-1(6H)-yl)benzamide, N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-

((R)-3-methyl-2,3-dihydropyrrolo[3',2':5,6]pyrido[2,3-b][1,4]thiazin-1(6H)-yl)benzamide,
N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-3-(trifluoromethyl)-2,3-dihydropyrrolo[3',2':5,6]pyrido[2,3-b][1,4]thiazin-1(6H)-yl)benzamide,
N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-3-(trifluoromethyl)-2,3-dihydropyrrolo[3',2':5,6]pyrido[2,3-b][1,4]thiazin-1(6H)-yl)benzamide,
(S)—N-((4-(((1,4-dioxan-2-yl)methyl)amino)-3-nitrophenyl)sulfonyl)-4-(4-((2-(4-chlorophenyl)cyclohept-1-en-1-yl)methyl)piperazin-1-yl)-2-(3,4-dihydro-2H-pyrrolo[3',2':5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-4-(4-((4'-chloro-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-4-(4-((4'-chloro-4,4-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-4-(4-((4-(4-chlorophenyl)-6,6-dimethyl-5,6-dihydro-2H-pyran-3-yl)methyl)piperazin-1-yl)-2-(3,4-dihydro-2H-pyrrolo[3',2':5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-4-(4-((4'-chloro-5,5-difluoro-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-4-(4-((2-(4-chlorophenyl)cyclopent-1-en-1-yl)methyl)piperazin-1-yl)-2-(3,4-dihydro-2H-pyrrolo[3',2':5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-4-(4-((2-(4-chlorophenyl)-5,5-difluorocyclohept-1-en-1-yl)methyl)piperazin-1-yl)-2-(3,4-dihydro-2H-pyrrolo[3',2':5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-4-(4-((7-(4-chlorophenyl)-1,4-dithiaspiro[4.5]dec-7-en-8-yl)methyl)piperazin-1-yl)-2-(3,4-dihydro-2H-pyrrolo[3',2':5,6]pyrido[2,3-b][1,4]oxazepin-1(7H)-yl)benzamide,
4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N-((3-nitro-4-(((S)-1-(tetrahydro-2H-pyran-4-yl)ethyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N-((3-nitro-4-(((R)-1-(tetrahydro-2H-pyran-4-yl)ethyl)amino)phenyl)sulfonyl)benzamide,
N-((4-((((5r,8r)-1-oxaspiro[4.5]decan-8-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide,
N-((4-((((5s,8s)-1-oxaspiro[4.5]decan-8-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide,
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((3-(hydroxymethyl)tetrahydrofuran-3-yl)methyl)amino)-3-nitrophenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((3-(hydroxymethyl)oxetan-3-yl)methyl)amino)-3-nitrophenyl)sulfonyl)benzamide,
(R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(pyridin-2-yl)-3,4-dihydro-2H-pyrrolo[3',2':5,6]pyrido[2,3-b][1,4]oxazepin-1(7H)-yl)benzamide,
4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(pyridin-3-yl)-2,3-dihydropyrrolo[3',2':5,6]pyrido[2,3-b][1,4]oxazin-1(6H)-yl)benzamide,
4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl-2,2,3,3,4,4-d6)-N-((3-nitro-4-(((tetrahydro-2H-pyran-4-yl)methyl)amino)phenyl)sulfonyl)benzamide,
2-(4-(2-aminopropan-2-yl)-3,4-dihydro-2H-pyrrolo[3',2':5,6]pyrido[2,3-b][1,4]oxazepin-1(7H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(4-(2-hydroxypropan-2-yl)-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(1,1,1-trifluoro-2-methylpropan-2-yl)-3,4-dihydro-2H-pyrrolo[3',2':5,6]pyrido[2,3-b][1,4]oxazepin-1(7H)-yl)benzamide,
4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(1,1,1-trifluoro-2-methylpropan-2-yl)-3,4-dihydro-2H-pyrrolo[3',2':5,6]pyrido[2,3-b][1,4]oxazepin-1(7H)-yl)benzamide,
(R)-4-(4-((4'-chloro-5,5-dimethyl-3,4,5,6-tetrahydro-[1,1'-biphenyl]-2-yl)methyl)piperazin-1-yl)-2-(3-(2-fluoropropan-2-yl)-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(3-(1-(2-(dimethylamino)ethoxy)-2-methylpropan-2-yl)-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide,
4-(4-((4'-chloro-5,5-dimethyl-3,4,5,6-tetrahydro-[1,1'-biphenyl]-2-yl)methyl)piperazin-1-yl)-2-(4-(2-cyanopropan-2-yl)-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3-(1-(4,4-difluoropiperidin-1-yl)-2-methylpropan-2-yl)-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide.

4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2,3,5,7-tetrahydro-1H-pyrrolo[3',2':5,6]pyrido[3,2-e][1,4]oxazepin-1-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(9,9-difluoro-6,7,8,9-tetrahydropyrrolo[3',2':5,6]pyrido[3,2-b]azepin-5(1H)-yl)benzamide, 4-(4-((4'-chloro-5,5-dimethyl-3,4,5,6-tetrahydro-[1,1'-biphenyl]-2-yl)methyl)piperazin-1-yl)-2-(1,1-dioxido-3,4-dihydro-2H-pyrrolo[3',2':5,6]pyrido[3,2-f][1,2,5]thiadiazepin-5(9H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-oxo-5,7-dihydro-2H-pyrrolo[3',2':5,6]pyrido[3,2-d][1,3]oxazepin-1(4H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2,3,5,7-tetrahydro-1H-pyrrolo[3',2':5,6]pyrido[3,2-e][1,4]thiazepin-1-yl)benzamide, 4-(4-((4'-chloro-5,5-dimethyl-3,4,5,6-tetrahydro-[1,1'-biphenyl]-2-yl)methyl)piperazin-1-yl)-2-(1-methyl-1-oxido-3,9-dihydro-1l4-pyrrolo[3',2':5,6]pyrido[3,2-f][1,2,5]thiadiazepin-5(4H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,2-dioxido-1,3,4,9-tetrahydro-5H-pyrrolo[3',2':5,6]pyrido[2,3-c][1,2,5]thiadiazepin-5-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-oxo-3,4,5,7-tetrahydropyrrolo[3',2':5,6]pyrido[3,2-d][1,3]diazepin-1(2H)-yl)benzamide, 4-(4-((4'-chloro-5,5-dimethyl-3,4,5,6-tetrahydro-[1,1'-biphenyl]-2-yl)methyl)piperazin-1-yl)-2-(2,2-dioxido-3,4-dihydropyrrolo[3',2':5,6]pyrido[3,2-f][1,4,5]oxathiazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-oxo-4,6-dihydro-1H-pyrrolo[2,3-b][1,5]naphthyridin-1-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-oxo-4,6-dihydro-1H-pyrrolo[3',2':5,6]pyrido[3,2-d]pyrimidin-1-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-oxo-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(2,2-dioxido-3H-pyrrolo[3',2':5,6]pyrido[3,2-e][1,3,4]oxathiazin-1(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(1,1-dioxido-2,3-dihydropyrrolo[3',2':5,6]pyrido[3,2-e][1,2,4]thiadiazin-4(8H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(1,1-dioxidopyrrolo[3',2':5,6]pyrido[3,2-e][1,2,4]thiadiazin-4(8H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(4,4-dimethyl-2-oxo-4,6-dihydropyrrolo[3',2':5,6]pyrido[3,2-d][1,3]oxazin-1(2H)-yl)-N-((3-nitro-4-(((tetrahydro-2H-pyran-4-yl)methyl)amino)phenyl)sulfonyl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(4-methyl-3-oxo-2,3,4,6-tetrahydro-1H-pyrido[2,3-b]pyrazin-1-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(4-oxo-4H-pyrrolo[1,2-a]pyrrolo[3',2':5,6]pyrido[3,2-e]pyrazin-5(9H)-yl)benzamide, 4-(4-((4'-chloro-5,5-dimethyl-3,4,5,6-tetrahydro-[1,1'-biphenyl]-2-yl)methyl)piperazin-1-yl)-2-(7,7-difluoro-6,7,8,8a-tetrahydro-1H-cyclopenta[b]pyrrolo[3',2':5,6]pyrido[3,2-e][1,4]oxazin-5(5aH)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(8,8-difluoro-6,6a,7,8,9,9a-hexahydrocyclopenta[f]pyrrolo[3',2':5,6]pyrido[2,3-b][1,4]oxazepin-5(1H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-((6aS,9aS)-8,8-difluoro-6,6a,7,8,9,9a-hexahydrocyclopenta[f]pyrrolo[3',2':5,6]pyrido[2,3-b][1,4]oxazepin-5(1H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-((6aR,9aR)-8,8-difluoro-6,6a,7,8,9,9a-hexahydrocyclopenta[f]pyrrolo[3',2':5,6]pyrido[2,3-b][1,4]oxazepin-5(1H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-((6aR,9aS)-8,8-difluoro-6,6a,7,8,9,9a-hexahydrocyclopenta[f]pyrrolo[3',2':5,6]pyrido[2,3-b][1,4]oxazepin-5(1H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-((6aS,9aR)-8,8-difluoro-6,6a,7,8,9,9a-hexahydrocyclopenta[f]pyrrolo[3',2':5,6]pyrido[2,3-b][1,4]oxazepin-5(1H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-((6aS,8R,9aS)-8-hydroxy-8-methyl-6,6a,7,8,9,9a-hexahydrocyclopenta[f]pyrrolo[3',2':5,6]pyrido[2,3-b][1,4]oxazepin-5(1H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-((6aS,8S,9aS)-8-hydroxy-8-methyl-6,6a,7,8,9,9a-hexahydrocyclopenta[f]pyrrolo[3',2':5,6]pyrido[2,3-b][1,4]oxazepin-5(1H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-((6aS,8R,9aS)-8-cyano-8-methyl-6,6a,7,8,9,9a-hexahydrocyclopenta[f]pyrrolo[3',2':5,6]pyrido[2,3-b][1,4]oxazepin-5(1H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-((6aS,8S,9aS)-8-cyano-8-methyl-6,6a,7,8,9,9a-hexahydrocyclopenta[f]pyrrolo[3',2':5,6]pyrido[2,3-b][1,4]oxazepin-5(1H)-yl)-N-((3-nitro-4-(((tetrahydro-2H-pyran-4-yl)methyl)amino)phenyl)sulfonyl)benzamide, 2-((6aS,8R,9aS)-8-amino-8-methyl-6,6a,7,8,9,9a-hexahydrocyclopenta[f]pyrrolo[3',2':5,6]pyrido[2,3-b][1,4]oxazepin-5(1H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, 2-((6aS,8S,9aS)-8-amino-8-methyl-6,6a,7,8,9,9a-hexahydrocyclopenta[f]pyrrolo[3',2':5,6]pyrido[2,3-b][1,4]oxazepin-5(1H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((5aS,8aS)-6,7,8,8a-tetrahydro-1H-cyclopenta[b]pyrrolo[3',2':5,6]pyrido[3,2-e][1,4]oxazin-5(5aH)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((5aS,8aS)-5a,6,8,8a-tetrahydrofuro[3,4-b]pyrrolo[3',2':5,6]pyrido[3,2-e][1,4]oxazin-5(1H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((5aS,8aR)-5a,6,8,8a-tetrahydrofuro[3,4-b]pyrrolo[3',2':5,6]pyrido[3,2-e][1,4]oxazin-5(1H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((5aR,8aR)-5a,6,8,8a-tetrahydrofuro[3,4-b]pyrrolo[3',2':5,6]pyrido[3,2-e][1,4]oxazin-5(1H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((5aR,8aS)-5a,6,8,8a-tetrahydrofuro[3,4-b]pyrrolo[3',2':5,6]pyrido[3,2-e][1,4]oxazin-5(1H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((6,6a,7,8,10,10a-hexahydropyrano[4,3-f]pyrrolo[3',2':5,6]pyrido[2,3-b][1,4]oxazepin-5(1H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(6a,7,9,9a-tetrahydro-1H-furo[3,4-f]pyrrolo[3',2':5,6]pyrido[2,3-b][1,4]oxazepin-5(6H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((5aR,8aR)-6,7,8,8a-tetrahydro-1H-cyclopenta[b]pyrrolo[3',2':5,6]pyrido[3,2-e][1,4]oxazin-5(5aH)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(6,7,9,9a-tetrahydro-1H-pyrano[3,4-b]pyrrolo[3',2':5,6]pyrido[3,2-e][1,4]oxazin-5(5aH)-yl)benzamide, 4-(4-((4'-chloro-5,5-dimethyl-3,4,5,6-tetrahydro-[1,1'-biphenyl]-2-yl)methyl)piperazin-1-yl)-2-(2,3-dihydro-4H-benzo[b][1,4]oxazin-4-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydro-4H-pyrido[3,2-b][1,4]oxazin-4-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydro-1H-pyrido[3,4-b][1,4]oxazin-1-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydro-4H-pyrido[4,3-b][1,4]oxazin-4-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydro-1H-pyrido[2,3-b][1,4]oxazin-1-yl)-N-((3-nitro-4-(((tetrahydro-2H-pyran-4-yl)methyl)amino)phenyl)sulfonyl)benzamide,4-(4-((4'-chloro-5,5-dimethyl-3,4,5,6-tetrahydro-[1,1'-biphenyl]-2-yl)methyl)piperazin-1-yl)-2-(3,4-dihydrobenzo[b][1,4]oxazepin-5(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydropyrido[2,3-b][1,4]oxazepin-1(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydropyrido[4,3-h][1,4]oxazepin-5(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydropyrido[3,2-h][1,4]oxazepin-5(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydropyrido[3,4-b][1,4]oxazepin-1(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydropyrimido[4,5-b][1,4]oxazepin-5(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydropyrazino[2,3-b][1,4]oxazepin-9(6H)-yl)-N-((3-nitro-4-(((tetrahydro-2H-pyran-4-yl)methyl)amino)phenyl)sulfonyl)benzamide, 2-(7-amino-3,4-dihydropyrido[2,3-b][1,4]oxazepin-1(2H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7-(methylamino)-3,4-dihydropyrido[2,3-b][1,4]oxazepin-1(2H)-yl)-N-((3-nitro-4-(((tetrahydro-2H-pyran-4-yl)methyl)amino)phenyl)sulfonyl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(7-((2,2,2-trifluoroethyl)amino)-3,4-dihydropyrido[2,3-b][1,4]oxazepin-1(2H)-yl)benzamide, (S)—N-((4-(((1,4-dioxan-2-yl)methyl)amino)-3-nitrophenyl)sulfonyl)-2-(7-amino-8-methyl-3,4-dihydropyrido[2,3-b][1,4]oxazepin-1(2H)-yl)-4-(4-((4'-chloro-5,5-dimethyl-3,4,5,6-tetrahydro-[1,1'-biphenyl]-2-yl)methyl)piperazin-1-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(7-methoxy-3,4-dihydropyrido[2,3-b][1,4]oxazepin-1(2H)-yl)benzamide, 2-(2-amino-7,8-dihydropyrimido[4,5-b][1,4]oxazepin-5(6H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, 2-(3-amino-7,8-dihydropyrazino[2,3-b][1,4]oxazepin-9(6H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-[1,4]oxazepino[2,3-b][1,8]naphthyridin-1(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydro-1H-pyrrolo[3',2':5,6]pyrazino[2,3-b][1,4]oxazepin-5(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydro-1H-pyrrolo[2',3':5,6]pyrido[3,2-b][1,4]oxazepin-5(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydro-3H-imidazo[4',5':5,6]pyrazino[2,3-b][1,4]oxazepin-9(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3,4,8,9-tetrahydro-2H-[1,4]oxazino[2',3':5,6]pyrido[2,3-b][1,4]oxazepin-10(7H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2,3,8,9-tetrahydro-[1,4]dioxin[2',3':5,6]pyrido[2,3-b][1,4]oxazepin-10(7H)-yl)benzamide, 4-(4-((4'-chloro-5,5-dimethyl-3,4,5,6-tetrahydro-[1,1'-biphenyl]-2-yl)methyl)piperazin-1-yl)-2-(7,8-dihydro-[1,3]dioxolo[4',5':5,6]pyrido[2,3-b][1,4]oxazepin-9(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydropyrazolo[1',5':1,6]pyridazino[3,4-b][1,4]oxazepin-1(2H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(8,9-dihydro-[1,2,4]triazolo[1',5':1,6]pyridazino[3,4-b][1,4]oxazepin-10(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydro-[1,2,3]triazolo[1',5':1,6]pyridazino[3,4-b][1,4]oxazepin-5(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(8,9-dihydro-[1,2,4]triazolo[1',5':1,6]pyridazino[3,4-b][1,4]oxazepin-10(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(8,9-dihydroimidazo[1',2':1,2]pyrimido[4,5-b][1,4]oxazepin-6(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydro-[1,2,4]triazolo[1',5':1,2]pyrimido[4,5-b][1,4]oxazepin-9(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(8,9-dihydro-[1,2,4]triazolo[4',3':1,2]pyrimido[4,5-b][1,4]oxazepin-6(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydrotetrazolo[1',5':1,2]pyrimido[4,5-b][1,4]oxazepin-9(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3,4,6,7,10,10a-hexahydro-2H-pyrrolo[3',2':5,6]pyrido[2,3-b][1,4]oxazepin-1(5aH)-yl)benzamide, 4-(4-((4'-chloro-[1,1'-biphenyl]-2-yl)(hydroxy)methyl)piperidin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-[1,1'-biphenyl]-2-yl)(hydroxy)methyl)piperidin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, N-((4-((((S)-1,4-dioxan-2-yl)methyl)amino)-3-nitrophenyl)sulfonyl)-4-(4-((R)-(4'-chloro-[1,1'-biphenyl]-2-yl)(hydroxy)methyl)piperidin-1-yl)-2-(3,4-dihydro-2H-pyrrolo[3',2':5,6]pyrido[2,3-b][1,4]oxazepin-1(7H)-yl)benzamide, N-((4-((((R)-1,4-dioxan-2-yl)methyl)amino)-3-nitrophenyl)sulfonyl)-4-(4-((R)-(4'-chloro-[1,1'-biphenyl]-2-yl)(hydroxy)methyl)piperidin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((R)-(4'-chloro-[1,1'-biphenyl]-2-yl)(hydroxy)methyl)piperidin-1-yl)-2-((R)-3-methyl-2,3-dihydropyrrolo[3',2':5,6]pyrido[2,3-b][1,4]oxazin-1(6H)-yl)benzamide, N-((4-((((S)-1,4-dioxan-2-yl)methyl)amino)-3-nitrophenyl)sulfonyl)-4-(4-((R)-(4'-chloro-[1,1'-biphenyl]-2-yl)(hydroxy)methyl)piperidin-1-yl)-2-((S)-3-methyl-2,3-dihydropyrrolo[3',2':5,6]pyrido[2,3-b][1,4]oxazin-1(6H)-yl)benzamide, N-((4-((((R)-1,4-dioxan-2-yl)methyl)amino)-3-nitrophenyl)sulfonyl)-4-(4-((R)-(4'-chloro-[1,1'-biphenyl]-2-yl)(hydroxy)methyl)piperidin-1-yl)-2-((R)-3-methyl-2,3-dihydropyrrolo[3',2':5,6]pyrido[2,3-b][1,4]oxazin-1(6H)-yl)benzamide, N-((4-((((R)-1,4-dioxan-2-yl)methyl)amino)-3-nitrophenyl)sulfonyl)-4-(4-((R)-(4'-chloro-[1,1'-biphenyl]-2-yl)(hydroxy)methyl)piperidin-1-yl)-2-((S)-3-methyl-2,3-dihydropyrrolo[3',2':5,6]pyrido[2,3-b][1,4]oxazin-1(6H)-yl)benzamide, N-((4-((((R)-1,4-dioxan-2-yl)methyl)amino)-3-nitrophenyl)sulfonyl)-4-(4-((R)-(4'-chloro-5,5-dimethyl-3,4,5,6-tetrahydro-[1,1'-biphenyl]-2-yl)(hydroxy)methyl)piperidin-1-yl)-2-((R)-3-methyl-2,3-dihydropyrrolo[3',2':5,6]pyrido[2,3-b][1,4]oxazin-1(6H)-yl)benzamide, N-((4-((((R)-1,4-dioxan-2-yl)methyl)amino)-3-nitrophenyl)sulfonyl)-4-(4-((R)-(6-(4-chlorophenyl)spiro[3.5]non-6-en-7-yl)(hydroxy)methyl)piperidin-1-yl)-2-((R)-3-methyl-2,3-dihydropyrrolo[3',2':5,6]pyrido[2,3-b][1,4]oxazin-1(6H)-yl)benzamide, N-((4-((((R)-1,4-dioxan-2-yl)methyl)amino)-3-nitrophenyl)sulfonyl)-4-(4-((R)-(6-(4-chlorophenyl)-2-oxaspiro[3.5]non-6-en-7-yl)(hydroxy)methyl)piperidin-1-yl)-2-((R)-3-methyl-2,3-dihydropyrrolo[3',2':5,6]pyrido[2,3-b][1,4]oxazin-1(6H)-yl)benzamide, N—(((S)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N—(((S)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N—(((R)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N—(((R)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((5-nitro-3-(tetrahydro-2H-pyran-4-yl)-3,4-dihydro-2H-benzo[b][1,4]oxazin-7-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((5-nitro-3-(tetrahydro-2H-pyran-4-yl)-3,4-dihydro-2H-benzo[b][1,4]oxazin-7-yl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-((4-methylpiperazin-1-yl)methyl)-5-nitro-3,4-dihydro-2H-benzo[b][1,4]oxazin-7-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-(2-morpholinoethyl)-5-nitro-3,4-dihydro-2H-benzo[b][1,4]oxazin-7-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-(4-hydroxy-4-methylcyclohexyl)-5-nitro-3,4-dihydro-2H-benzo[b][1,4]oxazin-7-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-(morpholinomethyl)-5-nitro-3,4-dihydro-2H-benzo[b][1,4]oxazin-7-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-((4-hydroxy-4-methylpiperidin-1-yl)methyl)-5-nitro-3,4-dihydro-2H-benzo[b][1,4]oxazin-7-yl)sulfonyl)benzamide, (S)-4-(4-((4'-chloro-5,5-dimethyl-3,4,5,6-tetrahydro-[1,1'-biphenyl]-2-yl)methyl)piperazin-1-yl)-N-((3-cyclopropyl-5-nitro-3,4-dihydro-2H-benzo[b][1,4]oxazin-7-yl)sulfonyl)-2-(3,4-dihydro-2H-pyrrolo[3',2':5,6]pyrido[2,3-b][1,4]oxazepin-1(7H)-yl)benzamide, N—(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((5-nitro-3-(pyridin-2-ylmethyl)-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-((4-methylpiperazin-1-yl)methyl)-5-nitro-3,4-dihydro-2H-benzo[b][1,4]thiazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((2-(morpholinomethyl)-8-nitro-2,3-dihydrobenzo[b][1,4]dioxin-6-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro- 2H-pyrrolo[3',2':5,6]pyrido[2,3-b][1,4]oxazepin-1(7H)-yl)-N-((2-((4-methylpiperazin-1-yl)methyl)-7-nitroindolin-5-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((2-(morpholino methyl)-7-nitroindolin-5-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((2-(morpholino methyl)-7-nitro-1H-indol-5-yl)sulfonyl)benzamide, N—(((S)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide, N—(((S)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide, N—(((R)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide, N—(((R)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((S)-5-nitro-3-(tetrahydro-2H-pyran-4-yl)-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((R)-5-nitro-3-(tetrahydro-2H-pyran-4-yl)-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((S)-3-(morpholinomethyl)-5-nitro-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((R)-3-(morpholino methyl)-5-nitro-3,4-dihydro-2H-benzo[b][1,4]oxazin-7-yl)sulfonyl)benzamide, N—(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide, N—(((S)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide, N—(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide, N—(((R)-3-(((1R,4R)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((S)-3-((4-methylpiperazin-1-yl)methyl)-5-nitro-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((R)-3-((4-methylpiperazin-1-yl)methyl)-5-nitro-3,4-dihydro-2H-benzo[b][1,4]oxazin-7-yl)sulfonyl)benzamide, N—(((S)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((S)-3-(trifluoromethyl)-2,3-dihydropyrrolo[3',2':5,6]pyrido[2,3-b][1,4]oxazin-1(6H)-yl)benzamide, N—(((S)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((S)-3-(trifluoromethyl)-2,3-dihydropyrrolo[3',2':5,6]pyrido[2,3-b][1,4]oxazin-1(6H)-yl)benzamide, N—(((R)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((S)-3-(trifluoromethyl)-2,3-dihydropyrrolo[3',2':5,6]pyrido[2,3-b][1,4]oxazin-1(6H)-yl)benzamide, N—(((R)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((S)-3-(trifluoromethyl)-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N—(((S)-5-nitro-3-(tetrahydro-2H-pyran-4-yl)-3,4-dihydro-2H-benzo[b][1,4]oxazin-7-yl)sulfonyl)-2-((S)-3-(trifluoromethyl)-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N—(((R)-5-nitro-3-(tetrahydro-2H-pyran-4-yl)-3,4-dihydro-2H-benzo[b][1,4]oxazin-7-yl)sulfonyl)-2-((S)-3-(trifluoromethyl)-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N—(((R)-3-(morpholinomethyl)-5-nitro-3,4-dihydro-2H-benzo[b][1,4]

oxazin-7-yl)sulfonyl)-2-((S)-3-(trifluoromethyl)-2,3-dihydropyrrolo[3',2':5,6]pyrido[2,3-b][1,4]oxazin-1(6H)-yl)benzamide, N—(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-((S)-3-(trifluoromethyl)-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N—(((S)-3-((4-methylpiperazin-1-yl)methyl)-5-nitro-3,4-dihydro-2H-benzo[b][1,4]oxazin-7-yl)sulfonyl)-2-((S)-3-(trifluoromethyl)-2,3-dihydropyrrolo[3',2':5,6]pyrido[2,3-b][1,4]oxazin-1(6H)-yl)benzamide, N—(((S)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, N—(((S)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, N—(((R)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, N—(((R)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((5-nitro-3-(tetrahydro-2H-pyran-4-yl)-3,4-dihydro-2H-benzo[b][1,4]oxazin-7-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((5-nitro-3-(tetrahydro-2H-pyran-4-yl)-3,4-dihydro-2H-benzo[b][1,4]oxazin-7-yl)sulfonyl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-(morpholino methyl)-5-nitro-3,4-dihydro-2H-benzo[b][1,4]oxazin-7-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-(morpholino methyl)-5-nitro-3,4-dihydro-2H-benzo[b][1,4]oxazin-7-yl)sulfonyl)benzamide, N—(((S)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, N—(((R)-3-(((1S,4S)-2-oxa-5-azabicyclo[2.2.1]heptan-5-yl)methyl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)benzamide, (S)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-((4-methylpiperazin-1-yl)methyl)-5-nitro-3,4-dihydro-2H-benzo[b][1,4]oxazin-7-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-((4-methylpiperazin-1-yl)methyl)-5-nitro-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((R)-3-(2-morpholinoethyl)-5-nitro-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-N—(((R)-3-(4-hydroxy-4-methylcyclohexyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N—(((R)-3-((4-hydroxy-4-methylpiperidin-1-yl)methyl)-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-N—(((S)-3-cyclopropyl-5-nitro-3,4-dihydro-2H-benzo[b][1,4]oxazin-7-yl)sulfonyl)-2-((R)-3-methyl-2,3-dihydropyrrolo[3',2':5,6]pyrido[2,3-b][1,4]oxazin-1(6H)-yl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((S)-5-nitro-3-(pyridin-2-ylmethyl)-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N-((3-((4-methylpiperazin-1-yl)methyl)-5-nitro-3,4-dihydro-2H-benzo[b][1,4]thiazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N-((2-(morpholinomethyl)-8-nitro-2,3-dihydrobenzo[b][1,4]dioxin-6-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((R)-2-((4-methylpiperazin-1-yl)methyl)-7-nitroindolin-5-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((R)-2-(morpholinomethyl)-7-nitroindolin-5-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((2-(morpholinomethyl)-7-nitro-1H-indol-5-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H- pyrrolo[3',2':5,6]pyrido[2,3-b][1,4]oxazepin-1(7H)-yl)-N-((7-nitro-2-((tetrahydro-2H-pyran-4-yl)methyl)indolin-5-yl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((5-nitro-4-((tetrahydro-2H-pyran-4-yl)methyl)-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((7-nitro-2-(oxetan-3-yl)iso indolin-5-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((7-nitro-3-oxoisoindolin-5-yl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((7-nitro-3-oxo-2-((tetrahydro-2H-pyran-4-yl)methyl)isoindolin-5-yl)sulfonyl)benzamide, 4-(4-((6-(4-chlorophenyl)spiro[3.5]non-6-en-7-yl)methyl)piperazin-1-yl)-N-((2-cyclopropyl-7-nitro-1H-benzo[d]imidazol-5-yl)sulfonyl)-2-(2,3-dihydropyrrolo[3',2':5,6]pyrido[2,3-b][1,4]oxazin-1(6H)-yl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((7-nitro-2-((tetrahydro-2H-pyran-4-yl)methyl)-2H-indazol-5-yl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((7-nitro-1-((tetrahydro-2H-pyran-4-yl)methyl)-1H-indazol-5-yl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((4-nitro-1-((tetrahydro-2H-pyran-4-yl)methyl)-1H-indazol-6-yl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((4-nitro-1-(tetrahydro-2H-pyran-4-yl)-1H-indazol-6-yl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((2-isopropyl-7-nitro-1H-benzo[d]imidazol-5-yl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((4-nitro-2-(tetrahydro-2H-pyran-4-yl)-2H-indazol-6-yl)sulfonyl)benzamide, 4-(4-((6-(4-chlorophenyl)spiro[3.5]non-6-en-7-yl)methyl)piperazin-1-yl)-2-(2,3-dihydropyrrolo[3',2':5,6]pyrido[2,3-b][1,4]oxazin-1(6H)-yl)-N-((3-fluoro-2-(2-methoxyethyl)-4-nitro-2H-indazol-6-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((7-nitro-2-(oxetan-3-yl)isoindolin-5-yl)sulfonyl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((5-nitro-4-((tetrahydro-2H-pyran-4-yl)methyl)-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((7-nitro-3-oxoisoindolin-5-yl)sulfonyl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((7-nitro-3-oxo-2-((tetrahydro-2H-pyran-4-yl)methyl)isoindolin-5-yl)sulfonyl)benzamide, 4-(4-((6-(4-chlorophenyl)spiro[3.5]non-6-en-7-yl)methyl)piperazin-1-yl)-N-((2-cyclopropyl-7-nitro-1H-benzo[d]imidazol-5-yl)sulfonyl)-2-(3,4-dihydro-2H-pyrrolo[3',2':5,6]pyrido[2,3-b][1,4]oxazepin-1(7H)-yl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((7-nitro-1-((tetrahydro-2H-pyran-4-yl)methyl)-1H-indazol-5-yl)sulfonyl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((2-isopropyl-7-nitro-1H-benzo[d]imidazol-5-yl)sulfonyl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((4-nitro-1-(tetrahydro-2H-pyran-4-yl)-1H-indazol-6-yl)sulfonyl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((4-nitro-1-((tetrahydro-2H-pyran-4-yl)methyl)-1H-indazol-6-yl)sulfonyl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((7-nitro-2-((tetrahydro-2H-pyran-4-yl)methyl)-2H-indazol-5-yl)sulfonyl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((4-nitro-2-(tetrahydro-2H-pyran-4-yl)-2H-indazol-6-yl)sulfonyl)benzamide, 4-(4-((6-(4-chlorophenyl)spiro[3.5]non-6-en-7-yl)methyl)piperazin-1-yl)-2-(3,4-dihydro-2H-pyrrolo[3',2':5,6]pyrido[2,3-b][1,4]oxazepin-1(7H)-yl)-N-((3-fluoro-2-(2-methoxyethyl)-4-nitro-2H-indazol-6-yl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(6,7,8,9-tetrahydropyrrolo[3',2':5,6]pyrido[2,3-b][1,4]oxazocin-5(1H)-yl)benzamide, 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(6,7,8,9-tetrahydropyrrolo[3',2':5,6]pyrido[2,3-b][1,4]oxazocin-5(1H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(6,7,8,9-tetrahydropyrrolo[3',2':5,6]pyrido[2,3-b][1,4]oxazocin-5(1H)-yl)benzamide, (R)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(6,7,8,9-tetrahydropyrrolo[3',2':5,6]pyrido[2,3-b][1,4]oxazocin-5(1H)-yl)benzamide, (R)-4-(4-((4'-chloro-5,5-dimethyl-3,4,5,6-tetrahydro-[1,1'-biphenyl]-2-yl)methyl)piperazin-1-yl)-N-((4-(((2-fluoro-1,4-dioxan-2-yl)methyl)amino)-3-nitrophenyl)sulfonyl)-2-(6,7,8,9-tetrahydropyrrolo[3',2':5,6]pyrido[2,3-b][1,4]oxazocin-5(1H)-yl)benzamide, (S)-4-(4-((4'-chloro-5,5-dimethyl-3,4,5,6-tetrahydro-[1,1'-biphenyl]-2-yl)methyl)piperazin-1-yl)-N-((4-(((2-fluoro-1,4-dioxan-2-yl)methyl)amino)-3-nitrophenyl)sulfonyl)-2-(6,7,8,9-tetrahydropyrrolo[3',2':5,6]pyrido[2,3-b][1,4]oxazocin-5(1H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(7,8,9,10-tetrahydro-1H-pyrrolo[3',2':5,6]pyrido[2,3-b][1,4]oxazonin-5(6H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(7,8,9,10-tetrahydro-1H-pyrrolo[3',2':5,6]pyrido[2,3-b][1,4]oxazonin-5(6H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2,3,5,6-tetrahydropyrrolo[3',2':5,6]pyrido[2,3-e][1,4,7]dioxazonin-1(9H)-yl)benzamide, (2S,4R)-1-((S)-14-(tert-butyl)-1-(4-(2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)ethyl)piperazin-1-yl)-12-oxo-3,6,9-trioxa-13-azapentadecan-15-oyl)-4-hydroxy-N-(4-(4-methylthiazol-5-yl)benzyl)pyrrolidine-2-carboxamide, (2S,4R)-1-((S)-2-(3-(2-(2-(4-(2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)ethyl)piperazin-1-yl)ethoxy)ethoxy)propanamido)-3,3-dimethylbutanoyl)-4-hydroxy-N-(4-(4-methylthiazol-5-yl)benzyl)pyrrolidine-2-carboxamide, (2S,4R)-1-((S)-2-(3-(2-(4-(2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)ethyl)piperazin-1-yl)ethoxy)propanamido)-3,3-dimethylbutanoyl)-4-hydroxy-N-(4-(4-methylthiazol-5-yl)benzyl)pyrrolidine-2-carboxamide, (2S,4R)-1-((S)-20-(tert-butyl)-1-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)-18-oxo-3,6,9,12,15-pentaoxa-19-azahenicosan-21-oyl)-4-hydroxy-N-(4-(4-methylthiazol-5-yl)benzyl)pyrrolidine-2-carboxamide, (2S,4R)-1-((S)-17-(tert-butyl)-1-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)-15-oxo-3,6,9,12-tetraoxa-16-azaoctadecan-18-oyl)-4-hydroxy-N-(4-(4-methylthiazol-5-yl)benzyl)pyrrolidine-2-carboxamide, (2S,4R)-1-((S)-14-(tert-butyl)-1-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl)sulfamoyl)-2-nitrophenyl)amino)-12-oxo-3,6,9-trioxa-13-azapentadecan-15-oyl)-4-hydroxy-N-(4-(4-methylthiazol-5-yl)benzyl)pyrrolidine-2-carboxamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(4-(2-(2-(2-((2-(2,6-dioxopiperidin-3-yl)-1,3-dioxoisoindolin-4-yl)amino)ethoxy)ethoxy)ethoxy)ethyl)piperazin-1-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(4-(2-(2-(2-((2-(2,6-dioxopiperidin-3-yl)-1,3-dioxoisoindolin-4-yl)amino)ethoxy)ethoxy)ethyl)piperazin-1-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(4-(2-(2-((2-(2,6-dioxopiperidin-3-yl)-1,3-dioxoisoindolin-4-yl)amino)ethoxy)ethyl)piperazin-1-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((17-((2-(2,6-dioxopiperidin-3-yl)-1,3-dioxoisoindolin-4-yl)amino)-3,6,9,12,15-pentaoxaheptadecyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((14-((2-(2,6-dioxopiperidin-3-yl)-1,3-dioxoisoindolin-4-yl)amino)-3,6,9,12-tetraoxatetradecyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((2-(2-(2-(2-((2-(2,6-dioxopiperidin-3-yl)-1,3-dioxoisoindolin-4-yl)amino)ethoxy)ethoxy)ethoxy)ethyl)amino)-3-nitrophenyl)sulfonyl)benzamide, 4-(4-(3-(2-(4-chlorophenyl)-1-isopropyl-5-methyl-4-(methylsulfonyl)-1H-pyrrol-3-yl)-5-fluorophenyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-(3-(2-(4-chlorophenyl)-1-isopropyl-5-methyl-4-(methylsulfonyl)-1H-pyrrol-3-yl)-5-fluorophenyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)—N-((4-(((1,4-dioxan-2-yl)methyl)amino)-3-nitrophenyl)sulfonyl)-4-(4-(3-(2-(4-chlorophenyl)-1-isopropyl-5-methyl-4-(methylsulfonyl)-1H-pyrrol-3-yl)-5-fluorophenyl)piperazin-1-yl)-2-(3,4-dihydro-2H-pyrrolo[3',2':5,6]pyrido[2,3-b][1,4]oxazepin-1(7H)-yl)benzamide, (R)—N-((4-(((1,4-dioxan-2-yl)methyl)amino)-3-nitrophenyl)sulfonyl)-4-(4-(3-(2-(4-chlorophenyl)-1-isopropyl-5-methyl-4-(methylsulfonyl)-1H-pyrrol-3-yl)-5-fluorophenyl)piperazin-1-yl)-2-(3,4-dihydro-2H-pyrrolo[3',2':5,6]pyrido[2,3-b][1,4]oxazepin-1(7H)-yl)benzamide, 4-(4-(3-(2-(4-chlorophenyl)-1-isopropyl-5-methyl-4-(methylsulfonyl)-1H-pyrrol-3-yl)-5-fluorophenyl)piperazin-1-yl)-2-(3,4-dihydro-2H-pyrrolo[3',2':5,6]pyrido[2,3-b][1, 4]oxazepin-1(7H)-yl)-N-((5-nitro-3-(tetrahydro-2H-pyran-4-yl)-3,4-dihydro-2H-benzo[b][1,4]oxazin-7-yl)sulfonyl)benzamide, (S)—N-((4-(((1,4-dioxan-2-yl)methyl)amino)-3-nitrophenyl)sulfonyl)-4-(4-(3-(2-(4-chlorophenyl)-1-isopropyl-5-methyl-4-(methylsulfonyl)-1H-pyrrol-3-yl)-5-fluorophenyl)piperazin-1-yl)-2-(2,3-dihydropyrrolo[3',2':5,6]pyrido[2,3-b][1,4]oxazin-1(6H)-yl)benzamide, (R)—N-((4-(((1,4-dioxan-2-yl)methyl)amino)-3-nitrophenyl)sulfonyl)-4-(4-(3-(2-(4-chlorophenyl)-1-isopropyl-5-methyl-4-(methylsulfonyl)-1H-pyrrol-3-yl)-5-fluorophenyl)piperazin-1-yl)-2-(2,3-dihydropyrrolo[3',2':5,6]pyrido[2,3-b][1,4]oxazin-1(6H)-yl)benzamide, 4-(4-(3-(2-(4-chlorophenyl)-1-isopropyl-5-methyl-4-(methylsulfonyl)-1H-pyrrol-3-yl)-5-fluorophenyl)piperazin-1-yl)-2-(2,3-dihydropyrrolo[3',2':5,6]pyrido[2,3-b][1,4]oxazin-1(6H)-yl)-N-((5-nitro-3-(tetrahydro-2H-pyran-4-yl)-3,4-dihydro-2H-benzo[b][1,4]oxazin-7-yl)sulfonyl)benzamide, 5-(4-chlorophenyl)-4-(3-(4-(3-(2,3-dihydropyrrolo[3',2':5,6]pyrido[2,3-b][1,4]oxazin-1(6H)-yl)-4-(((3-nitro-4-(((tetrahydro-2H-pyran-4-yl)methyl)amino)phenyl)sulfonyl)carbamoyl)phenyl)piperazin-1-yl)phenyl)-1,2-dimethyl-1H-pyrrole-3-carboxylic acid, 5-(4-chlorophenyl)-4-(3-(4-(3-(2,3-dihydropyrrolo[3',2':5,6]pyrido[2,3-b][1,4]oxazin-1(6H)-yl)-4-(((3-nitro-4-(((tetrahydro-2H-pyran-4-yl)methyl)amino)phenyl)sulfonyl)carbamoyl)phenyl)piperazin-1-yl)phenyl)-1-ethyl-2-methyl-1H-pyrrole-3-carboxylic acid, 2-(2,3-dihydropyrrolo[3',2':5,6]pyrido[2,3-b][1,4]oxazin-1(6H)-yl)-4-(4-(3-(1-ethyl-2-(4-fluorophenyl)-5-methyl-4-(methylsulfonyl)-1H-pyrrol-3-yl)-5-fluorophenyl)piperazin-1-yl)-N-((3-nitro-4-(((tetrahydro-2H-pyran-4-yl)methyl)amino)phenyl)sulfonyl)benzamide, 2-(2,3-dihydropyrrolo[3',2':5,6]pyrido[2,3-b][1,4]oxazin-1(6H)-yl)-4-(4-(3-fluoro-5-(2-(4-fluorophenyl)-1-isopropyl-5-methyl-4-(methylsulfonyl)-1H-pyrrol-3-yl)phenyl)piperazin-1-yl)-N-((3-nitro-4-(((tetrahydro-2H-pyran-4-yl)methyl)amino)phenyl)sulfonyl)benzamide, 5-(4-chlorophenyl)-4-(3-(4-(3-(2,3-dihydropyrrolo[3',2':5,6]pyrido[2,3-b][1,4]oxazin-1(6H)-yl)-4-(((3-nitro-4-(((tetrahydro-2H-pyran-4-yl)methyl)amino)phenyl)sulfonyl)carbamoyl)phenyl)piperazin-1-yl)phenyl)-1-isopropyl-2-methyl-1H-pyrrole-3-carboxylic acid, 5-(4-chlorophenyl)-4-(3-(4-(3-(2,3-dihydropyrrolo[3',2':5,6]pyrido[2,3-b][1,4]oxazin-1(6H)-yl)-4-(((3-nitro-4-(((tetrahydro-2H-pyran-4-yl)methyl)amino)phenyl)sulfonyl)carbamoyl)phenyl)piperazin-1-yl)phenyl)-1-isopropyl-2-methyl-N-(methylsulfonyl)-1H-pyrrole-3-carboxamide, 4-(4-(3-(2-(4-chlorophenyl)-1-isopropyl-5-methyl-4-(morpholine-4-carbonyl)-1H-pyrrol-3-yl)phenyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, 5-(4-chlorophenyl)-4-(3-(4-(3-(2,3-dihydropyrrolo[3',2':5,6]pyrido[2,3-b][1,4]oxazin-1(6H)-yl)-4-(((3-nitro-4-(((tetrahydro-2H-pyran-4-yl)methyl)amino)phenyl)sulfonyl)carbamoyl)phenyl)piperazin-1-yl)phenyl)-1-isopropyl-N,N,2-trimethyl-1H-pyrrole-3-carboxamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(1-oxido-2,3,6-trihydro-[1,4]oxaphosphinino[2,3-b]pyrrolo[3,2-e]pyridin-1-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(1-oxido-2,3,4,7-tetrahydro-[1,4]oxaphosphepino[2,3-b]pyrrolo[3,2-e]pyridin-1-yl)benzamide, 4-(4-[[2-(4-chlorophenyl)-5-methoxy-5-methylcyclohex-1-en-1-yl]methyl]piperazin-1-yl)-N-(4-[[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide, 4-(4-[[2-(4-chlorophenyl)-4,4-dimethylcyclohex-1-en-1-yl]methyl]piperazin-1-yl)-N-(4-[[[(2S)-1,4-dioxan-2-ylmethyl]amino]-3-nitrobenzenesulfonyl)-2-[11-oxo-13-oxa-2,4,10-triazatricyclo[7.4.0.0^[3,7]]trideca-1(9),2,5,7-tetraen-10-yl]benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((5,5-dimethyl-4'-(1,1,1-trifluoro-2-methylpropan-2-yl)-3,4,5,6-tetrahydro-[1,1'-biphenyl]-2-yl)methyl)piperazin-1-yl)benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((4,4-dimethyl-2-(2-oxo-2,3-dihydropyridin-4-yl)cyclohex-1-en-1-yl)methyl)piperazin-1-yl)benzamide, (S)—N-((4-(((1,4-dioxan-2-yl)methyl)amino)-3-nitrophenyl)sulfonyl)-4-(4-((2-(5-chlorothiophen-2-yl)-4,4-dimethylcyclohex-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((2-(4-chlorophenyl)cyclopent-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((5,5-dimethyl-3,4,5,6-tetrahydro-[1,1'-biphenyl]-2-yl)methyl)piperazin-1-yl)benzamide, (S)—N-((4-(((1,4-dioxan-2-yl)methyl)amino)-3-nitrophenyl)sulfonyl)-4-(4-((4'-chloro-3'-fluoro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((4'-chloro-2'-fluoro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((4'-chloro-3',5,5-trimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((4'-chloro-5,5-dimethyl-3'-(trifluoromethyl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((5,5-dimethyl-4'-(trifluoromethyl)-3,4,5,6-tetrahydro-[1,1'-biphenyl]-2-yl)methyl)piperazin-1-yl)benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((4,4-dimethyl-2-(pyridin-2-yl)cyclohex-1-en-1-yl)methyl)piperazin-1-yl)benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((4,4-dimethyl-2-(pyridin-3-yl)cyclohex-1-en-1-yl)methyl)piperazin-1-yl)benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((4,4-dimethyl-2-(pyridin-4-yl)cyclohex-1-en-1-yl)methyl)piperazin-1-yl)benzamide, N-((4-((((S)-1,4-dioxan-2-yl)methyl)amino)-3-nitrophenyl)sulfonyl)-4-(4-(((R)-4'-chloro-5-(trifluoromethyl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((S)-4'-chloro-5-(trifluoromethyl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((S)-4'-chloro-4-(trifluoromethyl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((R)-4'-chloro-4-(trifluoromethyl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((S)-4'-chloro-5-(1,1,1-trifluoro-2-methylpropan-2-yl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((R)-4'-chloro-5-(1,1,1-trifluoro-2-methylpropan-2-yl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((S)-4'-chloro-4-(1,1,1-trifluoro-2-methylpropan-2-yl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((R)-4'-chloro-4-(1,1,1-trifluoro-2-methylpropan-2-yl)-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((S)-2-(4-chlorophenyl)-5-(trifluoromethyl)cyclohept-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((S)-2-(4-chlorophenyl)-6-(trifluoromethyl)cyclohept-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((R)-2-(4-chlorophenyl)-4-(trifluoromethyl)cyclohept-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((S)-2-(4-chlorophenyl)-6-(1,1,1-trifluoro-2-methylpropan-2-yl)cyclohept-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((R)-2-(4-chlorophenyl)-4-(1,1,1-trifluoro-2-methylpropan-2-yl)cyclohept-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((S)-2-(4-chlorophenyl)-5-(1,1,1-trifluoro-2-methylpropan-2-yl)cyclohept-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-4-(1,1,1-trifluoro-2-methylpropan-2-yl)-3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-4-(1,1,1-trifluoro-2-methylpropan-2-yl)-3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-3-(1,1,1-trifluoro-2-methylpropan-2-yl)-3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-3-(1,1,1-trifluoro-2-methylpropan-2-yl)-3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-3-(trifluoromethyl)-3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-3-(trifluoromethyl)-3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-5-(4-((4'-chloro-5,5-dimethyl-3,4,5,6-tetrahydro-[1,1'-biphenyl]-2-yl)methyl)piperazin-1-yl)-3-(3,4-dihydro-2H-pyrrolo[3',2':5,6]pyrido[2,3-b][1,4]oxazepin-1(7H)-yl)thiophene-2-carboxamide, (S)—N-((5-(((1,4-dioxan-2-yl)methyl)amino)-4-nitrothiophen-2-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((4'-chloro-4,4-difluoro-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-(((R)-4'-chloro-5-methyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((6-(4-chlorophenyl)-2,3,3a,4,7,7a-hexahydro-1H-inden-5-yl)methyl)piperazin-1-yl)-2-(3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((6-(4-chlorophenyl)-1,3,3a,4,7,7a-hexahydroisobenzofuran-5-yl)methyl)piperazin-1-yl)-2-(3,4-dihydro-2H-pyrrolo[3',2':5,6]pyrido[2,3-b][1,4]oxazepin-1(7H)-yl)benzamide.

N-((4-((((S)-1,4-dioxan-2-yl)methyl)amino)-3-nitrophenyl)sulfonyl)-4-(4-((6-(4-chlorophenyl)-3a,4,7,7a-tetrahydrobenzo[d][1,3]dioxol-5-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((2-(4-chlorophenyl)-5,5-dimethylcyclohept-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(2-oxo-3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-oxo-3,4,5,7-tetrahydropyrrolo[3',2':5,6]pyrido[3,2-e][1,4]diazepin-1(2H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,3-dimethyl-2-oxo-3,5-dihydrodipyrrolo[2,3-b:2',3'-e]pyridin-1(2H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(7-methyl-3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydrofuro[3',2':5,6]pyrido[2,3-b][1,4]oxazepin-1(2H)-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydrothieno[3',2':5,6]pyrido[2,3-b][1,4]oxazepin-1(2H)-yl)benzamide, (S)—N-((4-(((1,4-dioxan-2-yl)methyl)amino)-3-nitrophenyl)sulfonyl)-4-(4-((4'-chloro-3,3,4,4,5,5,6,6-octafluoro-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-4-(4-((4'-chloro-2',3',5',6'-tetrafluoro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (R)-4-(4-((2-(3-chlorobicyclo[1.1.1]pentan-1-yl)-4,4-dimethylcyclohex-1-en-1-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((4,4-dimethyl-2-(3-methylbicyclo[1.1.1]pentan-1-yl)cyclohex-1-en-1-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((2-(3-(tert-butyl)bicyclo[1.1.1]pentan-1-yl)-4,4-dimethylcyclohex-1-en-1-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((4,4-dimethyl-2-(3-(trifluoromethyl)bicyclo[1.1.1]pentan-1-yl)cyclohex-1-en-1-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((4,4-dimethyl-2-(3-(1,1,1-trifluoro-2-methylpropan-2-yl)bicyclo[1.1.1]pentan-1-yl)cyclohex-1-en-1-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((4,4-dimethyl-2-(3-phenylbicyclo[1.1.1]pentan-1-yl)cyclohex-1-en-1-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((4,4-dimethyl-2-(3-morpholinobicyclo[1.1.1]pentan-1-yl)cyclohex-1-en-1-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((2-(3-(2-aminopropan-2-yl)bicyclo[1.1.1]pentan-1-yl)-4,4-dimethylcyclohex-1-en-1-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (R)-4-(4-((2-(3-(2-cyanopropan-2-yl)bicyclo[1.1.1]pentan-1-yl)-4,4-dimethylcyclohex-1-en-1-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide, (S)—N-((4-(((1,4-dioxan-2-yl)methyl)amino)-3-nitrophenyl)sulfonyl)-4-(4-((2-(4-chlorobicyclo[2.2.1]heptan-1-yl)-4,4-dimethylcyclohex-1-en-1-yl)methyl)piperazin-1-yl)-2-(3,4-dihydro-2H-pyrrolo[3',2':5,6]pyrido[2,3-b][1,4]oxazepin-1(7H)-yl)benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((4,4-dimethyl-2-(4-methylbicyclo[2.2.1]heptan-1-yl)cyclohex-1-en-1-yl)methyl)piperazin-1-yl)benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((4,4-dimethyl-2-(4-(trifluoromethyl)bicyclo[2.2.1]heptan-1-yl)cyclohex-1-en-1-yl)methyl)piperazin-1-yl)benzamide, (S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((4,4-dimethyl-2-(4-(1,1,1-trifluoro-2-methylpropan-2-yl)bicyclo[2.2.1]heptan-1-yl)cyclohex-1-en-1-yl)methyl)piperazin-1-yl)benzamide, (S)—N-((4-(((1,4-dioxan-2-yl)methyl)amino)-3-nitrophenyl)sulfonyl)-4-(4-((2-(4-(2-aminopropan-2-yl)bicyclo[2.2.1]heptan-1-yl)-4,4-dimethylcyclohex-1-en-1-yl)

methyl)piperazin-1-yl)-2-(3,4-dihydro-2H-pyrrolo[3',2':
5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-4-(4-((2-(4-(2-cyanopropan-2-yl)bicyclo[2.2.1]heptan-1-yl)-4,4-dimethylcyclohex-1-en-1-yl)methyl)piperazin-1-yl)-2-(3,4-dihydro-2H-pyrrolo[3',2':5,6]pyrido[2,3-b][1,4]oxazepin-1(7H)-yl)benzamide,
(S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((2-(4-(dimethylamino)bicyclo[2.2.1]heptan-1-yl)-4,4-dimethylcyclohex-1-en-1-yl)methyl)piperazin-1-yl)benzamide,
(S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((4,4-dimethyl-2-(4-morpholinobicyclo[2.2.1]heptan-1-yl)cyclohex-1-en-1-yl)methyl)piperazin-1-yl)benzamide,
(S)—N-((4-(((1,4-dioxan-2-yl)methyl)amino)-3-nitrophenyl)sulfonyl)-2-(3,4-dihydro-2H-pyrrolo[3',2':5,6]pyrido[2,3-b][1,4]oxazepin-1(7H)-yl)-4-(4-((4,4-dimethyl-2-(4-(trifluoromethyl)bicyclo[2.2.2]octan-1-yl)cyclohex-1-en-1-yl)methyl)piperazin-1-yl)benzamide.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration, and both of these configurations are within the scope of the invention.

Compounds having one or more chiral centers can exist in various stereoisomeric forms. Stereoisomers are compounds that differ only in their spatial arrangement. Stereoisomers include all diastereomeric, enantiomeric, and epimeric forms as well as racemates and mixtures thereof.

The term "geometric isomer" refers to cyclic compounds having at least two substituents, wherein the two substituents are both on the same side of the ring (cis) or wherein the substituents are each on opposite sides of the ring (trans). When a disclosed compound is named or depicted by structure without indicating stereochemistry, it is understood that the name or the structure encompasses one or more of the possible stereoisomers, or geometric isomers, or a mixture of the encompassed stereoisomers or geometric isomers.

When a geometric isomer is depicted by name or structure, it is to be understood that the named or depicted isomer exists to a greater degree than another isomer, that is that the geometric isomeric purity of the named or depicted geometric isomer is greater than 50%, such as at least 60%, 70%, 80%, 90%, 99%, or 99.9% pure by weight. Geometric isomeric purity is determined by dividing the weight of the named or depicted geometric isomer in the mixture by the total weight of all of the geometric isomers in the mixture.

Racemic mixture means 50% of one enantiomer and 50% of is corresponding enantiomer. When a compound with one chiral center is named or depicted without indicating the stereochemistry of the chiral center, it is understood that the name or structure encompasses both possible enantiomeric forms (e.g., both enantiomerically-pure, enantiomerically-enriched or racemic) of the compound. When a compound with two or more chiral centers is named or depicted without indicating the stereochemistry of the chiral centers, it is understood that the name or structure encompasses all possible diasteriomeric forms (e.g., diastereomerically pure, diastereomerically enriched and equimolar mixtures of one or more diastereomers (e.g., racemic mixtures) of the compound.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers also can be obtained from diastereomerically- or enantiomerically-pure intermediates, reagents, and catalysts by well-known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers is included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery*, 2008, Volume 7, p255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters*, 1994, Vol. 4, p. 1985.

Deuterium-enriched compounds: deuterium (D or $^2$H) is H) a stable, non-radioactive isotope of hydrogen and has an atomic weight of 2.0144. Hydrogen naturally occurs as a mixture of the isotopes $^X$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. The invention encompasses any pharmaceutically acceptable salts and solvates of any one of the above-described compounds and modifications thereof. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as ($C_{1-4}$) alkyl halides, e.g., methyl, ethyl, iso-propyl and tert-butyl chlorides, bromides and iodides; di-($C_{1-4}$) alkyl sulfates, e.g., dimethyl, diethyl and diamyl sulfates; alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The compounds disclosed therein are inhibitors for Bcl-2 family proteins, such as Bcl-2. For simplicity, the term "Bcl-2 inhibitor" includes compounds that inhibits one activity of at least one Bcl-2 family member, especially Bcl-2 family member with anti-apoptotic activity, such as Bcl-2.

Bcl-2 family proteins have a general structure that consists of a hydrophobic α-helix surrounded by amphipathic α-helices. Some members of the family have transmembrane domains at their c-terminus, which primarily function to localize them to the mitochondrion. For example, Bcl-x (L) has 233 residues and exhibits a single highly hydrophobic putative transmembrane α-helical segment (residues 210-226) when in the membrane. Related family members include Bax and Bak, which also influence apoptosis.

All members of the Bcl-2 family share one or more of the four characteristic domains of homology entitled the Bcl-2 homology (BH) domains (named BH1, BH2, BH3 and BH4). The BH domains are known to be crucial for function, as deletion of these domains via molecular cloning affects survival/apoptosis rates. The anti-apoptotic Bcl-2 proteins, such as Bcl-2 and Bcl-xL, conserve all four BH domains. Structural homology suggests that Bcl-2 family members that contain the BH1 and BH2 domains (Bcl-X(L), Bcl-2, and Bax) function similarly. On the other hand, the BH domains also serve to subdivide the pro-apoptotic Bcl-2 proteins into those with several BH domains (e.g. Bax and Bak) or those proteins that have only the BH3 domain (e.g., Bim, Bid, and BAD).

All anti-apoptotic Bcl-2 family proteins (such as Bcl-2, Bcl-xL, Bcl-w, Mcl-1, CED-9, A1, and Bfl-1) contain BH1 and BH2 domains, some of them contain an additional N-terminal BH4 domain (Bcl-2, Bcl-x(L) and Bcl-w), which is also seen in some pro-apoptotic proteins like Bcl-x(S), Diva, Bok-L and Bok-S. On the other hand, all pro-apoptotic Bcl-2 family proteins (such as Bcl-xS, Bax, Bak, Diva, Bik, Bim, BAD, Bid, and Egl-1) contain a BH3 domain necessary for dimerization with other proteins of Bcl-2 family and crucial for their killing activity, some of them also contain BH1 and BH2 domains (e.g., Diva, Bax and Bak). The BH3 domain is also present in some anti-apoptotic protein, such as Bcl-2 or Bcl-x(L). The three functionally important Bcl-2 homology regions (BH1, BH2 and BH3) are in close spatial proximity. They form an elongated cleft that may provide the binding site for other Bcl-2 family members.

In certain embodiments, the compounds of the invention function as BH3 mimetic to inhibit the function of one or more Bcl-2 family members that are anti-apoptotic, such as Bcl-2, Bcl-x(L), and/or Bcl-w, thus enhancing apoptosis (e.g., enhances an apoptotic signal).

The pharmaceutical composition of the present invention comprises one or more BCL-2 inhibitors, or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present invention optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

The pharmaceutical compositions of the present invention may further comprise other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions of the present invention may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPfβCD and SBEfβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$, $C_1$-$C_6$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$, $C_2$-$C_6$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$, $C_2$-$C_6$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group. "Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a saturated or unsaturated nonaromatic 5-8 membered monocyclic, 8-12 membered bicyclic, or 11-14 membered tricyclic ring system having 1 to 4 heteroatoms (such as O, N, S, B, P, Si, or Se), which may be the same or different. Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, B, Si, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{20}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NR$_a$R$_b$ where R$_a$ and R$_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —C=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(=NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —NO$_2$. "Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyltotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), antimicrotubule agents (Estramustine), and retinoids (Bexarotene, Isotretinoin, Tretinoin (ATRA)).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK (A1/B1/G1), AMPK (A1/B1/G2), AMPK (A1/B1/G3), AMPK (A1/B2/G1), AMPK (A2/B1/G1), AMPK (A2/B2/G1), AMPK (A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin Ti, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CSF1R, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa, CDC42BPA, MRCKb, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg (p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKGla, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1 (E255K), ABL1 (F317I), ABL1 (G250E), ABL1 (H396P), ABL1 (M351T), ABL1 ($Q_{252}$H), ABL1 (T315I), ABL1 (Y253F), ALK (C1156Y), ALK (L1196M), ALK (F1174L), ALK (R1275Q), BRAF (V599E), BTK (E41K), CHK2 (I157T), c-Kit (A829P), c-KIT (D816H), c-KIT (D816V), c-Kit (D820E), c-Kit (N822K), C-Kit (T670I), c-Kit (V559D), c-Kit (V559D/V654A), c-Kit (V559D/T670I), C-Kit (V560G), c-KIT (V654A), C-MET (D1228H), C-MET (D1228N), C-MET (F1200I), c-MET (M1250T), C-MET (Y1230A), C-MET (Y1230C), C-MET (Y1230D), C-MET (Y1230H), c-Src (T341M), EGFR (G719C), EGFR (G719S), EGFR (L858R), EGFR (L861Q), EGFR (T790M), EGFR, (L858R, T790M), EGFR (d746-750/T790M), EGFR (d746-750), EGFR (d747-749/A750P), EGFR (d747-752/P753S), EGFR (d752-759), FGFR1 (V561M), FGFR2 (N549H), FGFR3 (G697C), FGFR3 (K650E), FGFR3 (K650M), FGFR4 (N535K), FGFR4 (V550E), FGFR4 (V550L), FLT3 (D835Y), FLT3 (ITD), JAK2 (V617F), LRRK2 (G2019S), LRRK2 (12020T), LRRK2 (R1441C), p38a (T106M), PDGFRa (D842V), PDGFRa (T674I), PDGFRa (V561D), RET (E762Q), RET (G691S), RET (M918T), RET (R749T), RET (R813Q), RET (V804L), RET (V804M), RET (Y791F), TIF2 (R849W), TIF2 (Y897S), and TIF2 (Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g.HSP90), poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway (e.g Bcl-xL, BCL-2, Bcl-w), histone deacetylases (HDAC), histone acetyltransferases (HAT), and methyltransferase (e.g., histone lysine methyltransferases, histone arginine methyltransferase, DNA methyltransferase, etc), and other immunotherapies (e.g anti-PD1, anti-PDL1, anti-CTLA4, CAR-T, IDO, A2A antagonist etc).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), antibody conjugate (e.g brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, anti-metabolites, topoisomerase inhibitors, anti-microtubule agents, kinase inhibitors, epigenetic agents, HSP90 inhibitors, PARP inhibitors, and antibodies targeting VEGF, HER2, EGFR, LD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, pembrolizumab, nivolumab, atezolizumab, durvalumab, avelumab, as tisagenlecleucel, axicabtagene ciloleucel, radiation therapy, or surgery.

The invention further provides methods for the prevention or treatment of a neoplastic disease or autoimmune disease. In one embodiment, the invention relates to a method of treating a neoplastic disease or autoimmune disease, in a subject in need of treatment comprising administering to said subject a therapeutically effective amount of a compound of the invention. In one embodiment, the invention further provides for the use of a compound of the invention in the manufacture of a medicament for halting or decreasing a neoplastic disease or autoimmune disease.

In certain embodiments, the neoplastic disease is a lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease.

The autoimmune diseases that can be affected using compounds and compositions according to the invention include, but are not limited to allergy, Alzheimer's disease, acute disseminated encephalomyelitis, Addison's disease, ankylosing spondylitis, antiphospholipid antibody syndrome, asthma, atherosclerosis, autoimmune hemolytic anemia, autoimmune hemolytic and thrombocytopenic states, autoimmune hepatitis, autoimmune inner ear disease, bullous pemphigoid, coeliac disease, chagas disease, chronic obstructive pulmonary disease, chronic Idiopathic thrombocytopenic purpura (ITP), churg-strauss syndrome, Crohn's disease, dermatomyositis, diabetes mellitus type 1, endometriosis, Goodpasture's syndrome (and associated glomerulonephritis and pulmonary hemorrhage), graves' disease, guillain-barre syndrome, hashimoto's disease, hidradenitis suppurativa, idiopathic thrombocytopenic purpura, interstitial cystitis, irritable bowel syndrome, lupus erythematosus, morphea, multiple sclerosis, myasthenia gravis, narcolepsy, neuromyotonia, Parkinson's disease, pemphigus vulgaris, pernicious anaemia, polymyositis, primary biliary cirrhosis, psoriasis, psoriatic arthritis, rheumatoid arthritis, schizophrenia, septic shock, scleroderma, Sjogren's disease, systemic lupus erythematosus (and associated glomerulonephritis), temporal arteritis, tissue graft rejection and hyperacute rejection of transplanted organs, vasculitis (ANCA-associated and other vasculitides), vitiligo, and wegener's granulomatosis.

It should be understood that the invention is not limited to the particular embodiments shown and described herein, but that various changes and modifications may be made without departing from the spirit and scope of the invention as defined by the claims.

The compounds according to the present invention may be synthesized according to a variety of schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach to synthesize of the intermediate

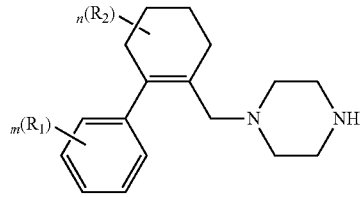

is described in Scheme 1-1 below: $R_1$, $R_2$, m, and n, in general Scheme 1-1 are the same as those described in the Summary section above.

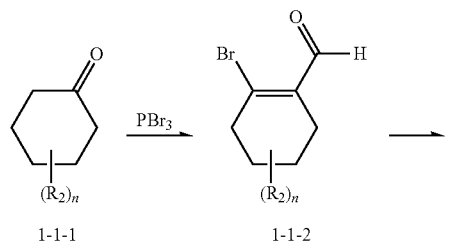

1-1-1  1-1-2

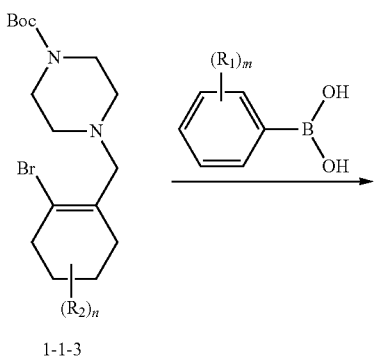

1-1-3

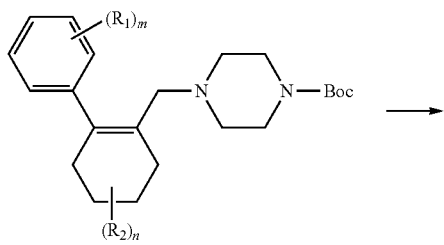

1-1-4

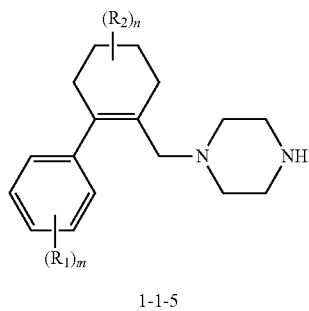

1-1-5

In Scheme 1-1, the appropriate ketone starting material 1-1-1 can react with tribromophosphine to form the aldehyde intermediate 1-1-2, which can couple with Boc-protected piperazine to form the intermediate 1-1-3. After that, 1-1-3 will couple with appropriate phenylboronic acid via a Suzuki reaction to form intermediate 1-1-4, followed by a de-boc process to yield key intermediate 1-1-5.

A typical approach to synthesize of the intermediate

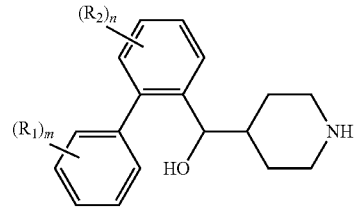

was described in U.S. Pat. No. 9,018,381 (e.g Scheme 2, Scheme 3, Scheme 5, Scheme 6).

The intermediate of

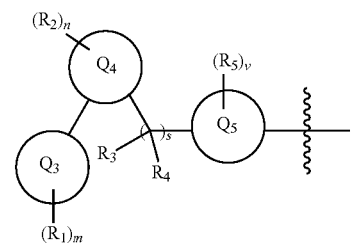

can be prepared by the method similar to the Scheme 1-1, and those described in US9,018,381 by using appropriate staring materials and intermediates.

A typical approach to synthesize of the intermediate

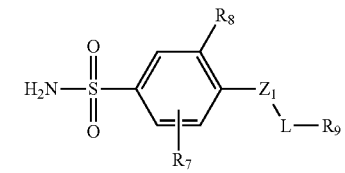

in which $R_8$ is $NO_2$ is described in Scheme 2-1 below. $R_7$, $R_8$, L, and $R_9$, in general Scheme 2-1 are the same as those described in the Summary section above.

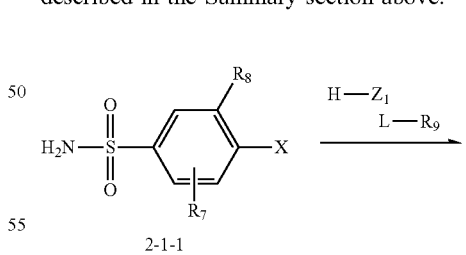

2-1-1

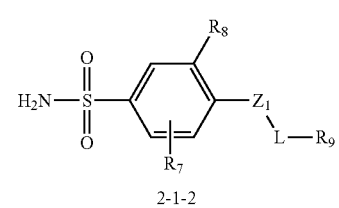

2-1-2

In Scheme 2-1, the starting material 2-1-1 reacts with appropriate alcohol or amine will yield 2-1-2.

A typical approach to synthesize of the intermediate

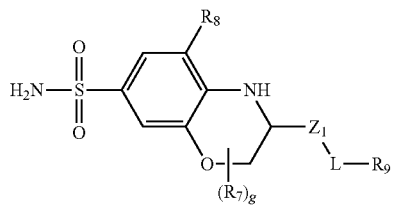

in which $R_8$ is $NO_2$ is described in Scheme 2-2 below. $R_8$, $Z_1$, L, and $R_9$, in general Scheme 2-2 are the same as those described in the Summary section above.

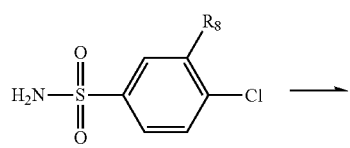

2-2-1

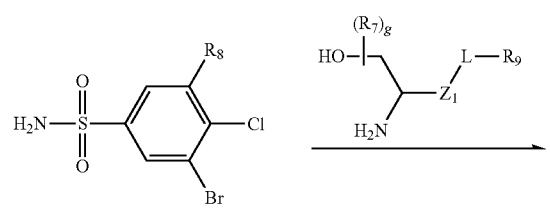

2-2-2

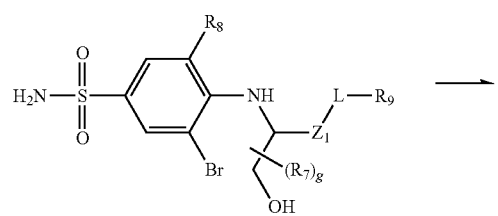

2-2-3

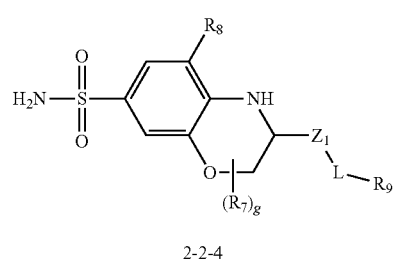

2-2-4

In Scheme 2-2, the bromination of the commercially available 2-2-1 results in 2-2-2, and then the reaction of 2-2-2 with appropriate amine provides 2-2-3. Intramolecular cyclization of 2-2-3 using metal catalyzed coupling conditions such as Buchwald reaction or other coupling reaction known in the literature give 2-2-4. Alternatively, 2-2-4 can be obtained via a 3 step sequence of mesylation of the hydroxyl group of 2-2-3, SN2 reaction and intramolecular cyclization.

Similarly, the intermediate of

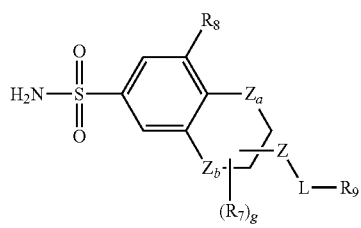

with different $Z_a$ and $Z_b$ can be prepared by the method similar to the Scheme 2-2 by using appropriate staring materials, intermediates, and intramolecular cyclization.

Similarly, the intermediate of

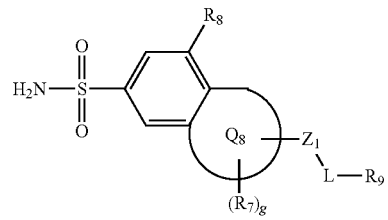

with different $Q_8$ can be prepared by the method similar to the Scheme 2-2 by using appropriate staring materials, intermediates, and intramolecular cyclization.

Similarly, the intermediate of

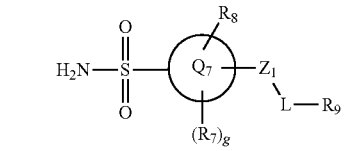

with different $R_7$ and $Q_7$ can be prepared by the method similar to the Scheme 2-1 and 2-2 by using appropriate staring materials, intermediates, and intramolecular cyclization.

A typical approach to synthesize of the intermediate
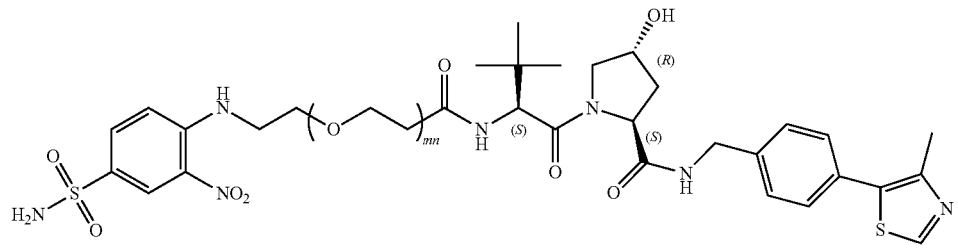
is described in Scheme 2-3 below. The mn in general Scheme 2-3 are the same as those described in the Summary section above.
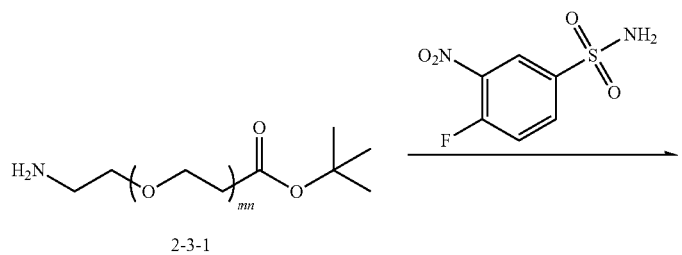
2-3-1
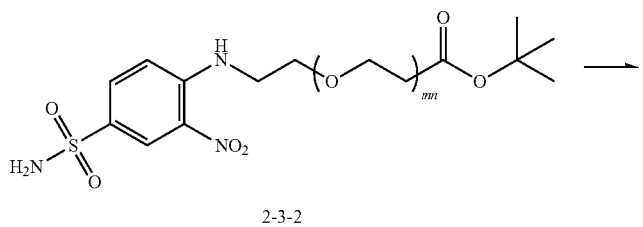
2-3-2
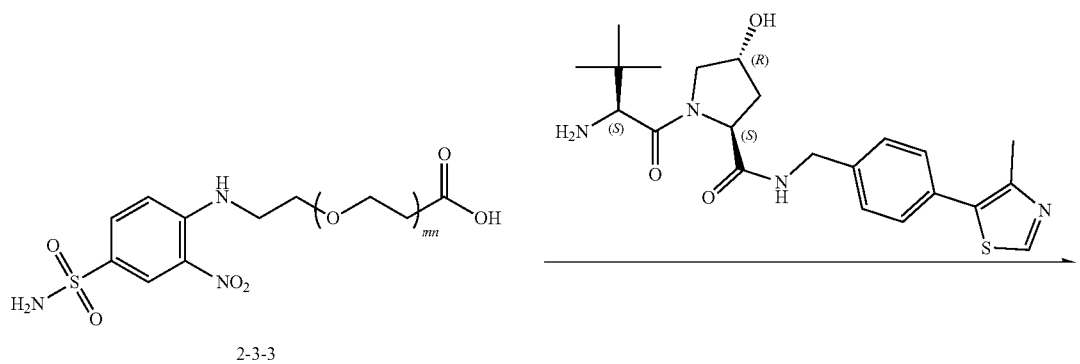
2-3-3
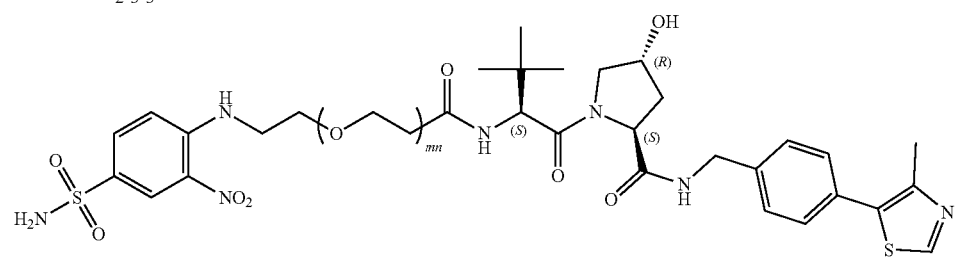
2-3-4

In Scheme 2-3, the appropriate staring material 2-3-1 can react with 4-fluoro-3-nitrobenzenesulfonamide to form the intermediate 2-3-2, which can be easily converted into carboxylic acid intermediate 2-3-3. Finally, 2-3-3 can react with the commercially available reagent (2S,4R)-1-((S)-2-amino-3,3-dimethylbutanoyl)-4-hydroxy-N-(4-(4-methylthiazol-5-yl)benzyl)pyrrolidine-2-carboxamide to form the target intermediate 2-3-4.

Similarly, the intermediate of

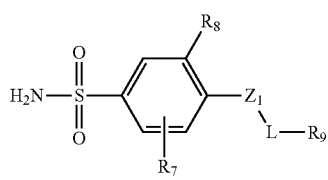

in which R₉ is

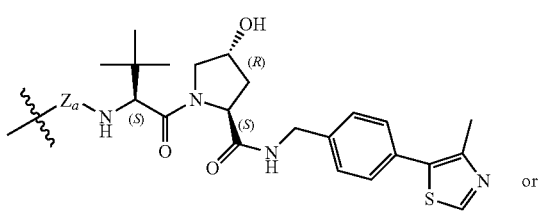

or

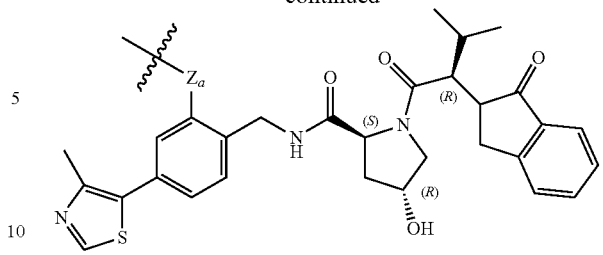

can be prepared by the method similar to the Scheme 2-3 by using appropriate staring materials, and intermediates.

A typical approach to synthesize of the intermediate

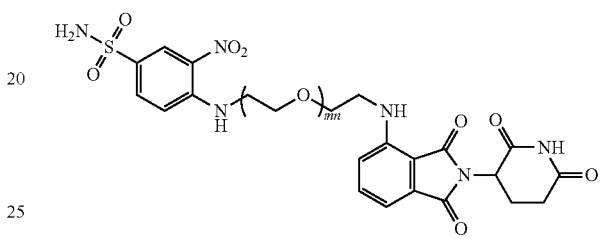

is described in Scheme 2-4 below. The mn in general Scheme 2-4 are the same as those described in the Summary section above.

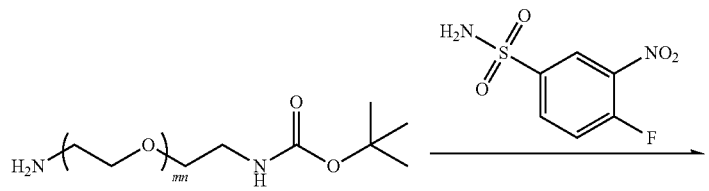

2-4-1

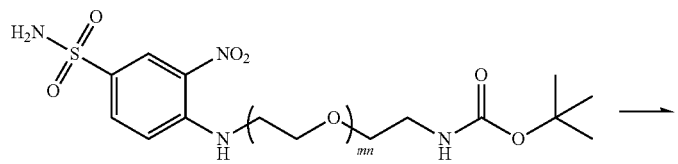

2-4-2

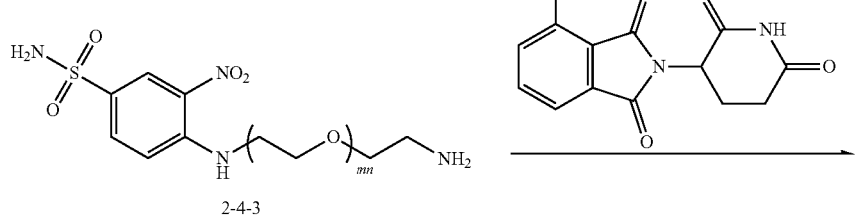

2-4-3

-continued

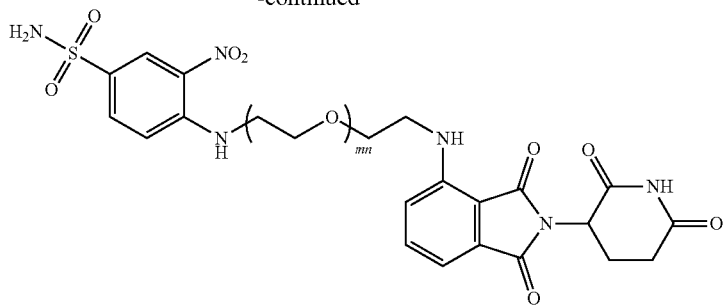

2-4-4

In Scheme 2-4, the appropriate staring material 2-4-1 can react with 4-fluoro-3-nitrobenzenesulfonamide to form the intermediate 2-4-2, which can be easily converted into amine intermediate 2-4-3. Finally, 2-4-3 can react with the commercially available reagent 2-(2,6-dioxopiperidin-3-yl)-4-fluoroisoindoline-1,3-dione to form the target intermediate 2-4-4.

Similarly, the intermediate of

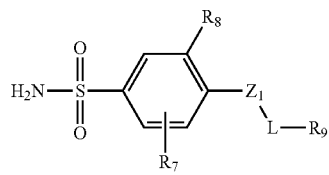

in which $R_9$ is

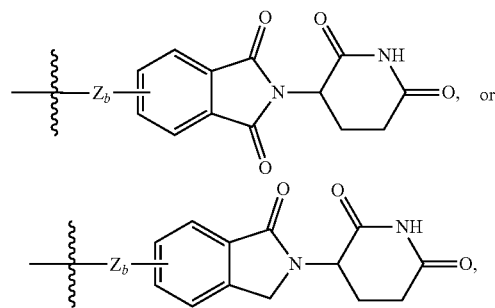

can be prepared by the method similar to the Scheme 2-4 by using appropriate staring materials, and intermediates.

A typical approach to synthesize of the intermediate

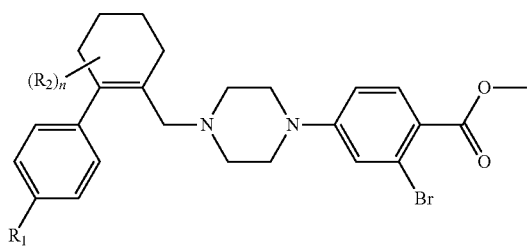

is described in Scheme 3-1 below. $R_2$, and n, in general Scheme 3-1 are the same as those described in the Summary section above.

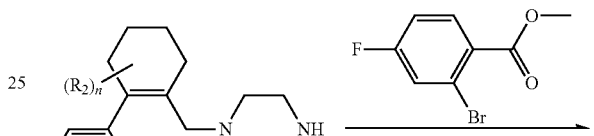

1-1-5

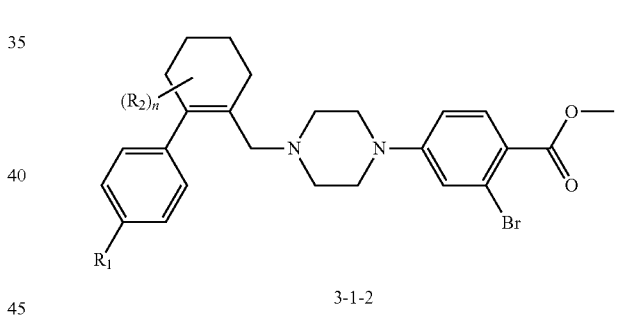

3-1-2

In Scheme 3-1, the intermediate 1-1-5 undergoes nucleophilic aromatic substitution with selected p-fluoro-2-bromobenzoate to give 3-1-2.

A typical approach to synthesize of the intermediate

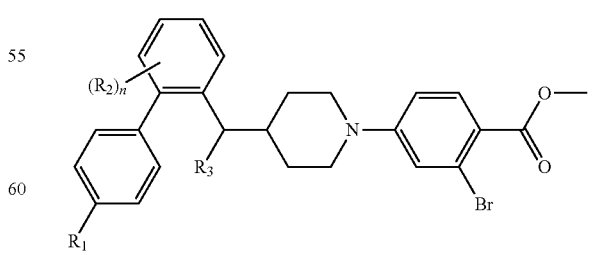

is described in Scheme 3-2 below. $R_1$, $R_2$, $R_3$, and n, in general Scheme 3-2 are the same as those described in the Summary section above.

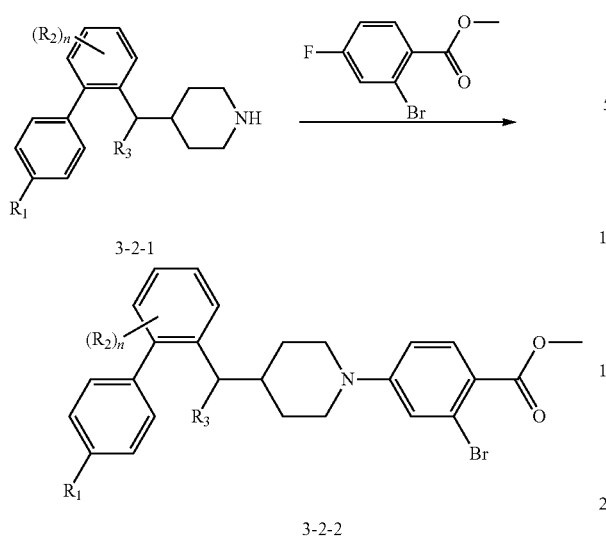

In Scheme 3-2, the intermediate 3-2-1 undergoes nucleophilic aromatic substitution with selected p-fluoro-2-bromobenzoate to give 3-2-2.

A typical approach to synthesize of the intermediate

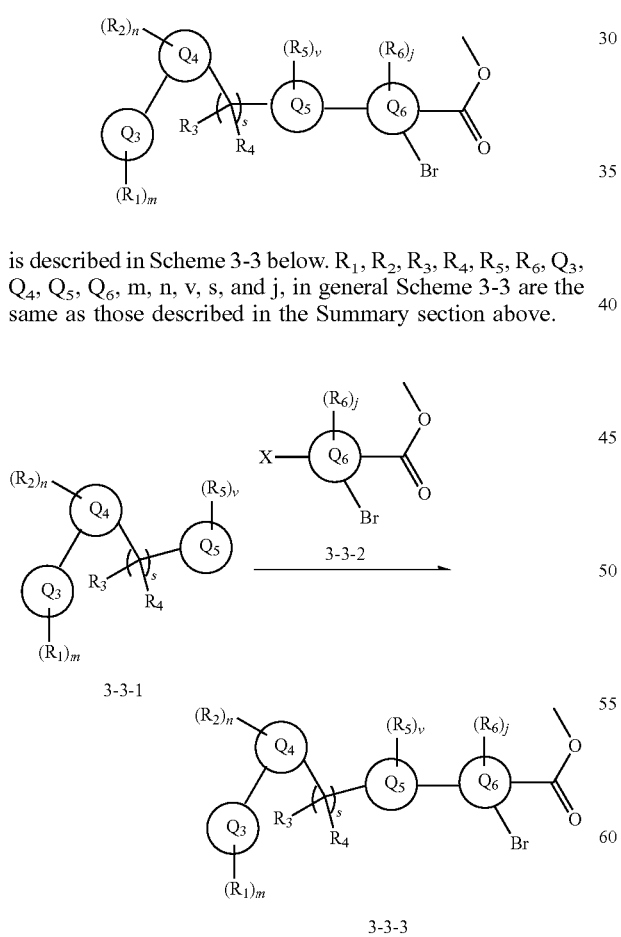

is described in Scheme 3-3 below. $R_1$, $R_2$, $R_3$, $R_4$, $R_5$, $R_6$, $Q_3$, $Q_4$, $Q_5$, $Q_6$, m, n, v, s, and j, in general Scheme 3-3 are the same as those described in the Summary section above.

In Scheme 3-3, the intermediate 3-3-1 undergoes nucleophilic aromatic substitution or metal catalyzed coupling condition such as Buchwald reaction or other coupling reaction known in the literature with appropriate intermediate 3-3-2 to give 3-3-3.

A typical approach to synthesize of the intermediate in which W is N is described in Scheme 1. The intermediate with N is CH can be made similarly.

In Scheme 1, the starting material 1-1 is protected with SEM group to give intermediate 1-2, which is followed by Buchwald coupling to yield intermediate 1-3. Hydrolysis of imine 1-3 gives aniline intermediate 1-4. Condensation of 1-4 with acetic acid anhydride results in SEM-protected tricyclic intermediate 1-5.

A typical approach to synthesize of the intermediate is described in Scheme 3:

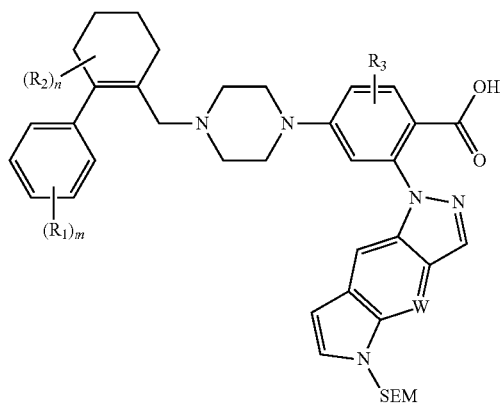

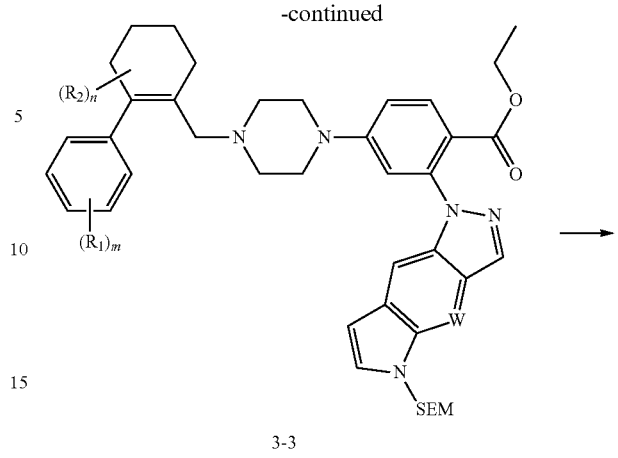

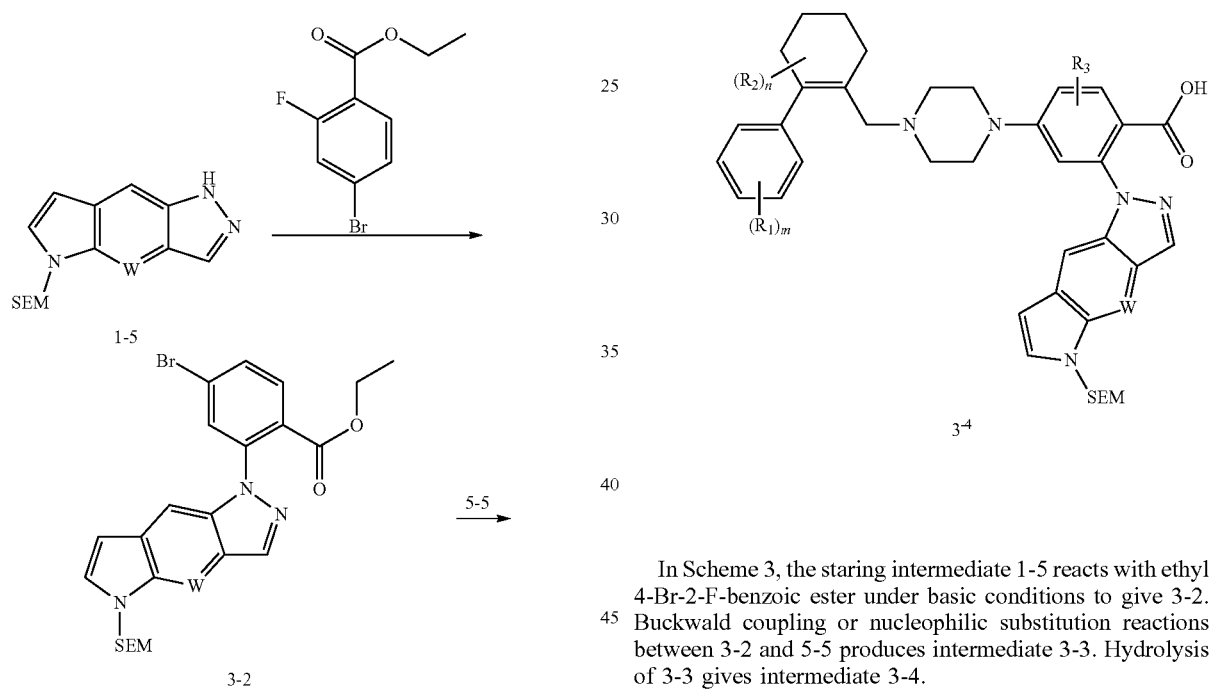

In Scheme 3, the staring intermediate 1-5 reacts with ethyl 4-Br-2-F-benzoic ester under basic conditions to give 3-2. Buckwald coupling or nucleophilic substitution reactions between 3-2 and 5-5 produces intermediate 3-3. Hydrolysis of 3-3 gives intermediate 3-4.

A typical approach to synthesize the compounds of

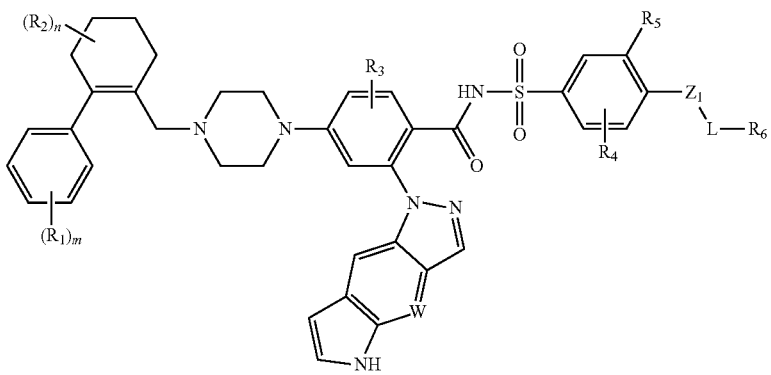

with $Z_1$=NH or O is described in Scheme A:

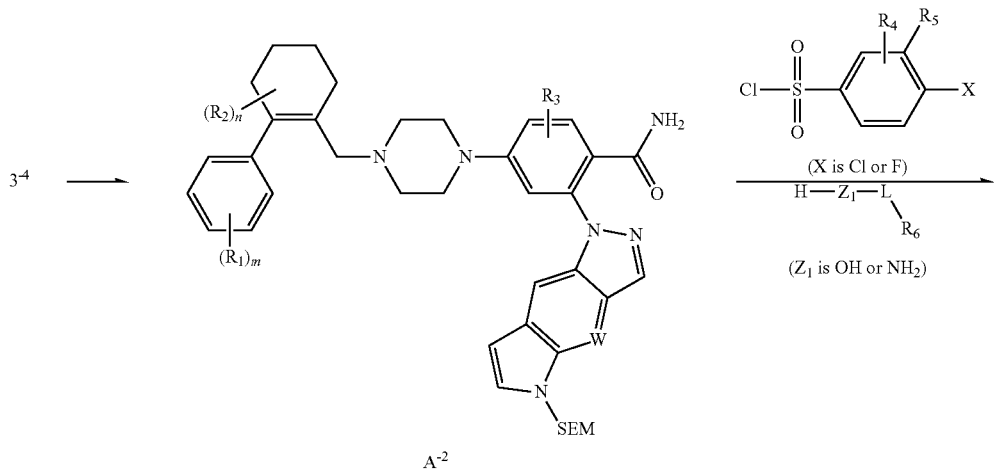

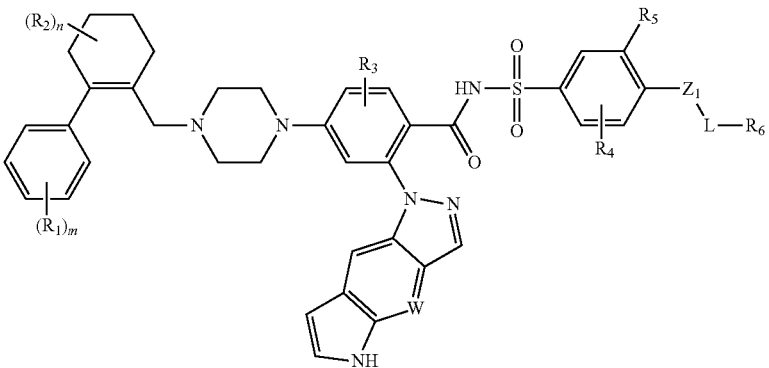

The intermediate 3-4 can undergo an amide coupling with ammonia gives intermediate A-2. Sequential substitution reaction of chlorobenzene sulfonyl halides (X is Cl or F) with appropriate amine $NH_2LR_4$ or alcohol $HO-L-R_4$ and coupling reaction with intermediate A-2 followed by deprotection of SEM group leads to target compounds.

Similarly, a typical approach to synthesize the compounds of

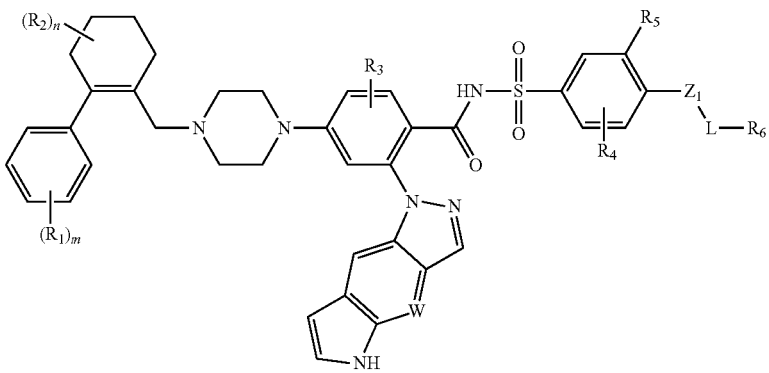

is described in Scheme C:
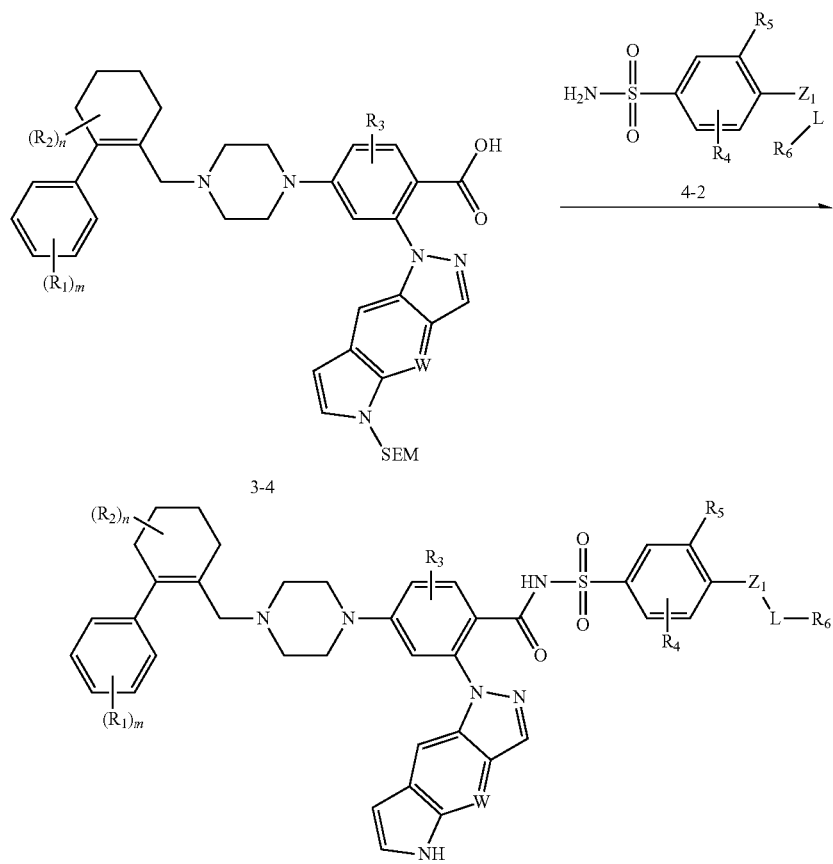
In Scheme C, the amide coupling of 3-4 and 4-2 leads to target compounds.
A typical approach to synthesize of target compounds (A-2) is described in Scheme A-2:
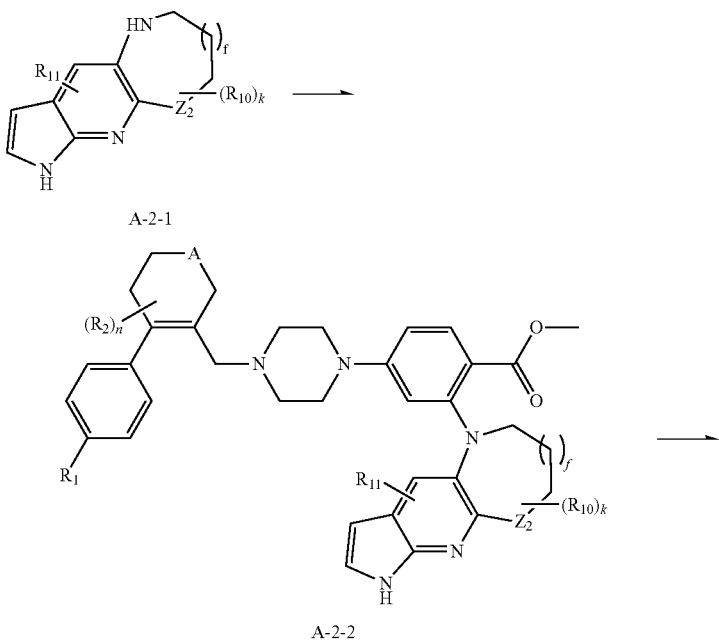

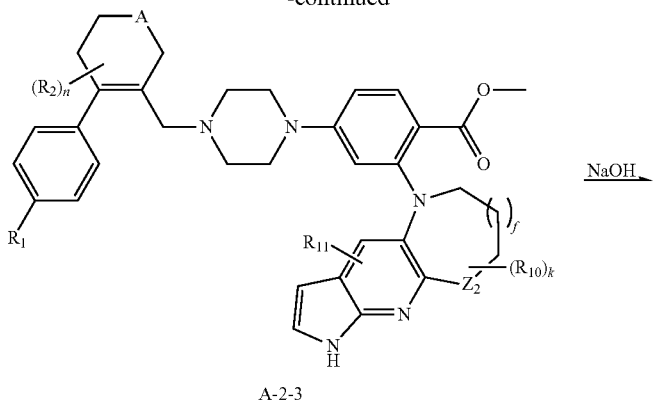

A-2-3

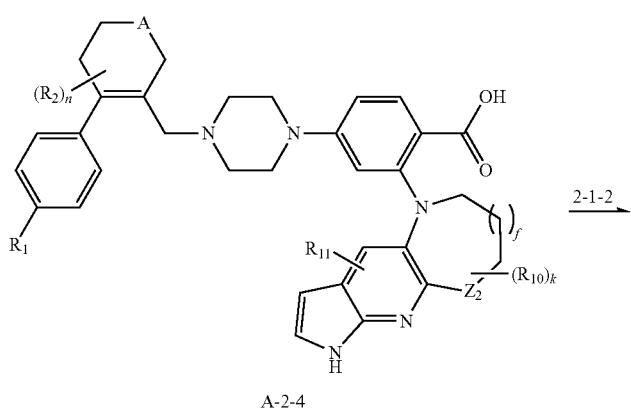

A-2-4

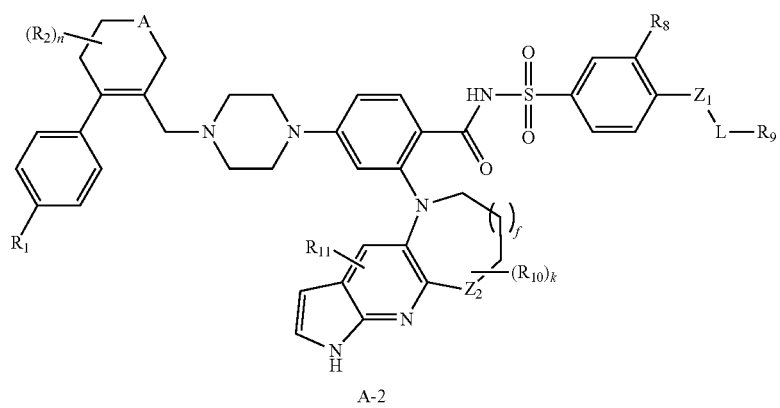

A-2

In Scheme A-2, the intermediate A-2-1 can be prepared by standard organic reactions or by the methods similar to those described in International Application Publication Nos. WO2019/040550 and WO2019/040573. The Buckwald coupling of A-2-1 with 3-1-2 yields A-2-2. A-2-2 is deprotected sequentially with TFA to remove SEM group and NaOH to remove ester group, producing free carboxylic acid intermediate A-2-4. Finally, the coupling of A-2-4 with 2-1-2 affords target compounds A-2.

A typical approach to synthesize target compounds of G-2 is described in Scheme G-2
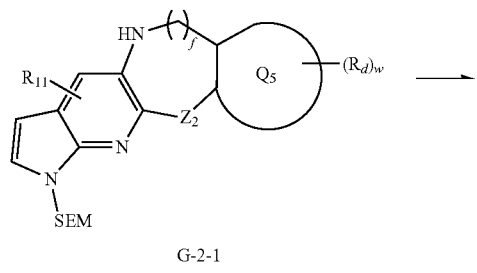
G-2-1
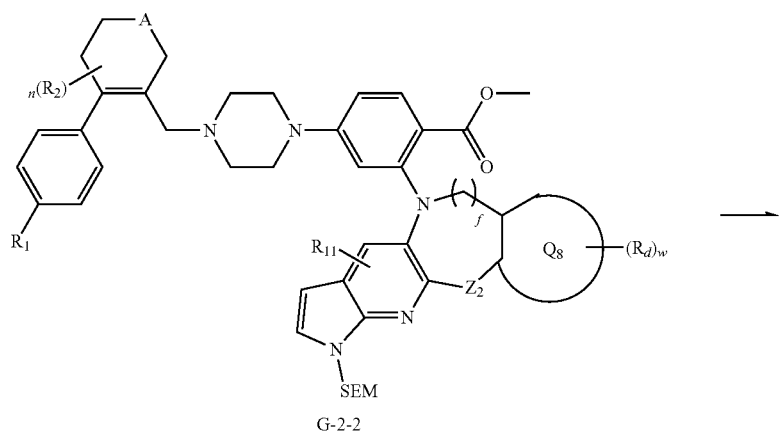
G-2-2
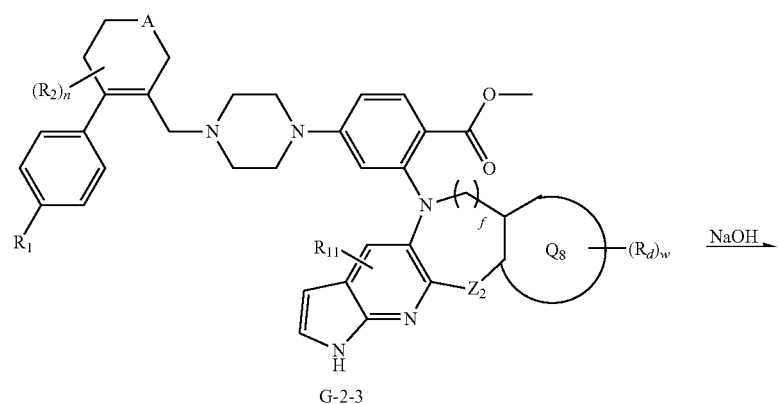
G-2-3
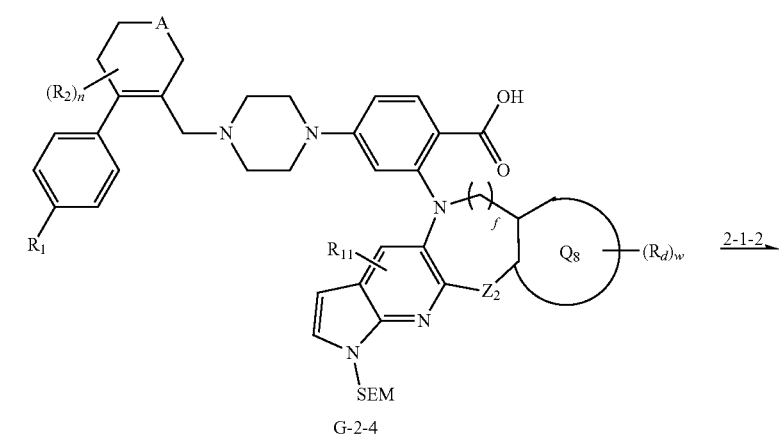
G-2-4

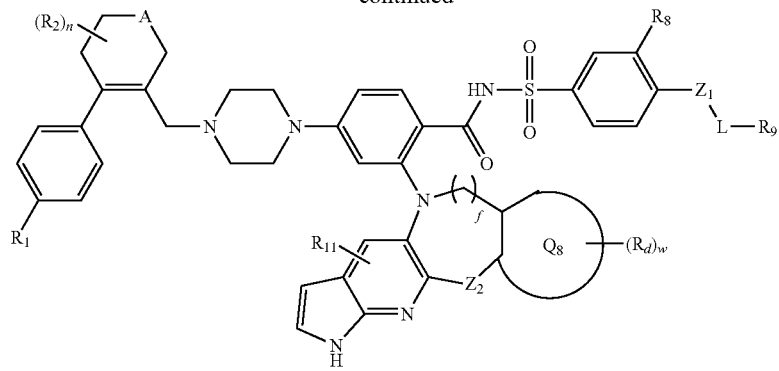

G-2

In Scheme G-2, the intermediate G-2-1 can be prepared by standard organic reactions. The Buckwald coupling of G-2-1 with 3-2 yields G-2-2. G-2-2 is deprotected sequentially with TFA to remove SEM group and NaOH to remove ester group, producing free carboxylic acid intermediate G-2-4. Finally, the coupling of G-2-4 with appropriate side chain affords target compounds of G-2.

Similarly, the compound of can be prepared by the method similar to the General Scheme II by using appropriate staring materials and intermediates.

A typical approach to synthesize of target compounds of E-2 is described in Scheme E-2:

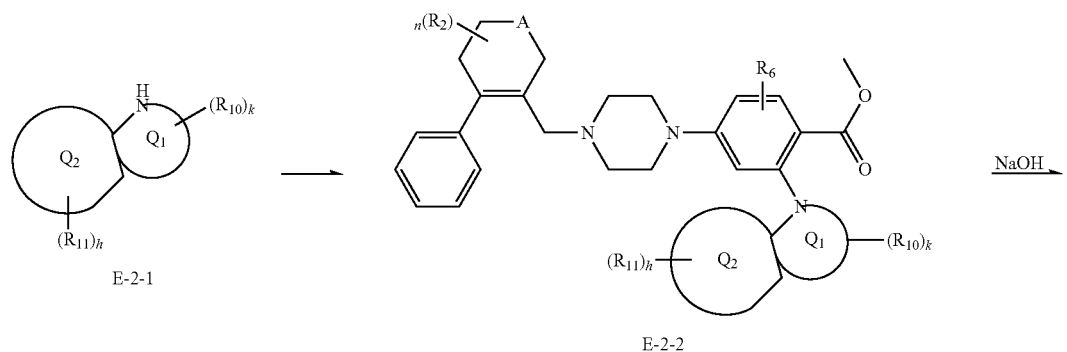

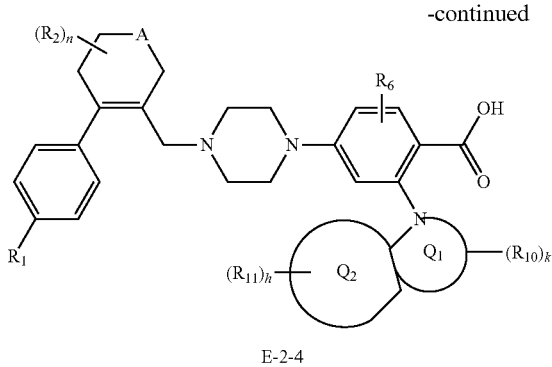

E-2-4

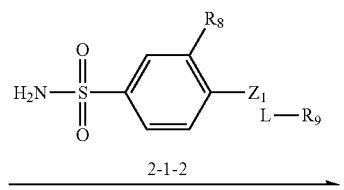

2-1-2

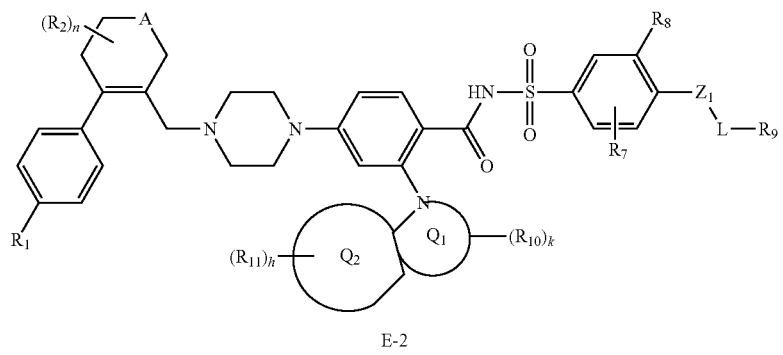

E-2

In Scheme E-2, the appropriate staring material E-2-1 are either commercially available or can be prepared by standard organic reactions, or by the methods similar to those described in International Application Publication Nos. WO2019/040550 and WO2019/040573. The Buckwald coupling of E-2-1 with 3-1-2 yields E-2-2, which is deprotected with NaOH to remove ester group, producing free carboxylic acid intermediate E-2-4. Finally, the coupling of E-2-4 with appropriate side chain affords target compounds of E-2.

A typical approach to synthesize of C-2 compounds is described in Scheme C-2:

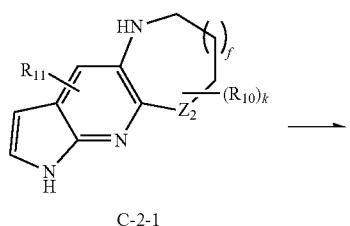

C-2-1

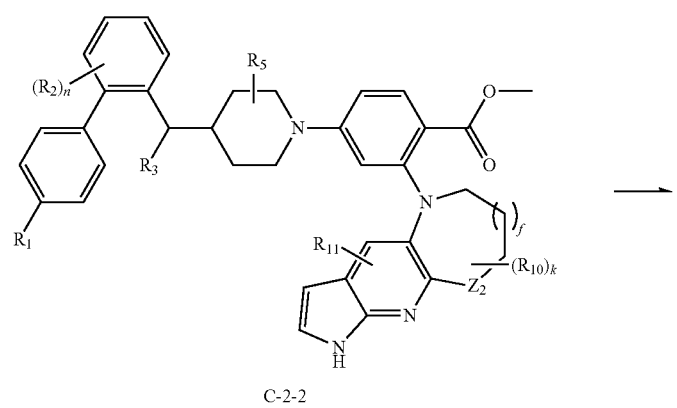

C-2-2

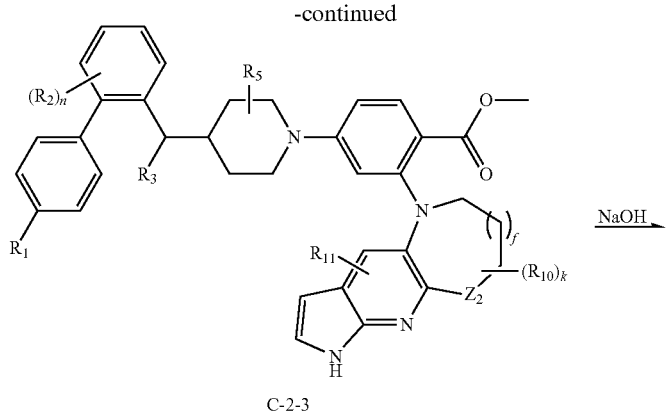

C-2-3

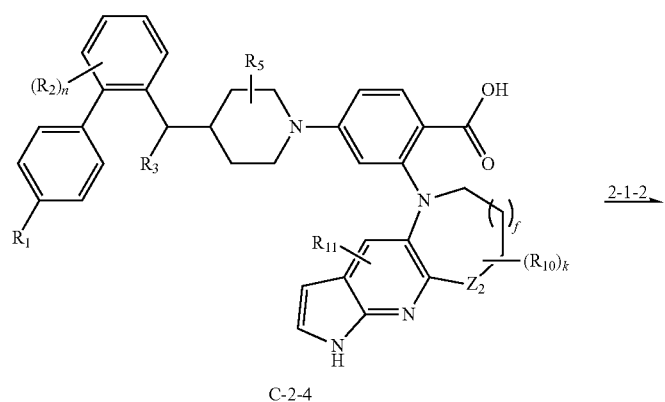

C-2-4

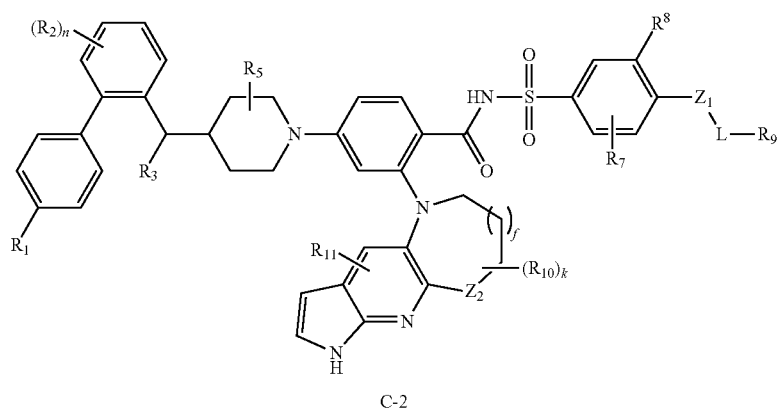

C-2

In Scheme C-2, the intermediate C-2-1 can be prepared by standard organic reactions or by the methods similar to those described in International Application Publication Nos. WO2019/040550 and WO2019/040573. The Buckwald coupling of C-2-1 with 3-2-2 yields C-2-2. C-2-2 is deprotected sequentially with TFA to remove SEM group and NaOH to remove ester group, producing free carboxylic acid intermediate C-2-4. Finally, the coupling of C-2-4 with 2-1-2 affords target compound C-2.

Similarly, the compound of
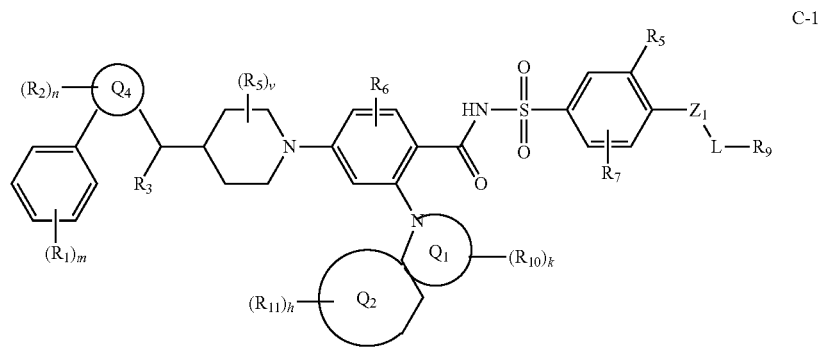
C-1
can be prepared by the method similar to Scheme C-2 by using appropriate staring materials and intermediates.
A typical approach to synthesize of target compounds (D-4) is described in Scheme D-4
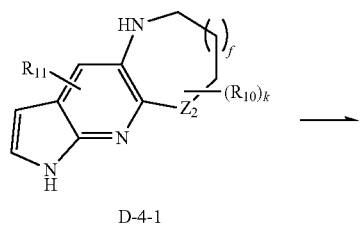
D-4-1
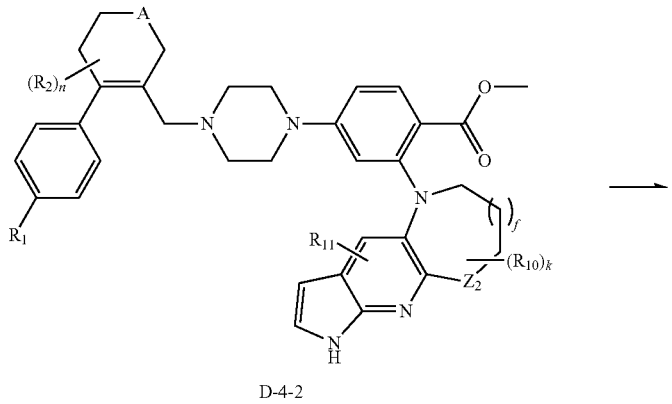
D-4-2
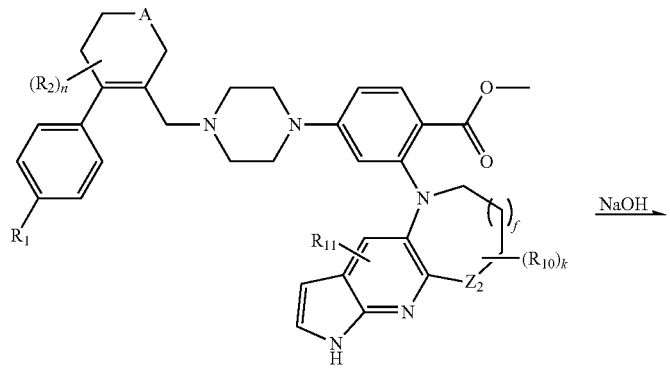
D-4-3

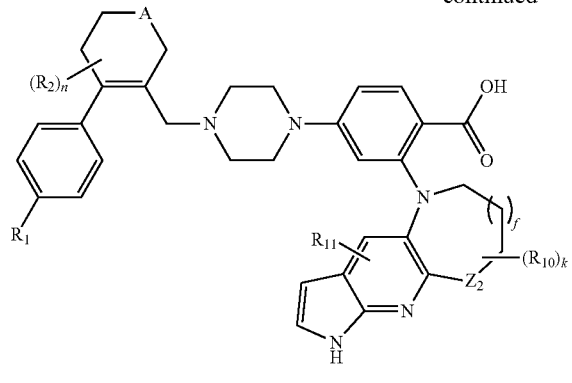
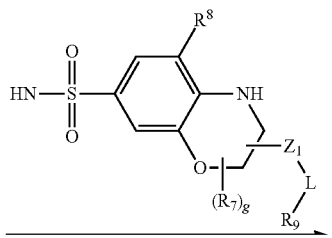

D-4-4

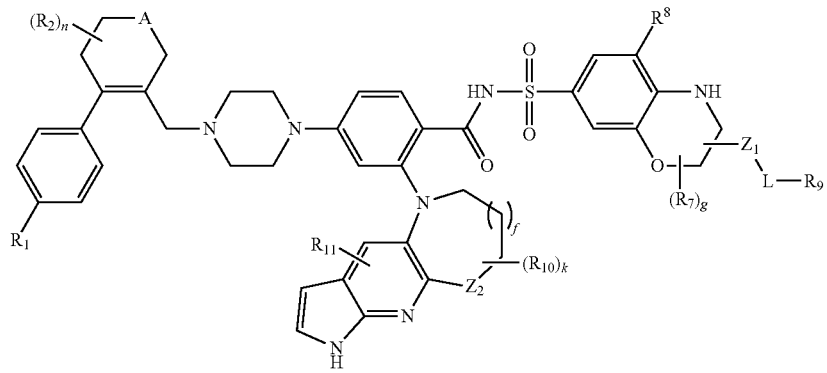

D-4

In Scheme D-4, the intermediate D-4-1 can be prepared by standard organic reactions or by the methods similar to those described in International Application Publication Nos. WO2019/040550 and WO2019/040573. The Buckwald coupling of D-4-1 with 3-1-2 yields D-4-2. D-4-2 is deprotected sequentially with TFA to remove SEM group and NaOH to remove ester group, producing free carboxylic acid intermediate D-4-4. Finally, the coupling of D-4-4 with appropriate side chain affords target compounds of D-4.

Similarly, the compound of

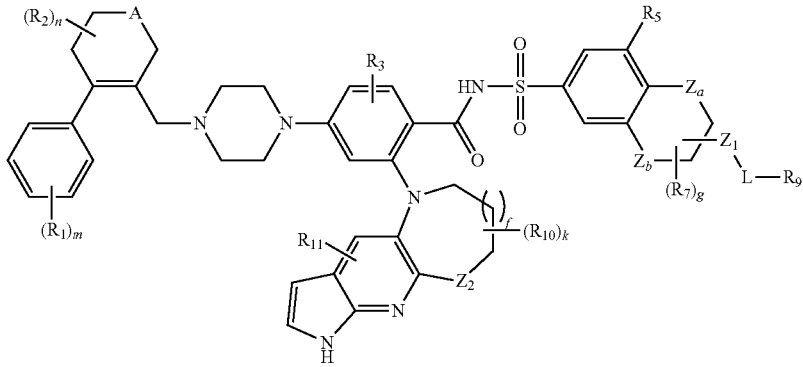

can be prepared by the method similar to Scheme D-4 by using appropriate staring materials and intermediates.

Similarly, the compound of
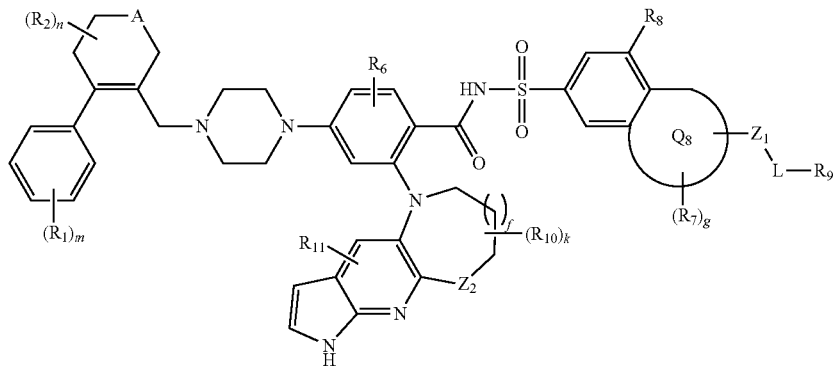
can be prepared by the method similar to Scheme D-4 by using appropriate staring materials and intermediates.
Similarly, the compound of
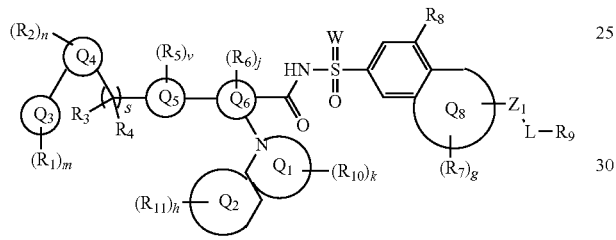
can be prepared by the method similar to Scheme D-4 by using appropriate staring materials and intermediates.
A typical approach to synthesize of Formula (B-1) compounds of is described in Scheme B-1:
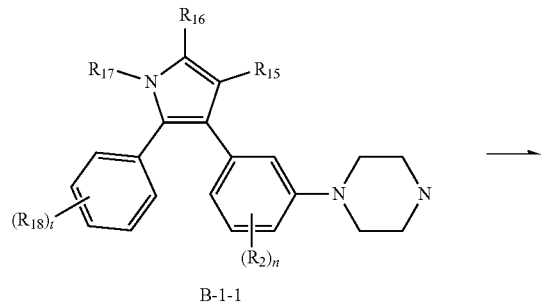
B-1-1
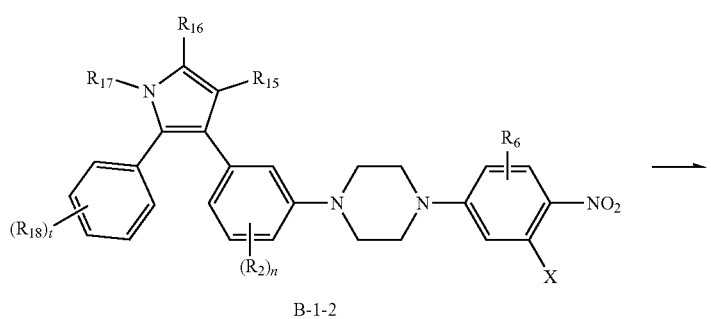
B-1-2

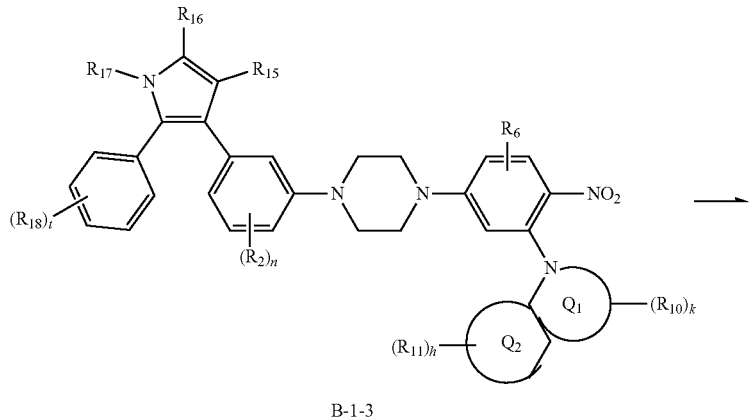
B-1-3
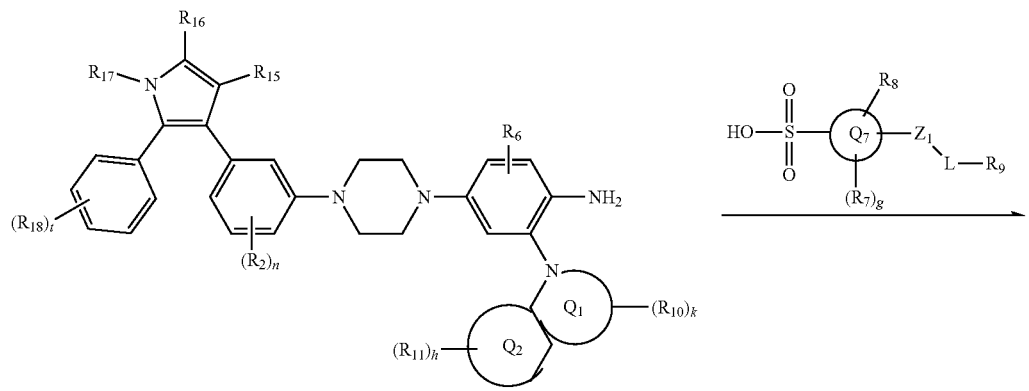
B-1-4
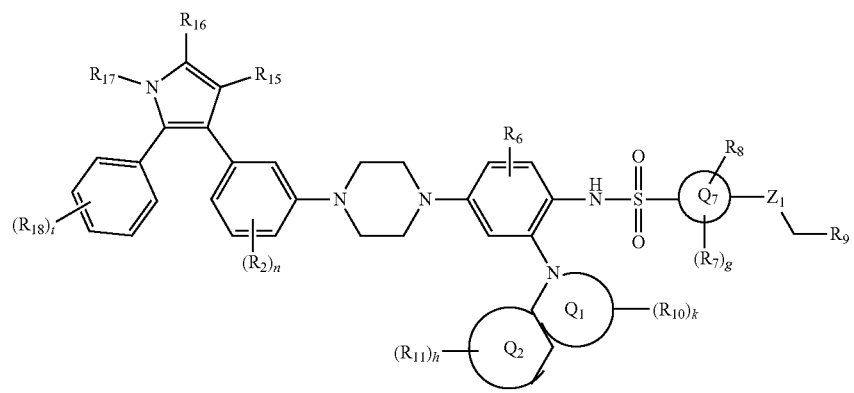
Formula (B-1)

In Scheme B-1, the appropriate staring material B-1-1 can be prepared by the methods similar to those described in US/2012/0189539 and WO2014/113413. B-1-1 undergoes nucleophilic aromatic substitution reaction to give B-1-2, which can react with appropriate amine to obtain B-1-3. After that B-1-3 can be reduced to the amine intermediate B-1-4, which can finally react with appropriate sulfuric acid intermediate to afford the final product with Formula (B-1).

Similarly, the compounds of

Formula (A-3)

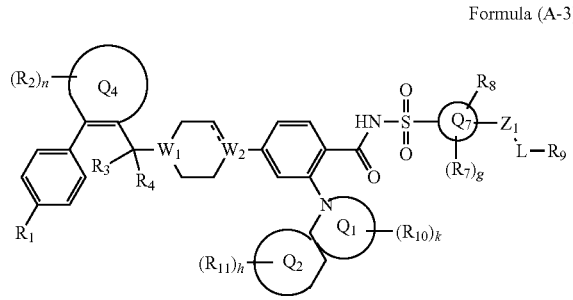

can be prepared by the method similar to above Schemes by using appropriate staring materials and intermediates.

Similarly, the compounds of

Formula (A-2)

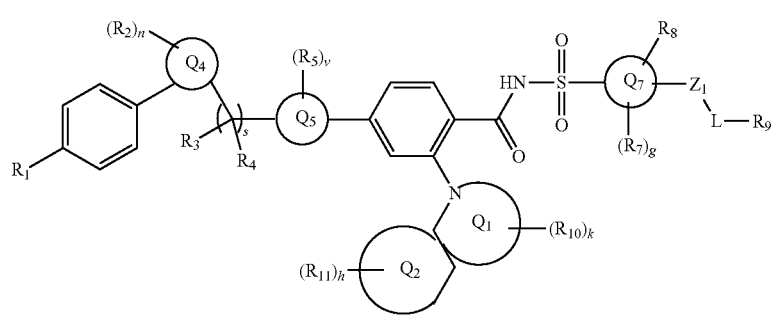

can be prepared by the method similar to above the Schemes by using appropriate staring materials and intermediates.

Similarly, the compounds of

Formula (A-1)

can be prepared by the method similar to above Schemes by using appropriate staring materials and intermediates.

Similarly, the compounds of

Formula (A)

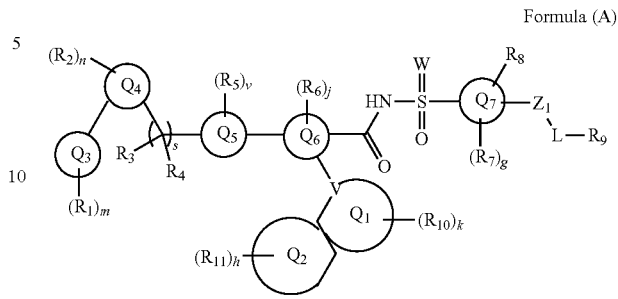

can be prepared by the method similar to above the Schemes by using appropriate staring materials and intermediates.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1$H spectra were obtained on XL400 (400 MHz) and are reported as ppm down field from Me₄Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column:

Example Int-1

Preparation of 1-((4'-chloro-5,5-dimethyl-3,4,5,6-tetrahydro-[1,1'-biphenyl]-2-yl)methyl)piperazine Synthesis of 2-bromo-4,4-dimethylcyclohex-1-enecarbaldehyde 2: A solution of anhydrous chloroform (57 ml) and anhydrous N,N-dimethylformamide (9 mL) were cooled to 3° C. (internal temperature) under nitrogen before phosphorus tribromide (10 mL, 0.1 mol) was introduced dropwise at a rate so that the reaction was maintained at 3° C. After the addition was complete the reaction was allowed to warm slowly to 10° C. and then the temperature was raised to 70° C. where it was maintained for 30 min. The reaction was cooled to rt and 3,3-dimethylcyclohexanone 1 (5 g, 0.04 mol) was added slowly over 20 min. After the addition was complete the reaction was warmed to 70° C. and it was stirred for 1.5 h. The mixture was then cooled to 0° C. and a solution of 4M sodium acetate (53 ml) was added slowly. The pH of the resulting solution was adjusted to 7 using a solution of 5M NaOH and the mixture was then extracted with heptanes (100 mL×3). The combined organic fractions were dried ($Na_2SO_4$), filtered and concentrated under reduced pressure to give 2-bromo-4,4-dimethylcyclohex-1-enecarbaldehyde 2 (4 g, 49%) as a yellow oil.

Synthesis of 2-(4-chlorophenyl)-4,4-dimethylcyclohex-1-enecarbaldehyde 3: To a degassed solution of 2-bromo-4,4-dimethylcyclohex-1-enecarbaldehyde 2 (5 g, 0.023 mol) and 4-chlorophenyl boronic acid (3.6 g, 0.023 mol) in 1,4-dioxane (50 mL) at rt was added a solution of 2M $Na_2CO_3$ (20.4 ml). Nitrogen was bubbled through the mixture for 2 min and then $PdCl_2(dppf)$ (0.5 g) was added. The reaction flask was heated to 120° C. where it was maintained for 3 h. After this time the suspension was cooled to rt and filtered through Celite. The collected solids were washed with additional dichloromethane and the combined filtrate and washings were concentrated under reduced pressure. Purification by column chromatography on silica with PE:EA=20:1 gave 2-(4-chlorophenyl)-4,4-dimethylcyclohex-1-enecarbaldehyde 3 (3 g, 53%) as a white solid. MS: 249[M+H]⁺

Synthesis of (2-(4-chlorophenyl)-4,4-dimethylcyclohex-1-enyl)methanol 4: A solution of 2-(4-chlorophenyl)-4,4-dimethylcyclohex-1-enecarbaldehyde 3 (20 g, 80.6 mmol) in MeOH (100 mL) was cooled to 0° C., $NaBH_4$ (3.1 g, 80.6 mmol) was added portionwise to the reaction at a rate so that the reaction was maintained at 0~5° C. After added, the mixture was stirred for 1 h at 0° C. Water was added slowly to the mixture and extracted with EA (200 mL×3), the organic layer was washed with brine and dried $Na_2SO_4$, filtered and concentrated under reduced pressure to give (2-(4-chlorophenyl)-4,4-dimethylcyclohex-1-enyl)methanol 4 (15 g, 75%) as a white solid. MS: 233[M+H–$H_2O$]⁺.

Synthesis of 1-(2-(bromomethyl)-5,5-dimethylcyclohex-1-enyl)-4-chlorobenzene 5: A solution of (2-(4-chlorophenyl)-4,4-dimethylcyclohex-1-enyl)methanol 4 (15 g, 0.060 mol) and in $Et_2O$ (300 ml) was cooled to 0° C. before phosphorus tribromide (7.5 mL) was added dropwise to the mixture, after added, the mixture was stirred for 1 h at 0° C. for 90 minutes. The reaction mixture was added $H_2O$ before being extracted with EA. The organic layer was washed with a saturated $NaHCO_3$ solution and brine and dried $Na_2SO_4$, filtered and concentrated under reduced pressure to give 1-(2-(bromomethyl)-5,5-dimethylcyclohex-1-enyl)-4-chlorobenzene 5 (18 g, 96%) as a colorless oil.

Synthesis of tert-butyl 4-((2-(4-chlorophenyl)-4,4-dimethylcyclohex-1-enyl)methyl)piperazine-1-carboxylate—To a solution of 1-bromo-2-(bromomethyl)-5,5-dimethylcyclohex-1-ene 5 (21 g, 0.067 mol) and tert-butyl piperazine-1-carboxylate (12.4 g, 0.067 mol) in dichloromethane (200 ml) at rt was added TEA (12.2 g, 0.12 mol). The reaction was stirred for 2 h. The reaction mixture was concentrated under reduced pressure to give the crude product. Purification by column chromatography on silica with PE:EA=20:1 provided tert-butyl 4-((2-(4-chlorophenyl)-4,4-dimethylcyclohex-1-enyl)methyl)piperazine-1-carboxylate 6 (21 g, 75%).

Synthesis of 1-((2-(4-chlorophenyl)-4,4-dimethylcyclohex-1-enyl)methyl)piperazine hydrogen chloride: To a solution of tert-butyl 44(2-(4-chlorophenyl)-4,4-dimethylcyclohex-1-enyl)methyl)piperazine-1-carboxylate 6 (30 g, 0.072 mol) in MeOH (20 ml) was added conc. HCl (50 mL). The reaction was stirred for 24 hours and then concentrated under reduced pressure. A saturated solution of $Na_2CO_3$ was added to adjust the pH to 8-9 and the mixture was extracted with dichloromethane (×2). The combined extracts were washed with brine, dried ($Na_2SO_4$), filtered and concentrated under reduced pressure. The oil product was treated with MeOH/HCl (g) (3M, 500 mL) and stirred for 1 hour, then concentrated under reduced pressure to get the product 1-((2-(4-chlorophenyl)-4,4-dimethylcyclohex-1-enyl) methyl)piperazine hydrogen chloride IM-14-1 (23 g, 83%). MS: 319[M+H]⁺ ¹H NMR (400 MHz, DMSO) δ 11.51 (s, 1H), 9.60 (s, 1H), 9.18 (s, 1H), 7.45 (d, J=8.2 Hz, 2H), 7.15 (d, J=8.0 Hz, 2H), 3.43 (s, 8H), 2.84 (s, 2H), 2.39 (s, 2H), 2.03 (s, 2H), 1.45 (t, J=6.0 Hz, 2H), 0.96 (s, 6H).

Example Int-2

Preparation of 3-nitro-4-(((tetrahydro-2H-pyran-4-yl)methyl)amino)benzenesulfonamide To a 500 mL three-neck RB flask equipped with a mechanical stirrer were charged the 4-chloro-3-nitrobenzenesulfonamide (23.7 g, 100 mmol), DIPEA (12.9 g, 100 mmol), (tetrahydro-2H-pyran-4-yl)methanamine (11.5 g, 100 mmol) and acetonitrile (200 mL). The reaction mixture was adjusted to an internal temperature of 80° C. and agitated for no less than 12 hours. The product solution was cooled down to 40° C. and agitated for no less than 1 hour until precipitation observed. The product slurry was further cooled to 20° C. Water (80 mL) was slowly charged over no less than 1 hour, and the mixture cooled to 10° C. and agitated for no less than 2 hours before collected by filtration. The wet cake was washed with 1:1 mix of acetonitrile:water (40 mL). The wet cake was rinsed with water (80 mL) at 40° C. for no less than 1 hour before collected by filtration. The wet cake was rinsed with water (20 mL), and dried at 75° C. under vacuum to give the 3-nitro-4-(((tetrahydro-2H-pyran-4-yl)methyl)amino)benzenesulfonamide (24.5 g, 78%) as an orange solid. ¹H NMR (400 MHz, DMSO) δ 8.60 (t, J=5.9 Hz, 1H), 8.48 (d, J=2.2 Hz, 1H), 7.84 (dd, J=9.2, 2.0 Hz, 1H), 7.54-7.18 (m, 3H), 3.86 (dd, J=11.3, 3.2 Hz, 2H), 3.35 (s, 2H), 3.27 (t, J=10.9 Hz, 2H), 1.92 (ddd, J=11.2, 7.4, 3.9 Hz, 1H), 1.62 (d, J=11.4 Hz, 2H), 1.27 (qd, J=12.3, 4.4 Hz, 2H).

Example Int-3

Preparation of 4-[[(4-fluorooxan-4-yl)methyl]amino]-3-nitrobenzene-1-sulfonamide Into a 50-mL round-bottom flask, was placed (4-fluorooxan-4-yl)methanamine hydrochloride (500 mg, 2.95 mmol, 1.00 equiv), 4-fluoro-3-nitrobenzene-1-sulfonamide (650 mg, 2.95 mmol, 1.00 equiv), tetrahydrofuran (15 mL), $Cs_2CO_3$ (2.8 g, 8.59 mmol, 3.00 equiv). The resulting solution was stirred for 14 h at 50° C. in an oil bath. The reaction mixture was cooled to room temperature. The resulting mixture was filtered and concentrated under vacuum. The residue was applied onto a silica gel column with ethyl acetate/petroleum ether (4:1). This resulted in 650 mg (66%) of 4-[[(4-fluorooxan-4-yl)methyl]amino]-3-nitrobenzene-1-sulfonamide as a yellow solid. LCMS (ES, m/z): M+1: 334. H-NMR: (300 MHz, DMSO, ppm): δ 8.58 (t, J=6.3 Hz, 1H), 8.49 (d, J=2.1 Hz, 1H), 7.90-7.80 (m, 1H), 7.44 (d, J=9.3 Hz, 1H), 7.34 (s, 2H), 3.87-3.70 (m, 4H), 3.61-3.50 (m, 2H), 1.95-1.70 (m, 4H).

Example Int-4

Preparation of (S)-4-((1,4-dioxan-2-yl)methylamino)-3-nitrobenzenesulfonamide

Synthesis of (R)-1-chloro-3-(2-chloroethoxy)propan-2-ol: (R)-2-(chloromethyl)oxirane (500.0 g, 5.4 mol, 1.00 equiv) was slowly added to a stirred solution of 2-chloroethanol (870.0 g, 10.8 mol, 2.00 equiv) and $BF_3 \cdot Et_2O$ (38.0 g, 27 mmol, 0.05 equiv) at 45° C. The reaction mixture was heated on an oil bath for 3 h at 45° C. The reaction mixture was cooled to R,T and Diethyl ether (100 mL) was added to this solution. The organic layer was washed with water (2×300 mL), dried over magnesium sulfate, and concentrated to yield a light brown liquid (R)-1-chloro-3-(2-chloroethoxy)propan-2-ol (800.0 g, quantitative). H-NMR: (300 MHz, DMSO-$d_6$, ppm) δ: 3.85-3.47 (m, 9H).

Synthesis of (R)-2-((2-chloroethoxy)methyl)oxirane. (R)-1-chloro-3-(2-chloroethoxy)propan-2-ol (800.0 g, crude, 4.7 mol, 1.0 eq) was added dropwise to a stirred solution of NaOH (465.0 g, 11.6 mol, 2.5 eq) in water (500 mL) on an ice-bath. The ice-bath was immediately removed after addition of (R)-1-chloro-3-(2-chloroethoxy)propan-2-ol. After stirring 2 h at an ambient temperature, diethyl ether (1.5 L) and water (500 mL) were added. The organic layer was washed with water (1×50 mL), dried over sodium sulfate, and concentrated to give a light brown liquid (R)-2-((2-chloroethoxy)methyl)oxirane (400.0 g). H-NMR: (300 MHz, CDCL3, ppm) δ: 3.82-3.52 (m, 5H), 3.40-3.35 (m, 1H), 3.11-3.09 (m, 1H), 2.75-2.73.

Synthesis of (S)-(1,4-dioxan-2-yl)methanol. (R)-2-((2-chloroethoxy)methyl)oxirane (400.0 g, 2.94 mol, 1.0 eq) was added to a solution of NaOH (294.0 g, 7.35 mol, 2.5 eq) in water (2900 mL) at room temperature. The reaction mixture was heated on an oil bath for 2 h at 90° C. The resulting solution was cooled to R,T and adjusted PH value to 5 by HCl (6 M). The mixture was concentrated and the residue was distilled (90-95° C., 0.1 kPa) under vacuum pump to give a colorless oil (S)-(1,4-dioxan-2-yl)methanol (110 g, 31.7%). H-NMR: (300 MHz, CDCL3, ppm) δ: 3.85-3.42 (m, 9H), 2.15 (bs, 1H).

Synthesis of (R)-(1,4-dioxan-2-yl)methyl methanesulfonate. A mixture of (S)-(1,4-dioxan-2-yl)methanol (50.0 g, 0.42 mol, 1.0 eq), TEA (63.6 g, 0.63 mol, 1.5 eq) and DCM (500 mL) at ice-bath, MsCl (48.1 g, 0.42 mol, 1.0 eq) was added dropwise. And then, the ice-bath removed and the mixture was stirred at R,T for 2 hours. The reaction mixture was washed by water (2×50 mL) and the organic phase was dried over sodium sulfate, and concentrated to give a light brown oil (R)-(1,4-dioxan-2-yl)methyl methanesulfonate (71.0 g, 83%). H-NMR: (300 MHz, CDCL3, ppm) δ: 4.23-4.20 (m, 2H), 3.82-3.56 (m, 6H), 3.50-3.40 (m, 1H), 3.02 (m, 3H).

Synthesis of (S)-(1,4-dioxan-2-yl)methanamine: In 1000 mL autoclave, to a solution of (R)-(1,4-dioxan-2-yl)methyl methanesulfonate (70.0 g, 0.36 mol, 1.0 eq) in $NH_3 \cdot MeOH$ (7 M, 500 mL) was stirred at 80° C. for 12 hours, the reaction mixture was cooled to R,T and concentrated to give a light brown oil (S)-(1,4-dioxan-2-yl)methanamine (30.0 g, 73%). NMR: (300 MHz, DMSO-$d_6$, ppm) δ: 8.27 (bs, 2H), 3.82-3.42 (m, 6H), 3.24-3.20 (m, 1H), 2.98-2.62 (m, 2H).

Synthesis of (S)-4-((1,4-dioxan-2-yl)methylamino)-3-nitrobenzenesulfonamide: A mixture of (S)-(1,4-dioxan-2-yl)methanamine (25.0 g, 0.21 mol, 1.0 eq), 4-fluoro-3-nitrobenzenesulfonamide (46.0 g, 0.21 mol, 1.0 eq) and $Cs_2CO_3$ (137.3 g, 0.42 mol, 2.0 eq) in THF (700 mL) was stirred at 50° C. for 6 hours, LCMS showed material was consumed completely, the reaction mixture was cooled R,T and poured into water (3500 mL). The mixture was filtered and collected filtrate cake and dried by oven to give a yellow solid (5)-4-((1,4-dioxan-2-yl)methylamino)-3-nitrobenzenesulfonamide (60.0 g, 89.5%). H-NMR: (300 MHz, DMSO-$d_6$, ppm) δ: 8.52-8.47 (m, 2H), 7.86-7.83 (m, 1H), 7.28-7.00 (m, 3H), 3.82-3.29 (m, 9H).

Example Int-5

Preparation of methyl 2-bromo-4-(4-[[2-(4-chlorophenyl)-4,4-dimethylcyclohex-1-en-1-yl]methy]piperazin-1-yl)benzoate Into a 250-mL round-bottom flask, was placed a solution of Example 1-1, i.e, 1-[[2-(4-chlorophenyl)-4,4-dimethylcyclohex-1-en-1-yl]methyl]piperazine (15.09 g, 47.32 mmol, 1.00 equiv) in DMA (150 mL), DIEA (12.9 g, 99.81 mmol, 2.00 equiv), methyl 2-bromo-4-fluorobenzoate (11.6 g, 49.78 mmol, 1.00 equiv). The resulting solution was stirred for 12 h at 100 degree. The reaction mixture was cooled to room temperature. The reaction was then quenched by the addition of 50 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 7 g (crude) of methyl 2-bromo-4-[[2-(4-chlorophenyl-4,4-dimethylcyclohex-1-en-1-yl]methyl]piperazin-1-yl)benzoate as yellow oil. LC-MS: (ES, m/z): M+1=533, 531.

Example Int-6

Preparation of 2-bromo-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide Synthesis of methyl 2-bromo-4-(4-((2-(4-chlorophenyl)-4,4-dimethylcyclohex-1-enyl)methyl)piperazin-1-yl)benzoate Into a 20000-mL round-bottom flask, was placed 1-((2-(4-chlorophenyl)-4,4-dimethylcyclohex-1-enyl)methyl)piperazine dihydrochloride (600 g, 1.53 mol, 1 equiv), methyl 2-bromo-4-fluorobenzoate (357 g, 1.53 mol, 1 equiv), DBU (319 g, 6.12 mol, 4 equiv) and DMSO (8000 mL). The resulting solution was stirred for 20 h at 70 degrees C. LCMS showed material was completely consumed. The resulting mixture was cooled to R,T and poured into water (32 L). The mixture was filtrated, collection of filter cake and the filter cake was washed by water (3000 mL×3) and dried by oven to give product 740 g (Y: 91%) methyl 2-bromo-4-(4-((2-(4-chlorophenyl)-4,4-dimethylcyclohex-1-enyl)methyl)piperazin-1-yl)benzoate as a white solid. H-NMR-PH-PHNW-4-55-400: (300 MHz, DMSO-$d_6$, ppm) δ: 7.73 (d, J=9.0 Hz, 1H), 7.42-7.39 (m, 2H), 7.18-7.12 (m, 3H), 6.97-6.94 (m, 1H), 4.00-3.84 (m, 2H), 3.76 (s, 2H), 3.57 (s, 3H), 3.51-3.33 (m, 4H), 2.79-2.60 (m, 2H), 2.32-2.30 (m, 2H), 2.03-1.97 (m, 2H), 1.47-1.45 (m, 2H), 0.96 (s, 6H).

Synthesis of 2-bromo-4-(4-((2-(4-chlorophenyl)-4,4-dimethylcyclohex-1-enyl)methyl)piperazin-1-yl)benzoic acid: Into a 20000-mL round-bottom flask, was placed methyl 2-bromo-4-(4-((2-(4-chlorophenyl)-4,4-dimethylcyclohex-1-enyl)methyl)piperazin-1-yl)benzoate (730 g, 1.37 mol, 1 equiv), LiOH (131.5 g, 5.48 mol, 4 equiv) and MeOH/THF/water (4500 mL/3000 mL/1000 mL). The resulting solution was stirred for 16 h at 70 degrees C. LCMS showed material was completely consumed. The resulting mixture was cooled to R,T and concentrated. The residue was diluted with water (5000 mL) and the mixture was adjust PH to 3-5 with HCl (6 M), followed by filtrated, collection of filter cake and dried by oven to give product 650 g (Y: 93%) 2-bromo-4-(4-((2-(4-chlorophenyl)-4,4-dimethylcyclohex-1-enyl)methyl)piperazin-1-yl)benzoic acid as a white solid. H-NMR-PH-PHNW-4-55-400: (300 MHz, DMSO-$d_6$, ppm) δ: 10.60 (bs, 1H), 7.73 (d, J=8.4 Hz, 1H), 7.42-7.39 (m, 2H), 7.14-7.11 (m, 3H), 6.95-6.92 (m, 1H), 4.00-3.84 (m, 2H), 3.76 (s, 2H), 3.51-3.33 (m, 4H), 2.79-2.60 (m, 2H), 2.32-2.30 (m, 2H), 2.03-1.97 (m, 2H), 1.47-1.45 (m, 2H), 0.97 (s, 6H).

Synthesis of 2-bromo-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide: Into a 20000-mL round-bottom flask, was placed 2-bromo-4-(4-((2-(4-chlorophenyl)-4,4-dimethylcyclohex-1-enyl)methyl)piperazin-1-yl)benzoic acid (583 g, 1.13 mol, 1 equiv), DCM (10 L), 3-nitro-4-[[(oxan-4-yl)methyl]amino]benzene-1-sulfonamide (338 g, 1.07 mol, 0.95 equiv), EDCI (326 g, 1.7 mol, 1.5 equiv), DMAP (551 g, 4.52 mol, 4 equiv). The resulting solution was stirred for overnight at 25 degrees C. LCMS showed material was completely consumed. The resulting mixture is followed by dilute hydrochloric acid (1.0 M) (1000 mL×3), saturated sodium bicarbonate (1000 mL×3) and brine (1000 mL×1), and then the organic phase was dried by $Na_2SO_4$, filtrated. The filtrate was concentrated to give product 857 g (Y: 93%) as a light brown yellow solid 2-bromo-4-(4-((2-(4-chlorophenyl)-4,4-dimethylcyclohex-1-enyl)methyl)piperazin-1-yl)-N-(3-nitro-4-((tetrahydro-2H-pyran-4-yl)methylamino)phenylsulfonyl)benzamide as a brown yellow solid. LC-MS: (ES, m/z): M+1=814/816/818, R,T=2.01 min. H-NMR-PH-PHNW-4-55-400: (300 MHz, DMSO-$d_6$, ppm) δ: 8.63-8.61 (m, 2H), 7.94-7.92 (m, 1H), 7.37-7.35 (m, 3H), 7.27-7.24 (m, 1H), 7.05-7.02 (m, 3H), 6.86-6.83 (m, 1H), 3.87-3.82 (m, 2H), 3.37-3.23 (m, 8H), 2.92 (s, 2H), 2.50-2.38 (m, 4H), 2.22-2.20 (m, 2H), 2.00-1.97 (m, 2H), 1.64-1.60 (m, 2H), 1.48-1.46 (m, 2H), 1.26-1.20 (m, 2H), 0.97 (s, 6H).

Example Int-7

Preparation of 4-[[2-(trimethylsilyl)ethoxy]methyl]-16-oxa-2,4,10-triazatricyclo[7.7.0.0^[3,7]]hexadeca-1(9),2,5,7-tetraene Synthesis of 5-[(5-bromo-1-[[2-(trimethylsilyl)ethoxy]methyl]-1H-pyrrolo[2,3-b]pyridin-6-yl)oxy]pentan-1-ol:
Into a 500-mL round-bottom flask purged and maintained with an inert atmosphere of nitrogen, was placed pentane-1,5-diol (9.07 g, 87.087 mmol, 2.00 equiv), THF (200 mL). This was followed by the addition of NaH (5.23 g, 130.762 mmol, 3.01 equiv, 60%), in portions at 0 degrees C. The resulting solution was stirred for 0.5 h at 0 degrees C. To this was added 5-bromo-6-fluoro-1-[[2-(trimethylsilyl)ethoxy]methyl]-1H-pyrrolo[2,3-b]pyridine (15 g, 43.442 mmol, 1 equiv) at 0 degrees C. The resulting solution was stirred overnight at 60 degrees C. in an oil bath. The reaction mixture was cooled to 25 degree C. The reaction was then quenched by the addition of 1000 mL of water. The resulting solution was extracted with 3×300 mL of ethyl acetate and the organic layers combined. The resulting mixture was washed with 2×1000 ml of brine. The mixture was dried over anhydrous sodium sulfate and concentrated under vacuum. The residue was applied onto a silica gel column with ethyl acetate/petroleum ether (1:3). This resulted in 7 g (37.52%) of 5-[(5-bromo-1-[[2-(trimethylsilyl)ethoxy]methyl]-1H-pyrrolo[2,3-b]pyridin-6-yl)oxy]pentan-1-ol as yellow oil. LC-MS (ES, m/z): 429.1 [M+H]

Synthesis of N-[6-[(5-hydroxypentyl)oxy]-1-[[2-(trimethylsilyl)ethoxy]methyl]-1H-pyrrolo[2,3-b]pyridin-5-yl]-4-methylbenzene-1-sulfonamide: Into a 250-mL round-bottom flask purged and maintained with an inert atmosphere of nitrogen, was placed 5-[(5-bromo-1-[[2-(trimethylsilyl)ethoxy]methyl]-1H-pyrrolo[2,3-b]pyridin-6-yl)oxy]pentan-1-ol (7 g, 16.301 mmol, 1 equiv), DMSO (50 mL), 4-methylbenzene-1-sulfonamide (5.6 g, 32.708 mmol, 2.01 equiv), methyl[2-(methylamino)ethyl]amine (864 mg, 9.801 mmol, 0.60 equiv), CuI (1.87 g, 9.819 mmol, 0.60 equiv), $K_2CO_3$ (6.77 g, 48.985 mmol, 3.01 equiv). The resulting solution was stirred for 7 days at 125 degrees C. in an oil bath. The reaction mixture was cooled to 25 degree C. The resulting solution was diluted with 500 mL of water. The resulting solution was extracted with 3×200 mL of ethyl acetate and the organic layers combined. The resulting mixture was washed with 2×1000 ml of brine. The mixture was dried over anhydrous sodium sulfate and concentrated under vacuum. The residue was applied onto a silica gel column with ethyl acetate/petroleum ether (1:1). This resulted in 3 g (35.41%) of N-[6-[(5-hydroxypentyl)oxy]-1-[[2-(trimethylsilyl)ethoxy]methyl]-1H-pyrrolo[2,3-b]pyridin-5-yl]-4-methylbenzene-1-sulfonamide as a yellow solid. LC-MS (ES, m/z): 520.2 [M+H]

Synthesis of 5-[[5-(4-methylbenzenesulfonamido)-1-[[2-(trimethylsilyl)ethoxy]methyl]pyrrolo[2,3-b]pyridin-6-yl]oxy]pentyl methanesulfonate: Into a 250-mL 3-necked round-bottom flask purged and maintained with an inert atmosphere of nitrogen, was placed N-[6-[(5-hydroxypentyl)oxy]-1-[[2-(trimethylsilyl)ethoxy]methyl]pyrrolo[2,3-b]pyridin-5-yl]-4-methylbenzenesulfonamide (3.00 g, 5.772 mmol, 1.00 equiv), DCM (30.00 mL), TEA (1.17 g, 11.562 mmol, 2.00 equiv). This was followed by the addition of MsCl (725.00 mg, 6.329 mmol, 1.10 equiv) dropwise with stirring at 0 degrees C. The resulting solution was stirred for 2 hr at 25 degrees C. The resulting solution was poured into 200 mL of aqueous $NaHCO_3$. The resulting solution was extracted with 2×200 mL of dichloromethane and the organic layers combined and dried over anhydrous sodium sulfate. The solids were filtered out. The resulting mixture was concentrated under vacuum. The residue was applied onto a silica gel column with ethyl acetate/petroleum ether (1:1). This resulted in 2.6 g (75.35%) of 5-[[5-(4-methyl-benzenesulfonamido)-1-[[2-(trimethylsilyl)ethoxy]methyl]pyrrolo[2,3-b]pyridin-6-yl]oxy]pentyl methanesulfonate as yellow oil. LC-MS (ES, m/z): 598.2 [M+H]

Synthesis of 10-(4-methylbenzenesulfonyl)-4-[[2-(trimethylsilyl)ethoxy]methyl]-16-oxa-2,4,10-triazatricyclo[7.7.0.0ˆ[3,7]]hexadeca-1(9),2,5,7-tetraene: Into a 100-mL round-bottom flask, was placed 5-[[5-(4-methylbenzenesulfonamido)-1-[[2-(trimethylsilyl)ethoxy]methyl]pyrrolo[2,3-b]pyridin-6-yl]oxy]pentyl methanesulfonate (2.36 g, 3.948 mmol, 1.00 equiv), DMF (30 mL), $Cs_2CO_3$ (2.57 g, 7.888 mmol, 2.00 equiv). The resulting solution was stirred overnight at 25 degrees C. The reaction was then quenched by the addition of 300 mL of water. The resulting solution was extracted with 3×100 mL of ethyl acetate and the organic layers combined. The resulting mixture was washed with 1×500 ml of brine. The mixture was dried over anhydrous sodium sulfate. The solids were filtered out. The resulting mixture was concentrated under vacuum. The residue was applied onto a silica gel column with ethyl acetate/petroleum ether (1:3). This resulted in 230 mg (11.61%) of 10-(4-methylbenzenesulfonyl)-4-[[2-(trimethylsilyl)ethoxy]methyl]-16-oxa-2,4,10-triazatricyclo[7.7.0.0ˆ[3,7]]hexadeca-1(9),2,5,7-tetraene as yellow oil. LC-MS: (ES, m/z): 502.2 [M+H]. $^1$H NMR (300 MHz, Chloroform-d, ppm): δ 7.89 (s, 1H), 7.66-7.51 (m, 2H), 7.27-7.20 (m, 3H), 6.48 (d, J=3.6 Hz, 1H), 5.58 (s, 2H), 4.39 (s, 2H), 3.84-3.69 (m, 2H), 3.64-3.44 (m, 2H), 2.43 (s, 3H), 1.68 (s, 2H), 1.50 (s, 4H), 1.01-0.85 (m, 2H), −0.04 (s, 9H).

Synthesis of 4-[[2-(trimethylsilyl)ethoxy]methyl]-16-oxa-2,4,10-triazatricyclo[7.7.0.0ˆ[3,7]]hexadeca-1(9),2,5,7-tetraene: Into a 40-mL vial purged and maintained with an inert atmosphere of nitrogen, was placed Na (63.00 mg, 2.740 mmol, 5.98 equiv), Naphthalene (353.00 mg, 2.754 mmol, 6.01 equiv), DME (5.00 mL). The mixture was stirred at room temperature for 40 min until the formation of Na/naphthalene was complete. Another 40-mL vial purged and maintained with an inert atmosphere of nitrogen, was placed 10-(4-methylbenzenesulfonyl)-4-[[2-(trimethylsilyl)ethoxy]methyl]-16-oxa-2,4,10-triazatricyclo[7.7.0.0ˆ[3,7]]hexadeca-1(9),2,5,7-tetraene (230.00 mg, 0.458 mmol, 1.00 equiv), THF (5.00 mL). This was followed by the addition of above Na/naphthalene solution at −78 degrees C. The resulting solution was stirred for 2 hr at 25 degrees C. The reaction was then quenched by the addition of 100 mL of aqueous $NH_4Cl$. The resulting solution was extracted with 2×50 mL of ethyl acetate and the organic layers combined. The resulting mixture was washed with 1×100 ml of brine. The mixture was dried over anhydrous sodium sulfate and concentrated under vacuum. The residue was applied onto a silica gel column with ethyl acetate/petroleum ether (1:3). This resulted in 138 mg (86.62%) of 4-[[2-(trimethylsilyl)ethoxy]methyl]-16-oxa-2,4,10-triazatricyclo[7.7.0.0ˆ[3,7]]hexadeca-1(9),2,5,7-tetraene as yellow oil. LC-MS (ES, m/z): 348.2 [M+H].

Example INT-8

Preparation of 54(2-(trimethylsilyl)ethoxy)methyl)-1,5-dihydropyrazolo[4,3-b]pyrrolo[3,2-e]pyridine General procedure for preparation of compound 2: To a solution of 5-bromo-6-methyl-1H-pyrrolo[2,3-b]pyridine (10 g, 47.4 mmol, 1.00 eq) in DMF (150.00 mL), the mixture was cooled to 0° C. and NaH (2.84 g, 71 mmol, 60% purity, 1.50 eq) was added to the mixture. The reaction mixture was stirred at 0° C. for 1 hr, 2-(chloromethoxy)ethyl-trimethyl-silane (10.3 g, 61.6 mmol, 11 mL, 1.30 eq) was added dropwise to the mixture. The mixture was stirred at 25° C. for 3 hr. TLC indicated 0% of Reactant 1 was remained, and one major new spot with larger polarity (Petroleum ether: Ethyl acetate=5:1, Rf=0.51) was detected. The mixture was poured into $NH_4Cl$ solution (40 ml), concentrated, then extracted with EA (30 ml×3), combine the organic layers, washed with brine (20 ml), and concentrated to give crude product. The residue was purified by column chromatography (SiO2, Petroleum ether/Ethyl acetate=100/1 to 5:1). Compound 2 (10.00 g, 29.30 mmol, 61.84% yield) was obtained. $^1$H NMR: ET6225-38-P1A 400 MHz $CDCl_3$ δ 8.01 (s, 1H), 7.26 (d, J=3.2 Hz, 1H), 6.40 (d, J=3.2 Hz, 1H), 5.62 (s, 2H), 3.55 (t, J=16 Hz, 2H), 2.75 (s, 3H), 0.91 (t, J=16 Hz, 2H), 0.07 (s, 9H).

General procedure for preparation of compound 3: A mixture of compound 2 (5.50 g, 16.1 mmol, 1.00 eq), diphenylmethanimine (3.50 g, 19.3 mmol, 1.20 eq), Xantphos (1.86 g, 3.22 mmol, 0.20 eq), $Cs_2CO_3$ (10.5 g, 32.2 mmol, 2.00 eq) in dioxane (150 mL) was degassed and purged with $N_2$ for 3 times, and then $Pd_2(dba)_3$ (885 mg, 966 umol, 0.06 eq) was added to the mixture. Then the mixture was stirred at 100° C. for 15 hour under $N_2$ atmosphere. TLC (Petroleum ether/Ethyl acetate=5:1) showed many spot. The desired compound was detected by LCMS (RT=1.363). The reaction mixture was concentrated under reduced pressure to give a residue. The crude product 3 was used into the next step without further purification General procedure for preparation of compound 4: A mixture of crude compound 3 (8.00 g, 11.8 mmol, 1.00 eq), 0.5 N HCl (100 mL), in THF (100 mL) was degassed and purged with $N_2$ for 3 times, and then the mixture was stirred at 25° C. for 14 hour under $N_2$ atmosphere. TLC (Petroleum ether/Ethyl acetate=3:1) showed the desired product was detected. The mixture was quenched by aq. $NaHCO_3$ (200 ml) to adjust pH=8, then extracted with Ethyl acetate (100 ml×3), combine the organic layers, washed with brine (100 ml), dried over sodium sulfate, concentrated to give crude product. The residue was purified by column chromatography (SiO2, Petroleum ether/Ethyl acetate=100/1 to 5:1) Compound 4 (3 g, 8.65 mmol, 73.5% yield, 80% purity) was obtained as a solid. $^1$H NMR: ET6225-46-P1A 400 MHz $CDCl_3$ δ 7.25 (s, 2H), 6.42 (s, 1H), 5.67 (s, 2H), 3.60 (t, J=8 Hz, 2H), 2.62 (s, 3H), 0.98 (t, J=8 Hz, 2H), 0.04 (s, 9H).

General procedure for preparation of compound 5: A mixture of compound 4 (2.00 g, 7.21 mmol, 1.00 eq) and $Ac_2O$ (1.6 g, 15.6 mmol, 2.2 eq) in $CHCl_3$ (50.00 mL) was added AcOK (7.08 g, 72.10 mmol, 10 eq), and then the mixture was stirred at 25° C. for 3 hr, under $N_2$ atmosphere. then isoamyl nitrate (3.38 g, 28.8 mmol, 4 eq) was added, heated to 60° C. for 14 hr, TLC (Petroleum ether/Ethyl acetate=3:1, Rf (product=0.43) showed the starting material was consumed completely. The mixture was quenched by aq. $NaHCO_3$ (200 ml), then extracted with DCM (100 ml×3), combine the organic layers, washed with brine (100 ml), dried over sodium sulfate, concentrated to give crude product. The residue was purified by column chromatography (SiO2, Petroleum ether/Ethyl acetate=100/1 to 5:1). Compound 5Ac (600 mg, 21.36% yield, 85% purity) and N-[6-methyl-1-(2-trimethylsilylethoxymethyl)pyrrolo[2,3-b]pyridin-5-yl]acetamide (1.50 g, 4.70 mmol, 65.12% yield) were obtained.

A mixture of Compound 5_Ac (600 mg, 1.82 mmol, 1.00 eq) in MeOH (5 mL) was added K₂CO₃ (753 mg, 5.45 mmol, 3.00 eq), and then the mixture was stirred at 25° C. for 2 hr, under N₂ atmosphere. TLC showed none of Compound 5 was remained. The mixture was poured into water (200 ml), and then extracted with DCM (100 ml×3), combine the organic layers, washed with brine (100 ml), and dried over sodium sulfate, concentrated to give crude product. The residue was purified by column chromatography (SiO2, Petroleum ether/Ethyl acetate=100/1 to 5:1). Compound 5 (500 mg, 95.25% yield) was obtained as a yellow solid. ¹H NMR: ET6225-47-P1A 400 MHz CDCl₃ δ 9.05 (s, 1H), 8.45 (s, 1H), 7.64 (s, 1H), 6.77 (s, 1H), 5.82 (s, 2H), 3.65 (t, J=8 Hz, 2H), 2.90 (s, 3H), 1.01 (t, J=8 Hz, 2H), 0.01 (s, 9H). ¹H NMR: ET6225-51-P1A 400 MHz CDCl₃ δ 8.05 (s, 1H), 7.60 (s, 1H), 6.66 (s, 1H), 5.82 (s, 2H), 3.67 (t, J=16 Hz, 2H), 1.01 (t, J=16 Hz, 2H), 0.04 (s, 9H).

Example 1

Preparation of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(pyrazolo[4,3-b]pyrrolo[3,2-e]pyridin-1(5H)-yl)benzamide A mixture of compound IM-14-3 (500 mg, 1.73 mmol, 1.00 eq), ethyl 4-bromo-2-fluoro-benzoate (641 mg, 2.60 mmol, 1.50 eq), Cs₂CO₃ (1.69 g, 5.19 mmol, 3.00 eq) in DMF (10 mL) was degassed and purged with N₂ for 3 times, and then the mixture was stirred at 125° C. for 1 hour under N₂ atmosphere under microwave condition. TLC indicated the desired compound (Rf: 0.24). The reaction mixture was filtered and the filtrate was concentrated under reduced pressure to give a residue. The residue was purified by silica gel column chromatography (Petroleum ether/Ethyl acetate=100:1 to 3:1). ethyl 4-bromo-2-(54(2-(trimethylsilyl)ethoxy)methyl)pyrazolo[4,3-b]pyrrolo[3,2-e]pyridin-1(5H)-yl)benzoate (400 mg, 659 umol, 38.1% yield, 85% purity) was obtained as a yellow oil. ¹H NMR: ET6225-63-P1A 400 MHz CDCl₃ 68.50 (s, 1H) 7.90-7.96 (m, 3H) 7.72 (d, J=8.38 1H) 7.60 (d, J=3.53 Hz, 1H) 6.60 (d, J=4 Hz, 1H) 5.81 (s, 2H) 3.97-4.07 (m, 2H) 3.62-3.70 (m, 2H) 0.97-1.05 (m, 2H) 0.83 (t, J=7.28 Hz, 3H) 0.01 (s, 9H).

A mixture of ethyl 4-bromo-2-(54(2-(trimethylsilyl)ethoxy)methyl)pyrazolo[4,3-b]pyrrolo[3,2-e]pyridin-1(5H)-yl)benzoate (800 mg, 1.55 mmol, 1.00 eq), compound 7 (594 mg, 1.86 mmol, 1.20 eq), Xantphos (359 mg, 621 umol, 0.40 eq), Cs₂CO₃ (1.52 g, 4.66 mmol, 3.00 eq) in dioxane (20 mL) was degassed and purged with N₂ for 3 times, and then Pd₂(dba)₃ (284 mg, 310 umol, 0.20 eq) was added to the mixture, the mixture was stirred at 100° C. for 15 hour under N₂ atmosphere. TLC showed the reaction was completed. The desired compound (Rf: 0.24) was detected. The reaction mixture was filtered and the filtrate was concentrated under reduced pressure to give a residue. The residue was purified by silica gel chromatography (100-200 mesh silica gel, Petroleum ether/Ethyl acetate=100/1-3/1). Ethyl 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoate (600 mg, 637 umol, 41.1% yield, 80% purity) was obtained as a yellow solid. ¹H NMR: ET6225-84-p1a 400 MHz CDCl₃ δ 8.46 (s, 1H) 8.04 (d, J=8.8 Hz, 1H) 7.73-7.86 (m, 1H) 7.55 (d, J=3.5 Hz, 1H) 6.95-7.05 (m, 4H) 6.57 (d, J=3.5 Hz, 1H) 5.80 (s, 2H) 3.88 (q, J=7 Hz, 2H) 3.61-3.70 (m, 2H) 3.37 (d, J=4.8 Hz, 4H) 2.89 (s, 2H) 2.42 (d, J=4.8 Hz, 4H) 2.29 (s, 2H) 2.07 (s, 2H) 1.63 (s, 7H) 1.52 (t, J=6.39 Hz, 2H) 0.85-1.08 (m, 16H) 0.68 (t, J=7.2 Hz, 3H) 0.00 (s, 9H).

A mixture of ethyl 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoate (500 mg, 664 umol, 1.00 eq), NaOH (79.6 mg, 1.99 mmol, 3.00 eq) in MeOH (10 mL), THF (10 mL), H₂O (5 mL) was stirred at 0-25° C. for 2 hour under N₂ atmosphere. The desired compound was detected. The reaction mixture was concentrated under reduced pressure to give a residue. this residue was dissolved in water, then was adjusted to pH=4-5 with 0.5 M HCl and extracted with Ethyl acetate (20 ml×3) combine the organic layers, washed with brine, dried over sodium sulfate, concentrated to give 4-(4-((4'-chloro-5,5-dimethyl-3,4,5,6-tetrahydro-[1,1'-biphenyl]-2-yl)methyl)piperazin-1-yl)-2-(54(2-(trimethylsilyl)ethoxy)methyl)pyrazolo[4,3-b]pyrrolo[3,2-e]pyridin-1(5H)-yl)benzoic acid (400 mg, 74.8% yield, 90% purity) was obtained as a white solid. ¹H NMR: ET6225-85-p1a 400 MHz CDCl₃ δ8.45 (s, 1H) 8.07 (d, J=9.2 Hz, 1H) 7.85 (s, 1H) 7.53 (d, J=3.9 Hz, 1H) 7.30-7.34 (m, 3H) 7.00 (d, J=8.4 Hz, 2H) 6.84-6.93 (m, 2H) 6.52-6.57 (m, 1H) 5.76 (s, 2H) 3.61-3.69 (m, 2H) 3.35 (s, 3H) 2.47 (s, 2H) 2.28 (s, 2H) 2.06 (s, 2H) 1.49 (t, J=5.9 Hz, 2H) 1.27-1.36 (m, 1H) 0.96-1.05 (m, 9H), 0.01 (s, 9H).

A mixture of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoic acid (400 mg, 551 umol, 1.00 eq), and HATU (629 mg, 1.65 mmol, 3.00 eq) NH₄Cl (147 mg, 2.76 mmol, 5.00 eq) Et₃N (558 mg, 5.51 mmol, 10.00 eq) in DMF (3 mL) was stirred at 25° C. for 15 hr under N₂ atmosphere. The desired compound was detected by TLC. The reaction mixture was filtered and the filtrate was concentrated under reduced pressure to give a residue. The residue was purified by column chromatography (SiO2, DCM:MeOH=200/1 to 20:1). 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (300 mg, 75% yield) was obtained as a yellow solid. ¹H NMR: ET6225-86-p1a 400 MHz CDCl₃ δ 8.44 (s, 1H) 7.88-7.94 (m, 1H) 7.83 (d, J=8.8 Hz, 1H) 7.55-7.60 (m, 1H) 7.39 (d, J=7.9 Hz, 2H) 7.05 (d, J=7.9 Hz, 2H) 6.87 (s, 1H) 6.65 (d, J=3.5 Hz, 1H) 5.74-5.80 (s, 2H) 3.66 (m, 4H) 3.53 (br. s., 2H) 3.21-3.34 (m, 11H) 2.09-2.32 (m, 3H) 1.41 (m, 17H) 0.01 (s, 9H).

A mixture of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (300 mg, 414 umol, 1.00 eq) in THF (8 mL), then NaH (49.7 mg, 1.24 mmol, 60% purity, 3.00 eq) was added at 0° C., stirred for 0.5 hr, then 4-chloro-3-nitro-benzenesulfonyl chloride (117 mg, 456 umol, 1.10 eq) in THF (2 mL) was added, the mixture was stirred at 25° C. for 2 hr under N₂ atmosphere. The desired compound was detected. The reaction mixture was concentrated under reduced pressure to give a residue. The residue was purified by prep-TLC (SiO2, DCM/MeOH=10/1). N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200.00 mg, 211.86 umol, 51.16% yield) was obtained as yellow solid. ¹H NMR: ET6215-89-p1a 400 MHz CDCl₃ δ 8.44 (s, 1H) 7.95 (s, 1H) 7.76 (s, 1H) 7.40-7.53 (m, 1H) 6.95

(d, J=7.8 Hz, 5H) 6.75 (s, 1H) 6.51 (s, 1H) 5.71 (s, 3H) 5.30 (s, 2H) 3.50-3.65 (m, 5H) 3.26 (s, 3H) 3.06 (d, J=6.65 Hz, 2H) 2.85 (s, 1H) 2.36 (s, 2H) 2.21 (s, 1H) 2.00 (s, 4H) 1.44 (s, 1H) 1.14-1.31 (m, 8H) 0.96 (m, 13H) 0.07 (s, 9H)

A mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200 mg, 212 umol, 1.00 eq) in TFA (3.00 mL) and DCM (3.00 mL) was stirred at 25° C. for 14 hr under $N_2$ atmosphere. The desired compound (Rt=1.146) was detected on LC-MS. The reaction mixture was concentrated under reduced pressure to give a crude as a yellow solid. A mixture of the crude (150 mg, 204 umol, 1.00 eq) and cyclohexylmethanamine (69.5 mg, 614 umol, 3.00 eq) in $CH_3CN$ (4 mL) in a microwave tube, then DIPEA (79.3 mg, 614 umol, 3.00 eq) was added, the mixture was stirred at 125° C. for 14 hr under $N_2$ atmosphere under microwave. The desired compound was detected by LCMS (Rt=0.573), The reaction mixture was concentrated under reduced pressure to give a residue. The residue was purified by prep-HPLC (neutral) and the recovered product was purified by Re-prep-HPLC (TFA). Two batches of target compound CY-1401 were obtained as yellow solid. The first batch is 11 mg; the second batch is 23 mg. $^1$H NMR: ET6225-91-p1c 400 MHz DMSO 611.50 (br. s., 1H) 8.64 (s, 1H) 8.40 (s, 1H) 7.97 (s, 1H) 7.89 (s, 1H) 7.60-7.69 (m, 2H) 7.56 (m, 1H) 7.40 (m, 2H) 6.98-7.16 (m, 5H) 6.35 (s, 1H) 3.81-4.03 (m, 3H) 3.12-3.41 (m, 6H) 2.24 (m, 2H) 2.05 (s, 2H) 1.65 (m, 3H) 1.44-1.53 (m, 2H) 1.19-1.38 (m, 3H) 0.96 (s, 6H), LCMS: (M+H)$^+$: 892.2.

Example 2

Preparation of 4-(4-((4'-chloro-5,5-dimethyl-3,4,5,6-tetrahydro-[1,1'-biphenyl]-2-yl)methyl)piperazin-1-yl)-N-((3-nitro-4-((1-(tetrahydro-2H-pyran-4-yl)piperidin-4-yl)amino)phenyl)sulfonyl)-2-(pyrazolo[4,3-b]pyrrolo[3,2-e]pyridin-1(5H)-yl)benzamide To a mixture of N-((4-chloro-3-nitrophenyl)sulfonyl)-4-(4-((4'-chloro-5-methyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (1.00 g, 1.06 mmol, 1.00 eq) in dichloromethane (10 mL) was added Trifluoroacetic Acid (15.40 g, 135 mmol, 10.00 mL) in one portion at 20° C. The mixture was stirred at 20° C. for 14 hrs, LCMS showed the product was detected. The reaction mixture was concentrated under reduced pressure to remove dichloromethane, and then diluted with water (100 mL), and extracted with ethyl acetate (20 mL*3). The combined organic layers were washed with brine (100 mL), dried over $Na_2SO_4$, filtered and concentrated under reduced pressure to give the crude product Compound N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (800.00 mg, crude) was used into the next step without further purification.

A mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (100 mg, 118 umol, 1.00 eq) and 1-tetrahydropyran-4-ylpiperidin-4-amine (65.5 mg, 355 umol, 3.00 eq) in $CH_3CN$ (1.0 mL) in a microwave tube, then DIPEA (153 mg, 1.19 mmol, 206 uL, 10 eq) was added, the mixture was stirred at 125° C. for 14 hr under $N_2$ atmosphere under microwave. LCMS and HPLC showed the product was detected. The reaction mixture was concentrated under reduced pressure to remove $CH_3CN$, and then diluted with water (10 mL) and extracted with dichloromethane (5 mL*3). The combined organic layers were washed with brine (10 mL), dried over $Na_2SO_4$, filtered and concentrated under reduced pressure to give a residue. The residue was purified by prep-HPLC (prep-HPLC (column: YMC-Actus Triart C18 150*30 5u; liquid phase: [A—10 mM $NH_4HCO_3$ in $H_2O$; B—ACN]B %: 45%-65%, 12 min])) to give Compound CY-1402 (2.60 mg, 2% yield) was obtained as a white solid. LCMS: (M/2+1): 481.1 $^1$H NMR: $CDCl_3$ 400 MHz δ 8.45 (s, 1H) 8.22-8.38 (m, 2H) 7.81 (d, J=8.0 Hz, 1H) 7.54 (s, 2H) 7.43 (d, J=8.0 Hz, 1H) 6.87 (d, J=8.0 Hz, 4H) 6.67 (s, 1H) 6.31 (s, 1H) 3.98 (d, J=8.0 Hz, 2H) 3.29-3.35 (m, 3H) 3.20 (s, 5H) 2.74 (s, 3H) 2.25 (s, 5H) 2.14 (s, 3H) 1.92 (s, 5H) 1.18 (s, 2H) 0.89 (s, 9H).

Example 3

Preparation of 4-(4-((4'-chloro-5,5-dimethyl-3,4,5,6-tetrahydro-[1,1'-biphenyl]-2-yl)methyl)piperazin-1-yl)-N-((4-((3-morpholinopropyl)amino)-3-nitrophenyl)sulfonyl)-2-(pyrazolo[4,3-b]pyrrolo[3,2-e]pyridin-1(5H)-yl)benzamide A mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (100 mg, 118 umol, 1.00 eq) and 3-morpholinopropan-1-amine (51 mg, 355 umol, 3.00 eq) in $CH_3CN$ (1.00 mL) in a microwave tube, then DIPEA (60 mg, 464 umol, 3.92 eq) was added, the mixture was stirred at 125° C. for 14 hr under $N_2$ atmosphere under microwave. LCMS and HPLC showed the product was detected. The reaction mixture was concentrated under reduced pressure to remove $CH_3CN$, and then diluted with water (10 mL) and extracted with dichloromethane (5 mL*3). The combined organic layers were washed with brine (10 mL), dried over $Na_2SO_4$, filtered and concentrated under reduced pressure to give a residue. The residue was purified by prep-HPLC (prep-HPLC (column: YMC-Actus Triart C18 150*30 5 u; liquid phase: [A—10 mM $NH_4HCO_3$ in $H_2O$; B—ACN]B %: 45%-75%, 12 min])) to give Compound CY-1404 (2.0 mg, 2% yield) was obtained as a yellow solid. LCMS: (M/2+1): 461.1 $^1$H NMR: ET10360-22-P1A1 $CDCl_3$ 400 MHz δ 9.06 (s, 1H) 8.46 (s, 1H) 8.23-8.39 (m, 2H) 7.81 (d, J=8.0 Hz, 1H) 7.50-7.59 (m, 2H) 7.34 (s, 1H) 6.80-6.92 (m, 3H) 6.68 (s, 1H) 6.46 (d, J=8.0 Hz, 1H) 6.28 (s, 1H) 3.64-3.78 (m, 4H) 3.12-3.29 (m, 6H) 2.66-2.84 (m, 4H) 2.44 (s, 7H) 2.26 (s, 4H) 2.08-2.17 (m, 3H) 1.92 (s, 2H) 1.30-1.43 (m, 4H) 1.06-1.21 (m, 4H) 0.89 (s, 7H).

Example 4

Preparation of 4-(4-((4'-chloro-5,5-dimethyl-3,4,5,6-tetrahydro-[1,1'-biphenyl]-2-yl)methyl)piperazin-1-yl)-N-((4-morpholino-3-nitrophenyl)sulfonyl)-2-(pyrazolo[4,3-b]pyrrolo[3,2-e]pyridin-1(5H)-yl)benzamide N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200.00 mg, 211.86 µmol, 1.00 eq) was dissolved in DCM (3.00 mL), to which TFA (4.62 g, 40.52 mmol, 3.00 mL, 191.25 eq) was added in one portion. The mixture was then stirred at 25° C. under $N_2$ atmosphere for 14 h. After removal of the solvent, N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (180.00 mg, crude) was obtained as a dark yellow solid which was confirmed by LC-MS and used directly for the next step without further purification.

To the mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (170.00 mg, 201.47 µmol, 1.00 eq) and morpholine (52.66 mg, 604.41 µL, 53.194, 3.00 eq) in $CH_3CN$ (4.00 mL), DIEA (78.12 mg, 604.41 µmol, 105.574, 3.00 eq) was added. The resulting mixture was taken up into a microwave tube, and heated under microwave at 80° C. under $N_2$ atmosphere for 2 h. After removal of the solvent, the crude 4-(4-((4'-chloro-5,5-dimethyl-3,4,5,6-tetrahydro-[1,1'-biphenyl]-2-yl)methyl)piperazin-1-yl)-N-((4-morpholino-3-nitrophenyl)sulfonyl)-2-(pyrazolo[4,3-b]pyrrolo[3,2-e]pyridin-1(5H)-yl)benzamide (300.00 mg, crude) was obtained as a black brown oil which was purified together with EW5403-10 by Prep-HPLC (HCl as additive) to afford CY-1406 HCl salt (41.40 mg) as a yellow solid. The product was confirmed by $^1$H NMR and LC-MS.

Example 5

Preparation of 4-(4-((4'-chloro-5,5-dimethyl-3,4,5,6-tetrahydro-[1,1'-biphenyl]-2-yl)methyl)piperazin-1-yl)-N-((4-(3-morpholinoazetidin-1-yl)-3-nitrophenyl)sulfonyl)-2-(pyrazolo[4,3-b]pyrrolo[3,2-e]pyridin-1(5H)-yl)benzamide Synthesis of Tert-butyl 3-morpholinoazetidine-1-carboxylate A mixture of tert-butyl 3-oxoazetidine-1-carboxylate (3.50 g, 20.45 mmol, 1.00 eq) and morpholine (2.32 g, 26.59 mmol, 2.34 mL, 1.30 eq) in DCE (250.00 mL) was stirred at 30° C. for 1 h, and then $NaBH(OAc)_3$ (5.63 g, 26.59 mmol, 1.30 eq) was added. The mixture was stirred at 30° C. for additional 15 h. Sat. $Na_2CO_3$ solution (200 mL) was added to the mixture, and the mixture was stirred at 30° C. for 10 min. The organic layer was separated, washed with $H_2O$ (200 mL) and brine (200 mL), and then concentrated under reduced pressure. The residue was purified by silica gel chromatography eluted with PE to PE:EA=1:1 to give tert-butyl 3-morpholinoazetidine-1-carboxylate (4.50 g, 18.57 mmol, 90.81% yield) as a light yellow oil which was confirmed by $^1$H NMR.

Synthesis of 4-(azetidin-3-yl)morpholine TFA salt: A mixture of tert-butyl 3-morpholinoazetidine-1-carboxylate (500.00 mg, 2.06 mmol, 1.00 eq) and TFA (7.70 g, 67.53 mmol, 5.00 mL, 32.78 eq) in DCM (20.00 mL) was stirred at 30° C. for 15 h. After removal of the solvent, 4-(azetidin-3-yl)morpholine TFA salt (280.00 mg, crude) was obtained as a yellow oil which was confirmed by LC-MS used directly without further purification.

Synthesis of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide: N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200.00 mg, 211.86 µmol, 1.00 eq) was dissolved in DCM (3.00 mL), to which TFA (4.62 g, 40.52 mmol, 3.00 mL, 191.25 eq) was added in one portion. The resulting mixture was then stirred at 25° C. under $N_2$ atmosphere for 14 h. After removal of the solvent, N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (200.00 mg, crude) was obtained as a dark yellow solid which was confirmed by LC-MS and used directly for the next step without further purification.

Synthesis of CY-1407: 4-(4-((4'-chloro-5,5-dimethyl-3,4,5,6-tetrahydro-[1,1'-biphenyl]-2-yl)methyl)piperazin-1-yl)-N-((4-(3-morpholinoazetidin-1-yl)-3-nitrophenyl)sulfonyl)-2-(pyrazolo[4,3-b]pyrrolo[3,2-e]pyridin-1(5H)-yl)benzamide HCl salt: A mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (78.37 mg, 551.10 µmol, 3.00 eq) in $CH_3CN$ (4.00 mL) was added DIEA (71.22 mg, 551.10 µmol, 96.24 µL, 3.00 eq). The resulting mixture was taken up into a microwave tube and heated using microwave at 80° C. for 2 h under $N_2$ atmosphere. After removal of the solvent, 4-[4-[[2-(4-chlorophenyl)-4,4-dimethyl-cyclohexen-1-yl]methyl]piperazin-1-yl]-N-[4-(3-morpholinoazetidin-1-yl)-3-nitro-phenyl]sulfonyl-2-(5H-pyrazolo[BLAH]pyrrolo[BLAH]-pyridin-1-yl)benzamide (300.00 mg, crude) was obtained as a black brown oil which was purified together with EW5403-7 by Prep-HPLC (HCl) and then by SFC (column: Phenomenex Gemini 150*25 mm*10 um; mobile phase: [water (0.05% ammonia hydroxide v/v)-ACN]; B %: 35%-65%, 10 min) to afford 4-(4-((4'-chloro-5,5-dimethyl-3,4,5,6-tetrahydro-[1,1'-biphenyl]-2-yl)methyl)piperazin-1-yl)-N-((4-(3-morpholinoazetidin-1-yl)-3-nitrophenyl)sulfonyl)-2-(pyrazolo[4,3-b]pyrrolo[3,2-e]pyridin-1(5H)-yl)benzamide HCl salt (2.40 mg, 2.51 µmol, 7.69% yield, HCl) as a yellow solid. The product was confirmed by LC-MS and $^1$H NMR.

Example 6

Preparation of 4-(4-((4'-chloro-5,5-dimethyl-3,4,5,6-tetrahydro-[1,1'-biphenyl]-2-yl)methyl)piperazin-1-yl)-N-((3-nitro-4-(7-oxa-2-azaspiro[3.5]nonan-2-yl)phenyl)sulfonyl)-2-(pyrazolo[4,3-b]pyrrolo[3,2-e]pyridin-1(5H)-yl)benzamide Synthesis of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide: N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (100.00 mg, 105.93 µmol, 1.00 eq) was dissolved in DCM (3.00 mL), to which TFA (2.31 g, 20.26 mmol, 1.50 mL, 191.25 eq) was added in one portion. The resulting mixture was then stirred at 25° C. under $N_2$ atmosphere for 14 h. After removal of the solvent, N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (101.00 mg, crude) was obtained as a dark yellow solid which was confirmed by LC-MS and used directly for the next step without further purification.

Synthesis of CY-1408: 4-(4-((4'-chloro-5,5-dimethyl-3,4,5,6-tetrahydro-[1,1'-biphenyl]-2-yl)methyl)piperazin-1-yl)-N-((3-nitro-4-(7-oxa-2-azaspiro[3.5]nonan-2-yl)phenyl) sulfonyl)-2-(pyrazolo[4,3-b]pyrrolo[3,2-e]pyridin-1(5H)-yl)benzamide HCl salt: The mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)benzamide (101.00 mg, 119.70 µmol, 1.00 eq) and 7-oxa-2-azaspiro[3.5]nonane (78.00 mg, 359.10 µmol, 3.00 eq, OXALIC ACID salt) were dissolved in $CH_3CN$ (4.00 mL), to which DIEA (92.82 mg, 718.20 µmol, 125.43 µL, 6.00 eq) was added. The resulting mixture was taken up into a microwave tube. The tube was heated under $N_2$ atmosphere at 80° C. for 3 h. After removal of the solvent, the residue was purified by Prep-HPLC (HCl, column: Phenomenex Synergi $C_{18}$ 150*25*10 µm; mobile phase: [water (0.05% HCl)-ACN]; B %: 35%-55%, 7.8 min) to afford 4-(4-((4'-chloro-5,5-dimethyl-3,4,5,6-tetrahydro-[1,1'-biphenyl]-2-yl)methyl)piperazin-1-yl)-N-((3-nitro-4-(7-oxa-2-azaspiro[3.5]nonan-2-yl)phenyl)sulfonyl)-2-(pyrazolo[4,3-b]pyrrolo[3,2-e]pyridin-1(5H)-yl)benzamide (6.10 mg, 6.48 µmol, 5.42% yield, HCl) as a yellow solid. The product was confirmed by LC-MS and $^1$H NMR.

Example 7

Preparation of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide Synthesis of S-(tetrahydropyran-4-ylmethyl) ethanethioate: A mixture of 4-(bromomethyl)tetrahydropyran (300.00 mg, 1.68 mmol, 1.00 eq) and potassium thioacetate (575.62 mg, 5.04 mmol, 3.00 eq) were dissolved in DMF (10.00 mL). The resulting mixture was then stirred at 25° C. for 3 h under $N_2$ atmosphere. The reacting solution was quenched with sat. aq. $NaHCO_3$ solution (50 mL) and extracted with DCM (50 mL×3). The combined organic layers were concentrated under reduced pressure to afford S-(tetrahydropyran-4-ylmethyl)ethanethioate (245.00 mg, 1.41 mmol, 83.69% yield) as black brown oil. The product was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(5-((2-(trimethylsilyl)ethoxy)methyl)pyrazolo[4,3-b]pyrrolo[3,2-e]pyridin-1(5H)-yl)benzamide: The mixture of N-((4-chloro-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (100.00 mg, 105.93 µmol, 1.00 eq) and S-(tetrahydropyran-4-ylmethyl)ethanethioate (55.38 mg, 317.79 µmol, 3.00 eq) were dissolved in $CH_3CN$ (4.00 mL), to which t-BuOK (59.43 mg, 529.65 µmol, 5.00 eq) was added in one portion. The resulting mixture was taken up into a microwave tube and heated under $N_2$ atmosphere at 80° C. for 2 h. The reacting solution was poured onto silica gel chromatography and eluted with pure PE to EA:MeOH=5:1. The eluent was concentrated under reduced pressure, and the residue was suspended in MeOH (4 mL) and stirred for 30 min. The precipitate was collected to afford 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(5-((2-(trimethylsilyl)ethoxy)methyl)pyrazolo[4,3-b]pyrrolo[3,2-e]pyridin-1(5H)-yl)benzamide (70.00 mg, crude) as an off-white solid. The crude product was confirmed by LC-MS and used directly for the next step without further purification.

Synthesis of CY-1409: 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide HCl salt: 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(5-((2-(trimethylsilyl)ethoxy)methyl)pyrazolo[4,3-b]pyrrolo[3,2-e]pyridin-1(5H)-yl)benzamide (30.00 mg, 28.85 µmol, 1.00 eq) was dissolved in DCM (5.00 mL), to which TFA (13.86 g, 121.53 mmol, 9.00 mL, 4211.98 eq) was added. The resulting mixture was then stirred at 25° C. for 14 h. After removal of the solvent, the residue was then dissolved in $CH_3CN$ (5.00 mL), to which DIEA (111.87 mg, 865.58 µmol, 151.17 µL, 30.00 eq) was added in one portion. The resulting mixture was then stirred at 80° C. for 3 h, and then the solvent and excess reagent were removed under reduced pressure to afford 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide (60.00 mg, crude) as a black brown oil which was purified together with EW5403-56 by Prep-HPLC (HCl) to afford 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)thio)phenyl)sulfonyl)-2-(pyrazolo[4,3-b]pyrrolo[3,2-e]pyridin-1(5H)-yl)benzamide HCl salt (21.40 mg, 22.62 µmol, 29.39% yield, HCl) as a yellow solid. The product was confirmed by LC-MS and $^1$H NMR.

Example 8

Preparation of 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(pyrazolo[4,3-b]pyrrolo[3,2-e]pyridin-1(5H)-yl)benzamide Synthesis of 4-[4-[[2-(4-chlorophenyl)-4,4-dimethyl-cyclohexen-1-yl]methyl]piperazin-1-yl]-2-fluoro-benzonitrile: A mixture of 1-[[2-(4-chlorophenyl)-4,4-dimethyl-cyclohexen-1-yl]methyl]piperazine (2.54 g, 7.15 mmol, 1.00 eq, HCl), 4-bromo-2-fluoro-benzonitrile (8.44 g, 42.21 mmol, 1.50 eq), Xantphos (6.51 g, 11.26 mmol, 0.40 eq), Pd(dba)$_2$ (3.24 g, 5.63 mmol, 0.20 eq) and $Cs_2CO_3$ (27.51 g, 84.42 mmol, 3.00 eq) in dioxane (300.00 mL) was stirred at 100° C. for 16 h under $N_2$ atmosphere. After removal of the solvent, the residue was purified by silica gel chromatography eluted with PE to PE:EA=5:1 to give 4-[4-[[2-(4-chlorophenyl)-4,4-dimethyl-cyclohexen-1-yl]methyl]piperazin-1-yl]-2-fluoro-benzonitrile (8.20 g, 18.72 mmol, 66.53% yield) as a yellow oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile: A mixture of 4-[4-[[2-(4- chlorophenyl)-4,4-dimethyl-cyclohexen-1-yl]methyl]piperazin-1-yl]-2-fluoro-benzonitrile (8.20 g, 18.72 mmol, 1.00 eq), 54(2-(trimethylsilyl)ethoxy)methyl)-1,5-dihydropyrazolo[4,3-b]pyrrolo[3,2-e]pyridine (5.40 g, 18.72 mmol, 1.00 eq) and $Cs_2CO_3$ (12.20 g, 37.44 mmol, 2.00 eq) in DMF (100.00 mL) was stirred at 120° C. for 3 h. After cooling to 15° C., the mixture was filtered. The filtrate was concentrated under reduced pressure. The residue was purified by silica gel chromatography eluted with PE to PE:EA=3:1 to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile (9.60 g, 13.59 mmol, 72.60% yield) as a black oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide: To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile (2.60 g, 3.68 mmol, 1.00 eq) in a mixture of DMSO (30.00 mL) and EtOH (30.00 mL), KOH (412.97 mg, 7.36 mmol, 2.00 eq) in $H_2O$ (10.00 mL) was added. After addition, $H_2O_2$ (3.34 g, 29.44 mmol, 2.83 mL, 30% purity, 8.00 eq) was added dropwise. The mixture was stirred at 25° C. for 14 h. $H_2O$ (100 mL) was added to the mixture, and the mixture was extracted with EA (100 mL×3). The combined organic layers were washed with $H_2O$ (500 mL), and concentrated under reduced pressure. The residue was purified by reverse phase column with TFA as additive to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (1.20 g, 1.66 mmol, 45.01% yield) as a yellow solid which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (500.00 mg, 690.22 umol, 1.00 eq) in THF (10.00 mL), LiHMDS (1 M, 1.52 mL, 2.20 eq) in THF was added at 0° C. The mixture was stirred at 0° C. for 30 min, and then 4-fluoro-3-nitro-benzenesulfonyl chloride (181.92 mg, 759.24 umol, 1.10 eq) was added. The mixture was stirred at 25° C. for 14 h. The reacting solution was quenched with sat. aq. $NH_4Cl$ (50 mL) and extracted with EA (50 mL×3). The combined organic layers were concentrated under reduced pressure. The residue was purified by silica gel chromatography (pure PE to DCM:MeOH=10:1) to afford 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (90.00 mg, 97.03 μmol, 14.06% yield) as a yellow oil. The product was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: A mixture of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (20.00 mg, 21.56 μmol, 1.00 eq), (4-fluorotetrahydropyran-4-yl)-methanamine (3.99 mg, 29.97 μmol, 1.39 eq) and DIEA (27.86 mg, 215.60 μmol, 37.65 μL, 10.00 eq) in DMF (5.00 mL) was stirred at 50° C. for 14 h. The reacting solution was diluted with water (20 mL) and extracted with DCM (50 mL×3). The combined organic layers were concentrated under reduced pressure. The residue was purified by silica gel chromatography (pure PE to PE:EA=1:2) to afford 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (40.00 mg, crude) as a yellow oil. The crude product was confirmed by LC-MS and used directly for the next step without further purification.

Synthesis of CY-1413: 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(pyrazolo[4,3-b]pyrrolo[3,2-e]pyridin-1(5H)-yl)benzamide HCl salt: 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (40.00 mg, 38.44 μmol, 1.00 eq) was dissolved in DCM (5.00 mL), to which TFA (43.83 mg, 384.40 μmol, 28.46 μL, 10.00 eq) was added in one portion. The resulting mixture was then stirred at 25° C. for 14 h. After removal of the solvent, crude 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide (30.00 mg, crude, TFA) was obtained as a yellow oil which was re-dissolved in MeCN (10.00 mL). To the solution, DIEA (36.77 mg, 284.50 μmol, 49.69 μL, 10.00 eq) was added in one portion. The resulting mixture was then stirred at 80° C. for 2 h. The solvent and excess reagent were removed under reduced pressure. The residue was purified by Prep-HPLC (HCl) to afford 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(pyrazolo[4,3-b]pyrrolo[3,2-e]pyridin-1(5H)-yl)benzamide HCl salt (6.90 mg, 7.29 μmol, 25.61% yield, HCl) as a light yellow solid which was confirmed by LC-MS and $^1H$ NMR.

Example 9

Preparation of 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(pyrazolo[4,3-b]pyrrolo[3,2-e]pyridin-1(5H)-yl)benzamide Synthesis of 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: The mixture of N-((4-chloro-3-nitrophenyl)sulfonyl)-4-(4-((4'-chloro-5,5-dimethyl-3,4,5,6-tetrahydro-[1,1'-biphenyl]-2- yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (200.00 mg, 211.86 μmol, 1.00 eq) and (1-methyl-4-piperidyl)methanamine (81.49 mg, 635.58 μmol, 3.00 eq) were dissolved in CH$_3$CN (10.00 mL), to which DIEA (82.14 mg, 635.58 μmol, 111.004, 3.00 eq) was added in one portion. The resulting mixture was taken up into a microwave tube and heated at 80° C. under N$_2$ atmosphere for 2 h. The reacting solution was poured onto silica gel chromatography and eluted with pure DCM to DCM:MeOH=5:1 to afford crude 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (50.00 mg, 48.27 μmol, 22.79% yield) as a yellow oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-(((1-methylpiperidin-4-yl)methyl)amino)-3-nitrophenyl)sulfonyl)benzamide: 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (50.00 mg, 48.27 μmol, 1.00 eq) was dissolved in DCM (10.00 mL), to which TFA (16.51 mg, 144.81 μmol, 10.724, 3.00 eq) was added. The resulting mixture was then stirred at 25° C. for 1 h. The solvent and excess reagent was removed under reduced pressure to afford 4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-(((1-methylpiperidin-4-yl)methyl)amino)-3-nitrophenyl)sulfonyl)benzamide (40.00 mg, crude) as a yellow oil which was used directly in the next step.

Synthesis of 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(pyrazolo[4,3-b]pyrrolo[3,2-e]pyridin-1(5H)-yl)benzamide HCl salt: The mixture of 4-(4-((4'-chloro-5,5-dimethyl-3,4,5,6-tetrahydro-[1,1'-biphenyl]-2-yl)methyl)piperazin-1-yl)-2-(5-hydroxymethyl)pyrazolo[4,3-b]pyrrolo[3,2-e]pyridin-1(5H)-yl)-N-((4-(((1-methylpiperidin-4-yl)methyl)amino)-3-nitrophenyl)sulfonyl)benzamide (40.00 mg, 42.76 μmol, 1.00 eq) and DIEA (16.58 mg, 128.28 μmol, 22.414, 3.00 eq) in CH$_3$CN (10.00 mL) was stirred at 80° C. for 5 h. After removal of the solvent, the residue was purified by Prep-HPLC (HCl as additive) and SFC to afford 4-(4-((4'-chloro-5,5-dimethyl-3,4,5,6-tetrahydro-[1,1'-biphenyl]-2-yl)methyl)piperazin-1-yl)-N-((4-(((1-methylpiperidin-4-yl)methyl)amino)-3-nitrophenyl)sulfonyl)-2-(pyrazolo[4,3-b]pyrrolo[3,2-e]pyridin-1(5H)-yl)benzamide HCl salt (23.60 mg, 26.06 μmol, 92.19% yield) as a light yellow solid which was confirmed by LC-MS and $^1$H NMR.

Example 10

Preparation of 4-(4-((4'-chloro-5,5-dimethyl-3,4,5,6-tetrahydro-[1,1'-biphenyl]-2-yl)methyl)piperazin-1-yl)-N-((4-(((4-fluoro-1-(oxetan-3-yl)piperidin-4-yl)methyl)amino)-3-nitrophenyl)sulfonyl)-2-(pyrazolo[4,3-b]pyrrolo[3,2-e]pyridin-1(5H)-yl)benzamide Synthesis of 9H-fluoren-9-ylmethyl 4-[(tert-butoxycarbonylamino)methyl]-4-fluoro-piperidine-1-carboxylate: The mixture of tert-butyl N-[(4-fluoro-4-piperidyl)methyl]carbamate (150.00 mg, 645.74 μmol, 1.00 eq) and 9H-fluoren-9-ylmethyl carbonochloridate (250.58 mg, 968.61 μmol, 1.50 eq) were dissolved in THF (20.00 mL) and H$_2$O (4.00 mL), to which NaHCO$_3$ (162.75 mg, 1.94 mmol, 75.35 μL, 3.00 eq) was added in one portion. The resulting mixture was then stirred at 15° C. for 14 h. The reacting solution was diluted with water (50 mL) and extracted with EA (50 mL×3). The combined organic layers were concentrated under reduced pressure. The residue was purified by silica gel chromatography (pure PE to PE:EA=5:1) to afford 9H-fluoren-9-ylmethyl 4-[(tert-butoxycarbonylamino)methyl]-4-fluoro-piperidine-1-carboxylate (163.00 mg, 358.61 μmol, 55.54% yield) as an off-white solid. The product was confirmed by LC-MS and used directly for the next step without further purification.

Synthesis of 4-(aminomethyl)-4-fluoro-piperidine-1-carboxylate TFA salt: 9H-fluoren-9-ylmethyl 4-[(tert-butoxycarbonylamino)methyl]-4-fluoro-piperidine-1-carboxylate (163.00 mg, 358.61 μmol, 1.00 eq) was dissolved in DCM (10.00 mL), to which TFA (204.44 mg, 1.79 mmol, 132.764, 5.00 eq) was added in one portion. The resulting mixture was then stirred at 15° C. for 14 h. The solvent and excess reagent were removed under reduced pressure to afford 9H-fluoren-9-ylmethyl 4-(aminomethyl)-4-fluoro-piperidine-1-carboxylate (200.00 mg, crude, TFA) as a yellow oil. The crude product was used directly for the next step without further purification.

Synthesis of 4-[4-[[2-(4-chlorophenyl)-4,4-dimethyl-cyclohexen-1-yl]methyl]piperazin-1-yl]-2-fluoro-benzonitrile: A mixture of 1-[[2-(4-chlorophenyl)-4,4-dimethyl-cyclohexen-1-yl]methyl]piperazine (2.54 g, 7.15 mmol, 1.00 eq, HCl), 4-bromo-2-fluoro-benzonitrile (8.44 g, 42.21 mmol, 1.50 eq), Xantphos (6.51 g, 11.26 mmol, 0.40 eq), Pd(dba)$_2$ (3.24 g, 5.63 mmol, 0.20 eq) and Cs$_2$CO$_3$ (27.51 g, 84.42 mmol, 3.00 eq) in dioxane (300.00 mL) was stirred at 100° C. for 16 h under N$_2$ atmosphere. After removal of the solvent, the residue was purified by silica gel chromatography eluted with PE to PE:EA=5:1 to give 4-[4-[[2-(4-chlorophenyl)-4,4-dimethyl-cyclohexen-1-yl]methyl]piperazin-1-yl]-2-fluoro-benzonitrile (8.20 g, 18.72 mmol, 66.53% yield) as a yellow oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile: A mixture of 4-[4-[[2-(4-chlorophenyl)-4,4-dimethyl-cyclohexen-1-yl]methyl]piperazin-1-yl]-2-fluoro-benzonitrile (8.20 g, 18.72 mmol, 1.00 eq), 54(2-(trimethylsilyl)ethoxy)methyl)-1,5-dihydropyrazolo[4,3-b]pyrrolo[3,2-e]pyridine (5.40 g, 18.72 mmol, 1.00 eq) and Cs$_2$CO$_3$ (12.20 g, 37.44 mmol, 2.00 eq) in DMF (100.00 mL) was stirred at 120° C. for 3 h. After cooling to 15° C., the mixture was filtered. The filtrate was concentrated under reduced pressure. The residue was purified by silica gel chromatography eluted with PE to PE:EA=3:1 to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile (9.60 g, 13.59 mmol, 72.60% yield) as a black oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyridin-1(5H)-yl)benzamide: To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)

methyl)pyrazolo[4,3-b]pyrrolo[3,2-e]pyridin-1(5H)-yl) benzonitrile (2.60 g, 3.68 mmol, 1.00 eq) in a mixture of DMSO (30.00 mL) and EtOH (30.00 mL), KOH (412.97 mg, 7.36 mmol, 2.00 eq) in $H_2O$ (10.00 mL) was added. After addition, $H_2O_2$ (3.34 g, 29.44 mmol, 2.83 mL, 30% purity, 8.00 eq) was added dropwise. The mixture was stirred at 25° C. for 14 h. $H_2O$ (100 mL) was added to the mixture, and the mixture was extracted with EA (100 mL×3). The combined organic layers were washed with $H_2O$ (500 mL), and concentrated under reduced pressure. The residue was purified by reverse phase column with TFA as additive to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (1.20 g, 1.66 mmol, 45.01% yield) as a yellow solid which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (500.00 mg, 690.22 µmol, 1.00 eq) in THF (10.00 mL), LiHMDS (1 M, 1.52 mL, 2.20 eq) in THF was added at 0° C. The mixture was stirred at 0° C. for 30 min, and then 4-fluoro-3-nitro-benzenesulfonyl chloride (181.92 mg, 759.24 µmol, 1.10 eq) was added. The mixture was stirred at 25° C. for 14 h. The reacting solution was quenched with sat. aq. $NH_4Cl$ (50 mL) and extracted with EA (50 mL×3). The combined organic layers were concentrated under reduced pressure. The residue was purified by silica gel chromatography (pure PE to DCM:MeOH=10:1) to afford 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (90.00 mg, 97.03 µmol, 14.06% yield) as a yellow oil. The product was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: The mixture of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (250.00 mg, 269.53 µmol, 1.00 eq) and 9H-fluoren-9-ylmethyl 4-(aminomethyl)-4-fluoro-piperidine-1-carboxylate (143.29 mg, 404.29 µmol, 1.50 eq) were dissolved in DMF (50.00 mL), to which DIEA (348.34 mg, 2.70 mmol, 470.73 µL, 10.00 eq) was added in one portion. The resulting mixture was then stirred at 50° C. for 14 h. The reacting solution was diluted with water (50 mL) and extracted with DCM (50 mL×3). The combined organic layers were concentrated under reduced pressure to afford crude (9H-fluoren-9-yl)methyl 4-(((4-(N-(4-(4-((4'-chloro-5,5-dimethyl-3,4,5,6-tetrahydro-[1,1'-biphenyl]-2-yl) methyl)piperazin-1-yl)-2-(5-((2-(trimethylsilyl)ethoxy) methyl)pyrazolo[4,3-b]pyrrolo[3,2-e]pyridin-1(5H)-yl) benzoyl)sulfamoyl)-2-nitrophenyl)amino)methyl)-4-fluoropiperidine-1-carboxylate (400.00 mg, crude) as a yellow oil which was re-dissolved in DMF (20.00 mL). To the above solution, piperidine (134.95 mg, 1.58 mmol, 156.924, 5.00 eq) was added in one portion. The resulting mixture was then stirred at 15° C. for 14 h. The reacting solution was poured onto silica gel chromatography and eluted with pure PE to DCM:MeOH=5:1 to afford 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl) methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (268.00 mg, 257.76 µmol, 81.32% yield) as a yellow oil which was confirmed by LC-MS and used directly for the next step without further purification.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl) sulfonyl)-2-(5-(hydroxymethyl)pyrazolo[4,3-b]pyrrolo[3,2-e]pyridin-1(5H)-yl)benzamide: 4-(4-((4'-chloro-5,5-dimethyl-3,4,5,6-tetrahydro-[1,1'-biphenyl]-2-yl)methyl) piperazin-1-yl)-N-((4-(((4-fluoropiperidin-4-yl)methyl) amino)-3-nitrophenyl)sulfonyl)-2-(5-((2-(trimethylsilyl) ethoxy)methyl)pyrazolo[4,3-b]pyrrolo[3,2-e]pyridin-1(5H)-yl)benzamide (268.00 mg, 257.76 µmol, 1.00 eq) was dissolved in DCM (20.00 mL), to which TFA (146.95 mg, 1.29 mmol, 95.424, 5.00 eq) was added in one portion. The resulting mixture was then stirred at 15° C. for 14 h. The solvent and excess reagent were removed under reduced pressure to afford 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl) sulfonyl)-2-(5-(hydroxymethyl)pyrazolo[4,3-b]pyrrolo[3,2-e]pyridin-1(5H)-yl)benzamide (240.00 mg, crude) as a yellow oil which was confirmed by LC-MS and used directly for the next step without further purification.

Synthesis of CY-1417: 4-(4-((4'-chloro-5,5-dimethyl-3,4,5,6-tetrahydro-[1,1'-biphenyl]-2-yl)methyl)piperazin-1-yl)-N-((4-(((4-fluoro-1-(oxetan-3-yl)piperidin-4-yl)methyl) amino)-3-nitrophenyl)sulfonyl)-2-(pyrazolo[4,3-b]pyrrolo [3,2-e]pyridin-1(5H)-yl)benzamide: The mixture of 4-(4-((4'-chloro-5,5-dimethyl-3,4,5,6-tetrahydro-[1,1'-biphenyl]-2-yl)methyl)piperazin-1-yl)-N-((4-(((4-fluoropiperidin-4-yl)methyl)amino)-3-nitrophenyl)sulfonyl)-2-(5-(hydroxymethyl)pyrazolo[4,3-b]pyrrolo[3,2-e]pyridin-1 (5H)-yl)benzamide (120.00 mg, 127.73 µmol, 1.00 eq) and oxetan-3-one (27.61 mg, 383.19 µmol, 3.00 eq) were dissolved in MeOH (10.00 mL), to which $NaBH_3CN$ (40.13 mg, 638.65 µmol, 5.00 eq) was added in one portion. The resulting mixture was then stirred at 15° C. for 14 h. The reacting solution was diluted with water (50 mL) and extracted with DCM (50 mL×3). The combined organic layers were concentrated under reduced pressure to afford crude 4-(4-((4'-chloro-5,5-dimethyl-3,4,5,6-tetrahydro-[1, 1'-biphenyl]-2-yl)methyl)piperazin-1-yl)-N-((4-(((4-fluoro-1-(oxetan-3-yl)piperidin-4-yl)methyl)amino)-3-nitrophenyl)sulfonyl)-2-(5-(hydroxymethyl)pyrazolo[4,3-b]pyrrolo [3,2-e]pyridin-1(5H)-yl)benzamide (120.00 mg, crude) as a yellow oil which was re-dissolved in $CH_3CN$ (20.00 mL). To the above solution DIEA (77.89 mg, 602.70 µmol, 105.264, 5.00 eq) was added in one portion. The resulting mixture was then stirred under $N_2$ atmosphere at 80° C. for 14 h. The reacting solution was diluted with water (50 mL) and extracted with DCM (50 mL×3). The combined organic layers were concentrated under reduced pressure. The residue was purified by Prep-TLC (EA/MeOH=10:1 and then EA:MeOH=5:1) to afford 4-(4-((4'-chloro-5,5-dimethyl-3,4, 5,6-tetrahydro-[1,1'-biphenyl]-2-yl)methyl)piperazin-1-yl)-N-((4-(((4-fluoro-1-(oxetan-3-yl)piperidin-4-yl)methyl)

amino)-3-nitrophenyl)sulfonyl)-2-(pyrazolo[4,3-b]pyrrolo [3,2-e]pyridin-1(5H)-yl)benzamide (2.80 mg, 2.90 μmol, 2.41% yield) as a yellow solid. The product was confirmed by LC-MS and $^1$H NMR.

Example 11

Preparation of (R)-4-(4-((4'-chloro-5,5-dimethyl-3,4, 5,6-tetrahydro-[1,1'-biphenyl]-2-yl)methyl)piperazin-1-yl)-N-((3-nitro-4-(((4-(oxetan-3-yl)morpholin-2-yl)methyl)amino)phenyl)sulfonyl)-2-(pyrazolo[4,3-b]pyrrolo[3,2-e]pyridin-1(5H)-yl)benzamide Synthesis of 9H-fluoren-9-ylmethyl (2R)-2-[(tert-butoxycarbonylamino)methyl]morpholine-4-carboxylate: A mixture of tert-butyl N-[[(2S)-morpholin-2-yl]methyl]carbamate (64.00 mg, 295.91 μmol, 1.00 eq), Fmoc-Cl (114.83 mg, 443.87 μmol, 1.50 eq) and Na$_2$CO$_3$ (94.09 mg, 887.74 μmol, 3.00 eq) in a mixture off THF (10.00 mL) and H$_2$O (2.00 mL) was stirred at 20° C. for 12 h. The mixture was extracted with EA (20 mL×3), and the combined organic layers were concentrated under reduced pressure. The residue was purified by Prep-TLC (PE:EA=3:1) to give 9H-fluoren-9-ylmethyl (2R)-2-[(tert-butoxycarbonylamino) methyl]morpholine-4-carboxylate (111.00 mg, 253.13 μmol, 85.54% yield) as a colorless oil which was confirmed by LC-MS.

Synthesis of 9H-fluoren-9-ylmethyl (2R)-2-(aminomethyl)morpholine-4-carboxylate TFA salt: A mixture of 9H-fluoren-9-ylmethyl (2R)-2-[(tert-butoxycarbonylamino) methyl]morpholine-4-carboxylate (111.00 mg, 253.12 μmol, 1.00 eq) and TFA (577.21 mg, 5.06 mmol, 374.814, 20.00 eq) in DCM (10.00 mL) was stirred at 15° C. for 3 h. After removal of the solvent, crude 9H-fluoren-9-ylmethyl (2R)-2-(aminomethyl)morpholine-4-carboxylate TFA salt (80.00 mg) was obtained as a light yellow oil which was used directly in the next step.

Synthesis of 4-[4-[[2-(4-chlorophenyl)-4,4-dimethyl-cyclohexen-1-yl]methyl]piperazin-1-yl]-2-fluoro-benzonitrile: A mixture of 1-[[2-(4-chlorophenyl)-4,4-dimethyl-cyclohexen-1-yl]methyl]piperazine (2.54 g, 7.15 mmol, 1.00 eq, HCl), 4-bromo-2-fluoro-benzonitrile (8.44 g, 42.21 mmol, 1.50 eq), Xantphos (6.51 g, 11.26 mmol, 0.40 eq), Pd(dba)$_2$ (3.24 g, 5.63 mmol, 0.20 eq) and Cs$_2$CO$_3$ (27.51 g, 84.42 mmol, 3.00 eq) in dioxane (300.00 mL) was stirred at 100° C. for 16 h under N$_2$ atmosphere. After removal of the solvent, the residue was purified by silica gel chromatography eluted with PE to PE:EA=5:1 to give 4-[4-[[2-(4-chlorophenyl)-4,4-dimethyl-cyclohexen-1-yl]methyl]piperazin-1-yl]-2-fluoro-benzonitrile (8.20 g, 18.72 mmol, 66.53% yield) as a yellow oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzonitrile: A mixture of 4-[4-[[2-(4-chlorophenyl)-4,4-dimethyl-cyclohexen-1-yl]methyl] piperazin-1-yl]-2-fluoro-benzonitrile (8.20 g, 18.72 mmol, 1.00 eq), 54(2-(trimethylsilyl)ethoxy)methyl)-1,5-dihydropyrazolo[4,3-b]pyrrolo[3,2-e]pyridine (5.40 g, 18.72 mmol, 1.00 eq) and Cs$_2$CO$_3$ (12.20 g, 37.44 mmol, 2.00 eq) in DMF (100.00 mL) was stirred at 120° C. for 3 h. After cooling to 15° C., the mixture was filtered. The filtrate was concentrated under reduced pressure. The residue was purified by silica gel chromatography eluted with PE to PE:EA=3:1 to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1 (5H)-yl)benzonitrile (9.60 g, 13.59 mmol, 72.60% yield) as a black oil which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide: To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy) methyl)pyrazolo[4,3-b]pyrrolo[3,2-e]pyridin-1(5H)-yl) benzonitrile (2.60 g, 3.68 mmol, 1.00 eq) in a mixture of DMSO (30.00 mL) and EtOH (30.00 mL), KOH (412.97 mg, 7.36 mmol, 2.00 eq) in H$_2$O (10.00 mL) was added. After addition, H$_2$O$_2$ (3.34 g, 29.44 mmol, 2.83 mL, 30% purity, 8.00 eq) was added dropwise. The mixture was stirred at 25° C. for 14 h. H$_2$O (100 mL) was added to the mixture, and the mixture was extracted with EA (100 mL×3). The combined organic layers were washed with H$_2$O (500 mL), and concentrated under reduced pressure. The residue was purified by reverse phase column with TFA as additive to give 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (1.20 g, 1.66 mmol, 45.01% yield) as a yellow solid which was confirmed by LC-MS.

Synthesis of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl) ethoxy)methyl)pyrazolo[4,3-b]pyrrolo[3,2-e]pyridin-1(5H)-yl)benzamide:

To a solution of 4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzamide (500.00 mg, 690.22 μmol, 1.00 eq) in THF (10.00 mL), LiHMDS (1 M, 1.52 mL, 2.20 eq) in THF was added at 0° C. The mixture was stirred at 0° C. for 30 min, and then 4-fluoro-3-nitro-benzenesulfonyl chloride (181.92 mg, 759.24 μmol, 1.10 eq) was added. The mixture was stirred at 25° C. for 14 h. The reacting solution was quenched with sat. aq. NH$_4$Cl (50 mL) and extracted with EA (50 mL×3). The combined organic layers were concentrated under reduced pressure. The residue was purified by silica gel chromatography (pure PE to DCM: MeOH=10:1) to afford 4-(4-((4'-chloro-5,5-dimethyl-3,4,5, 6-tetrahydro-[1,1'-biphenyl]-2-yl)methyl)piperazin-1-yl)-N-((4-fluoro-3-nitrophenyl)sulfonyl)-2-(5-((2-(trimethylsilyl) ethoxy)methyl)pyrazolo[4,3-b]pyrrolo[3,2-e]pyridin-1(5H)-yl)benzamide (90.00 mg, 97.03 μmol, 14.06% yield) as a yellow oil. The product was confirmed by LC-MS and used directly for the next step without further purification.

Synthesis of (S)-4-(4-((4'-chloro-5,5-dimethyl-3,4,5,6-tetrahydro-[1,1'-biphenyl]-2-yl)methyl)piperazin-1-yl)-N-((4-((morpholin-2-ylmethyl)amino)-3-nitrophenyl)sulfonyl)-2-(5-((2-(trimethylsilyl)ethoxy)methyl)pyrazolo[4,3-b] pyrrolo[3,2-e]pyridin-1(5H)-yl)benzamide: A mixture of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl) pyrazolo[4,3-b]pyrrolo[3,2-e]pyridin-1(5H)-yl)benzamide (80.00 mg, 86.25 μmol, 1.00 eq), 9H-fluoren-9-ylmethyl (2R)-2-(aminomethyl)morpholine-4-carboxylate (67.13 mg, 198.38 μmol, 2.30 eq) and DIEA (55.73 mg, 431.25 μmol, 75.31 μL, 5.00 eq) in DMF (10.00 mL) was stirred at 50° C. under N$_2$ atmosphere for 14 h. The reacting solution was diluted with water (20 mL) and extracted with DCM (50 mL×3). The combined organic layers were concentrated under reduced pressure to afford (R)-(9H-fluoren-9-yl) methyl 2-(((4-(N-(4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoyl)sulfamoyl)-2-nitrophenyl)amino)methyl)morpholine-4-carboxylate (100.00 mg, crude) as a yellow oil. Next, (R)-(9H-fluoren-9-yl)methyl 2-(((4-(N-(4-(4-((4'-chloro-5,5-dimethyl-3,4,5,6-tetrahydro-[1,1'-biphenyl]-2-yl)methyl)piperazin-1-yl)-2-(5-((2-(trimethylsilyl)ethoxy)methyl)pyrazolo[4,3-b]pyrrolo[3,2-e]pyridin-1(5H)-yl)benzoyl)sulfamoyl)-2-nitrophenyl)amino)methyl)morpholine-4-carboxylate (130.00 mg, 104.34 µmol, 1.00 eq) was dissolved in DMF (20.00 mL), to which piperidine (88.85 mg, 1.04 mmol, 103.314, 10.00 eq) was added in one portion. The resulting mixture was then stirred at 15° C. for 14 h. The reacting solution was poured onto silica gel chromatography (pure PE to DCM:MeOH=5:1) to afford (S)-4-(4-((4'-chloro-5,5-dimethyl-3,4,5,6-tetrahydro-[1,1'-biphenyl]-2-yl)methyl)piperazin-1-yl)-N-((4-((morpholin-2-ylmethyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (100.00 mg, crude) as a yellow oil. The crude product was confirmed by LC-MS and used directly for the next step without further purification.

Synthesis of (S)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-((morpholin-2-ylmethyl)amino)-3-nitrophenyl)sulfonyl)benzamide: (S)-4-(4-((4'-chloro-5,5-dimethyl-3,4,5,6-tetrahydro-[1,1'-biphenyl]-2-yl)methyl)piperazin-1-yl)-N-((4-((morpholin-2-ylmethyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (100.00 mg, 97.68 µmol, 1.00 eq) was dissolved in DCM (20.00 mL), to which TFA (111.38 mg, 976.84 µmol, 72.324, 10.00 eq) was added in one portion. The resulting mixture was then stirred at 15° C. for 14 h. The solvent and excess reagent were removed under reduced pressure to afford (S)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-((morpholin-2-ylmethyl)amino)-3-nitrophenyl)sulfonyl)benzamide (100.00 mg, crude, TFA) as a yellow oil. The crude product was used directly for the next step without further purification.

Synthesis of CY-1419-R: (R)-4-(4-((4'-chloro-5,5-dimethyl-3,4,5,6-tetrahydro-[1,1'-biphenyl]-2-yl)methyl)piperazin-1-yl)-N-((3-nitro-4-(((4-(oxetan-3-yl)morpholin-2-yl)methyl)amino)phenyl)sulfonyl)-2-(pyrazolo[4,3-b]pyrrolo[3,2-e]pyridin-1(5H)-yl)benzamide: The mixture of (S)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((4-((morpholin-2-ylmethyl)amino)-3-nitrophenyl)sulfonyl)benzamide (100.00 mg, 108.29 µmol, 1.00 eq) and oxetan-3-one (23.41 mg, 324.87 µmol, 3.00 eq) were dissolved in MeOH (20.00 mL), to which NaBH$_3$CN (20.41 mg, 324.87 µmol, 3.00 eq) was added in one portion. The resulting mixture was then stirred at 15° C. under N$_2$ atmosphere for 14 h. The reacting solution was diluted with water (20 mL) and extracted with DCM (50 mL×3). The combined organic layers were concentrated under reduced pressure to afford crude (R)-4-(4-((4'-chloro-5,5-dimethyl-3,4,5,6-tetrahydro-[1,1'-biphenyl]-2-yl)methyl)piperazin-1-yl)-2-(5-(hydroxymethyl)pyrazolo[4,3-b]pyrrolo[3,2-e]pyridin-1(5H)-yl)-N-((3-nitro-4-(((4-(oxetan-3-yl)morpholin-2-yl)methyl)amino)phenyl)sulfonyl)benzamide (100.00 mg, crude) as a yellow oil which was then suspended in CH$_3$CN (20.00 mL). To the above solution, DIEA (131.94 mg, 1.02 mmol, 178.304, 10.00 eq) was added in one portion. The resulting mixture was then stirred at 80° C. for 14 h. The solvent and excess reagent were removed under reduced pressure. The residue was purified by Prep-HPLC (neutral) to afford (R)-4-(4-((4'-chloro-5,5-dimethyl-3,4,5,6-tetrahydro-[1,1'-biphenyl]-2-yl)methyl)piperazin-1-yl)-N-((3-nitro-4-(((4-(oxetan-3-yl)morpholin-2-yl)methyl)amino)phenyl)sulfonyl)-2-(pyrazolo[4,3-b]pyrrolo[3,2-e]pyridin-1(5H)-yl)benzamide (1.10 mg, 1.16 µmol, 1.13% yield) as a yellow solid. The product was confirmed by LC-MS and $^1$H NMR. 11 mg of crude product was also obtained.

Example 12

Preparation of 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(pyrazolo[4,3-b]pyrrolo[3,2-e]pyridin-1(5H)-yl)benzamide Synthesis of Tert-butyl ((4-fluoro-1-methylpiperidin-4-yl)methyl)carbamate: A mixture of tert-butyl ((4-fluoropiperidin-4-yl)methyl)carbamate (330.00 mg, 1.42 mmol, 1.00 eq) and aq. HCHO (37%, 172.88 mg, 2.13 mmol, 158.61 µL, 1.50 eq) in CH$_3$CN (10.00 mL) was stirred at 30° C. for 30 min, and then NaBH$_3$CN (178.47 mg, 2.84 mmol, 2.00 eq) and AcOH (104.88 mg, 1.75 mmol, 99.89 µL, 1.23 eq) were added in portions. The mixture was stirred at 15° C. for 13.5 h. The reacting solution was diluted with water (100 mL) and extracted with EA (100 mL×4). The combined organic layers were concentrated under reduced pressure and purified by silica gel chromatography (PE:EA=1:1 to EA:MeOH=5:1) to afford tert-butyl ((4-fluoro-1-methylpiperidin-4-yl)methyl)carbamate (290.00 mg, 1.18 mmol, 82.91% yield) as a colorless oil, which was confirmed by LC-MS.

Synthesis of (4-fluoro-1-methylpiperidin-4-yl)methanamine: Tert-butyl ((4-fluoro-1-methylpiperidin-4-yl)methyl)carbamate (290.00 mg, 1.18 mmol, 1.00 eq) was dissolved in DCM (10.00 mL), to which TFA (3.08 g, 27.01 mmol, 2.00 mL, 22.89 eq) was added in portions. The resulting mixture was then stirred at 15° C. for 15 h. The solvent and excess reagent were removed under reduced pressure to afford (4-fluoro-1-methylpiperidin-4-yl)methanamine (320.00 mg, crude) as a yellow oil.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide: The mixture of 4-(4-((4'-chloro-5,5-dimethyl-3,4,5,6-tetrahydro-[1,1'-biphenyl]-2-yl)methyl)piperazin-1-yl)-N-((4-fluoro-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (140.00 mg, 150.94 µmol, 1.00 eq) and (4-fluoro-1-methylpiperidin-4-yl)methanamine (66.21 mg, 452.82 µmol, 3.00 eq) were dissolved in DMF (20.00 mL), to which DIEA (195.07 mg, 1.51 mmol, 263.614, 10.00 eq) was added in one portion. The resulting mixture was then stirred under N$_2$ atmosphere at 50° C. for 14 h. The solvent and excess reagent were removed under reduced pressure. The residue was purified by silica gel chromatography (pure DCM to DCM:MeOH=3:1) to afford 4-(4-((4'-chloro-5,5-dimethyl-3,4,5,6-tetrahydro-[1,1'-biphenyl]-2-yl)methyl)

piperazin-1-yl)-N-((4-(((4-fluoro-1-methylpiperidin-4-yl) methyl)amino)-3-nitrophenyl)sulfonyl)-2-(5-((2-(trimethylsilyl)ethoxy)methyl)pyrazolo[4,3-b]pyrrolo[3,2-e]pyridin-1(5H)-yl)benzamide (141.00 mg, 133.81 µmol, 88.65% yield) as a yellow oil, which was confirmed by LC-MS. LC-MS: EW5403-312-P1A00 (M+H$^+$=1054, M/2+H$^+$=527).

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide: 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl) sulfonyl)-2-(5-((2-(trimethylsilyl)ethoxy)methyl)pyrazolo [4,3-b]pyrrolo[3,2-e]pyridin-1(5H)-yl)benzamide (141.00 mg, 133.81 µmol, 1.00 eq) was dissolved in DCM (10.00 mL), to which TFA (152.57 mg, 1.34 mmol, 99.07 µL, 10.00 eq) was added in one portion. The resulting mixture was then stirred at 15° C. for 14 h. The solvent and excess reagent were removed under reduced pressure to afford 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide (150.00 mg, crude) as a yellow oil, which was confirmed by LC-MS. LC-MS: EW5403-317-P1Z (M+H$^+$=953).

Synthesis of CY-1415: 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(pyrazolo[4,3-b]pyrrolo[3,2-e]pyridin-1(5H)-yl)benzamide: The mixture of 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(5-(hydroxymethyl)pyrazolo[4,3-b]pyrrolo[3,2-e]pyridin-1(5H)-yl)benzamide (150.00 mg, 157.31 µmol, 1.00 eq) and DIEA (203.31 mg, 1.57 mmol, 274.74 µL, 10.00 eq) were dissolved in CH$_3$CN (20.00 mL). The resulting mixture was then stirred at 80° C. under N$_2$ atmosphere for 14 h. The solvent and excess reagent were removed under reduced pressure. The residue was purified by column: Phenomenex Synergi C$_{18}$ 150*25*10, µm; mobile phase: [water (0.05% HCl)-ACN]; B %: 42%-62%, 7.8 min to afford 4-(4-((4'-chloro-5,5-dimethyl-3,4,5,6-tetrahydro-[1,1'-biphenyl]-2-yl)methyl)piperazin-1-yl)-N-((4-(((4-fluoro-1-methylpiperidin-4-yl)methyl)amino)-3-nitrophenyl)sulfonyl)-2-(pyrazolo[4,3-b]pyrrolo[3,2-e]pyridin-1(5H)-yl)benzamide (1.8 mg, 1.95 µmol, 1.24% yield) as a yellow solid, which was confirmed by LC-MS and $^1$H NMR. LC-MS: EW5403-318-P1A0 (M+H$^+$=924M/2+H$^+$=462). $^1$H NMR: EW5403-318-P1A0 400 MHz DMSO-d$_6$, δ 11.43 (brs, 1H), 10.65 (brs, 1H), 8.54 (s, 1H), 8.30 (s, 1H), 8.05 (s, 1H), 7.77 (s, 1H), 7.36-7.59 (m, 4H), 7.07-7.09 (m, 3H), 6.95-6.97 (m, 2H), 6.30 (s, 1H), 3.71-3.77 (m, 2H), 3.24-3.27 (m, 3H), 3.03-3.17 (m, 3H), 2.87-2.89 (m, 2H), 2.10-2.12 (m, 4H), 2.21-2.50 (m, 4H), 1.99 (s, 3H), 1.41-1.45 (m, 2H), 1.16-1.23 (m, 6H), 0.95 (s, 6H).

Example 13

Preparation of 4-(4-((4'-chloro-5,5-dimethyl-3,4,5,6-tetrahydro-[1,1'-biphenyl]-2-yl)methyl)piperazin-1-yl)-N-((4-((4-fluoro-1-(oxetan-3-yl)piperidin-4-yl)methoxy)-3-nitrophenyl)sulfonyl)-2-(pyrazolo[4,3-b]pyrrolo[3,2-e]pyridin-1(5H)-yl)benzamide Step 1: Tert-butyl 4-fluoro-4-((2-nitro-4-sulfamoylphenoxy)methyl)piperidine-1-carboxylate: The mixture of 4-fluoro-3-nitro-benzenesulfonamide (300.00 mg, 1.36 mmol, 1.00 eq) and tert-butyl 4-fluoro-4-(hydroxymethyl) piperidine-1-carboxylate (317.26 mg, 1.36 mmol, 1.00 eq) were dissolved in THF (50.00 mL), to which NaH (163.20 mg, 4.08 mmol, 60% purity, 3.00 eq) was added at 0° C. in one portion. The resulting mixture was then stirred at 15° C. for 14 h. The reacting solution was quenched with EtOH (10 mL), diluted with water (50 mL) and extracted with DCM (100 mL×3). The combined organic layers were concentrated under reduced pressure and purified together with EW5403-280-P1 by silica gel chromatography (pure PE to PE:EA=1:1) to afford tert-butyl 4-fluoro-4-((2-nitro-4-sulfamoylphenoxy)methyl)piperidine-1-carboxylate (560 mg, 1.29 mmol, 85.69% yield) as an off-white solid, which was confirmed by LC-MS. LC-MS: EW5403-286-P1A0 (M+Na$^+$=456)

Step 2: 4-((4-fluoropiperidin-4-yl)methoxy)-3-nitrobenzenesulfonamide Tert-butyl 4-fluoro-4-((2-nitro-4-sulfamoylphenoxy)methyl)piperidine-1-carboxylate (100.00 mg, 230.71 µmol, 1.00 eq) was dissolved in DCM (20.00 mL), to which TFA (131.53 mg, 1.15 mmol, 85.414, 5.00 eq) was added in one portion. The resulting mixture was then stirred at 15° C. for 14 h. The solvent and excess reagent were removed under reduced pressure to afford 4-((4-fluoropiperidin-4-yl)methoxy)-3-nitrobenzenesulfonamide (80 mg, crude) as an off-white solid. LC-MS: EW5403-287-P1Z0 (M+H$^+$=334).

Step 3: 4-((4-fluoro-1-(oxetan-3-yl)piperidin-4-yl) methoxy)-3-nitrobenzenesulfonamide: The mixture of 4-[(4-fluoro-4-piperidyl)methoxy]-3-nitro-benzenesulfonamide (70.00 mg, 156.47 µmol, 1.00 eq, TFA) and oxetan-3-one (67.65 mg, 938.82 µmol, 6.00 eq) were dissolved in MeOH (10.00 mL), to which NaBH$_3$CN (98.33 mg, 1.56 mmol, 10.00 eq) was added in one portion. The resulting mixture was then stirred at 15° C. for 14 h. The solvent and excess reagent were removed under reduced pressure. The residue was purified together with EW5403-288-P1 by silica gel chromatography (pure DCM to DCM:MeOH=10:1) to afford 44(4-fluoro-1-(oxetan-3-yl)piperidin-4-yl)methoxy)-3-nitrobenzenesulfonamide (100 mg, crude) as a light yellow oil, which was confirmed by LC-MS. LC-MS: EW5403-289-P1A2 (M+H$^+$=390).

Step 4: The synthesis of CY-1418: 4-(4-((4'-chloro-5,5-dimethyl-3,4,5,6-tetrahydro-[1,1'-biphenyl]-2-yl)methyl) piperazin-1-yl)-N-((4-((4-fluoro-1-(oxetan-3-yl)piperidin-4-yl)methoxy)-3-nitrophenyl)sulfonyl)-2-(pyrazolo[4,3-b] pyrrolo[3,2-e]pyridin-1(5H)-yl)benzamide: The mixture of 4-[[4-fluoro-1-(oxetan-3-yl)-4-piperidyl]methoxy]-3-nitrobenzenesulfonamide (50.00 mg, 128.40 µmol, 1.00 eq), 4-[4-[[2-(4-chlorophenyl)-4,4-dimethyl-cyclohexen-1-yl] methyl]piperazin-1-yl]-2-(5H-pyrazolo[BLAH]pyrrolo [BLAH]pyridin-1-yl)benzoic acid (76.42 mg, 128.40 µmol, 1.00 eq), DMAP (31.37 mg, 256.81 µmol, 2.00 eq) and EDCI (49.23 mg, 256.81 µmol, 2.00 eq) were dissolved in DCM (20.00 mL). The resulting mixture was then stirred at 15° C. for 14 h. The reacting solution was poured onto silica gel chromatography and eluted with DCM to DCM: MeOH=5:1, and then purified by column: Phenomenex Synergi C18 150*25*10 µm; mobile phase: [water (0.05% HCl)-ACN]; B %: 42%-62%, 7.8 min to afford 4-(4-((4'-chloro-5,5-dimethyl-3,4,5,6-tetrahydro-[1,1'-biphenyl]-2-yl)methyl)piperazin-1-yl)-N-((4-((4-fluoro-1-(oxetan-3-yl) piperidin-4-yl)methoxy)-3-nitrophenyl)sulfonyl)-2-(pyrazolo[4,3-b]pyrrolo[3,2-e]pyridin-1(5H)-yl)benzamide (8.4 mg, 8.69 µmol, 6.8% yield) as a light yellow solid, which was confirmed by LC-MS and $^1$H NMR. LC-MS: EW5403-300-P1C0 (M/2+H$^+$=483). $^1$H NMR: EW5403-

300-P1A0 400 MHz CD$_3$OD, δ 8.26 (s, 1H), 8.18 (s, 2H), 7.99-8.00 (m, 1H), 7.67-7.70 (m, 1H), 7.65 (s, 1H), 7.15-7.37 (m, 7H), 6.52 (s, 1H), 4.44-4.49 (m, 2H), 4.12-4.18 (m, 3H), 3.95 (s, 2H), 3.54-3.82 (m, 8H), 3.35 (m, 2H), 2.90 (s, 3H), 2.38-2.49 (m, 6H), 2.14 (s, 2H), 1.60 (s, 2H), 1.29 (s, 1H), 1.03 (s, 6H).

Example 14

Preparation of 4-(4-((4'-chloro-5,5-dimethyl-3,4,5,6-tetrahydro-[1,1'-biphenyl]-2-yl)methyl)piperazin-1-yl)-N-((3-nitro-4-((tetrahydro-2H-pyran-4-yl)methoxy)phenyl)sulfonyl)-2-(pyrazolo[4,3-b]pyrrolo[3,2-e]pyridin-1(5H)-yl)benzamide Step 1: the synthesis of 3-nitro-4-((tetrahydro-2H-pyran-4-yl)methoxy)benzenesulfonamide: To a solution of (tetrahydro-2H-pyran-4-yl)methanol (263.68 mg, 2.27 mmol, 1.00 eq) in THF (20.00 mL), NaH (272.40 mg, 6.81 mmol, 60% purity, 3.00 eq) was added at 0° C. The mixture was stirred at 0° C. for 30 min, and then 4-fluoro-3-nitrobenzenesulfonamide (500.00 mg, 2.27 mmol, 1.00 eq) was added. The mixture was stirred at 25° C. for 15 h, and then the reaction mixture was quenched by MeOH (10 mL). After removal of the solvent, the residue was purified by silica gel chromatography eluted with PE:EA=5:1 to 1:1 to give 3-nitro-4-((tetrahydro-2H-pyran-4-yl)methoxy)benzenesulfonamide (446.00 mg, 1.41 mmol, 62.11% yield) as yellow solid which was confirmed by LC-MS. LC-MS: EW6259-87-P1A2 (M+H$^+$=317.0).

Step 2, the synthesis of CY-1426: 4-(4-((4'-chloro-5,5-dimethyl-3,4,5,6-tetrahydro-[1,1'-biphenyl]-2-yl)methyl)piperazin-1-yl)-N-((3-nitro-4-((tetrahydro-2H-pyran-4-yl)methoxy)phenyl)sulfonyl)-2-(pyrazolo[4,3-b]pyrrolo[3,2-e]pyridin-1(5H)-yl)benzamide: To a mixture of 3-nitro-4-((tetrahydro-2H-pyran-4-yl)methoxy)benzenesulfonamide (296.00 mg, 935.73 μmol, 1.50 eq) and 4-(4-((4'-chloro-5,5-dimethyl-3,4,5,6-tetrahydro-[1,1'-biphenyl]-2-yl)methyl)piperazin-1-yl)-2-(pyrazolo[4,3-b]pyrrolo[3,2-e]pyridin-1(5H)-yl)benzoic acid (371.25 mg, 623.82 μmol, 1.00 eq) in THF (20.00 mL) was added EDCI (358.76 mg, 1.87 mmol, 3.00 eq) and DMAP (228.64 mg, 1.87 mmol, 3.00 eq). The mixture was stirred at 25° C. for 12 h. After removal of the solvent, the residue was purified together with EW6259-90 by Prep-HPLC (column: Phenomenex Synergi C$_{18}$ 150*25*10 μm; mobile phase: [water (0.05% HCl)-ACN]; B %: 38%-58%, 7.8 min) to give 4-(4-((4'-chloro-5,5-dimethyl-3,4,5,6-tetrahydro-[1,1'-biphenyl]-2-yl)methyl)piperazin-1-yl)-N-((3-nitro-4-((tetrahydro-2H-pyran-4-yl)methoxy)phenyl)sulfonyl)-2-(pyrazolo[4,3-b]pyrrolo[3,2-e]pyridin-1(5H)-yl)benzamide (68.4 mg, 50.81 μmol, 8.15% yield) as yellow solid which was confirmed by LC-MS and $^1$H NMR. LC-MS: EW6259-91-P1G (M+H$^+$=893.2) 1HNMR: EW6259-91-P1P 400 MHz CD$_3$OD, δ 8.43 (s, 1H), 8.22 (s, 1H), 8.17 (d, J=2.0 Hz, 1H), 8.01-8.04 (m, 1H), 7.69-7.71 (m, 2H), 7.33-7.39 (m, 3H), 7.24 (s, 1H), 7.13-7.15 (m, 3H), 6.64-6.65 (m, 1H), 4.11-4.13 (m, 2H), 3.75-4.04 (m, 5H), 3.75 (s, 2H), 3.54-3.56 (m, 2H), 3.48-3.51 (m, 2H), 3.31-3.41 (m, 2H), 2.39 (s, 2H), 2.14-2.17 (m, 3H), 1.80-1.83 (m, 2H), 1.52-1.59 (m, 5H), 1.03 (s, 6H).

Example 15

Preparation of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide Into a 250-mL round-bottom flask, was placed a solution of 1-[[2-(4-chlorophenyl)-4,4-dimethylcyclohex-1-en-1-yl]methyl]piperazine (15.09 g, 47.32 mmol, 1.00 equiv) in DMA (150 mL), DIEA (12.9 g, 99.81 mmol, 2.00 equiv), methyl 2-bromo-4-fluorobenzoate (11.6 g, 49.78 mmol, 1.00 equiv). The resulting solution was stirred for 12 h at 100 degree. The reaction mixture was cooled to room temperature. The reaction was then quenched by the addition of 50 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 7 g (crude) of methyl 2-bromo-4-(4-[[2-(4-chlorophenyl)-4,4-dimethylcyclohex-1-en-1-yl]methyl]piperazin-1-yl)benzoate as yellow oil.
LC-MS (ES, m/z): M+1=533, 531.

Into a 40-mL round-bottom flask, was placed a solution of 4-[[2-(trimethylsilyl)ethoxy]methyl]-13-oxa-2,4,10-triazatricyclo[7.4.0.0^[3,7]]trideca-1,3(7),5,8-tetraene (175 mg, 0.57 mmol, 1.00 equiv) in dioxane (10 mL), Cs$_2$CO$_3$ (560 mg, 1.72 mmol, 3.00 equiv), XantPhos Pd G2 (CAS: 1375325-77-1) (53 mg, 0.06 mmol, 0.10 equiv), methyl 2-bromo-4-(4-[2-(4-chlorophenyl)-4,4-dimethylcyclohex-1-en-1-yl]methylpiperazin-1-yl)benzoate (334.7 mg, 0.63 mmol, 1.10 equiv). The resulting solution was stirred for 2 h at 110 degree. The reaction mixture was cooled to room temperature. The solids were filtered out. The resulting mixture was concentrated under vacuum. The residue was applied onto a silica gel column with ethyl acetate/petroleum ether (0:1-1:3). This resulted in 200 mg (46%) of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-13-oxa-2,4,10-triazatricyclo[7.4.0.0^[3,7]]trideca-1,3(7),5,8-tetraen-10-yl)benzoate as yellow oil. LC-MS: (ES, m/z): M+1=756, R,T=1.252 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Into a 50-mL round-bottom flask, was placed a solution of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-13-oxa-2,4,10-triazatricyclo[7.4.0.0^[3,7]]trideca-1,3(7),5,8-tetraen-10-yl)benzoate (200 mg, 0.26 mmol, 1.00 equiv) in tetrahydrofuran (20 mL), TBAF (3 mg, 0.01 mmol), ethane-1,2-diamine (3 mL). The resulting solution was stirred for 24 h at 60 degree. The reaction mixture was cooled to room temperature. The reaction was then quenched by the addition of 30 mL of water. The resulting solution was extracted with 2×30 mL of ethyl acetate and the organic layers combined. The resulting mixture was washed with 2×30 mL of brine. The mixture was dried over anhydrous sodium sulfate and concentrated under vacuum. The residue was applied onto a silica gel column with ethyl acetate/petroleum ether (0:1-1:2). This resulted in 90 mg (54%) of methyl 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0ˆ[3,7]]trideca-1,3(7),5,8-tetraen-10-yl] benzoate as a yellow solid. LC-MS (ES, m/z): M+1=626, R,T=1.052 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Into a 8-mL round-bottom flask, was placed a solution of methyl 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0ˆ[3,7]]trideca-1,3(7),5,8-tetraen-10-yl]benzoate (90 mg, 0.14 mmol, 1.00 equiv) in tetrahydrofuran/MeOH/H$_2$O (2/2/2 mL), sodium hydroxide (23 mg, 0.57 mmol, 4.00 equiv). The resulting solution was stirred for overnight at 60 degree. The reaction mixture was cooled to room temperature. The reaction was then quenched by the addition of 5 mL of water. The pH value of the solution was adjusted to 6 with hydrogen chloride (1 mol/L). The resulting solution was extracted with 2×10 mL of ethyl acetate and the organic layers combined. The resulting mixture was washed with 3×10 mL of brine. The mixture was dried over anhydrous sodium sulfate and concentrated under vacuum. The residue was applied onto a silica gel column with ethyl acetate/petroleum ether (0:1-1:1). This resulted in 70 mg (80%) of 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0ˆ[3,7]]trideca-1,3(7),5,8-tetraen-10-yl]benzoic acid as a yellow solid.

LC-MS (ES, m/z): M+1=612, R,T=1.005 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Into a 8-mL round-bottom flask, was placed a solution of 4-(4-[[2-(4-chlorophenyl)-4,4-dimethylcyclohex-1-en-1-yl]methyl]piperazin-1-yl)-N-([3-oxa-2,4,10-triazatricyclo[7.4.0.0ˆ[3,7]]trideca-1,3(7),5,8-tetraen-10-yl]benzoic acid (35 mg, 0.06 mmol, 1.00 equiv) in dichloromethane (5 mL), 4-dimethylaminopyridine (27.8 mg, 0.23 mmol, 4.00 equiv), 3-nitro-4-[(oxan-4-ylmethyl)amino]benzene-1-sulfonamide (21.7 mg, 0.07 mmol, 1.20 equiv), EDCI (22 mg, 0.11 mmol, 2.00 equiv). The resulting solution was stirred for overnight at room temperature. The resulting mixture was concentrated under vacuum. The crude product was purified by Prep-HPLC with the following conditions (Waters-2767): Column, X-bridge RP18, 5 um, 19*100 mm; mobile phase, 0.03% ammonia in water (0.03% NH4HCO3 & NH4OH) and CH3CN (32% CH3CN up to 52% in 6 min); Detector, UV 254 nm. This resulted in 28.3 mg (54%) of 4-(4-[[2-(4-chlorophenyl)-4,4-dimethylcyclohex-1-en-1-yl]methyl]piperazin-1-yl)-N-([3-nitro-4-[(oxan-4-ylmethyl)amino]benzene]sulfonyl)-2-[13-oxa-2,4,10-triazatricyclo[7.4.0.0ˆ[3,7]]trideca-1,3(7),5,8-tetraen-10-yl]benzamide as a yellow solid. LC-MS-: (ES, m/z): (ES, m/z): M+1=909, R.T=1.52 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient. H-NMR: (CDCl$_3$, 300 MHz) δ: 8.70 (s, 1H), 8.46 (m, 2H), 8.10-8.06 (m, 1H), 7.89-7.60 (m, 1H), 7.10 (s, 1H), 6.94-6.71 (m, 5H), 6.49 (s, 1H), 6.16 (s, 1H), 4.70-4.65 (m, 2H), 4.00-4.10 (m, 2H), 3.67-3.19 (m, 7H), 3.20-3.00 (m, 4H), 2.78 (s, 1H), 2.58-2.52 (m, 2H), 2.27-2.17 (m, 3H), 2.05-1.98 (m, 4H), 1.74-1.70 (m, 3H), 1.55-1.40 (m, 3H), 0.98 (s, 6H). The measurements of the NMR spectra were done with BrukerAvanceIII HD 300 MHz with a probe head of BBOF.

Example 16

Preparation of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((4-(((4-fluorotetrahydro-2H-pyran-4-yl)methyl)amino)-3-nitrophenyl)sulfonyl)benzamide Into a 8-mL round-bottom flask, was placed a solution of 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0ˆ[3,7]]trideca-1,3(7),5,8-tetraen-10-yl]benzoic acid (35 mg, 0.06 mmol, 1.00 equiv) in dichloromethane (5 mL), 4-dimethylaminopyridine (27.8 mg, 0.23 mmol, 4.00 equiv), EDCI (22 mg, 0.11 mmol, 2.00 equiv), 4-[(4-fluorooxan-4-yl)methyl]amino-3-nitrobenzene-1-sulfonamide (22.7 mg, 0.07 mmol, 1.20 equiv). The resulting solution was stirred for overnight at room temperature. The resulting mixture was concentrated under vacuum. The crude product was purified by Prep-HPLC with the following conditions (Waters-2767): Column, X-bridge RP18, 5 um, 19*100 mm; mobile phase, 0.03% ammonia in water (0.03% NH$_4$HCO$_3$ & NH$_4$OH) and CH$_3$CN (32% CH$_3$CN up to 52% in 6 min); Detector, UV 254 nm. This resulted in 26.2 mg (50%) of 4-(4-[[2-(4-chlorophenyl)-4,4-dimethylcyclohex-1-en-1-yl]methyl]piperazin-1-yl)-N-[(4-[[(4-fluorooxan-4-yl)methyl]amino]-3-nitrobenzene)sulfonyl]-2-[13-oxa-2,4,10-triazatricyclo[7.4.0.0ˆ[3,7]]trideca-1,3(7),5,8-tetraen-10-yl] benzamide as a yellow solid. LC-MS: (ES, m/z): (ES, m/z): M+1=927, R,T=1.27 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR: (CDCl$_3$, 300 MHz) δ: 12.38 (bs, 1H), 8.69 (d, J=2.1 Hz, 1H), 8.58 (t, J=6.3 Hz, 1H), 8.44 (s, 1H), 8.07 (d, J=9.0 Hz 1H), 7.90-7.87 (m, 1H), 7.24-7.22 (m, 2H), 7.08 (s, 1H), 6.94 (m, 2H), 6.85 (s, 1H), 6.80-6.77 (m, 2H), 6.49 (s, 1H), 6.14 (s, 1H), 4.74-4.67 (m, 2H), 3.91-3.80 (m, 2H), 3.80-3.44 (m, 6H), 3.17 (m, 4H), 2.77 (s, 1H), 2.22-2.10 (m, 6H), 2.00 (s, 2H), 1.98-1.75 (m, 3H), 1.80-1.60 (m, 2H), 1.55-1.40 (m, 2H), 0.94 (s, 6H). The measurements of the NMR spectra were done with BrukerAvanceIII HD 300 MHz with a probe head of BBOF.

Example 17

Preparation of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl-2,2,3,3-d4)-N-((4-(((4-fluorotetrahydro-2H-pyran-4-yl)methyl)amino)-3-nitrophenyl)sulfonyl)benzamide Synthesis of 4-[[2-(trimethylsilyl)ethoxy]methyl](12,12-2H2)-13-oxa-2,4,10-triazatricyclo[7.4.0.0ˆ[3,7]]trideca-1(9),2,5,7-tetraen-11-one: Into a 8-mL vial, was placed 4-[[2-(trimethylsilyl)ethoxy]methyl]-13-oxa-2,4,10-triazatricyclo[7.4.0.0ˆ[3,7]]trideca-1(9),2,5,7-tetraen-11-one (90 mg, 0.28 mmol, 1 equiv), D$_2$O (1 mL), MeOD (1 mL), Na$_2$CO$_3$ (89.6 mg, 0.85 mmol, 3.00 equiv). The resulting solution was stirred for 48 h at 60° C. in an oil bath. The resulting solution was extracted with 3×3 mL of dichloromethane. The organic layer was dried over anhydrous sodium sulfate and concentrated under vacuum. This resulted in 60 mg (66%) of 4-[[2-(trimethylsilyl)ethoxy]methyl](12,12-2H2)-13-oxa-2,4,10-triazatricyclo[7.4.0.0^[3,7]]trideca-1(9),2,5,7-tetraen-11-one as a yellow solid. LC-MS-PH-PHNW-4-34-1: (ES, m/z): M+1=322, The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-34-2: (d-DMSO, 300 ppm): 7.44-7.41 (m, 2H), 6.43-6.42 (d, J=6 Hz, 1H), 5.46-5.41 (m, 2H), 3.51-3.46 (m, 2H), 1.24 (s, 1H), 0.86-0.79 (m, 4H), −0.04-0.05 (m, 9H).

Synthesis of 4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraene: Into a 8-mL vial, was placed 4-[[2-(trimethylsilyl)ethoxy]methyl](12,12-2H2)-13-oxa-2,4,10-triazatricyclo[7.4.0.0^[3,7]]trideca-1(9),2,5,7-tetraen-11-one (60 mg, 0.19 mmol, 1 equiv), THF (3 mL). This was followed by the addition of LiAlD$_4$ (31.3 mg, 0.75 mmol, 3.99 equiv) in portions at 0° C. The resulting solution was stirred for overnight at room temperature. The reaction was then quenched by the addition of 1 mL of D$_2$O. The resulting solution was extracted with 3×5 mL of ethyl acetate. The organic layer was dried over anhydrous sodium sulfate and concentrated under vacuum. This resulted in 25 mg (43.28%) of 4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraene as a yellow solid. LC-MS-PH-PHNW-4-34-2: (ES, m/z): M+1=931. H-NMR-PH-PHNW-4-34-2: (CDCl$_3$, 300 ppm): 7.35 (s, 1H), 7.17-7.15 (d, J=6 Hz, 1H), 6.35-6.34 (d, J=3 Hz, 1H), 5.56-5.53 (m, 2H), 3.58-3.52 (m, 2H), 2.08 (s, 1H), 1.28 (s, 1H), 0.93-0.88 (m, 3H), −0.04--0.05 (m, 9H).

Synthesis of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraen-10-yl)benzoate: Into a 8-mL vial, was placed 4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraene (25 mg, 0.08 mmol, 1 equiv), methyl 2-bromo-4-(4-[[2-(4-chlorophenyl)-4,4-dimethylcyclohex-1-en-1-yl]methyl]piperazin-1-yl)benzoate (55.9 mg, 0.11 mmol, 1.3 equiv), Dioxane (5 mL), Cs$_2$CO$_3$ (52.6 mg, 0.16 mmol, 2 equiv), Chloro[9,9-dimethyl-4,5-bis(diphenylphosphino)xanthene][2-amino-1,1-biphenyl-2-yl]palladium(II) (5 mg). The resulting solution was stirred for 2 h at 100° C. in an oil bath. After the reaction completed, the crude solution is concentrated and the residue was applied onto a silica gel column with ethyl acetate/petroleum ether (0:1-1:1). This resulted in 20 mg (32.56%) of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl](11,11,12,12-2H4)-13-oxa-2,4,10-triazatricyclo[7.4.0.0^[3,7]]trideca-1(9),2,5,7-tetraen-10-yl)benzoate as a yellow solid. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of methyl 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoate. Into a 8-mL vial, was placed methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl](11,11,12,12-2H4)-13-oxa-2,4,10-triazatricyclo[7.4.0.0^[3,7]]trideca-1(9), (20 mg, 0.03 mmol, 1 equiv), THF (2 mL), TBAF (100 mg, 0.38 mmol, 14.54 equiv), ethane-1,2-diamine (1 mL, 0.02 mmol, 0.63 equiv). The resulting solution was stirred for overnight at 70° C. The resulting mixture was concentrated under vacuum. The residue was applied onto a silica gel column with ethyl acetate/petroleum ether (0:1-1:1). This resulted in 12 mg (72.40%) of methyl 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoate as a yellow solid. LC-MS-PH-PHNW-4-34-4: (ES, m/z): M+1=630. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoic acid: Into a 8-mL vial, was placed methyl 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoate (12 mg, 0.02 mmol, 1 equiv), MeOH (1 mL), H$_2$O (1 mL), THF (1 mL), NaOH (3.0 mg, 0.08 mmol, 3.94 equiv). The resulting solution was stirred for overnight at 60° C. in an oil bath. The pH value of the solution was adjusted to 5 with HCl (1 mol/L). The reaction mixture was concentrated under vacuum. The residue was applied on a silica gel column and eluted with PE/EA (1:0-2:3). This resulted in 9 mg (76.71%) of 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1(9),2,5,7-tetraen-10-yl]benzoic acid as an off-white solid. LC-MS-PH-PHNW-4-34-5: (ES, m/z): M+1=616. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzene sulfonyl)-2-[(11,11,12,12-2H4)-13-oxa-2,4,10-triazatricyclo[7.4.0.0.0^[3,7]]trideca-1(9),2,5,7-tetraen-10-yl]benzamide: Into a 8-mL vial, was placed 4-(4-[[2-(4-chlorophenyl)-4,4-dimethylcyclohex-1-en-1-yl]methyl]piperazin-1-yl)-2-[(11,11,12,12-2H4)-13-oxa-2,4,10-triazatricyclo[7.4.0.0^[3,7]]trideca-1,3(7),5,8-tetraen-10-yl]benzoic acid (9 mg, 0.01 mmol, 1 equiv), 4-[[(4-fluorooxan-4-yl)methyl]amino]-3-nitrobenzene-1-sulfonamide (6.3 mg, 0.02 mmol, 1.3 equiv), DCM (2 mL), DMAP (7.1 mg, 0.06 mmol, 3.98 equiv), EDCI (5.6 mg, 0.03 mmol, 2 equiv). The resulting solution was stirred for overnight at room temperature. The resulting mixture was concentrated under vacuum. The residue was applied onto a silica gel column with dichloromethane/methanol (10:1). This resulted in 6 mg (44.10%) of 4-(4-[[2-(4-chlorophenyl)-4,4-dimethylcyclohex-1-en-1-yl]methyl]piperazin-1-yl)-N-(4-[[(4-fluorooxan-4-yl)methyl]

amino]-3-nitrobenzenesulfonyl)-2-[(11,11,12,12-2H4)-13-oxa-2,4,10-triazatricyclo[7.4.0.0.0`[3,7]]trideca-1(9),2,5,7-tetraen-10-yl]benzamide as a yellow solid. LC-MS-PH-PHNW-4-34-0: (ES, m/z): M+1=931. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-34-0: (d-DMSO, 300 ppm): 8.57 (s, 1H), 8.37 (s, 1H), 7.58-7.55 (m, 1H), 7.37-7.35 (m, 3H), 7.08-7.05 (m, 3H), 6.87-6.76 (m, 3H), 3.76-3.73 (m, 6H), 3.57-3.53 (m, 6H), 3.33 (m, 3H), 2.76-2.73 (m, 2H), 2.26-2.20 (m, 6H), 1.98 (m, 2H), 1.81-1.76 (m, 5H), 1.41-1.39 (m, 5H), 1.39 (m, 4H), 0.91-0.88 (m, 6H).

Example 18

Preparation of 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-methyl-2,3-dihydropyrrolo[3',2':5,6]pyrido[2,3-b][1,4]oxazin-1(6H)-yl)benzamide Synthesis of tert-butyl 1-(5-bromo-1-((2-(trimethylsilyl)ethoxy)methyl)-1H-pyrrolo[2,3-b]pyridin-6-yloxy)propan-2-ylcarbamate. Into a 250 mL round-bottom flask was placed tert-butyl 1-hydroxypropan-2-ylcarbamate (2.28 g, 13.05 mmol, 1.50 equiv), DMF (30 mL), NaH (0.87 g, 21.75 mmol, 2.50 equiv) at 0° C. for 10 min. 5-bromo-6-fluoro-14(2-(trimethylsilyl)ethoxy)methyl)-1H-pyrrolo[2,3-b]pyridine (3.0 g, 8.70 mmol, 1.00 equiv) was added. The resulting solution was stirred overnight at room temperature. The resulting solution was diluted with 200 mL of H₂O. The resulting solution was extracted with 3×300 mL of ethyl acetate and the organic layers combined. The resulting mixture was washed with 1×200 mL of H₂O and 1×200 mL sodium chloride(aq). The resulting mixture was concentrated under vacuum. The residue was applied onto a silica gel column with PE/EA (5:1). This resulted in 2.2 g (50%) of tert-butyl 1-(5-bromo-1-((2-(trimethylsilyl)ethoxy)methyl)-1H-pyrrolo[2,3-b]pyridin-6-yloxy)propan-2-ylcarbamate as a yellow oil. LC-MS-PH-PHNW-4-35-1 (ES, m/z): LC-MS (M+1): 502; RT=1.50 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 2.0 minutes; Oven temperature 40° C.; flow: 1.5 mL/min.

Synthesis of tert-butyl 2-methyl-64(2-(trimethylsilyl)ethoxy)methyl)-2,3-dihydropyrrolo[3',2':5,6]pyrido[2,3-b][1,4]oxazine-1(6H)-carboxylate. Into a 100 mL round-bottom flask was placed tert-butyl 1-(5-bromo-14(2-(trimethylsilyl)ethoxy)methyl)-1H-pyrrolo[2,3-b]pyridin-6-yloxy)propan-2-ylcarbamate (2.2 g, 4.39 mmol, 1.00 equiv), dioxane (25 mL), Cs₂CO₃ (4.30 g, 13.17 mmol, 3.00 equiv), X-phosPd 3G (1.04 g, 1.317 mmol, 0.30 equiv). The resulting solution was stirred overnight at 100° C. under N₂. The resulting mixture was concentrated under vacuum. The residue was applied onto a silica gel column with PE/EA (3:1). This resulted in 1.26 g (68%) of tert-butyl 2-methyl-64(2-(trimethylsilyl)ethoxy)methyl)-2,3-dihydropyrrolo[3',2':5,6]pyrido[2,3-b][1,4]oxazine-1(6H)-carboxylate as a yellow oil. LC-MS-PH-PHNW-4-35-2 (ES, m/z): LC-MS (M+1): 420; RT=1.84 min. The measurements of the retention were done with a reversed phase column (C18). Shimadzu LCMS 2020; 50*3.0 Kinetex 2.6u XB-ODS, 2.6 microm; Eluent A: water (0.05% TFA); Eluent B: Acetonitrile; linear gradient from 5% acetonitrile to 100% acetonitrile in 2.6 minutes; Oven temperature 40° C.; flow: 1.0 mL/min.

Synthesis of 2-methyl-64(2-(trimethylsilyl)ethoxy)methyl)-1,2,3,6-tetrahydropyrrolo[3',2':5,6]pyrido[2,3-b][1,4]oxazine: Into a 250 mL round-bottom flask was placed tert-butyl 2-methyl-64(2-(trimethylsilyl)ethoxy)methyl)-2,3-dihydropyrrolo[3',2':5,6]pyrido[2,3-b][1,4]oxazine-1(6H)-carboxylate (1.26 g, 3.00 mmol, 1.00 equiv), DCM (15 mL), ZnBr₂ (10.0 g, 30 mmol, 10.0 equiv). The resulting solution was stirred at room temperature for 3 h. The resulting solution was diluted with 50 mL of NaHCO₃. The resulting solution was extracted with 3×50 mL of DCM and the organic layers combined. The resulting mixture was washed with 1×50 mL of H₂O and 1×50 mL sodium chloride(aq). The resulting mixture was concentrated under vacuum. The residue was applied onto a silica gel column with PE/EA (1:1). This resulted in 800 mg (83%) of 2-methyl-64(2-(trimethylsilyl)ethoxy)methyl)-1,2,3,6-tetrahydropyrrolo[3',2':5,6]pyrido[2,3-b][1,4]oxazine as a yellow oil. LC-MS-PH-PHNW-4-35-3 (ES, m/z): LC-MS (M+1): 320; RT=1.54 min. The measurements of the retention were done with a reversed phase column (C18). Shimadzu LCMS 2020; 50*3.0 Kinetex 2.6u XB-ODS, 2.6 microm; Eluent A: water (0.05% TFA); Eluent B: Acetonitrile; linear gradient from 5% acetonitrile to 100% acetonitrile in 2.6 minutes; Oven temperature 40° C.; flow: 1.0 mL/min.

Synthesis of methyl 4-(4-((4'-chloro-5,5-dimethyl-3,4,5,6-tetrahydro-[1,1'-biphenyl]-2-yl)methyl) piperazin-1-yl)-2-(2-methyl-64(2-(trimethylsilyl)ethoxy)methyl)-2,3-dihydropyrrolo[3',2':5,6]pyrido[2,3-b][1,4]oxazin-1(6H)-yl)benzoate: Into a 100 mL round-bottom flask was placed tert-butyl 1-(5-bromo-14(2-(trimethylsilyl)ethoxy)methyl)-1H-pyrrolo[2,3-b]pyridin-6-yloxy)propan-2-ylcarbamate (300 mg, 0.94 mmol, 1.00 equiv), dioxane (15 mL), Cs₂CO₃ (920 mg, 2.82 mmol, 3.00 equiv), XantphosPd 2G (83 mg, 0.094 mmol, 0.10 equiv), methyl 2-bromo-4-(4-((4'-chloro-5,5-dimethyl-3,4,5,6-tetrahydro-[1,1'-biphenyl]-2-yl)methyl)piperazin-1-yl)benzoate (1.0 g, 1.88 mmol, 2.00 equiv). The resulting solution was stirred overnight at 110° C. under N₂. The resulting mixture was concentrated under vacuum. The residue was applied onto a silica gel column with PE/EA (5:1). This resulted in 360 mg (50%) of methyl 4-(4-((4'-chloro-5,5-dimethyl-3,4,5,6-tetrahydro-[1,1'-biphenyl]-2-yl)methyl)piperazin-1-yl)-2-(2-methyl-6-((2-(trimethylsilyl)ethoxy)methyl)-2,3-dihydropyrrolo[3',2':5,6]pyrido[2,3-b][1,4]oxazin-1(6H)-yl)benzoate as a yellow oil. LC-MS-PH-PHNW-4-35-4 (ES, m/z): LC-MS (M+1): 770; RT=1.56 min. The measurements of the retention were done with a reversed phase column (C18). Shimadzu LCMS 2020; 50*3.0 Kinetex 2.6u XB-ODS, 2.6 microm; Eluent A: water (0.05% TFA); Eluent B: Acetonitrile; linear gradient from 5% acetonitrile to 100% acetonitrile in 2.6 minutes; Oven temperature 40° C.; flow: 1.0 mL/min Synthesis of methyl 4-(4-((4'-chloro-5,5-dimethyl-3,4,5,6-tetrahydro-[1,1'-biphenyl]-2-yl)methyl) piperazin-1-yl)-2-(2-methyl-2,3-dihydropyrrolo[3',2':5,6]pyrido[2,3-b][1,4]oxazin-1(6H)-yl)benzoate Into a 100 mL round-bottom flask was placed tert-butyl methyl 4-(4-((4'-chloro-5,5-dimethyl-3,4,5,6-tetrahydro-[1,1'-biphenyl]-2-yl)methyl)piperazin-1-yl)-2-(2-methyl-6-((2-(trimethylsilyl)ethoxy)methyl)-2,3-dihydropyrrolo[3',2':5,6]pyrido[2,3-b][1,4]oxazin-1(6H)-yl)benzoate (300 mg, 0.39 mmol, 1.00 equiv), THF (10 mL), TBAF (3.0 g), ethane-1,2-diamine (5 mL). The resulting solution was stirred overnight at 60° C. The resulting mixture was concentrated under vacuum. The mixture was adjust PH<7 by 2N HCl. The resulting solution was extracted with 3×200 mL of EA and the organic layers combined. The resulting mixture was washed with 1×10 mL of $H_2O$ and 1×10 mL sodium chloride(aq). The resulting mixture was concentrated under vacuum. This resulted in 120 mg (48%) of methyl 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoate as a yellow oil. LC-MS-PH-PHNW-4-35-5 (ES, m/z): LC-MS (M+1): 640; RT=2.82 min. The measurements of the retention were done with a reversed phase column (C18). Shimadzu LCMS 2020; 50*3.0 Kinetex 2.6u HPH-C18, 2.6 microm; Eluent A: water (0.05% $NH_4HCO_3$); Eluent B: Methanol; linear gradient from 10% acetonitrile to 98% acetonitrile in 3.5 minutes; Oven temperature 40° C.; flow: 0.8 mL/min.

Synthesis of 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoic acid. Into a 50 mL round-bottom flask was methyl 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoate (70 mg, 0.11 mmol, 1.00 equiv), $MeOH/H_2O$ (5/5 mL), NaOH (44 mg, 1.10 mmol, 10 equiv). The resulting solution was stirred at 60° C. for 3 h. The resulting mixture was concentrated under vacuum. The residue was applied onto a silica gel column with dichloromethane/methanol (10:1). This resulted in 50 mg (73%) of 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoic acid as a white solid. LC-MS-PH-PHNW-4-35-6 (ES, m/z): LC-MS (M+1): 626; RT=2.45 min. The measurements of the retention were done with a reversed phase column (C18). Shimadzu LCMS 2020; 50*3.0 Kinetex 2.6u HPH-C18, 2.6 microm; Eluent A: water (0.05% $NH_4HCO_3$); Eluent B: Methanol; linear gradient from 10% acetonitrile to 98% acetonitrile in 3.5 minutes; Oven temperature 40° C.; flow: 0.8 mL/min.

Synthesis of 4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(2-methyl-2,3-dihydropyrrolo[3',2':5,6]pyrido[2,3-b][1,4]oxazin-1(6H)-yl)benzamide: Into a 50-mL 1-necked round-bottom flask was placed 4-(4-((4'-chloro-5,5-dimethyl-3,4,5,6-tetrahydro-[1,1'-biphenyl]-2-yl)methyl)piperazin-1-yl)-2-(2-methyl-2,3-dihydropyrrolo[3',2':5,6]pyrido[2,3-b][1,4]oxazin-1(6H)-yl)benzoic acid (40 mg, 0.064 mol, 1.00 equiv), DCM (4 mL), EDCI (49 mg, 0.256 mmol, 4.00 equiv), DMAP (16 mg, 0.128 mmol, 2.00 equiv), 4-(((4-fluorotetrahydro-2H-pyran-4-yl)methyl) amino)-3-nitrobenzenesulfonamide (28 mg, 0.0832 mol, 1.30 equiv). The resulting solution was stirred overnight at 40° C. The resulting mixture was concentrated under vacuum. This resulted in 2.9 mg (70%) of 4-(4-((4'-chloro-5,5-dimethyl-3,4,5,6-tetrahydro-[1,1'-biphenyl]-2-yl) methyl)piperazin-1-yl)-N-((4-(((4-fluorotetrahydro-2H-pyran-4-yl)methyl)amino)-3-nitrophenyl)sulfonyl)-2-(2-methyl-2,3-dihydropyrrolo[3',2':5,6]pyrido[2,3-b][1,4]oxazin-1(6H)-yl)benzamide as a yellow solid. LC-MS-PH-PHNW-4-35-0A (ES, m/z): LC-MS (M+1):941; RT=5.02 min. The measurements of the retention were done with a reversed phase column (C18). Shimadzu LCMS 2020; 50*3.0 Kinetex 2.6u Ascentis Express C18, 2.6 microm; Eluent A: water (0.05% TFA); Eluent B: Methanol; linear gradient from 5% acetonitrile to 95% acetonitrile in 7.0 minutes; Oven temperature 40° C.; flow: 1.0 mL/min.

Example 19

Preparation of (S)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-2,3-dihydropyrrolo[3',2':5,6]pyrido[2,3-b][1,4]oxazin-1(6H)-yl)benzamide and (R)-4-(4-((4'-chloro-5,5-dimethyl-3,4,5,6-tetrahydro-[1,1'-biphenyl]-2-yl)methyl)piperazin-1-yl)-N-((4-(((4-fluorotetrahydro-2H-pyran-4-yl)methyl)amino)-3-nitrophenyl)sulfonyl)-2-(3-methyl-2,3-dihydropyrrolo[3',2':5,6]pyrido[2,3-b][1,4]oxazin-1(6H)-yl)benzamide Synthesis of 12-methyl-4-[[2-(trimethylsilyl)ethoxy]methyl]-13-oxa-2,4,10-triazatricyclo[7.4.0.0^[3,7]]trideca-1(9),2,5,7-tetraen-11-one: Into a 100-mL round-bottom flask, was placed 5-amino-1-[[2-(trimethylsilyl)ethoxy]methyl]-1H-pyrrolo[2,3-b]pyridin-6-ol (1.5 g, 5.37 mmol, 1 equiv), DMF (50 mL), $K_2CO_3$ (2.2 g, 16.11 mmol, 3 equiv). This was followed by the addition of 2-chloropropanoyl chloride (1.4 g, 10.74 mmol, 2 equiv) dropwise with stirring at 0° C. The resulting solution was stirred for overnight at room temperature. The reaction was then quenched by the addition of 50 mL of water. The resulting solution was extracted with 2×50 mL of ethyl acetate. The resulting mixture was washed with 2×50 mL of brine. The mixture was dried over anhydrous sodium sulfate and filtrate and concentrated under vacuum. The residue was applied onto a silica gel column with ethyl acetate/petroleum ether (0:1-1:3). This resulted in 500 mg (27.93%) of 12-methyl-4-[[2-(trimethylsilyl)ethoxy]methyl]-13-oxa-2,4,10-triazatricyclo[7.4.0.0^[3,7]]trideca-1(9),2,5,7-tetraen-11-one as a yellow solid. LC-MS-PH-PHNW-4-37-1: (ES, m/z): M+1=334, R,T=1.123 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-37-1: (CDCl3, 300 ppm): 8.34 (s, 1H), 7.63 (d, J=3 Hz, 1H), 7.42-7.28 (m, 1H), 6.46 (d, J=3 Hz, 1H), 5.68 (s, 2H), 4.92-4.85 (m, 1H), 3.63-3.53 (m, 2H), 1.85-1.81 (d, J=12 Hz, 3H), 0.94-0.89 (m, 2H), −0.154 (s, 9H). The measurements of the NMR spectra were done with BrukerAvanceIII HD 300 MHz with a probe head of BBOF.

Synthesis of 12-methyl-4-[[2-(trimethylsilyl)ethoxy] methyl]-13-oxa-2,4,10-triazatricyclo[7.4.0.0^[3,7]]trideca-1(9),2,5,7-tetraene & (12R or 5)-12-methyl-4-[[2-(trimethylsilyl)ethoxy]methyl]-13-oxa-2,4,10-triazatricyclo[7.4.0.0^[3,7]]trideca-1(9),2,5,7-tetraene (Assumed) & (12S or R)-12-methyl-4-[[2-(trimethylsilyl)ethoxy]methyl]-13-oxa-2,4,10-triazatricyclo[7.4.0.0^[3,7]]trideca-1(9),2,5,7-tetraene (Assumed): Into a 100-mL 3-necked round-bottom flask, was placed 12-methyl-4-[[2-(trimethylsilyl)ethoxy]methyl]-13-oxa-2,4,10-triazatricyclo[7.4.0.0^[3,7]]trideca-1(9),2,5,7-tetraen-11-one (500 mg, 1.50 mmol, 1 equiv), THF (20 mL). This was followed by the addition of $LiAlH_4$ (113.8 mg, 3.00 mmol, 2 equiv), in portions at 0° C. The resulting solution was stirred for 1 overnight at room temperature. The reaction was then quenched by the addition of 20 mL of water. The solids were filtered out. The resulting solution was extracted with 2×20 mL of ethyl acetate. The resulting mixture was washed with 2×20 mL of brine. The mixture was dried over anhydrous sodium sulfate and filtrate and concentrated under vacuum. The residue was applied onto a silica gel column with ethyl acetate/petroleum ether (0:1-1:3). This resulted in 450 mg (93%) of 12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a yellow solid.

The crude 12-methyl-4-[[2-(trimethylsilyl)ethoxy]methyl]-13-oxa-2,4,10-triazatricyclo[7.4.0.0ˆ[3,7]]trideca-1(9),2,5,7-tetraene (450 mg) was purified by Chiral-Prep-HPLC with the following conditions: (SHIMADZU LC-20AT): Column, CHIRALPAK IC; mobile phase A: n-hexane, Phase B: ethanol; Detector, 220 nm. This resulted in 200 mg (44%) of (12R or S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a yellow solid (Assumed).

This resulted in 200 mg (44%) of (12S or R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a yellow solid (Assumed).

LC-MS-PH-PHNW-4-37-2: (ES, m/z): M+1=320, R,T=1.107 min.

The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

H-NMR-PH-PHNW-4-37-2: (CDCl3, 300 ppm): 7.63 (s, 1H), 7.17 (s, 1H), 6.36-6.35 (d, J=3 Hz, 1H), 5.57-5.52 (m, 2H), 4.59-4.55 (m, 1H), 3.62-3.46 (m, 3H), 3.18-3.14 (m, 1H), 1.62-1.44 (m, 3H), 0.93-0.88 (m, 2H), −0.17 (s, 9H).

Synthesis of methyl 4-(4-[[2-(4-chlorophenyl)-4,4-dimethylcyclohex-1-en-1-yl]methyl]piperazin-1-yl)-2-[(12R or S)-12-methyl-4-[[2-(trimethylsilyl)ethoxy]methyl]-13-oxa-2,4,10-triazatricyclo[7.4.0.0ˆ[3,7]]trideca-1(9),2,4,10-triazatricyclo[7.4.0.0ˆ3,7]trideca-1(9),2,5,7-tetraen-10-yl]benzoate (Assumed): Into a 8-mL vial, was placed (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene (200 mg, 0.63 mmol, 1 equiv), methyl 2-bromo-4-(4-[[2-(4-chlorophenyl)-4,4-dimethylcyclohex-1-en-1-yl]methyl]piperazin-1-yl)benzoate (399.6 mg, 0.75 mmol, 1.2 equiv), CS2CO3 (611.9 mg, 1.88 mmol, 3 equiv), Dioxane (5 mL), Chloro[9,9-dimethyl-4,5-bis(diphenylphosphino)xanthene][2-amino-1,1-biphenyl-2-yl]palladium(II) (120 mg). The resulting solution was stirred for 2 hr at 110° C. in an oil bath. The resulting mixture was concentrated under vacuum. The residue was applied onto a silica gel column with ethyl acetate/petroleum ether (0:1-1:10). This resulted in 250 mg (51.83%) of methyl 4-(4-[[2-(4-chlorophenyl)-4,4-dimethylcyclohex-1-en-1-yl]methyl]piperazin-1-yl)-2-[(12R or S)-12-methyl-4-[[2-(trimethylsilyl)ethoxy]methyl]-13-oxa-2,4,10-triazatricyclo[7.4.0.0ˆ[3,7]]trideca-1(9),2,4,10-triazatricyclo[7.4.0.0ˆ3,7]trideca-1(9),2,5,7-tetraen-10-yl]benzoate as a yellow solid (Assumed).

Synthesis of methyl 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoate (Assumed) Into a 100-mL round-bottom flask, was placed methyl 4-(4-[[2-(4-chlorophenyl)-4,4-dimethylcyclohex-1-en-1-yl]methyl]piperazin-1-yl)-2-[(12R or S)-12-methyl-4-[[2-(trimethylsilyl)ethoxy]methyl]-13-oxa-2,4,10-triazatricyclo[7.4.0.0ˆ[3,7]]trideca-1(9),2 (250 mg, 0.32 mmol, 1 equiv), TBAF (3 g, 11.47 mmol, 35.36 equiv), THF (30 mL), ethane-1,2-diamine (2 g, 33.28 mmol, 102.56 equiv). The resulting solution was stirred for 12 h at 70° C. in an oil bath. The reaction was then quenched by the addition of 50 mL of water. The resulting solution was extracted with 2×50 mL of ethyl acetate. The resulting mixture was washed with 3×50 mL of brine. The mixture was dried over anhydrous sodium sulfate and filtrate and concentrated under vacuum. The residue was applied onto a silica gel column with ethyl acetate/petroleum ether (0:1-1:3). This resulted in 90 mg (43%) of methyl 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoate as a yellow solid (Assumed). H-NMR-PH-PHNW-4-37-50: (CDCl3, 300 ppm): 8.24 (s, 1H), 7.89-7.86 (d, J=9 Hz, 1H), 7.32-7.24 (m, 6H), 7.14-7.01 (m, 1H), 6.97-6.94 (m, 2H), 6.73-6.65 (m, 2H), 6.18 (s, 1H), 3.67-3.53 (m, 3H), 3.32-3.18 (m, 3H), 2.98-2.80 (m, 1H), 2.30-2.04 (m, 6H), 1.99 (s, 2H), 1.56-1.50 (m, 5H), 0.91-0.88 (m, 6H).

Synthesis of 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoic acid (Assumed). Into a 8-mL vial, was placed methyl 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoate (90 mg, 0.14 mmol, 1 equiv), MeOH (1 mL), H2O (1 mL), THF (1 mL), NaOH (22.5 mg, 0.56 mmol, 4 equiv). The resulting solution was stirred for overnight at 60° C. in an oil bath. The pH value of the solution was adjusted to 5 with HCl (1 mol/L). The resulting mixture was concentrated under vacuum. The residue was applied onto a silica gel column with dichloromethane/methanol (1:0-10:1). This resulted in 80 mg (90%) of 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoic acid as a yellow solid (Assumed). LC-MS-PH-PHNW-4-37-60: (ES, m/z): M+1=626, R,T=1.035 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzene sulfonyl)-2-[(12R or S)-12-methyl-13-oxa-2,4,10-triazatricyclo[7.4.0.0ˆ[3,7]]trideca-1(9),2,5,7-tetraen-10-yl]benzamide (Assumed): Into a 8-mL vial, was placed 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoic acid (90 mg, 0.14 mmol, 1 equiv), 4-[[(4-fluorooxan-4-yl)methyl]amino]-3-nitrobenzene-1-sulfonamide (57.5 mg, 0.17 mmol, 1.2 equiv), DCM (5 mL), DMAP (70.2 mg, 0.57 mmol, 4 equiv), EDCI (55.1 mg, 0.29 mmol, 2.00 equiv). The resulting solution was stirred for overnight at room temperature. The resulting mixture was concentrated. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min, hold 48.0% in 1 min) within 5 min; Detector, UV 254 nm. This resulted in 28 mg (20%) of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzene sulfonyl)-2-[(12R or S)-12-methyl-13-oxa-2,4,10-triazatricyclo[7.4.0.0^[3,7]]trideca-1(9),2,5,7-tetraen-10-yl]benzamide as a yellow solid (Assumed). 19.8 mg product was submitted (Assumed). LC-MS-PH-PHNW-4-37-0: (ES, m/z): M+1=941, R,T=3.04 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-37-0: (d-DMSO, 300 ppm): 8.59 (s, 1H), 8.54 (s, 1H), 7.55-7.53 (m, 1H), 7.36-7.29 (d, J=6 Hz, 3H), 7.12-7.06 (m, 3H), 6.80-6.72 (m, 3H), 5.95 (m, 1H), 4.53-4.51 (m, 1H), 3.78-3.43 (m, 7H), 3.21-3.00 (m, 5H), 2.22-2.17 (m, 5H), 1.96-1.75 (m, 6H), 1.58-1.56 (m, 5H), 0.93-0.88 (m, 6H).

Synthesis of methyl 4-(4-[[2-(4-chlorophenyl)-4,4-dimethylcyclohex-1-en-1-yl]methyl]piperazin-1-yl)-2-[(12S or R)-12-methyl-4-[[2-(trimethylsilyl)ethoxy]methyl]-13-oxa-2,4,10-triazatricyclo[7.4.0.0^[3,7]]trideca-1(9),2,2,5,7-tetraen-10-yl]benzoate (Assumed): Into a 8-mL vial, was placed (12S or R)-12-methyl-4-[[2-(trimethylsilyl)ethoxy]methyl]-13-oxa-2,4,10-triazatricyclo[7.4.0.0^[3,7]]trideca-1(9),2,5,7-tetraene (200 mg, 0.63 mmol, 1 equiv), methyl 2-bromo-4-(4-[[2-(4-chlorophenyl)-4,4-dimethylcyclohex-1-en-1-yl]methyl]piperazin-1-yl)benzoate (399.6 mg, 0.75 mmol, 1.2 equiv), $Cs_2CO_3$ (611.9 mg, 1.88 mmol, 3 equiv), Dioxane (5 mL), Chloro[9,9-dimethyl-4,5-bis(diphenylphosphino)xanthene][2-amino-1,1-biphenyl-2-yl]palladium(II) (120 mg). The resulting solution was stirred for 2 h at 110° C. in an oil bath. The resulting mixture was concentrated under vacuum. The residue was applied onto a silica gel column with ethyl acetate/petroleum ether (0:1-1:10). This resulted in 250 mg (51%) of methyl 4-(4-[[2-(4-chlorophenyl)-4,4-dimethylcyclohex-1-en-1-yl]methyl]piperazin-1-yl)-2-[(12S or R)-12-methyl-4-[[2-(trimethylsilyl)ethoxy]methyl]-13-oxa-2,4,10-triazatricyclo[7.4.0.0^[3,7]]trideca-1(9),2,2,5,7-tetraen-10-yl]benzoate as a yellow solid (Assumed).

Synthesis of methyl 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0^[3,7]]trideca-1(9),2,5,7-tetraen-10-yl]benzoate (Assumed): into a 100-mL round-bottom flask, was placed methyl 4-(4-[[2-(4-chlorophenyl)-4,4-dimethylcyclohex-1-en-1-yl]methyl]piperazin-1-yl)-2-[(12S or R)]-12-methyl-4-[[2-(trimethylsilyl)ethoxy]methyl]-13-oxa-2,4,10-triazatricyclo[7.4.0.0^[3,7]]trideca-1(9),2 (250 mg, 0.32 mmol, 1 equiv), TBAF (3 g, 11.47 mmol, 35.36 equiv), THF (30 mL), ethane-1,2-diamine (2 g, 33.28 mmol, 102.56 equiv). The resulting solution was stirred for 12 h at 70° C. in an oil bath. The reaction was then quenched by the addition of 50 mL of water. The resulting solution was extracted with 2×50 mL of ethyl acetate. The resulting mixture was washed with 3×50 mL of brine. The mixture was dried over anhydrous sodium sulfate and filtrate and concentrated under vacuum. The residue was applied onto a silica gel column with ethyl acetate/petroleum ether (0:1-1:3). This resulted in 90 mg (43%) of methyl 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0^[3,7]]trideca-1(9),2,5,7-tetraen-10-yl]benzoate as a yellow solid (Assumed).

LC-MS-PH-PHNW-4-38-50: (ES, m/z): M+1=640, R,T=1.424 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-38-50: (CDCl3, 300 ppm): 8.24 (s, 1H), 7.89-7.86 (d, J=9 Hz, 1H), 7.32-7.24 (m, 6H), 7.14-7.01 (m, 1H), 6.97-6.94 (m, 2H), 6.73-6.65 (m, 2H), 6.18 (s, 1H), 3.67-3.53 (m, 3H), 3.32-3.18 (m, 3H), 2.98-2.80 (m, 1H), 2.30-2.04 (m, 6H), 1.99 (s, 2H), 1.56-1.50 (m, 5H), 0.91-0.88 (m, 6H).

Synthesis of 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0^[3,7]]trideca-1(9),2,5,7-tetraen-10-yl]benzoic acid (Assumed): Into a 8-mL vial, was placed methyl 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0^[3,7]]trideca-1(9),2,5,7-tetraen-10-yl]benzoate (90 mg, 0.14 mmol, 1 equiv), MeOH (1 mL), $H_2O$ (1 mL), THF (1 mL), NaOH (22.5 mg, 0.56 mmol, 4.00 equiv). The resulting solution was stirred for overnight at 60° C. in an oil bath. The pH value of the solution was adjusted to 5 with HCl (1 mol/L). The resulting mixture was concentrated under vacuum. The residue was applied onto a silica gel column with chloroform/methanol (1:0-10:1). This resulted in 80 mg (90%) of 4-(4-[[2-(4-chlorophenyl)-4,4-dimethylcyclohex-1-en-1-yl]methyl]piperazin-1-yl)-2-[(12S or R)-12-methyl-13-oxa-2,4,10-triazatricyclo[7.4.0.0^[3,7]]trideca-1(9),2,5,7-tetraen-10-yl]benzoic acid as a solid (Assumed): LC-MS-PH-PHNW-4-38-60: (ES, m/z): M+1=626, R,T=1.039 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzene sulfonyl)-2-[(12S or R)-12-methyl-13-oxa-2,4,10-triazatricyclo[7.4.0.0^[3,7]]trideca-1(9),2,5,7-tetraen-10-yl]benzamide (Assumed): Into a 8-mL vial, was placed 4-(4-[[2-(4-chlorophenyl)-4,4-dimethylcyclohex-1-en-1-yl]ethyl]piperazin-1-yl)-2-[(12S or R)-12-methyl-13-oxa-2,4,10-triazatricyclo[7.4.0.0^[3,7]]trideca-1(9),2,5,7-tetraen-10-yl]benzoic acid (90 mg, 0.14 mmol, 1 equiv), 4-[[(4-fluorooxan-4-yl)methyl]amino]-3-nitrobenzene-1-sulfonamide (57.5 mg, 0.17 mmol, 1.2 equiv), DCM (5 mL), DMAP (70.2 mg, 0.57 mmol, 4 equiv), EDCI (55.1 mg, 0.29 mmol, 2 equiv). The resulting solution was stirred for overnight at room temperature. The resulting mixture was concentrated. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min, hold 48.0% in 1 min) within 5 min; Detector, UV 254 nm. This resulted in 26 mg (19%) of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzene sulfonyl)-2-[(12S or R)-12-methyl-13-oxa-2,4,10-triazatricyclo[7.4.0.0^[3,7]]trideca-1(9),2,5,7-tetraen-10-yl]benzamide as a yellow solid. 19.6 mg product was submitted (Assumed). LC-MS-PH-PHNW-4-38-0: (ES, m/z): M+1=941, R,T=3.036 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-38-0: (d-DMSO, 300 ppm): 8.56 (s, 1H), 8.36 (s, 1H), 7.62-7.54 (m, 1H), 7.37-7.30 (m, 3H), 7.14-7.04 (m, 3H), 6.98-6.92 (m, 3H), 5.94 (m, 1H), 4.53 (m, 1H), 3.79-3.71 (m, 4H), 3.65-3.54 (m, 3H), 3.44 (m, 4H), 2.78-2.73 (m, 2H), 2.23-2.18 (m, 6H), 1.97-1.91 (m, 2H), 1.87-1.81 (m, 4H), 1.50-1.20 (m, 5H), 0.91-0.88 (m, 6H).

Example 20: Preparation of 4-(4-((4'-chloro-5,5-dimethyl-3,4,5,6-tetrahydro-[1,1'-biphenyl]-2-yl) methyl)piperazin-1-yl)-2-(3,3-dimethyl-2,3-dihydropyrrolo[3',2':5,6]pyrido[2,3-b][1,4]oxazin-1(6H)-yl)-N-((4-(((4-fluorotetrahydro-2H-pyran-4-yl)methyl) amino)-3-nitrophenyl)sulfonyl)benzamide Synthesis of 12,12-dimethyl-4-[[2-(trimethylsilyl)ethoxy]methyl]-13-oxa-2,4,10-triazatricyclo[7.4.0.0ˆ[3,7]]trideca-1,3(7),5,8-tetraen-11-one: Into a 100-mL round-bottom flask, was placed 5-amino-1-[[2-(trimethylsilyl)ethoxy] methyl]-1H-pyrrolo[2,3-b]pyridin-6-ol (1 g, 3.58 mmol, 1 equiv), $CH_3CN$ (20 mL), methyl 2-bromo-2-methylpropanoate (647.9 mg, 3.58 mmol, 1.0 equiv), $Cs_2CO_3$ (1.7 g, 5.37 mmol, 1.5 equiv). The resulting solution was stirred for 2 h at 80° C. in an oil bath. The resulting mixture was concentrated under vacuum. The residue was applied onto a silica gel column with ethyl acetate/petroleum ether (1:3). This resulted in 270 mg (21%) of 12,12-dimethyl-4-[[2-(trimethylsilyl)ethoxy]methyl]-13-oxa-2,4,10-triazatricyclo [7.4.0.0ˆ[3,7]]trideca-1,3(7),5,8-tetraen-11-one as a light yellow solid. LC-MS-PH-PHNW-4-40-2: (ES, m/z): M+1=348, R,T=1.164 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 12,12-dimethyl-4-[[2-(trimethylsilyl)ethoxy] methyl]-13-oxa-2,4,10-triazatricyclo[7.4.0.0ˆ[3,7]]trideca-1,3(7),5,8-tetraene: Into a 8-mL vial, was placed 12,12-dimethyl-4-[[2-(trimethylsilyl)ethoxy]methyl]-13-oxa-2,4,10-triazatricyclo[7.4.0.0ˆ[3,7]]trideca-1,3(7),5,8-tetraen-11-one (250 mg, 0.72 mmol, 1 equiv), THF (3 mL). This was followed by the addition of $LiAlH_4$ (54.6 mg, 1.44 mmol, 2 equiv), in portions at 0° C. The resulting solution was stirred for overnight at room temperature. The reaction was then quenched by the addition of 5 mL of water. The solids were filtered out. The resulting solution was extracted with 2×10 mL of ethyl acetate. The organic layer was dried over anhydrous sodium sulfate and concentrated under vacuum. The residue was applied onto a silica gel column with ethyl acetate/petroleum ether (0:1-1:5). This resulted in 140 mg (58%) of 12,12-dimethyl-4-[[2-(trimethylsilyl)ethoxy] methyl]-13-oxa-2,4,10-triazatricyclo[7.4.0.0ˆ[3,7]]trideca-1,3(7),5,8-tetraene as a yellow solid.

Synthesis of 4-(4-[[2-(4-chlorophenyl)-4,4-dimethylcyclohex-1-en-1-yl]methyl]piperazin-1-yl)-2-(12,12-dimethyl-4-[[2-(trimethylsilyl)ethoxy]ethyl]-13-oxa-2,4,10-triazatricyclo[7.4.0.0ˆ[3,7]]trideca-1,3(7), 5,8-tetraen-10-yl) benzoate: Into a 8-mL vial, was placed 12,12-dimethyl-4-[[2-(trimethylsilyl)ethoxy]methyl]-13-oxa-2,4,10-triazatricyclo[7.4.0.0ˆ[3,7]]trideca-1,3(7),5,8-tetraene (140 mg, 0.42 mmol, 1 equiv), methyl 2-bromo-4-(4-[[2-(4-chlorophenyl)-4,4-dimethylcyclohex-1-en-1-yl]methyl]piperazin-1-yl)benzoate (267.9 mg, 0.50 mmol, 1.2 equiv), $Cs_2CO_3$ (410.3 mg, 1.26 mmol, 3 equiv), Dioxane (2 mL), Chloro[9,9-dimethyl-4,5-bis(diphenylphosphino)xanthene] [2-amino-1,1-biphenyl-2-yl]palladium(II) (80 mg). The resulting solution was stirred for 2 h at 110° C. in an oil bath. The resulting mixture was concentrated under vacuum. The residue was applied onto a silica gel column with ethyl acetate/petroleum ether (0:1-1:3). This resulted in 130 mg (39%) of methyl 4-(4-[[2-(4-chlorophenyl)-4,4-dimethylcyclohex-1-en-1-yl]methyl]piperazin-1-yl)-2-(12,12-dimethyl-4-[[2-(trimethylsilyl)ethoxy]methyl]-13-oxa-2,4,10-triazatricyclo[7.4.0.0ˆ[3,7]]trideca-1,3(7), 5,8-tetraen-10-yl) benzoate as a yellow solid. LC-MS-PH-PHNW-4-40-4: (ES, m/z): M+1=784, R,T=1.331 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of methyl 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3(7),5,8-tetraen-10-yl]benzoate: Into a 40-mL vial, was placed methyl 4-(4-[[2-(4-chlorophenyl)-4,4-dimethylcyclohex-1-en-1-yl]methyl]piperazin-1-yl)-2-(12,12-dimethyl-4-[[2-(trimethylsilyl)ethoxy]methyl]-13-oxa-2,4,10-triazatricyclo[7.4.0.0ˆ[3,7]]trideca-1,3(7), (130 mg, 0.17 mmol, 1 equiv), TBAF (3 g), THF (10 mL), ethane-1,2-diamine (2 g). The resulting solution was stirred for overnight at 60° C. in an oil bath. The reaction was then quenched by the addition of 10 mL of water. The resulting solution was extracted with 2×10 mL of ethyl acetate. The resulting mixture was washed with 3×10 mL of brine. The mixture was dried over anhydrous sodium sulfate and filtrate and concentrated under vacuum. The residue was applied onto a silica gel column with ethyl acetate/petroleum ether (0:1-1:3). This resulted in 110 mg (crude) of methyl 4-(4-[[2-(4-chlorophenyl)-4,4-dimethylcyclohex-1-en-1-yl] methyl]piperazin-1-yl)-2-[12,12-dimethyl-13-oxa-2,4,10-triazatricyclo[7.4.0.0ˆ[3,7]]trideca-1,3(7),5,8-tetraen-10-yl] benzoate as a yellow solid. LC-MS-PH-PHNW-4-40-5: (ES, m/z): M+1=654, R,T=1.107 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3 (7),5,8-tetraen-10-yl]benzoic acid: Into a 8-mL vial, was placed methyl 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3 (7),5,8-tetraen-10-yl]benzoate (80 mg, 0.12 mmol, 1 equiv), MeOH (1 mL), THF (1 mL), $H_2O$ (1 mL), NaOH (19.6 mg, 0.49 mmol, 4 equiv). The resulting solution was stirred for overnight at 60° C. in an oil bath. The pH value of the solution was adjusted to 5 with HCl (1 mol/L). The resulting mixture was concentrated under vacuum. The residue was applied onto a silica gel column with dichloromethane/ methanol (1:0-10:1). This resulted in 60 mg (76.64%) of 4-(4-[[2-(4-chlorophenyl)-4,4-dimethylcyclohex-1-en-1-yl]

methyl]piperazin-1-yl)-2-[12,12-dimethyl-13-oxa-2,4,10-triazatricyclo[7.4.0.0ˆ[3,7]]trideca-1,3(7),5,8-tetraen-10-yl]benzoic acid as a yellow solid. LC-MS-PH-PHNW-4-40-6: (ES, m/z): M+1=640, R,T=1.359 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1(9),2,5,7-tetraen-10-yl]-N-(4-[[(4-fluorooxan-4-yl)methyl]amino]-3-nitrobenzenesulfonyl)benzamide: Into a 8-mL vial, was placed 4-[[(4-fluorooxan-4-yl)methyl]amino]-3-nitrobenzene-1-sulfonamide (37.5 mg, 0.11 mmol, 1.2 equiv), DCM (5 mL), 4-(4-[[2-(4-chlorophenyl)-4,4-dimethylcyclohex-1-en-1-yl]methyl]piperazin-1-yl)-2-[12,12-dimethyl-13-oxa-2,4,10-triazatricyclo[7.4.0.0ˆ[3,7]]trideca-1,3(7),5,8-tetraen-10-yl]benzoic acid (60 mg, 0.09 mmol, 1 equiv), EDCI (35.9 mg, 0.19 mmol, 2 equiv), DMAP (45.8 mg, 0.37 mmol, 4 equiv). The resulting solution was stirred for overnight at room temperature. The resulting mixture was concentrated under vacuum. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min within 5; Detector, UV 254 nm. This resulted in 25 mg (27%) of 4-(4-[[2-(4-chlorophenyl)-4,4-dimethylcyclohex-1-en-1-yl]ethyl]piperazin-1-yl)-2-[12,12-dimethyl-13-oxa-2,4,10-triazatricyclo[7.4.0.0ˆ[3,7]]trideca-1(9),2,5,7-tetraen-10-yl]-N-(4-[[(4-fluorooxan-4-yl)methyl]amino]-3-nitrobenzenesulfonyl)benzamide as a yellow solid. 20.6 mg product was submitted. LC-MS-PH-PHNW-4-40-0: (ES, m/z): M+1=955, R,T=2.655 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-40-0: (d-DMSO, 300 ppm): 8.56 (s, 1H), 8.36 (s, 1H), 7.56-7.49 (m, 2H), 7.36-7.33 (m, 2H), 7.06-7.00 (m, 3H), 6.93-6.90 (m, 1H), 6.88-6.74 (M, 2H), 5.99 (m, 1H), 3.78-3.74 (m, 4H), 3.67-3.50 (m, 2H), 3.23 (m, 4H), 2.76-2.72 (m, 2H), 2.22-2.16 (m, 6H), 1.96-1.75 (m, 6H), 1.41-1.39 (m, 8H), 0.91-0.88 (m, 6H).

Example 21

Preparation of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-3-yl)methyl)amino)phenyl)sulfonyl)benzamide Synthesis of 3-nitro-4-(((tetrahydro-2H-pyran-3-yl)methyl)amino)benzenesulfonamide: Into a 50-mL round-bottom flask, was placed (tetrahydro-2H-pyran-3-yl)methanamine (200 mg, 1.74 mmol, 1.00 equiv), THF (5 mL), 4-fluoro-3-nitrobenzene-1-sulfonamide (383 mg, 1.74 mmol, 1.00 equiv), $Cs_2CO_3$ (1.134 g, 3.48 mmol, 2.00 equiv). The resulting solution was stirred for 3 h at 50 degrees C. in an oil bath. The resulting mixture was concentrated under vacuum. The residue was applied onto a silica gel column with ethyl acetate/petroleum ether (1/1). This resulted in 270 mg (49.3%) of 3-nitro-4-(((tetrahydro-2H-pyran-3-yl)methyl)amino)benzenesulfonamide as a yellow solid. LC-MS-PH-PHNW-4-41-1: (ES, m/z): M+1=316, R,T=1.25 min. The measurements of the retention were done with a reversed phase column (C18). Shimadzu LCMS 2020; 50*3.0 Kinetex 2.6u XB-ODS, 2.6 microm; Eluent A: water (0.5% FA); Eluent B: Acetonitrile (0.05 TFA); linear gradient from 5% acetonitrile to 100% acetonitrile in 2.6 minutes; Oven temperature 40° C.; flow: 1.0 mL/min.

Synthesis of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-3-yl)methyl)amino)phenyl)sulfonyl)benzamide: Into a 100-mL round-bottom flask, was placed 4-(4-[[2-(4-chlorophenyl)-4,4-dimethylcyclohex-1-en-1-yl]methyl]piperazin-1-yl)-2-[13-oxa-2,4,10-triazatricyclo[7.4.0.0ˆ[3,7]]trideca-1,3(7),5,8-tetraen-10-yl]benzoic acid (50 mg, 0.082 mmol, 1.00 equiv) in dichloromethane (5 mL), EDCI (63 mg, 0.328 mmol, 4.00 equiv), 4-dimethylaminopyridine (20 mg, 0.164 mmol, 2.00 equiv), 3-nitro-4-(((tetrahydro-2H-pyran-4-yl)methyl)amino)benzenesulfonamide (26 mg, 0.082 mmol, 1.00 equiv). The resulting solution was stirred for overnight at 40° C. The resulting mixture was concentrated under vacuum. The crude product was purified by Prep-HPLC with the following conditions (Waters-2767): Column, X-bridge RP18, 5 um, 19*100 mm; mobile phase, 0.03% ammonia in water (0.03% $NH_4HCO_3$ & $NH_4OH$) and $CH_3CN$ (32% $CH_3CN$ up to 52% in 6 min); Detector, UV 254 nm. This resulted in 12.8 mg (17%) of 4-(4-((4'-chloro-5,5-dimethyl-3,4,5,6-tetrahydro-[1,1'-biphenyl]-2-yl)methyl)piperazin-1-yl)-2-(2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide as a yellow solid. LC-MS-PH-PHNW-4-41-0: (ES, m/z): M+1=909, R,T=1.60 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.0 minutes; Oven temperature 40° C.; flow: 1.5 mL/min. 1H NMR (300 MHz, Chloroform-d) δ 12.40 (s, 1H), 8.72 (s, 1H), 8.63 (s, 1H), 8.44 (t, J=5.5 Hz, 1H), 8.10 (d, J=9.0 Hz, 1H), 7.93-7.82 (m, 1H), 7.25 (s, 4H), 7.13 (t, J=2.9 Hz, 1H), 7.00-6.68 (m, 6H), 6.52 (s, 1H), 6.17 (d, J=3.3 Hz, 1H), 4.71 (dd, J=23.6, 10.7 Hz, 2H), 3.99-3.79 (m, 3H), 3.70 (s, 1H), 3.57 (dd, J=18.5, 10.9 Hz, 3H), 3.46-3.17 (m, 7H), 2.80 (s, 2H), 2.29 (s, 3H), 2.21 (s, 2H), 2.03 (d, J=12.3 Hz, 5H), 1.75-1.60 (m, 4H), 1.44 (d, J=8.7 Hz, 3H), 1.28 (s, 1H), 0.97 (s, 6H), 0.87 (s, 1H). The measurements of the NMR spectra were done with BrukerAvanceIII HD 300 MHz with a probe head of BBOF.

Example 22

Preparation of (S)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide Synthesis of 6-(tert-butoxy)-N-(diphenylmethylidene)-1-[[2-(trimethylsilyl)ethoxy]methyl]-1H-pyrrolo[2,3-b]pyridin-5-amine: Into a 250-mL round-bottom flask, was placed a solution of 5-bromo-6-fluoro-1-[[2-(trimethylsilyl)ethoxy]

methyl]-1H-pyrrolo[2,3-b]pyridine (20.7 g, 60 mmol, 1.00 equiv) in dioxane (300 mL), t-BuOK (20.5 g, 180 mmol, 3.00 equiv), xantphos (6.9 g, 12 mmol, 0.20 equiv), $Pd_2(dba)_3 \cdot CHCl_3$ (5.7 g, 0.10 equiv), diphenylmethanimine (14.04 g, 78 mmol, 1.20 equiv). The resulting solution was stirred for overnight at 100° C. The resulting mixture was concentrated under vacuum. The residue was applied onto a silica gel column with ethyl acetate/petroleum ether (0:1-1:20). This resulted in 15 g (crude) of 6-(tert-butoxy)-N-(diphenylmethylidene)-1-[[2-(trimethylsilyl)ethoxy]methyl]-1H-pyrrolo[2,3-b]pyridin-5-amine as white oil. LC-MS-PH-PHNW-4-7-9: (ES, m/z): M+1=500.

Synthesis of 5-amino-1-[[2-(trimethylsilyl)ethoxy]methyl]-1H-pyrrolo[2,3-b]pyridin-6-ol hydrogen chloride salt: Into a 500-mL round-bottom flask, was placed 6-(tert-butoxy)-N-(diphenylmethylidene)-1-[[2-(trimethylsilyl)ethoxy]methyl]-1H-pyrrolo[2,3-b]pyridin-5-amine (15 g, 30.02 mmol, 1.00 equiv) in dioxane (120 mL), HCl/dioxane (4M, 30 mL). The resulting solution was stirred for 5 h at room temperature. The resulting solution was diluted with 500 mL of ether. The solids were collected by filtration. This resulted in 5 g (crude) of 5-amino-1-[[2-(trimethylsilyl)ethoxy]methyl]-1H-pyrrolo[2,3-b]pyridin-6-ol hydrogen chloride salt as a red solid, Q-NMR show it might converted into 3 hydrogen chloride salt. LC-MS-PH-PHNW-4-10-1: (ES, m/z): M+1=280, R,T=0.811 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Synthesis of 12-methyl-4-[[2-(trimethylsilyl)ethoxy]methyl]-13-oxa-2,4,10-triazatricyclo[7.4.0.0^[3,7]]trideca-1(9),2,5,7-tetraen-11-one: Into a 100-mL round-bottom flask, was placed 5-amino-1-[[2-(trimethylsilyl)ethoxy]methyl]-1H-pyrrolo[2,3-b]pyridin-6-ol (1.5 g, 5.37 mmol, 1 equiv), DMF (50 mL), $K_2CO_3$ (2.2 g, 16.11 mmol, 3 equiv). This was followed by the addition of 2-chloropropanoyl chloride (1.4 g, 10.74 mmol, 2 equiv) dropwise with stirring at 0° C. The resulting solution was stirred for overnight at room temperature. The reaction was then quenched by the addition of 50 mL of water. The resulting solution was extracted with 2×50 mL of ethyl acetate. The resulting mixture was washed with 2×50 mL of brine. The mixture was dried over anhydrous sodium sulfate and filtrate and concentrated under vacuum. The residue was applied onto a silica gel column with ethyl acetate/petroleum ether (0:1-1:3). This resulted in 500 mg (27.93%) of 12-methyl-4-[[2-(trimethylsilyl)ethoxy]methyl]-13-oxa-2,4,10-triazatricyclo[7.4.0.0^[3,7]]trideca-1(9),2,5,7-tetraen-11-one as a yellow solid. LC-MS-PH-PHNW-4-37-1: (ES, m/z): M+1=334, R,T=1.123 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-37-1: (CDCl3, 300 ppm): 8.34 (s, 1H), 7.63 (d, J=3 Hz, 1H), 7.42-7.28 (m, 1H), 6.46 (d, J=3 Hz, 1H), 5.68 (s, 2H), 4.92-4.85 (m, 1H), 3.63-3.53 (m, 2H), 1.85-1.81 (d, J=12 Hz, 3H), 0.94-0.89 (m, 2H), −0.154 (s, 9H).

Synthesis of 12-methyl-4-[[2-(trimethylsilyl)ethoxy]methyl]-13-oxa-2,4,10-triazatricyclo[7.4.0.0^[3,7]]trideca-1(9),2,5,7-tetraene & (12 S)-12-methyl-4-[[2-(trimethylsilyl)ethoxy]methyl]-13-oxa-2,4,10-triazatricyclo[7.4.0.0^[3,7]]trideca-1(9),2,5,7-tetraene & (12R)-12-methyl-4-[[2-(trimethylsilyl)ethoxy]methyl]-13-oxa-2,4,10-triazatricyclo[7.4.0.0^[3,7]]trideca-1(9),2,5,7-tetraene: Into a 100-mL 3-necked round-bottom flask, was placed 12-methyl-4-[[2-(trimethylsilyl)ethoxy]methyl]-13-oxa-2,4,10-triazatricyclo[7.4.0.0^[3,7]]trideca-1(9),2,5,7-tetraen-11-one (500 mg, 1.50 mmol, 1 equiv), THF (20 mL). This was followed by the addition of $LiAlH_4$ (113.8 mg, 3.00 mmol, 2 equiv), in portions at 0° C. The resulting solution was stirred for 1 overnight at room temperature. The reaction was then quenched by the addition of 20 mL of water. The solids were filtered out. The resulting solution was extracted with 2×20 mL of ethyl acetate. The resulting mixture was washed with 2×20 mL of brine. The mixture was dried over anhydrous sodium sulfate and filtrate and concentrated under vacuum. The residue was applied onto a silica gel column with ethyl acetate/petroleum ether (0:1-1:3). This resulted in 450 mg (93%) of 12-methyl-4-[[2-(trimethylsilyl)ethoxy]methyl]-13-oxa-2,4,10-triazatricyclo[7.4.0.0^[3,7]]trideca-1(9),2,5,7-tetraene as a yellow solid.

The crude 12-methyl-4-[[2-(trimethylsilyl)ethoxy]methyl]-13-oxa-2,4,10-triazatricyclo[7.4.0.0^[3,7]]trideca-1(9),2,5,7-tetraene (450 mg) was purified by Chiral-Prep-HPLC with the following conditions: (SHIMADZU LC-20AT): Column, CHIRALPAK IC; mobile phase A: n-hexane, Phase B: ethanol; Detector, 220 nm. This resulted in 200 mg (44%) of (12S)-12-methyl-4-[[2-(trimethylsilyl)ethoxy]methyl]-13-oxa-2,4,10-triazatricyclo[7.4.0.0^[3,7]]trideca-1(9),2,5,7-tetraene as a yellow solid.

This resulted in 200 mg (44%) of (12R)-12-methyl-4-[[2-(trimethylsilyl)ethoxy]methyl]-13-oxa-2,4,10-triazatricyclo[7.4.0.0^[3,7]]trideca-1(9),2,5,7-tetraene as a yellow solid. LC-MS-PH-PHNW-4-37-2: (ES, m/z): M+1=320, R,T=1.107 min.

The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-4-37-2: (CDCl3, 300 ppm): 7.63 (s, 1H), 7.17 (s, 1H), 6.36-6.35 (d, J=3 Hz, 1H), 5.57-5.52 (m, 2H), 4.59-4.55 (m, 1H), 3.62-3.46 (m, 3H), 3.18-3.14 (m, 1H), 1.62-1.44 (m, 3H), 0.93-0.88 (m, 2H), −0.17 (s, 9H).

Synthesis of methyl 4-(4-[[2-(4-chlorophenyl)-4,4-dimethylcyclohex-1-en-1-yl]methyl]piperazin-1-yl)-2-[(12 S)-12-methyl-4-[[2-(trimethylsilyl)ethoxy]methyl]-13-oxa-2,4,10-triazatricyclo[7.4.0.0^[3,7]]trideca-1(9),2,4,10-triazatricyclo[7.4.0.0^3,7]trideca-1(9),2,5,7-tetraen-10-yl]benzoate: Into a 8-mL vial, was placed (12S)-12-methyl-4-[[2-(trimethylsilyl)ethoxy]methyl]-13-oxa-2,4,10-triazatricyclo[7.4.0.0^[3,7]]trideca-1(9),2,5,7-tetraene (200 mg, 0.63 mmol, 1 equiv), methyl 2-bromo-4-(4-[[2-(4-chlorophenyl)-4,4-dimethylcyclohex-1-en-1-yl]methyl]piperazin-1-yl)benzoate (399.6 mg, 0.75 mmol, 1.2 equiv), $CS_2CO_3$ (611.9 mg, 1.88 mmol, 3 equiv), Dioxane (5 mL), Chloro[9,9-dimethyl-4,5-bis(diphenylphosphino)xanthene][2-amino-1,1-biphenyl-2-yl]palladium(II) (120 mg). The resulting solution was stirred for 2 hr at 110° C. in an oil bath. The resulting mixture was concentrated under vacuum. The residue was applied onto a silica gel column with ethyl acetate/petroleum ether (0:1-1:10). This resulted in 250 mg (51.83%) of methyl 4-(4-[[2-(4-chlorophenyl)-4,4-dimethylcyclohex-1-en-1-yl]methyl]piperazin-1-yl)-2-[(12S)-12-methyl-4-[[2-(trimethylsilyl)ethoxy]methyl]-13-oxa-2,4,10-triazatricyclo[7.4.0.0^[3,7]]trideca-1(9),2,4,10-triazatricyclo[7.4.0.0^3,7]trideca-1(9),2,5,7-tetraen-10-yl]benzoate as a yellow solid.

Synthesis of methyl 4-(4-[[2-(4-chlorophenyl)-4,4-dimethylcyclohex-1-en-1-yl]methyl]piperazin-1-yl)-2-[(12S)-

12-methyl-13-oxa-2,4,10-triazatricyclo[7.4.0.0ˆ[3,7]]tri-deca-1(9),2,5,7-tetraen-10-yl]benzoate. Into a 100-mL round-bottom flask, was placed methyl 4-(4-[[2-(4-chlorophenyl)-4,4-dimethylcyclohex-1-en-1-yl]methyl]piperazin-1-yl)-2-[(12S)-12-methyl-4-[[2-(trimethylsilyl)ethoxy]methyl]-13-oxa-2,4,10-triazatricyclo[7.4.0.0ˆ[3,7]]trideca-1(9),2 (250 mg, 0.32 mmol, 1 equiv), TBAF (3 g, 11.47 mmol, 35.36 equiv), THF (30 mL), ethane-1,2-diamine (2 g, 33.28 mmol, 102.56 equiv). The resulting solution was stirred for 12 h at 70° C. in an oil bath. The reaction was then quenched by the addition of 50 mL of water. The resulting solution was extracted with 2×50 mL of ethyl acetate. The resulting mixture was washed with 3×50 mL of brine. The mixture was dried over anhydrous sodium sulfate and filtrate and concentrated under vacuum. The residue was applied onto a silica gel column with ethyl acetate/petroleum ether (0:1-1:3). This resulted in 90 mg (43%) of methyl 4-(4-[[2-(4-chlorophenyl)-4,4-dimethylcyclohex-1-en-1-yl]methyl]piperazin-1-yl)-2-[(12S)-12-methyl-13-oxa-2,4,10-triazatricyclo[7.4.0.0ˆ[3,7]]trideca-1(9),2,5,7-tetraen-10-yl]benzoate as a yellow solid. H-NMR-PH-PHNW-4-37-50: (CDCl3, 300 ppm): 8.24 (s, 1H), 7.89-7.86 (d, J=9 Hz, 1H), 7.32-7.24 (m, 6H), 7.14-7.01 (m, 1H), 6.97-6.94 (m, 2H), 6.73-6.65 (m, 2H), 6.18 (s, 1H), 3.67-3.53 (m, 3H), 3.32-3.18 (m, 3H), 2.98-2.80 (m, 1H), 2.30-2.04 (m, 6H), 1.99 (s, 2H), 1.56-1.50 (m, 5H), 0.91-0.88 (m, 6H).

Synthesis of 4-(4-[[2-(4-chlorophenyl)-4,4-dimethylcyclohex-1-en-1-yl]methyl]piperazin-1-yl)-2-[(12 S)-12-methyl-13-oxa-2,4,10-triazatricyclo[7.4.0.0ˆ[3,7]]trideca-1(9),2,5,7-tetraen-10-yl]benzoic acid. Into a 8-mL vial, was placed methyl 4-(4-[[2-(4-chlorophenyl)-4,4-dimethylcyclohex-1-en-1-yl]methyl]piperazin-1-yl)-2-[(12S)-12-methyl-13-oxa-2,4,10-triazatricyclo[7.4.0.0ˆ[3,7]]trideca-1(9),2,5,7-tetraen-10-yl]benzoate (90 mg, 0.14 mmol, 1 equiv), MeOH (1 mL), H₂O (1 mL), THF (1 mL), NaOH (22.5 mg, 0.56 mmol, 4 equiv). The resulting solution was stirred for overnight at 60° C. in an oil bath. The pH value of the solution was adjusted to 5 with HCl (1 mol/L). The resulting mixture was concentrated under vacuum. The residue was applied onto a silica gel column with dichloromethane/methanol (1:0-10:1). This resulted in 80 mg (90%) of 4-(4-[[2-(4-chlorophenyl)-4,4-dimethylcyclohex-1-en-1-yl]ethyl]piperazin-1-yl)-2-[(12S)-12-methyl-13-oxa-2,4,10-triazatricyclo[7.4.0.0ˆ[3,7]]trideca-1(9),2,5,7-tetraen-10-yl]benzoic acid as a yellow solid. LC-MS: (ES, m/z): M+1=626, R,T=1.035 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Synthesis of (S)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide. Into a 8-mL vial, was placed 4-(4-[[2-(4-chlorophenyl)-4,4-dimethylcyclohex-1-en-1-yl]methyl]piperazin-1-yl)-2-[(12R or S)-12-methyl-13-oxa-2,4,10-triazatricyclo[7.4.0.0ˆ[3,7]]trideca-1(9),2,5,7-tetraen-10-yl]benzoic acid (90 mg, 0.14 mmol, 1 equiv), 4-[[(4-fluorooxan-4-yl)methyl]amino]-3-nitrobenzene-1-sulfonamide (57.5 mg, 0.17 mmol, 1.2 equiv), DCM (5 mL), DMAP (70.2 mg, 0.57 mmol, 4 equiv), EDCI (55.1 mg, 0.29 mmol, 2.00 equiv). The resulting solution was stirred for overnight at room temperature. The resulting mixture was concentrated. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min, hold 48.0% in 1 min) within 5 min; Detector, UV 254 nm. This resulted in 22 mg (20%) of (S)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide. LC-MS: (ES, m/z): M+1=923, R,T=2.653 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR: (d-CDCl₃, 300 ppm): 8.62 (s, 1H), 8.44-8.42 (m, 2H), 8.09-8.06 (m, 1H), 7.85-7.70 (m, 1H), 7.28-7.22 (m, 2H), 6.94-6.80 (m, 3H), 6.72-6.62 (m, 2H), 6.10 (s, 1H), 4.05-4.00 (m, 2H), 3.50-3.17 (m, 10H), 2.95-2.35 (m, 2H), 2.27-2.19 (m, 4H), 1.98-1.70 (m, 5H), 1.60-1.26 (m, 11H), 0.95 (s, 6H).

Example 23

Preparation of (R)-4-(4-((4'-chloro-5,5-dimethyl-3,4,5,6-tetrahydro-[1,1'-biphenyl]-2-yl)methyl)piperazin-1-yl)-2-(3-methyl-2,3-dihydropyrrolo[3',2':5,6]pyrido[2,3-b][1,4]oxazin-1(6H)-yl)-N-((3-nitro-4-(((tetrahydro-2H-pyran-4-yl)methyl)amino)phenyl)sulfonyl)benzamide Synthesis of N-[(2R)-2-hydroxypropyl]-4-methylbenzene-1-sulfonamide: Into a 250-mL round-bottom flask, was placed (2R)-1-aminopropan-2-ol (5 g, 1 equiv), DCM (70 mL), TsCl (12.67 g, 1 equiv). This was followed by the addition of TEA (7.41 g, 1.1 equiv) at 0° C. The resulting solution was stirred for 3 hr at 0° C. The resulting mixture was concentrated. The residue was applied onto a silica gel column with ethyl acetate/petroleum ether (1/1). This resulted in 8 g of N-(2R)-2-hydroxypropyl]-4-methylbenzene-1-sulfonamide as a white solid. ¹H NMR ((300 MHz, DMSO-d6, ppm): δ 7.74-7.63 (m, 2H), 7.52-7.34 (m, 3H), 4.66 (d, J=4.7 Hz, 1H), 3.58 (qd, J=6.3, 4.8 Hz, 1H), 2.73-2.50 (m, 2H), 2.39 (s, 3H), 0.99 (d, J=6.2 Hz, 3H).

Synthesis of methyl 2-bromo-4-(4-[[2-(4-chlorophenyl)-4,4-dimethylcyclohex-1-en-1-yl]methyl]piperazin-1-yl)benzoate: Into a 250-mL round-bottom flask, was placed a solution of 1-[[2-(4-chlorophenyl)-4,4-dimethylcyclohex-1-en-1-yl]methyl]piperazine (15.09 g, 47.32 mmol, 1.00 equiv) in DMA (150 mL), DIEA (12.9 g, 99.81 mmol, 2.00 equiv), methyl 2-bromo-4-fluorobenzoate (11.6 g, 49.78 mmol, 1.00 equiv). The resulting solution was stirred for 12 h at 100 degree. The reaction mixture was cooled to room temperature. The reaction was then quenched by the addition of 50 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 7 g (crude) of methyl 2-bromo-4-(4-[[2-(4-chlorophenyl)-4,4-dimethylcyclohex-1-en-1-yl]methyl]piperazin-1-yl)benzoate as yellow oil. LC-MS: (ES, m/z): M+1=533, 531.

Synthesis of N-[(2R)-2-[(5-bromo-1-[[2-(trimethylsilyl)ethoxy]methyl]-1H-pyrrolo[2,3-b]pyridin-6-yl)oxy]propyl]-4-methylbenzene-1-sulfonamide: Into a 100-mL round-bottom flask, was placed N-[(2R)-2-hydroxypropyl]-4-methylbenzene-1-sulfonamide (1 g, 1.5 equiv), DMF (3 mL). This was followed by the addition of NaH (0.35 g, 3 equiv) at 0° C. in 10 min. To this was added 5-bromo-6-fluoro-1-[[2-(trimethylsilyl)ethoxy]methyl]-1H-pyrrolo[2,3-b]pyridine (1 g, 1 equiv) at 0° C. The resulting solution was stirred for 4 hr at room temperature. The reaction was then quenched by the addition of 20 mL of water. The resulting solution was extracted with 3×50 mL of ethyl acetate and the organic layers combined and concentrated. The residue was applied onto a silica gel column with ethyl acetate/petroleum ether (1/3). This resulted in 400 mg of N-[(2R)-2-[(5-bromo-1-[[2-(trimethylsilyl)ethoxy]methyl]-1H-pyrrolo[2,3-b]pyridin-6-yl)oxy]propyl]-4-methylbenzene-1-sulfonamide as a yellow solid. $^1$H-NMR (300 MHz, DMSO-d6, ppm): δ 8.18 (s, 1H), 7.72-7.62 (m, 2H), 7.41 (d, J=3.5 Hz, 1H), 7.28 (d, J=8.0 Hz, 2H), 6.42 (d, J=3.6 Hz, 1H), 5.50 (q, J=10.8 Hz, 2H), 5.16 (q, J=6.1 Hz, 1H), 3.53-3.38 (m, 2H), 3.13 (dd, J=13.4, 6.0 Hz, 1H), 2.98 (dd, J=13.4, 5.8 Hz, 1H), 2.29 (s, 3H), 1.28 (d, J=6.2 Hz, 3H), 0.80 (ddt, J=16.1, 14.1, 7.1 Hz, 2H), 0.13 (s, 9H).

Synthesis of (12R)-12-methyl-10-(4-methylbenzenesulfonyl)-4-[[2-(trimethylsilyl)ethoxy]methyl]-13-oxa-2,4,10-triazatricyclo[7.4.0.0ˆ[3,7]]trideca-1(9),2,5,7-tetraene: Into a 100-mL round-bottom flask purged and maintained with an inert atmosphere of nitrogen, was placed N-[(2R)-2-[(5-bromo-1-[[2-(trimethylsilyl)ethoxy]methyl]-1H-pyrrolo[2,3-b]pyridin-6-yl)oxy]propyl]-4-methylbenzene-1-sulfonamide (3.9 g, 1 equiv), dioxane (50 mL), t-BuXPhos 3G (560 mg, 0.1 equiv), Cs$_2$O$_3$ (6.9 g, 3 equiv). The resulting solution was stirred for 4 hr at 90° C. The resulting mixture was concentrated. The residue was applied onto a silica gel column with ethyl acetate/petroleum ether (1/3). This resulted in 3.3 g of (12R)-12-methyl-10-(4-methylbenzenesulfonyl)-4-[[2-(trimethylsilyl)ethoxy]methyl]-13-oxa-2,4,10-triazatricyclo[7.4.0.0ˆ[3,7]]trideca-1(9),2,5,7-tetraene as colorless oil. $^1$H-NMR (300 MHz, DMSO-d6, ppm): δ 8.28 (s, 1H), 7.56-7.39 (m, 3H), 7.39-7.30 (m, 2H), 6.52 (d, J=3.6 Hz, 1H), 5.43 (s, 2H), 4.28 (dd, J=14.6, 2.6 Hz, 1H), 3.61-3.41 (m, 3H), 3.26-3.11 (m, 1H), 2.35 (s, 3H), 1.32-1.11 (m, 3H), 0.89-0.74 (m, 2H), 0.11 (s, 9H).

Synthesis of (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene: Into a 100-mL 3-necked round-bottom flask, was placed Na (1.31 g, 9.4 equiv), naphthalene (0.76 g, 6 equiv). This was followed by the addition of DME (15 mL) for 30 min at room temperature. To this was added the solution (12R)-12-methyl-10-(4-methylbenzenesulfonyl)-4-[[2-(trimethylsilyl)ethoxy]methyl]-13-oxa-2,4,10-triazatricyclo[7.4.0.0ˆ[3,7]]trideca-1(9),2,5,7-tetraene (2.8 g, 1 equiv) in THF (15 mL) at −78° C. The resulting solution was stirred for 3 hr at room temperature. The reaction was then quenched by the addition of 30 mL of NH$_4$Cl. The resulting solution was extracted with 3×100 mL of ethyl acetate and the organic layers combined and concentrated. The residue was applied onto a silica gel column with ethyl acetate/petroleum ether (1/3). This resulted in 1.4 g of (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene as a colorless oil. LC-MS (ES, m/z): 320 [M+1]$^+$; RT=1.61 min.

Synthesis of methyl 4-(4-[[2-(4-chlorophenyl)-4,4-dimethylcyclohex-1-en-1-yl]methyl]piperazin-1-yl)-2-[(12S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraen-10-yl]benzoate: Into a 250-mL round-bottom flask purged and maintained with an inert atmosphere of nitrogen, was placed (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene (1.178 g, 1 equiv), methyl 2-bromo-4-(4-[[2-(4-chlorophenyl)-4,4-dimethylcycloohex-1-en-1-yl]methyl] piperazin-1-yl)benzoate (2.35 g, 1.2 equiv), dioxane (15 mg, 15 equiv), Cs$_2$CO$_3$ (3.62 g, 3 equiv), XantPhos (328 mg, 0.1 equiv). The resulting solution was stirred for 2 hr at 110° C. The resulting mixture was concentrated. The residue was applied onto a silica gel column with ethyl acetate/petroleum ether (1/3). This resulted in 3.2 g of methyl 4-(4-[[2-(4-chlorophenyl)-4,4-dimethylcyclohex-1-en-1-yl]methyl]piperazin-1-yl)-2-[(12S)-12-methyl-4-[[2-(trimethylsilyl)ethoxy]methyl]-13-oxa-2,4,10-triazatricyclo[7.4.0.0ˆ[3,7]]trideca-1(9),2,5,7-tetraen-10-yl]benzoate as a yellow solid. LC-MS (ES, m/z): 770 [M+1]$^+$; RT=1.33 min.

Synthesis of methyl 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoate: Into a 250-mL round-bottom flask, was placed methyl 4-(4-[[2-(4-chlorophenyl)-4,4-dimethylcyclohex-1-en-1-yl]methyl]piperazin-1-yl)-2-[(12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraen-10-yl]benzoate (3.2 g, 1 equiv), THF (50 mL), TBAF (20 g), ethane-1,2-diamine (33 g). The resulting solution was stirred for 5 hr at 70° C. The reaction was then quenched by the addition of 50 mL of water. The resulting solution was extracted with 3×100 mL of ethyl acetate and the organic layers combined and concentrated. The residue was applied onto a silica gel column with dichloromethane/methanol (10/1). This resulted in 2.2 g of methyl 4-(4-[[2-(4-chlorophenyl)-4,4-dimethylcyclohex-1-en-1-yl]ethyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoate as a yellow solid. LC-MS-(ES, m/z): 640 [M+1]$^+$; RT=2.51 min.

Synthesis of 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoic acid: Into a 250-mL round-bottom flask, was placed methyl 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoate (2.2 g, 1 equiv), MEOH/H$_2$O/THF (10 mL/10 ml/10 mL). The resulting solution was stirred for 5 hr at 60° C. The resulting mixture was concentrated. The resulting solution was extracted with 3×100 mL of dichloromethane and the organic layers combined and concentrated. The residue was applied onto a silica gel column with dichloromethane/methanol (10/1). This resulted in 1.6 g of 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoic acid as yellow oil. LC-MS (ES, m/z): 626 [M+1]$^+$; RT=2.47 min.

Synthesis of 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]-N-(3-nitro-4-[[(oxan-4-yl)methyl] amino]benzenesulfonyl)benzamide: Into a 250-mL round-bottom flask, was placed 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoic acid (1.6 g, 1 equiv), DCM (20 mL), 3-nitro-4-[[(oxan-4-yl)methyl]amino]benzene-1-sulfonamide (890 mg, 1.2 equiv), DMAP (1.25 g, 4 equiv), EDCI (980 mg, 2 equiv). The resulting solution was stirred for 14 hr at room temperature. The resulting mixture was concentrated. The residue was applied onto a silica gel column with EA/DCM (1/10). This resulted in 0.82 g of 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]-N-(3-nitro-4-[[(oxan-4-yl)methyl]amino]benzenesulfonyl)benzamide as a yellow solid. LC-MS (ES, m/z): 923 [M+1]$^+$; RT=3.50 min. $^1$H NMR (300 MHz, CDCl$_3$, ppm): δ 12.48 (s, 1H), 8.62 (d, J=2.4 Hz, 2H), 8.54-8.38 (m, 1H), 8.16-7.95 (m, 1H), 7.81-7.71 (m, 1H), 7.32-7.12 (m, 6H), 7.07 (t, J=2.9 Hz, 1H), 6.97-6.77 (m, 3H), 6.76-6.60 (m, 2H), 6.52 (s, 1H), 6.09 (d, J=3.0 Hz, 1H), 4.88 (d, J=7.7 Hz, 1H), 4.02 (dd, J=11.8, 4.2 Hz, 2H), 3.55-3.34 (m, 4H), 3.32-3.14 (m, 5H), 3.08 (s, 1H), 2.77 (d, J=9.6 Hz, 2H), 2.28 (s, 3H), 2.19 (s, 2H), 1.99 (d, J=7.6 Hz, 4H), 1.72 (d, J=12.7 Hz, 2H), 1.45 (ddd, J=24.5, 12.3, 5.8 Hz, 6H), 0.94 (d, J=2.1 Hz, 6H).

Example 24

Preparation of 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide Synthesis of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate: Into a 100-mL round-bottom flask purged and maintained with an inert atmosphere of nitrogen, was placed methyl 2-bromo-4-(4-[[2-(4-chlorophenyl)-4,4-dimethylcyclohex-1-en-1-yl]methyl]piperazin-1-yl)benzoate (999.0 mg, 1.88 mmol, 4.00 equiv), toluene (20 mL), 4-[[2-(trimethylsilyl)ethoxy]methyl]-14-oxa-2,4,10-triazatricyclo[7.5.0.0^[3,7]]tetradeca-1(9),2,5,7-tetraene (150 mg, 0.47 mmol, 1 equiv), Cs$_2$CO$_3$ (764.9 mg, 2.35 mmol, 5 equiv), XantPhos Pd 2G (333.2 mg, 0.38 mmol, 0.8 equiv). The resulting solution was stirred for 1 overnight at 110° C. The resulting solution was diluted with 300 mL of water. The resulting solution was extracted with 2×100 mL of ethyl acetate. The resulting mixture was washed with 1×300 mL of brine. The mixture was dried over anhydrous sodium sulfate and concentrated under vacuum. The residue was applied onto a silica gel column with ethyl acetate/petroleum ether (1:2). This resulted in 200 mg (55.29%) of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate as a yellow solid. LC-MS: (ES, m/z): M+H=769, R,T=3.076 min. The measurements of the retention were done with a reversed phase column (C18). Shimadzu LCMS 2020; 50*3.0 Shim-pack XR-ODS, 2.2 microm; Eluent A: water (0.05% TFA); Eluent B: Acetonitrile; linear gradient from 5% acetonitrile to 100% acetonitrile in 5.0 minutes; Oven temperature 40° C.; flow: 1.5 mL/min.

Synthesis of methyl 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoate: Into a 40-mL vial, was placed methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate (200 mg, 0.26 mmol, 1 equiv), THF (20 mL), TBAF.3H$_2$O (2.5 g), ethane-1,2-diamine (1.5 g, 24.96 mmol, 96.15 equiv). The resulting solution was stirred for 2 overnight at 70° C. in an oil bath. The resulting solution was diluted with 200 mL of water. The resulting solution was extracted with 3×30 mL of ethyl acetate. The resulting mixture was washed with 2×200 mL of brine. The mixture was dried over anhydrous sodium sulfate and concentrated under vacuum. The residue was applied onto a silica gel column with ethyl acetate/petroleum ether (2:1). This resulted in 130 mg (78.22%) of methyl 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoate as a light yellow solid. LC-MS: (ES, m/z): M+H=639, R,T=1.388 min. The measurements of the retention were done with a reversed phase column (C18). Shimadzu LCMS 2020; 50*3.0 Shim-pack XR-ODS, 2.2 microm; Eluent A: water (0.05% TFA); Eluent B: Acetonitrile; linear gradient from 5% acetonitrile to 100% acetonitrile in 2.6 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoic acid: Into a 40-mL vial, was placed methyl 4-(4-[[2-(4-chlorophenyl)-4,4-dimethylcyclohex-1-en-1-yl]ethyl]piperazin-1-yl)-2-[14-oxa-2,4,10-triazatricyclo[7.5.0.0^[3,7]]tetradeca-1(9),2,5,7-tetraen-10-yl]benzoate (130 mg, 0.20 mmol, 1 equiv), MeOH (6 mL), THF (6 mL), H$_2$O (2 mL), NaOH (81.2 mg, 2.03 mmol, 10.00 equiv). The resulting solution was stirred for 1 overnight at 60° C. in an oil bath. The resulting mixture was concentrated under vacuum. The pH value of the solution was adjusted to 5-6 with HCl (2 mol/L). The resulting solution was extracted with 2×50 mL of dichloromethane/MeOH (v:v=10:1). The resulting mixture was washed with 2×200 mL of brine. The mixture was dried over anhydrous sodium sulfate and concentrated under vacuum. This resulted in 80 mg (62.92%) of 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoic acid as a light yellow solid. LC-MS: (ES, m/z): M+H=625, R,T=1.336 min. The measurements of the retention were done with a reversed phase column (C18). Shimadzu LCMS 2020; 50*3.0 Shim-pack XR-ODS, 2.2 microm; Eluent A: water (0.05% TFA); Eluent B: Acetonitrile; linear gradient from 5% acetonitrile to 100% acetonitrile in 2.6 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-N-(3-nitro-4-[[(oxan-4-yl)methyl]amino]benzene sulfonyl)-2-[14-oxa-2,4,10-triazatricyclo[7.5.0.0^[3,7]]tetradeca-1(9),2,5,7-tetraen-10-yl]benzamide: Into a 40-mL round-bottom flask, was placed 4-(4-[[2-(4-chlorophenyl)-4,4-dimethylcyclohex-1-en-1-yl]ethyl]piperazin-1-yl)-2-[14-oxa-2,4,10-triazatricyclo[7.5.0.0^[3,7]]tetradeca-1(9),2,5,7-tetraen-10-yl]benzoic acid (50 mg, 0.08 mmol, 1 equiv), DCM (3 mL), 3-nitro-4-[[(oxan-4-yl)methyl]amino]benzene-1-sulfonamide (25.2 mg, 0.08 mmol, 1.00 equiv), EDCI (30.6 mg, 0.16 mmol, 2 equiv), DMAP (39.0 mg, 0.32 mmol, 4 equiv). The resulting solution was stirred for overnight at 25 degrees C. The resulting mixture was concentrated under vacuum. The residue was applied onto a silica gel column with dichloromethane/methanol (10:1). The crude product was purified by Flash-Prep-HPLC with the following conditions (IntelFlash-1): Column, C18 reversed phase column; mobile phase, Water (10 MMOL/L NH$_4$HCO$_3$+0.05% NH$_3$·H$_2$O)

and CH₃CN (20.0% CH₃CN up to 90.0% in 30 min); Detector, UV 220 nm. This resulted in 19.1 mg (25.90%) of 4-(4-[[2-(4-chlorophenyl)-4,4-dimethylcyclohex-1-en-1-yl]methyl]piperazin-1-yl)-N-(3-nitro-4-[[(oxan-4-yl)methyl]amino]benzenesulfonyl)-2-[14-oxa-2,4,10-triazatricyclo[7.5.0.0^[3,7]]tetradeca-1(9),2,5,7-tetraen-10-yl]benzamide as a yellow solid. LC-MS: (ES, m/z): M+1=923, R,T=3.463 min. The measurements of the retention were done with a reversed phase column (C18). Shimadzu LCMS 2020; 50*3.0 Agilent Poroshell HPH-C18, 2.7 um; Eluent A: water (0.05% ammonia water); Eluent B: Acetonitrile; linear gradient from 5% acetonitrile to 95% acetonitrile in 7.0 minutes; Oven temperature 40° C.; flow: 1.5 mL/min. ¹H NMR (300 MHz, DMSO-$d_6$, ppm) δ 11.91 (s, 1H), 11.26 (s, 1H), 8.56 (s, 1H), 8.47 (d, J=2.1 Hz, 1H), 7.61 (d, J=9.0 Hz, 1H), 7.48 (d, J=9.2 Hz, 1H), 7.37 (d, J=8.3 Hz, 2H), 7.20 (s, 1H), 7.07 (d, J=8.3 Hz, 2H), 6.99-6.83 (m, 2H), 6.76 (d, J=29.2 Hz, 2H), 6.14 (s, 1H), 4.21 (s, 2H), 3.85 (d, J=9.3 Hz, 2H), 3.52 (s, 2H), 3.30-3.14 (m, 8H), 2.79 (s, 1H), 2.23 (d, J=20.0 Hz, 5H), 1.99 (s, 4H), 1.85 (s, 1H), 1.61 (d, J=11.3 Hz, 2H), 1.42 (s, 2H), 1.25 (s, 2H), 1.03-0.79 (m, 6H). The measurements of the NMR spectra were done with Bruker AvanceIII HD 300 MHz with a probe head of BBOF.

Example 25

Preparation of 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-(((4-fluorotetrahydro-2H-pyran-4-yl)methyl)amino)-3-nitrophenyl)sulfonyl)benzamide Into a 40-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoic acid (80 mg, 0.13 mmol, 1 equiv), DCM (3 mL), 4-[[(4-fluorooxan-4-yl)methyl]amino]-3-nitrobenzene-1-sulfonamide (42.6 mg, 0.13 mmol, 1.00 equiv), EDCI (49.0 mg, 0.26 mmol, 2 equiv), DMAP (62.4 mg, 0.51 mmol, 4 equiv). The resulting solution was stirred for 1 overnight at 25° C. The resulting mixture was concentrated under vacuum. The crude product was purified by Prep-HPLC with the following conditions (Prep-HPLC-006): Column, X Bridge Prep C18 OBD Column, 19×150 mm 5 um; mobile phase, Water (10 MMOL/L NH₄HCO₃+0.1% NH₃·H₂O) and CH₃CN (41.0% CH₃CN up to 61.0% in 6 min, hold 95.0% in 1 min, down to 41.0% in 1 min, hold 41.0% in 1 min); Detector, UV 210 nm. This resulted in 17 mg (14.13%) of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[14-oxa-2,4,10-triazatricyclo[7.5.0.0^[3,7]]tetradeca-1(9),2,5,7-tetraen-10-ylbenzamide as a yellow solid. LC-MS: (ES, m/z): M+1=940, R,T=1.583 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 3.0 minutes; Oven temperature 40° C.; flow: 1.5 mL/min. ¹H NMR (300 MHz, DMSO-$d_6$, ppm) δ 11.94 (s, 1H), 11.25 (s, 1H), 8.59 (s, 1H), 8.48 (d, J=2.3 Hz, 1H), 7.66 (d, J=9.1 Hz, 1H), 7.47 (d, J=8.9 Hz, 1H), 7.37 (d, J=8.2 Hz, 2H), 7.20 (s, 1H), 7.07 (dd, J=8.9, 3.8 Hz, 3H), 6.94 (s, 1H), 6.71 (s, 2H), 6.13 (d, J=3.1 Hz, 1H), 4.20 (d, J=6.5 Hz, 2H), 3.80-3.70 (m, 3H), 3.68-3.60 (m, 1H), 3.58-3.45 (m, 4H), 3.25-3.05 (m, 4H), 2.83-2.69 (m, 2H), 2.33-2.10 (m, 6H), 1.98 (s, 4H), 1.84-1.68 (m, 4H), 1.49-1.35 (m, 2H), 0.95 (s, 6H). The measurements of the NMR spectra were done with Bruker AvanceIII HD 300 MHz with a probe head of BBOF.

Example 26

Preparation of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide Synthesis of 4,4,4-trifluoro-3-hydroxybutanamide: Into a 50-mL round-bottom flask, was placed ethyl 4,4,4-trifluoro-3-hydroxybutanoate (500 mg, 2.7 mmol, 1 equiv), NH₃ in MeOH (5 mL, 4.0 M). The resulting solution was stirred for 16 hr at 60 degrees C. The resulting mixture was concentrated. This resulted in 500 mg of 4,4,4-trifluoro-3-hydroxybutanamide as a white solid. ¹H NMR (300 MHz, DMSO-$d_6$, ppm) δ 7.62 (ds, 1H), 7.01 (ds, 1H), 3.36-6.34 (m, 1H), 4.27-4.40 (m, 1H), 2.39-2.36 (m, 2H). The measurements of the NMR spectra were done with Bruker AvanceIII HD 300 MHz with a probe head of BBOF.

Synthesis of 4-amino-1,1,1-trifluorobutan-2-ol: Into a 50-mL 3-necked round-bottom flask, was placed 4,4,4-trifluoro-3-hydroxybutanamide (500 mg, 3.2 mmol, 1 equiv) and THF (10 mL), LAH (242 mg, 6.4 mmol, 2.00 equiv) was added little by little at ice-bath. The resulting solution was stirred for 16 hr at R,T. After the reaction was completed, the reaction mixture was quenched by the addition of 0.24 mL of water, 0.24 mL of NaOH (10% in H₂O) and 0.72 mL of water was added into the solution successively at ice-bath. The solids were filtered out. The resulting mixture was concentrated under vacuum. This resulted in 380 mg (83.43%) of 4-amino-1,1,1-trifluorobutan-2-ol as a colorless oil. ¹H NMR (300 MHz, CDCL3, ppm) 4.10-4.01 (m, 1H), 2.70-2.66 (m, 2H), 1.51-1.47 (m, 2H). The measurements of the NMR spectra were done with Bruker AvanceIII HD 300 MHz with a probe head of BBOF.

Synthesis of 4-methyl-N-(4,4,4-trifluoro-3-hydroxybutyl)benzenesulfonamide. Into a 100-mL round-bottom flask, was placed 4-amino-1,1,1-trifluorobutan-2-ol (350 mg, 2.4 mmol, 1 equiv), TEA (480 mg, 4.8 mmol, 2.0 equiv) and DCM (10 mL), TsCl (470 mg, 2.4 mmol, 1.0 equiv) was added at ice-bath. The resulting solution was stirred for 4 hr at R,T degrees C. The resulting solution was diluted with 50 mL of DCM. The resulting mixture was washed with 2×20 ml of water and 1×20 mL of brine. The mixture was dried over anhydrous sodium sulfate. The solids were filtered out. The resulting mixture was concentrated under vacuum. The residue was applied onto a silica gel column with ethyl acetate/petroleum ether (0-50%). This resulted in 600 mg (82.52%) of 4-methyl-N-(4,4,4-trifluoro-3-hydroxybutyl)benzene-1-sulfonamide as colorless oil. ¹H NMR (300 MHz, DMSO-$d_6$, ppm) δ 7.70-7.68 (m, 2H), 7.42-7.40 (m, 2H), 6.23-6.21 (m, 1H), 4.01-3.96 (m, 1H), 2.87-2.83 (m, 2H), 2.39 (s, 3H), 1.70-1.49 (m, 2H). The measurements of the NMR spectra were done with Bruker AvanceIII HD 300 MHz with a probe head of BBOF.

Synthesis of N-(3-(5-bromo-14(2-(trimethylsilyl)ethoxy)methyl)-1H-pyrrolo[2,3-b]pyridin-6-yloxy)-4,4,4-trifluorobutyl)-4-methylbenzenesulfonamide. Into a 100-mL round-bottom flask, was placed 5-bromo-6-fluoro-1-[[2-(trimethylsilyl)ethoxy]methyl]-1H-pyrrolo[2,3-b]pyridine (300 mg, 0.9 mmol, 1 equiv), 4-methyl-N-(4,4,4-trifluoro- 3-hydroxybutyl)benzene-1-sulfonamide (310 mg, 1.0 mmol, 1.2 equiv), $Cs_2CO_3$ (566 mg, 1.7 mmol, 2.0 equiv) and 1,4-Dioxane (10 mL). The resulting solution was stirred for 16 hr at 90 degrees C. in an oil bath. The reaction mixture was cooled. The solids were filtered out. The resulting solution was diluted with 100 mL of DCM. The resulting mixture was washed with 5×50 ml of water and 1×50 mL of brine. The mixture was dried over anhydrous sodium sulfate. The solids were filtered out. The resulting mixture was concentrated under vacuum. The residue was applied onto a silica gel column with ethyl acetate/petroleum ether (0-30%). This resulted in 400 mg (73.95%) of N-[3-[(5-bromo-1-[[2-(trimethylsilyl)ethoxy]methyl]-1H-pyrrolo[2,3-b]pyridin-6-yl)oxy]-4,4,4-trifluorobutyl]-4-methylbenzene-1-sulfonamide as a light yellow solid. $^1$H NMR (300 MHz, CDCL3, ppm) 8.17 (bs, 1H), 7.76-7.73 (m, 2H), 7.29-7.27 (m, 3H), 6.51-6.50 (m, 1H), 5.93-5.91 (m, 1H), 5.75-5.72 (m, 2H), 5.63-5.58 (m, 1H), 3.60-3.57 (m, 2H), 3.34-3.32 (m, 1H), 3.13-3.11 (m, 1H), 2.46 (s, 3H), 2.31-2.29 (m, 1H), 2.10-2.07 (m, 1H), 1.00-0.85 (m, 2H), 0.01 (s, 9H). The measurements of the NMR spectra were done with Bruker AvanceIII HD 300 MHz with a probe head of BBOF.

Synthesis of 1-tosyl-4-(trifluoromethyl)-7-((2-(trimethylsilyl)ethoxy)methyl)-1,3,4,7-tetrahydro-2H-pyrrolo[3',2':5,6]pyrido[2,3-b][1,4]oxazepane. Into a 250-mL round-bottom flask purged and maintained with an inert atmosphere of nitrogen, was placed N-[3-[(5-bromo-1-[[2-(trimethylsilyl)ethoxy]methyl]-1H-pyrrolo[2,3-b]pyridin-6-yl)oxy]-4,4,4-trifluorobutyl]-4-methylbenzene-1-sulfonamide (700 mg, 1.13 mmol, 1 equiv), $Cs_2CO_3$ (1.1 g, 3.39 mmol, 3.00 equiv), CuI (214 mg, 1.13 mmol, 1 equiv), 2-isobutyrylcyclohexan-1-one (80 mg, 0.56 mmol, 0.5 equiv), DMSO (10 mL), The resulting solution was stirred for 24 hr at 120° C. in an oil bath. The resulting solution was diluted with 20 mL of water. The resulting solution was extracted with 2×50 mL of ethyl acetate. The resulting mixture was washed with 1×50 mL of brine. The mixture was dried over anhydrous sodium sulfate and concentrated under vacuum. The residue was applied onto a silica gel column with ethyl acetate/petroleum ether (0-30%). This resulted in 350 mg (57.38%) of 1-tosyl-4-(trifluoromethyl)-7-((2-(trimethylsilyl)ethoxy)methyl)-1,3,4,7-tetrahydro-2H-pyrrolo[3',2':5,6]pyrido[2,3-b][1,4]oxazepine as light yellow solid. $^1$H NMR (300 MHz, CDCL3, ppm) 8.19 (bs, 1H), 7.50-7.47 (m, 2H), 7.39 (s, 1H), 7.24-7.22 (m, 2H), 6.58-6.57 (m, 1H), 5.69-5.66 (m, 1H), 5.55-5.51 (m, 1H), 4.57-4.52 (m, 1H), 3.96-3.94 (m, 1H), 3.59-3.56 (m, 2H), 3.48-3.44 (m, 1H), 2.41 (s, 3H), 2.31-2.29 (m, 1H), 1.95-1.91 (m, 1H), 0.97-0.91 (m, 2H), 0.05 (s, 9H). The measurements of the NMR spectra were done with Bruker AvanceIII HD 300 MHz with a probe head of BBOF.

Synthesis of 4-(trifluoromethyl)-74(2-(trimethylsilyl)ethoxy)methyl)-1,3,4,7-tetrahydro-2H-pyrrolo[3',2':5,6]pyrido[2,3-b][1,4]oxazepane. Into a 250 mL 3-necked round-bottom flask, was placed Na (150 mg, 6.5 mmol, 1.0 equiv), naphthalene (833 mg, 6.5 mmol, 10 equiv) and DME (3 ml) under $N_2$. The reaction mixture was stirred at room temperature until Na and naphthalene completely dissolved. To this was added the solution 1-tosyl-4-(trifluoromethyl)-7-((2-(trimethylsilyl)ethoxy)methyl)-1,3,4,7-tetrahydro-2H-pyrrolo[3',2':5,6]pyrido[2,3-b][1,4]oxazepine (350 mg, 0.65 mmol, 1 equiv) in THF (5 mL) at −78° C. The resulting solution was stirred for 2-3 hr at −60° C. to −40° C. unstill the starting material consumed by TLC. The reaction was then quenched by the addition of 5 mL of $NH_4Cl$ at −10° C. The resulting solution was extracted with 3×10 mL of ethyl acetate. The mixture was dried over anhydrous sodium sulfate and concentrated under vacuum. The residue was applied onto a silica gel column and eluted with ethyl acetate/petroleum ether (1/3). This resulted in 220 mg (88%) of 4-(trifluoromethyl)-7-((2-(trimethylsilyl)ethoxy)methyl)-1,3,4,7-tetrahydro-2H-pyrrolo[3',2':5,6]pyrido[2,3-b][1,4]oxazepine as a white solid.

Synthesis of methyl 4-(4-((4'-chloro-5,5-dimethyl-3,4,5,6-tetrahydro-[1,1'-biphenyl]-2-yl)methyl)piperazin-1-yl)-2-(4-(trifluoromethyl)-7-((2-(trimethylsilyl)ethoxy)methyl)-3,4-dihydro-2H-pyrrolo[3',2':5,6]pyrido[2,3-b][1,4]oxazepin-1(7H)-yl)benzoate. Into a 100-mL round-bottom flask purged and maintained with an inert atmosphere of nitrogen, was placed methyl 2-bromo-4-(4-[[2-(4-chlorophenyl)-4,4-dimethylcyclohex-1-en-1-yl]methyl]piperazin-1-yl)benzoate (1.2 g, 2.28 mmol, 4.00 equiv), toluene (20 mL), 4-(trifluoromethyl)-74(2-(trimethylsilyl)ethoxy)methyl)-1,3,4,7-tetrahydro-2H-pyrrolo[3',2':5,6]pyrido[2,3-b][1,4]oxazepine (220 mg, 0.57 mmol, 1 equiv), $Cs_2CO_3$ (923 mg, 2.84 mmol, 5 equiv), XantPhos Pd 2G (250 mg, 0.46 mmol, 0.8 equiv). The resulting solution was stirred for overnight at 110° C. The resulting solution was diluted with 30 mL of water. The resulting solution was extracted with 2×30 mL of ethyl acetate. The resulting mixture was washed with 1×30 mL of brine. The mixture was dried over anhydrous sodium sulfate and concentrated under vacuum. The residue was applied onto a silica gel column with ethyl acetate/petroleum ether (0-50%). This resulted in 380 mg crude (80.0%) of methyl 4-(4-((4'-chloro-5,5-dimethyl-3,4,5,6-tetrahydro-[1,1'-biphenyl]-2-yl)methyl)piperazin-1-yl)-2-(4-(trifluoromethyl)-7-((2-(trimethylsilyl)ethoxy)methyl)-3,4-dihydro-2H-pyrrolo[3',2':5,6]pyrido[2,3-b][1,4]oxazepin-1(7H)-yl)benzoate as a yellow solid. LC-MS: (ES, m/z): M+H=838, R,T=3.33 min. The measurements of the retention were done with a reversed phase column (C18). Shimadzu LCMS 2020; 50*3.0, Poroshell HPH-C18, 2.7 microm; Eluent A: water (0.05% NH4HCO3); Eluent B: Acetonitrile; linear gradient from 5% acetonitrile to 100% acetonitrile in 5.0 minutes; Oven temperature 40° C.; flow: 1.5 mL/min.

Synthesis of methyl 4-(4-((4'-chloro-5,5-dimethyl-3,4,5,6-tetrahydro-[1,1'-biphenyl]-2-yl)methyl)piperazin-1-yl)-2-(4-(trifluoromethyl)-3,4-dihydro-2H-pyrrolo[3',2':5,6]pyrido[2,3-b][1,4]oxazepin-1(7H)-yl)benzoate. Into a 40-mL vial, was placed methyl 4-(4-((4'-chloro-5,5-dimethyl-3,4,5,6-tetrahydro-[1,1'-biphenyl]-2-yl)methyl)piperazin-1-yl)-2-(4-(trifluoromethyl)-7-((2-(trimethylsilyl)ethoxy)methyl)-3,4-dihydro-2H-pyrrolo[3',2':5,6]pyrido[2,3-b][1,4]oxazepin-1(7H)-yl)benzoate (380 mg, 0.45 mmol, 1 equiv), THF (20 mL), TBAF.3H$_2$O (708 mg, 2.25 mmol, 5 equiv), ethane-1,2-diamine (540 mg, 9.0 mmol, 20 equiv). The resulting solution was stirred for overnight at 70° C. in an oil bath. The resulting solution was diluted with 20 mL of water. The resulting solution was extracted with 3×30 mL of ethyl acetate. The resulting mixture was washed with 2×20 mL of brine. The mixture was dried over anhydrous sodium sulfate and concentrated under vacuum. The residue was applied onto a silica gel column with ethyl acetate/petroleum ether (0-50%). This resulted in 300 mg (93%) of methyl 4-(4-((4'-chloro-5,5-dimethyl-3,4,5,6-tetrahydro-[1,1'-biphenyl]-2-yl)methyl)piperazin-1-yl)-2-(4-(trifluoromethyl)-3,4-dihydro-2H-pyrrolo[3',2':5,6]pyrido[2,3-b][1,4]oxazepin-1(7H)-yl)benzoate as a light yellow solid. $^1$H NMR (300 MHz, CDCL3, ppm) 10.78 (bs, 1H), 7.75-7.72 (m, 1H), 7.29-7.24 (m, 3H), 7.00-6.97 (m, 2H), 6.56-6.56 (m, 2H), 6.28-6.26 (m, 1H), 5.28-5.20 (m, 1H), 3.98-3.96 (m, 1H), 3.79-3.77 (m, 1H), 3.59 (s, 1H), 3.24-3.23 (m, 3H), 2.84 (m, 2H), 2.31-2.28 (m, 4H), 2.26-2.24 (m, 4H), 1.49-1.47 (m, 2H), 1.34-1.24 (m, 4H), 1.00 (s, 6H), 0.96-0.90 (m, 2H).

Synthesis of 4-(4-((4'-chloro-5,5-dimethyl-3,4,5,6-tetrahydro-[1,1'-biphenyl]-2-yl)methyl)piperazin-1-yl)-2-(4-(trifluoromethyl)-3,4-dihydro-2H-pyrrolo[3',2':5,6]pyrido[2,3-b][1,4]oxazepin-1(7H)-yl)benzoic acid. Into a 40-mL vial, was placed methyl 4-(4-((4'-chloro-5,5-dimethyl-3,4,5,6-tetrahydro-[1,1'-biphenyl]-2-yl)methyl)piperazin-1-yl)-2-(4-(trifluoromethyl)-3,4-dihydro-2H-pyrrolo[3',2':5,6]pyrido[2,3-b][1,4]oxazepin-1(7H)-yl)benzoate (200 mg, 0.28 mmol, 1 equiv), MeOH (6 mL), 1,4-dioxane (6 mL), $H_2O$ (2 mL), NaOH (67 mg, 1.68 mmol, 6.00 equiv). The resulting solution was stirred for overnight at 60° C. in an oil bath. The resulting mixture was concentrated under vacuum. The pH value of the solution was adjusted to 5-6 with HCl (2 mol/L). The resulting solution was extracted with 2×50 mL of dichloromethane/MeOH (v:v=10:1). The resulting mixture was washed with 2×200 mL of brine. The mixture was dried over anhydrous sodium sulfate and concentrated under vacuum. This resulted in 157 mg (81.0%) of 4-(4-((4'-chloro-5,5-dimethyl-3,4,5,6-tetrahydro-[1,1'-biphenyl]-2-yl)methyl)piperazin-1-yl)-2-(4-(trifluoromethyl)-3,4-dihydro-2H-pyrrolo[3',2':5,6]pyrido[2,3-b][1,4]oxazepin-1(7H)-yl)benzoic acid as a light yellow solid. LC-MS: (ES, m/z): M+H=694, R,T=2.43 min. The measurements of the retention were done with a reversed phase column (C18). Shimadzu LCMS 2020; 50*3.0, Poroshell HPH-C18, 2.7 microm; Eluent A: water (0.05% NH4HCO3); Eluent B: Acetonitrile; linear gradient from 5% acetonitrile to 100% acetonitrile in 5.0 minutes; Oven temperature 40° C.; flow: 1.5 mL/min.

Synthesis of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide. Into a 40-mL round-bottom flask, was placed 4-(4-((4'-chloro-5,5-dimethyl-3,4,5,6-tetrahydro-[1,1'-biphenyl]-2-yl)methyl)piperazin-1-yl)-2-(4-(trifluoromethyl)-3,4-dihydro-2H-pyrrolo[3',2':5,6]pyrido[2,3-b][1,4]oxazepin-1(7H)-yl)benzoic acid (57 mg, 0.08 mmol, 1 equiv), DCM (3 mL), 3-nitro-4-[[(oxan-4-yl)methyl]amino]benzene-1-sulfonamide (25.2 mg, 0.08 mmol, 1.00 equiv), EDCI (30.6 mg, 0.16 mmol, 2 equiv), DMAP (39.0 mg, 0.32 mmol, 4 equiv). The resulting solution was stirred for overnight at 25 degrees C. The resulting mixture was concentrated under vacuum. The residue was applied onto a silica gel column with dichloromethane/methanol (10:1). The crude product was purified by Flash-Prep-HPLC with the following conditions (Intel-Flash-1): Column, C18 reversed phase column; mobile phase, Water (10 MMOL/L $NH_4HCO_3$+0.05% $NH_3·H_2O$) and $CH_3CN$ (20.0% $CH_3CN$ up to 90.0% in 30 min); Detector, UV 220 nm. This resulted in 32 mg (40.0%) of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide as a yellow solid. LC-MS: (ES, m/z): M+1=991, R,T=2.41 min. The measurements of the retention were done with a reversed phase column (C18). Shimadzu LCMS 2020; 50*3.0 Agilent Poroshell HPH-C18, 2.7 um; Eluent A: water (0.05% ammonia water); Eluent B: Acetonitrile; linear gradient from 5% acetonitrile to 95% acetonitrile in 7.0 minutes; Oven temperature 40° C.; flow: 1.5 mL/min. $^1$H NMR (300 MHz, CDCL3, ppm) δ 11.43 (ds, 1H), 9.99 (ds, 1H), 8.72 (s, 1H), 8.40 (ds, 1H), 7.93-7.85 (m, 2H), 7.37-7.35 (m, 2H), 7.26 (s, 1H), 7.02-6.93 (m, 3H), 6.71-6.64 (m, 3H), 6.27 (s, 1H), 4.58 (s, 1H), 4.05-3.15 (m, 23H), 2.70-2.35 (m, 7H), 2.03 (s, 3H), 1.92-1.90 (m, 1H), 1.89-1.87 (m, 2H), 1.71-1.67 (m, 2H), 1.53-1.45 (m, 3H), 1.00 (s, 6H). The measurements of the NMR spectra were done with Bruker AvanceIII HD 300 MHz with a probe head of BBOF.

Example 27

Preparation of 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]thiazepin-1(7H)-yl)-N-((3-nitro-4-(((tetrahydro-2H-pyran-4-yl)methyl)amino)phenyl)sulfonyl)benzamide Synthesis of methyl 3-[(5-bromo-1-[[2-(trimethylsilyl)ethoxy]methyl]-1H-pyrrolo[2,3-b]pyridin-6-yl)sulfanyl]propanoate. Into a 40-mL round-bottom flask, was placed 5-bromo-6-fluoro-1-[[2-(trimethylsilyl)ethoxy]methyl]-1H-pyrrolo[2,3-b]pyridine (3 g, 8.7 mmol, 1 equiv), methyl 3-sulfanylpropanoate (2.1 g, 17.4 mmol, 2.0 equiv), ACN (30 mL), $Cs_2CO_3$ (7.1 g, 21.7 mmol, 2.5 equiv). The resulting solution was stirred for 1 hr at 70° C. The solids were filtered out. The resulting mixture was concentrated. The residue was applied onto a silica gel column with ethyl acetate/petroleum ether (0-10%). This resulted in 300 mg (7.75%) of methyl 3-[(5-bromo-1-[[2-(trimethylsilyl)ethoxy]methyl]-1H-pyrrolo[2,3-b]pyridin-6-yl)sulfanyl]propanoate as a colorless oil. LC-MS: (ES, m/z): M+1=445/447, R,T=1.47 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Synthesis of 3-[(5-bromo-1-[[2-(trimethylsilyl)ethoxy]methyl]-1H-pyrrolo[2,3-b]pyridin-6-yl)sulfanyl]propan-1-ol. Into a 8-mL round-bottom flask purged and maintained with an inert atmosphere of nitrogen, was placed methyl 3-[(5-bromo-1-[[2-(trimethylsilyl)ethoxy]methyl]-1H-pyrrolo[2,3-b]pyridin-6-yl)sulfanyl]propanoate (300 mg, 0.67 mmol, 1 equiv) and THF (10 mL). This was followed by the addition of $LiAlH_4$ (51 mg, 1.3 mmol, 2.00 equiv) at −78° C. carefully. The resulting solution was stirred for 1 hr at room temperature. After the reaction was completed, the reaction mixture was quenched by the addition of 0.5 mL of water, 0.5 mL of NaOH (10% in $H_2O$) and 1.5 mL of water was added into the solution successively at ice-bath. The solids were filtered out. The resulting mixture was concentrated under vacuum. This resulted in 200 mg (71.14%) of 3-[(5-bromo-1-[[2-(trimethylsilyl)ethoxy]methyl]-1H-pyrrolo[2,3-b]pyridin-6-yl)sulfanyl]propan-1-ol as yellow oil. H-NMR: (CDCl3, 300 ppm): 7.99 (s, 1H), 7.24-7.20 (m, 1H), 6.49-6.41 (m, 1H), 5.32 (s, 2H), 3.84-3.78 (m, 2H), 3.58-3.50 (m, 2H), 3.46-3.40 (m, 2H), 2.09-2.01 (m, 2H), 0.96-0.88 (m, 2H), 0.05 (s, 9H).

Synthesis of N-[6-[(3-hydroxypropyl)sulfanyl]-1-[[2-(trimethylsilyl)ethoxy]methyl]-1H-pyrrolo[2,3-b]pyridin-5-yl]-4-methylbenzene-1-sulfonamide. Into a 100-mL round-bottom flask purged and maintained with an inert atmosphere of nitrogen was placed 4-methylbenzene-1-sulfonamide (1.6 g, 9.6 mmol, 2 equiv), 3-[(5-bromo-1-[[2-(trimethylsilyl)ethoxy]methyl]-1H-pyrrolo[2,3-b]pyridin-6-yl)sulfanyl]propan-1-ol (2 g, 4.8 mmol, 1 equiv), 1,10-phenanthroline (0.17 g, 0.94 mmol, 0.20 equiv), CuI (0.18 g, 0.96 mmol, 0.2 equiv), $Cs_2CO_3$ (3.1 g, 9.6 mmol, 2 equiv) under DMSO (30 mL). The resulting solution was stirred for 72 hr at 120° C. The resulting solution was diluted with 30 mL of H₂O. The solids were filtered out. The resulting solution was extracted with 3×50 mL of ethyl acetate, The mixture was dried over anhydrous sodium sulfate and concentrated under vacuum. The residue was applied onto a silica gel column with ethyl acetate/petroleum ether (0:1-1:1). This resulted in 1.0 g (41.11%) of N-[6-[(3-hydroxypropyl)sulfanyl]-1-[[2-(trimethylsilyl)ethoxy]methyl]-1H-pyrrolo[2,3-b]pyridin-5-yl]-4-methylbenzene-1-sulfonamide as a white solid. LC-MS: (ES, m/z): M+1=508, R,T=2.845 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Synthesis of 10-(4-methylbenzenesulfonyl)-4-[[2-(trimethylsilyl)ethoxy]methyl]-14-thia-2,4,10-triazatricyclo [7.5.0.0^[3,7]]tetradeca-1(9),2,5,7-tetraene. Into a 8-mL round-bottom flask, was placed N-[6-[(3-hydroxypropyl)sulfanyl]-1-[[2-(trimethylsilyl)ethoxy]methyl]-1H-pyrrolo[2,3-b]pyridin-5-yl]-4-methylbenzene-1-sulfonamide (240 mg, 0.47 mmol, 1 equiv), THF (5 ml), PPh₃ (248 mg, 0.95 mmol, 2 equiv). This was followed by the addition of DEAD (164 mg, 0.95 mmol, 2.00 equiv) dropwise with stirring at 0° C. The resulting solution was stirred for 12 hrs at room temperature. The resulting mixture was concentrated. The residue was applied onto a silica gel column with ethyl acetate/petroleum ether (0:1-1:2). This resulted in 200 mg (86.40%) of 10-(4-methylbenzenesulfonyl)-4-[[2-(trimethylsilyl)ethoxy]methyl]-14-thia-2,4,10-triazatricyclo [7.5.0.0^[3,7]]tetradeca-1(9),2,5,7-tetraene as a colorless solid. H-NMR: (CDCl3, 300 ppm): 7.82 (s, 1H), 7.69-7.58 (m, 3H), 7.38-7.36 (d, J=6 Hz, 2H), 6.55-6.54 (d, J=3 Hz, 2H), 5.55 (s, 2H), 4.30-4.23 (m, 2H)4.06-4.02 (m, 2H), 3.57-3.49 (m, 2H), 2.77 (s, 2H), 2.50 (s, 3H), 2.07-1.99 (m, 3H), 1.24-1.04 (m, 9H), 0.87-0.84 (m, 3H), 0.02 (s, 9H).

Synthesis of 4-[[2-(trimethylsilyl)ethoxy]methyl]-14-thia-2,4,10-triazatricyclo[7.5.0.0^[3,7]]tetradeca-1(9),2,5,7-tetraene. Into a 8-mL round-bottom flask, was placed naphthalene (314 mg, 2.4 mmol, 6 equiv), Na (90 mg, 3.9 mmol, 9.6 equiv) and DME (5 mL), The resulting solution was stirred for 0.5 hr at room temperature. The resulting solution was added to 40-mL round-bottom flask of 10-(4-methylbenzenesulfonyl)-4-[[2-(trimethylsilyl)ethoxy]methyl]-14-thia-2,4,10-triazatricyclo[7.5.0.0^[3,7]]tetradeca-1(9),2,5,7-tetraene (200 mg, 0.41 mmol, 1 equiv), THF (10 mL). The resulting solution was stirred for 3 hr at room temperature. The reaction was then quenched by the addition of 1 mL of NH₄Cl. The resulting mixture was concentrated. The residue was applied onto a silica gel column with ethyl acetate/petroleum ether (0-50%). This resulted in 120 mg (87.57%) of 4-[[2-(trimethylsilyl)ethoxy]methyl]-14-thia-2,4,10-triazatricyclo[7.5.0.0^[3,7]]tetradeca-1(9),2,5,7-tetraene as a yellow solid. LC-MS: (ES, m/z): M+1=649, R,T=0.80 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Synthesis of methyl 4-(4-[[2-(4-chlorophenyl)-4,4-dimethylcyclohex-1-en-1-yl]ethyl]piperazin-1-yl)-2-(4-[[2-(trimethylsilyl)ethoxy]ethyl]-14-thia-2,4,10-triazatricyclo [7.5.0.0^[3,7]]tetradeca-1(9),2,5,7-tetraen-10-yl)benzoate. Into a 8-mL round-bottom flask purged and maintained with an inert atmosphere of nitrogen, was placed 4-[[2-(trimethylsilyl)ethoxy]methyl]-14-thia-2,4,10-triazatricyclo [7.5.0.0^[3,7]]tetradeca-1(9),2,5,7-tetraene (120 mg, 0.36 mmol, 1 equiv), methyl 2-bromo-4-(4-[[2-(4-chlorophenyl)-4,4-dimethylcyclohex-1-en-1-yl]methyl]piperazin-1-yl) benzoate (380 mg, 0.71 mmol, 2.00 equiv), caesio methaneperoxoate caesium (233 mg, 0.71 mmol, 2.00 equiv), toluene (3 mL), XantPhosPd (34 mg, 0.04 mmol, 0.1 equiv). The resulting solution was stirred for overnight at 110° C. The resulting mixture was concentrated. The residue was applied onto a silica gel column with ethyl acetate/petroleum ether (0-50%). This resulted in 150 mg (53.32%) of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-thia-2,4,10-triazatricyclo[7.5.0.0^[3,7]]tetradeca-1(9),2,5,7-tetraen-10-yl)benzoate as a yellow solid. LC-MS: (ES, m/z): M+1=786, R,T=1.26 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient. H-NMR: (CDCl3, 300 ppm): 7.64-7.61 (d, J=9 Hz, 1H), 7.35 (s, 1H), 7.28-7.26 (m, 2H), 7.19-7.18 (m, 1H), 6.99-6.97 (m, 2H), 6.52-6.47 (m, 2H), 6.27-6.26 (d, J=3 Hz, 1H), 5.61 (s, 2H), 3.96-3.84 (m, 2H), 3.60-3.54 (m, 5H), 3.28-3.16 (m, 6H), 2.82 (s, 2H), 2.33-2.24 (m, 6H), 2.06-2.02 (m, 4H), 1.49-1.45 (m, 2H), 1.28-1.19 (m, 4H), 1.03-0.88 (m, 6H), 0.00 (s, 9H).

Synthesis of methyl 4-(4-[[2-(4-chlorophenyl)-4,4-dimethylcyclohex-1-en-1-yl]methyl]piperazin-1-yl)-2-[14-thia-2,4,10-triazatricyclo[7.5.0.0^[3,7]]tetradeca-1(9),2,5,7-tetraen-10-yl]benzoate. Into a 8-mL round-bottom flask, was placed methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-thia-2,4,10-triazatricyclo [7.5.0.0^[3,7]]tetradeca-1(9),2,5,7-tetraen-10-yl)benzoate (150 mg, 0.19 mmol, 1 equiv), ethane-1,2-diamine (229 mg, 3.8 mmol, 20 equiv), TBAF (997 mg, 3.8 mmol, 20 equiv), THF (10 mL). The resulting solution was stirred for 14 hr at 70° C. The resulting mixture was concentrated. The residue was applied onto a silica gel column with ethyl acetate/petroleum ether (0-50%). This resulted in 50 mg (39.95%) of methyl 4-(4-[[2-(4-chlorophenyl)-4,4-dimethylcyclohex-1-en-1-yl]methyl]piperazin-1-yl)-2-[14-thia-2,4,10-triazatricyclo[7.5.0.0^[3,7]]tetradeca-1(9),2,5,7-tetraen-10-yl] benzoate as a yellow solid. LC-MS: (ES, m/z): M+1=656, R,T=1.05 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Synthesis of 4-(4-[[2-(4-chlorophenyl)-4,4-dimethylcyclohex-1-en-1-yl]methyl]piperazin-1-yl)-2-[14-thia-2,4,10-triazatricyclo[7.5.0.0^[3,7]]tetradeca-1(9),2,5,7-tetraen-10-yl]benzoic acid. Into a 8-mL round-bottom flask, was placed methyl 4-(4-[[2-(4-chlorophenyl)-4,4-dimethylcyclohex-1-en-1-yl]methyl]piperazin-1-yl)-2-[14-thia-2,4,10-triazatricyclo[7.5.0.0^[3,7]]tetradeca-1(9),2,5,7-tetraen-10-yl]benzoate (65 mg, 0.10 mmol, 1 equiv), 1,4-dioxane (1 mL), H₂O (1 mL), NaOH (23.95 mg, 0.60 mmol, 6.00 equiv). The resulting solution was stirred for 14 hr at 90° C. The pH value of the solution was adjusted to 5 with HCl (2 mol/L). The resulting mixture was concentrated. The residue was applied onto a silica gel column with dichloromethane/methanol (0-10%). This resulted in 30 mg (46.80%) of 4-(4-[[2-(4-chlorophenyl)-4,4-dimethylcyclohex-1-en-1-yl] ethyl]piperazin-1-yl)-2-[14-thia-2,4,10-triazatricyclo [7.5.0.0^[3,7]]tetradeca-1(9),2,5,7-tetraen-10-yl]benzoic acid as a yellow solid.

Synthesis of 4-(4-[[2-(4-chlorophenyl)-4,4-dimethylcyclohex-1-en-1-yl]methyl]piperazin-1-yl)-N-(3-nitro-4-[[(oxan-4-yl)methyl]amino]benzene sulfonyl)-2-[14-thia-2,4,10-triazatricyclo[7.5.0.0^[3,7]]tetradeca-1(9),2,5,7-tetraen-10-yl]benzamide. Into a 8-mL round-bottom flask, was placed 4-(4-[[2-(4-chlorophenyl)-4,4-dimethylcyclohex-1-en-1-yl]methyl]piperazin-1-yl)-2-[14-thia-2,4,10-triazatricyclo[7.5.0.0^[3,7]]tetradeca-1(9),2,5,7-tetraen-10-yl]benzoic acid (30 mg, 0.05 mmol, 1 equiv), 3-nitro-4-[[(oxan-4-yl)methyl]amino]benzene-1-sulfonamide (17 mg, 0.06 mmol, 1.20 equiv), EDCI (18 mg, 0.09 mmol, 2 equiv), DMAP (23 mg, 0.19 mmol, 4 equiv), DCM (3 mL). The resulting solution was stirred for overnight at room temperature. The resulting mixture was concentrated. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min within 5; Detector, UV 254 nm. This resulted in 10.6 mg (24.15%) of 4-(4-[[2-(4-chlorophenyl)-4,4-dimethylcyclohex-1-en-1-yl]methyl]piperazin-1-yl)-N-(3-nitro-4-[[(oxan-4-yl)methyl]amino]benzenesulfonyl)-2-[14-thia-2,4,10-triazatricyclo[7.5.0.0^[3,7]]tetradeca-1(9),2,5,7-tetraen-10-yl]benzamide as a yellow solid. LC-MS: (ES, m/z): M+1=939, R,T=3.55 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient. H-NMR: (CDCl3, 300 ppm): 8.71 (s, 1H), 8.49 (s, 1H), 7.99-7.97 (m, 1H), 7.81-7.77 (m, 1H), 7.38-7.28 (m, 4H), 7.01-6.93 (m, 2H), 6.88-6.72 (m, 3H), 3.36 (s, 1H), 4.06-3.26 (m, 18H), 2.73-2.22 (m, 6H), 2.13-1.73 (m, 3H), 1.79-1.25 (m, 6H), 1.00 (s, 6H).

Example 28

Preparation of 4-(4-[[2-(4-chlorophenyl)-4,4-dimethylcyclohex-1-en-1-yl]methyl]piperazin-1-yl)-2-[14,14-dioxo-14lambda6-thia-2,4,10-triazatricyclo[7.5.0.0^[3,7]]tetradeca-1(9),2,5,7-tetraen-10-yl]-N-(3-nitro-4-[[(oxan-4-yl)methyl]amino]benzenesulfonyl)benzamide Synthesis of methyl 4-(4-[[2-(4-chlorophenyl)-4,4-dimethylcyclohex-1-en-1-yl]methyl]piperazin-1-yl)-2-[14,14-dioxo-14lambda6-thia-2,4,10-triazatricyclo[7.5.0.0^[3,7]]tetradeca-1(9),2,5,7-tetraen-10-yl]benzoate: Into a 8-mL round-bottom flask, was placed methyl 4-(4-[[2-(4-chlorophenyl)-4,4-dimethylcyclohex-1-en-1-yl]methyl]piperazin-1-yl)-2-[14-thia-2,4,10-triazatricyclo[7.5.0.0^[3,7]]tetradeca-1(9),2,5,7-tetraen-10-yl]benzoate (30 mg, 0.046 mmol, 1 equiv), DCM (3 mL), m-CPBA (19.72 mg, 0.114 mmol, 2.50 equiv). The resulting solution was stirred for overnight at room temperature. The reaction was then quenched by the addition of 1 mL of water. The resulting solution was extracted with 2×5 mL of dichloromethane concentrated. The residue was applied onto a silica gel column with ethyl acetate/petroleum ether (0:1-1:1). This resulted in 20 mg (63.57%) of methyl 4-(4-[[2-(4-chlorophenyl)-4,4-dimethylcyclohex-1-en-1-yl]methyl]piperazin-1-yl)-2-[14,14-dioxo-14lambda6-thia-2,4,10-triazatricyclo[7.5.0.0^[3,7]]tetradeca-1(9),2,5,7-tetraen-10-yl]benzoate as a white solid. LC-MS-PH-PHNW-4-65-8: (ES, m/z): M+1=688, R,T=0.967 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Synthesis of 4-(4-[[2-(4-chlorophenyl)-4,4-dimethylcyclohex-1-en-1-yl]methyl]piperazin-1-yl)-2-[14,14-dioxo-14lambda6-thia-2,4,10-triazatricyclo[7.5.0.0^[3,7]]tetradeca-1(9),2,5,7-tetraen-10-yl]benzoic acid. Into a 8-mL round-bottom flask, was placed methyl 4-(4-[[2-(4-chlorophenyl)-4,4-dimethylcyclohex-1-en-1-yl]methyl]piperazin-1-yl)-2-[14,14-dioxo-14lambda6-thia-2,4,10-triazatricyclo[7.5.0.0^[3,7]]tetradeca-1(9),2,5,7-tetraen-10-yl]benzoate (20 mg, 0.029 mmol, 1 equiv), 1,4-dioxane (1 mL), water (1 mL), NaOH (6.97 mg, 0.174 mmol, 6.00 equiv). The resulting solution was stirred for overnight at 70° C. The pH value of the solution was adjusted to 5 with HCl (1 mol/L). The resulting solution was extracted with 2×3 mL of ethyl acetate. The organic layer was washed with 2×3 ml of Brine. The mixture was dried over anhydrous sodium sulfate and concentrated. This resulted in 13 mg (66.35%) of 4-(4-[[2-(4-chlorophenyl)-4,4-dimethylcyclohex-1-en-1-yl]methyl]piperazin-1-yl)-2-[14,14-dioxo-14 lambda6-thia-2,4,10-triazatricyclo[7.5.0.0^[3,7]]tetradeca-1(9),2,5,7-tetraen-10-yl]benzoic acid as a white solid. LC-MS-PH-PHNW-4-65-9: (ES, m/z): M+1=674, R,T=1.945 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Synthesis of 4-(4-[[2-(4-chlorophenyl)-4,4-dimethylcyclohex-1-en-1-yl]methyl]piperazin-1-yl)-2-[14,14-dioxo-14lambda6-thia-2,4,10-triazatricyclo[7.5.0.0^[3,7]]tetradeca-1(9),2,5,7-tetraen-10-yl]-N-(3-nitro-4-[[(oxan-4-yl)methyl]amino]benzenesulfonyl)benzamide. Into a 8-mL round-bottom flask, was placed 3-nitro-4-[[(oxan-4-yl)methyl]amino]benzene-1-sulfonamide (6.08 mg, 0.019 mmol, 1 equiv), 4-(4-[[2-(4-chlorophenyl)-4,4-dimethylcyclohex-1-en-1-yl]methyl]piperazin-1-yl)-2-[14,14-dioxo-14lambda6-thia-2,4,10-triazatricyclo[7.5.0.0^[3,7]]tetradeca-1(9),2,5,7-tetraen-10-yl]benzoic acid (13 mg, 0.019 mmol, 1 equiv), DCM (0.47 mL, 5.506 mmol, 381.56 equiv), DMAP (9.42 mg, 0.077 mmol, 4 equiv), EDCI (7.39 mg, 0.039 mmol, 2 equiv). The resulting solution was stirred for overnight at room temperature. The resulting mixture was concentrated. The crude product was further purified by Prep-HPLC with the following conditions (Waters I): Column, Xbridge Prep C18 OBD column, 5 um, 19*150 mm; mobile phase, Water (0.05% TFA) and CH3CN (46% CH3CN up to 51% in 7 min); Detector, UV 220 & 254 nm. This resulted in 2.5 mg (6.24%) of 4-(4-[[2-(4-chlorophenyl)-4,4-dimethylcyclohex-1-en-1-yl]methyl]piperazin-1-yl)-2-[14,14-dioxo-14lambda6-thia-2,4,10-triazatricyclo[7.5.0.0^[3,7]]tetradeca-1(9),2,5,7-tetraen-10-yl]-N-(3-nitro-4-[[(oxan-4-yl)methyl]amino]benzenesulfonyl)benzamide as a yellow solid. LC-MS-PH-PHNW-4-65-0: (ES, m/z): M+1=971.5, R,T=3.243 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Example 29

Preparation of 4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide Synthesis of 2-methoxypropane-1,3-diol. Into a 1000-mL 3-necked round-bottom flask purged and maintained with an inert atmosphere of nitrogen, was placed 1,3-dimethyl 2-methoxypropanedioate (20 g, 123 mmol, 1 equiv) and THF (250 mL). LiAlH4 (23.4 g, 616 mmol, 5.0 equiv) was added little by little at ice-bath. The resulting solution was stirred for 16 hr at R,T. After the reaction was completed, the reaction mixture was quenched by the addition of 23.4 mL of water, 23.4 mL of NaOH (10% in H$_2$O) and 70 mL of water was added into the solution successively at ice-bath. The solids were filtered out. The resulting mixture was concentrated under vacuum. This resulted in 12 g (91.67%) of 2-methoxypropane-1,3-diol as colorless oil. $^1$H NMR (300 MHz, CDCL3, ppm) δ 3.80-3.63 (m, 4H), 3.47 (s, 3H), 3.36-3.32 (m, 1H), 3.25 (bs, 2H).

Synthesis of 3-(5-bromo-1-((2-(trimethylsilyl)ethoxy) methyl)-1H-pyrrolo[2,3-b]pyridin-6-yloxy)-2-methoxypropan-1-ol. I Into a 250-mL 3-necked round-bottom flask, was placed 2-methoxypropane-1,3-diol (1.84 g, 17.4 mmol, 1.2 equiv) and THF (70 mL), NaH (0.87 g, 36.2 mmol, 2.5 equiv) was added at ice-bath, after the mixture was stirred at R,T for 30 min, and then 5-bromo-6-fluoro-1-[[2-(trimethylsilyl)ethoxy]methyl]-1H-pyrrolo[2,3-b]pyridine (5.0 g, 14.5 mmol, 1 equiv) was added at R,T. The resulting solution was stirred for 4 hr at 80 degrees C. The reaction was then quenched by the addition of 20 mL of water. The resulting solution was extracted with 3×50 mL of dichloromethane and the organic layers combined. The resulting mixture was washed with 1×50 mL of brine. The mixture was dried over anhydrous sodium sulfate. The solids were filtered out. The resulting mixture was concentrated. The residue was applied onto a silica gel column with ethyl acetate/petroleum ether (0-40%). This resulted in 4.0 g (64.03%) of 3-[(5-bromo-[[2-(trimethylsilyl)ethoxy] methyl]-1H-pyrrolo[2,3-b]pyridin-6-yl)oxy]-2-methoxypropan-1-ol as a white solid. $^1$H NMR (300 MHz, CDCL3, ppm) 8.09 (s, 1H), 7.20 (d, J=3.6 Hz, 1H), 6.44 (d, J=3.6 Hz, 1H), 5.62 (s, 2H), 4.60-4.58 (m, 2H), 3.97-3.95 (m, 1H), 3.92-3.90 (m, 2H), 3.79 (s, 3H), 3.65-3.60 (m, 2H), 0.98-0.93 (m, 2H), 0.01 (s, 9H).

Synthesis of N-(6-(3-hydroxy-2-methoxypropoxy)-1-((2-(trimethylsilyl)ethoxy)methyl)-1H-pyrrolo[2,3-b]pyridin-5-yl)-4-methylbenzenesulfonamide. Into a 250-mL 3-necked round-bottom flask purged and maintained with an inert atmosphere of nitrogen, was placed 3-[(5-bromo-1-[[2-(trimethylsilyl)ethoxy]methyl]-1H-pyrrolo[2,3-b]pyridin-6-yl)oxy]-2-methoxypropan-1-ol (4.0 g, 9.3 mmol, 1 equiv), T$_s$-NH$_2$ (4.76 g, 27.8 mmol, 3.00 equiv), Cs$_2$CO$_3$ (9.06 g, 27.8 mmol, 3.0 equiv), CuI (0.88 g, 4.6 mmol, 0.5 equiv), 1,10-phenanthroline (0.50 g, 2.8 mmol, 0.3 equiv) and DMSO (100 mL). The resulting solution was stirred for 24 hr at 120 degrees C. in an oil bath. The reaction mixture was cooled. The resulting solution was diluted with 500 mL of DCM. The solids were filtered out. The mixture was dried over anhydrous sodium sulfate. The solids were filtered out. The resulting mixture was concentrated. The residue was applied onto a silica gel column with ethyl acetate/petroleum ether (0-60%). This resulted in 2.7 g (55.82%) of N-[6-(3-hydroxy-2-methoxypropoxy)-1-[[2-(trimethylsilyl)ethoxy] methyl]-1H-pyrrolo[2,3-b]pyridin-5-yl]-4-methylbenzene-1-sulfonamide as a solid. $^1$H NMR (300 MHz, CDCL3, ppm) 8.09 (s, 1H), 7.61-7.59 (m, 2H), 7.17-7.15 (m, 3H), 6.75 (s, 1H), 6.46 (d, J=3.3 Hz, 1H), 5.48 (s, 2H), 4.28-4.23 (m, 2H), 3.59-3.44 (m, 8H), 2.37 (s, 3H), 0.92-0.86 (m, 3H), 0.01 (s, 9H).

Synthesis of 3-methoxy-1-tosyl-7-((2-(trimethylsilyl) ethoxy)methyl)-1,3,4,7-tetrahydro-2H-pyrrolo[3',2':5,6] pyrido[2,3-b][1,4]oxazepane. Into a 100-mL 3-necked round-bottom flask purged and maintained with an inert atmosphere of nitrogen, was placed N-[6-(3-hydroxy-2-methoxypropoxy)-1-[[2-(trimethylsilyl)ethoxy]methyl]-1H-pyrrolo[2,3-b]pyridin-5-yl]-4-methylbenzene-1-sulfonamide (500 mg, 0.96 mmol, 1 equiv), PPh$_3$ (1.2 g, 4.79 mmol, 5.0 equiv) and THF (10 mL), DEAD (834 mg, 4.79 mmol, 5.0 equiv) was added dropwise at ice-bath. The resulting solution was stirred for 2 hr at R,T. The resulting solution was diluted with 50 mL of DCM. The resulting mixture was washed with 3×20 ml of water and 1×20 mL of brine. The mixture was dried over anhydrous sodium sulfate. The solids were filtered out. The resulting mixture was concentrated under vacuum. The residue was applied onto a silica gel column with ethyl acetate/petroleum ether (0-60%). This resulted in 370 mg (76.65%) of 3-methoxy-1-tosyl-7-((2-(trimethylsilyl)ethoxy)methyl)-1,3,4,7-tetrahydro-2H-pyrrolo[3',2':5,6]pyrido[2,3-b][1,4]oxazepine as a white solid. LC-MS: (ES, m/z): M+H=504, R,T=2.40 min.

Synthesis of 3-methoxy-7-((2-(trimethylsilyl)ethoxy) methyl)-1,3,4,7-tetrahydro-2H-pyrrolo[3',2':5,6]pyrido[2,3-b][1,4]oxazepane. Into a 250 mL 3-necked round-bottom flask, was placed Na (158 mg, 6.9 mmol, 1.0 equiv), naphthalene (884 mg, 6.9 mmol, 10 equiv) and DME (3 ml) under N$_2$. The reaction mixture was stirred at room temperature until Na and naphthalene completely dissolved. To this was added the solution 3-methoxy-1-tosyl-7-((2-(trimethylsilyl)ethoxy)methyl)-1,3,4,7-tetrahydro-2H-pyrrolo[3',2':5,6]pyrido[2,3-b][1,4]oxazepine (350 mg, 0.69 mmol, 1 equiv) in THF (5 mL) at −78° C. The resulting solution was stirred for 2-3 hr at −60° C. to −40° C. unstill the starting material consumed by TLC. The reaction was then quenched by the addition of 5 mL of NH$_4$Cl at −10° C. The resulting solution was extracted with 3×10 mL of ethyl acetate. The mixture was dried over anhydrous sodium sulfate and concentrated under vacuum. The residue was applied onto a silica gel column and eluted with ethyl acetate/petroleum ether (1/3). This resulted in 214 mg (88%) of 3-methoxy-7-((2-(trimethylsilyl)ethoxy)methyl)-1,3,4,7-tetrahydro-2H-pyrrolo[3',2':5,6]pyrido[2,3-b][1,4]oxazepine as a white solid. LC-MS: (ES, m/z): M+H=350, R,T=2.26 min.

Synthesis of methyl 4-(4-((4'-chloro-5,5-dimethyl-3,4,5, 6-tetrahydro-[1,1'-biphenyl]-2-yl)methyl)piperazin-1-yl)-2-(3-methoxy-7-((2-(trimethylsilyl)ethoxy)methyl)-3,4-dihydro-2H-pyrrolo[3',2':5,6]pyrido[2,3-b][1,4]oxazepin-1 (7H)-yl)benzoate. Into a 100-mL round-bottom flask purged and maintained with an inert atmosphere of nitrogen, was placed methyl 2-bromo-4-(4-[[2-(4-chlorophenyl)-4,4-dimethylcyclohex-1-en-1-yl]methyl]piperazin-1-yl)benzoate (1.34 g, 2.52 mmol, 4.00 equiv), toluene (20 mL), 3-methoxy-7-((2-(trimethylsilyl)ethoxy)methyl)-1,3,4,7-tetrahydro-2H-pyrrolo[3',2':5,6]pyrido[2,3-b][1,4]oxazepine (220 mg, 0.63 mmol, 1 equiv), Cs$_2$CO$_3$ (1.02 g, 3.15 mmol, 5 equiv), XantPhos Pd 2G (25 mg, 0.06 mmol, 0.1 equiv). The resulting solution was stirred for overnight at 110° C. The resulting solution was diluted with 30 mL of water. The resulting solution was extracted with 2×30 mL of ethyl acetate. The resulting mixture was washed with 1×30 mL of brine. The mixture was dried over anhydrous sodium sulfate and concentrated under vacuum. The residue was applied onto a silica gel column with ethyl acetate/petroleum ether (0-50%). This resulted in 403 mg crude (80.0%) of methyl 4-(4-((4'-chloro-5,5-dimethyl-3,4,5,6-tetrahydro-[1,1'-biphenyl]-2-yl)methyl)piperazin-1-yl)-2-(3-methoxy-7-((2-(trimethylsilyl)ethoxy)methyl)-3,4-dihydro-2H-pyrrolo[3', 2':5,6]pyrido[2,3-b][1,4]oxazepin-1(7H)-yl)benzoate as a yellow solid.

Synthesis of methyl 4-(4-((4'-chloro-5,5-dimethyl-3,4,5, 6-tetrahydro-[1,1'-biphenyl]-2-yl)methyl)piperazin-1-yl)-2-(3-methoxy-3,4-dihydro-2H-pyrrolo[3',2':5,6]pyrido[2,3-b] [1,4]oxazepin-1(7H)-yl)benzoate. Into a 40-mL vial, was placed methyl 4-(4-((4'-chloro-5,5-dimethyl-3,4,5,6-tetrahydro-[1,1'-biphenyl]-2-yl)methyl)piperazin-1-yl)-2-(3- methoxy-7-((2-(trimethylsilyl)ethoxy)methyl)-3,4-dihydro-2H-pyrrolo[3',2':5,6]pyrido[2,3-b][1,4]oxazepin-1(7H)-yl)benzoate (380 mg, 0.48 mmol, 1 equiv), THF (20 mL), TBAF.3H₂O (756 mg, 2.4 mmol, 5 equiv), ethane-1,2-diamine (576 mg, 9.6 mmol, 20 equiv). The resulting solution was stirred for overnight at 70° C. in an oil bath. The resulting solution was diluted with 20 mL of water. The resulting solution was extracted with 3×30 mL of ethyl acetate. The resulting mixture was washed with 2×20 mL of brine. The mixture was dried over anhydrous sodium sulfate and concentrated under vacuum. The residue was applied onto a silica gel column with ethyl acetate/petroleum ether (0-50%). This resulted in 338 mg (93%) of methyl 4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)benzoate as a light yellow solid. LC-MS: (ES, m/z): M+H=670, R,T=2.00 min.

Synthesis of 4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)benzoic acid. Into a 40-mL vial, was placed methyl 4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)benzoate (200 mg, 0.30 mmol, 1 equiv), MeOH (6 mL), 1,4-dioxane (6 mL), H₂O (2 mL), NaOH (72 mg, 1.8 mmol, 6.00 equiv). The resulting solution was stirred for overnight at 60° C. in an oil bath. The resulting mixture was concentrated under vacuum. The pH value of the solution was adjusted to 5-6 with HCl (2 mol/L). The resulting solution was extracted with 2×50 mL of dichloromethane/MeOH (v:v=10:1). The resulting mixture was washed with 2×200 mL of brine. The mixture was dried over anhydrous sodium sulfate and concentrated under vacuum. This resulted in 152 mg (81.0%) of 4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)benzoic acid as a light yellow solid. LC-MS: (ES, m/z): M+H=656, R,T=2.43 min.

Synthesis of 4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide. Into a 40-mL round-bottom flask, was placed 4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)benzoic acid (50 mg, 0.08 mmol, 1 equiv), DCM (3 mL), 3-nitro-4-[[(oxan-4-yl)methyl]amino]benzene-1-sulfonamide (25.2 mg, 0.08 mmol, 1.00 equiv), EDCI (30.6 mg, 0.16 mmol, 2 equiv), DMAP (39.0 mg, 0.32 mmol, 4 equiv). The resulting solution was stirred for overnight at 25 degrees C. The resulting mixture was concentrated under vacuum. The residue was applied onto a silica gel column with dichloromethane/methanol (10:1). The crude product was purified by Flash-Prep-HPLC with the following conditions (IntelFlash-1): Column, C18 reversed phase column; mobile phase, Water (10 MMOL/L NH₄HCO₃+0.05% NH₃·H₂O) and CH₃CN (20.0% CH₃CN up to 90.0% in 30 min); Detector, UV 220 nm. This resulted in 32 mg (40.0%) of 4-(4-((4'-chloro-5,5-dimethyl-3,4,5,6-tetrahydro-[1,1'-biphenyl]-2-yl)methyl)piperazin-1-yl)-2-(3-methoxy-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl) sulfonyl)benzamide as a yellow solid. LC-MS: (ES, m/z): M+1=953, R,T=3.44 min. ¹H NMR (300 MHz, DMSO-d6, ppm) δ 11.00 (ds, 1H), 8.56 (s, 2H), 7.47-7.44 (m, 2H), 7.36-7.33 (m, 2H), 7.08-7.04 (m, 3H), 6.78-6.65 (m, 2H), 6.57-6.54 (m, 1H), 6.43 (s, 1H), 6.04 (s, 1H), 4.05-3.15 (m, 20H), 3.13 (s, 1H), 2.70-2.35 (m, 4H), 2.03 (s, 3H), 1.92-1.90 (m, 1H), 1.89-1.87 (m, 2H), 1.71-1.67 (m, 2H), 1.53-1.45 (m, 3H), 0.97 (s, 6H).

Example 30

Preparation of 4-(4-[[2-(4-chlorophenyl)-4,4-dimethylcyclohex-1-en-1-yl]methyl]piperazin-1-yl)-N-[4-([[(2R)-1,4-dioxan-2-yl]methyl]amino)-3-nitrobenzene sulfonyl]-2-[14-oxa-2,4,10-triazatricyclo [7.5.0.0ˆ[3,7]]tetradeca-1(9),2,5,7-tetraen-10-yl] benzamide Synthesis of 4-([[(2R)-1,4-dioxan-2-yl]methyl]amino)-3-nitrobenzene-1-sulfonamide. Into a 100-mL round-bottom flask, was placed 4-fluoro-3-nitrobenzene-1-sulfonamide (1.43 g, 0.007 mmol, 1 equiv), 1-[(2R)-1,4-dioxan-2-yl]methanamine hydrochloride (1 g, 6.510 mmol, 1 equiv), THF (30 mL), Cs₂CO₃ (8.48 g, 0.026 mmol, 4 equiv). The resulting solution was stirred overnight at 50° C. in an oil bath. The solids were collected by filtration. The solid was dried in an oven under reduced pressure. This resulted in 1.8 g (87.14%) of 4-([[(2R)-1,4-dioxan-2-yl]methyl]amino)-3-nitrobenzene-1-sulfonamide as a yellow solid. LC-MS: (ES, m/z): M+1=318, R,T=0.740 min.

Synthesis of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo [7.5.0.0ˆ[3,7]]tetradeca-1(9),2,5,7-tetraen-10-yl)benzoate. Into a 100-mL round-bottom flask purged and maintained with an inert atmosphere of nitrogen, was placed methyl 2-bromo-4-(4-[[2-(4-chlorophenyl)-4,4-dimethylcyclohex-1-en-1-yl]methyl]piperazin-1-yl)benzoate (4.35 g, 8.21 mmol, 1.87 equiv), toluene (50 mL), 4-[[2-(trimethylsilyl)ethoxy]methyl]-14-oxa-2,4,10-triazatricyclo[7.5.0.0ˆ[3,7]]tetradeca-1(9),2,5,7-tetraene (1.4 g, 4.39 mmol, 1 equiv), Cs₂CO₃ (7.1 g, 21.85 mmol, 4.98 equiv), XantPhos Pd 2G (584 mg, 0.66 mmol, 0.15 equiv). The resulting solution was stirred overnight at 110° C. The resulting solution was diluted with 300 mL of water. The resulting solution was extracted with 2×100 mL of ethyl acetate. The resulting mixture was washed with 1×300 mL of brine. The mixture was dried over anhydrous sodium sulfate and concentrated under vacuum. The residue was applied onto a silica gel column with ethyl acetate/petroleum ether (1:2). This resulted in 2.1 g (62%) of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0ˆ[3,7]]tetradeca-1(9),2,5,7-tetraen-10-yl) benzoate as a brown solid. LC-MS: (ES, m/z): M+H=770, R,T=1.318 min.

Synthesis of methyl 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoate. Into a 40-mL vial, was placed methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0ˆ[3,7]]tetradeca-1(9),2,5,7-tetraen-1(2.1 g, 3.29 mmol, 1 equiv), THF (20 mL), TBAF.3H₂O (5 g), ethane-1,2-diamine (1.4 g). The resulting solution was stirred overnight at 70° C. in an oil bath. The resulting solution was diluted with 200 mL of water. The resulting solution was extracted with 3×30 mL of ethyl acetate. The resulting mixture was washed with 2×200 mL of brine. The mixture was dried over anhydrous sodium sulfate and concentrated under vacuum. The residue was recrystallization with ethyl acetate/petroleum ether (1:5). This resulted in 1.4 g (80%) of methyl 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoate as a white solid. LC-MS: (ES, m/z): M+H=640, R,T=1.023 min.

Synthesis of 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoic acid. Into a 40-mL vial, was placed methyl 4-(4-[[2-(4-chlorophenyl)-4,4-dimethylcyclohex-1-en-1-yl]ethyl]piperazin-1-yl)-2-[14-oxa-2,4,10-triazatricyclo[7.5.0.0ˆ[3,7]]tetradeca-1(9),2,5,7-tetraen-10-yl]benzoate (1.4 g, 2.24 mmol, 1 equiv), EtOH (25 mL), dioxane (25 mL), 4M NaOH (5 mL). The resulting solution was stirred for 4 h at 80° C. in an oil bath. The resulting mixture was concentrated under vacuum. The pH value of the solution was adjusted to 5-6 with HCl (2 mol/L). The solids were collected by filtration. This resulted in 1.1 g (80%) of 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoic acid as a white solid. LC-MS: (ES, m/z): M+H=626, R,T=2.138 min.

Synthesis of 4-(4-[[2-(4-chlorophenyl)-4,4-dimethylcyclohex-1-en-1-yl]methyl]piperazin-1-yl)-N-[4-([[(2R)-1,4-dioxan-2-yl]methyl]amino)-3-nitrobenzene sulfonyl]-2-[14-oxa-2,4,10-triazatricyclo[7.5.0.0ˆ[3,7]]tetradeca-1(9),2,5,7-tetraen-10-yl]benzamide. Into a 40-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoic acid (150 mg, 0.240 mmol, 1 equiv), DCM (3 mL), 4-([[(2R)-1,4-dioxan-2-yl]methyl]amino)-3-nitrobenzene-1-sulfonamide (76 mg, 0.240 mmol, 1.00 equiv), EDCI (92 mg, 0.480 mmol, 2.00 equiv), DMAP (117 mg, 0.958 mmol, 4.00 equiv). The resulting solution was stirred overnight at 25° C. The resulting mixture was concentrated under vacuum. The crude product was purified by Prep-HPLC with the following conditions (2 #SHIMADZU (HPLC-01)): Column, XBridge Prep C18 OBD Column 5 um, 19*150 mm; mobile phase, ACN and Water (0.05% NH$_3$·H$_2$O) (20% Phase B up to 75% in 1 min, up to 95% in 7 min, hold 95% in 1 min, down to 20% in 1 min); Detector, 254/220 nm. This resulted in 28 mg (12.63%) of 4-(4-[[2-(4-chlorophenyl)-4,4-dimethylcyclohex-1-en-1-yl]methyl]piperazin-1-yl)-N-[4-([[(2R)-1,4-dioxan-2-yl]methyl]amino)-3-nitrobenzene-sulfonyl]-2-[14-oxa-2,4,10-triazatricyclo[7.5.0.0ˆ[3,7]]tetradeca-1(9),2,5,7-tetraen-10-yl]benzamide as a yellow solid. LC-MS: (ES, m/z): M+1=925, R,T=3.425 min. The measurements of the retention were done with a reversed phase column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 40° C.; flow: 1.5 mL/min. $^1$H NMR (300 MHz, DMSO-d$_6$, ppm) δ 11.90 (s, 1H), 11.20 (s, 1H), 8.60 8.41 (m, 2H), 7.64 (d, J=8.7 Hz, 1H), 7.47 (d, J=8.7 Hz, 1H), 7.36 (d, J=8.1 Hz, 2H), 7.20 (t, J=2.9 Hz, 1H), 7.07 (d, J=8.1 Hz, 2H), 6.90 (d, J=12.1 Hz, 2H), 6.70 (d, J=8.6 Hz, 2H), 6.19-6.06 (m, 1H), 4.20 (d, J=6.5 Hz, 2H), 3.88 3.71 (m, 3H), 3.69-3.32 (m, 8H), 3.28 (s, OH), 3.20 (s, 4H), 2.78 (s, 2H), 2.22 (d, J=18.1 Hz, 6H), 1.98 (s, 4H), 1.51-1.34 (m, 2H), 0.95 (s, 6H).

Example 31

Preparation of 4-(4-[[2-(4-chlorophenyl)-4,4-dimethylcyclohex-1-en-1-yl]methyl]piperazin-1-yl)-N-[4-([[(2S)-1,4-dioxan-2-yl]methyl]amino)-3-nitrobenzene sulfonyl]-2-[14-oxa-2,4,10-triazatricyclo[7.5.0.0[3,7]]tetradeca-1(9),2,5,7-tetraen-10-yl] benzamide Synthesis of 4-([[(2S)-1,4-dioxan-2-yl]methyl]amino)-3-nitrobenzene-1-sulfonamide. Into a 100-mL round-bottom flask, was placed 4-fluoro-3-nitrobenzene-1-sulfonamide (1.43 g, 0.007 mmol, 1 equiv), 1-[(2S)-1,4-dioxan-2-yl]methanamine hydrochloride (1 g, 6.510 mmol, 1 equiv), THF (30 mL), Cs$_2$CO$_3$ (8.48 g, 0.026 mmol, 4 equiv). The resulting solution was stirred overnight at 50° C. in an oil bath. The solids were collected by filtration. The solid was dried in an oven under reduced pressure. This resulted in 1.82 g (88.10%) of 4-([[(2S)-1,4-dioxan-2-yl]methyl]amino)-3-nitrobenzene-1-sulfonamide as a yellow solid. LC-MS: (ES, m/z): M+1=318, R,T=0.741 min.

Synthesis of 4-(4-[[2-(4-chlorophenyl)-4,4-dimethylcyclohex-1-en-1-yl]methyl]piperazin-1-yl)-N-[4-([[(2S)-1,4-dioxan-2-yl]methyl]amino)-3-nitrobenzene sulfonyl]-2-[14-oxa-2,4,10-triazatricyclo[7.5.0.0[3,7]]tetradeca-1(9),2,5,7-tetraen-10-yl]benzamide. Into a 40-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoic acid (150 mg, 0.240 mmol, 1 equiv), DCM (3 mL), 4-([[(2S)-1,4-dioxan-2-yl]methyl]amino)-3-nitrobenzene-1-sulfonamide (76 mg, 0.240 mmol, 1.00 equiv), EDCI (92 mg, 0.480 mmol, 2.00 equiv), DMAP (117 mg, 0.958 mmol, 4.00 equiv). The resulting solution was stirred overnight at 25° C. The resulting mixture was concentrated under vacuum. The crude product was purified by Prep-HPLC with the following conditions (2 #SHIMADZU (HPLC-01)): Column, XBridge Prep C18 OBD Column 5 um, 19*150 mm; mobile phase, ACN and Water (0.05% NH$_3$·H$_2$O) (20% Phase B up to 75% in 1 min, up to 95% in 7 min, hold 95% in 1 min, down to 20% in 1 min); Detector, 254/220 nm. This resulted in 29 mg (13.08%) of 4-(4-[[2-(4-chlorophenyl)-4,4-dimethylcyclohex-1-en-1-yl]methyl]piperazin-1-yl)-N-[4-([[(2S)-1,4-dioxan-2-yl]methyl]amino)-3-nitrobenzene-sulfonyl]-2-[14-oxa-2,4,10-triazatricyclo[7.5.0.0ˆ[3,7]]tetradeca-1(9),2,5,7-tetraen-10-yl]benzamide as a yellow solid. LC-MS: (ES, m/z): M+1=925, R,T=3.426 min. $^1$H NMR (300 MHz, DMSO-d$_6$, ppm) δ 11.90 (s, 1H), 11.20 (s, 1H), 8.60-8.41 (m, 2H), 7.64 (d, J=8.7 Hz, 1H), 7.47 (d, J=8.7 Hz, 1H), 7.36 (d, J=8.1 Hz, 2H), 7.20 (t, J=2.9 Hz, 1H), 7.07 (d, J=8.1 Hz, 2H), 6.90 (d, J=12.1 Hz, 2H), 6.70 (d, J=8.6 Hz, 2H), 6.19-6.06 (m, 1H), 4.20 (d, J=6.5 Hz, 2H), 3.88 3.71 (m, 3H), 3.69-3.32 (m, 8H), 3.28 (s, OH), 3.20 (s, 4H), 2.78 (s, 2H), 2.22 (d, J=18.1 Hz, 6H), 1.98 (s, 4H), 1.51-1.34 (m, 2H), 0.95 (s, 6H).

Example 32

Preparation of 4-(4-[[2-(4-chlorophenyl)-4,4-dimethylcyclohex-1-en-1-yl]methyl]piperazin-1-yl)-N-(4-[[[(2S)-1,4-dioxan-2-ylmethyl]amino]-3-nitrobenzene sulfonyl)-2-[13-thia-2,4,10-triazatricyclo[7.4.0.0ˆ[3,7]]trideca-1(9),2,5,7-tetraen-10-yl] benzamide Into a 250-mL round-bottom flask, was placed cysteamine hydrochloride (5.00 g, 44.014 mmol, 1.00 equiv), DCM (100.00 mL), TEA (13.36 g, 0.132 mmol, 3 equiv), acetic anhydride (4.94 g, 0.048 mmol, 1.1 equiv). The resulting solution was stirred for overnight at room temperature. The reaction was then quenched by the addition of 100 mL of water. The resulting solution was extracted with 3×50 mL of ethyl acetate dried over anhydrous sodium sulfate. The resulting solution was concentrated under vacuum. The residue was applied onto a silica gel column and eluted with ethyl acetate/petroleum ether (7:1). This resulted in 7.2 g (crude) of 2-acetamidoethanethiol as light yellow oil. $^1$H $^1$H NMR (300 MHz, DMSO-d$_6$) ∈ 7.99 (s, 1H), 3.20-3.214 (m, 2H), 2.54-2.47 (m, 2H), 1.90 (s, 1H), 1.81 (s, 3H).

Into a 100-mL round-bottom flask, was placed 2-acetamidoethanethiol (1.19 g, 9.985 mmol, 1.00 equiv), DMF (30.00 mL), 5-bromo-6-fluoro-1-[[2-(trimethylsilyl)ethoxy]methyl]pyrrolo[2,3-b]pyridine (3.45 g, 0.010 mmol, 1 equiv), CS$_2$CO$_3$ (9.76 g, 0.030 mmol, 3 equiv). The resulting solution was stirred for 5 h at 80 degrees C. in an oil bath. The reaction mixture was cooled to room temperature with a water/ice bath. The reaction was then quenched by the addition of 50 mL of water. The resulting solution was extracted with 3×50 mL of ethyl acetate dried over anhydrous sodium sulfate and concentrated. The residue was applied onto a silica gel column and eluted with ethyl acetate/petroleum ether (1:1). The collected fractions were combined and concentrated. This resulted in 2 g (45.07%) of N-[2-[(5-bromo-1-[[2-(trimethylsilyl)ethoxy]methyl]pyrrolo[2,3-b]pyridin-6-yl)sulfanyl]ethyl]acetamide as yellow oil. LCMS-PH-PHNW-4-121-2 (ES, m/z): M+1: 444/446.

Into a 50-mL round-bottom flask purged and maintained with an inert atmosphere of nitrogen, was placed N-[2-[(5-bromo-1-[[2-(trimethylsilyl)ethoxy]methyl]pyrrolo[2,3-b]pyridin-6-yl)sulfanyl]ethyl]acetamide (2.00 g, 0.004 mmol, 1.00 equiv), DMF (30 ml), Cs$_2$CO$_3$ (4.40 g, 0.013 mmol, 3 equiv), BrettPhos Pd G3 Precatalyst (0.61 mg, 0.001 mmol, 0.15 equiv). The resulting solution was stirred for overnight at 100 degrees C. in an oil bath. The reaction was cooled down to r.t then quenched by the addition of 30 mL of water. The resulting solution was extracted with 3×50 mL of ethyl acetate dried over anhydrous sodium sulfate and concentrated. The residue was applied onto a silica gel column and eluted with ethyl acetate/petroleum ether (5:2). The collected fractions were combined and concentrated. This resulted in 670 mg (40.96%) of 1-(4-[[2-(trimethylsilyl)ethoxy]methyl]-13-thia-2,4,10-triazatricyclo[7.4.0.0ˆ[3,7]]trideca-1(9),2,5,7-tetraen-10-yl)ethanone as yellow oil. LCMS-PH-PHNW-4-121-3 (ES, m/z): M+1: 364.

Into a 40-mL vial, was placed 1-(4-[[2-(trimethylsilyl)ethoxy]methyl]-13-thia-2,4,10-triazatricyclo[7.4.0.0ˆ[3,7]]trideca-1(9),2,5,7-tetraen-10-yl)ethanone (600.00 mg, 1.650 mmol, 1.00 equiv), MeOH (10.00 mL), NaOH (4M) (10.00 mL). The resulting solution was stirred for overnight at 80 degrees C. in an oil bath. The resulting mixture was concentrated. The resulting solution was extracted with 3×30 L of ethyl acetate dried over anhydrous sodium sulfate and concentrated. The residue was applied onto a silica gel column and eluted with ethyl acetate/petroleum ether (3:1). The collected fractions were combined and concentrated. This resulted in 410 mg (77.27%) of 4-[[2-(trimethylsilyl)ethoxy]methyl]-13-thia-2,4,10-triazatricyclo[7.4.0.0ˆ[3,7]]trideca-1(9),2,5,7-tetraene as yellow oil. LC-MS-PH-PHNW-4-121-4: (ES, m/z): M+1:322.

Into a 100-mL round-bottom flask purged and maintained with an inert atmosphere of nitrogen, was placed 4-[[2-(trimethylsilyl)ethoxy]methyl]-13-thia-2,4,10-triazatricyclo[7.4.0.0ˆ[3,7]]trideca-1(9),2,5,7-tetraene (200.00 mg, 0.622 mmol, 1.00 equiv), 2-bromo-4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)benzamide (1016.69 mg, 1.244 mmol, 2 equiv), DMF (20.00 mL), Cs$_2$CO$_3$ (608.04 mg, 1.866 mmol, 3 equiv), CuI (47.39 mg, 0.249 mmol, 0.4 equiv), 1,10-phenanthroline (22.42 mg, 0.124 mmol, 0.2 equiv). The resulting solution was stirred for 4 h at 95 degrees C. in an oil bath. The reaction was then quenched by the addition of 30 mL of water. The solids were filtered out. The resulting solution was extracted with 3×20 mL of ethyl acetate concentrated. The residue was applied onto a silica gel column and eluted with ethyl acetate/petroleum ether (2:1). The collected fractions were combined and concentrated. This resulted in 300 mg (45.59%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-13-thia-2,4,10-triazatricyclo[7.4.0.0ˆ[3,7]]trideca-1(9),2,5,7-tetraen-10-yl)benzamide as yellow oil. LC-MS-PH-PHNW-4-121-5: (ES, m/z): M+1:1057.

Into a 100-mL round-bottom flask, was placed 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-13-thia-2,4,10-triazatricyclo[7.4.0.0ˆ[3,7]]trideca-1(9),2,5,7-tetraen-10-yl)benzamide (300.00 mg, 0.284 mmol, 1.00 equiv), THF (20.00 mL), 0.277 mmol, 0.98 equiv), TBAF (741.53 mg, 2.836 mmol, 10.00 equiv), ethane-1,2-diamine (170.44 mg, 2.836 mmol, 10 equiv). The resulting solution was stirred for overnight at 70 degrees C. in an oil bath. The resulting mixture was concentrated. The crude product was purified by Chiral-Prep-HPLC with the following conditions: Column, XBridge Prep C18 OBD 19*150 mm 5 um; mobile phase, A: 0.1% HCl in water; B: ACN; Gradient: 24-95% B in 7.9 min; Flow rate: 20 ml/min; Detector, 220 nm. This resulted in 50 mg (18.29%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzene sulfonyl)-2-[13-thia-2,4,10-triazatricyclo[7.4.0.0ˆ[3,7]]trideca-1(9),2,5,7-tetraen-10-yl]benzamide hydrochloride as a yellow solid. LC-MS-PH-PHNW-4-121-0: (ES, m/z): M+1-HCl: 963. H-NMR-PH-PHNW-4-121-0: $^1$H $^1$H NMR (300 MHz, DMSO-d$_6$) δ 8.35 (d, J=2.4 Hz, 1H), 7.53 (d, J=8.7 Hz, 1H), 7.39 (d, J=8.4 Hz, 2H), 7.32 (dd, J=9.3, 2.4 Hz, 1H), 7.15-7.06 (m, 3H), 6.86 (d, J=8.7 Hz, 1H), 6.74 (s, 1H), 6.62 (d, J=9.3 Hz, 1H), 6.45 (s, 1H), 5.94 (d, J=3.3 Hz, 1H), 3.88-3.74 (m, 6H), 3.61 (d, J=9.9 Hz, 4H), 3.49 (dd, J=12.0, 9.6 Hz, 2H), 3.43-3.26 (m, 7H), 3.15 (s, 2H), 2.74 (s, 2H), 2.21 (s, 2H), 2.03 (s, 2H), 1.45 (d, J=6.9 Hz, 2H), 0.94 (s, 6H).

Example 33

Preparation of 4-(4-[[2-(4-chlorophenyl)-4,4-dimethylcyclohex-1-en-1-yl]methyl]piperazin-1-yl)-2-(3,4-dihydro-2H-1,4-benzoxazin-4-yl)-N-(3-nitro-4-[[(oxan-4-yl)methyl]amino]benzenesulfonyl)benzamide Into a 50-mL round-bottom flask purged and maintained with an inert atmosphere of nitrogen, was placed 2-bromo-4-(4-[[2-(4-chlorophenyl)-4,4-dimethylcyclohex-1-en-1-yl]methyl]piperazin-1-yl)-N-(3-nitro-4-[[(oxan-4-yl)methyl]amino]benzenesulfonyl)benzamide (1568.13 mg, 1.924 mmol, 1.30 equiv), 3,4-dihydro-2H-1,4-benzoxazine (200 mg, 1.480 mmol, 1.00 equiv), DMF (20.00 mL), CS$_2$CO$_3$ (1.45 g, 4.450 mmol, 3.011 equiv), CuI (112.00 mg, 0.588 mmol, 0.40 equiv), 1,10-phenanthroline (53.30 mg, 0.296 mmol, 0.20 equiv). The resulting solution was stirred for 5 h at 90 degrees C. in an oil bath. The solids were filtered out. The resulting solution was extracted with 3×40 mL of ethyl acetate concentrated. The residue was applied onto a silica gel column and eluted with ethyl acetate/petroleum ether (5:1). The collected fractions were combined and concentrated. This resulted in 100 mg (7.77%) of 4-(4-[[2-(4-chlorophenyl)-4,4-dimethylcyclohex-1-en-1-yl]methyl]piperazin-1-yl)-2-(3,4-dihydro-2H-1,4-benzoxazin-4-yl)-N-(3-nitro-4-[[(oxan-4-yl)methyl]amino]benzenesulfonyl) benzamide as a yellow solid. LC-MS-PH-PHNW-4-101-0: (ES, m/z): M+1: 869. H-NMR-PH-PHNW-4-101-0: $^1$H NMR (300 MHz, DMSO-$d_6$) δ 11.87 (s, 1H), 8.64 (t, J=6.0 Hz, 1H), 8.36 (d, J=2.4 Hz, 1H), 7.69-7.56 (m, 1H), 7.48 (d, J=8.7 Hz, 1H), 7.41-7.32 (m, 2H), 7.13-7.01 (m, 3H), 6.81 (dd, J=9.0, 2.4 Hz, 1H), 6.73 (d, J=2.4 Hz, 1H), 6.58 (dd, J=7.8, 1.8 Hz, 1H), 6.37 (dtd, J=20.1, 7.5, 1.8 Hz, 2H), 6.09 (dd, J=7.8, 1.8 Hz, 1H), 4.22 (s, 2H), 3.88 (dd, J=11.4, 4.2 Hz, 2H), 3.54 (s, 2H), 3.35 (d, J=7.2 Hz, 2H), 3.30 (s, 2H), 3.21 (s, 4H), 2.81 (s, 2H), 2.23 (d, J=24.3 Hz, 6H), 1.99 (d, J=2.1 Hz, 3H), 1.66 (d, J=12.6 Hz, 2H), 1.42 (t, J=6.3 Hz, 2H), 1.30 (tt, J=12.5, 6.3 Hz, 2H), 0.95 (s, 6H).

Example 34

Preparation of 4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]-2-[2H,3H-pyrido[4,3-b][1,4]oxazin-4-yl]benzamide Into a 8-mL vial purged and maintained with an inert atmosphere of nitrogen, was placed 2-bromo-4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]benzamide (233.51 mg, 0.286 mmol, 1.30 equiv), DMF (4.00 mL), 2H,3H,4H-pyrido[4,3-b][1,4]oxazine (30.00 mg, 0.220 mmol, 1.00 equiv), 1,10-phenanthroline (7.94 mg, 0.044 mmol, 0.2 equiv), CuI (16.79 mg, 0.088 mmol, 0.4 equiv), $Cs_2CO_3$ (215.37 mg, 0.661 mmol, 3 equiv). The resulting solution was stirred for 3 h at 95 degrees C. in an oil bath. The solids were filtered out. The resulting solution was quenched with 10 mL water and extracted with 3×10 mL of ethyl acetate concentrated. The crude product was purified by Prep-HPLC with the following conditions (2 #SHIMADZU (HPLC-01)): Column, SunFire Prep C18 OBD Column, 19*150 mm 5 um 10 nm; mobile phase, Water (0.1% HCl) and ACN (20% PhaseB up to 40% in 8 min); Detector, UV=254 nm. This resulted in 8 mg (4.17%) of 4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]-2-[2H,3H-pyrido[4,3-b][1,4]oxazin-4-yl]benzamide as a yellow solid as HCl salt. LC-MS-PH-PHNW-4-104-0: (ES, m/z): M+1-HCl: 870. H-NMR-PH-PHNW-4-104-0: $^1$H NMR (300 MHz, DMSO-$d_6$) δ 12.30 (s, 1H), δ 10.37 (s, 1H), 8.64 (d, J=6.3 Hz, 1H), 8.43 (d, J=2.4 Hz, 1H), 7.88 (d, J=6.3 Hz, 1H), 7.80-7.65 (m, 1H), 7.54 (d, J=9.3 Hz, 1H), 7.42 (d, J=8.1 Hz, 2H), 7.30 (s, 1H), 7.19-7.09 (m, 4H), 6.96 (s, 2H), 4.58 (s, 1H), 4.31 (s, 1H), 3.89 (dd, J=11.7, 4.2 Hz, 4H), 3.66-3.56 (m, 4H), 3.29 (d, J=12.0 Hz, 6H), 2.76 (d, J=16.8 Hz, 2H), 2.42-2.24 (m, 4H), 2.06 (s, 2H), 1.95 (s, 1H), 1.66 (d, J=13.2 Hz, 2H), 1.49 (d, J=6.6 Hz, 2H), 1.40-1.21 (m, 2H), 0.97 (s, 6H).

Example 35

Preparation of 4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]-2-[2H,3H,4H-pyrido[2,3-b][1,4]oxazepin-1-yl]benzamide Into a 250 mL 4-necked round-bottom flask purged and maintained with an inert atmosphere of nitrogen, was placed 3,3-diethoxypropan-1-ol (7.70 g, 64.437 mmol, 1.50 equiv), THF (60.00 mL). This was followed by the addition of NaH (3.40 g, 85.915 mmol, 2.00 equiv) in portions at 0 degrees C. To this was added 2-fluoro-3-nitropyridine (6.10 g, 42.958 mmol, 1.00 equiv) in portions at 0 degrees C. The resulting solution was stirred for 18 h at room temperature. The reaction was then quenched by the addition of 60 mL of water/ice. The resulting solution was extracted with 2×50 mL of ethyl acetate and the organic layers combined. The resulting mixture was washed with 30 ml of water. The resulting mixture was washed with 30 mL of brine. The mixture was dried over anhydrous sodium sulfate, filtered and concentrated. The residue was applied onto a silica gel column and eluted with ethyl acetate/petroleum ether (1:3). This resulted in 6.0 g (Y=51.7%) of 2-(3,3-diethoxypropoxy)-3-methylpyridine as light yellow oil.

Into a 250-mL 3-necked round-bottom flask purged and maintained with an inert atmosphere of $H_2$ (2 atm), was placed 1-(3,3-diethoxypropoxy)-2-nitrobenzene (6.00 g, 22.222 mmol, 1.00 equiv), Pd/C (700.00 mg, 2.222 mmol, 0.10 equiv) and EtOH (80 ml). The resulting solution was stirred for 3 h at room temperature. The solids were filtered out. The resulting mixture was concentrated. The residue was applied onto a silica gel column and eluted with ethyl acetate/petroleum ether (1:3). This resulted in 5.0 g (Y=94.3%) of 2-(3,3-diethoxypropoxy)aniline as light yellow oil.

Into a 100-mL 3-necked round-bottom flask, was placed 2-(3,3-diethoxypropoxy)pyridin-3-amine (650.00 mg, 2.708 mmol, 1.00 equiv), DCM (10.00 mL). This was followed by the addition of TFA (1.50 g, 13.542 mmol, 5.00 equiv) dropwise with stirring at −10 degrees C. To this was added Triethylsilane (1.50 g, 13.542 mmol, 5.00 equiv) dropwise with stirring at −10 degrees C. The resulting solution was stirred for 3 h at −10 degrees C. in an ice/salt bath. The reaction was then quenched by the addition of 10 mL of water/ice. The resulting solution was extracted with 2×20 mL of dichloromethane and the organic layers combined. The resulting mixture was washed with 20 ml of brine. The mixture was dried over anhydrous sodium sulfate and concentrated. The residue was applied onto a silica gel column and eluted with dichloromethane/methanol (10:1). This resulted in 80 mg (Y=19.7%) of 1H,2H,3H,4H-pyrido[2,3-b][1,4]oxazepine as colorless oil.

Into a 50-mL round-bottom flask purged and maintained with an inert atmosphere of nitrogen, was placed 1H,2H,3H,4H-pyrido[2,3-b][1,4]oxazepine (60.00 mg, 0.400 mmol, 1.00 equiv), methyl 2-bromo-4-(4-[[2-(4-chlorophenyl)-4,4-dimethylcyclohex-1-en-1-yl]methyl]piperazin-1-yl)benzoate (350.00 mg, 0.600 mmol, 1.50 equiv), $CS_2CO_3$ (455.00 mg, 1.000 mmol, 2.50 equiv), Toluene (12 ml), 2G-Xantphos-Pd Precatalyst (11.00 mg, 0.004 mmol, 0.01 equiv). The resulting solution was stirred for 18 h at 110 degrees C. in an oil bath. The reaction mixture was cooled to room temperature with a water bath. The solids were filtered out. The resulting mixture was concentrated. The residue was applied onto a silica gel column and eluted with ethyl acetate/petroleum ether (1:3). This resulted in 125 mg (crude) of methyl 4-(4-[[2-(4-chlorophenyl)-4,4-dimethylcyclohex-1-en-1-yl]methyl]piperazin-1-yl)-2-[2H,3H,4H-pyrido[2,3-b][1,4]oxazepin-1-yl]benzoate as colorless oil.

Into a 50-mL round-bottom flask, was placed methyl 4-(4-[[2-(4-chlorophenyl)-4,4-dimethylcyclohex-1-en-1-yl]ethyl]piperazin-1-yl)-2-[2H,3H,4H-pyrido[2,3-b][1,4]oxazepin-1-yl]benzoate (30.00 mg, 0.050 mmol, 1.00 equiv), 4 N NaOH (1.00 mL), EtOH (5.00 mL), Dioxane (5.00 mL). The resulting solution was stirred for 18 h at 50 degrees C. in an oil bath. The resulting mixture was concentrated. The pH value of the solution was adjusted to 2-3 with HCl (4 mol/L). The resulting solution was extracted with 2×20 mL of ethyl acetate and the organic layers combined. The resulting mixture was washed with 20 ml of brine. The mixture was dried over anhydrous sodium sulfate and concentrated. This resulted in 20 mg (Y=68.3%) of 4-(4-[[2-(4-chlorophenyl)-4,4-dimethylcyclohex-1-en-1-yl]methyl]piperazin-1-yl)-2-[2H,3H,4H-pyrido[2,3-b][1,4]oxazepin-1-yl]benzoic acid as colorless oil.

Into a 50-mL round-bottom flask, was placed 4-(4-[[2-(4-chlorophenyl)-4,4-dimethylcyclohex-1-en-1-yl]ethyl]piperazin-1-yl)-2-[2H,3H,4H-pyrido[2,3-b][1,4]oxazepin-1-yl]benzoic acid (20.00 mg, 0.034 mmol, 1.00 equiv), 3-nitro-4-[(oxan-4-ylmethyl)amino]benzenesulfonamide (12.00 mg, 0.038 mmol, 1.10 equiv), EDCI (13.00 mg, 0.068 mmol, 2.00 equiv), DMAP (9.00 mg, 0.068 mmol, 2.00 equiv), DCM (5.00 mL). The resulting solution was stirred for 4 h at room temperature. The resulting solution was diluted with 10 mL of water. The resulting solution was extracted with 2×20 mL of dichloromethane and the organic layers combined. The resulting mixture was washed with 10 ml of brine. The mixture was dried over anhydrous sodium sulfate and concentrated. The crude product was purified by Prep-HPLC with the following conditions: column, X-Bridge Prep C18 19*150 mm 5 um; mobile phase, A: water (it contains 10 mM $NH_4HCO_3$ 0.05% ammonia); B: ACN; Gradient: 20-45% B in 8 min; Flow rate: 20 mL/min; detector, UV 220 nm. The collected solution was concentrated under vacuum to remove $CH_3CN$ and the resulting solution was dried by lyophilization. This resulted in 7 mg (Y=23.2%) of 4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]-2-[2H,3H,4H-pyrido[2,3-b][1,4]oxazepin-1-yl]benzamide as a yellow solid. LC-MS-PH-PHNW-4-108-0: (ES, m/z): M+1=884, R.T=2.065 min. (DMSO, 300 ppm): 11.86 (s, 1H), 8.65 (s, 1H), 8.38 (s, 1H), 7.63-7.66 (d, J=9.0 Hz, 1H), 7.36-7.38 (m, 3H), 7.06-7.09 (m, 3H), 6.65-6.72 (m, 2H), 6.46-6.57 (m, 2H), 4.26-4.28 (m, 2H), 3.86-3.90 (m, 2H), 3.53-3.60 (m, 2H), 3.32 (s, 3H), 3.17 (s, 4H), 2.73-2.78 (m, 2H), 2.19-2.28 (m, 6H), 1.99 (s, 3H), 1.85 (s, 2H), 1.65-1.74 (m, 2H), 1.42 (s, 2H), 1.12-1.38 (m, 4H), 0.98 (s, 6H).

Example 36

Preparation of 4-(4-[[2-(4-chlorophenyl)-4,4-dimethylcyclohex-1-en-1-yl]methyl]piperazin-1-yl)-2-[12,12-difluoro-14-oxa-2,4,10-triazatricyclo[7.5.0.0^[3,7]]tetradeca-1(9),2,5,7-tetraen-10-yl]-N-(3-nitro-4-[[(oxan-4-yl)methyl]amino]benzene sulfonyl) benzamide Synthesis of N-(2,2-difluoro-3-hydroxypropyl)-4-methylbenzene-1-sulfonamide: Into a 40-mL round-bottom flask, was placed 3-amino-2,2-difluoropropan-1-ol (1 g, 9.002 mmol, 1 equiv), DCM (10 mL), $Et_3N$ (1.37 g, 13.539 mmol, 1.50 equiv), TsCl (1.72 g, 9.002 mmol, 1.0 equiv). The resulting solution was stirred for overnight at room temperature. The resulting mixture was concentrated. The residue was applied onto a silica gel column with ethyl acetate/petroleum ether (0:1-1:2). This resulted in 600 mg (25.13%) of N-(2,2-difluoro-3-hydroxypropyl)-4-methylbenzene-1-sulfonamide as a white solid. $^1$H-NMR-1 (300 MHz, $CDCl_3$, ppm) δ 7.76-7.73 (d, J=9.0 Hz, 2H), 7.35-7.32 (d, J=9.0 Hz, 2H), 5.04-5.00 (m, 1H), 3.9-3.83 (m, 2H), 3.46-3.35 (m, 2H), 2.45 (s, 3H).

Synthesis of N-[3-[(5-bromo-1-[[2-(trimethylsilyl)ethoxy]methyl]-1H-pyrrolo[2,3-b]pyridin-6-yl)oxy]-2,2-difluoropropyl]-4-methylbenzene-1-sulfonamide: Into a 10-mL round-bottom flask, was placed 5-bromo-6-fluoro-1-[[2-(trimethylsilyl)ethoxy]methyl]-1H-pyrrolo[2,3-b]pyridine (2.60 g, 7.530 mmol, 1.00 equiv), N-(2,2-difluoro-3-hydroxypropyl)-4-methylbenzene-1-sulfonamide (2 g, 7.539 mmol, 1 equiv), dioxane (20 mL, 236.082 mmol, 31.31 equiv), This was followed by the addition of NaH (453 mg, 11.3 mmol, 1.5 equiv, 60%), in portions at 0 degrees C. The resulting solution was stirred for overnight at 90 degrees C. The resulting mixture was concentrated. The residue was applied onto a silica gel column with ethyl acetate/petroleum ether (0:1-1:5). This resulted in 2.4 g (53.90%) of N-[3-[(5-bromo-1-[[2-(trimethylsilyl)ethoxy]methyl]-1H-pyrrolo[2,3-b]pyridin-6-yl)oxy]-2,2-difluoropropyl]-4-methylbenzene-1-sulfonamide as colorless oil. LC-MS (ES, m/z): M+1=590.

Synthesis of 12,12-difluoro-10-(4-methylbenzenesulfonyl)-4-[[2-(trimethylsilyl)ethoxy]methyl]-14-oxa-2,4,10-triazatricyclo[7.5.0.0^[3,7]]tetradeca-1,3(7),5,8-tetraene: Into a 100-mL round-bottom flask, was placed N-[3-[(5-bromo-1-[[2-(trimethylsilyl)ethoxy]methyl]-1H-pyrrolo[2,3-b]pyridin-6-yl)oxy]-2,2-difluoropropyl]-4-methylbenzene-1-sulfonamide (2.4 g, 4.064 mmol, 1 equiv), 2-(2-methylpropanoyl)cyclohexan-1-one (0.14 g, 0.832 mmol, 0.20 equiv), CuI (0.15 g, 0.813 mmol, 0.2 equiv), $Cs_2CO_3$ (2.65 g, 8.128 mmol, 2 equiv), DMSO (25 mL, 351.964 mmol, 86.61 equiv). The resulting solution was stirred for overnight at 120 degrees C. The resulting solution was diluted with 50 mL $H_2O$ and 50 mL EA. The solids were filtered out. The resulting solution was extracted with 3×50 mL of ethyl acetate. The organic layer was washed with 3×50 mL of Brine. The mixture was dried over anhydrous sodium sulfate and concentrated. The residue was applied onto a silica gel column with ethyl acetate/petroleum ether (0:1-1:1). This resulted in 1.5 g (72.42%) of 12,12-difluoro-10-(4-methylbenzenesulfonyl)-4-[[2-(trimethylsilyl)ethoxy]methyl]-14-oxa-2,4,10-triazatricyclo[7.5.0.0^[3,7]]tetradeca-1,3(7),5,8-tetraene as yellow oil. $^1$H NMR (300 MHz, $CDCl_3$, ppm): δ 8.37 (s, 1H), 7.42-7.39 (m, 3H), 7.16-7.14 (d, J=6.0 Hz, 2H), 6.61-6.60 (d, J=3.0 Hz, 1H), 5.58 (s, 1H), 4.23-4.15 (m, 2H), 3.98-3.91 (m, 1H), 3.58-3.52 (m, 2H), 2.37 (s, 3H), 0.95-0.89 (m, 2H), 0.00 (s, 9H).

Synthesis of 12,12-difluoro-4-[[2-(trimethylsilyl)ethoxy]methyl]-14-oxa-2,4,10-triazatricyclo[7.5.0.0^[3,7]]tetradeca-1(9),2,5,7-tetraene: Into a 8-mL round-bottom flask, was placed naphthalene (2.26 g, 17.660 mmol, 6 equiv), DME (20 mL, 206.633 mmol, 70.21 equiv), Na (0.65 g, 28.255 mmol, 9.6 equiv), The resulting solution was stirred for 0.5 h at room temperature. The resulting solution was added to a 40-mL round-bottom flask, was placed 12,12-difluoro-10-(4-methylbenzenesulfonyl)-4-[[2-(trimethylsilyl)ethoxy]methyl]-14-oxa-2,4,10-triazatricyclo[7.5.0.0^[3,7]]tetradeca-1(9),2,5,7-tetraene (1.5 g, 2.943 mmol, 1 equiv), THF (20 mL, 246.860 mmol, 83.87 equiv). The resulting solution was stirred for 1 h at room temperature.

The reaction was then quenched by the addition of 10 mL of NH₄Cl. The resulting solution was extracted with 3×50 mL of ethyl acetate concentrated. The residue was applied onto a silica gel column with ethyl acetate/petroleum ether (0:1-1:1). This resulted in 0.5 g (47.79%) of 12,12-difluoro-4-[[2-(trimethylsilyl)ethoxy]methyl]-14-oxa-2,4,10-triazatricyclo[7.5.0.0^[3,7]]tetradeca-1(9),2,5,7-tetraene as a white solid. ¹H-NMR (300 MHz, CDCl₃, ppm): δ 7.34-7.28 (m, 1H), 7.25-7.23 (d, J=6.0 Hz, 1H), 6.37-6.36 (m, 1H), 5.58-5.53 (m, 2H), 4.57-4.48 (m, 2H), 3.72-3.64 (m, 2H), 3.59-3.52 (m, 2H), 1.30-1.28 (m, 2H), 0.00 (s, 9H).

Synthesis of methyl 4-chloro-2-(12,12-difluoro-4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate:

Into a 8-mL round-bottom flask, was placed methyl 2-bromo-4-chlorobenzoate (210.56 mg, 0.844 mmol, 1.5 equiv), 12,12-difluoro-4-[[2-(trimethylsilyl)ethoxy]methyl]-14-oxa-2,4,10-triazatricyclo[7.5.0.0^[3,7]]tetradeca-1(9),2,5,7-tetraene (200 mg, 0.563 mmol, 1 equiv), pyridine-2-carboxylic acid (13.85 mg, 0.113 mmol, 0.2 equiv), DMSO (5 mL), Cs₂CO₃ (549.97 mg, 1.688 mmol, 3 equiv), CuI (21.43 mg, 0.113 mmol, 0.2 equiv). The resulting solution was stirred for 12 h at 130 degrees C. The reaction was then quenched by the addition of 10 mL of water. The resulting solution was extracted with 3×20 mL of ethyl acetate concentrated. The residue was applied onto a silica gel column with ethyl acetate/petroleum ether (0:1-1:10). This resulted in 180 mg (46.40%) of methyl 4-chloro-2-(12,12-difluoro-4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate as a white crude solid. LC-MS (ES, m/z): M+1=524.

Synthesis of methyl 4-(4-[[2-(4-chlorophenyl)-4,4-dimethylcyclohex-1-en-1-yl]methyl]piperazin-1-yl)-2-(12,12-difluoro-4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate: Into a 8-mL round-bottom flask, was placed methyl 4-chloro-2-(12,12-difluoro-4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate (180.00 mg, 0.343 mmol, 1.00 equiv), 1-[[2-(4-chlorophenyl)-4,4-dimethylcyclohex-1-en-1-yl]methyl]piperazine (131.44 mg, 0.412 mmol, 1.2 equiv), toluene (3.00 mL), Cs₂CO₃ (335.74 mg, 1.030 mmol, 3 equiv), tBuXPhos Pd G3 Precatalyst (27.29 mg, 0.034 mmol, 0.1 equiv). The resulting solution was stirred for overnight at room temperature. The resulting mixture was concentrated. The residue was applied onto a silica gel column with ethyl acetate/petroleum ether (0:1-1:1). This resulted in 100 mg of methyl 4-(4-[[2-(4-chlorophenyl)-4,4-dimethylcyclohex-1-en-1-yl]methyl]piperazin-1-yl)-2-(12,12-difluoro-4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate as a white solid. LC-MS (ES, m/z): M+1=806.4

Synthesis of methyl 4-(4-[[2-(4-chlorophenyl)-4,4-dimethylcyclohex-1-en-1-yl]methyl]piperazin-1-yl)-2-[12,12-difluoro-14-oxa-2,4,10-triazatricyclo[7.5.0.0^[3,7]]tetradeca-1(9),2,5,7-tetraen-10-yl]benzoate: Into a 40-mL round-bottom flask, was placed methyl 4-(4-[[2-(4-chlorophenyl)-4,4-dimethylcyclohex-1-en-1-yl]ethyl]piperazin-1-yl)-2-(12,12-difluoro-4-[[2-(trimethylsilyl)ethoxy]methyl]-14-oxa-2,4,10-triazatricyclo[7.5.0.0^[3,7]]tetraen-10-yl)benzoate (100 mg, 0.124 mmol, 1 equiv), TBAF (648.41 mg, 2.480 mmol, 20 equiv), THF (10 mL), ethane-1,2-diamine (149.04 mg, 2.480 mmol, 20 equiv). The resulting solution was stirred for 12 h at 70 degrees C. The resulting mixture was concentrated. The residue was applied onto a silica gel column with ethyl acetate/petroleum ether (0:1-1:1). This resulted in 50 mg (59.63%) of methyl 4-(4-[[2-(4-chlorophenyl)-4,4-dimethylcyclohex-1-en-1-yl]ethyl]piperazin-1-yl)-2-[12,12-difluoro-14-oxa-2,4,10-triazatricyclo[7.5.0.0^[3,7]]tetradeca-1(9),2,5,7-tetraen-10-yl]benzoate as a white solid. LC-MS (ES, m/z): M+1=676.3.

Synthesis of 4-(4-[[2-(4-chlorophenyl)-4,4-dimethylcyclohex-1-en-1-yl]methyl]piperazin-1-yl)-2-[12,12-difluoro-14-oxa-2,4,10-triazatricyclo[7.5.0.0^[3,7]]tetradeca-1(9),2,5,7-tetraen-10-yl]benzoic acid: Into a 8-mL round-bottom flask, was placed methyl 4-(4-[[2-(4-chlorophenyl)-4,4-dimethylcyclohex-1-en-1-yl]methyl]piperazin-1-yl)-2-[12,12-difluoro-14-oxa-2,4,10-triazatricyclo[7.5.0.0^[3,7]]tetradeca-1(9),2,5,7-tetraen-10-yl]benzoate (50 mg, 0.074 mmol, 1 equiv), Dioxane (1 mL), MeOH (1 mL), H₂O (1 mL), NaOH (17.74 mg, 0.444 mmol, 6.00 equiv). The resulting solution was stirred for 12 h at 70 degrees C. The pH value of the solution was adjusted to 6 with HCl (1 mol/L). The resulting mixture was concentrated. The residue was applied onto a silica gel column with ethyl acetate/petroleum ether (0:1-1:1). This resulted in 20 mg (40.85%) of 4-(4-[[2-(4-chlorophenyl)-4,4-dimethylcyclohex-1-en-1-yl]methyl]piperazin-1-yl)-2-[12,12-difluoro-14-oxa-2,4,10-triazatricyclo[7.5.0.0^[3,7]]tetradeca-1(9),2,5,7-tetraen-10-yl]benzoic acid as a white solid.

H-NMR (300 MHz, CDCl₃, ppm): 67.70-7.63 (m, 1H), 7.31-7.25 (m, 2H), 7.03-6.93 (m, 2H), 6.77 (s, 1H), 6.67-6.63 (m, 2H), 6.06 (s, 1H), 3.64-3.47 (m, 3H), 3.40-3.31 (m, 4H), 2.88 (s, 1H), 2.42-2.27 (m, 5H), 2.10-2.07 (m, 3H), 1.38-1.26 (m, 8H), 1.25-1.24 (m, 2H), 1.02 (s, 6H), 1.42 (m, 2H), 0.88-0.85 (m, 2H).

Synthesis of 4-(4-[[2-(4-chlorophenyl)-4,4-dimethylcyclohex-1-en-1-yl]methyl]piperazin-1-yl)-2-[12,12-difluoro-14-oxa-2,4,10-triazatricyclo[7.5.0.0^[3,7]]tetradeca-1(9),2,5,7-tetraen-10-yl]-N-(3-nitro-4-[[(oxan-4-yl)methyl]amino]benzenesulfonyl)benzamide: Into a 8-mL round-bottom flask, was placed 4-(4-[[2-(4-chlorophenyl)-4,4-dimethylcyclohex-1-en-1-yl]methyl]piperazin-1-yl)-2-[12,12-difluoro-14-oxa-2,4,10-triazatricyclo[7.5.0.0^[3,7]]tetradeca-1(9),2,5,7-tetraen-10-yl]benzoic acid (20.00 mg, 0.030 mmol, 1.00 equiv), 3-nitro-4-[[(oxan-4-yl)methyl]amino]benzene-1-sulfonamide (11.43 mg, 0.036 mmol, 1.2 equiv), DCM (3 mL), DMAP (14.76 mg, 0.121 mmol, 4 equiv), EDCI (11.58 mg, 0.060 mmol, 2 equiv). The resulting solution was stirred for 12 h at room temperature. The crude product was purified by Prep-HPLC with the following conditions (Waters-2767): Column, X-bridge RP18, 5 um, 19*100 mm; mobile phase, 0.03% ammonia in water (0.03% NH₄HCO₃ & NH₄OH) and CH₃CN (32% CH₃CN up to 52% in 6 min); Detector, UV 254 nm. This resulted in 11.5 mg (39.68%) of 4(4-[[2-(4-chlorophenyl)-4,4-dimethylcyclohex-1-en-1-yl]methyl]piperazin-1-yl)-2-[12,12-difluoro-14-oxa-2,4,10-triazatricyclo[7.5.0.0^[3,7]]tetradeca-1(9),2,5,7-tetraen-10-yl]-N-(3-nitro-4-[[(oxan-4-yl)methyl]amino]benzenesulfonyl)benzamide as a white solid. LC-MS-0: (ES, m/z): M+1=961.47. ¹H-NMR-O (300 MHz, d-DMSO, ppm): δ 11.01 (s, 1H), 8.34-8.33 (d, J=3.0 Hz, 1H), 7.47-7.45 (m, 2H), 7.38-7.35 (m, 2H), 6.82-6.80 (m, 3H), 6.02 (s, 1H), 3.86-3.51 (m, 7H), 3.39-3.17 (m, 5H), 2.77-2.73 (m, 2H), 2.24-2.20 (m, 6H), 2.00 (s, 2H), 1.42 (m, 2H), 1.30 (s, 1H), 0.95 (s, 6H).

Example 37

Preparation of 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((S)-5-nitro-3-(tetrahydro-2H-pyran-4-yl)-3,4-dihydro-2H-benzo[b][1,4]oxazin-7-yl)sulfonyl)benzamide, and 4-(4-((4'-chloro-5,5-dimethyl-3,4,5,6-tetrahydro-[1,1'-biphenyl]-2-yl)methyl)piperazin-1-yl)-2-((R)-3-methyl-2,3-dihydropyrrolo[3',2':5,6]pyrido[2,3-b][1,4]oxazin-1(6H)-yl)-N—(((R)-5-nitro-3-(tetrahydro-2H-pyran-4-yl)-3,4-dihydro-2H-benzo[b][1,4]oxazin-7-yl)sulfonyl)benzamide Synthesis of 3-bromo-4-chloro-5-nitrobenzenesulfonamide, Into a 50-mL round-bottom flask, was placed 4-chloro-3-nitrobenzenesulfonamide (20.00 g, 84.520 mmol, 1.00 equiv), $H_2SO_4$ (20.00 mL). This was followed by the addition of NBS (22.56 g, 126.753 mmol, 1.50 equiv), in portions at 50 degrees C. The resulting solution was stirred for 2 hr at 60 degrees C. The resulting solution was diluted with 200 mL of cold $H_2O$. The resulting solution was extracted with 3×30 mL of ethyl acetate. The resulting mixture was washed with 1×20 ml of $H_2O$. The resulting mixture was washed with 1×20 mL of NaCl (aq.). The residue was applied onto a silica gel column with ethyl and eluted with ethyl acetate/petroleum ether (1:3). This resulted in 5 g (18.75%) of 3-bromo-4-chloro-5-nitrobenzenesulfonamide as a white solid. LC-MS-1: (ES, m/z): 312.9 [M−H]

Synthesis of 2-amino-2-(oxan-4-yl)ethanol: Into a 100-mL round-bottom flask, was placed amino(oxan-4-yl)acetic acid (4.00 g, 25.128 mmol, 1.00 equiv), THF (50.00 mL), $LiAlH_4$ (1.91 g, 50.324 mmol, 2.00 equiv). The resulting solution was stirred for 3 hr at 60 degrees C. in an oil bath. The reaction was then quenched by the addition of 10 mL of water. The resulting mixture was concentrated. This resulted in 6 g (crude) of 2-amino-2-(oxan-4-yl)ethanol as a white solid. LC-MS-21: (ES, m/z): 146.2 [M+H]$^+$ Synthesis of 3-bromo-4-[[2-hydroxy-1-(oxan-4-yl)ethyl]amino]-5-nitrobenzenesulfonamide: Into a 100-mL round-bottom flask, was placed 3-bromo-4-chloro-5-nitrobenzenesulfonamide (5.00 g, 15.847 mmol, 1.00 equiv), 2-amino-2-(oxan-4-yl)ethanol (5.00 g), $CH_3CN$ (30.00 mL, 0.731 mmol), DIEA (6.10 g, 47.198 mmol, 2.98 equiv). The resulting solution was stirred for 48 hr at 80 degrees C. in an oil bath. The resulting mixture was concentrated. The residue was applied onto a silica gel column and eluted with dichloromethane/methanol (10:1). This resulted in 1.2 g (17.85%) of 3-bromo-4-[[2-hydroxy-1-(oxan-4-yl)ethyl]amino]-5-nitrobenzenesulfonamide as a yellow solid. LC-MS-2: (ES, m/z): 424.1 [M+H]$^+$.

Synthesis of methyl 4-(4-[[2-(4-chlorophenyl)-4,4-dimethylcyclohex-1-en-1-yl]methyl]piperazin-1-yl)-2-[(12R)-12-methyl-4-[[2-(trimethylsilyl)ethoxy]methyl]-13-oxa-2,4,10-triazatricyclo[7.4.0.0^[3,7]]trideca-1(9),2,5,7-tetraen-10-yl]benzoate. Into a 50-mL round-bottom flask, was placed (12R)-12-methyl-4-[[2-(trimethylsilyl)ethoxy]methyl]-13-oxa-2,4,10-triazatricyclo[7.4.0.0^[3,7]]trideca-1(9),2,5,7-tetraene (500.00 mg, 1.565 mmol, 1.00 equiv), methyl 2-bromo-4-(4-[[2-(4-chlorophenyl)-4,4-dimethylcyclohex-1-en-1-yl]methyl]piperazin-1-yl)benzoate (832.48 mg, 1.565 mmol, 1.00 equiv), xantphos Pd 2G (138.82 mg, 0.157 mmol, 0.10 equiv), $Cs_2CO_3$ (1529.77 mg, 4.695 mmol, 3.00 equiv), dioxane (10.00 mL). The resulting solution was stirred for 14 hr at 80 degrees C. The resulting solution was concentrated. The residue was applied onto a silica gel column and eluted with ethyl acetate/petroleum ether (1:3). This resulted in 611 mg (50.67%) of methyl 4-(4-[[2-(4-chlorophenyl)-4,4-dimethylcyclohex-1-en-1-yl]methyl]piperazin-1-yl)-2-[(12R)-12-methyl-4-[[2-(trimethylsilyl)ethoxy]methyl]-13-oxa-2,4,10-triazatricyclo[7.4.0.0^[3,7]]trideca-1(9),2,5,7-tetraen-10-yl]benzoate as a yellow solid. LC-MS-11: (ES, m/z): 770.4 [M+H]$^+$.

Synthesis of methyl 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]benzoate. Into a 8-mL vial, was placed methyl 4-(4-[[2-(4-chlorophenyl)-4,4-dimethylcyclohex-1-en-1-yl]methyl]piperazin-1-yl)-2-[(12R)-12-methyl-4-[[2-(trimethylsilyl)ethoxy]methyl]-13-oxa-2,4,10-triazatricyclo[7.4.0.0^[3,7]]trideca-1(9),2,5,7-tetraen-10-yl]benzoate (300.00 mg, 0.389 mmol), ethane-1,2-diamine (0.20 mL), TBAF in THF (1 ml, 2M). The resulting solution was stirred for 24 hr at 70 degrees C. in an oil bath. The resulting mixture was concentrated. The residue was applied onto a silica gel column with ethyl acetate/petroleum ether (1:1). This resulted in 100 mg (40.12%) of methyl 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]benzoate as a white solid. LC-MS-11: (ES, m/z): 640.3 [M+H]$^+$.

Synthesis of 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]benzoic acid. Into a 8-mL vial, was placed methyl 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]benzoate (100.00 mg, 0.156 mmol, 1.00 equiv), NaOH (37.49 mg, 0.937 mmol, 6.00 equiv), MeOH (0.50 mL), dioxane (0.50 mL), $H_2O$ (0.20 mL). The resulting solution was stirred for 14 hr at 70 degrees C. in an oil bath. The resulting mixture was concentrated. The resulting solution was diluted with 1 mL of $H_2O$. The pH value of the solution was adjusted to 6 with $CH_3COOH$. The resulting mixture was concentrated. The residue was applied onto a silica gel column and eluted with dichloromethane/methanol (10:1). This resulted in 60 mg of 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]benzoic acid as a brown solid. LC-MS-13: (ES, m/z): 626.3 [M+H]$^+$.

Synthesis of 5-nitro-3-(oxan-4-yl)-3,4-dihydro-2H-1,4-benzoxazine-7-sulfonamide. Into a 50-mL round-bottom flask purged and maintained with an inert atmosphere of nitrogen, was placed 3-bromo-4-[[2-hydroxy-1-(oxan-4-yl)ethyl]amino]-5-nitrobenzenesulfonamide (1.40 g, 3.300 mmol, 1.00 equiv), dioxane (20.00 mL), $Pd_2(dba)_3$ (604.34 mg, 0.660 mmol, 0.20 equiv), XantPhos (763.73 mg, 1.320 mmol, 0.40 equiv), $Cs_2CO_3$ (3.23 g, 9.913 mmol, 3.00 equiv). The resulting solution was stirred for 2 hr at 100 degrees C. in an oil bath. The resulting mixture was concentrated. The residue was applied onto a silica gel column and eluted with ethyl acetate/petroleum ether (1:1). This resulted in 230 mg (20.30%) of 5-nitro-3-(oxan-4-yl)-3,4-dihydro-2H-1,4-benzoxazine-7-sulfonamide as a yellow solid. LC-MS-3: (ES, m/z): 342.1 [M−H]$^−$ Synthesis of (3S)-5-nitro-3-(oxan-4-yl)-3,4-dihydro-2H-1,4-benzoxazine-7-sulfonamide and (3R)-5-nitro-3-(oxan-4-yl)-3,4-dihydro-2H-1,4-benzoxazine-7-sulfonamide. Into a 50-mL round-bottom flask, was placed 5-nitro-3-(oxan-4-yl)-3,4-dihydro-2H-1,4-benzoxazine-7-sulfonamide (150.00 mg) and DMF (10 ml). The sample was purified by Chiral-Prep-HPLC with the following conditions (WATERS 2767): Column, CHIRALPAK IA, 250*20 mm, 5 um; Mobile phase: A: n-Hexane:DMC=3:1, 0.1% DEA), B: EtOH; Gradient: 10% B in 20 min; Detector, 220 nm. This resulted in 30 mg of (3S)-5-nitro-3-(oxan-4-yl)-3,4-dihydro-2H-1,4-benzoxazine-7-sulfonamide as a yellow solid. This resulted in 32 mg of (3R)-5-nitro-3-(oxan-4-yl)-3,4-dihydro-2H-1,4-benzoxazine-7-sulfonamide as a yellow solid.

Synthesis of 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]-N-[(3S)-5-nitro-3-(oxan-4-yl)-3,4-dihydro-2H-1,4-benzoxazin-7-ylsulfonyl]benzamide hydrochloride: Into a 8-mL vial, was placed (3S)-5-nitro-3-(oxan-4-yl)-3,4-dihydro-2H-1,4-benzoxazine-7-sulfonamide (20 mg, 0.058 mmol, 1.00 equiv), 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoic acid (36.48 mg, 0.058 mmol, 1.00 equiv), DCM (0.5 mL), EDC.HCl (22.33 mg, 0.116 mmol, 2.00 equiv), DMAP (17.79 mg, 0.146 mmol, 2.50 equiv). The resulting solution was stirred for 14 hr at room temperature. The resulting mixture was concentrated. The residue was purified with Prep-TLC with dichloromethane/methanol (10:1). The crude product (30 mg) was purified by Prep-HPLC with the following conditions: Column, XBridge Prep C18 OBD 19*150 mm 5 um; Mobile phase, A: 0.1% HCl in water; B: ACN; Gradient: 38-58% B in 7 min; Flow rate: 20 ml/min; Detector, 220 nm. This resulted in 10 mg (17.38%) of 4-(4-[[2-(4-chlorophenyl)-4,4-dimethylcyclohex-1-en-1-yl]ethyl]piperazin-1-yl)-2-[(12R)-12-methyl-13-oxa-2,4,10-triazatricyclo[7.4.0.0ˆ[3,7]]trideca-1(9),2,5,7-tetraen-10-yl]-N-[(3S)-5-nitro-3-(oxan-4-yl)-3,4-dihydro-2H-1,4-benzoxazin-7-ylsulfonyl]benzamide hydrochloride as a yellow solid. LC-MS-0A: (ES, m/z): 951.4 [M–HCl+H]$^{+}$. $^1$H NMR-0A (300 MHz, DMSO, ppm): δ 12.15 (s, 1H), 10.86 (s, 1H), 9.68 (s, 1H), 8.78 (s, 1H), 8.05-7.81 (m, 1H), 7.58-7.31 (m, 1H), 7.21-6.72 (m, 6H), 6.70-6.40 (m, 1H), 6.02-5.81 (m, 1H), 4.61-4.11 (m, 3H), 3.92-3.78 (m, 4H), 3.65-3.61 (m, 2H), 3.38-3.13 (m, 8H), 2.90-2.72 (m, 2H), 2.30-2.21 (m, 2H), 2.13-1.94 (m, 2H), 1.92-1.51 (m, 3H), 1.51-1.23 (m, 8H), 0.96 (s, 6H).

Synthesis of 4-(4-[[2-(4-chlorophenyl)-4-methylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]-N-[(3R)-5-nitro-3-(oxan-4-yl)-3,4-dihydro-2H-1,4-benzoxazin-7-ylsulfonyl]benzamide hydrochloride. Into a 8-mL vial, was placed (3R)-5-nitro-3-(oxan-4-yl)-3,4-dihydro-2H-1,4-benzoxazine-7-sulfonamide (20.00 mg, 0.058 mmol, 1.00 equiv),4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]benzoic acid (36.48 mg, 0.058 mmol, 1.00 equiv), DCM, EDCI (22.33 mg, 0.116 mmol, 2.00 equiv), DMAP (17.79 mg, 0.146 mmol, 2.50 equiv). The resulting solution was stirred for 14 hr at room temperature. The resulting mixture was concentrated. The residue was purified with Prep-TLC with DCM/methanol (10:1). The crude product (30 mg) was purified by Prep-HPLC with the following conditions: Column, XBridge Prep C18 OBD 19*150 mm 5 um; Mobile phase, A: 0.1% HCl in water; B: ACN; Gradient: 38-58% B in 7 min; Flow rate: 20 ml/min; Detector, 220 nm. This resulted in 10.3 mg (18.16%) of 4-(4-[[2-(4-chlorophenyl)-4-methylcyclohex-1-en-1-yl]methyl]piperazin-1-yl)-2-[(12R)-12-methyl-13-oxa-2,4,10-triazatricyclo[7.4.0.0ˆ[3,7]]trideca-1(9),2,5,7-tetraen-10-yl]-N-[(3R)-5-nitro-3-(oxan-4-yl)-3,4-dihydro-2H-1,4-benzoxazin-7-ylsulfonyl]benzamide hydrochloride as a yellow solid. LC-MS-0B: (ES, m/z): 951.4 [M–HCl+H]$^{+}$ $^1$H NMR-0B (300 MHz, DMSO, ppm): δ 12.16 (s, 1H), 10.89 (s, 1H), 10.02 (s, 1H), 8.78 (s, 1H), 8.05-7.41 (m, 5H), 7.21-6.52 (m, 6H), 6.02-5.91 (m, 1H), 4.61-4.21 (m, 2H), 4.15-3.78 (m, 5H), 3.71-3.65 (m, 2H), 3.38-3.13 (m, 8H), 2.88-2.72 (m, 2H), 2.35-2.30 (m, 2H), 2.13-1.94 (m, 2H), 1.92-1.59 (m, 3H), 1.51-1.23 (m, 8H), 0.96 (s, 6H).

Example 38

Preparation of N-(4-[[[(2S)-1,4-dioxan-2-ylmethyl]amino]-3-nitrobenzene sulfonyl)-4-(4-[[2-(4-hydroxyphenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzamide Synthesis of 4-([[[(2S)-1,4-dioxan-2-yl]methyl]amino)-3-nitrobenzene-1-sulfonamide: Into a 100-mL round-bottom flask, was placed 4-fluoro-3-nitrobenzene-1-sulfonamide (1.43 g, 0.007 mmol, 1 equiv), 1-[(2S)-1,4-dioxan-2-yl]methanamine hydrochloride (1 g, 6.510 mmol, 1 equiv), THF (30 mL), Cs$_2$CO$_3$ (8.48 g, 0.026 mmol, 4 equiv). The resulting solution was stirred overnight at 50° C. in an oil bath. The solids were collected by filtration. The solid was dried in an oven under reduced pressure. This resulted in 1.82 g (88.10%) of 4-([[[(2S)-1,4-dioxan-2-yl]methyl]amino)-3-nitrobenzene-1-sulfonamide as a yellow solid. LC-MS (ES, m/z): M+1=318.

Synthesis of 2-[3-[(5-bromo-1-[[2-(trimethylsilyl)ethoxy]methyl]pyrrolo[2,3-b]pyridin-6-yl)oxy]propyl]isoindole-1,3-dione: Into a 1000-mL 3-necked round-bottom flask purged and maintained with an inert atmosphere of nitrogen, was placed 5-bromo-6-fluoro-1-[[2-(trimethylsilyl)ethoxy]methyl]pyrrolo[2,3-b]pyridine (53.50 g, 154.944 mmol, 1 equiv). This was followed by the addition of 2-(3-hydroxypropyl)isoindole-1,3-dione (31.80 g, 154.944 mmol, 1 equiv), in portions at degrees C. To this was added Dioxane (500.00 mL) at degrees C., NaH (9.30 g, 232.415 mmol, 1.50 equiv, 60%). The resulting solution was stirred for 4 h at 80 degrees C. The reaction mixture was cooled with a water/ice bath. The reaction was then quenched by the addition of 500 mL AcOH/ice/water. The resulting solution was extracted with 2×500 mL of ethyl acetate. The resulting mixture was washed with 3×500 ml of Brine. The mixture was dried over anhydrous sodium sulfate and concentrated. The residue was applied onto a silica gel column with ethyl acetate/petroleum ether (0:1-1:10). This resulted in 58 g (70.56%) of 2-[3-[(5-bromo-1-[[2-(trimethylsilyl)ethoxy]methyl]pyrrolo[2,3-b]pyridin-6-yl)oxy]propyl]isoindole-1,3-dione as colorless oil. LC-MS: (ES, m/z): M+1=554.

Synthesis of 3-[(5-bromo-1-[[2-(trimethylsilyl)ethoxy]methyl]pyrrolo[2,3-b]pyridin-6-yl)oxy]propan-1-amine: Into a 500-mL round-bottom flask, was placed 2-[3-[(5-bromo-1-[[2-(trimethylsilyl)ethoxy]methyl]pyrrolo[2,3-b]pyridin-6-yl)oxy]propyl]isoindole-1,3-dione (58.00 g, 109.332 mmol, 1.00 equiv), EtOH (300.00 mL), NH2NH2H2O (68.42 g, 1093.321 mmol, 10 equiv, 80%). The resulting solution was stirred for 4 h at room temperature. The resulting mixture was concentrated. The reaction was then quenched by the addition of 200 mL of water. The resulting solution was extracted with 2×500 mL of ethyl acetate The resulting mixture was washed with 2×300 ml of Brine. The mixture was dried over anhydrous sodium sulfate and concentrated. The residue was applied onto a silica gel column with ethyl acetate/petroleum ether (0:1-1:2). This resulted in 37.5 g (85.66%) of 3-[(5-bromo-1-[[2-(trimethylsilyl)ethoxy]methyl]pyrrolo[2,3-b]pyridin-6-yl)oxy]propan-1-amine as yellow oil.

Synthesis of 4-[[2-(trimethylsilyl)ethoxy]methyl]-14-oxa-2,4,10-triazatricyclo[7.5.0.0^[3,7]]tetradeca-1(9),2,5,7-tetraene: Into a 1000-mL round-bottom flask, was placed 3-[(5-bromo-1-[[2-(trimethylsilyl)ethoxy]methyl]pyrrolo[2,3-b]pyridin-6-yl)oxy]propan-1-amine (37.50 g, 93.658 mmol, 1.00 equiv), toluene (500.00 mL), t-BuONa (27.00 g, 280.947 mmol, 3.00 equiv), BrettPhos Pd G3 (4.25 g, 4.688 mmol, 0.05 equiv). The resulting solution was stirred for 4 h at 110 degrees C. The solids were filtered out. The resulting mixture was concentrated. The residue was applied onto a silica gel column with ethyl acetate/petroleum ether (0:1-1:1). This resulted in 16.1 g (53.81%) of 4-[[2-(trimethylsilyl)ethoxy]methyl]-14-oxa-2,4,10-triazatricyclo[7.5.0.0^[3,7]]tetradeca-1(9),2,5,7-tetraene as a brown solid. LC-MS: (ES, m/z): M+1=320.

Synthesis of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate: Into a 500-mL round-bottom flask, was placed methyl 2-bromo-4-(4-[[2-(4-chlorophenyl)-4,4-dimethylcyclohex-1-en-1-yl]methyl]piperazin-1-yl)benzoate (46.95 g, 88.268 mmol, 2 equiv), 4-[[2-(trimethylsilyl)ethoxy]methyl]-14-oxa-2,4,10-triazatricyclo[7.5.0.0^[3,7]]tetradeca-1(9),2,5,7-tetraene (14.10 g, 44.134 mmol, 1.00 equiv), $Cs_2CO_3$ (43.14 g, 132.403 mmol, 3 equiv), toluene (300 mL), xantphos Pd (2136.10 mg, 2.207 mmol, 0.05 equiv). The resulting solution was stirred for 6 h at 100 degrees C. The resulting mixture was concentrated. The residue was applied onto a silica gel column with (ethyl acetate/petroleum ether (0:1-1:1). This resulted in 35 g (102.93%) of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate as a brown crude solid. LC-MS: (ES, m/z): M+1=770.

Synthesis of 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid: Into a 1000-mL round-bottom flask, was placed methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate (35.00 g, 34.523 mmol, 1.00 equiv, 76%), Dioxane (200 mL), MeOH (200 mL), $H_2O$ (100 mL), NaOH (11.05 g, 276.270 mmol, 8.00 equiv). The resulting solution was stirred for overnight at 70 degrees C. The resulting mixture was concentrated. The reaction was then quenched by the addition of 100 mL of water. The pH value of the solution was adjusted to 6 with AcOH. The solids were collected by filtration. This resulted in 31 g (118.70%) of 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid as a white crude solid. LC-MS (ES, m/z): M+1=756.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide: Into a 250-mL Into a 2000-mL round-bottom flask, was placed 4-[[(2S)-1,4-dioxan-2-ylmethyl]amino]-3-nitrobenzenesulfonamide (13.00 g, 40.980 mmol, 1 equiv), 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid (31.00 g, 40.980 mmol, 1.00 equiv), DCM (1200.00 mL), DMAP (20.03 g, 163.921 mmol, 4 equiv), EDCI (15.71 g, 81.961 mmol, 2 equiv). The resulting solution was stirred for 5 days at 30 degrees C. The reaction was then quenched by the addition of 500 mL of water. The resulting solution was extracted with 2×300 mL of dichloromethane The resulting mixture was washed with 3×500 ml of Brine. The mixture was dried over anhydrous sodium sulfate and concentrated. The residue was applied onto a silica gel column with ethyl acetate/petroleum ether (0:1-1:1). This resulted in 17 g (39.29%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide as a yellow solid. LC-MS: (ES, m/z): M+1=1056.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide and N-(4-[[(2S)-1,4-dioxan-2-ylmethyl]amino]-3-nitrobenzenesulfonyl)-4-(4-[[2-(4-hydroxyphenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzamide: Into a 250-mL round-bottom flask, was placed 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide (17.00 g, 16.102 mmol, 1.00 equiv), THF (100 mL), TBAF (84.20 g, 322.035 mmol, 20.00 equiv), ethane-1,2-diamine (19.35 g, 322.043 mmol, 20 equiv). The resulting solution was stirred for 3 days at 70 degrees C. The reaction was then quenched by the addition of 200 mL of water. The resulting solution was extracted with 3×100 mL of ethyl acetate. The resulting mixture was washed with 3×100 ml of Brine. The mixture was dried over anhydrous sodium sulfate and concentrated. The residue was applied onto a silica gel column with ethyl acetate/petroleum ether (0:1-1:0). This resulted in 200 mg (1.37%) of N-(4-[[(2S)-1,4-dioxan-2-ylmethyl]amino]-3-nitrobenzenesulfonyl)-4-(4-[[4-hydroxyphenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzamide as a white solid. $^1$H NMR-200 (300 MHz, DMSO-$d_6$) δ 12.29 (s, 1H), 12.05 (s, 1H), 11.34 (s, 1H), 8.00 (s, 1H), 7.52-7.42 (m, 3H), 7.37 (d, J=8.4 Hz, 2H), 7.25 (d, J=3.0 Hz, 1H), 7.07 (d, J=8.3 Hz, 2H), 6.96 (s, 1H), 6.72-6.70 (m, 2H), 6.15 (d, J=3.4, 1.9 Hz, 1H), 4.98-4.94 (m, 1H), 4.18 (s, 2H), 3.96-3.94 (m, 2H), 3.91-3.76 (m, 3H), 3.69-3.65 (m, 1H), 3.47 (s, 2H), 3.21 (s, 4H), 2.77-2.73 (m, 2H), 2.24-2.19 (m, 6H), 1.98 (s, 4H), 1.43-1.39 (m, 2H), 0.95 (s, 6H).

Example 39

Preparation of 2-[7-amino-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)benzamide Synthesis of 5-bromo-6-fluoropyridin-2-amine: Into a 1000-mL round-bottom flask, was placed 6-fluoropyridin-2-amine (30 g, 267.601 mmol, 1 equiv), CH₃CN (500 mL), NBS (52 g, 292.161 mmol, 1.09 equiv). The resulting solution was stirred for 6 hr at 25 degrees C. The resulting solution was diluted with 1000 mL of water. The resulting solution was extracted with 3×500 mL of ethyl acetate and the organic layers combined. The resulting mixture was washed with 2×2000 ml of brine. The mixture was dried over anhydrous sodium sulfate and concentrated under vacuum. The crude product was re-crystallized from PE:EA in the ratio of 5:1. The solids were collected by filtration. This resulted in 33 g (64.56%) of 5-bromo-6-fluoropyridin-2-amine as a white solid. ¹H NMR (300 MHz, Chloroform-d, ppm) δ 7.61 (t, J=8.6 Hz, 1H), 6.28 (dd, J=8.3, 1.4 Hz, 1H), 4.45 (s, 2H).

Synthesis of tert-butyl N-(5-bromo-6-fluoropyridin-2-yl)carbamate: Into a 500-mL 3-necked round-bottom flask purged and maintained with an inert atmosphere of nitrogen, was placed 5-bromo-6-fluoropyridin-2-amine (10.00 g, 52.355 mmol, 1.00 equiv), THF (100.00 mL). This was followed by the addition of NaHMDS (42.00 mL, 84.000 mmol, 1.60 equiv) dropwise with stirring at 0 degrees C. The resulting solution was stirred for 0.5 h at 0 degrees C. To this was added Boc₂O (11.47 g, 52.555 mmol, 1.00 equiv) at 0 degrees C. The resulting solution was stirred overnight at 25 degrees C. The reaction was then quenched by the addition of aqueous NH₄Cl. The resulting solution was extracted with 3×300 mL of ethyl acetate and the organic layers combined. The resulting mixture was washed with 2×1000 ml of brine. The mixture was dried over anhydrous sodium sulfate. The solids were filtered out. The resulting mixture was concentrated under vacuum. The residue was applied onto a silica gel column with ethyl acetate/petroleum ether (1:3). This resulted in 8.7 g (57.08%) of tert-butyl N-(5-bromo-6-fluoropyridin-2-yl)carbamate as a white solid. ¹H NMR (300 MHz, DMSO-d₆, ppm) δ 10.23 (s, 1H), 8.17-8.11 (t, J=8.7 Hz, 1H), 7.67 (dd, J=8.6, 1.5 Hz, 1H), 1.47 (s, 9H).

Synthesis of tert-butyl N-[5-bromo-6-[3-(1,3-dioxoisoindol-2-yl)propoxy]pyridin-2-yl]carbamate: Into a 250-mL round-bottom flask purged and maintained with an inert atmosphere of nitrogen, was placed 2-(3-hydroxypropyl)isoindole-1,3-dione (6.53 g, 31.821 mmol, 1.10 equiv), THF (100.00 mL). This was followed by the addition of NaH (1.74 g, 43.504 mmol, 1.51 equiv, 60%), in portions at 0 degrees C. The resulting solution was stirred for 0.5 h at 0 degrees C. To this was added tert-butyl N-(5-bromo-6-fluoropyridin-2-yl)carbamate (8.40 g, 28.854 mmol, 1.00 equiv) at 0 degrees C. The resulting solution was stirred overnight at 70 degrees C. in an oil bath. The reaction mixture was cooled to room temperature. The reaction was then quenched by the addition of aqueous NH₄Cl. The resulting solution was extracted with 3×200 mL of ethyl acetate and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (1:4). This resulted in 10.9 g (79.31%) of tert-butyl N-[5-bromo-6-[3-(1,3-dioxoisoindol-2-yl)propoxy]pyridin-2-yl]carbamate as a white solid. ¹H-NMR (300 MHz, DMSO-d₆, ppm) δ 9.72 (s, 1H), 7.94-7.71 (m, 5H), 7.27 (d, J=8.4 Hz, 1H), 4.33 (t, J=5.9 Hz, 2H), 3.76 (t, J=6.7 Hz, 2H), 2.07 (p, J=6.4 Hz, 2H), 1.46 (s, 9H).

Synthesis of tert-butyl N-[6-(3-aminopropoxy)-5-bromopyridin-2-yl]carbamate: Into a 250-mL round-bottom flask, was placed tert-butyl N-[5-bromo-6-[3-(1,3-dioxoisoindol-2-yl)propoxy]pyridin-2-yl]carbamate (5.00 g, 10.497 mmol, 1.00 equiv), EtOH (50.00 mL), N₂H₄·H₂O (6.60 g, 105.600 mmol, 10.06 equiv, 80%). The resulting solution was stirred overnight at 50 degrees C. in an oil bath. The reaction mixture was cooled to room temperature. The resulting solution was diluted with 500 mL of water. The resulting solution was extracted with 3×200 mL of ethyl acetate and the organic layers combined. The resulting mixture was washed with 1×1000 ml of brine. The mixture was dried over anhydrous sodium sulfate and concentrated under vacuum. The residue was applied onto a silica gel column with dichloromethane/methanol (10:1). This resulted in 3.4 g (93.55%) of tert-butyl N-[6-(3-aminopropoxy)-5-bromopyridin-2-yl]carbamate as a yellow solid. ¹H NMR (300 MHz, DMSO-d₆, ppm) δ 7.87 (d, J=8.4 Hz, 1H), 7.28 (d, J=8.4 Hz, 1H), 4.35 (t, J=6.4 Hz, 2H), 2.67 (t, J=6.7 Hz, 2H), 1.77 (p, J=6.5 Hz, 2H), 1.47 (s, 9H).

Synthesis of tert-butyl N-[1H,2H,3H,4H-pyrido[2,3-b][1,4]oxazepin-7-yl]carbamate: Into a 100-mL round-bottom flask purged and maintained with an inert atmosphere of nitrogen, was placed tert-butyl N-[6-(3-aminopropoxy)-5-bromopyridin-2-yl]carbamate (3.40 g, 9.820 mmol, 1.00 equiv), toluene (40.00 mL), t-BuONa (2.84 g, 29.552 mmol, 3.01 equiv), Xphos Pd G3 (702.00 mg, 0.829 mmol, 0.08 equiv). The resulting solution was stirred for 2 hr at 90 degrees C. in an oil bath. The reaction mixture was cooled to room temperature. The resulting mixture was concentrated under vacuum. The residue was applied onto a silica gel column with ethyl acetate/petroleum ether (1:1). This resulted in 1.11 g (42.60%) of tert-butyl N-[1H,2H,3H,4H-pyrido[2,3-b][1,4]oxazepin-7-yl]carbamate as a yellow solid. ¹H-NMR (300 MHz, DMSO-d₆, ppm) δ 9.19 (s, 1H), 7.24 (d, J=8.3 Hz, 1H), 7.16 (d, J=8.3 Hz, 1H), 5.26 (t, J=3.2 Hz, 1H), 4.13-4.02 (m, 2H), 3.06 (td, J=5.8, 3.1 Hz, 2H), 1.87 (p, J=5.6 Hz, 2H), 1.44 (s, 9H).

Synthesis of methyl 2-[7-[(tert-butoxycarbonyl)amino]-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)benzoate: Into a 40-mL vial purged and maintained with an inert atmosphere of nitrogen, was placed methyl 2-bromo-4-(4-[[2-(4-chlorophenyl)-4,4-dimethylcyclohex-1-en-1-yl]methyl]piperazin-1-yl)benzoate (956.33 mg, 1.798 mmol, 1.80 equiv), toluene (10.00 mL), tert-butyl N-[1H,2H,3H,4H-pyrido[2,3-b][1,4]oxazepin-7-yl]carbamate (265.00 mg, 0.999 mmol, 1.00 equiv), Pd₂(dba)₃·CHCl₃ (206.78 mg, 0.200 mmol, 0.20 equiv), Xantphos (231.17 mg, 0.400 mmol, 0.40 equiv), Cs₂CO₃ (976.31 mg, 2.996 mmol, 3.00 equiv). The resulting solution was stirred for 2 hr at 100 degrees C. in an oil bath. The reaction mixture was cooled to room temperature. The resulting solution was diluted with 200 mL of water. The resulting solution was extracted with 3×50 mL of ethyl acetate and the organic layers combined. The resulting mixture was washed with 1×300 ml of brine. The mixture was dried over anhydrous sodium sulfate and concentrated under vacuum. The residue was applied onto a silica gel column with ethyl acetate/petroleum ether (1:2). This resulted in 430 mg (60.10%) of methyl 2-[7-[(tert-butoxycarbonyl)amino]-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)benzoate as a light yellow solid. LC-MS (ES, m/z): M+1=716.

Synthesis of 2-[7-[(tert-butoxycarbonyl)amino]-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)benzoic acid: Into a 40-mL vial, was placed methyl 2-[7-[(tert-butoxycarbonyl)amino]-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)benzoate (300.00 mg, 0.419 mmol, 1.00 equiv), MeOH (5.00 mL), dioxane (5.00 mL), NaOH (4M, 1.00 mL). The resulting solution was stirred for 4 hr at 70 degrees C. in an oil bath. The reaction mixture was cooled to room temperature. The resulting mixture was concentrated under vacuum. The pH value of the solution was adjusted to 6-7 with HCl (2 mol/L). The resulting solution was extracted with 3×50 mL of ethyl acetate and the organic layers combined. The resulting mixture was washed with 1×300 ml of brine. The mixture was dried over anhydrous sodium sulfate and concentrated under vacuum. The residue was applied onto a silica gel column with ethyl acetate/petroleum ether (2:1). This resulted in 190 mg (64.60%) of 2-[7-[(tert-butoxycarbonyl)amino]-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)benzoic acid as yellow oil. LC-MS (ES, m/z): M+1=702.

Synthesis of tert-butyl N-[1-[5-(4-[[2-(4-chlorophenyl)-4,4-dimethylcyclohex-1-en-1-yl]methyl]piperazin-1-yl)-2-[(4-[[(2S)-1,4-dioxan-2-ylmethyl]amino]-3-nitrobenzenesulfonyl)carbamoyl]phenyl]-2H,3H,4H-pyrido[2,3-b][1,4]oxazepin-7-yl]carbamate: Into a 40-mL vial, was placed 2-[7-[(tert-butoxycarbonyl)amino]-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)benzoic acid (180.00 mg, 0.256 mmol, 1.00 equiv), DCM (5.00 mL), 4-[[(2S)-1,4-dioxan-2-ylmethyl]amino]-3-nitrobenzenesulfonamide (81.40 mg, 0.257 mmol, 1.00 equiv), EDCI (99.00 mg, 0.516 mmol, 2.01 equiv), DMAP (125.00 mg, 1.023 mmol, 3.99 equiv). The resulting solution was stirred overnight at 30 degrees C. in an oil bath. The resulting mixture was concentrated under vacuum. The residue was applied onto a silica gel column with dichloromethane/ethyl acetate (included 5% $CH_3OH$) (4:1). This resulted in 120 mg (46.75%) of tert-butyl N-[1-[5-(4-[[2-(4-chlorophenyl)-4,4-dimethylcyclohex-1-en-1-yl]methyl]piperazin-1-yl)-2-[(4-[[(2S)-1,4-dioxan-2-ylmethyl]amino]-3-nitrobenzenesulfonyl)carbamoyl]phenyl]-2H,3H,4H-pyrido[2,3-b][1,4]oxazepin-7-yl]carbamate as a yellow solid. LC-MS (ES, m/z): M+1=1001.

Synthesis of 2-[7-amino-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)benzamide: Into a 8-mL vial, was placed tert-butyl N-[1-[5-(4-[[2-(4-chlorophenyl)-4,4-dimethylcyclohex-1-en-1-yl]methyl]piperazin-1-yl)-2-[(4-[[(2S)-1,4-dioxan-2-ylmethyl]amino]-3-nitrobenzenesulfonyl)carbamoyl]phenyl]-2H,3H,4H-pyrido[2,3-b][1,4]oxazepin-7-yl]carbamate (120.00 mg, 0.120 mmol, 1.00 equiv), HCl (gas) in 1,4-dioxane (3.00 mL). The resulting solution was stirred for 4 hr at 25 degrees C. The resulting mixture was concentrated under vacuum. The pH value of the solution was adjusted to 7 with $NH_3 \cdot H_2O$ (28%). The crude product was purified by Prep-HPLC with the following conditions (Prep-HPLC-006): Column, X Bridge Shield RP18 OBD Column, 5 um, 19*150 mm; mobile phase, Water (0.05% $NH_3 \cdot H_2O$) and $CH_3CN$ (40% Phase B up to 70% in 7 min); Detector, UV 254/220 nm. This resulted in 4.1 mg (3.80%) of 2-[7-amino-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)benzamide as a yellow solid. LC-MS (ES, m/z): M+1=901, $^1$H-NMR (300 MHz, DMSO-$d_6$, ppm) δ 11.85 (s, 1H), 8.73-8.47 (m, 2H), 7.81 (dd, J=9.2, 2.3 Hz, 1H), 7.46-7.30 (m, 3H), 7.17 (d, J=9.3 Hz, 1H), 7.08 (d, J=8.4 Hz, 2H), 6.69-6.42 (m, 3H), 5.91 (d, J=8.4 Hz, 1H), 5.66 (s, 2H), 4.10 (s, 2H), 3.88-3.73 (m, 3H), 3.69-3.60 (m, 2H), 3.59-3.33 (m, 6H), 3.15 (s, 4H), 2.75 (d, J=13.5 Hz, 2H), 2.22 (d, J=16.2 Hz, 6H), 1.99 (s, 2H), 1.88 (s, 2H), 1.42 (t, J=6.4 Hz, 2H), 0.95 (s, 6H).

Example 40

Preparation of 4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]-2-[13-(pyridin-2-yl)-14-oxa-2,4,10-triazatricyclo[7.5.0.0^[3,7]]tetradeca-1(9),2,5,7-tetraen-10-yl]benzamide hydrochloride Synthesis of 3-hydroxy-3-(pyridin-2-yl)propanenitrile: Into a 100-mL round-bottom flask, was placed 3-oxo-3-(pyridin-2-yl)propanenitrile (4.00 g, 27.369 mmol, 1.00 equiv), MeOH (40.00 mL). This was followed by the addition of $NaBH_4$ (2.07 g, 54.739 mmol, 2.00 equiv), in portions at 0 degrees C. The resulting solution was stirred for 3 hr at room temperature. The reaction was cooled to 0 degrees C. and quenched by the addition of 5 mL of water. The resulting mixture was concentrated. The residue was applied onto a silica gel column and eluted with ethyl acetate/petroleum ether (1:3). This resulted in 2.3 g (56.72%) of 3-hydroxy-3-(pyridin-2-yl)propanenitrile as a white solid. LC-MS-1: (ES, m/z): 149.1 [M+H]$^+$.

Synthesis of 3-amino-1-(pyridin-2-yl)propan-1-ol: Into a 100-mL round-bottom flask, was placed 3-hydroxy-3-(pyridin-2-yl)propanenitrile (2.30 g, 15.523 mmol, 1.00 equiv), THF (30.00 mL). This was followed by the addition of $LiAlH_4$ (1.18 g, 31.046 mmol, 2.00 equiv), in portions at 0 degrees C. The resulting solution was stirred for 2 hr at 0 degrees C. in a water/ice bath. The reaction was then quenched by the addition of 3 mL of water. The resulting mixture was concentrated. This resulted in 2.1 g (crude) of 3-amino-1-(pyridin-2-yl)propan-1-ol as a brown solid. LC-MS-2: (ES, m/z): 148.2 [M+H]$^+$.

Synthesis of tert-butyl N-[3-hydroxy-3-(pyridin-2-yl)propyl]carbamate: Into a 100-mL round-bottom flask, was placed 3-amino-1-(pyridin-2-yl)propan-1-ol (2.00 g, crude), DCM (30 mL), $Boc_2O$ (5.74 g, 26.282 mmol, 2.00 equiv), TEA (2.66 g, 26.287 mmol, 2.00 equiv). The resulting solution was stirred for 14 hr at room temperature. The resulting mixture was concentrated. The residue was applied onto a silica gel column and eluted with ethyl acetate/petroleum ether (1:2). This resulted in 700 mg (21.11%) of tert-butyl N-[3-hydroxy-3-(pyridin-2-yl)propyl]carbamate as an off-white solid. LC-MS-2: (ES, m/z): 253.1 [M+1-1]$^+$.

Synthesis of tert-butyl N-[3-[(5-bromo-1-[[2-(trimethylsilyl)ethoxy]methyl]pyrrolo[2,3-b]pyridin-6-yl)oxy]-3-(pyridin-2-yl)propyl]carbamate as brown oil: Into a 50-mL round-bottom flask, was placed tert-butyl N-[3-hydroxy-3-(pyridin-2-yl)propyl]carbamate (700.00 mg, 2.774 mmol, 1.00 equiv), dioxane (15.00 mL), NaH (222.00 mg, 9.251 mmol, 3.33 equiv), 5-bromo-6-fluoro-1-[[2-(trimethylsilyl)ethoxy]methyl]pyrrolo[2,3-b]pyridine (957.94 mg, 2.774 mmol, 1.00 equiv). The resulting solution was stirred for 3 hr at 70 degrees C. The reaction was cooled to room temperature then quenched by the addition of 2 mL of water. The resulting mixture was concentrated. The residue was applied onto a silica gel column and eluted with ethyl acetate/petroleum ether (1:3). This resulted in 600 mg (37.44%) of tert-butyl N-[3-[(5-bromo-1-[[2-(trimethylsilyl) ethoxy]methyl]pyrrolo[2,3-b]pyridin-6-yl)oxy]-3-(pyridin-2-yl)propyl]carbamate as brown oil. LC-MS-4 (ES, m/z): 577.2 [M+H]$^+$.

Synthesis of 3-[(5-bromo-1-[[2-(trimethylsilyl)ethoxy] methyl]pyrrolo[2,3-b]pyridin-6-yl)oxy]-3-(pyridin-2-yl) propan-1-amine: Into a 50-mL round-bottom flask, was placed tert-butyl N-[3-[(5-bromo-1-[[2-(trimethylsilyl) ethoxy]methyl]pyrrolo[2,3-b]pyridin-6-yl)oxy]-3-(pyridin-2-yl)propyl]carbamate (600.00 mg, 1.039 mmol, 1.00 equiv), CH$_3$CN (5.00 mL), ZnBr$_2$ (2.34 g, 10.388 mmol, 10.00 equiv). The resulting solution was stirred for 14 hr at 80 degrees C. in an oil bath. The resulting mixture was concentrated. The residue was applied onto a silica gel column and eluted with ethyl acetate/petroleum ether (1:2). This resulted in 350 mg (70.56%) of 3-[(5-bromo-[[2-(trimethylsilyl)ethoxy]methyl]pyrrolo[2,3-b]pyridin-6-yl) oxy]-3-(pyridin-2-yl)propan-1-amine as yellow oil. LC-MS-4: (ES, m/z): 477.2 [M+H]$^+$.

Synthesis of 13-(pyridin-2-yl)-4-[[2-(trimethylsilyl) ethoxy]methyl]-14-oxa-2,4,10-triazatricyclo[7.5.0.0^[3,7]] tetradeca-1(9),2,5,7-tetraene: Into a 50-mL round-bottom flask purged and maintained with an inert atmosphere of nitrogen, was placed 3-[(5-bromo-1-[[2-(trimethylsilyl) ethoxy]methyl]pyrrolo[2,3-b]pyridin-6-yl)oxy]-3-(pyridin-2-yl)propan-1-amine (300.00 mg, 0.628 mmol, 1.00 equiv), toluene (5.00 mL, 0.054 mmol, 0.09 equiv), BrettPhos Pd G3 (56.96 mg, 0.063 mmol, 0.10 equiv), t-BuONa (181.15 mg, 1.885 mmol, 3.00 equiv). The resulting solution was stirred for 6 hr at 80 degrees C. in an oil bath. The resulting mixture was concentrated. The residue was applied onto a silica gel column and eluted with ethyl acetate/petroleum ether (1:3). This resulted in 150 mg (60.20%) of 13-(pyridin-2-yl)-4-[[2-(trimethylsilyl)ethoxy]methyl]-14-oxa-2,4,10-triazatricyclo[7.5.0.0^[3,7]]tetradeca-1(9),2,5,7-tetraene as a brown solid. LC-MS-6: (ES, m/z): 397.2 [M+H]$^+$.

Synthesis of methyl 4-(4-[[2-(4-chlorophenyl)-4,4-dimethylcyclohex-1-en-1-yl]methyl]piperazin-1-yl)-2-[13-(pyridin-2-yl)-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoate as light yellow oil: Into a 8-mL vial purged and maintained with an inert atmosphere of nitrogen, was placed 13-(pyridin-2-yl)-4-[[2-(trimethylsilyl)ethoxy] methyl]-14-oxa-2,4,10-triazatricyclo[7.5.0.0^[3,7]]tetradeca-1(9),2,5,7-tetraene (80.00 mg, 0.202 mmol, 1.00 equiv), toluene (3.00 mL, 0.033 mmol, 0.16 equiv), methyl 2-bromo-4-(4-[[2-(4-chlorophenyl)-4,4-dimethylcyclohex-1-en-1-yl]methyl]piperazin-1-yl)benzoate (128.77 mg, 0.242 mmol, 1.20 equiv), Cs$_2$CO$_3$ (197.18 mg, 0.605 mmol, 3.00 equiv), xanphos Pd 2G (17.89 mg, 0.020 mmol, 0.10 equiv). The resulting solution was stirred for 3 hr at 110 degrees C. in an oil bath. The resulting mixture was concentrated. The residue was applied onto a silica gel column and eluted with ethyl acetate/petroleum ether (1:1). This resulted in 75 mg (43.86%) of methyl 4-(4-[[2-(4-chlorophenyl)-4,4-dimethylcyclohex-1-en-1-yl]methyl]piperazin-1-yl)-2-[13-(pyridin-2-yl)-4-[[2-(trimethylsilyl)ethoxy] methyl]-14-oxa-2,4,10-triazatricyclo[7.5.0.0^[3,7]] tetradeca-1(9),2,5,7-tetraen-10-yl]benzoate as light yellow oil. LC-MS-7 (ES, m/z): 847.5 [M+H]$^+$.

Synthesis of 4-(4-[[2-(4-chlorophenyl)-4,4-dimethylcyclohex-1-en-1-yl]methyl]piperazin-1-yl)-2-[13-(pyridin-2-yl)-4-[[2-(trimethylsilyl)ethoxy]methyl]-14-oxa-2,4,10-triazatricyclo[7.5.0.0^[3,7]]tetradeca-1(9),2,5,7-tetraen-10-yl] benzoic acid: Into a 8-mL round-bottom flask, was placed methyl 4-(4-[[2-(4-chlorophenyl)-4,4-dimethylcyclohex-1-en-1-yl]methyl]piperazin-1-yl)-2-[13-(pyridin-2-yl)-4-[[2-(trimethylsilyl)ethoxy]methyl]-14-oxa-2,4,10-triazatricyclo [7.5.0.0^[3,7]]tetradeca-1(9),2,5,7-tetraen-10-yl]benzoate (80.00 mg, 0.094 mmol, 1.00 equiv), MeOH (0.50 mL), Dioxane (0.50 mL), H$_2$O (0.25 mL, 0.014 mmol, 0.15 equiv), NaOH (15.10 mg, 0.378 mmol, 4.00 equiv). The resulting solution was stirred for 14 hr at 70 degrees C. in an oil bath. The resulting mixture was concentrated. The resulting solution was diluted with 2 mL of H$_2$O. The pH value of the solution was adjusted to 6 with AcOH. The resulting solution was extracted with 3×2 mL of dichloromethane concentrated. The residue was applied onto a silica gel column and eluted with dichloromethane/methanol (10:1). This resulted in 60 mg (76.26%) of 4-(4-[[2-(4-chlorophenyl)-4,4-dimethylcyclohex-1-en-1-yl]methyl]piperazin-1-yl)-2-[13-(pyridin-2-yl)-4-[[2-(trimethylsilyl)ethoxy] methyl]-14-oxa-2,4,10-triazatricyclo[7.5.0.0^[3,7]] tetradeca-1(9),2,5,7-tetraen-10-yl]benzoic acid as a white solid. LC-MS-8 (ES, m/z): 833.4 [M+H]$^+$.

Synthesis of 4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]-2-[13-(pyridin-2-yl)-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzamide: Into a 8-mL vial, was placed 4-(4-[[2-(4-chlorophenyl)-4,4-dimethylcyclohex-1-en-1-yl]methyl] piperazin-1-yl)-2-[13-(pyridin-2-yl)-4-[[2-(trimethylsilyl) ethoxy]ethyl]-14-oxa-2,4,10-triazatricyclo[7.5.0.0^[3,7]] tetradeca-1(9),2,5,7-tetraen-10-yl]benzoic acid (20.00 mg, 0.024 mmol, 1.00 equiv), 3-nitro-4-[(oxan-4-ylmethyl) amino]benzenesulfonamide (7.57 mg, 0.024 mmol, 1.00 equiv), DCM (1.00 mL), EDCI (9.20 mg, 0.048 mmol, 2.00 equiv), DMAP (5.86 mg, 0.048 mmol, 2.00 equiv). The resulting solution was stirred for 14 hr at room temperature. The resulting mixture was concentrated. The residue was purified by Prep-TLC with dichloromethane/methanol (10:1). This resulted in 17 mg (62.65%) of 4-(4-[[2-(4-chlorophenyl)-4,4-dimethylcyclohex-1-en-1-yl]methyl]piperazin-1-yl)-N-[3-nitro-4-[(oxan-4-ylmethyl)amino] benzenesulfonyl]-2-[13-(pyridin-2-yl)-4-[[2-(trimethylsilyl) ethoxy]methyl]-14-oxa-2,4,10-triazatricyclo[7.5.0.0^[3,7]] tetradeca-1(9),2,5,7-tetraen-10-yl]benzamide as a yellow solid. LC-MS-8 (ES, m/z): 1130.7 [M+H]$^+$.

Synthesis of 4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]-2-[13-(pyridin-2-yl)-14-oxa-2,4,10-triazatricyclo[7.5.0.0^[3,7]]tetradeca-1 (9),2,5,7-tetraen-10-yl]benzamide hydrochloride: Into a 8-mL round-bottom flask, was placed 4-(4-[[2-(4-chlorophenyl)-4,4-dimethylcyclohex-1-en-1-yl]ethyl]piperazin-1-yl)-N-[3-nitro-4-[(oxan-4-ylmethyl)amino]benzenesulfonyl]-2-[13-(pyridin-2-yl)-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzamide (15.00 mg), TBAF in THF (2M, 1.00 mL), ethane-1,2-diamine (0.25 mL). The resulting solution was stirred for 14 hr at 70 degrees C. in an oil bath. The resulting mixture was concentrated. The residue was purified by Prep-TLC with dichloromethane/methanol (10:1). The crude product was purified by Prep-HPLC with the following conditions: Column, XBridge Prep C18 OBD 19*150 mm 5 um; mobile phase, A: 0.1% HCl in water; B:

ACN; Gradient: 6-95% B in 7.9 min; Flow rate: 20 ml/min; Detector, 220 nm. This resulted in 3.2 mg (23.8%) of 4-(4-[[2-(4-chlorophenyl)-4,4-dimethylcyclohex-1-en-1-yl]methyl]piperazin-1-yl)-N-[3-nitro-4-[(oxan-4-ylmethyl)amino]benzenesulfonyl]-2-[13-(pyridin-2-yl)-14-oxa-2,4,10-triazatricyclo[7.5.0.0^[3,7]]tetradeca-1(9),2,5,7-tetraen-10-yl]benzamide hydrochloride as a yellow solid. LC-MS-0 (ES, m/z): 1000.5 [M−HCl+H]$^+$. $^1$H NMR-0 (300 MHz, CDCl$_3$, ppm): δ 8.81 (s, 1H), 8.62-8.57 (m, 1H), 8.42-8.25 (m, 1H), 8.01-8.75 (m, 3H), 7.45-7.34 (m, 3H), 7.18-7.10 (m, 1H), 7.05-6.88 (m, 3H), 6.83-6.55 (m, 3H), 6.27-6.17 (m, 1H), 5.19 (s, 1H), 4.13-3.90 (m, 3H), 3.82-3.33 (m, 10H), 3.24-3.02 (m, 2H), 2.70-2.48 (m, 2H), 2.43-2.31 (m, 2H), 2.17-2.08 (m, 2H), 1.96-1.8 (m, 1H), 1.70-1.63 (m, 2H), 1.58-1.52 (m, 2H), 1.46-1.20 (m, 6H), 1.01 (d, J=2.1 Hz, 6H).

Example 41

Preparation of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzene sulfonyl)-2-[13-oxa-2,4,10-triazatricyclo [7.5.0.0^[3,7]]tetradeca-1(9),2,5,7-tetraen-10-yl] benzamide hydrochloride Synthesis of methyl 6-amino-3-bromo-5-iodopyridine-2-carboxylate: Into a 500-mL round-bottom flask, was placed methyl 6-amino-3-bromopyridine-2-carboxylate (20.00 g, 86.562 mmol, 1.00 equiv), HOAc (200.00 mL), TFA (10.00 mL). This was followed by the addition of NIS (29.35 g, 130.453 mmol, 1.51 equiv), in portions at 25 degrees C. The resulting solution was stirred overnight at 25 degrees C. The resulting solution was diluted with 2000 mL of water. The resulting solution was extracted with 3×500 mL of ethyl acetate and the organic layers combined. The resulting mixture was washed with 2×2000 mL of brine. The mixture was dried over anhydrous sodium sulfate and concentrated under vacuum. The crude product was re-crystallized from PE:EA in the ratio of 1:1. The solids were collected by filtration. This resulted in 25.8 g (83.50%) of methyl 6-amino-3-bromo-5-iodopyridine-2-carboxylate as a red solid. $^1$H-NMR (300 MHz, Chloroform-d, ppm) δ 8.14 (s, 1H), 5.21 (br, 2H), 3.99 (s, 3H).

Synthesis of methyl 6-amino-3-bromo-5-(2-ethoxyethenyl)pyridine-2-carboxylate: Into a 500-mL round-bottom flask purged and maintained with an inert atmosphere of nitrogen, was placed methyl 6-amino-3-bromo-5-iodopyridine-2-carboxylate (24.00 g, 67.237 mmol, 1.00 equiv), 2-(2-ethoxyethenyl)-4,4,5,5-tetramethyl-1,3,2-dioxaborolane (26.50 g, 133.791 mmol, 1.99 equiv), i-PrOH (300 mL), K$_3$PO$_4$ (42.60 g, 200.691 mmol, 2.98 equiv), Pd(OAc)$_2$ (1.50 g, 6.681 mmol, 0.10 equiv), Ruphos (3.13 g, 6.708 mmol, 0.10 equiv). The resulting solution was stirred overnight at 30 degrees C. in an oil bath. The reaction mixture was cooled to room temperature. The solids were filtered out. The resulting mixture was concentrated. The residue was applied onto a silica gel column with ethyl acetate/petroleum ether (1:1). This resulted in 10.7 g (52.85%) of methyl 6-amino-3-bromo-5-(2-ethoxyethenyl)pyridine-2-carboxylate as brown oil. $^1$H NMR (300 MHz, Chloroform-d, ppm) δ 8.10 (s, 0.5H), 7.57 (s, 0.5H), 6.90 (d, J=12.6 Hz, 0.5H), 6.41 (d, J=7.1 Hz, 0.5H), 3.97 (s, 3H).

Synthesis of methyl 5-bromo-1H-pyrrolo[2,3-b]pyridine-6-carboxylate: Into a 250-mL round-bottom flask, was placed methyl 6-amino-3-bromo-5-(2-ethoxyethenyl)pyridine-2-carboxylate (10.70 g, 35.532 mmol, 1.00 equiv), MeOH (100.00 mL), Conc. HCl (20.00 mL, 12 N). The resulting solution was stirred overnight at 25 degrees C. The resulting mixture was concentrated under vacuum. The pH value of the solution was adjusted to 7 with NaOH (2 mol/L). The solids were collected by filtration. This resulted in 9 g (99.30%) of methyl 5-bromo-1H-pyrrolo[2,3-b]pyridine-6-carboxylate as a brown solid. $^1$H NMR (300 MHz, Chloroform-d, ppm) δ 11.60 (s, 1H), 8.29 (s, 1H), 7.69 (t, J=3.0 Hz, 1H), 6.54 (dd, J=3.4, 1.7 Hz, 1H), 4.10 (s, 3H).

Synthesis of methyl 5-bromo-1-[[2-(trimethylsilyl)ethoxy]methyl]pyrrolo[2,3-b]pyridine-6-carboxylate: Into a 250-mL round-bottom flask purged and maintained with an inert atmosphere of nitrogen, was placed methyl 5-bromo-1H-pyrrolo[2,3-b]pyridine-6-carboxylate (9.00 g, 35.284 mmol, 1.00 equiv), DMF (100.00 mL). This was followed by the addition of NaH (2.83 g, 70.757 mmol, 2.01 equiv, 60%), in portions at 0 degrees C. The resulting solution was stirred for 30 min at 0 degrees C. To this was added SEM-Cl (8.82 g, 52.903 mmol, 1.50 equiv) at 0 degrees C. The resulting solution was stirred for 2 hr at 25 degrees C. The reaction was then quenched by the addition of 500 mL of water. The resulting solution was extracted with 2×200 mL of ethyl acetate and the organic layers combined. The resulting mixture was washed with 1×500 mL of brine. The mixture was dried over anhydrous sodium sulfate and concentrated under vacuum. The residue was applied onto a silica gel column with ethyl acetate/petroleum ether (1:3). This resulted in 8.2 g (60.31%) of methyl 5-bromo-1-[[2-(trimethylsilyl)ethoxy]methyl]pyrrolo[2,3-b]pyridine-6-carboxylate as yellow oil. $^1$H NMR (300 MHz, Chloroform-d, ppm) δ 8.17 (s, 1H), 7.50 (d, J=3.7 Hz, 1H), 6.53 (d, J=3.6 Hz, 1H), 5.68 (s, 2H), 4.02 (s, 3H), 3.60-3.45 (m, 2H), 0.99-0.88 (m, 2H), −0.05 (s, 9H).

Synthesis of (5-bromo-1-[[2-(trimethylsilyl)ethoxy]methyl]pyrrolo[2,3-b]pyridin-6-yl)methanol: Into a 250-mL round-bottom flask, was placed methyl 5-bromo-1-[[2-(trimethylsilyl)ethoxy]methyl]pyrrolo[2,3-b]pyridine-6-carboxylate (5.00 g, 12.976 mmol, 1.00 equiv), THF (50.00 mL). This was followed by the addition of LAH (990.00 mg, 26.084 mmol, 2.01 equiv), in portions at 0 degrees C. The resulting solution was stirred for 2 hr at 25 degrees C. The reaction was then quenched by the addition of Na$_2$SO$_4$.10H$_2$O. The solids were filtered out. The resulting mixture was concentrated under vacuum. The residue was applied onto a silica gel column with ethyl acetate/petroleum ether (1:3). This resulted in 1.7 g (36.67%) of (5-bromo-1-[[2-(trimethylsilyl)ethoxy]methyl]pyrrolo[2,3-b]pyridin-6-yl)methanol as light yellow oil. $^1$H NMR (300 MHz, Chloroform-d, ppm) δ 8.10 (s, 1H), 7.36 (d, J=3.6 Hz, 1H), 6.51 (d, J=3.6 Hz, 1H), 5.68 (s, 2H), 4.85 (s, 2H), 3.63-3.50 (m, 2H), 0.98-0.88 (m, 2H), −0.05 (s, 9H).

Synthesis of ethyl 2-[(5-bromo-1-[[2-(trimethylsilyl)ethoxy]methyl]pyrrolo[2,3-b]pyridin-6-yl)methoxy]acetate: Into a 100-mL round-bottom flask purged and maintained with an inert atmosphere of nitrogen, was placed (5-bromo-1-[[2-(trimethylsilyl)ethoxy]methyl]pyrrolo[2,3-b]pyridin-6-yl)methanol (1.70 g, 4.758 mmol, 1.00 equiv), THF (20.00 mL). This was followed by the addition of NaH (669.00 mg, 16.727 mmol, 3.52 equiv, 60%), in portions at 0 degrees C. The resulting solution was stirred for 30 min at 0 degrees C. To this was added ethyl bromoacetate (2.38 g, 14.251 mmol, 3.00 equiv) at 0 degrees C. The resulting solution was stirred overnight at 70 degrees C. in an oil bath. The reaction mixture was cooled to room temperature. The reaction was then quenched by the addition of 200 mL of aqueous NH$_4$Cl. The resulting solution was extracted with 2×100 mL of ethyl acetate and the organic layers combined. The resulting mixture was washed with 1×500 mL of brine. The mixture was dried over anhydrous sodium sulfate and concentrated under vacuum. The residue was applied onto a silica gel column with ethyl acetate/petroleum ether (1:3). This resulted in 1.7 g (80.58%) of ethyl 2-[(5-bromo-1-[[2-(trimethylsilyl)ethoxy]methyl]pyrrolo[2,3-b]pyridin-6-yl)methoxy]acetate as light yellow oil.

$^1$H NMR (300 MHz, Chloroform-d, ppm) δ 8.10 (s, 1H), 7.39 (d, J=3.6 Hz, 1H), 6.48 (d, J=3.6 Hz, 1H), 5.68 (s, 2H), 4.99 (s, 2H), 4.28 (s, 2H), 4.23 (t, J=7.1 Hz, 2H), 3.58-3.51 (m, 2H), 1.34-1.27 (m, 3H), 0.95-0.88 (m, 2H), −0.05 (s, 9H).

Synthesis of 2-[(5-bromo-1-[[2-(trimethylsilyl)ethoxy]methyl]pyrrolo[2,3-b]pyridin-6-yl)methoxyacetamide: Into a 50-mL pressure tank reactor, was placed ethyl 2-[(5-bromo-1-[[2-(trimethylsilyl)ethoxy]methyl]pyrrolo[2,3-b]pyridin-6-yl)methoxy]acetate (1.70 g, 3.834 mmol, 1.00 equiv), NH$_3$ (g) in MeOH (20.00 mL). The resulting solution was stirred overnight at 60 degrees C. in an oil bath. The reaction mixture was cooled to room temperature. The resulting mixture was concentrated under vacuum. The crude product was re-crystallized from PE:EA in the ratio of 5:1. The solids were collected by filtration. This resulted in 1.2 g (75.53%) of 2-[(5-bromo-1-[[2-(trimethylsilyl)ethoxy]methyl]pyrrolo[2,3-b]pyridin-6-yl)methoxy]acetamide as a white solid. $^1$H NMR (300 MHz, Chloroform-d, ppm) δ 8.13 (s, 1H), 7.40 (d, J=3.6 Hz, 1H), 6.50 (d, J=3.6 Hz, 1H), 5.65 (s, 2H), 4.95 (s, 2H), 4.19 (s, 2H), 3.64-3.46 (m, 2H), 1.03-0.85 (m, 2H), −0.04 (s, 9H).

Synthesis of 4-[[2-(trimethylsilyl)ethoxy]methyl]-13-oxa-2,4,10-triazatricyclo[7.5.0.0^[3,7]]tetradeca-1(9),2,5,7-tetraen-11-one: Into a 100-mL round-bottom flask purged and maintained with an inert atmosphere of nitrogen, was placed 2-[(5-bromo-1-[[2-(trimethylsilyl)ethoxy]methyl]pyrrolo[2,3-b]pyridin-6-yl)methoxy]acetamide (1.20 g, 2.896 mmol, 1.00 equiv), dioxane (20.00 mL), methyl[2-(methylamino)ethyl]amine (256.00 mg, 2.904 mmol, 1.00 equiv), CuI (553.00 mg, 2.904 mmol, 1.00 equiv), K$_2$CO$_3$ (1.20 g, 8.683 mmol, 3.00 equiv). The resulting solution was stirred overnight at 100 degrees C. in an oil bath. The reaction mixture was cooled to room temperature. The resulting mixture was concentrated under vacuum. The residue was applied onto a silica gel column with ethyl acetate/petroleum ether (1:3). This resulted in 527 mg (54.57%) of 4-[[2-(trimethylsilyl)ethoxy]methyl]-13-oxa-2,4,10-triazatricyclo[7.5.0.0^[3,7]]tetradeca-1(9),2,5,7-tetraen-11-one as a white solid. $^1$H NMR (300 MHz, Chloroform-d, ppm) δ 8.65 (br, 1H), 7.55 (s, 1H), 7.38 (d, J=3.6 Hz, 1H), 6.49 (d, J=3.6 Hz, 1H), 5.65 (s, 2H), 5.00 (s, 2H), 4.64 (s, 2H), 3.66-3.45 (m, 2H), 0.98-0.87 (m, 2H), −0.04 (s, 9H).

Synthesis of 4-[[2-(trimethylsilyl)ethoxy]methyl]-13-oxa-2,4,10-triazatricyclo[7.5.0.0^[3,7]]tetradeca-1(9),2,5,7-tetraene: Into a 100-mL round-bottom flask, was placed 4-[[2-(trimethylsilyl)ethoxy]methyl]-13-oxa-2,4,10-triazatricyclo[7.5.0.0^[3,7]]tetradeca-1(9),2,5,7-tetraen-11-one (527.00 mg, 1.580 mmol, 1.00 equiv), THF (10.00 mL), LAH (150.00 mg, 3.952 mmol, 2.50 equiv). The resulting solution was stirred for 3 hr at 25 degrees C. The reaction was then quenched by the addition of Na$_2$SO$_4$.10H$_2$O. The solids were filtered out. The resulting mixture was concentrated under vacuum. The residue was applied onto a silica gel column with ethyl acetate/petroleum ether (1:3). This resulted in 350 mg (69.32%) of 4-[[2-(trimethylsilyl)ethoxy]methyl]-13-oxa-2,4,10-triazatricycloo[7.5.0.0[3,7]]tetradeca-1(9),2,5,7-tetraene as yellow oil. LC-MS (ES, m/z): M+1=320.

Synthesis of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-13-oxa-2,4,10-triazatricyclo[7.5.0.0^[3,7]]tetradeca-1(9),2,5,7-tetraen-10-yl)benzoate: Into a 40-mL vial purged and maintained with an inert atmosphere of nitrogen, was placed methyl 2-bromo-4-(4-[[2-(4-chlorophenyl)-4,4-dimethylcyclohex-1-en-1-yl]methyl]piperazin-1-yl)benzoate (1.16 g, 2.181 mmol, 1.99 equiv), toluene (20.00 mL), 4-[[2-(trimethylsilyl)ethoxy]methyl]-13-oxa-2,4,10-triazatricyclo[7.5.0.0^[3,7]]tetradeca-1(9),2,5,7-tetraene (350.00 mg, 1.096 mmol, 1.00 equiv), Cs$_2$CO$_3$ (1.07 g, 3.284 mmol, 3.00 equiv), Xantphos Pd 2G (146.00 mg, 0.165 mmol, 0.15 equiv). The resulting solution was stirred for 2 days at 110 degrees C. in an oil bath. The reaction mixture was cooled to room temperature. The resulting mixture was concentrated under vacuum. The residue was applied onto a silica gel column with ethyl acetate/petroleum ether (1:1). The crude product was purified by Flash-Prep-HPLC with the following conditions (IntelFlash-1): Column, C18 reversed phase column; mobile phase, water (0.01% TFA) and CH$_3$CN; Gradient: 20% CH$_3$CN increasing to 80% within 15 min; Flow rate: 80 mL/min; Detector, 254/220 nm. This resulted in 150 mg (17.77%) of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-13-oxa-2,4,10-triazatricyclo[7.5.0.0^[3,7]]tetradeca-1(9),2,5,7-tetraen-10-yl)benzoate as yellow oil. LC-MS (ES, m/z): M+1=770.

Synthesis of 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-13-oxa-2,4,10-triazatricyclo[7.5.0.0^[3,7]]tetradeca-1(9),2,5,7-tetraen-10-yl)benzoic acid: Into a 100-mL round-bottom flask, was placed methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-13-oxa-2,4,10-triazatricyclo[7.5.0.0^[3,7]]tetradeca-1(9),2,5,7-tetraen-10-yl)benzoate (150.00 mg, 0.195 mmol, 1.00 equiv), MeOH (5.00 mL), dioxane (5.00 mL), NaOH (1.00 mL, 4.000 mmol, 20.55 equiv). The resulting solution was stirred for 4 hr at 70 degrees C. in an oil bath. The reaction mixture was cooled to room temperature. The resulting mixture was concentrated under vacuum. The pH value of the solution was adjusted to 6-7 with HCl (2 mol/L). The resulting solution was extracted with 3×50 mL of ethyl acetate and the organic layers combined. The resulting mixture was washed with 1×200 mL of brine. The mixture was dried over anhydrous sodium sulfate and concentrated under vacuum. The residue was applied onto a silica gel column with ethyl acetate/petroleum ether (1:1). This resulted in 100 mg (67.90%) of 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-13-oxa-2,4,10-triazatricyclo[7.5.0.0^[3,7]]tetradeca-1(9),2,5,7-tetraen-10-yl)benzoic acid as light yellow oil. LC-MS: (ES, m/z): M+1=756.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-13-oxa-2,4,10-triazatricyclo[7.5.0.0^[3,7]]tetradeca-1(9),2,5,7-tetraen-10-yl)benzamide: Into a 40-mL vial, was placed 4-(4-[[2-(4-chlorophenyl)-4,4-dimethylcyclohex-1-en-1-yl]methyl]piperazin-1-yl)-2-(4-[[2-(trimethylsilyl)ethoxy]ethyl]-13-oxa-2,4,10-triazatricyclo[7.5.0.0^[3,7]]tetradeca-1(9),2,5,7-tetraen-10-yl)benzoic acid (100.00 mg, 0.132 mmol, 1.00 equiv), DCM (5.00 mL), 4-[[(2S)-1,4-dioxan-2-ylmethyl]amino]-3-nitrobenzenesulfonamide (42.00 mg, 0.132 mmol, 1.00 equiv), EDCI (51.00 mg, 0.266 mmol, 2.01 equiv), DMAP (64.00 mg, 0.524 mmol, 3.96 equiv). The resulting solution was stirred overnight at 30 degrees C. in an oil bath. The resulting mixture was concentrated under vacuum. The residue was applied onto a silica gel column with dichloromethane/ethyl acetate (1:1). This resulted in 50 mg (35.83%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-13-oxa-2,4,10-triazatricyclo[7.5.0.0^[3,7]]tetradeca-1(9),2,5,7-tetraen-10-yl)benzamide as a yellow solid.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[13-oxa-2,4,10-triazatricyclo[7.5.0.0^[3,7]]tetradeca-1(9),2,5,7-tetraen-10-yl]benzamide hydrochloride: Into a 40-mL vial, was placed 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-13-oxa-2,4,10-triazatricyclo[7.5.0.0^[3,7]]tetradeca-1(9),2,5,7-tetraen-10-yl)benzamide (50.00 mg, 0.047 mmol, 1.00 equiv), 1.0 M TBAF/THF (5.00 mL), ethylenediamine (100.00 mg, 1.664 mmol, 35.13 equiv). The resulting solution was stirred for 3.5 hr at 70 degrees C. in an oil bath. The reaction mixture was cooled to room temperature. The resulting solution was diluted with 100 mL of $H_2O$. The resulting solution was extracted with 3×30 mL of dichloromethane and the organic layers combined. The resulting mixture was washed with 1×200 mL of brine. The mixture was dried over anhydrous sodium sulfate and concentrated under vacuum. The residue was purified by Prep-TLC with dichloromethane/ethyl acetate (included 10% MeOH) (1:1). The crude product was purified by Prep-HPLC with the following conditions: Column, SunFire Prep C18, 19×150 mm, 5 um; Mobile phase, water (it contains 0.1% FA) and $CH_3CN$; Gradient: 20% up to 85% in 15 min; Flow rate: 15 mL/min; Detector: 254/220 nm. The collected solution was concentrated under vacuum to remove $CH_3CN$ and the resulting solution was dried by lyophilization (added with Conc. HCl (1 drop)). This resulted in 4.5 mg (9.88%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[13-oxa-2,4,10-triazatricyclo[7.5.0.0^[3,7]]tetradeca-1(9),2,5,7-tetraen-10-yl]benzamide hydrochloride as a yellow solid. LC-MS (ES, m/z): M+1=925. $^1H$ NMR (300 MHz, DMSO-$d_6$, ppm) δ 11.80 (s, 1H), 11.22 (s, 1H), 10.71 (d, J=10.0 Hz, 1H), 8.62 (t, J=5.2 Hz, 1H), 8.32 (d, J=2.0 Hz, 1H), 7.55-7.21 (m, 5H), 7.14 (d, J=7.9 Hz, 2H), 6.98-6.58 (m, 4H), 6.13 (s, 1H), 4.76 (s, 2H), 4.03-3.46 (m, 17H), 3.13 (d, J=30.4 Hz, 2H), 2.78 (q, J=11.2, 10.0 Hz, 2H), 2.40 (s, 2H), 2.05 (s, 2H), 1.46 (q, J=6.3 Hz, 2H), 1.23 (s, 2H), 0.97 (s, 6H).

Example 42

Preparation of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[7-(methylamino)-2H,3H,4H-pyrido[2,3-b][1,4]oxazepin-1-yl]benzamide hydrochloride Synthesis of tert-butyl N-(5-bromo-6-fluoropyridin-2-yl)-N-methylcarbamate: Into a 250-mL round-bottom flask purged and maintained with an inert atmosphere of nitrogen, was placed tert-butyl N-(5-bromo-6-fluoropyridin-2-yl)carbamate (3.30 g, 11.336 mmol, 1.00 equiv), DMF (50.00 mL). This was followed by the addition of NaH (570.00 mg, 14.251 mmol, 1.26 equiv, 60%), in portions at 0 degrees C. The resulting solution was stirred for 30 min at 0 degrees C. To this was added $CH_3I$ (1.86 g, 13.104 mmol, 1.16 equiv) at 0 degrees C. The resulting solution was stirred for 1 hr at 25 degrees C. The reaction was then quenched by the addition of 500 mL of aqueous $NH_4Cl$. The resulting solution was extracted with 2×200 mL of ethyl acetate and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (1:3). This resulted in 3.48 g (100.61%) of tert-butyl N-(5-bromo-6-fluoropyridin-2-yl)-N-methylcarbamate as a white solid. LC-MS (ES, m/z): M-t-Bu+1=249.

Synthesis of tert-butyl N-[5-bromo-6-[3-(1,3-dioxoisoindol-2-yl)propoxy]pyridin-2-yl]-N-methylcarbamate: Into a 250-mL round-bottom flask purged and maintained with an inert atmosphere of nitrogen, was placed 2-(3-hydroxypropyl)isoindole-1,3-dione (2.58 g, 12.572 mmol, 1.10 equiv), THF (40.00 mL). This was followed by the addition of NaH (687.00 mg, 17.177 mmol, 1.50 equiv, 60%), in portions at 0 degrees C. The resulting solution was stirred for 30 min at 0 degrees C. To this was added tert-butyl N-(5-bromo-6-fluoropyridin-2-yl)-N-methylcarbamate (3.49 g, 11.437 mmol, 1.00 equiv) at 0 degrees C. The resulting solution was stirred for 2 hr at 70 degrees C. in an oil bath. The reaction mixture was cooled to room temperature. The reaction was then quenched by the addition of 500 mL of aqueous $NH_4Cl$. The resulting solution was extracted with 2×200 mL of ethyl acetate and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (1:3). This resulted in 4.2 g (74.89%) of tert-butyl N-[5-bromo-6-[3-(1,3-dioxoisoindol-2-yl)propoxy]pyridin-2-yl]-N-methylcarbamate as a white solid. $^1H$ NMR (300 MHz, DMSO-$d_6$, ppm) δ 7.90-7.78 (m, 5H), 7.20 (d, J=8.4 Hz, 1H), 4.35 (t, J=6.0 Hz, 2H), 3.77 (t, J=6.6 Hz, 2H), 3.22 (s, 3H), 2.09 (p, J=6.4 Hz, 2H), 1.46 (s, 9H).

Synthesis of tert-butyl N-[6-(3-aminopropoxy)-5-bromopyridin-2-yl]-N-methylcarbamate: Into a 250-mL round-bottom flask, was placed tert-butyl N-[5-bromo-6-[3-(1,3-dioxoisoindol-2-yl)propoxy]pyridin-2-yl]-N-methylcarbamate (4.20 g, 8.565 mmol, 1.00 equiv), EtOH (50.00 mL), $N_2H_4 \cdot H_2O$ (5.37 g, 85.909 mmol, 10.03 equiv, 80%). The resulting solution was stirred overnight at 50 degrees C. in an oil bath. The reaction mixture was cooled to room temperature. The resulting solution was diluted with 500 mL of water. The resulting solution was extracted with 2×200 mL of ethyl acetate and the organic layers combined. The resulting mixture was washed with 1×1000 ml of brine. The mixture was dried over anhydrous sodium sulfate and concentrated under vacuum. This resulted in 3.02 g (97.87%) of tert-butyl N-[6-(3-aminopropoxy)-5-bromopyridin-2-yl]-N-methylcarbamate as yellow oil. LC-MS (ES, m/z): M+1=360.

Synthesis of tert-butyl N-methyl-N-[1H,2H,3H,4H-pyrido[2,3-b][1,4]oxazepin-7-yl]carbamate: Into a 100-mL round-bottom flask purged and maintained with an inert atmosphere of nitrogen, was placed tert-butyl N-[6-(3-aminopropoxy)-5-bromopyridin-2-yl]-N-methylcarbamate (3.00 g, 8.328 mmol, 1.00 equiv), toluene (30.00 mL), Xphos Pd G3 (600.00 mg, 0.709 mmol, 0.09 equiv), t-BuONa (2.41 g, 25.077 mmol, 3.01 equiv). The resulting solution was stirred for 2 hr at 90 degrees C. in an oil bath. The reaction mixture was cooled to room temperature. The resulting mixture was concentrated under vacuum. The residue was applied onto a silica gel column with ethyl acetate/petroleum ether (1:2). This resulted in 1 g (42.99%) of tert-butyl N-methyl-N-[1H,2H,3H,4H-pyrido[2,3-b][1,4] oxazepin-7-yl]carbamate as a brown solid. $^1$H NMR (300 MHz, DMSO-$d_6$, ppm) δ 7.16 (d, J=8.2 Hz, 1H), 6.97 (d, J=8.2 Hz, 1H), 5.47 (t, J=3.2 Hz, 1H), 4.11 (dd, J=6.1, 4.8 Hz, 2H), 3.18-3.08 (m, 2H), 3.12 (s, 3H), 1.89 (p, J=5.7 Hz, 2H), 1.42 (s, 9H).

Synthesis of methyl 2-[7-[(tert-butoxycarbonyl)(methyl) amino]-2H,3H,4H-pyrido[2,3-b][1,4]oxazepin-1-yl]-4-(4-[[2-(4-chlorophenyl)-4,4-dimethylcyclohex-1-en-1-yl] methyl]piperazin-1-yl)benzoate: Into a 40-mL vial purged and maintained with an inert atmosphere of nitrogen, was placed tert-butyl N-methyl-N-[1H,2H,3H,4H-pyrido[2,3-b] [1,4]oxazepin-7-yl]carbamate (500.00 mg, 1.790 mmol, 1.00 equiv), toluene (20.00 mL), methyl 2-bromo-4-(4-[[2-(4-chlorophenyl)-4,4-dimethylcyclohex-1-en-1-yl]methyl] piperazin-1-yl)benzoate (1.71 g, 3.215 mmol, 1.80 equiv), Pd$_2$(dba)$_3$·CHCl$_3$ (369.00 mg, 0.356 mmol, 0.20 equiv), Xantphos (414.00 mg, 0.715 mmol, 0.40 equiv), Cs$_2$CO$_3$ (1.75 g, 5.371 mmol, 3.00 equiv). The resulting solution was stirred for 2 hr at 100 degrees C. in an oil bath. The reaction mixture was cooled to room temperature. The resulting mixture was concentrated under vacuum. The residue was applied onto a silica gel column with ethyl acetate/petroleum ether (1:2). This resulted in 1.1 g (84.14%) of methyl 2-[7-[(tert-butoxycarbonyl)(methyl)amino]-2H,3H,4H-pyrido[2,3-b][1,4]oxazepin-1-yl]-4-(4-[[2-(4-chlorophenyl)-4,4-dimethylcycloohex-1-en-1-yl]ethyl]piperazin-1-yl) benzoate as a yellow solid. LC-MS (ES, m/z): M+1=730.

Synthesis of 2-[7-[(tert-butoxycarbonyl)(methyl)amino]-2H,3H,4H-pyrido[2,3-b][1,4]oxazepin-1-yl]-4-(4-[[2-(4-chlorophenyl)-4,4-dimethylcyclohex-1-en-1-yl]methyl]piperazin-1-yl)benzoic acid: Into a 100-mL round-bottom flask, was placed methyl 2-[7-[(tert-butoxycarbonyl)(methyl) amino]-2H,3H,4H-pyrido[2,3-b][1,4]oxazepin-1-yl]-4-(4-[[2-(4-chlorophenyl)-4,4-dimethylcyclohex-1-en-1-yl] methyl]piperazin-1-yl)benzoate (700.00 mg, 0.958 mmol, 1.00 equiv), dioxane (5.00 mL), MeOH (5.00 mL), NaOH (1.00 mL, 4.000 mmol, 4.17 equiv). The resulting solution was stirred for 4 hr at 70 degrees C. in an oil bath. The reaction mixture was cooled to room temperature. The resulting mixture was concentrated under vacuum. The resulting solution was diluted with 100 mL of water. The pH value of the solution was adjusted to 6-7 with HCl (2 mol/L). The resulting solution was extracted with 3×100 mL of ethyl acetate and the organic layers combined. The resulting mixture was washed with 1×500 ml of brine. The mixture was dried over anhydrous sodium sulfate and concentrated under vacuum. The crude product was re-crystallized from EtOAc:PE in the ratio of 1:10. The solids were collected by filtration. This resulted in 415 mg (60.45%) of 2-[7-[(tert-butoxycarbonyl)(methyl)amino]-2H,3H,4H-pyrido[2,3-b] [1,4]oxazepin-1-yl]-4-(4-[[2-(4-chlorophenyl)-4,4-dimethylcyclohex-1-en-1-yl]methyl]piperazin-1-yl)benzoic acid as a yellow solid. LC-MS (ES, m/z): M+1=716.

Synthesis of tert-butyl N-[1[5-(4-[[2-(4-chlorophenyl)-4,4-dimethylcyclohex-1-en-1-yl]methyl]piperazin-1-yl)-2-[(4-[[(2S)-1,4-dioxan-2-ylmethyl]amino]-3-nitrobenzenesulfonyl)carbamoyl]phenyl]-2H,3H,4H-pyrido[2,3-b][1,4] oxazepin-7-yl]-N-methylcarbamate: Into a 40-mL vial, was placed 2-[7-[(tert-butoxycarbonyl)(methyl)amino]-2H,3H, 4H-pyrido[2,3-b][1,4]oxazepin-1-yl]-4-(4-[[2-(4-chlorophenyl)-4,4-dimethylcyclohex-1-en-1-yl]methyl]piperazin-1-yl)benzoic acid (200.00 mg, 0.279 mmol, 1.00 equiv), DCM (5.00 mL), 4-[[(2S)-1,4-dioxan-2-ylmethyl]amino]-3-nitrobenzenesulfonamide (89.00 mg, 0.280 mmol, 1.00 equiv), EDCI (108.00 mg, 0.563 mmol, 2.02 equiv), DMAP (137.00 mg, 1.121 mmol, 4.02 equiv). The resulting solution was stirred overnight at 30 degrees C. in an oil bath. The reaction mixture was cooled to room temperature. The resulting mixture was concentrated under vacuum. The residue was applied onto a silica gel column with dichloromethane/methanol (10:1). This resulted in 120 mg (42.32%) of tert-butyl N-[1-[5-(4-[[2-(4-chlorophenyl)-4,4-dimethylcyclohex-1-en-1-yl]methyl]piperazin-1-yl)-2-[(4-[[(2S)-1,4-dioxan-2-ylmethyl]amino]-3-nitrobenzenesulfonyl)carbamoyl]phenyl]-2H,3H,4H-pyrido[2,3-b][1,4] oxazepin-7-yl]-N-methylcarbamate as a yellow solid. LC-MS (ES, m/z): M+1=1015.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[7-(methylamino)-2H,3H,4H-pyrido[2,3-b][1,4]oxazepin-1-yl] benzamide hydrochloride: Into a 50-mL round-bottom flask, was placed tert-butyl N-[1-[5-(4-[[2-(4-chlorophenyl)-4,4-dimethylcyclohex-1-en-1-yl]methyl]piperazin-1-yl)-2-[(4-[[(2S)-1,4-dioxan-2-ylmethyl]amino]-3-nitrobenzenesulfonyl)carbamoyl]phenyl]-2H,3H,4H-pyrido[2,3-b][1,4] oxazepin-7-yl]-N-methylcarbamate (120.00 mg, 0.118 mmol, 1.00 equiv), HCl (gas) in 1,4-dioxane (5.00 mL). The resulting solution was stirred for 4 hr at 25 degrees C. The resulting mixture was concentrated under vacuum. The pH value of the solution was adjusted to 8 with NH$_3$·H$_2$O. The crude product was purified by Prep-HPLC with the following conditions (Prep-HPLC-006): Column, XBridge Shield RP18 OBD Column, 5 um, 19*150 mm; mobile phase, Water (0.05% FA) and ACN (40% Phase B up to 70% in 7 min); Detector, UV 254/220 nm. The collected solution was concentrated under vacuum to remove CH$_3$CN and the resulting solution was dried by lyophilization (added with Conc. HCl (1 drop)). This resulted in 20 mg (18.49%) of 4-(4-[[2-(4-chlorophenyl)-4,4-dimethylcyclohex-1-en-1-yl] methyl]piperazin-1-yl)-N-(4-[[(2S)-1,4-dioxan-2-ylmethyl] amino]-3-nitrobenzenesulfonyl)-2-[7-(methylamino)-2H, 3H,4H-pyrido[2,3-b][1,4]oxazepin-1-yl]benzamide hydrochloride as a yellow solid. LC-MS (ES, m/z): M−HCl+ 1=915, $^1$H NMR (300 MHz, DMSO-$d_6$, ppm) δ 11.95 (s, 1H), 10.87 (s, 1H), 8.63 (s, 1H), 8.55 (d, J=2.1 Hz, 1H), 7.93-7.76 (m, 1H), 7.42 (d, J=7.9 Hz, 2H), 7.29 (d, J=8.7 Hz, 1H), 7.22 (d, J=9.3 Hz, 1H), 7.14 (d, J=7.9 Hz, 2H), 6.91 (s, 1H), 6.59 (d, J=7.9 Hz, 2H), 6.12 (s, 1H), 4.41 (s, 2H), 4.08-3.06 (m, 19H), 2.73 (s, 5H), 2.41 (s, 2H), 2.01 (d, J=21.8 Hz, 4H), 1.47 (s, 2H), 0.97 (s, 6H).

Example 43

Preparation of 4-(4-[[2-(4-chlorophenyl)-4,4-dimethylcyclohex-1-en-1-yl]methyl]piperazin-1-yl)-N-[(3S)-3-[(2S)-1,4-dioxan-2-yl]-5-nitro-3,4-dihydro-2H-1,4-benzoxazin-7-ylsulfonyl]-2-[(12R)-12-methyl-13-oxa-2,4,10-triazatricyclo[7.4.0.0ˆ[3,7]] trideca-1(9),2,5,7-tetraen-10-yl]benzamide hydrochloride, and 4-(4-[[2-(4-chlorophenyl)-4,4-dimethylcycloohex-1-en-1-yl]ethyl]piperazin-1-yl)-N-[(3R)-3-[(2S)-1,4-dioxan-2-yl]-5-nitro-3,4-dihydro-2H-1,4-benzoxazin-7-ylsulfonyl]-2-[(12R)-12-methyl-13-oxa-2,4,10-triazatricyclo[7.4.0.0ˆ[3,7]] trideca-1(9),2,5,7-tetraen-10-yl]benzamide hydrochloride Synthesis of (2R)-1,4-dioxane-2-carbaldehyde: Into a 100-mL round-bottom flask, was placed (2S)-1,4-dioxan-2- ylmethanol (2.36 g, 19.978 mmol, 1.00 equiv), CH₃CN (50.00 mL, 1.218 mmol, 0.0 equiv), IBX (9.51 g, 33.962 mmol, 1.70 equiv). The resulting solution was stirred for 4 h at 70 degrees C. in an oil bath. The solids were filtered out. The resulting mixture was concentrated. This resulted in 2.0 g (86.22%) of (2R)-1,4-dioxane-2-carbaldehyde as colorless oil. H-NMR-1: ¹H NMR (300 MHz, CDCl₃, ppm) δ 9.66 (s, 1H), 4.12-3.77 (m, 7H).

Synthesis of 2-amino-2-[(2S)-1,4-dioxan-2-yl]acetonitrile: Into a 100-mL pressure tank reactor, was placed (2R)-1,4-dioxane-2-carbaldehyde (2.00 g, 17.224 mmol, 1.00 equiv). NH₃/MeOH (7M) (40.00 mL). This was followed by the addition of TMSCN (2.97 g, 29.970 mmol, 1.74 equiv). The resulting solution was stirred for overnight at 70 degrees C. in an oil bath. The resulting mixture was concentrated. The residue was applied onto a silica gel column and eluted with ethyl acetate/petroleum ether (3:1). The collected fractions were combined and concentrated. This resulted in 2.0 g (81.68%) of 2-amino-2-[(2S)-1,4-dioxan-2-yl]acetonitrile as brown oil. LCMS-2 (ES, m/z): M+1: 143.

Synthesis of amino((2S)-1,4-dioxan-2-yl)acetic acid: Into a 20-mL round-bottom flask, was placed 2-amino-2-[(2S)-1,4-dioxan-2-yl]acetonitrile (2.00 g, 14.069 mmol, 1.00 equiv), NaOH (4M) (5.00 mL). The resulting solution was stirred for overnight at 70 degrees C. in an oil bath. The pH value of the solution was adjusted to 6 with HOAc. The solids were collected by filtration. The solid was dried in an oven under reduced pressure. This resulted in 1.2 g (52.93%) of amino((2S)-1,4-dioxan-2-yl)acetic acid as a white solid. LCMS-3 (ES, m/z): M+1: 162.

Synthesis of 2-amino-2-[(2S)-1,4-dioxan-2-yl]ethanol: Into a 100-mL round-bottom flask, was placed amino((2S)-1,4-dioxan-2-yl)acetic acid (1.20 g, 7.446 mmol, 1.00 equiv), THF (40.00 mL, 0.555 mmol, 0.07 equiv), LiAlH₄ (0.85 g, 22.396 mmol, 3.01 equiv). The resulting solution was stirred for 4 h at 60 degrees C. in an oil bath. The reaction was then quenched by the addition of 2.4 g of Na₂SO₄.10H₂O. The solids were filtered out. The resulting mixture was concentrated. This resulted in 1.8 g (crude) of 2-amino-2-[(2S)-1,4-dioxan-2-yl]ethanol as colorless oil. LCMS-4 (ES, m/z): M+1: 148.

Synthesis of 3-bromo-4-([1-[(2S)-1,4-dioxan-2-yl]-2-hydroxyethyl]amino)-5-nitrobenzenesulfonamide: Into a 50-mL round-bottom flask, was placed 3-bromo-4-chloro-5-nitrobenzenesulfonamide (1.19 g, 3.772 mmol, 1.00 equiv), 2-amino-2-[(2S)-1,4-dioxan-2-yl]ethanol (0.72 g, 0.005 mmol, 1.3 equiv), CH₃CN (30.00 mL), DIEA (1.46 g, 0.011 mmol, 3 equiv). The resulting solution was stirred for 48 h at 80 degrees C. in an oil bath. The resulting mixture was concentrated. The residue was applied onto a silica gel column and eluted with ethyl acetate/petroleum ether (9:1). The collected fractions were combined and concentrated. This resulted in 120 mg (7.46%) of 3-bromo-4-([1-(2S)-1,4-dioxan-2-yl]-2-hydroxyethyl]amino)-5-nitrobenzenesulfonamide as a yellow solid. LCMS-5 (ES, m/z): M-1: 424

Synthesis of (3S)-3-[(2S)-1,4-dioxan-2-yl]-5-nitro-3,4-dihydro-2H-1,4-benzoxazine-7-sulfonamide &(3R)-3-[(2S)-1,4-dioxan-2-yl]-5-nitro-3,4-dihydro-2H-1,4-benzoxazine-7-sulfonamide (assumed): Into a 8-mL round-bottom flask purged and maintained with an inert atmosphere of nitrogen, was placed 3-bromo-4-([1-[(2S)-1,4-dioxan-2-yl]-2-hydroxyethyl]amino)-5-nitrobenzenesulfonamide (120.00 mg, 0.282 mmol, 1.00 equiv), dioxane (8.00 mL), CS₂CO₃ (229.32 mg, 0.704 mmol, 2.50 equiv), t-BuXPhos Pd G3 (22.33 mg, 0.028 mmol, 0.1 equiv). The resulting solution was stirred for 8 h at 100 degrees C. in an oil bath. The reaction was then quenched by the addition of water (8 mL). The resulting solution was extracted with 3×8 mL of ethyl acetate concentrated. The crude product was purified by Prep-HPLC with the following conditions: Column, X-bridge RP18; mobile phase, 0.05% ammonia in water and CH₃CN (45% CH₃CN up to 60% in 5 min); Detector, UV 254 nm. This resulted in 7 mg (7.20%) of (3S or 3R)-3-[(2S)-1,4-dioxan-2-yl]-5-nitro-3,4-dihydro-2H-1,4-benzoxazine-7-sulfonamide as a yellow solid. This resulted in 10 mg (10.29%) of (3R or 3S)-3-[(2S)-1,4-dioxan-2-yl]-5-nitro-3,4-dihydro-2H-1,4-benzoxazine-7-sulfonamide as a yellow solid. LC-MS-6: (ES, m/z): M−1:344.

Synthesis of 4-(4-[[2-(4-chlorophenyl)-4,4-dimethylcyclohex-1-en-1-yl]methyl]piperazin-1-yl)-N-[(3S)-3-[(2S)-1,4-dioxan-2-yl]-5-nitro-3,4-dihydro-2H-1,4-benzoxazin-7-ylsulfonyl]-2-[(12R)-12-methyl-13-oxa-2,4,10-triazatricyclo[7.4.0.0^[3,7]]trideca-1(9),2,5,7-tetraen-10-yl]benzamide hydrochloride (assumed): Into a 8-mL round-bottom flask, was placed 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]benzoic acid (12.69 mg, 0.020 mmol, 1.00 equiv), (3S)-3-[(2S)-1,4-dioxan-2-yl]-5-nitro-3,4-dihydro-2H-1,4-benzoxazine-7-sulfonamide (7.00 mg, 0.020 mmol, 1.00 equiv), DCM (5.00 mL), EDCI (7.77 mg, 0.041 mmol, 2.00 equiv), DMAP (7.43 mg, 0.061 mmol, 3.00 equiv). The resulting solution was stirred for overnight at room temperature. The resulting mixture was concentrated. The crude product was purified by Prep-HPLC with the following conditions (2 #SHIMADZU (HPLC-01)): Column, Sun Fire Prep C18 OBD Column, 19*150 mm 5 um 10 nm; mobile phase, Water (0.05% TFA) and ACN (38% Phase B up to 58% in 7 min); Detector, UV 254 nm. The collected solution was concentrated under vacuum to remove CH3CN and the resulting solution was dried by lyophilization (added with con. HCl (1 drop)). This resulted in 5 mg (24.92%) of 4-(4-[[2-(4-chlorophenyl)-4,4-dimethylcyclohex-1-en-1-yl]methyl]piperazin-1-yl)-N-[(3S)-3-[(2S)-1,4-dioxan-2-yl]-5-nitro-3,4-dihydro-2H-1,4-benzoxazin-7-ylsulfonyl]-2-[(12R)-12-methyl-13-oxa-2,4,10-triazatricyclo[7.4.0.0^[3,7]]trideca-1(9),2,5,7-tetraen-10-yl]benzamide hydrochloride as a yellow solid. LC-MS-0A: (ES, m/z): M+1−HCl: 953.

Synthesis of 4-(4-[[2-(4-chlorophenyl)-4,4-dimethylcyclohex-1-en-1-yl]methyl]piperazin-1-yl)-N-[(3R)-3-[(2S)-1,4-dioxan-2-yl]-5-nitro-3,4-dihydro-2H-1,4-benzoxazin-7-ylsulfonyl]-2-[(12R)-12-methyl-13-oxa-2,4,10-triazatricyclo[7.4.0.0^[3,7]]trideca-1(9),2,5,7-tetraen-10-yl]benzamide hydrochloride (assumed): Into a 8-mL round-bottom flask, was placed (3R)-3-[(2S)-1,4-dioxan-2-yl]-5-nitro-3,4-dihydro-2H-1,4-benzoxazine-7-sulfonamide (10.00 mg, 0.029 mmol, 1.00 equiv), 4-(4-[[2-(4-chlorophenyl)-4,4-dimethylcyclohex-1-en-1-yl]methyl]piperazin-1-yl)-2-[(12R)-12-methyl-13-oxa-2,4,10-triazatricyclo[7.4.0.0^[3,7]]trideca-1(9),2,5,7-tetraen-10-yl]benzoic acid (18.13 mg, 0.029 mmol, 1.00 equiv), DCM (5.00 mL), EDCI (11.10 mg, 0.058 mmol, 2 equiv), DMAP (14.15 mg, 0.116 mmol, 4 equiv). The resulting solution was stirred for overnight at room temperature. The resulting mixture was concentrated. The crude product was purified by Prep-HPLC with the following conditions (2 #SHIMADZU (HPLC-01)): Column, Sun Fire Prep C18 OBD Column, 19??150 mm 5 um 10 nm; mobile phase, Water (0.05% TFA) and ACN (38% Phase B up to 58% in 7 min); Detector, UV=254 nm. The collected solution was concentrated under vacuum to remove CH₃CN and the resulting solution was dried by lyophilization (added with con. HCl (1 drop)). This resulted in 10 mg of 4-(4-[[2-(4-chlorophenyl)-4,4-dimethylcyclohex-1-en-1-yl]methyl]piperazin-1-yl)-N-[(3R)-3-[(2S)-1,4-dioxan-2-yl]-5-nitro-3,4-dihydro-2H-1,4-benzoxazin-7-ylsulfonyl]-2-[(12R)-12-methyl-13-oxa-2,4,10-triazatricyclo[7.4.0.0^[3,7]]trideca-1(9),2,5,7-tetraen-10-yl]benzamide hydrochloride as a yellow solid. LC-MS-0B: (ES, m/z): M+1-HCl: 953; H-NMR-0B: $^1$H NMR (300 MHz, Methanol-4 ppm) δ 8.01 (s, 1H), 7.65 (d, J=8.4 Hz, 1H), 7.41 (d, J=8.4 Hz, 1H), 7.25 (s, 1H), 7.13 (d, J=8.4 Hz, 2H), 6.94 (s, 2H), 6.82 (s, 1H), 6.66 (s, 1H), 5.94 (s, 1H), 4.70 (s, 1H), 4.31 (s, 1H), 4.04 (s, 1H), 3.98-3.58 (m, 12H), 3.48 (s, 3H), 3.22 (s, 2H), 2.90 (s, 2H), 2.33 (s, 2H), 2.16 (s, 2H), 1.62 (t, J=6.3 Hz, 2H), 1.51 (d, J=6.3 Hz, 3H), 1.32 (s, 1H), 1.05 (s, 6H).

Example 44

Preparation of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzene sulfonyl)-2-[(11S,15S)-16-oxa-2,4,10-triazatetracyclo[7.7.0.0^[3,7]0.^[11,15]]hexadeca-1(9),2,5,7-tetraen-10-yl]benzamide (Assumed) and 4-(4-[[2-(4-chlorophenyl)-4,4-dimethylcycloohex-1-en-1-yl]methyl]piperazin-1-yl)-N-(4-[[(2S)-1,4-dioxan-2-ylmethyl]amino]-3-nitrobenzene sulfonyl)-2-[(11R,15R)-16-oxa-2,4,10-triazatetracyclo[7.7.0.0^[3,7].0^[11,15]]hexadeca-1(9),2,5,7-tetraen-10-yl]benzamide (Assumed Synthesis of N-[(trans)-2-hydroxycyclopentyl]-4-methylbenzenesulfonamide: Into a 250-mL round-bottom flask purged and maintained with an inert atmosphere of nitrogen, was placed (trans)-2-aminocyclopentan-1-ol (2.10 g, 20.761 mmol, 1.00 equiv), DCM (30.00 mL), TEA (3.18 g, 31.426 mmol, 1.51 equiv). This was followed by the addition of P-toluenesulfonyl chloride (4.35 g, 22.818 mmol, 1.10 equiv), in portions at 0 degrees C. The resulting solution was stirred for 3 hr at 25 degrees C. The resulting mixture was concentrated under vacuum. The residue was applied onto a silica gel column with ethyl acetate/petroleum ether (1.5:1). This resulted in 5 g (94.32%) of N-[(trans)-2-hydroxycyclopentyl]-4-methylbenzenesulfonamide as light yellow oil. $^1$H NMR (300 MHz, Chloroform-d, ppm) δ 7.84-7.77 (m, 2H), 7.38-7.30 (m, 2H), 5.27 (s, 1H), 4.06 (dt, J=7.2, 6.3 Hz, 1H), 3.25 (q, J=7.7 Hz, 1H), 2.91 (s, 1H), 2.45 (s, 3H), 2.06-1.81 (m, 2H), 1.72-1.46 (m, 3H), 1.45-1.23 (m, 1H).

Synthesis of N-[(trans)-2-[(5-bromo-1-[[2-(trimethylsilyl)ethoxy]methyl]pyrrolo[2,3-b]pyridin-6-yl)oxy]cyclopentyl]-4-methylbenzenesulfonamide: Into a 250-mL round-bottom flask purged and maintained with an inert atmosphere of nitrogen, was placed N-[(trans)-2-hydroxycyclopentyl]-4-methylbenzenesulfonamide (5.00 g, 19.583 mmol, 1.30 equiv), THF (50.00 mL). This was followed by the addition of NaH (1.81 g, 45.254 mmol, 3.01 equiv, 60%), in portions at 0 degrees C. The resulting solution was stirred for 0.5 h at 0 degrees C. To this was added 5-bromo-6-fluoro-1-[[2-(trimethylsilyl)ethoxy]methyl]pyrrolo[2,3-b]pyridine (5.19 g, 15.031 mmol, 1.00 equiv) at 0 degrees C. The resulting solution was stirred for 2 hr at 70 degrees C. in an oil bath. The reaction mixture was cooled to room temperature. The reaction was then quenched by the addition of aqueous NH$_4$Cl. The resulting solution was extracted with 3×200 mL of ethyl acetate and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (1:3). This resulted in 4.8 g (55.00%) of N-[(trans)-2-[(5-bromo-1-[[2-(trimethylsilyl)ethoxy]ethyl]pyrrolo[2,3-b]pyridin-6-yl)oxy]cyclopentyl]-4-methylbenzenesulfonamide as yellow oil. $^1$H NMR (300 MHz, Chloroform-d, ppm) δ 8.00 (s, 1H), 7.56-7.47 (m, 2H), 7.19 (d, J=3.6 Hz, 1H), 7.11-7.02 (m, 2H), 6.42 (d, J=3.6 Hz, 1H), 5.70 (d, J=10.9 Hz, 1H), 5.49 (d, J=10.9 Hz, 1H), 5.33-5.20 (m, 1H), 3.69-3.43 (m, 3H), 2.31 (s, 3H), 1.93-1.63 (m, 4H), 1.01-0.93 (m, 2H), 0.89 (dd, J=7.0, 1.5 Hz, 2H), 0.01 (s, 9H).

Synthesis of (trans)-10-(4-methylbenzenesulfonyl)-4-[[2-(trimethylsilyl)ethoxy]methyl]-16-oxa-2,4,10-triazatetracyclo[7.7.0.0^[3,7].0[11,15]]hexadeca-1(9),2,5,7-tetraene: Into a 100-mL round-bottom flask purged and maintained with an inert atmosphere of nitrogen, was placed N-[(trans)-2-[(5-bromo-1-[[2-(trimethylsilyl)ethoxy]methyl]pyrrolo[2,3-b]pyridin-6-yl)oxy]cyclopentyl]-4-methylbenzenesulfonamide (2.90 g, 4.995 mmol, 1.00 equiv), DMF (30.00 mL), phen (902.00 mg, 5.005 mmol, 1.00 equiv), CuI (952.00 mg, 4.999 mmol, 1.00 equiv), K$_2$CO$_3$ (2.07 g, 14.978 mmol, 3.00 equiv). The resulting solution was stirred overnight at 120 degrees C. in an oil bath. The reaction mixture was cooled to room temperature. The resulting solution was diluted with 500 mL of water. The resulting solution was extracted with 3×200 mL of ethyl acetate and the organic layers combined. The resulting mixture was washed with 1×1000 ml of brine. The mixture was dried over anhydrous sodium sulfate and concentrated under vacuum. The residue was applied onto a silica gel column with ethyl acetate/petroleum ether (1:3). This resulted in 2.1 g (84.14%) of (trans)-10-(4-methylbenzenesulfonyl)-4-[[2-(trimethylsilyl)ethoxy]methyl]-16-oxa-2,4,10-triazatetracyclo[7.7.0.0^[3,7].0^[11,15]]hexadeca-1(9),2,5,7-tetraene as colorless oil. $^1$H NMR (300 MHz, Chloroform-d, ppm) δ 8.68 (s, 1H), 7.43-7.34 (m, 2H), 7.24 (d, J=3.6 Hz, 1H), 7.15 (d, J=8.0 Hz, 2H), 6.53 (d, J=3.6 Hz, 1H), 5.54 (d, J=1.4 Hz, 2H), 4.00 (td, J=10.0, 7.6 Hz, 1H), 3.52 (t, J=8.2 Hz, 2H), 3.43-3.28 (m, 1H), 2.68-2.49 (m, 1H), 2.35 (s, 3H), 2.21-1.88 (m, 4H), 1.77 (td, J=10.8, 7.6 Hz, 1H), 0.97-0.86 (m, 2H), −0.05 (s, 9H).

Synthesis of (11S,15S)-4-[[2-(trimethylsilyl)ethoxy]methyl]-16-oxa-2,4,10-triazatetracyclo[7.7.0.0^[3,7].0^[11,15]]hexadeca-1(9),2,5,7-tetraene (Assumed) and (11R,15R)-4-[[2-(trimethylsilyl)ethoxy]methyl]-16-oxa-2,4,10-triazatetracyclo[7.7.0.0^[3,7].0^[11,15]]hexadeca-1(9),2,5,7-tetraene (Assumed): Into a 100-mL round-bottom flask, was placed Mg (1.92 g, 78.996 mmol, 19.74 equiv), MeOH (20.00 mL), (trans)-10-(4-methylbenzenesulfonyl)-4-[[2-(trimethylsilyl)ethoxy]methyl]-16-oxa-2,4,10-triazatetracyclo[7.7.0.0^[3,7].0[11,15]]hexadeca-1(9),2,5,7-tetraene (2.00 g, 4.002 mmol, 1.00 equiv). The resulting solution was stirred for 2 hr at 60 degrees C. in an oil bath. The reaction mixture was cooled to room temperature. The resulting solution was diluted with 300/300 mL of NaHCO$_3$ and CH$_2$Cl$_2$. The solids were filtered out and the organic was separated. The mixture was dried over anhydrous sodium sulfate and concentrated under vacuum. The residue was applied onto a silica gel column with ethyl acetate/petroleum ether (1:3). The crude product was purified by Chiral-Prep-HPLC with the following conditions: Mobile phase: A: n-Hexane B: ETOH; Flow rate: 20 mL/min; Column: DAICEL CHIRALPAK OD, 250*20 mm, 5 um; Gradient: 20% B in 15 min; 220 nm. This resulted in 360 mg (26.03%) of (11S,15S)-4-[[2-(trimethylsilyl)ethoxy]methyl]-16-oxa-2,4,10-triazatetracyclo[7.7.0.0^[3,7].0[11,15]]hexadeca-1(9),2,5,7-tetraene (Assumed) as yellow oil. This resulted in 400 mg (28.92%) of (11R,15R)-4-[[2-(trimethylsilyl)ethoxy]

methyl]-16-oxa-2,4,10-triazatetracyclo[7.7.0.0^[3,7].0^[11,15]]hexadeca-1(9),2,5,7-tetraene (Assumed) as yellow oil. Peak 1: LC-MS (ES, m/z): M+1=346, $^1$H NMR (300 MHz, Chloroform-d, ppm) δ 7.28 (s, 1H), 7.15 (d, J=3.5 Hz, 1H), 6.33 (d, J=3.5 Hz, 1H), 5.56 (s, 2H), 4.30-4.07 (m, 1H), 3.55 (dd, J=8.8, 7.5 Hz, 2H), 3.29 (dt, J=11.4, 7.5 Hz, 1H), 2.37-2.19 (m, 1H), 2.18-2.04 (m, 1H), 2.04-1.79 (m, 3H), 1.68-1.40 (m, 1H), 0.90 (dd, J=8.7, 7.5 Hz, 2H), −0.06 (s, 9H). Peak 2: LC-MS (ES, m/z): M+1=346, $^1$H NMR (300 MHz, Chloroform-d, ppm) δ 7.28 (s, 1H), 7.15 (d, J=3.5 Hz, 1H), 6.33 (d, J=3.5 Hz, 1H), 5.56 (s, 2H), 4.30-4.07 (m, 1H), 3.55 (dd, J=8.8, 7.5 Hz, 2H), 3.29 (dt, J=11.4, 7.5 Hz, 1H), 2.37-2.19 (m, 1H), 2.18-2.04 (m, 1H), 2.04-1.79 (m, 3H), 1.68-1.40 (m, 1H), 0.90 (dd, J=8.7, 7.5 Hz, 2H), −0.06 (s, 9H).

Synthesis of methyl 4-(4-[[2-(4-chlorophenyl)-4,4-dimethylcyclohex-1-en-1-yl]methyl]piperazin-1-yl)-2-[(11S,15S)-4-[[2-(trimethylsilyl)ethoxy]methyl]-16-oxa-2,4,10-triazatetracyclo[7.7.0.0^[3,7].0^[11,15]]hexadeca-1(9),2,5,7-tetraen-10-yl]benzoate (Assumed): Into a 40-mL vial purged and maintained with an inert atmosphere of nitrogen, was placed (11S,15S)-4-[[2-(trimethylsilyl)ethoxy]methyl]-16-oxa-2,4,10-triazatetracyclo[7.7.0.0^[3,7].0^[11,15]]hexadeca-1(9),2,5,7-tetraene (Assumed) (340.00 mg, 0.984 mmol, 1.00 equiv), toluene (15.00 mL), methyl 2-bromo-4-(4-[[2-(4-chlorophenyl)-4,4-dimethylcyclohex-1-en-1-yl]methyl]piperazin-1-yl)benzoate (1.04 g, 1.955 mmol, 1.99 equiv), Pd$_2$(dba)$_3$·CHCl$_3$ (204.00 mg, 0.197 mmol, 0.20 equiv), Xantphos (228.00 mg, 0.394 mmol, 0.40 equiv), Cs$_2$CO$_3$ (961.00 mg, 2.949 mmol, 3.00 equiv). The resulting solution was stirred for 4 hr at 100 degrees C. in an oil bath. The reaction mixture was cooled to room temperature. The resulting mixture was concentrated under vacuum. The residue was applied onto a silica gel column with ethyl acetate/petroleum ether (1:2). This resulted in 630 mg (80.38%) of methyl 4-(4-[[2-(4-chlorophenyl)-4,4-dimethylcyclohex-1-en-1-yl]methyl]piperazin-1-yl)-2-[(11S,15S)-4-[[2-(trimethylsilyl)ethoxy]ethyl]-16-oxa-2,4,10-triazatetracyclo[7.7.0.0^[3,7].0[11,15]]hexadeca-1(9),2,5,7-tetraen-10-yl]benzoate (Assumed as a yellow solid. LC-MS (ES, m/z): M+1=796.

Synthesis of methyl 4-(4-[[2-(4-chlorophenyl)-4,4-dimethylcyclohex-1-en-1-yl]methyl]piperazin-1-yl)-2-[(11S,15S)-16-oxa-2,4,10-triazatetracyclo[7.7.0.0^[3,7].0^[11,15]]hexadeca-1(9),2,5,7-tetraen-10-yl]benzoate (Assumed): Into a 40-mL vial, was placed methyl 4-(4-[[2-(4-chlorophenyl)-4,4-dimethylcyclohex-1-en-1-yl]methyl]piperazin-1-yl)-2-[(11S,15S)-4-[[2-(trimethylsilyl)ethoxy]methyl]-16-oxa-2,4,10-triazatetracyclo[7.7.0.0^[3,7].0^[11,15]]hexadeca-1(9),2,5,7-tetraen-10-yl]benzoate (Assumed) (630.00 mg, 0.791 mmol, 1.00 equiv), TBAF in THF (10.00 mL, 1.0 M), ethylenediamine (1.30 g, 21.631 mmol, 27.35 equiv). The resulting solution was stirred for 8 hr at 70 degrees C. in an oil bath. The reaction mixture was cooled to room temperature. The resulting mixture was concentrated under vacuum. The residue was applied onto a silica gel column with ethyl acetate/petroleum ether (2:1). This resulted in 300 mg (56.93%) of methyl 4-(4-[[2-(4-chlorophenyl)-4,4-dimethylcyclohex-1-en-1-yl]methyl]piperazin-1-yl)-2-[(11S,15S)-16-oxa-2,4,10-triazatetracyclo[7.7.0.0^[3,7].0^[11,15]]hexadeca-1(9),2,5,7-tetraen-10-yl]benzoate (Assumed) as a yellow solid. LC-MS: (ES, m/z): M+1=666.

Synthesis of 4-(4-[[2-(4-chlorophenyl)-4,4-dimethylcyclohex-1-en-1-yl]methyl]piperazin-1-yl)-2-[(11S,15S)-16-oxa-2,4,10-triazatetracyclo[7.7.0.0^[3,7].0^[11,15]]hexadeca-1(9),2,5,7-tetraen-10-yl]benzoic acid (Assumed): Into a 40-mL vial, was placed methyl 4-(4-[[2-(4-chlorophenyl)-4,4-dimethylcyclohex-1-en-1-yl]methyl]piperazin-1-yl)-2-[(11S,15S)-16-oxa-2,4,10-triazatetracyclo[7.7.0.0^[3,7].0^[11,15]]hexadeca-1(9),2,5,7-tetraen-10-yl]benzoate (Assumed) (300.00 mg, 0.450 mmol, 1.00 equiv), dioxane (5.00 mL), MeOH (5.00 mL), NaOH (1.00 mL, 4.000 mmol, 8.88 equiv). The resulting solution was stirred for 4 hr at 70 degrees C. in an oil bath. The reaction mixture was cooled to room temperature.

The resulting mixture was concentrated under vacuum. The pH value of the solution was adjusted to 6-7 with HCl (2 mol/L). The resulting solution was extracted with 3×50 mL of ethyl acetate and the organic layers combined. The resulting mixture was washed with 1×300 ml of brine. The mixture was dried over anhydrous sodium sulfate and concentrated under vacuum. The residue was purified by Prep-TLC with ethyl acetate. This resulted in 130 mg (44.26%) of 4-(4-[[2-(4-chlorophenyl)-4,4-dimethylcyclohex-1-en-1-yl]methyl]piperazin-1-yl)-2-[(11S,15S)-16-oxa-2,4,10-triazatetracyclo[7.7.0.0^[3,7].0^[11,15]]hexadeca-1(9),2,5,7-tetraen-10-yl]benzoic acid (Assumed) as a white solid. LC-MS: (ES, m/z): M+1=652.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(11S,15S or 11R, 15R)-16-oxa-2,4,10-triazatetracyclo[7.7.0.0^[3,7].0[11,15]]hexadeca-1(9),2,5,7-tetraen-10-yl]benzamide (Assumed): Into a 40-mL vial, was placed 4-(4-[[2-(4-chlorophenyl)-4,4-dimethylcyclohex-1-en-1-yl]methyl]piperazin-1-yl)-2-[(11S,15S)-16-oxa-2,4,10-triazatetracyclo[7.7.0.0^[3,7].0^[11,15]]hexadeca-1(9),2,5,7-tetraen-10-yl]benzoic acid (Assumed) (50.00 mg, 0.077 mmol, 1.00 equiv), DCM (5.00 mL), 4-[[(2S)-1,4-dioxan-2-ylmethyl]amino]-3-nitrobenzenesulfonamide (24.00 mg, 0.076 mmol, 0.99 equiv), EDCI (30.00 mg, 0.156 mmol, 2.04 equiv), DMAP (38.00 mg, 0.311 mmol, 4.06 equiv). The resulting solution was stirred overnight at 30 degrees C. in an oil bath. The resulting mixture was concentrated under vacuum. The crude product was purified by Prep-HPLC with the following conditions (Prep-HPLC-006): Column, X Bridge Shield RP18 OBD Column, 5 um, 19*150 mm; mobile phase, Water (0.05% NH$_3$·H$_2$O) and ACN (40% Phase B up to 70% in 7 min); Detector, UV 254/220 nm. This resulted in 25 mg (34.27%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(11S,15S or 11R, 15R)-16-oxa-2,4,10-triazatetracyclo[7.7.0.0^[3,7].0[11,15]]hexadeca-1(9),2,5,7-tetraen-10-yl]benzamide (Assumed) as a yellow solid. LC-MS (ES, m/z): M+1=951, $^1$H NMR (300 MHz, DMSO-d$_6$, ppm) δ 12.90 (s, 1H), 11.21 (s, 1H), 8.54 (s, 1H), 8.35 (d, J=2.3 Hz, 1H), 7.75 (d, J=8.6 Hz, 1H), 7.46-7.30 (m, 3H), 7.18-6.99 (m, 3H), 6.93 (d, J=9.2 Hz, 1H), 6.80 (s, 2H), 6.49 (s, 1H), 6.07-5.99 (m, 1H), 4.33 (d, J=7.2 Hz, 1H), 3.79 (dd, J=9.9, 5.9 Hz, 4H), 3.73-3.33 (m, 7H), 3.27 (d, J=13.6 Hz, 4H), 3.12 (d, J=6.5 Hz, 1H), 2.75 (s, 2H), 2.20 (s, 6H), 1.97 (s, 2H), 1.83 (s, 2H), 1.68 (s, 1H), 1.40 (s, 3H), 0.94 (d, J=2.2 Hz, 6H).

Synthesis of methyl 4-(4-[[2-(4-chlorophenyl)-4,4-dimethylcyclohex-1-en-1-yl]methyl]piperazin-1-yl)-2-[(11R,15R)-4-[[2-(trimethylsilyl)ethoxy]methyl]-16-oxa-2,4,10-triazatetracyclo[7.7.0.0^[3,7].0[11,15]]hexadeca-1(9),2,5,7-tetraen-10-yl]benzoate (Assumed): Into a 40-mL vial purged and maintained with an inert atmosphere of nitrogen, was placed (11R,15R)-4-[[2-(trimethylsilyl)ethoxy]methyl]-16-oxa-2,4,10-triazatetracyclo[7.7.0.0^[3,7].0[11,15]]hexadeca-1(9),2,5,7-tetraene (Assumed) (400.00 mg, 1.158 mmol, 1.00 equiv), toluene (15 mL), methyl 2-bromo-4-(4-

[[2-(4-chlorophenyl)-4,4-dimethylcyclohex-1-en-1-yl] methyl]piperazin-1-yl)benzoate (1.23 g, 2.312 mmol, 2.00 equiv), Pd$_2$(dba)$_3$·CHCl$_3$ (239.00 mg, 0.231 mmol, 0.20 equiv), Xantphos (268.00 mg, 0.463 mmol, 0.40 equiv), Cs$_2$CO$_3$ (1.13 g, 3.468 mmol, 3.00 equiv). The resulting solution was stirred for 4 hr at 100 degrees C. in an oil bath. The reaction mixture was cooled to room temperature. The resulting mixture was concentrated under vacuum. The residue was applied onto a silica gel column with ethyl acetate/petroleum ether (1:2). This resulted in 680 mg (73.74%) of methyl 4-(4-([[2-4-chlorophenyl)-4,4-dimethylcyclohex-1-en-1-yl]methyl]piperazin-1-yl)-2-[(11R,15R)-4-[[2-(trimethylsilyl)ethoxy]ethyl]-16-oxa-2,4,10-triazatetracyclo[7.7.0.0ˆ[3,7].0ˆ[11,15]]hexadeca-1(9),2,5,7-tetraen-10-yl]benzoate (Assumed) as a yellow solid. LC-MS (ES, m/z): M+1=796.

Synthesis of methyl 4-(4-[[2-(4-chlorophenyl)-4,4-dimethylcyclohex-1-en-1-yl]methyl]piperazin-1-yl)-2-[(11R,15R)-16-oxa-2,4,10-triazatetracyclo[7.7.0.0ˆ[3,7].0[11,15]]hexadeca-1(9),2,5,7-tetraen-10-yl]benzoate (Assumed): Into a 40-mL vial, was placed methyl 4-(4-[[2-(4-chlorophenyl)-4,4-dimethylcyclohex-1-en-1-yl]ethyl]piperazin-1-yl)-2-[(11R,15R)-4-[[2-(trimethylsilyl)ethoxy]methyl]-16-oxa-2,4,10-triazatetracyclo[7.7.0.0ˆ[3,7].0ˆ[11,15]]hexadeca-1(9),2,5,7-tetraen-10-yl]benzoate (Assumed) (670.00 mg, 0.841 mmol, 1.00 equiv), TBAF in THF (10.00 mL, 1.0 M), ethylenediamine (1.30 g, 21.631 mmol, 25.72 equiv). The resulting solution was stirred for 8 hr at 70 degrees C. in an oil bath. The reaction mixture was cooled to room temperature. The resulting mixture was concentrated under vacuum. The residue was applied onto a silica gel column with ethyl acetate/petroleum ether (2:1). This resulted in 320 mg (57.10%) of methyl 4-(4-[[2-(4-chlorophenyl)-4,4-dimethylcyclohex-1-en-1-yl]methyl]piperazin-1-yl)-2-[(11R,15R)-16-oxa-2,4,10-triazatetracyclo[7.7.0.0ˆ[3,7].0ˆ[11,15]]hexadeca-1(9),2,5,7-tetraen-10-yl]benzoate (Assumed) as a yellow solid. LC-MS (ES, m/z): M+1=666.

Synthesis of 4-(4-[[2-(4-chlorophenyl)-4,4-dimethylcyclohex-1-en-1-yl]methyl]piperazin-1-yl)-2-[(11R,15R)-16-oxa-2,4,10-triazatetracyclo[7.7.0.0ˆ[3,7].0[11,15]]hexadeca-1(9),2,5,7-tetraen-10-yl]benzoic acid (Assumed): Into a 40-mL vial, was placed methyl 4-(4-[[2-(4-chlorophenyl)-4,4-dimethylcyclohex-1-en-1-yl]methyl]piperazin-1-yl)-2-[(11R,15R)-16-oxa-2,4,10-triazatetracyclo[7.7.0.0ˆ[3,7].0[11,15]]hexadeca-1(9),2,5,7-tetraen-10-yl]benzoate (Assumed) (140.00 mg, 0.210 mmol, 1.00 equiv), dioxane (3.00 mL), MeOH (3.00 mL), NaOH (0.60 mL, 2.400 mmol, 11.42 equiv). The resulting solution was stirred for 4 hr at 70 degrees C. in an oil bath. The reaction mixture was cooled to room temperature. The resulting mixture was concentrated under vacuum. The pH value of the solution was adjusted to 6-7 with HCl (2 mol/L). The resulting solution was extracted with 3×50 mL of ethyl acetate and the organic layers combined. The resulting mixture was washed with 1×300 ml of brine. The mixture was dried over anhydrous sodium sulfate and concentrated under vacuum. The residue was purified by Prep-TLC with ethyl acetate. This resulted in 80 mg (58.37%) of 4-(4-[[2-(4-chlorophenyl)-4,4-dimethylcyclohex-1-en-1-yl]methyl]piperazin-1-yl)-2-[(11R,15R)-16-oxa-2,4,10-triazatetracyclo[7.7.0.0ˆ[3,7]0.0[11,15]]hexadeca-1(9),2,5,7-tetraen-10-yl]benzoic acid (Assumed) as a white solid. LC-MS (ES, m/z): M+1=652.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(11R,15R or 11S, 15S)-16-oxa-2,4,10-triazatetracyclo[7.7.0.0ˆ[3,7].0[11,15]]hexadeca-1(9),2,5,7-tetraen-10-yl] benzamide: Into a 40-mL vial, was placed 4-(4-[[2-(4-chlorophenyl)-4,4-dimethylcyclohex-1-en-1-yl]methyl] piperazin-1-yl)-2-[(11R,15R)-16-oxa-2,4,10-triazatetracyclo[7.7.0.0ˆ[3,7].0ˆ[11,15]]hexadeca-1(9),2,5, 7-tetraen-10-yl]benzoic acid (20.00 mg, 0.031 mmol, 1.00 equiv), DCM (5.00 mL), 4-[[(2S)-1,4-dioxan-2-ylmethyl] amino]-3-nitrobenzenesulfonamide (Assumed) (9.70 mg, 0.031 mmol, 1.00 equiv), EDCI (12.00 mg, 0.063 mmol, 2.04 equiv), DMAP (15.00 mg, 0.123 mmol, 4.00 equiv). The resulting solution was stirred overnight at 30 degrees C. in an oil bath. The resulting mixture was concentrated under vacuum. The crude product was purified by Prep-HPLC with the following conditions (Prep-HPLC-006): Column, X Bridge Shield RP18 OBD Column, 5 um, 19*150 mm; mobile phase, Water (0.05% NH$_3$·H$_2$O) and ACN (40% Phase B up to 70% in 7 min); Detector, UV 254/220 nm. This resulted in 4.7 mg (16.11%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(11R,15R or 11S, 15S)-16-oxa-2,4,10-triazatetracyclo[7.7.0.0ˆ[3,7].0[11,15]]hexadeca-1(9),2,5,7-tetraen-10-yl]benzamide (Assumed) as a yellow solid. LC-MS (ES, m/z): M+1=951, $^1$H NMR (300 MHz, DMSO-d$_6$, ppm) δ 12.90 (s, 1H), 11.21 (s, 1H), 8.54 (s, 1H), 8.35 (d, J=2.3 Hz, 1H), 7.75 (d, J=8.6 Hz, 1H), 7.46-7.30 (m, 3H), 7.18-6.99 (m, 3H), 6.93 (d, J=9.2 Hz, 1H), 6.80 (s, 2H), 6.49 (s, 1H), 6.07-5.99 (m, 1H), 4.33 (d, J=7.2 Hz, 1H), 3.79 (dd, J=9.9, 5.9 Hz, 4H), 3.73-3.33 (m, 7H), 3.27 (d, J=13.6 Hz, 4H), 3.12 (d, J=6.5 Hz, 1H), 2.75 (s, 2H), 2.20 (s, 6H), 1.97 (s, 2H), 1.83 (s, 2H), 1.68 (s, 1H), 1.40 (s, 3H), 0.94 (d, J=2.2 Hz, 6H).

Example 45

Preparation of 4-(4-[[2-(4-chlorophenyl)-4,4-dimethylcycloohex-1-en-1-yl]methyl]piperazin-1-yl)-2-[(11R,15S)-13,16-dioxa-2,4,10-triazatetracyclo [7.7.0.0ˆ[3,7]. 0ˆ[11,15]]hexadeca-1(9),2,5,7-tetraen-10-yl]-N-(4-[[(2S)-1,4-dioxan-2-ylmethyl]amino]-3-nitrobenzenesulfonyl)benzamide (assumed) and 4-(4-[[2-(4-chlorophenyl)-4,4-dimethylcycloohex-1-en-1-yl]ethyl]piperazin-1-yl)-2-[(11S,15R)-13,16-dioxa-2,4,10-triazatetracyclo[7.7.0.0ˆ[3,7].0ˆ[11,15]] hexadeca-1(9),2,5,7-tetraen-10-yl]-N-(4-[[(2S)-1,4-dioxan-2-ylmethyl]amino]-3-nitrobenzenesulfonyl) benzamide (Assumed Synthesis of N-[(trans)-4-hydroxyoxolan-3-yl]-4-methylbenzenesulfonamide: Into a 250-mL round-bottom flask purged and maintained with an inert atmosphere of nitrogen, was placed 3,6-dioxabicyclo[3.1.0]hexane (5.00 g, 58.079 mmol, 1.00 equiv), dioxane (100.00 mL), p-toluenesulfonamide (11.93 g, 69.681 mmol, 1.20 equiv), TEBAC (1.33 g, 5.833 mmol, 0.10 equiv), K$_2$CO$_3$ (0.80 g, 5.788 mmol, 0.10 equiv). The resulting solution was stirred for 3 days at 90 degrees C. in an oil bath. The reaction mixture was cooled to room temperature. The solids were filtered out. The resulting mixture was concentrated under vacuum. The residue was applied onto a silica gel column with ethyl acetate/petroleum ether (2:1). This resulted in 10.69 g (25.75%) of N-[(trans)-4-hydroxyoxolan-3-yl]-4-methylbenzenesulfonamide as a white solid. LC-MS: (ES, m/z): M+1=258.

Synthesis of N-[(trans)-4-[(5-bromo-1-[[2-(trimethylsilyl)ethoxy]methyl]pyrrolo[2,3-b]pyridin-6-yl)oxy]oxolan-3-yl]-4-methylbenzenesulfonamide: Into a 250-mL round-bottom flask purged and maintained with an inert atmosphere of nitrogen, was placed N-[(trans)-4-hydroxyoxolan-3-yl]-4-methylbenzenesulfonamide (10.50 g, 14.691 mmol, 1.30 equiv, 36%), THF (100 mL). This was followed by the addition of NaH (2.71 g, 67.756 mmol, 6.01 equiv, 60%), in portions at 0 degrees C. The resulting solution was stirred for 30 min at 0 degrees C. To this was added 5-bromo-6-fluoro-1-[[2-(trimethylsilyl)ethoxy]methyl]pyrrolo[2,3-b]pyridine (3.89 g, 11.266 mmol, 1.00 equiv) at 0 degrees C. The resulting solution was stirred for 4 hr at 70 degrees C. in an oil bath. The reaction mixture was cooled to room temperature. The reaction was then quenched by the addition of 500 mL of aqueous NH₄Cl. The resulting solution was extracted with 3×300 mL of ethyl acetate and the organic layers combined. The resulting mixture was washed with 1×1500 mL of brine. The mixture was dried over anhydrous sodium sulfate and concentrated under vacuum. The residue was applied onto a silica gel column with ethyl acetate/petroleum ether (1:2). This resulted in 3 g (45.71%) of N-[(trans)-4-[(5-bromo-1-[[2-(trimethylsilyl)ethoxy]methyl]pyrrolo[2,3-b]pyridin-6-yl)oxy]oxolan-3-yl]-4-methylbenzenesulfonamide as light yellow oil. $^1$H NMR (300 MHz, Chloroform-d, ppm) δ 8.04 (s, 1H), 7.78-7.61 (m, 2H), 7.25-7.10 (m, 3H), 6.43 (d, J=3.6 Hz, 1H), 5.67 (d, J=10.8 Hz, 1H), 5.60 (d, J=5.7 Hz, 1H), 5.49 (d, J=10.8 Hz, 1H), 5.40 (dt, J=6.1, 3.1 Hz, 1H), 4.27 (dd, J=10.5, 5.9 Hz, 1H), 4.21-4.03 (m, 1H), 4.03-3.86 (m, 2H), 3.70-3.52 (m, 3H), 2.32 (s, 3H), 0.93 (ddt, J=10.6, 5.5, 2.6 Hz, 2H), −0.02 (s, 9H).

Synthesis of (trans)-10-(4-methylbenzenesulfonyl)-4-[[2-(trimethylsilyl)ethoxy]methyl]-13,16-dioxa-2,4,10-triazatetracyclo[7.7.0.0ˆ[3,7].0[11,15]]hexadeca-1(9),2,5,7-tetraene: Into a 250-mL round-bottom flask purged and maintained with an inert atmosphere of nitrogen, was placed N-[(trans)(3S,4R)-4-[(5-bromo-1-[[2-(trimethylsilyl)ethoxy]methyl]pyrrolo[2,3-b]pyridin-6-yl)oxy]oxolan-3-yl]-4-methylbenzenesulfonamide (3.00 g, 5.149 mmol, 1.00 equiv), DMF (50.00 mL), phen (743.00 mg, 4.123 mmol, 0.80 equiv), CuI (785.00 mg, 4.122 mmol, 0.80 equiv), K₂CO₃ (2.14 g, 15.484 mmol, 3.01 equiv). The resulting solution was stirred for 2 days at 120 degrees C. in an oil bath. The reaction mixture was cooled to room temperature. The resulting solution was diluted with 500 mL of water. The resulting solution was extracted with 3×200 mL of ethyl acetate and the organic layers combined. The resulting mixture was washed with 1×1000 mL of brine. The mixture was dried over anhydrous sodium sulfate and concentrated under vacuum. The residue was applied onto a silica gel column with ethyl acetate/petroleum ether (1:2). This resulted in 2.5 g (82.26%) of (trans)-10-(4-methylbenzenesulfonyl)-4-[[2-(trimethylsilyl)ethoxy]methyl]-13,16-dioxa-2,4,10-triazatetracyclo[7.7.0.0ˆ[3,7].0[11,15]]hexadeca-1(9),2,5,7-tetraene as yellow oil. LC-MS: (ES, m/z) M+1=502.

Synthesis of (11S,15R)-4-[[2-(trimethylsilyl)ethoxy]methyl]-13,16-dioxa-2,4,10-triazatetracyclo[7.7.0.0ˆ[3,7].0ˆ[11,15]]hexadeca-1(9),2,5,7-tetraene (assumed) and (11R,15S)-4-[[2-(trimethylsilyl)ethoxy]methyl]-13,16-dioxa-2,4,10-triazatetracyclo[7.7.0.0ˆ[3,7].0ˆ[11,15]]hexadeca-1(9),2,5,7-tetraene (assumed): Into a 100-mL round-bottom flask, was placed Mg (2.04 g, 83.933 mmol, 19.81 equiv), MeOH (30.00 mL), (trans)-10-(4-methylbenzenesulfonyl)-4-[[2-(trimethylsilyl)ethoxy]methyl]-13,16-dioxa-2,4,10-triazatetracyclo[7.7.0.0ˆ[3,7].0[11,15]]hexadeca-1(9),2,5,7-tetraene (2.50 g, 4.236 mmol, 1.00 equiv, 85%). The resulting solution was stirred for 2 hr at 60 degrees C. in an oil bath. The reaction mixture was cooled to room temperature. The resulting solution was diluted with 300/300 mL of NaHCO₃ and CH₂Cl₂. The solids were filtered out and the organic was separated. The mixture was dried over anhydrous sodium sulfate and concentrated under vacuum. The residue was applied onto a silica gel column with ethyl acetate/petroleum ether (1:3). The crude product was purified by Chiral-Prep-HPLC with the following conditions: Mobile phase: A: n-Hexane (0.1% DEA) B: ETOH; Flow rate: 20 mL/min; Column: DAICEL CHIRALPAK IA, 250*20 mm, 5 um; Gradient: 12% B in 20 min; 220 nm. This resulted in 350 mg (23.78%) of (11R,15S)-4-[[2-(trimethylsilyl)ethoxy]methyl]-13,16-dioxa-2,4,10-triazatetracyclo[7.7.0.0ˆ[3,7].0[11,15]]hexadeca-1(9),2,5,7-tetraene (assumed) as yellow oil and 400 mg (27.18%) of (11S,15R)-4-[[2-(trimethylsilyl)ethoxy]methyl]-13,16-dioxa-2,4,10-triazatetracyclo[7.7.0.0ˆ[3,7].0[11,15]]hexadeca-1(9),2,5,7-tetraene (assumed) as yellow oil. Peak 1: LC-MS: (ES, m/z) M+1=348. $^1$H NMR (300 MHz, Chloroform-d, ppm) δ 7.39 (s, 1H), 7.21 (d, J=3.6 Hz, 1H), 6.37 (d, J=3.6 Hz, 1H), 5.57 (s, 2H), 4.60 (dt, J=10.1, 7.6 Hz, 1H), 4.39-4.22 (m, 2H), 3.94 (dd, J=9.9, 7.9 Hz, 1H), 3.86-3.69 (m, 2H), 3.64-3.45 (m, 2H), 0.91 (dd, J=8.8, 7.5 Hz, 2H), −0.04 (s, 9H). Peak 2: LC-MS: (ES, m/z) M+1=348. $^1$H NMR (300 MHz, Chloroform-d, ppm) δ 7.39 (s, 1H), 7.21 (d, J=3.6 Hz, 1H), 6.37 (d, J=3.6 Hz, 1H), 5.57 (s, 2H), 4.60 (dt, J=10.1, 7.6 Hz, 1H), 4.39-4.22 (m, 2H), 3.94 (dd, J=9.9, 7.9 Hz, 1H), 3.86-3.69 (m, 2H), 3.64-3.45 (m, 2H), 0.91 (dd, J=8.8, 7.5 Hz, 2H), −0.04 (s, 9H).

Synthesis of methyl 4-(4-[[2-(4-chlorophenyl)-4,4-dimethylcyclohex-1-en-1-yl]methyl]piperazin-1-yl)-2-[(11R,15S)-4-[[2-(trimethylsilyl)ethoxy]methyl]-13,16-dioxa-2,4,10-triazatetracyclo[7.7.0.0ˆ[3,7].0[11,15]]hexadeca-1(9),2,5,7-tetraen-10-yl]benzoate (assumed): Into a 40-mL vial purged and maintained with an inert atmosphere of nitrogen, was placed (11R,15S)-4-[[2-(trimethylsilyl)ethoxy]methyl]-13,16-dioxa-2,4,10-triazatetracyclo[7.7.0.0ˆ[3,7].0[11,15]]hexadeca-1(9),2,5,7-tetraene (assumed) (350.00 mg, 1.007 mmol, 1.00 equiv), toluene (15.00 mL), methyl 2-bromo-4-(4-[[2-(4-chlorophenyl)-4,4-dimethylcyclohex-1-en-1-yl]methyl]piperazin-1-yl)benzoate (1.07 g, 2.012 mmol, 2.00 equiv), Pd₂(dba)₃.CHCl₃ (208.00 mg, 0.201 mmol, 0.20 equiv), Xantphos (234.00 mg, 0.404 mmol, 0.40 equiv), Cs₂CO₃ (985.00 mg, 3.023 mmol, 3.00 equiv). The resulting solution was stirred for 3 hr at 100 degrees C. in an oil bath. The reaction mixture was cooled to room temperature. The resulting mixture was concentrated under vacuum. The residue was applied onto a silica gel column with ethyl acetate/petroleum ether (1:2). This resulted in 720 mg (89.52%) of methyl 4-(4-[[2-(4-chlorophenyl)-4,4-dimethylcyclohex-1-en-1-yl]methyl]piperazin-1-yl)-2-[(11R,15S)-4-[[2-(trimethylsilyl)ethoxy]ethyl]-13,16-dioxa-2,4,10-triazatetracyclo[7.7.0.0ˆ[3,7].0ˆ[11,15]]hexadeca-1(9),2,5,7-tetraen-10-yl]benzoate (assumed) as a yellow solid. LC-MS: (ES, m/z) M+1=798.

Synthesis of methyl 4-(4-[[2-(4-chlorophenyl)-4,4-dimethylcyclohex-1-en-1-yl]methyl]piperazin-1-yl)-2-[(11R,15S)-13,16-dioxa-2,4,10-triazatetracyclo[7.7.0.0ˆ[3,7].0ˆ[11,15]]hexadeca-1(9),2,5,7-tetraen-10-yl]benzoate (assumed): Into a 40-mL vial, was placed methyl 4-(4-[[2-(4-chlorophenyl)-4,4-dimethylcyclohex-1-en-1-yl]methyl]piperazin-1-yl)-2-[(11R,15S)-4-[[2-(trimethylsilyl)ethoxy]methyl]-13,16-dioxa-2,4,10-triazatetracyclo[7.7.0.0ˆ[3,7].0ˆ[11,15]]hexadeca-1(9),2,5,7-tetraen-10-yl]benzoate (assumed) (720.00 mg, 0.902 mmol, 1.00 equiv), 1.0 M TBAF/THF (15.00 mL), ethylenediamine (1.30 g, 21.631 mmol, 23.99 equiv). The resulting solution was stirred for 8 hr at 70 degrees C. in an oil bath. The reaction mixture was cooled to room temperature. The resulting mixture was concentrated under vacuum. The residue was applied onto a silica gel column with ethyl acetate/petroleum ether (2:1). This resulted in 350 mg (58.09%) of methyl 4-(4-[[2-(4-chlorophenyl)-4,4-dimethylcyclohex-1-en-1-yl]methyl]piperazin-1-yl)-2-[(11R,15S)-13,16-dioxa-2,4,10-triazatetracyclo[7.7.0.0^[3,7].0^[11,15]]hexadeca-1(9),2,5,7-tetraen-10-yl]benzoate (assumed) as a light yellow solid. LC-MS: (ES, m/z) M+1=668.

Synthesis of 4-(4-[[2-(4-chlorophenyl)-4,4-dimethylcyclohex-1-en-1-yl]methyl]piperazin-1-yl)-2-[(11R,15S)-13,16-dioxa-2,4,10-triazatetracyclo[7.7.0.0^[3,7].0^[11,15]]hexadeca-1(9),2,5,7-tetraen-10-yl]benzoic acid (assumed): Into a 40-mL vial, was placed methyl 4-(4-[[2-(4-chlorophenyl)-4,4-dimethylcyclohex-1-en-1-yl]methyl]piperazin-1-yl)-2-[(11R,15S)-13,16-dioxa-2,4,10-triazatetracyclo[7.7.0.0^[3,7].0^[11,15]]hexadeca-1(9),2,5,7-tetraen-10-yl]benzoate (assumed) (150.00 mg, 0.224 mmol, 1.00 equiv), dioxane (3.00 mL), MeOH (3.00 mL), NaOH (0.60 mL, 2.400 mmol, 10.69 equiv). The resulting solution was stirred for 4 hr at 70 degrees C. in an oil bath. The reaction mixture was cooled to room temperature. The resulting mixture was concentrated under vacuum. The pH value of the solution was adjusted to 5-6 with HCl (2 mol/L). The resulting solution was extracted with 3×50 mL of ethyl acetate and the organic layers combined. The resulting mixture was washed with 1×300 mL of brine. The mixture was dried over anhydrous sodium sulfate and concentrated under vacuum. The residue was purified by Prep-TLC with dichloromethane/methanol (10:1). This resulted in 80 mg (54.48%) of 4-(4-[[2-(4-chlorophenyl)-4,4-dimethylcyclohex-1-en-1-yl]ethyl]piperazin-1-yl)-2-[(11R,15S)-13,16-dioxa-2,4,10-triazatetracyclo[7.7.0.0^[3,7].0^[11,15]]hexadeca-1(9),2,5,7-tetraen-10-yl]benzoic acid (assumed) as a white solid. LC-MS: (ES, m/z) M+1=654.

Synthesis of 4-(4-[[2-(4-chlorophenyl)-4,4-dimethylcyclohex-1-en-1-yl]methyl]piperazin-1-yl)-2-[(11R,15S)-13,16-dioxa-2,4,10-triazatetracyclo[7.7.0.0^[3,7].0^[11,15]]hexadeca-1(9),2,5,7-tetraen-10-yl]-N-(4-[[(2S)-1,4-dioxan-2-ylmethyl]amino]-3-nitrobenzenesulfonyl)benzamide (assumed): Into a 40-mL vial, was placed 4-(4-[[2-(4-chlorophenyl)-4,4-dimethylcyclohex-1-en-1-yl]methyl]piperazin-1-yl)-2-[(11R,15S)-13,16-dioxa-2,4,10-triazatetracyclo[7.7.0.0^[3,7].0^[11,15]]hexadeca-1(9),2,5,7-tetraen-10-yl]benzoic acid (assumed) (50.00 mg, 0.076 mmol, 1.00 equiv), DCM (5.00 mL), 4-[[(2S)-1,4-dioxan-2-ylmethyl]amino]-3-nitrobenzenesulfonamide (24.00 mg, 0.076 mmol, 0.99 equiv), EDCI (29.00 mg, 0.151 mmol, 1.98 equiv), DMAP (37.00 mg, 0.303 mmol, 3.96 equiv). The resulting solution was stirred overnight at 30 degrees C. in an oil bath. The resulting mixture was concentrated under vacuum. The crude product was purified by Prep-HPLC with the following conditions (Prep-HPLC-006): Column, XBridge Shield RP18 OBD Column, 5 um, 19*150 mm; mobile phase, Water (0.05% NH$_3$·H$_2$O) and ACN (40% Phase B up to 70% in 7 min); Detector, UV 254/220 nm. This resulted in 25 mg (34.31%) of 4-(4-[[2-(4-chlorophenyl)-4,4-dimethylcyclohex-1-en-1-yl]methyl]piperazin-1-yl)-2-[(11R,15S)-13,16-dioxa-2,4,10-triazatetracyclo[7.7.0.0^[3,7].0^[11,15]]hexadeca-1(9),2,5,7-tetraen-10-yl]-N-(4-[[(2S)-1,4-dioxan-2-ylmethyl]amino]-3-nitrobenzenesulfonyl)benzamide (assumed) as a yellow solid. LC-MS: (ES, m/z) M+1=953. $^1$H NMR (300 MHz, DMSO-d$_6$, ppm) δ 12.27 (s, 1H), 11.05 (d, J=66.1 Hz, 1H), 8.42 (d, J=30.6 Hz, 1H), 8.32 (d, J=2.3 Hz, 1H), 7.57 (s, 1H), 7.36 (dd, J=8.4, 4.1 Hz, 3H), 7.08 (ddd, J=14.1, 5.9, 2.6 Hz, 3H), 6.78 (t, J=29.3 Hz, 3H), 6.57 (s, 1H), 6.06-5.94 (m, 1H), 4.45 (dd, J=98.7, 9.1 Hz, 3H), 3.96-3.34 (m, 12H), 3.19 (d, J=16.7 Hz, 4H), 2.81-2.71 (m, 2H), 2.24 (d, J=19.4 Hz, 6H), 1.98 (s, 2H), 1.41 (s, 2H), 0.94 (s, 6H).

Synthesis of methyl 4-(4-[[2-(4-chlorophenyl)-4,4-dimethylcyclohex-1-en-1-yl]methyl]piperazin-1-yl)-2-[(11S,15R)-4-[[2-(trimethylsilyl)ethoxy]methyl]-13,16-dioxa-2,4,10-triazatetracyclo[7.7.0.0^[3,7].0[11,15]]hexadeca-1(9),2,5,7-tetraen-10-yl]benzoate (assumed): Into a 40-mL vial purged and maintained with an inert atmosphere of nitrogen, was placed (11S,15R)-4-[[2-(trimethylsilyl)ethoxy]methyl]-13,16-dioxa-2,4,10-triazatetracyclo[7.7.0.0^[3,7].0[11,15]]hexadeca-1(9),2,5,7-tetraene (assumed) (400.00 mg, 1.151 mmol, 1.00 equiv), toluene (15.00 mL), methyl 2-bromo-4-(4-[[2-(4-chlorophenyl)-4,4-dimethylcyclohex-1-en-1-yl]methyl]piperazin-1-yl)benzoate (1.22 g, 2.294 mmol, 1.99 equiv), Pd$_2$(dba)$_3$·CHCl$_3$ (237.00 mg, 0.229 mmol, 0.20 equiv), Xantphos (266.00 mg, 0.460 mmol, 0.40 equiv), Cs$_2$CO$_3$ (1.12 g, 3.437 mmol, 2.99 equiv). The resulting solution was stirred for 3 hr at 100 degrees C. in an oil bath. The reaction mixture was cooled to room temperature. The resulting mixture was concentrated under vacuum. The residue was applied onto a silica gel column with ethyl acetate/petroleum ether (1:2). This resulted in 820 mg (89.21%) of methyl 4-(4-[[2-(4-chlorophenyl)-4,4-dimethylcyclohex-1-en-1-yl]methyl]piperazin-1-yl)-2-[(11S,15R)-4-[[2-(trimethylsilyl)ethoxy]ethyl]-13,16-dioxa-2,4,10-triazatetracyclo[7.7.0.0^[3,7].0^[11,15]]hexadeca-1(9),2,5,7-tetraen-10-yl]benzoate (assumed) as a yellow solid. LC-MS: (ES, m/z) M+1=798.

Synthesis of methyl 4-(4-[[2-(4-chlorophenyl)-4,4-dimethylcyclohex-1-en-1-yl]methyl]piperazin-1-yl)-2-[(11S,15R)-13,16-dioxa-2,4,10-triazatetracyclo[7.7.0.0^[3,7].0[11,15]]hexadeca-1(9),2,5,7-tetraen-10-yl]benzoate (assumed): Into a 40-mL vial, was placed methyl 4-(4-[[2-(4-chlorophenyl)-4,4-dimethylcyclohex-1-en-1-yl]methyl]piperazin-1-yl)-2-[(11S,15R)-4-[[2-(trimethylsilyl)ethoxy]methyl]-13,16-dioxa-2,4,10-triazatetracyclo[7.7.0.0^[3,7].0[11,15]]hexadeca-1(9),2,5,7-tetraen-10-yl]benzoate (assumed) (820.00 mg, 1.027 mmol, 1.00 equiv), TBAF in THF (15.00 mL), ethylenediamine (1.30 g, 21.631 mmol, 21.06 equiv). The resulting solution was stirred for 8 hr at 70 degrees C. in an oil bath. The reaction mixture was cooled to room temperature. The resulting mixture was concentrated under vacuum. The residue was applied onto a silica gel column with ethyl acetate/petroleum ether (2:1). This resulted in 380 mg (55.37%) of methyl 4-(4-[[2-(4-chlorophenyl)-4,4-dimethylcyclohex-1-en-1-yl]methyl]piperazin-1-yl)-2-[(11S,15R)-13,16-dioxa-2,4,10-triazatetracyclo[7.7.0.0^[3,7].0^[11,15]]hexadeca-[(9),2,5,7-tetraen-10-yl]benzoate (assumed) as a light yellow solid. LC-MS: (ES, m/z) M+1=668.

Synthesis of 4-(4-[[2-(4-chlorophenyl)-4,4-dimethylcyclohex-1-en-1-yl]methyl]piperazin-1-yl)-2-[(11S,15R)-13,16-dioxa-2,4,10-triazatetracyclo[7.7.0.0^[3,7].0^[11,15]]hexadeca-1(9),2,5,7-tetraen-10-yl]benzoic acid (assumed): Into a 40-mL vial, was placed methyl 4-(4-[[2-(4-chlorophenyl)-4,4-dimethylcyclohex-1-en-1-yl]methyl]piperazin-1-yl)-2-[(11S,15R)-13,16-dioxa-2,4,10-triazatetracyclo[7.7.0.0^[3,7].0^[11,15]]hexadeca-1(9),2,5,7-tetraen-10-yl]benzoate (assumed) (150.00 mg, 0.224 mmol, 1.00 equiv), dioxane (3.00 mL), MeOH (3.00 mL), NaOH (0.60 mL, 2.400 mmol, 10.69 equiv). The resulting solution was stirred for 4 hr at 70 degrees C. in an oil bath. The reaction mixture was cooled to room temperature. The resulting mixture was concentrated under vacuum. The pH value of the solution was adjusted to 5-6 with HCl (2 mol/L). The resulting solution was extracted with 3×50 mL of ethyl acetate and the organic layers combined. The resulting mixture was washed with 1×300 mL of brine. The mixture was dried over anhydrous sodium sulfate and concentrated under vacuum. The residue was purified by Prep-TLC with dichloromethane/methanol (10:1). This resulted in 80 mg (54.48%) of 4-(4-[[2-(4-chlorophenyl)-4,4-dimethylcyclohex-1-en-1-yl]ethyl]piperazin-1-yl)-2-[(11S,15R)-13,16-dioxa-2,4,10-triazatetracyclo[7.7.0.0^[3,7].0^[11,15]]hexadeca-1(9),2,5,7-tetraen-10-yl]benzoic acid (assumed) as a white solid. LC-MS: (ES, m/z) M+1=654.

Synthesis of 4-(4-[[2-(4-chlorophenyl)-4,4-dimethylcyclohex-1-en-1-yl]methyl]piperazin-1-yl)-2-[(11S,15R)-13,16-dioxa-2,4,10-triazatetracyclo[7.7.0.0^[3,7].0^[11,15]]hexadeca-1(9),2,5,7-tetraen-10-yl]-N-(4-[[(2S)-1,4-dioxan-2-ylmethyl]amino]-3-nitrobenzenesulfonyl)benzamide (assumed): Into a 40-mL vial, was placed 4-(4-[[2-(4-chlorophenyl)-4,4-dimethylcyclohex-1-en-1-yl]methyl]piperazin-1-yl)-2-[(11S,15R)-13,16-dioxa-2,4,10-triazatetracyclo[7.7.0.0^[3,7].0[11,15]]hexadeca-1(9),2,5,7-tetraen-10-yl]benzoic acid (assumed) (50.00 mg, 0.076 mmol, 1.00 equiv), DCM (5.00 mL), 4-[[(2S)-1,4-dioxan-2-ylmethyl]amino]-3-nitrobenzenesulfonamide (24.00 mg, 0.076 mmol, 0.99 equiv), EDCI (29.00 mg, 0.151 mmol, 1.98 equiv), DMAP (37.00 mg, 0.303 mmol, 3.96 equiv). The resulting solution was stirred overnight at 30 degrees C. in an oil bath. The resulting mixture was concentrated under vacuum. The crude product was purified by Prep-HPLC with the following conditions (Prep-HPLC-006): Column, XBridge Shield RP18 OBD Column, 5 um, 19*150 mm; mobile phase, Water (0.05% $NH_3 \cdot H_2O$) and ACN (40% Phase B up to 70% in 7 min); Detector, UV 254/220 nm. This resulted in 25 mg (34.31%) of 4-(4-[[2-(4-chlorophenyl)-4,4-dimethylcyclohex-1-en-1-yl]methyl]piperazin-1-yl)-2-[(11S,15R)-13,16-dioxa-2,4,10-triazatetracyclo[7.7.0.0^[3,7].0^[11,15]]hexadeca-1(9),2,5,7-tetraen-10-yl]-N-(4-[[(2S)-1,4-dioxan-2-ylmethyl]amino]-3-nitrobenzenesulfonyl)benzamide (assumed) as a yellow solid. LC-MS: (ES, m/z) M+1=953. $^1$H NMR (300 MHz, DMSO-$d_6$, ppm) δ 12.27 (s, 1H), 11.05 (d, J=66.1 Hz, 1H), 8.42 (d, J=30.6 Hz, 1H), 8.32 (d, J=2.3 Hz, 1H), 7.57 (s, 1H), 7.36 (dd, J=8.4, 4.1 Hz, 3H), 7.08 (ddd, J=14.1, 5.9, 2.6 Hz, 3H), 6.78 (t, J=29.3 Hz, 3H), 6.57 (s, 1H), 6.06-5.94 (m, 1H), 4.45 (dd, J=98.7, 9.1 Hz, 3H), 3.96-3.34 (m, 12H), 3.19 (d, J=16.7 Hz, 4H), 2.81-2.71 (m, 2H), 2.24 (d, J=19.4 Hz, 6H), 1.98 (s, 2H), 1.41 (s, 2H), 0.94 (s, 6H).

Example 46

Preparation of 4-(4-[[2-(4-chlorophenyl)-4,4-dimethylcyclohex-1-en-1-yl]methyl]piperazin-1-yl)-N-[(3S or 3R)-5-nitro-3-(oxan-4-yl)-3,4-dihydro-2H-1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide & 4-(4-[[2-(4-chlorophenyl)-4,4-dimethylcyclohex-1-en-1-yl]methyl]piperazin-1-yl)-N-[(3R or 3S)-5-nitro-3-(oxan-4-yl)-3,4-dihydro-2H-1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide Synthesis of 4-(4-[[2-(4-chlorophenyl)-4,4-dimethylcyclohex-1-en-1-yl]methyl]piperazin-1-yl)-N-[(3S)-5-nitro-3-(oxan-4-yl)-3,4-dihydro-2H-1,4-benzoxazin-7-ylsulfonyl]-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide (Assumed) Into a 8-mL vial, was placed 4-(4-[[2-(4-chlorophenyl)-4,4-dimethylcyclohex-1-en-1-yl]methyl]piperazin-1-yl)-2-(4-[[2-(trimethylsilyl)ethoxy]ethyl]-14-oxa-2,4,10-triazatricyclo[7.5.0.0^[3,7]]tetradeca-1(9),2,5,7-tetraen-10-yl)benzoic acid (25.00 mg, 0.033 mmol, 1.00 equiv), (3S)-5-nitro-3-(oxan-4-yl)-3,4-dihydro-2H-1,4-benzoxazine-7-sulfonamide (11.35 mg, 0.033 mmol, 1.00 equiv), EDCI (12.67 mg, 0.066 mmol, 2.00 equiv), DMAP (12.11 mg, 0.099 mmol, 3.00 equiv), DCM (1.00 mL). The resulting solution was stirred for 14 hr at 35 degrees C. in an oil bath. The resulting mixture was concentrated. The residue was purified by Prep-TLC with dichloromethane/methanol (10:1). This resulted in 22 mg (61.53%) of 4-(4-[[2-(4-chlorophenyl)-4,4-dimethylcyclohex-1-en-1-yl]methyl]piperazin-1-yl)-N-[(3S)-5-nitro-3-(oxan-4-yl)-3,4-dihydro-2H-1,4-benzoxazin-7-ylsulfonyl]-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide as a yellow solid.

LC-MS (ES, m/z): 1081 [M+H].

Synthesis of 4-(4-[[2-(4-chlorophenyl)-4,4-dimethylcyclohex-1-en-1-yl]methyl]piperazin-1-yl)-N-[(3S)-5-nitro-3-(oxan-4-yl)-3,4-dihydro-2H-1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide Into a 8-mL vial, was placed 4-(4-[[2-(4-chlorophenyl)-4,4-dimethylcyclohex-1-en-1-yl]methyl]piperazin-1-yl)-N-[(3S)-5-nitro-3-(oxan-4-yl)-3,4-dihydro-2H-1,4-benzoxazin-7-ylsulfonyl]-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide (20.00 mg, 0.018 mmol, 1.00 equiv), ethane-1,2-diamine (0.20 mL), TBAF in THF (1 ml, 2M). The resulting solution was stirred for 48 hr at 70 degrees C. in an oil bath. The resulting mixture was concentrated. The residue was purified by Prep-TLC with dichloromethane/methanol (10:1). The crude product was purified by Prep-HPLC with the following conditions: Column, X Bridge Prep C18 OBD 19*150 mm 5 um; mobile phase, A: 0.1% $NH_3$—$H_2O$ in water; B: ACN; Gradient: 6-85% B in 7.9 min; Flow rate: 20 ml/min; Detector, 220 nm. This resulted in 6 mg (34.11%) of 4-(4-[[2-(4-chlorophenyl)-4,4-dimethylcyclohex-1-en-1-yl]ethyl]piperazin-1-yl)-N-[(3S)-5-nitro-3-(oxan-4-yl)-3,4-dihydro-2H-1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide as a yellow solid.

LC-MS (ES, m/z): 951.4 [M+H] $^1$H NMR (300 MHz, CDCl$_3$, ppm): δ 12.22 (s, 1H), 8.73 (s, 1H), 8.47 (d, J=2.1 Hz, 1H), 8.37 (s, 1H), 8.00 (d, J=9.6 Hz, 1H), 7.50 (s, 1H), 7.27 (s, 1H), 7.18 (s, 1H), 7.07 (s, 1H), 7.02-6.98 (m, 2H), 6.76-6.72 (m, 2H), 6.25 (s, 1H), 4.40 (s, 1H), 4.10-3.90 (m, 4H), 3.78-3.20 (m, 9H), 2.85 (s, 2H), 2.45-2.14 (m, 6H), 2.03 (s, 2H), 1.90-1.32 (m, 10H), 0.96 (s, 6H).

Synthesis of 4-(4-[[2-(4-chlorophenyl)-4,4-dimethylcyclohex-1-en-1-yl]methyl]piperazin-1-yl)-N-[(3R)-5-nitro-3-(oxan-4-yl)-3,4-dihydro-2H-[1,4-benzoxazin-7-ylsulfonyl]-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide. Into a 8-mL vial, was placed 4-(4-[[2-(4-chlorophenyl)-4,4-dimethylcyclohex-1-en-1-yl]methyl]pipera-zin-1-yl)-2-(4-[[2-(trimethylsilyl)ethoxy]ethyl]-14-oxa-2,4,10-triazatricyclo[7.5.0.0^[3,7]]tetradeca-1(9),2,5,7-tetraen-10-yl)benzoic acid (25.00 mg, 0.033 mmol, 1.00 equiv), (3R)-5-nitro-3-(oxan-4-yl)-3,4-dihydro-2H-1,4-benzoxazine-7-sulfonamide (11.35 mg, 0.033 mmol, 1.00 equiv), EDCI (12.67 mg, 0.066 mmol, 2.00 equiv), DMAP (12.11 mg, 0.099 mmol, 3.00 equiv), DCM (1.00 mL). The resulting solution was stirred for 14 hr at 35 degrees C. in an oil bath. The resulting mixture was concentrated. The residue was purified with Prep-TLC with dichloromethane/ methanol (10:1). This resulted in 20 mg (55.94%) of 4-(4-[[2-(4-chlorophenyl)-4,4-dimethylcyclohex-1-en-1-yl]methyl]piperazin-1-yl)-N-[(3R)-5-nitro-3-(oxan-4-yl)-3,4-dihydro-2H-1,4-benzoxazin-7-ylsulfonyl]-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide as a yellow solid.

LC-MS (ES, m/z): 1081 [M+H].

Synthesis of 4-(4-[[2-(4-chlorophenyl)-4,4-dimethylcyclohex-1-en-1-yl]methyl]piperazin-1-yl)-N-[(3R)-5-nitro-3-(oxan-4-yl)-3,4-dihydro-2H-[1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide Into a 8-mL vial, was placed 4-(4-[[2-(4-chlorophenyl)-4,4-dimethylcyclohex-1-en-1-yl]methyl]piperazin-1-yl)-N-[(3R)-5-nitro-3-(oxan-4-yl)-3,4-dihydro-2H-1,4-benzoxazin-7-ylsulfonyl]-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide (18.00 mg, 1 equiv), ethane-1,2-diamine (0.20 mL), TBAF in THF (1 ml, 2M). The resulting solution was stirred for 48 hr at 70 degrees C. in an oil bath. The resulting mixture was concentrated. The residue was purified by Prep-TLC with dichloromethane/methanol (10:1). The crude product was purified by Prep-HPLC with the following conditions: Column, X Bridge Prep C18 OBD 19*150 mm 5 um; mobile phase, A: 0.1% $NH_3$—$H_2O$ in water; B: ACN; Gradient: 6-80% B in 7.9 min; Flow rate: 20 ml/min; Detector, 220 nm. This resulted in 7 mg (44.21%) of 4-(4-[[2-(4-chlorophenyl)-4,4-dimethylcyclohex-1-en-1-yl]ethyl]piperazin-1-yl)-N-[(3R)-5-nitro-3-(oxan-4-yl)-3,4-dihydro-2H-1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide as a yellow solid. LC-MS-PH-PHNW-4-141-0: (ES, m/z): 951.4 [M+H] $^1$H NMR-PH-PHNW-4-141-0 (300 MHz, $CDCl_3$, ppm): δ 12.23 (s, 1H), 8.68 (s, 1H), 8.48 (d, J=2.1 Hz, 1H), 8.37 (s, 1H), 8.00 (d, J=9.6 Hz, 1H), 7.51 (s, 1H), 7.27 (s, 1H), 7.17 (s, 1H), 7.07 (s, 1H), 7.02-6.98 (m, z, 2H), 6.77-6.71 (m, 2H), 6.25 (s, 1H), 4.40 (s, 1H), 4.10-3.90 (m, 4H), 3.78-3.20 (m, 9H), 2.45-2.13 (m, 6H), 2.03 (s, 2H), 1.89-1.37 (m, 10H), 0.98 (s, 6H).

Example 47

Preparation of 4-(4-[[2-(4-chlorophenyl)-4,4-dimethylcyclohex-1-en-1-yl]methyl]piperazin-1-yl)-N-[(3S or 3R)-3-[(2S)-1,4-dioxan-2-yl]-5-nitro-3,4-dihydro-2H-1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide & 4-(4-[[2-(4-chlorophenyl)-4,4-dimethylcyclohex-1-en-1-yl]methyl]piperazin-1-yl)-N-[(3R or 3S)-3-[(2S)-1,4-dioxan-2-yl]-5-nitro-3,4-dihydro-2H-1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide Synthesis of (2R)-1,4-dioxane-2-carbaldehyde, Into a 500-mL round-bottom flask, was placed (2S)-1,4-dioxan-2-ylmethanol (30.00 g, 253.953 mmol, 1.00 equiv), $CH_3CN$ (250.00 mL), IBX (120.89 g, 431.724 mmol, 1.70 equiv). The resulting solution was stirred for 4 h at 70 degrees C. in an oil bath. The solids were filtered out. The resulting mixture was concentrated. This resulted in 30 g (crude) of (2R)-1,4-dioxane-2-carbaldehyde as colorless oil. H-NMR-1: $^1$H NMR (300 MHz, $CDCl_3$, ppm) δ 9.66 (s, 1H), 4.12-3.77 (m, 7H).

Synthesis of 2-amino-2-[(2S)-1,4-dioxan-2-yl]acetonitrile, Into a 500-mL pressure tank reactor, was placed (2R)-1,4-dioxane-2-carbaldehyde (30.00 g, 258.362 mmol, 1.00 equiv). $NH_3$/MeOH (7M) (300.00 mL). This was followed by the addition of TMSCN (38.40 g, 387.071 mmol, 1.50 equiv). The resulting solution was stirred for overnight at 70 degrees C. in an oil bath. The resulting mixture was concentrated. The residue was applied onto a silica gel column and eluted with ethyl acetate/petroleum ether (3:1). The collected fractions were combined and concentrated. This resulted in 18 g (49.01%) of (2S)-2-amino-2-[(2S)-1,4-dioxan-2-yl]acetonitrile as yellow oil. LCMS-2 (ES, m/z): M+1: 143.

Synthesis of amino((2S)-1,4-dioxan-2-yl)acetic acid: Into a 100-mL round-bottom flask, was placed 2-amino-2-[(2S)-1,4-dioxan-2-yl]acetonitrile (18.00 g, 126.620 mmol, 1.00 equiv), NaOH (4M) (40.00 mL). The resulting solution was stirred for overnight at 70 degrees C. in an oil bath. The pH value of the solution was adjusted to 6 with HOAc. The solids were collected by filtration. The solid was dried in an oven under reduced pressure. This resulted in 8.8 g (43.13%) of amino((2S)-1,4-dioxan-2-yl)acetic acid as a white solid LCMS-3 (ES, m/z): M+1: 162.

Synthesis of 2-amino-2-[(2S)-1,4-dioxan-2-yl]ethanol: Into a 250-mL round-bottom flask, was placed amino((2S)-1,4-dioxan-2-yl)acetic acid (8.80 g, 54.605 mmol, 1.00 equiv), THF (120.00 mL, 1.664 mmol, 0.03 equiv). This was followed by the addition of LiAlH4 (6.22 g, 163.883 mmol, 3.00 equiv) in several batches at 0 degrees C. The resulting solution was stirred for 6 h at 60 degrees C. in an oil bath. The reaction was then quenched by the addition of 12 g of Na2SO4.10H2O. The solids were filtered out. The resulting mixture was concentrated. This resulted in 4.5 g (55.99%) of 2-amino-2-[(2S)-1,4-dioxan-2-yl]ethanol as a white solid. LCMS-4 (ES, m/z): M+1: 148.

Synthesis of 3-bromo-4-([1-[(2S)-1,4-dioxan-2-yl]-2-hydroxyethyl]amino)-5-nitrobenzenesulfonamide: Into a 250-mL round-bottom flask, was placed 3-bromo-4-chloro-5-nitrobenzenesulfonamide (4.00 g, 12.677 mmol, 1.00 equiv), $CH_3CN$ (120.00 mL), DIEA (6.55 g, 0.051 mmol, 4 equiv), 2-amino-2-[(2S)-1,4-dioxan-2-yl]ethanol (4.48 g, 0.030 mmol, 2.4 equiv). The resulting solution was stirred for 48 h at 80 degrees C. in an oil bath. The resulting mixture was concentrated. The residue was applied onto a silica gel column and eluted with ethyl acetate/petroleum ether (9:1). The collected fractions were combined and concentrated. This resulted in 3.2 g (59.22%) of 3-bromo-4-(1-[(2S)-1,4-dioxan-2-yl-2-hydroxyethyl]amino)-5-nitrobenzenesulfonamide as a yellow solid. LCMS-5 (ES, m/z): M-1: 424.

Synthesis of (3S or 3R)-3-[(2S)-1,4-dioxan-2-yl]-5-nitro-3,4-dihydro-2H-1,4-benzoxazine-7-sulfonamide & (3R or 3S)-3-[(2S)-1,4-dioxan-2-yl]-5-nitro-3,4-dihydro-2H-1,4-benzoxazine-7-sulfonamide: Into a 100-mL round-bottom flask purged and maintained with an inert atmosphere of nitrogen, was placed 3-bromo-4-([1-[(2S)-1,4-dioxan-2-yl]-2-hydroxyethyl]amino)-5-nitrobenzenesulfonamide (1.00 g, 2.346 mmol, 1.00 equiv), dioxane (40.00 mL), $Cs_2CO_3$ (1911.01 mg, 5.865 mmol, 2.50 equiv), t-BuXPhos Pd G3 (186.05 mg, 0.235 mmol, 0.10 equiv). The resulting solution was stirred for 8 h at 100 degrees C. in an oil bath. The reaction was then quenched by the addition of 40 mL of water. The resulting solution was extracted with 3×40 mL of ethyl acetate dried over anhydrous sodium sulfate and concentrated. The residue was applied onto a silica gel column and eluted with ethyl acetate/petroleum ether (1:1).

The collected fractions were combined and concentrated. The crude product was purified by Prep-HPLC with the following conditions:

Column, X-bridge RP18; mobile phase, 0.05% ammonia in water and $CH_3CN$ (45% $CH_3CN$ up to 60% in 5 min); Detector, UV 254 nm. This resulted in 20 mg (2.47%) of (3S or 3R)-3-[(2S)-1,4-dioxan-2-yl]-5-nitro-3,4-dihydro-2H-1,4-benzoxazine-7-sulfonamide as a yellow solid and 40 mg (4.94%) of (3R or 3S)-3-[(2S)-1,4-dioxan-2-yl]-5-nitro-3,4-dihydro-2H-1,4-benzoxazine-7-sulfonamide as a yellow solid LC-MS-6: (ES, m/z): M−1:344.

Synthesis of 4-(4-[[2-(4-chlorophenyl)-4,4-dimethylcyclohex-1-en-1-yl]methyl]piperazin-1-yl)-N-[(3S or 3R)-3-[(2S)-1,4-dioxan-2-yl]-5-nitro-3,4-dihydro-2H-[1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide: Into a 8-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoic acid (18.13 mg, 0.029 mmol, 1 equiv), (3S or 3R)-3-[(2S)-1,4-dioxan-2-yl]-5-nitro-3,4-dihydro-2H-1,4-benzoxazine-7-sulfonamide (10.00 mg, 0.029 mmol, 1.00 equiv), DCM (3.00 mL), EDCI (11.10 mg, 0.058 mmol, 2.00 equiv), DMAP (14.15 mg, 0.116 mmol, 4.00 equiv). The resulting solution was stirred for overnight at room temperature. The resulting mixture was concentrated. The crude product was purified by Prep-HPLC with the following conditions: Column, X-bridge RP18; mobile phase, 0.05% ammonia in water and $CH_3CN$ (45% $CH_3CN$ up to 60% in 5 min); Detector, UV 254 nm. This resulted in 3.2 mg (11.59%) of 4-(4-[[2-(4-chlorophenyl)-4,4-dimethylcyclohex-1-en-1-yl]methyl]piperazin-1-yl)-N-[(3S or 3R)-3-[(2S)-1,4-dioxan-2-yl]-5-nitro-3,4-dihydro-2H-1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide as a yellow solid. LC-MS-0: (ES, m/z): M+1: 953. $^1$H NMR (300 MHz, Chloroform-d, ppm) δ 12.09 (d, J=26.1 Hz, 1H), 8.61 (s, 1H), 8.50 (s, 1H), 8.23 (s, 1H), 7.99 (d, J=8.4 Hz, 1H), 7.63 (s, 1H), 7.35 (s, 2H), 7.16 (s, 1H), 7.00 (d, J=8.4 Hz, 3H), 6.74 (d, J=8.1 Hz, 2H), 6.25 (d, J=15.9 Hz, 1H), 4.38 (s, 1H), 4.00-3.37 (m, 14H), 3.31 (s, 2H), 2.86 (s, 1H), 2.63 (s, 2H), 2.32 (d, J=35.6 Hz, 5H), 2.08 (d, J=25.8 Hz, 2H), 1.48 (s, 1H),1.28 (s, 2H), 1.01 (s, 6H).

Synthesis of 4-(4-[[2-(4-chlorophenyl)-4,4-dimethylcyclohex-1-en-1-yl]methyl]piperazin-1-yl)-N-[(3R or 3S)-3-[(2S)-1,4-dioxan-2-yl]-5-nitro-3,4-dihydro-2H-[1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide: Into a 8-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoic acid (18.13 mg, 0.029 mmol, 1 equiv), (3S or 3S)-3-[(2S)-1,4-dioxan-2-yl]-5-nitro-3,4-dihydro-2H-1,4-benzoxazine-7-sulfonamide (10.00 mg, 0.029 mmol, 1.00 equiv), DCM (3.00 mL), EDCI (11.10 mg, 0.058 mmol, 2.00 equiv), DMAP (14.15 mg, 0.116 mmol, 4.00 equiv). The resulting solution was stirred for overnight at room temperature. The resulting mixture was concentrated. The crude product was purified by Prep-HPLC with the following conditions: Column, X-bridge RP18; mobile phase, 0.05% ammonia in water and $CH_3CN$ (45% $CH_3CN$ up to 60% in 5 min); Detector, UV 254 nm. This resulted in 3.1 mg (11.23%) of 4-(4-[[2-(4-chlorophenyl)-4,4-dimethylcyclohex-1-en-1-yl]methyl]piperazin-1-yl)-N-[(3R or 3S)-3-[(2S)-1,4-dioxan-2-yl]-5-nitro-3,4-dihydro-2H-1,4-benzoxazin-7-ylsulfonyl]-2-[14-oxa-2,4,10-triazatricyclo[7.5.0.0^[3,7]]tetradeca-1(9),2,5,7-tetraen-10-yl]benzamide as a yellow solid. LC-MS-0: (ES, m/z): M+1: 953. $^1$H NMR (300 MHz, Chloroform-d, ppm) δ 12.05 (d, J=29.4 Hz, 1H), 8.82 (s, 1H), 8.49 (s, 2H), 7.98 (d, J=9.0 Hz, 1H), 7.58 (s, 1H), 7.36 (s, 1H), 7.17 (s, 1H), 7.00 (d, J=7.5 Hz, 3H), 6.74 (d, J=8.1 Hz, 2H), 6.25 (d, J=14.4 Hz, 1H), 4.15-3.44 (m, 16H), 3.31 (s, 2H), 2.86 (s, 1H), 2.64 (s, 2H), 2.32 (d, J=37.5 Hz, 4H), 2.08 (d, J=25.3 Hz, 2H), 1.50 (s, 4H), 1.28 (s, 1H), 1.01 (s, 6H).

Example 48

Preparation of 4-(4-[[2-(4-chlorophenyl)-4,4-dimethylcyclohex-1-en-1-yl]methyl]piperazin-1-yl)-N-[4-([2-[4-(2-[2-[2-(2-[[2-(2,6-dioxopiperidin-3-yl)-1,3-dioxoisoindol-4-yl]amino]ethoxy)ethoxy]ethyl)piperazin-1-yl]ethyl]amino)-3-nitrobenzenesulfonyl]-2-[14-oxa-2,4,10-triazatricyclo[7.5.0.0^[3,7]]tetradeca-1(9),2,5,7-tetraen-10-yl]benzamide hydrochloride Synthesis of 2-(2,6-dioxopiperidin-3-yl)-4-(12-hydroxy-4,7,10-trioxa-1-azadodecan-1-yl)isoindole-1,3-dione: Into a 40-mL vial, was placed 2-[2-[2-(2-aminoethoxy)ethoxy]ethoxy]ethanol (500.00 mg, 2.587 mmol, 1.00 equiv), DMF (10.00 mL), 2-(2,6-dioxopiperidin-3-yl)-4-fluoroisoindole-1,3-dione (718.00 mg, 2.599 mmol, 1.00 equiv), DIEA (1.67 g, 12.921 mmol, 4.99 equiv). The resulting solution was stirred for 2 hr at 90 degrees C. in an oil bath. The reaction mixture was cooled to room temperature. The resulting solution was diluted with 100 mL of water. The pH value of the solution was adjusted to 4-5 with $KHSO_4$ (10%). The resulting solution was extracted with 3×50 mL of ethyl acetate and the organic layers combined. The resulting mixture was washed with 1×300 mL of brine. The mixture was dried over anhydrous sodium sulfate and concentrated under vacuum. The residue was applied onto a silica gel column with dichloromethane/methanol (3:1). This resulted in 220 mg (18.92%) of 2-(2,6-dioxopiperidin-3-yl)-4-(12-hydroxy-4,7,10-trioxa-1-azadodecan-1-yl)isoindole-1,3-dione as yellow oil. LC-MS (ES, m/z): M+1=450. $^1$H NMR (300 MHz, DMSO-$d_6$, ppm) δ 11.09 (s, 1H), 7.59 (dd, J=8.6, 7.1 Hz, 1H), 7.15 (d, J=8.6 Hz, 1H), 7.05 (d, J=7.0 Hz, 1H), 6.61 (t, J=5.8 Hz, 1H), 5.06 (dd, J=12.8, 5.4 Hz, 1H), 4.55 (d, J=5.6 Hz, 1H), 3.67-3.36 (m, 17H), 2.89 (ddd, J=17.2, 13.8, 5.3 Hz, 1H), 2.67-2.53 (m, 2H), 2.13-1.95 (m, 1H).

Synthesis of 2-[2-[2-(2[[2-(2,6-dioxopiperidin-3-yl)-[1,3-dioxoisoindol-4-yl]amino]ethoxy)ethoxy]ethyl methanesulfonate: Into a 100-mL round-bottom flask, was placed 2-(2,6-dioxopiperidin-3-yl)-4-(12-hydroxy-4,7,10-trioxa-1-azadodecan-1-yl)isoindole-1,3-dione (220.00 mg, 0.489 mmol, 1.00 equiv), DCM (15.00 mL), TEA (148.00 mg, 1.463 mmol, 2.99 equiv), MsCl (67.00 mg, 0.585 mmol, 1.19 equiv). The resulting solution was stirred for 3 hr at 25 degrees C. The resulting solution was diluted with 100 mL of $NaHCO_3$. The resulting solution was extracted with 3×50 mL of dichloromethane and the organic layers combined. The resulting mixture was washed with 1×200 mL of brine. The mixture was dried over anhydrous sodium sulfate and concentrated under vacuum. This resulted in 258 mg (99.91%) of 2-[2-[2-(2-[[2-(2,6-dioxopiperidin-3-yl)-1,3-dioxoisoindol-4-yl]amino]ethoxy)ethoxy]ethoxy]ethyl methanesulfonate as yellow oil. LC-MS: (ES, m/z): M+1=528.

Synthesis of 4-([2-[4-(2-[2-[2-(2-[[2-(2,6-dioxopiperidin-3-yl)-1,3-dioxoisoindol-4-yl]amino]ethoxy)ethoxy]ethoxy]ethyl)piperazin-1-yl]ethyl]amino)-3-nitrobenzenesulfona mide: Into a 40-mL vial, was placed 3-nitro-4-[[2-(piperazin-1-yl)ethyl]amino]benzenesulfonamide hydrochloride (173.00 mg, 0.473 mmol, 1.00 equiv), CH$_3$CN (10.00 mL), 2-[2-[2-(2-[[2-(2,6-dioxopiperidin-3-yl)-1,3-dioxoisoindol-4-yl]amino]ethoxy)ethoxy]ethoxy]ethyl methanesulfonate (250.00 mg, 0.474 mmol, 1.00 equiv), DIEA (367.00 mg, 2.840 mmol, 5.99 equiv). The resulting solution was stirred overnight at 80 degrees C. The reaction mixture was cooled to room temperature and concentrated under vacuum. The residue was applied onto a silica gel column with dichloromethane/methanol (10:1). The crude product was purified by Flash-Prep-HPLC with the following conditions (Intel-Flash-1): Column, C18 reversed phase column; mobile phase, H$_2$O (10 mm NH$_4$HCO$_3$) and CH$_3$CN (50% CH$_3$CN in H$_2$O); Detector, 254 nm. This resulted in 35 mg (9.71%) of 4-([2-[4-(2-[2-[2-(2-[[2-(2,6-dioxopiperidin-3-yl)-1,3-dioxoisoindol-4-yl]amino]ethoxy)ethoxy]ethoxy]ethyl)piperazin-1-yl]ethyl]amino)-3-nitrobenzenesulfonamide as a yellow solid. LC-MS: (ES, m/z): M+1=761.

Synthesis of 4-(4-[[2-(4-chlorophenyl)-4,4-dimethylcyclohex-1-en-1-yl]methyl]piperazin-1-yl)-N-[4-([2-[4-(2-[2-[2-(2-[[2-(2,6-dioxopiperidin-3-yl)-1,3-dioxoisoindol-4-yl]amino]ethoxy)ethoxy]ethoxy]ethyl)piperazin-1-yl]ethyl]amino)-3-nitrobenzenesulfonyl]-2-[14-oxa-2,4,10-triazatricyclo[7.5.0.0^[3,7]]tetradeca-1(9),2,5,7-tetraen-10-yl]benzamide hydrochloride: Into a 40-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoic acid (29.00 mg, 0.046 mmol, 1.01 equiv), DCM (5.00 mL), 4-([2-[4-(2-[2-[2-(2-[[2-(2,6-dioxopiperidin-3-yl)-1,3-dioxoisoindol-4-yl]amino]ethoxy)ethoxy]ethoxy]ethyl)piperazin-1-yl]ethyl]amino)-3-nitrobenzenesulfonamide (35.00 mg, 0.046 mmol, 1.00 equiv), EDCI (18.00 mg, 0.094 mmol, 2.04 equiv), DMAP (22.00 mg, 0.180 mmol, 3.91 equiv). The resulting solution was stirred overnight at 30 degrees C. in an oil bath. The resulting mixture was concentrated under vacuum. The crude product was purified by Prep-HPLC with the following conditions (Prep-HPLC-006): Column, XBridge Shield RP18 OBD Column, 5 um, 19*150 mm; mobile phase, Water (0.05% FA) and ACN (40% Phase B up to 70% in 7 min); Detector, UV 254/220 nm. The collected solution was concentrated under vacuum to remove CH$_3$CN and the resulting solution was dried by lyophilization (added with Conc. HCl (1 drop)). This resulted in 7 mg (10.75%) of 4-(4-[[2-(4-chlorophenyl)-4,4-dimethylcyclohex-1-en-1-yl]methyl]piperazin-1-yl)-N-[4-([2-[4-(2-[2-[2-(2-[[2-(2,6-dioxopiperidin-3-yl)-1,3-dioxoisoindol-4-yl]amino]ethoxy)ethoxy]ethoxy]ethyl)piperazin-1-yl]ethyl]amino)-3-nitrobenzene sulfonyl]-2-[14-oxa-2,4,10-triazatricyclo[7.5.0.0^[3,7]]tetradeca-1(9),2,5,7-tetraen-10-yl]benzamide hydrochloride as a yellow solid. LC-MS: (ES, m/z): M+1=1369. $^1$H NMR (300 MHz, DMSO-d$_{6, ppm}$) δ 11.95 (s, 1H), 11.23 (s, 1H), 11.10 (s, 1H), 10.68 (s, 1H), 8.69 (s, 1H), 8.36 (s, 1H), 7.69-7.52 (m, 2H), 7.43 (dd, J=8.4, 4.3 Hz, 3H), 7.20-7.09 (m, 4H), 7.08-6.96 (m, 2H), 6.90 (s, 1H), 6.71 (d, J=13.4 Hz, 2H), 6.59 (s, 1H), 6.09 (dd, J=3.4, 1.8 Hz, 1H), 5.06 (dd, J=12.9, 5.4 Hz, 1H), 4.28 (s, 2H), 3.66-3.28 (m, 30H), 3.00-2.59 (m, 6H), 2.40 (s, 3H), 2.02 (d, J=19.1 Hz, 6H), 1.49 (d, J=6.4 Hz, 3H), 1.24 (s, 2H), 0.97 (s, 6H).

Example 49

Preparation of 4-(4-[[2-(4-chlorophenyl)-4,4-dimethylcyclohex-1-en-1-yl]methyl]piperazin-1-yl)-N-[4-(18-[[2-(2,6-dioxopiperidin-3-yl)-1,3-dioxoisoindol-4-yl]amino]-4,7,10,13,16-pentaoxa-1-azaoctadecan-1-yl)-3-nitrobenzenesulfonyl]-2-[14-oxa-2,4,10-triazatricyclo[7.5.0.0^[3,7]]tetradeca-1(9),2,5,7-tetraen-10-yl]benzamide Synthesis of tert-butylN-[17-[(2-nitro-4-sulfamoylphenyl)amino]-3,6,9,12,15-pentaoxaheptadecan-1-yl]carbamate: Into a 50-mL round-bottom flask, was placed tert-butyl N-(17-amino-3,6,9,12,15-pentaoxaheptadecan-1-yl)carbamate (500.00 mg, 1.314 mmol, 1.00 equiv), 4-fluoro-3-nitrobenzenesulfonamide (289.33 mg, 1.314 mmol, 1.00 equiv), CH$_3$CN (5.00 mL), DIEA (509.52 mg, 3.942 mmol, 3.00 equiv). The resulting solution was stirred for 14 hr at 70 degrees C. in an oil bath. The resulting mixture was concentrated. The residue was applied onto a silica gel column and eluted with ethyl acetate/petroleum ether (1:1). This resulted in 650 mg (85.18%) of tert-butyl N-[17-[(2-nitro-4-sulfamoylphenyl)amino]-3,6,9,12,15-pentaoxaheptadecan-1-yl]carbamate as a yellow solid. LCMS-1 (ES, m/z): M+1: 581.

Synthesis of 4-(18-amino-4,7,10,13,16-pentaoxa-1-azaoctadecan-1-yl)-3-nitrobenzenesulfonamide: Into a 8-mL vial, was placed tert-butyl N-[17-[(2-nitro-4-sulfamoylphenyl)amino]-3,6,9,12,15-pentaoxaheptadecan-1-yl] carbamate (650 mg), HCl in dioxane (2M 10 ml). The resulting solution was stirred for 3 hr at room temperature. The resulting mixture was concentrated. This resulted in 650 mg 4-(18-amino-4,7,10,13,16-pentaoxa-1-azaoctadecan-1-yl)-3-nitrobenzenesulfonamide as a yellow solid. LCMS-2 (ES, m/z): M+1: 481.

Synthesis of 4-(18-[[2-(2,6-dioxopiperidin-3-yl)-1,3-dioxoisoindol-4-yl]amino]-4,7,10,13,16-pentaoxa-1-azaoctadecan-1-yl)-3-nitrobenzenesulfonamide: Into a 8-mL vial, was placed 4-(18-amino-4,7,10,13,16-pentaoxa-1-azaoctadecan-1-yl)-3-nitrobenzenesulfonamide (200.00 mg, 0.416 mmol, 1.00 equiv), 2-(2,6-dioxopiperidin-3-yl)-4-fluoroisoindole-1,3-dione (114.97 mg, 0.416 mmol, 1.00 equiv), DIEA (107.58 mg, 0.832 mmol, 2.00 equiv), DMF (2.00 mL). The resulting solution was stirred for 14 hr at 80 degrees C. in an oil bath. The resulting mixture was concentrated. The residue was purified by Prep-TLC with PE:EA=1:1. This resulted in 32 mg (10.44%) of 4-(18-[[2-(2,6-dioxopiperidin-3-yl)-1,3-dioxoisoindol-4-yl]amino]-4,7,10,13,16-pentaoxa-1-azaoctadecan-1-yl)-3-nitrobenzenesulfonamide as a yellow solid. LCMS-3 (ES, m/z): M$_+$1: 737.

Synthesis of 4-(4-[[2-(4-chlorophenyl)-4,4-dimethylcyclohex-1-en-1-yl]methyl]piperazin-1-yl)-N-[4-(18-[[2-(2,6-dioxopiperidin-3-yl)-1,3-dioxoisoindol-4-yl]amino]-4,7,10,13,16-pentaoxa-1-azaoctadecan-1-yl)-3-nitrobenzenesulfonyl]-2-[14-oxa-2,4,10-triazatricyclo[7.5.0.0^[3,7]]tetradeca-1(9),2,5,7-tetraen-10-yl]benzamide: Into a 8-mL vial, was placed 4-(18-[[2-(2,6-dioxopiperidin-3-yl)-1,3-dioxoisoindol-4-yl]amino]-4,7,10,13,16-pentaoxa-1-azaoctadecan-1-yl)-3-nitrobenzenesulfonamide (28.00 mg, 0.038 mmol, 1.00 equiv), 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoic acid (23.80 mg, 0.038 mmol, 1.00 equiv), DCM (1.00 mL), EDC.HCl (14.57 mg, 0.076 mmol, 2.00 equiv), DMAP (11.61 mg, 0.095 mmol, 2.50 equiv). The resulting solution was stirred for 14 hr at 30 degrees C. in an oil bath. The resulting mixture was concentrated. The residue was purified with Prep-TLC with dichloromethane/methanol (10:1). The crude product was purified by Prep-HPLC with the following conditions (WATERS 2767): Column, X Bridge Prep C18 OBD 19*150 mm 5 um; Mobile phase, A: 0.1% NH$_3$—H$_2$O in water; B: ACN; Gradient: 15-85% B in 7.9 min; Flow rate: 20 ml/min; Detector, 220 nm. This resulted in 2.4 mg (4.70%) of 4-(4-[[2-(4-chlorophenyl)-4,4-dimethylcyclohex-1-en-1-yl]ethyl]piperazin-1-yl)-N-[4-(18-[[2-(2,6-dioxopiperidin-3-yl)-1,3-dioxoisoindol-4-yl]amino]-4,7,10,13,16-pentaoxa-1-azaoctadecan-1-yl)-3-nitrobenzene sulfonyl]-2-[14-oxa-2,4,10-triazatricyclo[7.5.0.0ˆ[3,7]]tetradeca-1(9),2,5,7-tetraen-10-yl]benzamide as a yellow solid. LCMS-0: (ES, m/z): M+1: 1444.5 H-NMR-0: $^1$H NMR (300 MHz, Chloroform-d, ppm) δ 11.82 (s, 1H), 9.49 (s, 1H), 9.35 (s, 1H), 8.82 (s, 1H), 8.53-8.41 (m, 1H), 8.01-7.82 (m, 2H), 7.57-7.47 (m, 1H), 7.40-7.32 (m, 3H), 7.30-7.20 (m, 2H), 7.08-6.90 (m, 3H), 6.85 (s, 1H), 6.80-6.70 (m, 2H), 6.62-6.40 (m, 2H), 6.11 (s, 1H), 5.05-4.93 (m, 1H), 3.82-3.35 (m, 34H), 2.96-2.78 (m, 3H), 2.62-2.05 (m, 12H), 1.55-1.50 (m, 2H), 1.01 (s, 6H).

Example 50

Preparation of 4-(4-[[2-(4-chlorophenyl)-4,4-dimethylcyclohex-1-en-1-yl]methyl]piperazin-1-yl)-N-(4-[[2-(4-[2-[2-(2-[[2-(2,6-dioxopiperidin-3-yl)-1,3-dioxoisoindol-4-yl]amino]ethoxy)ethoxy]ethyl]piperazin-1-yl)ethyl]amino]-3-nitrobenzene sulfonyl)-2-[14-oxa-2,4,10-triazatricyclo[7.5.0.0ˆ[3,7]]tetradeca-1(9),2,5,7-tetraen-10-yl]benzamide Synthesis of 2-(2,6-dioxopiperidin-3-yl)-4-([2-[2-(2-hydroxyethoxy)ethoxy]ethyl]amino)isoindole-1,3-dione: Into a 50-mL round-bottom flask, was placed 2-[2-(2-aminoethoxy)ethoxy]ethanol (500.00 mg, 3.351 mmol, 1.00 equiv), DMSO (20.00 mL), 2-(2,6-dioxopiperidin-3-yl)-4-fluoroisoindole-1,3-dione (925.74 mg, 3.351 mmol, 1.00 equiv), DIEA (1299.45 mg, 10.054 mmol, 3 equiv). The resulting solution was stirred for overnight at 70 degrees C. in an oil bath. The reaction was then quenched by the addition of 20 mL of water. The resulting solution was extracted with 3×30 mL of ethyl acetate concentrated. The residue was applied onto a silica gel column and eluted with dichloromethane/methanol (10:1). The collected fractions were combined and concentrated. This resulted in 800 mg (58.88%) of 2-(2,6-dioxopiperidin-3-yl)-4-([2-[2-(2-hydroxyethoxy)ethoxy]ethyl]amino)isoindole-1,3-dione as a yellow solid. LCMS-1 (ES, m/z): M+1: 406.

Synthesis of 2-[2-(2-[[2-(2,6-dioxopiperidin-3-yl)-1,3-dioxoisoindol-4-yl]amino]ethoxy)ethoxy]ethyl methanesulfonate: Into a 50-mL round-bottom flask, was placed 2-(2,6-dioxopiperidin-3-yl)-4-([2-[2-(2-hydroxyethoxy)ethoxy]ethyl]amino)isoindole-1,3-dione (800.00 mg, 1.973 mmol, 1.00 equiv), DCM (20.00 mL), TEA (599.04 mg, 5.920 mmol, 3.00 equiv). This was followed by the addition of MsCl (226.05 mg, 1.973 mmol, 1.00 equiv) dropwise with stirring at 0 degrees C. The resulting solution was stirred for 3 h at room temperature. The resulting mixture was concentrated. The residue was applied onto a silica gel column and eluted with ethyl acetate/petroleum ether (4:1). The collected fractions were combined and concentrated. This resulted in 600 mg (62.89%) of 2-[2-(2-[[2-(2,6-dioxopiperidin-3-yl)-1,3-dioxoisoindol-4-yl]amino]ethoxy)ethoxy]ethyl methanesulfonate as a yellow solid. LCMS-2 (ES, m/z): M+1: 484.

Synthesis of 4-[[2-(4-[2-[2-(2-[[2-(2,6-dioxopiperidin-3-yl)-1,3-dioxoisoindol-4-yl]amino]ethoxy)ethoxy]ethyl]piperazin-1-yl)ethyl]amino]-3-nitrobenzenesulfonamide: Into a 50-mL round-bottom flask, was placed 2-[2-(2-[[2-(2,6-dioxopiperidin-3-yl)-1,3-dioxoisoindol-4-yl]amino]ethoxy)ethoxy]ethyl methanesulfonate (300.00 mg, 0.620 mmol, 1.00 equiv), 3-nitro-4-[[2-(piperazin-1-yl)ethyl]amino]benzene sulfonamide (204.38 mg, 0.620 mmol, 1.00 equiv), CH$_3$CN (15.00 mg), DIEA (481.16 mg, 3.723 mmol, 6.00 equiv). The resulting solution was stirred for overnight at 70 degrees C. in an oil bath. The resulting mixture was concentrated. The residue was applied onto a silica gel column and eluted with dichloromethane/methanol (10:1). The collected fractions were combined and concentrated. This resulted in 200 mg (44.97%) of 4-[[2-(4-[2-[2-(2-[[2-(2,6-dioxopiperidin-3-yl)-1,3-dioxoisoindol-4-yl]amino]ethoxy)ethoxy]ethyl]piperazin-1-yl)ethyl]amino]-3-nitrobenzenesulfonamide as a yellow solid. LCMS-3 (ES, m/z): M+1: 717.

Synthesis of 4-(4-[[2-(4-chlorophenyl)-4,4-dimethylcyclohex-1-en-1-yl]methyl]piperazin-1-yl)-N-(4-[[2-(4-[2-[2-(2-[[2-(2,6-dioxopiperidin-3-yl)-1,3-dioxoisoindol-4-yl]amino]ethoxy)ethoxy]ethyl]piperazin-1-yl)ethyl]amino]-3-nitrobenzenesulfonyl)-2-[14-oxa-2,4,10-triazatricyclo[7.5.0.0ˆ[3,7]]tetradeca-1(9),2,5,7-tetraen-10-yl]benzamide: Into a 40-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoic acid (40.00 mg, 0.064 mmol, 1.00 equiv), DCM (6.00 mL), 4-[[2-(4-[2-[2-(2-[[2-(2,6-dioxopiperidin-3-yl)-1,3-dioxoisoindol-4-yl]amino]ethoxy)ethoxy]ethyl]piperazin-1-yl)ethyl]amino]-3-nitrobenzenesulfonamide (45.79 mg, 0.064 mmol, 1.00 equiv), EDCI (24.49 mg, 0.128 mmol, 2.00 equiv), DMAP (31.21 mg, 0.25 mmol, 4.00 equiv). The resulting solution was stirred for overnight at 30 degrees C. in an oil bath. The resulting mixture was concentrated. The crude product was purified by Prep-HPLC with the following conditions: Column, X-bridge RP18; mobile phase, 0.05% ammonia in water and CH$_3$CN (45% CH$_3$CN up to 60% in 5 min); Detector 254 nm. This resulted in 5 mg (5.91%) of 4-(4-[[2-(4-chlorophenyl)-4,4-dimethylcyclohex-1-en-1-yl]methyl]piperazin-1-yl)-N-(4-[[2-(4-[2-[2-(2-[[2-(2,6-dioxopiperidin-3-yl)-1,3-dioxoisoindol-4-yl]amino]ethoxy)ethoxy]ethyl]piperazin-1-yl)ethyl]amino]-3-nitrobenzenesulfonyl)-2-[14-oxa-2,4,10-triazatricyclo[7.5.0.0ˆ[3,7]]tetradeca-1(9),2,5,7-tetraen-10-yl]benzamide as a yellow solid. LC-MS-0: (ES, m/z): M+1: 1325. $^1$H NMR (300 MHz, Chloroform-d, ppm) ϵ 8.39 (d, J=2.1 Hz, 1H), 7.66-7.46 (m, 2H), 7.37-7.31 (m, 3H), 7.16-6.97 (m, 5H), 6.94 (s, 1H), 6.78 (d, J=9.3 Hz, 1H), 6.60 (s, 1H), 6.50 (s, 1H), 6.08 (d, J=3.3 Hz, 1H), 5.00 (dd, J=12.9, 5.3 Hz, 1H), 4.18 (s, 2H), 3.65-3.30 (m, 15H), 3.07 (s, 4H), 2.90-2.58 (m, 8H), 2.21 (t, J=20.4 Hz, 7H), 1.98 (d, J=28.5 Hz, 6H), 1.37 (s, 2H), 0.91 (s, 6H).

Example 51

Preparation of 4-(4-[[2-(4-chlorophenyl)-4,4-dimethylcyclohex-1-en-1-yl]methyl]piperazin-1-yl)-N-[4-(15-[[2-(2,6-dioxopiperidin-3-yl)-1,3-dioxoisoindol-4-yl]amino]-4,7,10,13-tetraoxa-1-azapentadecan-1-yl)-3-nitrobenzenesulfonyl]-2-[14-oxa-2,4,10-triazatricyclo[7.5.0.0ˆ[3,7]]tetradeca-1(9),2,5,7-tetraen-10-yl]benzamide Synthesis of tert-butyl N-[14-[(2-nitro-4-sulfamoylphenyl)amino]-3,6,9,12-tetraoxatetradecan-1-yl]carbamate:

Into a 50-mL round-bottom flask, was placed tert-butyl N-(14-amino-3,6,9,12-tetraoxatetradecan-1-yl)carbamate (500.00 mg, 1.488 mmol, 1.00 equiv), 4-fluoro-3-nitrobenzenesulfonamide (327.00 mg, 1.488 mmol, 1.00 equiv), DIEA (385.00 mg, 2.976 mmol, 2.00 equiv), ACN (5.00 mL). The resulting solution was stirred for 18 h at 50 degrees C. in an oil bath. The resulting mixture was concentrated. The residue was applied onto a silica gel column with ethyl acetate/petroleum ether (5:1). This resulted in 680 mg (90%) of tert-butyl N-[14-[(2-nitro-4-sulfamoylphenyl)amino]-3,6,9,12-tetraoxatetradecan-1-yl]carbamate as yellow oil. LCMS-1 (ES, m/z): M−1: 535.

Synthesis of 4-(15-amino-4,7,10,13-tetraoxa-1-azapentadecan-1-yl)-3-nitrobenzenesulfonamide: Into a 50-mL round-bottom flask, was placed tert-butyl N-[14-[(2-nitro-4-sulfamoylphenyl)amino]-3,6,9,12-tetraoxatetradecan-1-yl]carbamate (680.00 mg, 1.269 mmol, 1.00 equiv), TFA (3.00 mL), DCM (12.00 mL). The resulting solution was stirred for 3 h at room temperature. The reaction was then quenched by the addition of 20 mL of water. The resulting solution was extracted with 2×20 mL of dichloromethane and the organic layers combined. The resulting mixture was washed with 2×20 ml of NaHCO$_3$. The mixture was dried over anhydrous sodium sulfate and concentrated. This resulted in 450 mg (92%) of 4-(15-amino-4,7,10,13-tetraoxa-1-azapentadecan-1-yl)-3-nitrobenzene sulfonamide as yellow oil. LCMS-2 (ES, m/z): M−1: 435.

Synthesis of 4-(15-[[2-(2,6-dioxopiperidin-3-yl)-1,3-dioxoisoindol-4-yl]amino]-4,7,10,13-tetraoxa-1-azapentadecan-1-yl)-3-nitrobenzenesulfonamide: Into a 50-mL round-bottom flask, was placed 4-(15-amino-4,7,10,13-tetraoxa-1-azapentadecan-1-yl)-3-nitrobenzenesulfonamide (310.00 mg, 0.711 mmol, 1.00 equiv), 2-(2,6-dioxopiperidin-3-yl)-4-fluoroisoindole-1,3-dione (196.00 mg, 0.711 mmol, 1.00 equiv), DIEA (185.00 mg, 1.422 mmol, 2.00 equiv), DMSO (5.00 mL). The resulting solution was stirred for 18 h at 90 degrees C. in an oil bath. The reaction mixture was cooled to room temperature with a water bath. The reaction was then quenched by the addition of 20 mL of water. The resulting solution was extracted with 2×30 mL of ethyl acetate and the organic layers combined. The resulting mixture was washed with 1×20 ml of brine. The mixture was dried over anhydrous sodium sulfate and concentrated. The residue was applied onto a silica gel column with dichloromethane/methanol (10:1). This resulted in 180 mg (87%) of 4-(15-[[2-(2,6-dioxopiperidin-3-yl)-1,3-dioxoisoindol-4-yl]amino]-4,7,10,13-tetraoxa-1-azapentadecan-1-yl)-3-nitrobenzenesulfonamide as yellow oil. LCMS-3 (ES, m/z): M−1: 691.

Synthesis of 4-(4-[[2-(4-chlorophenyl)-4,4-dimethylcyclohex-1-en-1-yl]methyl]piperazin-1-yl)-N-[4-(15-[[2-(2,6-dioxopiperidin-3-yl)-1,3-dioxoisoindol-4-yl]amino]-4,7,10,13-tetraoxa-1-azapentadecan-1-yl)-3-nitrobenzenesulfonyl]-2-[14-oxa-2,4,10-triazatricyclo[7.5.0.0ˆ[3,7]]tetradeca-1(9),2,5,7-tetraen-10-yl]benzamide: Into a 8-mL vial, was placed 4-(15-[[2-(2,6-dioxopiperidin-3-yl)-1,3-dioxoisoindol-4-yl]amino]-4,7,10,13-tetraoxa-1-azapentadecan-1-yl)-3-nitrobenzenesulfonamide (30.00 mg, 0.043 mmol, 1.00 equiv), 4-(4-[[2-(4-chlorophenyl)-4,4-dimethylcyclohex-1-en-1-yl]methyl]piperazin-1-yl)-2-[14-oxa-2,4,10-triazatricycloo[7.5.0.0[3,7]]tetradeca-1(9),2,5,7-tetraen-10-yl]benzoic acid (27.00 mg, 0.043 mmol, 1.00 equiv), EDCI (17.00 mg, 0.086 mmol, 2.00 equiv), DMAP (11.00 mg, 0.086 mmol, 2.00 equiv), DCM (2.00 mL). The resulting solution was stirred for 18 hr at room temperature. The resulting mixture was concentrated. The crude product was purified by Prep-HPLC with the following conditions: column, X-Bridge Prep C18 19*150 mm 5 um; mobile phase, A: water (it contains 10 mM NH$_4$HCO$_3$ 0.05% ammonia); B: ACN; Gradient: 20-45% B in 8 min; Flow rate: 20 mL/min; detector, UV 220 nm. The collected solution was concentrated under vacuum to remove CH$_3$CN and the resulting solution was dried by lyophilization. This resulted in 6 mg of 4-(4-[[2-(4-chlorophenyl)-4,4-dimethylcyclohex-1-en-1-yl]methyl]piperazin-1-yl)-N-[4-(15-[[2-(2,6-dioxopiperidin-3-yl)-1,3-dioxoisoindol-4-yl]amino]-4,7,10,13-tetraoxa-1-azapentadecan-1-yl)-3-nitrobenzenesulfonyl]-2-[14-oxa-2,4,10-triazatricyclo[7.5.0.0ˆ[3,7]]tetradeca-1(9),2,5,7-tetraen-10-yl]benzamide as a yellow solid.

LCMS-0: (ES, m/z): M+1: 1300. $^1$H NMR (300 MHz, DMSO-d$_6$, ppm) δ 11.14 (s, 1H), 11.09 (s, 1H), 8.44-8.45 (m, 2H), 7.62-7.65 (d, J=9.0 Hz, 1H), 7.53-7.56 (d, J=9.0 Hz, 1H), 7.43-7.46 (d, J=9.0 Hz, 1H), 7.34-7.37 (d, J=9.0 Hz, 2H), 7.01-7.18 (m, 6H), 6.95 (s, 1H), 6.87-6.90 (d, J=9.0 Hz, 1H), 6.52-6.72 (m, 3H), 6.10 (s, 1H), 5.01-5.09 (m, 1H), 4.22 (s, 2H), 3.44-3.66 (m, 22H), 3.07-3.18 (m, 5H), 2.72-2.78 (m, 2H), 2.58-2.62 (m, 2H), 2.11-2.35 (m, 6H), 1.90-2.08 (m, 5H), 1.39-1.43 (m, 2H), 0.95 (s, 6H).

Example 52

Preparation of 4-(4-[[2-(4-chlorophenyl)-4,4-dimethylcyclohex-1-en-1-yl]methyl]piperazin-1-yl)-N-[4-[(2-[4-[2-(2-[[2-(2,6-dioxopiperidin-3-yl)-1,3-dioxoisoindol-4-yl]amino]ethoxy)ethyl]piperazin-1-yl]ethyl)amino]-3-nitrobenzenesulfonyl]-2-[14-oxa-2,4,10-triazatricyclo[7.5.0.0ˆ[3,7]]tetradeca-1(9),2,5,7-tetraen-10-yl]benzamide Synthesis of 2-(2,6-dioxopiperidin-3-yl)-4-[[2-(2-hydroxyethoxy)ethyl]amino]isoindole-1,3-dione: Into a 50-mL round-bottom flask, was placed 2-(2-aminoethoxy)ethanol (383.00 mg, 3.643 mmol, 1.00 equiv), DMSO (20.00 mL), 2-(2,6-dioxopiperidin-3-yl)-4-fluoroisoindole-1,3-dione (1006.24 mg, 3.643 mmol, 1.00 equiv), DIEA (1412.45 mg, 10.929 mmol, 3 equiv). The resulting solution was stirred for overnight at 70 degrees C. in an oil bath. The reaction was then quenched by the addition of 30 mL of water. The resulting solution was extracted with 3×40 mL of ethyl acetate concentrated. The residue was applied onto a silica gel column and eluted with dichloromethane/methanol (10:1). The collected fractions were combined and concentrated. This resulted in 900 mg (68.37%) of 2-(2,6-dioxopiperidin-3-yl)-4-[[2-(2-hydroxyethoxy)ethyl]amino]isoindole-1,3-dione as a yellow solid. LCMS-1 (ES, m/z): M+1: 362.

Synthesis of 2-(2-[[2-(2,6-dioxopiperidin-3-yl)-1,3-dioxoisoindol-4-yl]amino]ethoxy)ethyl methanesulfonate: Into a 50-mL round-bottom flask, was placed 2-(2,6-dioxopiperidin-3-yl)-4-[[2-(2-hydroxyethoxy)ethyl]amino]isoindole-1,3-dione (500.00 mg, 1.384 mmol, 1.00 equiv), DCM (20.00 mL), TEA (420.05 mg, 4.151 mmol, 3 equiv). This was followed by the addition of MsCl (158.50 mg, 1.384 mmol, 1.00 equiv) dropwise with stirring at 0 degrees C. The resulting solution was stirred for 3 h at room temperature. The resulting mixture was concentrated. The residue was applied onto a silica gel column and eluted with ethyl acetate/petroleum ether (4:1). The collected fractions were combined and concentrated. This resulted in 300 mg (49.34%) of 2-(2-[[2-(2,6-dioxopiperidin-3-yl)-1,3-dioxoisoindol-4-yl]amino]ethoxy)ethyl methanesulfonate as a yellow solid. LCMS-2 (ES, m/z): M+1: 440.

Synthesis of 4-[(2-[4-[2-(2-[[2-(2,6-dioxopiperidin-3-yl)-1,3-dioxoisoindol-4-yl]amino]ethoxy)ethyl]piperazin-1-yl]ethyl)amino]-3-nitrobenzenesulfonamide: Into a 50-mL round-bottom flask, was placed 3-nitro-4-[[2-(piperazin-1-yl)ethyl]amino]benzenesulfonamide (225.00 mg, 0.683 mmol, 1.00 equiv), CH$_3$CN (20.00 mL), DIEA (529.72 mg, 4.099 mmol, 6 equiv), 2-(2-[[2-(2,6-dioxopiperidin-3-yl)-1,3-dioxoisoindol-4-yl]amino]ethoxy)ethyl methanesulfonate (300.18 mg, 0.683 mmol, 1.00 equiv). The resulting solution was stirred for overnight at 70 degrees C. in an oil bath. The resulting mixture was concentrated. The residue was applied onto a silica gel column and eluted with dichloromethane/methanol (10:1). The collected fractions were combined and concentrated. This resulted in 130 mg (28.29%) of 4-[(2-[4-[2-(2-[[2-(2,6-dioxopiperidin-3-yl)-1,3-dioxoisoindol-4-yl]amino]ethoxy)ethyl]piperazin-1-yl]ethyl)amino]-3-nitrobenzenesulfonamide as a yellow solid. LCMS-3 (ES, m/z): M+1: 673

Synthesis of 4-(4-[[2-(4-chlorophenyl)-4,4-dimethylcyclohex-1-en-1-yl]methyl]piperazin-1-yl)-N-[4-[(2-[4-[2-(2-[[2-(2,6-dioxopiperidin-3-yl)-1,3-dioxoisoindol-4-yl]amino]ethoxy)ethyl]piperazin-1-yl]ethyl)amino]-3-nitrobenzenesulfonyl]-2-[14-oxa-2,4,10-triazatricyclo[7.5.0.0ˆ[3,7]]tetradeca-1(9),2,5,7-tetraen-10-yl]benzamide: Into a 40-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoic acid (40.00 mg, 0.064 mmol, 1.00 equiv), DCM (8.00 mL), 4-[(2-[4-[2-(2-[[2-(2,6-dioxopiperidin-3-yl)-1,3-dioxoisoindol-4-yl]amino]ethoxy)ethyl]piperazin-1-yl]ethyl)amino]-3-nitrobenzenesulfonamide (42.97 mg, 0.064 mmol, 1.00 equiv), EDCI (24.49 mg, 0.128 mmol, 2 equiv), DMAP (31.21 mg, 0.256 mmol, 4 equiv). The resulting solution was stirred for overnight at 30 degrees C. in an oil bath. The resulting mixture was concentrated. The crude product was purified by Prep-HPLC with the following conditions: Column, X-bridge RP18; mobile phase, 0.05% ammonia in water and CH$_3$CN (45% CH$_3$CN up to 60% in 5 min); Detector, UV 254 nm. This resulted in 5 mg (6.11%) of 4-(4-[[2-(4-chlorophenyl)-4,4-dimethylcyclohex-1-en-1-yl]methyl]piperazin-1-yl)-N-[4-[(2-[4-[2-(2-[[2-(2,6-dioxopiperidin-3-yl)-1,3-dioxoisoindol-4-yl]amino]ethoxy)ethyl]piperazin-1-yl]ethyl)amino]-3-nitrobenzenesulfonyl]-2-[14-oxa-2,4,10-triazatricyclo[7.5.0.0ˆ[3,7]]tetradeca-1(9),2,5,7-tetraen-10-yl]benzamide as a yellow solid. LC-MS-0: (ES, m/z): M+1: 1281, $^1$H NMR (300 MHz, Chloroform-d, ppm) δ 8.40 (d, J=2.1 Hz, 1H), 7.66-7.51 (m, 2H), 7.42 (d, J=8.4 Hz, 1H), 7.34 (d, J=8.4 Hz, 2H), 7.18-7.10 (m, 2H), 7.03 (dd, J=11.7, 7.8 Hz, 3H), 6.92 (s, 1H), 6.80 (d, J=9.4 Hz, 1H), 6.62 (s, 2H), 6.08 (d, J=3.4 Hz, 1H), 5.01 (dd, J=12.6, 5.4 Hz, 1H), 4.19 (s, 2H), 3.60 (s, 6H), 3.42 (d, J=24.9 Hz, 6H), 3.12 (s, 4H), 2.89-2.57 (m, 12H), 2.48-2.43 (m, 4H) 2.19 (d, J=20.7 Hz, 6H), 1.95 (s, 6H), 1.38 (s, 2H), 0.92 (s, 6H).

Example 53

Preparation of 4-(4-[[2-(4-chlorophenyl)-4,4-dimethylcyclohex-1-en-1-yl]methyl]piperazin-1-yl)-N-[4-(12-[[2-(2,6-dioxopiperidin-3-yl)-1,3-dioxoisoindol-4-yl]amino]-4,7,10-trioxa-1-azadodecan-1-yl)-3-nitrobenzenesulfonyl]-2-[14-oxa-2,4,10-triazatricyclo[7.5.0.0ˆ[3,7]]tetradeca-1(9),2,5,7-tetraen-10-yl]benzamide Synthesis of tert-butyl N-[2-[2-(2-[2-[(2-nitro-4-sulfamoylphenyl)amino]ethoxy]ethoxy) ethoxy]ethyl]carbamate: Into a 50-mL 3-necked round-bottom flask purged and maintained with an inert atmosphere of nitrogen, was placed tert-butyl N-(2-[2-[2-(2-aminoethoxy)ethoxy]ethoxy]ethyl)carbamate (500.00 mg, 1.711 mmol, 1.00 equiv), 4-fluoro-3-nitrobenzenesulfonamide (377.00 mg, 1.711 mmol, 1.00 equiv), DIEA (442.00 mg, 3.422 mmol, 2.00 equiv), ACN (10.00 mL). The resulting solution was stirred for 18 h at 50 degrees C. in an oil bath. The reaction mixture was cooled to room temperature with a water bath. The resulting mixture was concentrated. The residue was applied onto a silica gel column with ethyl acetate/petroleum ether (20:1). This resulted in 1.2 g (99%) of tert-butyl N-[2-[2-(2-[2-[(2-nitro-4-sulfamoylphenyl)amino]ethoxy]ethoxy) ethoxy]ethyl]carbamate as yellow oil. LCMS-1 (ES, m/z): M−1: 491.

Synthesis of 4-(12-amino-4,7,10-trioxa-1-azadodecan-1-yl)-3-nitrobenzenesulfonamide: Into a 50-mL round-bottom flask, was placed tert-butyl N-[2-[2-(2-[2-[(2-nitro-4-sulfamoylphenyl)amino]ethoxy]ethoxy) ethoxy]ethyl]carbamate (1.60 g, 3.252 mmol, 1.00 equiv), DCM (12.00 mL), TFA (4.00 mL). The resulting solution was stirred for 3 h at room temperature. The resulting mixture was concentrated. This resulted in 1.1 g (95%) of 4-(12-amino-4,7,10-trioxa-1-azadodecan-1-yl)-3-nitrobenzenesulfonamide as yellow oil. LCMS-2 (ES, m/z): M−1: 391.

Synthesis of 4-(12-[[2-(2,6-dioxopiperidin-3-yl)-1,3-dioxoisoindol-4-yl]amino]-4,7,10-trioxa-1-azadodecan-1-yl)-3-nitrobenzenesulfonamide: Into a 50-mL round-bottom flask, was placed 4-(12-amino-4,7,10-trioxa-1-azadodecan-1-yl)-3-nitrobenzenesulfonamide (300.00 mg, 0.765 mmol, 1.00 equiv), 2-(2,6-dioxopiperidin-3-yl)-4-fluoroisoindole-1,3-dione (211.00 mg, 0.765 mmol, 1.00 equiv), DIEA (197.00 mg, 1.531 mmol, 2.00 equiv), DMSO (5.00 mL). The resulting solution was stirred for 18 h at 90 degrees C. in an oil bath. The reaction mixture was cooled to room temperature with a water bath. The reaction was then quenched by the addition of 20 mL of water. The resulting solution was extracted with 2×20 mL of ethyl acetate and the organic layers combined. The resulting mixture was washed with 3×20 ml of water and 1×20 mL of brine. The mixture was dried over anhydrous sodium sulfate and concentrated. The residue was applied onto a silica gel column with dichloromethane/methanol (10:1). This resulted in 160 mg (70%) of 4-(12-[[2-(2,6-dioxopiperidin-3-yl)-1,3-dioxoisoindol-4-yl]amino]-4,7,10-trioxa-1-azadodecan-1-yl)-3-nitrobenzenesulfonamide as yellow oil. LCMS-3 (ES, m/z): M−1: 647.

Synthesis of 4-(4-[[2-(4-chlorophenyl)-4,4-dimethylcyclohex-1-en-1-yl]methyl]piperazin-1-yl)-N-[4-(12-[[2-(2,6-dioxopiperidin-3-yl)-1,3-dioxoisoindol-4-yl]amino]-4,7,10-trioxa-1-azadodecan-1-yl)-3-nitrobenzenesulfonyl]-2-[14-oxa-2,4,10-triazatricyclo[7.5.0.0ˆ[3,7]]tetradeca-1(9),2,5,7-tetraen-10-yl]benzamide: Into a 8-mL vial, was placed 4-(12-[[2-(2,6-dioxopiperidin-3-yl)-1,3-dioxoisoindol-4-yl]amino]-4,7,10-trioxa-1-azadodecan-1-yl)-3-nitrobenzenesulfonamide (30.00 mg, 0.046 mmol, 1.00 equiv), 4-(4-[[2-(4-chlorophenyl)-4,4-dimethylcyclohex-1-en-1-yl]methyl]piperazin-1-yl)-2-[14-oxa-2,4,10-triazatricycloo[7.5.0.0[3,7]]tetradeca-1(9),2,5,7-tetraen-10-yl]benzoic acid (29.00 mg, 0.046 mmol, 1.00 equiv), EDCI (18.00 mg, 0.092 mmol, 2.00 equiv), DMAP (11.00 mg, 0.092 mmol, 2.00 equiv), DCM (2.00 mL). The resulting solution was stirred for 18 h at room temperature. The resulting mixture was concentrated. The crude product was purified by Prep-HPLC with the following conditions: column, X-Bridge Prep C18 19*150 mm 5 um; mobile phase, A: water (it contains 10 mM NH$_4$HCO$_3$ 0.05% ammonia); B: ACN; Gradient: 20-45% B in 8 min; Flow rate: 20 mL/min; detector, UV 220 nm. The collected solution was concentrated under vacuum to remove $CH_3CN$ and the resulting solution was dried by lyophilization. This resulted in 6 mg (92%) of 4-(4-[[2-(4-chlorophenyl)-4,4-dimethylcyclohex-1-en-1-yl]methyl]piperazin-1-yl)-N-[4-(12-[[2-(2,6-dioxopiperidin-3-yl)-1,3-dioxoisoindol-4-yl]amino]-4,7,10-trioxa-1-azadodecan-1-yl)-3-nitrobenzenesulfonyl]-2-[14-oxa-2,4,10-triazatricyclo[7.5.0.0^[3,7]]tetradeca-1(9),2,5,7-tetraen-10-yl]benzamide as a yellow solid. LCMS-0: (ES, m/z): M+1: 1256. $^1$H NMR (300 MHz, DMSO-$d_6$, ppm) δ 11.89 (s, 1H), 11.12 (s, 1H), 11.09 (s, 1H), 8.52 (s, 1H), 8.44 (s, 1H), 7.60-7.68 (m, 1H), 7.52-7.57 (m, 1H), 7.41-7.48 (m, 1H), 7.35-7.35 (d, J=9.0 Hz, 2H), 7.18 (s, 1H), 7.00-7.11 (m, 4H), 6.89-6.91 (m, 2H), 6.72 (s, 1H), 6.56-6.60 (m, 1H), 6.10 (s, 1H), 5.02-5.08 (m, 1H), 4.22 (s, 2H), 4.06-4.12 (m, 1H), 3.32-3.65 (m, 19H), 3.21-3.26 (m, 2H), 3.16-3.18 (m, 3H), 2.80-2.98 (m, 2H), 2.73-2.77 (m, 1H), 2.60-2.64 (m, 2H), 2.12-2.28 (m, 5H), 1.98-2.04 (m, 4H), 1.39-1.41 (m, 2H), 0.95 (s, 6H).

Example 54

Preparation of (2S,4R)-1-[(2S)-2-[3-(2-[2-[2-(4-[2-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]phenyl]formamidosulfonyl]-2-nitrophenyl)amino]ethyl]piperazin-1-yl]ethoxy]ethoxy]ethoxy)propanamido]-3,3-dimethylbutanoyl]-4-hydroxy-N-[[4-(4-methyl-1,3-thiazol-5-yl)phenyl]methyl]pyrrolidine-2-carboxamide Synthesis of tert-butyl 3-(2-[2-[2-(methanesulfonyloxy)ethoxy]ethoxy]ethoxy)propanoate: Into a 100-mL round-bottom flask purged and maintained with an inert atmosphere of nitrogen, was placed tert-butyl 3-[2-[2-(2-hydroxyethoxy)ethoxy]ethoxy]propanoate (1.00 g, 3.593 mmol, 1.00 equiv), DCM (20.00 mL), TEA (1.09 g, 10.772 mmol, 3.00 equiv), MsCl (492.00 mg, 4.295 mmol, 1.20 equiv). The resulting solution was stirred for 2 hr at 25 degrees C. The resulting solution was diluted with 200 mL of aqueous $NaHCO_3$. The resulting solution was extracted with 3×50 mL of dichloromethane and the organic layers combined. The resulting mixture was washed with 1×300 mL of brine. The mixture was dried over anhydrous sodium sulfate and concentrated under vacuum. This resulted in 1.3 g (101.52%) of tert-butyl 3-(2-[2-[2-(methanesulfonyloxy)ethoxy]ethoxy]ethoxy)propanoate as light yellow oil. $^1$H NMR (300 MHz, Chloroform-d, ppm) δ 4.48-4.31 (m, 2H), 3.89-3.57 (m, 12H), 3.09 (s, 3H), 2.51 (t, J=6.5 Hz, 2H), 1.46 (s, 9H).

Synthesis of tert-butyl 3-(2-[2-[2-(4-[2-[(2-nitro-4-sulfamoylphenyl)amino]ethyl]piperazin-1-yl)ethoxy]ethoxy]ethoxy)propanoate: Into a 40-mL vial, was placed tert-butyl 3-(2-[2-[2-(methanesulfonyloxy)ethoxy]ethoxy]ethoxy)propanoate (500.00 mg, 1.403 mmol, 1.00 equiv), $CH_3CN$ (10.00 mL), 3-nitro-4-[[2-(piperazin-1-yl)ethyl]amino]benzenesulfonamide hydrochloride (513.00 mg, 1.402 mmol, 1.00 equiv), DIEA (1.09 g, 8.431 mmol, 6.01 equiv). The resulting solution was stirred overnight at 80 degrees C. in an oil bath. The reaction mixture was cooled to room temperature. The resulting mixture was concentrated under vacuum. The residue was applied onto a silica gel column with dichloromethane/methanol (10:1). This resulted in 700 mg (84.62%) of tert-butyl 3-(2-[2-[2-(4-[2-[(2-nitro-4-sulfamoylphenyl)amino]ethyl]piperazin-1-yl)ethoxy]ethoxy]ethoxy)propanoate as yellow oil. LC-MS: (ES, m/z): M+1=590.

Synthesis of 3-(2-[2-[2-(4-[2-[(2-nitro-4-sulfamoylphenyl)amino]ethyl]piperazin-1-yl)ethoxy]ethoxy]ethoxy)propanoic acid: Into a 100-mL round-bottom flask, was placed tert-butyl 3-(2-[2-[2-(4-[2-[(2-nitro-4-sulfamoylphenyl)amino]ethyl]piperazin-1-yl)ethoxy]ethoxy]ethoxy)propanoate (680.00 mg, 1.153 mmol, 1.00 equiv), DCM (4.00 mL), TFA (1.00 mL). The resulting solution was stirred for 4 hr at 25 degrees C. The resulting mixture was concentrated under vacuum. This resulted in 600 mg (crude) of 3-(2-[2-[2-(4-[2-[(2-nitro-4-sulfamoylphenyl)aminoethyl]piperazin-1-yl)ethoxy]ethoxy]ethoxy)propanoic acid as yellow oil. LC-MS: (ES, m/z): M+1=534.

Synthesis of (2S,4R)-1-[(2S)-3,3-dimethyl-2-[3-(2-[2-[2-(4[2-[(2-nitro-4-sulfamoylphenyl)amino]ethyl]piperazin-1-yl)ethoxy]ethoxy]ethoxy)propanamido]butanoyl]-4-hydroxy-N-[[4-(4-methyl-1,3-thiazol-5-yl)phenyl]methyl]pyrrolidine-2-carboxamide: Into a 40-mL vial, was placed 3-(2-[2-[2-(4-[2-[(2-nitro-4-sulfamoylphenyl)amino]ethyl]piperazin-1-yl)ethoxy]ethoxy]ethoxy)propanoic acid (600.00 mg, 1.124 mmol, 1.00 equiv), DMF (10.00 mL), DIEA (872.00 mg, 6.747 mmol, 6.00 equiv), HATU (470.00 mg, 1.236 mmol, 1.10 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (525.00 mg, 1.124 mmol, 1.00 equiv). The resulting solution was stirred for 1.5 hr at 25 degrees C. The crude product was purified by Flash-Prep-HPLC with the following conditions (IntelFlash-1): Column, C18 reversed phase column; mobile phase, $H_2O$ (10 mm $NH_4HCO_3$) and $CH_3CN$ (40% $CH_3CN$ in $H_2O$); Detector, 254 nm. This resulted in 250 mg (13.39%) of (2S,4R)-1-[(2S)-3,3-dimethyl-2-[3-(2-[2-[2-(4-[2-[(2-nitro-4-sulfamoylphenyl)amino]ethyl]piperazin-1-yl)ethoxy]ethoxy]ethoxy)propanamido]butanoyl]-4-hydroxy-N-[[4-(4-methyl-1,3-thiazol-5-yl)phenyl]methyl]pyrrolidine-2-carboxamide as a yellow solid. LC-MS: (ES, m/z): M+1=946.

Synthesis of (2S,4R)-1-[(2S)-2-[3-(2-[2-[2-(4-[2-[(4-[[4-(4-[[2-(4-chlorophenyl)-4,4-dimethylcyclohex-1-en-1-yl]methyl]piperazin-1-yl)-2-[14-oxa-2,4,10-triazatricyclo]7.5.0.0^[3,7]]tetradeca-1(9),2,5,7-tetraen-10-yl]phenyl]formamidosulfonyl]-2-nitrophenyl)amino]ethyl]piperazin-1-yl]ethoxy[ethoxy]ethoxy)propanamido]-3,3-dimethylbutanoyl]-4-hydroxy-N-[[4-(4-methyl-1,3-thiazol-5-yl)phenyl]methyl]pyrrolidine-2-carboxamide: Into a 40-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoic acid (40.00 mg, 0.064 mmol, 1.00 equiv), DCM (5.00 mL), (2S,4R)-1-[(2S)-3,3-dimethyl-2-[3-(2-[2-[2-(4-[2-[(2-nitro-4-sulfamoylphenyl)amino]ethyl]piperazin-1-yl)ethoxy]ethoxy]ethoxy)propanamido]butanoyl]-4-hydroxy-N-[[4-(4-methyl-1,3-thiazol-5-yl)phenyl]methyl]pyrrolidine-2-carboxamide (106.00 mg, 0.064 mmol, 1.00 equiv, 57%), EDCI (24.00 mg, 0.125 mmol, 1.96 equiv), DMAP (31.00 mg, 0.254 mmol, 3.97 equiv). The resulting solution was stirred overnight at 30 degrees C. in an oil bath. The resulting mixture was concentrated under vacuum. The crude product was purified by Prep-HPLC with the following conditions: The crude product was purified by Prep-HPLC with the following conditions (Prep-HPLC-006): Column, XBridge Shield RP18 OBD Column, 5 um, 19*150 mm; mobile phase, Water (0.05% $NH_3 \cdot H_2O$) and ACN (40% Phase B up to 70% in 7 min); Detector, UV 254/220 nm. This resulted in 20 mg (20.14%) of (2S,4R)-1-[(2S)-2-[3-(2-[2-[2-(4-[2-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]ethyl]piperazin-1-yl)ethoxy]ethoxy]ethoxy)propanamido]-3,3-dimethylbutanoyl]-4-hydroxy-N-[[4-(4-methyl-1,3-thiazol-5-yl)phenyl]methyl]pyrrolidine-2-carboxamide as a yellow solid. LC-MS: (ES, m/z): M+1=1554. $^1$H NMR (300 MHz, DMSO-$d_{6, ppm}$) δ 11.21 (s, 1H), 8.98 (s, 1H), 8.66 (s, 1H), 8.56 (s, 1H), 8.44 (d, J=2.2 Hz, 1H), 7.91 (d, J=9.2 Hz, 1H), 7.64 (d, J=9.2 Hz, 1H), 7.40 (td, J=14.2, 7.9 Hz, 7H), 7.17 (d, J=3.7 Hz, 1H), 7.07 (d, J=8.2 Hz, 2H), 6.94 (s, 1H), 6.83 (d, J=9.5 Hz, 1H), 6.66 (d, J=10.1 Hz, 2H), 6.10 (d, J=3.1 Hz, 1H), 5.12 (s, 1H), 4.58-4.18 (m, 7H), 3.71-3.38 (m, 18H), 3.13 (d, J=9.4 Hz, 4H), 2.70 (d, J=37.9 Hz, 10H), 2.46-1.89 (m, 22H), 1.41 (s, 2H), 0.94 (s, 15H).

Example 55

Preparation of (2S,4R)-1-[(2S)-2-[1-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]-3,6,9,12,15-pentaoxaoctadecan-18-amido]-3,3-dimethylbutanoyl]-4-hydroxy-N-[[4-(4-methyl-1,3-thiazol-5-yl)phenyl]methyl]pyrrolidine-2-carboxamide Synthesis of tert-butyl 1-[(2-nitro-4-sulfamoylphenyl)amino]-3,6,9,12,15-pentaoxaoctadecan-18-oate: Into a 50-mL 3-necked round-bottom flask purged and maintained with an inert atmosphere of nitrogen, was placed tert-butyl 1-amino-3,6,9,12,15-pentaoxaoctadecan-18-oate (1.00 g, 2.740 mmol, 1.00 equiv), 4-fluoro-3-nitrobenzenesulfonamide (0.60 g, 2.740 mmol, 1.00 equiv), DIEA (0.71 g, 5.480 mmol, 2.00 equiv), ACN (15.00 mL). The resulting solution was stirred for 18 hr at 50 degrees C. in an oil bath. The reaction mixture was cooled to room temperature with a water bath. The resulting mixture was concentrated. The residue was applied onto a silica gel column with ethyl acetate/petroleum ether (10:1). This resulted in 1.8 g (91%) of tert-butyl 1-[(2-nitro-4-sulfamoylphenyl)amino]-3,6,9,12,15-pentaoxaoctadecan-18-oate as yellow oil. LCMS-1 (ES, m/z): M−1: 564.

Synthesis of 1-[(2-nitro-4-sulfamoylphenyl)amino]-3,6,9,12,15-pentaoxaoctadecan-18-oic acid: Into a 50-mL round-bottom flask, was placed tert-butyl 1-[(2-nitro-4-sulfamoylphenyl)amino]-3,6,9,12,15-pentaoxaoctadecan-18-oate (1.80 g, 3.186 mmol, 1.00 equiv), TFA (4.00 mL), DCM (12.00 mL). The resulting solution was stirred for 3 hr at room temperature. The resulting mixture was concentrated. This resulted in 1.2 g (90.5%) of 1-[(2-nitro-4-sulfamoylphenyl)amino]-3,6,9,12,15-pentaoxaoctadecan-18-oic acid as yellow oil. LCMS-2 (ES, m/z): M−1: 508.

Synthesis of (2S,4R)-1-[(2S)-3,3-dimethyl-2-[1-[(2-nitro-4-sulfamoylphenyl)amino]-3,6,9,12,15-pentaoxaoctadecan-18-amido]butanoyl]-4-methyl-N-[[4-(4-methyl-1,3-thiazol-5-yl)phenyl]methyl]pyrrolidine-2-carboxamide: Into a 50-mL round-bottom flask, was placed 1-[(2-nitro-4-sulfamoylphenyl)amino]-3,6,9,12,15-pentaoxaoctadecan-18-oic acid (240.00 mg, 0.465 mmol, 1.00 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (200.00 mg, 0.465 mmol, 1.00 equiv), DIEA (150.00 mg, 1.163 mmol, 2.50 equiv), HATU (195.00 mg, 0.512 mmol, 1.10 equiv), DMF (5.00 mL). The resulting solution was stirred for 2 h at room temperature. The reaction was then quenched by the addition of 30 mL of water. The resulting solution was extracted with 2×30 mL of ethyl acetate and the organic layers combined. The resulting mixture was washed with 3×30 ml of water and 1×30 mL of brine. The mixture was dried over anhydrous sodium sulfate and concentrated. The residue was applied onto a silica gel column with dichloromethane/methanol (10:1). This resulted in 200 mg (86.3%) of (2S,4R)-1-[(2S)-3,3-dimethyl-2-[1-[(2-nitro-4-sulfamoylphenyl)amino]-3,6,9,12,15-pentaoxaoctadecan-18-amido]butanoyl]-4-methyl-N-[[4-(4-methyl-1,3-thiazol-5-yl)phenyl]methyl]pyrrolidine-2-carboxamide as yellow oil. LCMS-3 (ES, m/z): M−1: 920.

Synthesis of (2S,4R)-1-[(2S)-2-[1-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]-3,6,9,12,15-pentaoxaoctadecan-18-amido]-3,3-dimethylbutanoyl]-4-hydroxy-N-[[4-(4-methyl-1,3-thiazol-5-yl)phenyl]methyl]pyrrolidine-2-carboxamide: Into a 8-mL sealed tube, was placed (2S,4R)-1-[(2S)-3,3-dimethyl-2-[1-[(2-nitro-4-sulfamoylphenyl)amino]-3,6,9,12,15-pentaoxaoctadecan-18-amido]butanoyl]-4-hydroxy-N-[[4-(4-methyl-1,3-thiazol-5-yl)phenyl]methyl]pyrrolidine-2-carboxamide (30.00 mg, 0.032 mmol, 1.00 equiv), 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-2,5,7-trien-10-yl]benzoic acid (20.00 mg, 0.032 mmol, 1.00 equiv), EDCI (12.00 mg, 0.065 mmol, 2.00 equiv), DMAP (8.00 mg, 0.065 mmol, 2.00 equiv), DCM (2.00 mL). The resulting solution was stirred for 18 hr at room temperature. The resulting mixture was concentrated. The crude product. The crude product was purified by Prep-HPLC with the following conditions: column, X-Bridge Prep C18 19*150 mm 5 um; mobile phase, 0.05% ammonia in water and CH$_3$CN (45% CH$_3$CN up to 60% in 5 min); Flow rate: 20 mL/min; detector, UV 220 nm. The collected solution was concentrated under vacuum to remove CH$_3$CN and the resulting solution was dried by lyophilization. This resulted in 2.8 mg (94.2%) of (2S,4R)-1-[(2S)-2-[1-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]-3,6,9,12,15-pentaoxaoctadecan-18-amido]-3,3-dimethylbutanoyl]-4-hydroxy-N-[[4-(4-methyl-1,3-thiazol-5-yl)phenyl]methyl]pyrrolidine-2-carboxamide as a yellow solid. LCMS-0: (ES, m/z): M+1: 1530. $^1$H NMR (300 MHz, DMSO-$d_6$, ppm) δ 11.89 (s, 1H), 11.19 (s, 1H), 8.98 (s, 2H), 8.52-8.58 (m, 2H), 8.43-8.48 (br, 1H), 7.90-7.93 (d, J=9.0 Hz, 1H), 7.66 (s, 1H), 7.32-7.49 (m, 8H), 7.16-7.20 (m, 1H), 7.06-7.09 (d, J=9.0 Hz, 2H), 6.88-6.92 (m, 2H), 6.68-6.78 (m, 1H), 6.11 (s, 1H), 5.12 (s, 1H), 4.52-4.57 (m, 1H), 4.31-4.48 (m, 4H), 4.17-4.24 (m, 3H), 3.65-3.67 (m, 5H), 3.54-3.59 (m, 8H), 3.44-3.48 (m, 14H), 3.16-3.26 (m, 1H), 3.73-3.81 (m, 2H), 2.44 (s, 3H), 2.11-2.28 (m, 6H), 1.89-2.17 (m, 6H), 1.38-1.46 (m, 2H), 1.24 (s, 2H), 0.93 (s, 15H).

Example 56

Preparation of (2S,4R)-1-[(2S)-2-(3-[2-[2-(4-[2-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]phenyl]formamidosulfonyl]-2-nitrophenyl)amino]ethyl]piperazin-1-yl)ethoxy]ethoxy]propanamido)-3,3-dimethylbutanoyl]-4-hydroxy-N-[[4-(4-methyl-1,3-thiazol-5-yl)phenyl]methyl]pyrrolidine-2-carboxamide Synthesis of tert-butyl 3-[2-[2-(methanesulfonyloxy)ethoxy]ethoxy]propanoate: Into a 50-mL round-bottom flask, was placed tert-butyl 3-[2-(2-hydroxyethoxy)ethoxy]propanoate (500.00 mg, 2.134 mmol, 1.00 equiv), DCM (20.00 mL), TEA (647.85 mg, 6.402 mmol, 3.00 equiv), MsCl (317.80 mg, 2.774 mmol, 1.30 equiv). The resulting solution was stirred for overnight at room temperature. The resulting mixture was concentrated. The residue was applied onto a silica gel column and eluted with ethyl acetate/petroleum ether (1:1). The collected fractions were combined and concentrated. This resulted in 600 mg (90.00%) of tert-butyl 3-[2-[2-(methanesulfonyloxy)ethoxy]ethoxy]propanoate as colorless oil. LCMS-1 (ES, m/z): M+1: 313.

Synthesis of tert-butyl 4-[2-[(2-nitro-4-sulfamoylphenyl)amino]ethyl]piperazine-1-carboxylate: Into a 250-mL round-bottom flask, was placed 4-fluoro-3-nitrobenzenesulfonamide (8.72 g, 39.606 mmol, 1.00 equiv), tert-butyl 4-(2-aminoethyl)piperazine-1-carboxylate (9.99 g, 43.563 mmol, 1.10 equiv), $CH_3CN$ (120.00 mL), DIEA (15.36 g, 118.817 mmol, 3 equiv). The resulting solution was stirred for 4 h at 70 degrees C. in an oil bath. The resulting mixture was concentrated. The product was precipitated by the addition of water. The solids were collected by filtration. The solid was dried in an oven under reduced pressure. This resulted in 12 g (70.55%) of tert-butyl 4-[2-[(2-nitro-4-sulfamoylphenyl)amino]ethyl]piperazine-1-carboxylate as a yellow solid.

LCMS-2 (ES, m/z): M−1: 428.

Synthesis of 3-nitro-4-[[2-(piperazin-1-yl)ethyl]amino]benzenesulfonamide: Into a 100-mL round-bottom flask, was placed tert-butyl 4-[2-[(2-nitro-4-sulfamoylphenyl)amino]ethyl]piperazine-1-carboxylate (2.00 g, 4.65 mmol, 1.00 equiv), HCl (gas) in 1,4-dioxane (20.00 mL). The resulting solution was stirred for 3 h at room temperature. The resulting mixture was concentrated. The pH value of the solution was adjusted to 7 with $NaHCO_3$ (6 mol/L). The resulting solution was extracted with 3×20 mL of dichloromethane concentrated. This resulted in 1.8 g (crude) of 3-nitro-4-[[2-(piperazin-1-yl)ethyl]amino]benzenesulfonamide as a yellow solid. LCMS-3 (ES, m/z): M+1: 330

Synthesis of tert-butyl 3-[2-[2-(4-[2-[(2-nitro-4-sulfamoylphenyl)amino]ethyl]piperazin-1-yl)ethoxy]ethoxy]propanoate: Into a 50-mL round-bottom flask, was placed 3-nitro-4-[[2-(piperazin-1-yl)ethyl]amino]benzenesulfonamide (329.00 mg, 0.999 mmol, 1.00 equiv), tert-butyl 3-[2-[2-(methanesulfonyloxy)ethoxy]ethoxy]propanoate (312.02 mg, 0.999 mmol, 1.00 equiv), $CH_3CN$ (20.00 mL), DIEA (774.56 mg, 5.993 mmol, 6 equiv). The resulting solution was stirred for overnight at 70 degrees C. in an oil bath. The resulting mixture was concentrated. The residue was applied onto a silica gel column and eluted with dichloromethane/methanol (10:1). The collected fractions were combined and concentrated. This resulted in 400 mg (73.39%) of tert-butyl 3-[2-[2-(4-[2-[(2-nitro-4-sulfamoylphenyl)amino]ethyl]piperazin-1-yl)ethoxy]ethoxy]propanoate as yellow oil. LC-MS-4: (ES, m/z): M−1: 544.

Synthesis of 3-[2-[2-(4-[2-[(2-nitro-4-sulfamoylphenyl)amino]ethyl]piperazin-1-yl)ethoxy]ethoxy]propanoic acid: Into a 50-mL round-bottom flask, was placed tert-butyl 3-[2-[2-(4-[2-[(2-nitro-4-sulfamoylphenyl)amino]ethyl]piperazin-1-yl)ethoxy]ethoxy]propanoate (200.00 mg, 0.367 mmol, 1.00 equiv), DCM (8.00 mL), TFA (2.00 mL, 0.018 mmol, 0.05 equiv). The resulting solution was stirred for 3 h at room temperature. The resulting mixture was concentrated. The pH value of the solution was adjusted to 7 with $NaHCO_3$ (3 mol/L). The resulting solution was extracted with 3×100 mL of dichloromethane concentrated. This resulted in 150 mg (83.60%) of 3-[2-[2-(4[2-[(2-nitro-4-sulfamoylphenyl)amino]ethyl]piperazin-1-yl)ethoxy]ethoxy]propanoic acid as yellow oil. LC-MS-5: (ES, m/z): M−1: 488.

Synthesis of (2S,4R)-1-[(2S)-3,3-dimethyl-2-(3-[2-[2-(4-[2-[(2-nitro-4-sulfamoylphenyl)amino]ethyl]piperazin-1-yl)ethoxy]ethoxy]propanamido)butanoyl]-4-hydroxy-N-[[4-(4-methyl-1,3-thiazol-5-yl)phenyl[methyl]pyrrolidine-2-carboxamide: Into a 8-mL round-bottom flask, was placed 3-[2-[2-(4-[2-[(2-nitro-4-sulfamoylphenyl)amino]ethyl]piperazin-1-yl)ethoxy]ethoxy]propanoic acid (150.00 mg, 0.306 mmol, 1.00 equiv), DMF (5.00 mL), HATU (128.16 mg, 0.337 mmol, 1.1 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (131.93 mg, 0.306 mmol, 1.0 equiv), DIEA (158.41 mg, 1.226 mmol, 4 equiv). The resulting solution was stirred for overnight at room temperature. The reaction was then quenched by the addition of 10 mL of water. The resulting solution was extracted with 3×30 mL of ethyl acetate concentrated. The residue was applied onto a silica gel column with dichloromethane/methanol (5:1). The collected fractions were combined and concentrated. This resulted in 50 mg (18.09%) of (2S,4R)-1-[(2S)-3,3-dimethyl-2-(3-[2-[2-(4-[2-[(2-nitro-4-sulfamoylphenyl)amino]ethyl]piperazin-1-yl)ethoxy]ethoxy]propanamido)butanoyl]-4-hydroxy-N-[[4-(4-methyl-1,3-thiazol-5-yl)phenyl]methyl]pyrrolidine-2-carboxamide as a yellow solid. LC-MS-6: (ES, m/z): M−1: 900.

Synthesis of (2S,4R)-1-[(2S)-2-(3-[2-[2-(4-[2-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]phenyl]formamidosulfonyl]-2-nitrophenyl)amino]ethyl]piperazin-1-yl)ethoxy]ethoxy]propanamido)-3,3-dimethylbutanoyl]-4-hydroxy-N-[[4-(4-methyl-1,3-thiazol-5-yl)phenyl]methyl]pyrrolidine-2-carboxamide: Into a 40-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0^[3,7]]tetradeca-1(9),2,5,7-tetraen-10-yl]benzoic acid (30.00 mg, 0.048 mmol, 1.00 equiv), DCM (8.00 mL), (2S,4R)-1-[(2S)-3,3-dimethyl-2-(3-[2-[2-(4-[2-[(2-nitro-4-sulfamoylphenyl)amino]ethyl]piperazin-1-yl)ethoxy]propanamido)butanoyl]-4-hydroxy-N-[[4-(4-methyl-1,3-thiazol-5-yl)phenyl]methyl]pyrrolidine-2-carboxamide (43.22 mg, 0.048 mmol, 1.00 equiv), EDCI (18.37 mg, 0.096 mmol, 2 equiv), DMAP (23.41 mg, 0.192 mmol, 4 equiv). The resulting solution was stirred for overnight at 30 degrees C. in an oil bath. The resulting mixture was concentrated. The crude product was purified by Prep-HPLC with the following conditions: Column, X-bridge RP18; mobile phase, 0.05% ammonia in water and $CH_3CN$ (45% $CH_3CN$ up to 60% in 6 min); Detector, UV 254 nm. This resulted in 5 mg (6.91%) of (2S,4R)-1-[(2S)-2-(3-[2-[2-(4-[2-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl) aminoethyl]piperazin-1-yl)ethoxy]ethoxy]propanamido)-3,3-dimethylbutanoyl]-4-hydroxy-N-[[4-(4-methyl-1,3-thiazol-5-yl)phenyl]methyl]pyrrolidine-2-carboxamide as a yellow solid. LC-MS-0: (ES, m/z): M+1: 1510. $^1$H NMR (300 MHz, DMSO-$d_6$, ppm)) δ 8.92 (s, 1H), 8.56 (s, 1H), 8.38 (d, J=2.1 Hz, 1H), 7.86 (d, J=9.3 Hz, 1H), 7.64-7.55 (m, 1H), 7.36-7.32 (m, 7H), 7.12 (d, J=3.6 Hz, 1H), 7.07-6.96 (m, 3H), 6.78 (d, J=9.3 Hz, 1H), 6.55 (s, 1H), 6.08 (d, J=3.6 Hz, 1H), 4.55-4.11 (m, 6H), 3.67-3.31 (m, 13H), 3.00 (s, 4H), 2.66 (d, J=33.6 Hz, 6H), 2.41 (s, 7H), 2.22-1.74 (m, 12H), 1.36 (s, 2H), 0.90 (s, 14H).

Example 57

Preparation of (2S,4R)-1-[(2S)-2-[1-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]-3,6,9,12-tetraoxapentadecan-15-amido]-3,3-dimethylbutanoyl]-4-hydroxy-N-[[4-(4-methyl-1,3-thiazol-5-yl)phenyl]methyl]pyrrolidine-2-carboxamide Synthesis of tert-butyl 1-[(2-nitro-4-sulfamoylphenyl)amino]-3,6,9,12-tetraoxapentadecan-15-oate: Into a 50-mL round-bottom flask, was placed tert-butyl 1-amino-3,6,9,12-tetraoxapentadecan-15-oate (500.22 mg, 1.556 mmol, 1.10 equiv), 4-fluoro-3-nitrobenzenesulfonamide (311.50 mg, 1.415 mmol, 1.00 equiv), $CH_3CN$ (20.00 mL), DIEA (548.57 mg, 4.244 mmol, 3 equiv). The resulting solution was stirred for overnight at 50 degrees C. in an oil bath. The resulting mixture was concentrated. The residue was applied onto a silica gel column and eluted with ethyl acetate/petroleum ether (1:1). The collected fractions were combined and concentrated. This resulted in 700 mg (94.86%) of tert-butyl 1-[(2-nitro-4-sulfamoylphenyl)amino]-3,6,9,12-tetraoxapentadecan-15-oate as yellow oil.

LCMS-1 (ES, m/z): M−1: 520.

Synthesis of 1-[(2-nitro-4-sulfamoylphenyl)amino]-3,6,9,12-tetraoxapentadecan-15-oic acid: Into a 100-mL round-bottom flask, was placed tert-butyl 1-[(2-nitro-4-sulfamoylphenyl)amino]-3,6,9,12-tetraoxapentadecan-15-oate (700.00 mg, 1.342 mmol, 1.00 equiv), DCM (24.00 mL), TFA (6.00 mL). The resulting solution was stirred for 3 h at room temperature. The pH value of the solution was adjusted to 7 with $NaHCO_3$ (6 mol/L). The resulting solution was extracted with 3×20 mL of dichloromethane concentrated. This resulted in 500 mg (80.04%) of 1-[(2-nitro-4-sulfamoylphenyl)amino]-3,6,9,12-tetraoxapentadecan-15-oic acid as yellow oil. LCMS-2 (ES, m/z): M+1: 466.

Synthesis of (2S,4R)-1-[(2S)-3,3-dimethyl-2-[1-[(2-nitro-4-sulfamoylphenyl)amino]-3,6,9,12-tetraoxapentadecan-15-amido]butanoyl]-4-hydroxy-N-[[4-(4-methyl-1,3-thiazol-5-yl)phenyl]methyl]pyrrolidine-2-carboxamide: Into a 50-mL round-bottom flask, was placed 1-[(2-nitro-4-sulfamoylphenyl)amino]-3,6,9,12-tetraoxapentadecan-15-oic acid (220.00 mg, 0.473 mmol, 1.00 equiv), DMF (10.00 mL), DIEA (244.34 mg, 1.891 mmol, 4 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (203.50 mg, 0.473 mmol, 1.00 equiv), HATU (197.68 mg, 0.520 mmol, 1.1 equiv). The resulting solution was stirred for 4 h at room temperature. The reaction was then quenched by the addition of 30 mL of water. The resulting solution was extracted with 3×30 mL of ethyl acetate dried over anhydrous sodium sulfate and concentrated. The residue was applied onto a silica gel column and eluted with dichloromethane/methanol (10:1). The collected fractions were combined and concentrated. This resulted in 200 mg (48.19%) of (2S,4R)-1-[(2S)-3,3-dimethyl-2-[1-[(2-nitro-4-sulfamoylphenyl)amino]-3,6,9,12-tetraoxapentadecan-15-amido]butanoyl]-4-hydroxy-N-[[4-(4-methyl-1,3-thiazol-5-yl)phenyl]methyl]pyrrolidine-2-carboxamide as yellow oil. LCMS-3 (ES, m/z): M−1: 876.

Synthesis of (2S,4R)-1-[(2S)-2-[1-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]-3,6,9,12-tetraoxapentadecan-15-amido]-3,3-dimethylbutanoyl]-4-hydroxy-N-[[4-(4-methyl-1,3-thiazol-5-yl)phenyl]methyl]pyrrolidine-2-carboxamide: Into a 8-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoic acid (20.80 mg, 0.033 mmol, 1.00 equiv), DCM (3.00 mL), (2S,4R)-1-[(2S)-3,3-dimethyl-2-[1-[(2-nitro-4-sulfamoylphenyl)amino]-3,6,9,12-tetraoxapentadecan-15-amido]butanoyl]-4-hydroxy-N-[[4-(4-methyl-1,3-thiazol-5-yl)phenyl]methyl]pyrrolidine-2-carboxamide (29.16 mg, 0.033 mmol, 1.00 equiv), EDCI (12.74 mg, 0.066 mmol, 2.00 equiv), DMAP (12.17 mg, 0.100 mmol, 3.00 equiv). The resulting solution was stirred for overnight at room temperature. The resulting mixture was concentrated. The crude product was purified by Prep-HPLC with the following conditions: Column, X-bridge RP18; mobile phase, 0.05% ammonia in water and $CH_3CN$ (45% $CH_3CN$ up to 60% in 5 min); Detector, UV 254 nm. This resulted in 6 mg (12.15%) of (2S,4R)-1-[(2S)-2-[1-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]-3,6,9,12-tetraoxapentadecan-15-amido]-3,3-dimethylbutanoyl]-4-hydroxy-N-[[4-(4-methyl-1,3-thiazol-5-yl)phenyl]methyl]pyrrolidine-2-carboxamide as a yellow solid. LC-MS-0: (ES, m/z): M+1: 1486. $^1$H NMR (300 MHz, Chloroform-d, ppm) δ 11.82 (s, 1H), 9.95 (s, 1H), 8.69 (s, 2H), 8.41 (s, 1H), 7.96 (d, J=9.6 Hz, 1H), 7.63 (s, 2H), 7.36 (s, 5H), 7.17 (s, 1H), 7.00 (d, J=8.1 Hz, 2H), 6.85 (s, 1H), 6.74 (s, 2H), 6.49 (s, 1H), 6.11 (s, 1H),4.93 (s, 1H), 4.62 (s, 2H), 4.56 (s, 1H), 4.47-4.34 (m, 1H), 4.26 (s, 1H), 3.68 (d, J=5.1 Hz, 21H), 3.34 (s, 5H), 2.86 (s, 1H), 2.52 (s, 7H), 2.39 (s, 4H), 2.27 (s, 3H), 2.08 (d, J=26.7 Hz, 2H), 1.49 (s, 2H), 1.28 (s, 1H), 1.01 (s, 15H).

Example 58

Preparation of (2S,4R)-1-[(2S)-2-[3-[2-(4-[2-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]ethyl]piperazin-1-yl)ethoxy]propanamido]-3,3-dimethylbutanoyl]-4-hydroxy-N-[[4-(4-methyl-1,3-thiazol-5-yl)phenyl]methyl]pyrrolidine-2-carboxamide Synthesis of tert-butyl 3-[2-(methanesulfonyloxy)ethoxy]propanoate: Into a 50-mL round-bottom flask, was placed tert-butyl 3-(2-hydroxyethoxy)propanoate (500.00 mg, 2.628 mmol, 1.00 equiv), DCM (20.00 mL), TEA (797.86 mg, 7.885 mmol, 3 equiv), MsCl (391.39 mg, 3.417 mmol, 1.30 equiv). The resulting solution was stirred for overnight at room temperature. The resulting mixture was concentrated. The residue was applied onto a silica gel column and eluted with ethyl acetate/petroleum ether (1:1). The collected fractions were combined and concentrated. This resulted in 600 mg (85.08%) of tert-butyl 3-[2-(methanesulfonyloxy)ethoxy]propanoate as colorless oil. LCMS-1 (ES, m/z): M+1: 269.

Synthesis of tert-butyl 3-[2-(4[2-[(2-nitro-4-sulfamoylphenyl)amino]ethyl]piperazin-1-yl)ethoxy]propanoate: Into a 50-mL round-bottom flask, was placed 3-nitro-4-[[2-(piperazin-1-yl)ethyl]amino]benzenesulfonamide (329.00 mg, 0.999 mmol, 1.00 equiv), tert-butyl 3-[2-(methanesulfonyloxy)ethoxy]propanoate (268.01 mg, 0.999 mmol, 1.00 equiv), $CH_3CN$ (20.00 mL), DIEA (774.56 mg, 5.993 mmol, 6 equiv). The resulting solution was stirred for overnight at 70 degrees C. in an oil bath. The resulting mixture was concentrated. The residue was applied onto a silica gel column and eluted with dichloromethane/methanol (10:1). The collected fractions were combined and concentrated. This resulted in 400 mg (79.84%) of tert-butyl 3-[2-(4-[2-[(2-nitro-4-sulfamoylphenyl)amino]ethyl]piperazin-1-yl)ethoxy]propanoate as yellow oil. LCMS-2 (ES, m/z): M−1: 500.

Synthesis of 3-[2-(4-[2-[(2-nitro-4-sulfamoylphenyl)amino]ethyl]piperazin-1-yl)ethoxy]propanoic acid: Into a 50-mL round-bottom flask, was placed 1-[(2-nitro-4-sulfamoylphenyl)amino]-3,6,9,12-tetraoxapentadecan-15-oic acid (220.00 mg, 0.473 mmol, 1.00 equiv), DMF (10.00 mL), DIEA (244.34 mg, 1.891 mmol, 4 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (203.50 mg, 0.473 mmol, 1.00 equiv), HATU (197.68 mg, 0.520 mmol, 1.1 equiv). The resulting solution was stirred for 4 h at room temperature. The reaction was then quenched by the addition of 30 mL of water. The resulting solution was extracted with 3×30 mL of ethyl acetate dried over anhydrous sodium sulfate and concentrated. The residue was applied onto a silica gel column and eluted with dichloromethane/methanol (10:1). The collected fractions were combined and concentrated. This resulted in 200 mg (48.19%) of (2S,4R)-1-[(2S)-3,3-dimethyl-2-[1-[(2-nitro-4-sulfamoylphenyl)amino]-3,6,9,12-tetraoxapentadecan-15-amido]butanoyl]-4-hydroxy-N-[[4-(4-methyl-1,3-thiazol-5-yl)phenyl]methyl]pyrrolidine-2-carboxamide as yellow oil.

LCMS-3 (ES, m/z): M−1: 444.

Synthesis of (2S,4R)-1-[(2S)-3,3-dimethyl-2-[3-[2-(4-[2-[(2-nitro-4-sulfamoylphenyl)amino]ethyl]piperazin-1-yl)ethoxy]propanamido]butanoyl]-4-hydroxy-N-[[4-(4-methyl-1,3-thiazol-5-yl)phenyl]methyl]pyrrolidine-2-carboxamide: Into a 8-mL round-bottom flask, was placed 3-[2-(4-[2-[(2-nitro-4-sulfamoylphenyl)amino]ethyl]piperazin-1-yl)ethoxy]propanoic acid (150.00 mg, 0.337 mmol, 1.00 equiv), DMF (5.00 mL), HATU (140.83 mg, 0.370 mmol, 1.1 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (144.98 mg, 0.337 mmol, 1.00 equiv), DIEA (174.07 mg, 1.347 mmol, 4 equiv). The resulting solution was stirred for overnight at room temperature. The reaction was then quenched by the addition of 10 mL of water. The resulting solution was extracted with 3×30 mL of ethyl acetate concentrated. The residue was applied onto a silica gel column and eluted with dichloromethane/methanol (5:1). The collected fractions were combined and concentrated. This resulted in 55 mg (19.04%) of (2S,4R)-1-[(2S)-3,3-dimethyl-2-[3-[2-(4-[2-[(2-nitro-4-sulfamoylphenyl)amino]ethyl]piperazin-1-yl)ethoxy]propanamido]butanoyl]-4-hydroxy-N-[[4-(4-methyl-1,3-thiazol-5-yl)phenyl]methyl]pyrrolidine-2-carboxamide as a yellow solid.

LCMS-4 (ES, m/z): M−1: 857.

Synthesis of (2S,4R)-1-[(2S)-2-[3-[2-(4-[2-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]ethyl]piperazin-1-yl)ethoxy]propanamido]-3,3-dimethylbutanoyl]-4-hydroxy-N-[[4-(4-methyl-1,3-thiazol-5-yl)phenyl]methyl]pyrrolidine-2-carboxamide: Into a 40-mL vial, was placed 4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]benzoic acid (30.00 mg, 0.048 mmol, 1.00 equiv), DCM (8.00 mL), (2S,4R)-1-[(2S)-3,3-dimethyl-2-[3-[2-(4-[2-[(2-nitro-4-sulfamoylphenyl)amino]ethyl]piperazin-1-yl)ethoxy]propanamido]butanoyl]-4-hydroxy-N-[[4-(4-methyl-1,3-thiazol-5-yl)phenyl]methyl]pyrrolidine-2-carboxamide (41.11 mg, 0.048 mmol, 1.00 equiv), EDCI (18.37 mg, 0.096 mmol, 2 equiv), DMAP (23.41 mg, 0.192 mmol, 4 equiv). The resulting solution was stirred for overnight at 30 degrees C. in an oil bath. The resulting mixture was concentrated. The crude product was purified by Prep-HPLC with the following conditions: Column, X-bridge RP18; mobile phase, 0.05% ammonia in water and $CH_3CN$ (45% $CH_3CN$ up to 60% in 6 min); Detector, UV 254 nm. This resulted in 6 mg (8.54%) of (2S,4R)-1-[(2S)-2-[3-[2-(4-[2-[(4-[[4-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]ethyl]piperazin-1-yl)ethoxy]propanamido]-3,3-dimethylbutanoyl]-4-hydroxy-N-[[4-(4-methyl-1,3-thiazol-5-yl)phenyl]methyl]pyrrolidine-2-carboxamide as a yellow solid. LC-MS-0: (ES, m/z): M+1: 1466. $^1$H NMR (300 MHz, DMSO-$d_6$, ppm) δ 8.90 (s, 1H), 8.56 (s, 1H), 8.37 (d, J=2.1 Hz, 1H), 7.88 (d, J=9.0 Hz, 1H), 7.62 (d, J=9.0 Hz, 1H), 7.36-7.31 (m, 6H), 7.11-7.02 (m, 3H), 6.78 (d, J=9.3 Hz, 1H), 6.51 (d, J=9.0 Hz, 1H), 6.28 (s, 1H), 6.07 (d, J=3.6 Hz, 1H), 4.55-4.10 (m, 6H), 3.67-3.25 (m, 9H), 2.94 (s, 3H), 2.70 (s, 5H), 2.40 (s, 11H), 2.23-1.65 (m, 12H), 1.36 (s, 2H), 0.89 (s, 14H).

Example 59

Preparation of (2S,4R)-1-[(2S)-2-[3-[2-(2-[2-[(4-[[5-(4-[[2-(4-chlorophenyl)-4,4-dimethylcyclohex-1-en-1-yl]ethyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]ethoxy]ethoxy)ethoxy]propanamido]-3,3-dimethylbutanoyl]-4-methyl-N-[[4-(4-methyl-1,3-thiazol-5-yl)phenyl]methyl]pyrrolidine-2-carboxamide Synthesis of tert-butyl 3-(2-(2-(2-(2-nitro-4-sulfamoylphenylamino)ethoxy)ethoxy)ethoxy)propanoate: Into a 50-mL 3-necked round-bottom flask purged and maintained with an inert atmosphere of nitrogen, was placed tert-butyl 3-[2-[2-(3-aminopropoxy)ethoxy]ethoxy]propanoate (1.00 g, 3.608 mmol, 1.00 equiv), 4-fluoro-3-nitrobenzenesulfonamide (0.79 g, 3.608 mmol, 1.00 equiv), DIEA (0.93 g, 7.215 mmol, 2.00 equiv), ACN (15.00 mL). The resulting solution was stirred for 18 hr at 50 degrees C. in an oil bath. The reaction mixture was cooled to room temperature with a water bath. The resulting mixture was concentrated. The residue was applied onto a silica gel column with ethyl acetate/petroleum ether (10:1). This resulted in 1.67 g (96%) of tert-butyl 3-[2-(2-[2-[(2-nitro-4-sulfamoylphenyl)amino] ethoxy]ethoxy)ethoxy]propanoate as yellow oil. LCMS-1 (ES, m/z): M−1: 476.

Synthesis of 3-(2-(2-(2-(2-nitro-4-sulfamoylphenylamino)ethoxy)ethoxy)ethoxy)propanoic acid: Into a 50-mL round-bottom flask, was placed tert-butyl 3-[2-(2-[2-[(2-nitro-4-sulfamoylphenyl)amino]ethoxy]ethoxy)ethoxy] propanoate (1.60 g, 3.245 mmol, 1.00 equiv), TFA (4.00 mL), DCM (12.00 mL). The resulting solution was stirred for 3 hr at room temperature. The resulting mixture was concentrated. This resulted in 1.0 g (79.6%) of 3-[2-(2-[2-[(2-nitro-4-sulfamoylphenyl)amino]ethoxy]ethoxy)ethoxy] propanoic acid as yellow oil. LCMS-2 (ES, m/z): M−1: 420.

Synthesis of (2S,4R)-1-[(2S)-3,3-dimethyl-2-[3-[2-(2-[2-[(2-nitro-4-sulfamoylphenyl)amino]ethoxy]ethoxy)ethoxy] propanamido]butanoyl]-4-methyl-N-[[4-(4-methyl-1,3-thiazol-5-yl)phenyl]methyl]pyrrolidine-2-carboxamide: Into a 50-mL round-bottom flask, was placed 3-[2-(2[2-[(2-nitro-4-sulfamoylphenyl)amino]ethoxy]ethoxy)ethoxy]propanoic acid (200.00 mg, 0.475 mmol, 1.00 equiv), (2S,4R)-1-[(2S)-2-amino-3,3-dimethylbutanoyl]-4-methyl-N-[[4-(4-methyl-1,3-thiazol-5-yl)phenyl]methyl]pyrrolidine-2-carboxamide (200.00 mg, 0.475 mmol, 1.00 equiv), DIEA (186.00 mg, 1.188 mmol, 2.50 equiv), HATU (200.00 mg, 0.523 mmol, 1.10 equiv), DMF (5.00 mL). The resulting solution was stirred for 2 hr at room temperature. The reaction was then quenched by the addition of 10 mL of water/ice. The resulting solution was extracted with 2×15 mL of ethyl acetate The resulting mixture was washed with 4×20 ml of water and 1×20 mL of brine. The mixture was dried over anhydrous sodium sulfate and concentrated. The residue was applied onto a silica gel column with dichloromethane/methanol (10:1). This resulted in 380 mg (85%) of (2S,4R)-1-[(2S)-3,3-dimethyl-2-[3-[2-(2-[2-[(2-nitro-4-sulfamoylphenyl)amino]ethoxy]ethoxy)ethoxy]propanamido] butanoyl]-4-methyl-N-[[4-(4-methyl-1,3-thiazol-5-yl) phenyl]methyl]pyrrolidine-2-carboxamide as yellow oil. LCMS-3 (ES, m/z): M−1: 832.

Synthesis of (2S,4R)-1-[(2S)-2-[3-[2-(2-[2-[(4-[[5-(4-[[2-(4-chlorophenyl)-4,4-dimethylcyclohex-1-en-1-yl]methyl] piperazin-1-yl)-2-[14-oxa-2,4,10-triazatricyclo[7.5.0.0ˆ[3,7]]tetradeca-1(9),2,5,7-tetraen-10-yl]phenyl] formamidosulfonyl]-2-nitrophenyl)amino]ethoxy]ethoxy) ethoxy]propanamido]-3,3-dimethylbutanoyl]-4-methyl-N-[[4-(4-methyl-1,3-thiazol-5-yl)phenyl]methyl]pyrrolidine-2-carboxamide: Into a 8-mL vial, was placed (2S,4R)-1-[(2S)-3,3-dimethyl-2-[3-[2-(2-[2-[(2-nitro-4-sulfamoylphenyl)amino]ethoxy]ethoxy)ethoxy] propanamido]butanoyl]-4-methyl-N-[[4-(4-methyl-1,3-thiazol-5-yl)phenyl]methyl]pyrrolidine-2-carboxamide (30.00 mg, 0.036 mmol, 1.00 equiv), 5-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1 (9),2,5,7-tetraen-10-yl]benzoic acid (23.00 mg, 0.036 mmol, 1.00 equiv), EDCI (14.00 mg, 0.072 mmol, 2.00 equiv), DMAP (9.00 mg, 0.072 mmol, 2.00 equiv), DCM (2.00 mL). The resulting solution was stirred for 18 hr at room temperature. The resulting mixture was concentrated. The crude product was purified by Prep-HPLC with the following conditions: column, X-Bridge Prep C18 19*150 mm 5 um; mobile phase, 0.05% ammonia in water and CH$_3$CN (45% CH$_3$CN up to 60% in 5 min); Flow rate: 20 mL/min; detector, UV 220 nm. The collected solution was concentrated under vacuum to remove CH$_3$CN and the resulting solution was dried by lyophilization. This resulted in 4 mg of (2S,4R)-1-[(2S)-2-[3-[2-(2-[2-[(4-[[5-(4-[[2-(4-chlorophenyl)-4,4-dimethylcyclohex-1-en-1-yl]methyl]piperazin-1-yl)-2-[14-oxa-2,4,10-triazatricyclo[7.5.0.0ˆ[3,7]]tetradeca-1(9),2,5,7-tetraen-10-yl]phenyl]formamidosulfonyl]-2-nitrophenyl)amino]ethoxy]ethoxy)ethoxy]propanamido]-3,3-dimethylbutanoyl]-4-methyl-N-[[4-(4-methyl-1,3-thiazol-5-yl)phenyl]methyl]pyrrolidine-2-carboxamide as a yellow solid. LCMS-0: (ES, m/z): M+1: 1442. $^1$H NMR (300 MHz, DMSO-d$_6$, ppm) δ 11.87 (s, 1H), 11.19 (s, 1H), 8.95-8.98 (d, J=9.0 Hz, 1H), 8.56 (s, 2H), 8.45-8.46 (m, 1H), 7.89 (s, 1H), 7.61 (s, 2H), 7.31-7.55 (m, 8H), 7.05-7.09 (m, 2H), 6.82-6.92 (m, 2H), 6.69-6.73 (m, 1H), 6.11 (s, 1H), 5.11 (s, 1H), 4.55 (s, 1H), 4.31-4.50 (m, 3H), 4.22-4.26 (m, 3H), 3.40-3.70 (m, 10H), 3.22 (s, 3H), 2.70-2.80 (m, 7H), 2.15-2.30 (m, 9H), 1.93-2.07 (m, 8H), 1.38-1.42 (m, 2H), 1.20-1.30 (m, 4H), 0.93 (s, 15H).

Example 60

Preparation of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzene sulfonyl)-2-[(12R)-12-methyl-13-oxa-2,4,10-triazatricyclo[7.4.0.0ˆ[3,7]]trideca-1(9),2,5,7-tetraen-10-yl]benzamide Synthesis of (E)-2-(2-ethoxyvinyl)-4,4,5,5-tetramethyl-1,3,2-dioxaborolane: Into a 3 L 4-necked round-bottom flask, was placed ethyl vinyl ether (2000.00 g, 27777.778 mmol, 3.00 equiv), 4,4,5,5-tetramethyl-1,3,2-dioxaborolane (508.00 g, 9259.259 mmol, 1.00 equiv). This solution was cooled to 5 degrees C. in an ice/salt bath. This followed by the addition of Pd(OAc)$_2$ (10.39 g, 46.296 mmol, 0.005 equiv) in portions at 0-5 degrees C. The resulting solution was stirred for 18 h at room temperature. The resulting mixture was concentrated. This resulted in 1500 g (crude) and purify by rectification, collect 65-70 degree at 25 mm Hg, got 890 g (Y=50%, LCMS OK, Q-NMR=87%) of 2-[(Z,E mixtures)-2-ethoxyethenyl]-4,4,5,5-tetramethyl-1,3-dioxolane as light yellow oil. LC-MS: (ES, m/z): M+1=199, R.T=1.979 min, 2.440 min. H-NMR: (300 MHz, DMSO-d$_6$, ppm): δ 6.71-6.95 (m, 1H), 4.29-4.34 (m, 1H), 3.80-3.93 (m, 2H), 1.15-1.21 (m, 16H).

Synthesis of N-[(2R)-2-hydroxypropyl]acetamide: Into a 250-mL 3-necked round-bottom flask purged and maintained with an inert atmosphere of nitrogen, was placed (2R)-1-aminopropan-2-ol (10 g, 133.136 mmol, 1 equiv), DCM (100 mL), TEA (16 g, 159.764 mmol, 1.2 equiv). This was followed by the addition of a solution of acetyl acetate (13.6 g, 133.136 mmol, 1.0 equiv) in DCM (10 mL) dropwise with stirring at 0° C. The resulting solution was stirred for 14 hr at room temperature. The resulting mixture was concentrated. The residue was applied onto a silica gel column with dichloromethane/methanol (100:5). This resulted in 13.5 g (69.25%) of N-[(2R)-2-hydroxypropyl] acetamide as a yellow oil. LC-MS: (ES, m/z): M+1=118.

Synthesis of 4-([[(2S)-1,4-dioxan-2-yl]methyl]amino)-3-nitrobenzene-1-sulfonamide: Into a 100-mL round-bottom flask, was placed 4-fluoro-3-nitrobenzene-1-sulfonamide (1.43 g, 0.007 mmol, 1 equiv), 1-[(2S)-1,4-dioxan-2-yl] methanamine hydrochloride (1 g, 6.510 mmol, 1 equiv), THF (30 mL), Cs$_2$CO$_3$ (8.48 g, 0.026 mmol, 4 equiv). The resulting solution was stirred overnight at 50° C. in an oil bath. The solids were collected by filtration. The solid was dried in an oven under reduced pressure. This resulted in 1.82 g (88.10%) of 4-([[(2S)-1,4-dioxan-2-yl]methyl]amino)-3-nitrobenzene-1-sulfonamide as a yellow solid. LC-MS: (ES, m/z): M+1=318, R,T=0.741 min.

Synthesis of methyl 2-bromo-4-(4-((2-(4-chlorophenyl)-4,4-dimethylcyclohex-1-enyl)methyl)piperazin-1-yl)benzoate: Into a 20000-mL round-bottom flask, was placed 1-((2-(4-chlorophenyl)-4,4-dimethylcyclohex-1-enyl)methyl)piperazine dihydrochloride (600 g, 1.53 mol, 1 equiv), methyl 2-bromo-4-fluorobenzoate (357 g, 1.53 mol, 1 equiv), DBU (319 g, 6.12 mol, 4 equiv) and DMSO (8000 mL). The resulting solution was stirred for 20 h at 70 degrees C. LCMS showed material was completely consumed. The resulting mixture was cooled to R,T and poured into water (32 L). The mixture was filtered, collection of filter cake and the filter cake was washed by water (3000 mL×3) and dried by oven to give product 740 g (Y=91%) methyl 2-bromo-4-(4-((2-(4-chlorophenyl)-4,4-dimethylcyclohex-1-enyl)methyl)piperazin-1-yl)benzoate as a white solid. H-NMR: (300 MHz, DMSO-$d_6$, ppm) δ: 7.73 (d, J=9.0 Hz, 1H), 7.42-7.39 (m, 2H), 7.18-7.12 (m, 3H), 6.97-6.94 (m, 1H), 4.00-3.84 (m, 2H), 3.76 (s, 3H), 3.57 (s, 3H), 3.51-3.33 (m, 4H), 2.79-2.60 (m, 2H), 2.32-2.30 (m, 2H), 2.03-1.97 (m, 2H), 1.47-1.45 (m, 2H), 0.96 (s, 6H).

Synthesis of 2-bromo-4-(4-((2-(4-chlorophenyl)-4,4-dimethylcyclohex-1-enyl)methyl)piperazin-1-yl)benzoic acid: Into a 20000-mL round-bottom flask, was placed methyl 2-bromo-4-(4-((2-(4-chlorophenyl)-4,4-dimethylcyclohex-1-enyl)methyl)piperazin-1-yl)benzoate (730 g, 1.37 mol, 1 equiv), LiOH (131.5 g, 5.48 mol, 4 equiv) and MeOH/THF/water (4500 mL/3000 mL/1000 mL). The resulting solution was stirred for 16 h at 70 degrees C. LCMS showed material was completely consumed. The resulting mixture was cooled to R,T and concentrated. The residue was diluted with water (5000 mL) and the mixture was adjust PH to 3-5 with HCl (6 M), followed by filtrated, collection of filter cake and dried by oven to give product 650 g 2-bromo-4-(4-((2-(4-chlorophenyl)-4,4-dimethylcyclohex-1-enyl)methyl)piperazin-1-yl)benzoic acid as a white solid. H-NMR-PH-PHNW-4-55-400: (300 MHz, DMSO-$d_6$, ppm) δ: 10.60 (bs, 1H), 7.73 (d, J=8.4 Hz, 1H), 7.42-7.39 (m, 2H), 7.14-7.11 (m, 3H), 6.95-6.92 (m, 1H), 4.00-3.84 (m, 2H), 3.76 (s, 2H), 3.51-3.33 (m, 4H), 2.79-2.60 (m, 2H), 2.32-2.30 (m, 2H), 2.03-1.97 (m, 2H), 1.47-1.45 (m, 2H), 0.97 (s, 6H).

Synthesis of 5-bromo-6-fluoropyridin-2-amine: Into a 100 L 4-necked round-bottom flask, was placed 6-fluoropyridin-2-amine (4500.00 g, 40178.571 mmol, 1.00 equiv), ACN (25000.00 mL). This was followed by the addition of NBS (7100.00 g, 41764.706 mmol, 1.03 equiv) in portions (2 h) at 5-15 degrees C. The resulting solution was stirred for 3 h at room temperature. The resulting solution was diluted with 50 L of water. The resulting solution was extracted with 2×32 L of ethyl acetate. The resulting mixture was washed with 10 L of brine. The mixture was dried over anhydrous sodium sulfate and concentrated. The resulting mixture was washed with 3×13 L of PE. This mixture was dried by oven to give product 6900 g (Y=90%) of 5-bromo-6-fluoropyridin-2-amine as a light brown solid. LC-MS: (ES, m/z): M+1=191, 193, R.T=0.851 min. H-NMR: (300 MHz, DMSO-$d_6$, ppm): δ 7.63-7.71 (m, 1H), 6.57 (s, 2H), 6.27-631 (m, 1H).

Synthesis of 5-bromo-6-fluoro-3-iodopyridin-2-amine: Into a 100 L 4-necked round-bottom flask, was placed 5-bromo-6-fluoropyridin-2-amine (6500.00 g, 34219.531 mmol, 1.00 equiv), AcOH (39000.00 mL). The solution was cooled to 15 degree C. in a water/ice bath. This was followed by the addition of NIS (8470.00 g, 37641.484 mmol, 1.10 equiv) in portions (3 h) at 10-20 degrees C. The resulting solution was stirred for 3 h at room temperature. The resulting solution was added into 100 L of water. The mixture was filtered, collection of filter cake and the filter cake was washed by water (25 L×3) and dried by oven to give product 9840 g (Y=85%) of 5-bromo-6-fluoro-3-iodopyridin-2-amine as a brown solid. LC-MS: (ES, m/z): M+1=317, 319, R.T=1.072 min. H-NMR: (300 MHz, DMSO-$d_6$, ppm): δ 8.17-8.20 (m, 1H), 6.69 (s, 2H).

Synthesis of 5-bromo-3-(2-ethoxyvinyl)-6-fluoropyridin-2-amine: Into a 20 L 4-necked round-bottom flask purged and maintained with an inert atmosphere of nitrogen, was placed 5-bromo-6-fluoro-3-iodopyridin-2-amine (855.00 g, 2705.696 mmol, 1.00 equiv), i-PrOH (10000.00 mL), 2-[(E)-2-ethoxyethenyl]-4,4,5,5-tetramethyl-1,3-dioxolane (1000.00 g, 5050.505 mmol, 1.87 equiv), $K_3PO_4$ (1720.00 g, 8113.207 mmol, 3.00 equiv), Ruphos (12.00 g, 27.060 mmol, 0.02 equiv), Pd(OAc)2 (10.00 g, 44.643 mmol, 0.02 equiv). The resulting solution was stirred for 12 h at room temperature in a liquid nitrogen bath. The solids were filtered out. The filter cake was washed by 3×2 L DCM. The organic layer was collected and concentrated. The residue was applied onto a silica gel column and eluted with ethyl acetate/petroleum ether (1:5). This concentrated and resulted in 680 g (80%) of 5-bromo-3-[(Z,E mixtures)-2-ethoxyethenyl]-6-fluoropyridin-2-amine as dark brown oil. LC-MS: (ES, m/z): M+1=261, 263, R.T=1.090 min.

Synthesis of 5-bromo-6-fluoro-1H-pyrrolo[2,3-b]pyridine: Into a 10 L 4-necked round-bottom flask purged and maintained with an inert atmosphere of nitrogen, was placed 5-bromo-3-[(E)-2-ethoxyethenyl]-6-fluoropyridin-2-amine (680.00 g, 2605.364 mmol, 1.00 equiv), EtOH (5000.00 mL), HCl (1000.00 mL). The resulting solution was stirred for 5 h at room temperature. The resulting mixture was concentrated. The pH value of the solution was adjusted to 6 with NaOH (4 mol/L). The solids were collected by filtration and washed with 3×500 mL water. This resulted in 410 g (Y=75%) of 5-bromo-6-fluoro-1H-pyrrolo[2,3-b]pyridine as a light brown solid. LC-MS: (ES, m/z): M+1=215, 217, R.T=0.993 min. H-NMR: (300 MHz, DMSO-$d_6$, ppm): δ 9.53 (brs, 1H), 8.19-8.22 (d, J=9.0 Hz, 1H), 7.32 7.34 (m, 1H), 6.50-6.52 (m, 1H).

Synthesis of 5-bromo-6-fluoro-14(2-(trimethylsilyl)ethoxy)methyl)-1H-pyrrolo[2,3-b]pyridine: Into a 5 L 4-necked round-bottom flask was placed 5-bromo-6-fluoro-1H-pyrrolo[2,3-b]pyridine (200.00 g, 930.232 mmol, 1.00 equiv), DMF (2500.00 mL). This solution was cooled to 0 degrees C. in a water/ice bath. This was followed by the addition of NaH (75.00 g, 1860.464 mmol, 2.00 equiv) in portions at 0 degrees C. To this was added SEM-Cl (233.00 g, 1395.210 mmol, 1.50 equiv) dropwise with stirring at 0 degrees C. The resulting solution was stirred for 1 h at room temperature. The reaction was then quenched by the addition of 1000 mL of water/ice. The resulting solution was diluted with 5 L of water. The resulting solution was extracted with 2×10 L of ethyl acetate and the organic layers combined. The resulting mixture was washed with 3×5 L of water. The resulting mixture was washed with 3 L of brine. The mixture was dried over anhydrous sodium sulfate and concentrated. The residue was applied onto a silica gel column and eluted with ethyl acetate/petroleum ether (1:20). This resulted in 298 g (87%) of 5-bromo-6-fluoro-1-[[2-(trimethylsilyl)ethoxy]ethyl]pyrrolo[2,3-b]pyridine as light yellow oil. LC-MS: (ES, m/z): M+1=345, 347, R.T=1.435 min. H-NMR (300 MHz, DMSO-d$_6$, ppm): δ 8.46-8.49 (d, J=9.0 Hz, 1H), 7.68-7.69 (m, 1H), 6.57-6.58 (m, 1H), 5.52-5.55 (m, 2H), 3.47-3.60 (m, 2H), 0.79-0.90 (m, 2H), 0.01 (s, 9H).

Synthesis of (R)—N-(2-(5-bromo-14(2-(trimethylsilyl) ethoxy)methyl)-1H-pyrrolo[2,3-b]pyridin-6-yloxy)propyl) acetamide: Into a 50-mL round-bottom flask, was placed N-[(2R)-2-hydroxypropyl]acetamide (680 mg, 5.8 mmol, 2.00 equiv), dioxane (10 mL). This was followed by the addition of NaH (348 mg, 8.7 mmol, 3 equiv), in portions at 15° C. The resulting solution was stirred for 10 min at RT. To this was added a solution of 5-bromo-6-fluoro-1-((2-(trimethylsilyl)ethoxy)methyl)-1H-pyrrolo[2,3-b]pyridine (1 g, 2.9 mmol, 1 equiv) in dioxane (5 mL). The resulting solution was stirred for 4 hr at 80° C. in an oil bath. The reaction was cooled to r.t then quenched by the addition of 5 mL of water. The resulting solution was extracted with 3×10 mL of ethyl acetate. The resulting mixture was washed with 3×5 ml of H$_2$O. The resulting mixture was washed with 1×10 mL of NaCl (aq). The mixture was dried over anhydrous sodium sulfate and concentrated. The residue was applied onto a silica gel column with PE/EA (100:20). This resulted in 880 mg (73%) of (R)—N-(2-(5-bromo-1-((2-(trimethylsilyl)ethoxy)methyl)-1H-pyrrolo[2,3-b]pyridin-6-yloxy)propyl)acetamide as a white solid.

Synthesis of 1-[(12R)-4-(trimethylsilyl)ethoxy)methyl)-12-methyl-13-oxa-2,4,10-triazatricyclo[7.4.0.0ˆ[3,7]]trideca-1(9),2,5,7-tetraen-10-yl]ethan-1-one: Into a 25-mL round-bottom flask purged and maintained with an inert atmosphere of nitrogen, was placed (R)—N-(2-(5-bromo-1-((2-(trimethylsilyl)ethoxy)methyl)-1H-pyrrolo[2,3-b]pyridin-6-yloxy)propyl)acetamide (500 mg, 1.13 mmol, 1 equiv), dioxane (8 mL), Cs2CO3 (1.1 g, 3.4 mmol, 3 equiv), BrettPhos Pd G3 (102 mg, 0.11 mmol, 0.10 equiv). The resulting solution was stirred for 14 hr at 80° C. in an oil bath. The resulting mixture was concentrated. The residue was applied onto a silica gel column with ethyl acetate/petroleum ether (50:50). This resulted in 300 mg (73.3%) of 1-[(12R)-4-(trimethylsilyl)ethoxy)methyl)-12-methyl-13-oxa-2,4,10-triazatricyclo[7.4.0.0ˆ[3,7]]trideca-1(9),2,5,7-tetraen-10-yl]ethan-1-one as light yellow oil.

Synthesis of (12R)-4-(trimethylsilyl)ethoxy)methyl)-12-methyl-13-oxa-2,4,10-triazatricyclo[7.4.0.0ˆ[3,7]]trideca-1(9),2,5,7-tetraene: Into a 8-mL vial, was placed 1-[(12R)-4-(trimethylsilyl)ethoxy)methyl)-12-methyl-13-oxa-2,4,10-triazatricyclo[7.4.0.0ˆ[3,7]]trideca-1(9),2,5,7-tetraen-10-yl]ethan-1-one (50 mg), methanol (0.5 mL), NaOH/H$_2$O (1M, 0.5 ml). The resulting solution was stirred for 14 hr at 80° C. in an oil bath. The resulting mixture was concentrated. The residue was applied onto a silica gel column with ethyl acetate/petroleum ether (1:1). This resulted in 15 mg (34%) of (12R)-4-(trimethylsilyl)ethoxy)methyl)-12-methyl-13-oxa-2,4,10-triazatricyclo[7.4.0.0ˆ[3,7]]trideca-1(9),2,5,7-tetraene as brown oil.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraen-10-yl]benzamide: Into a 8-mL vial purged and maintained with an inert atmosphere of nitrogen, was placed (12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraene (100.00 mg, 0.313 mmol, 1.00 equiv), 2-bromo-4-(4-[[2-(4-chlorophenyl)-4,4-dimethylcyclohex-1-en-1-yl]methyl]piperazin-1-yl)-N-(4-[[(2S)-1,4-dioxan-2-ylmethyl] amino]-3-nitrobenzenesulfonyl)benzamide (255.79 mg, 0.313 mmol, 1.00 equiv), DMF (2.00 mL), CuI (23.84 mg, 0.125 mmol, 0.40 equiv), N$_1$,N$_2$-bis(4-hydroxy-2,6-dimethylphenyl)oxalamide (20.53 mg, 0.063 mmol, 0.20 equiv), K$_2$CO$_3$ (129.78 mg, 0.939 mmol, 3.00 equiv). The resulting solution was stirred for 4 hr at 100 degrees C. in an oil bath. The resulting solution was diluted with 10 mL of H$_2$O. The resulting solution was extracted with 3×5 mL of ethyl acetate. The resulting mixture was washed with 3×5 ml of H$_2$O. The mixture was dried over anhydrous sodium sulfate. The residue was applied onto a silica gel column and eluted with dichloromethane/methanol (10:1). This resulted in 220 mg (66.57%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraen-10-yl]benzamide as a yellow solid. LC-MS: (ES, m/z): 1055.5 [M+H].

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(12R)-12-methyl-13-oxa-2,4,10-triazatricyclo[7.4.0.0ˆ[3,7]]trideca-1(9),2,5,7-tetraen-10-yl]benzamide: Into a 25-mL round-bottom flask, was placed 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(12R)-12-methyl-4-[[2-(trimethylsilyl)ethoxy]methyl]-13-oxa-2,4,10-triazatricyclo[7.4.0.0ˆ[3,7]]trideca-1(9),2,5,7-tetraen-10-yl]benzamide (210.00 mg), ethane-1,2-diamine (1.00 mL), TBAF in THF (3M, 5.00 mL). The resulting solution was stirred for 14 hr at 70 degrees C. in an oil bath. The resulting mixture was concentrated. The resulting solution was diluted with 20 mL of DCM. The resulting mixture was washed with 3×5 ml of H$_2$O. The mixture was dried over anhydrous sodium sulfate. The residue was purified with Prep-TLC with dichloromethane/methanol (100:5). This resulted in 70 mg (38.02%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(12R)-12-methyl-13-oxa-2,4,10-triazatricyclo[7.4.0.0ˆ[3,7]]trideca-1(9),2,5,7-tetraen-10-yl]benzamide as a yellow solid. LC-MS: (ES, m/z): 925.4 [M+H]. $^1$H NMR (300 MHz, CDCl$_3$, ppm): δ 12.38 (s, 1H), 8.68-8.46 (m, 3H), 8.16-7.97 (m, 1H), 7.90-7.81 (m, 1H), 7.28-7.05 (m, 3H), 7.02-6.78 (m, 3H), 6.77-6.63 (m, 2H), 6.54 (s, 1H), 6.11-6.03 (m, 1H), 4.98-4.83 (m, 1H), 4.10-2.99 (m, 17H), 2.91-2.79 (m, 2H), 2.40-2.17 (m, 6H), 2.10-2.02 (m, 2H), 1.70-1.61 (m, 3H), 0.97 (s, 6H).

Example 61

Synthesis of (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide Into a 50-mL round-bottom flask, was placed a solution of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide (15 mg, 0.015 mmol, 1.00 equiv) in methanol (5 mL). The resulting-solution was purified by Chiral-Prep-HPLC with the following conditions (SHIMADZU LC-20AT): Column, CHIRALPAK ID-3, 4.6*50 mm, 3 μm; mobile phase A: n-Hexane/DCM=5/1; Phase B: EtOH/MeOH=1/1; Detector, PDA. This resulted in 2.5 mg (33%) of (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide as a yellow solid. LC-MS: (ES, m/z): M+1=991, R,T=1.61 min. The measurements of the retention were done with a reversed phase column (C18). Shimadzu LCMS 2020; 50*3.0 Agilent Poroshell HPH-C18, 2.7 um; Eluent A: water (0.05% ammonia water); Eluent B: Acetonitrile; linear gradient from 5% acetonitrile to 95% acetonitrile in 7.0 minutes; Oven temperature 40° C.; flow: 1.5 mL/min. $^1$H NMR (300 MHz, CDCL3, ppm) δ 11.43 (ds, 1H), 9.99 (ds, 1H), 8.72 (s, 1H), 8.40 (ds, 1H), 7.93-7.85 (m, 2H), 7.37-7.35 (m, 2H), 7.26 (s, 1H), 7.02-6.93 (m, 3H), 6.71-6.64 (m, 3H), 6.27 (s, 1H), 4.58 (s, 1H), 4.05-3.15 (m, 23H), 2.70-2.35 (m, 7H), 2.03 (s, 3H), 1.92-1.90 (m, 1H), 1.89-1.87 (m, 2H), 1.71-1.67 (m, 2H), 1.53-1.45 (m, 3H), 1.00 (s, 6H).

Example 62

Synthesis of (S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide Into a 50-mL round-bottom flask, was placed a solution of 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide (15 mg, 0.015 mmol, 1.00 equiv) in methanol (5 mL). The resulting solution was purified by Chiral-Prep-HPLC with the following conditions (SHIMADZU LC-20AT): Column, CHIRALPAK ID-3, 4.6*50 mm, 3 μm; mobile phase A: n-Hexane/DCM=5/1; Phase B: EtOH/MeOH=1/1; Detector, PDA. This resulted in 2.5 mg (33%) of (S)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(trifluoromethyl)-3,4-dihydro-2H-pyrrolo[3',2':5,6]pyrido[2,3-b][1,4]oxazepin-1(7H)-yl)benzamide as a yellow solid LC-MS: (ES, m/z): M+1=991, R,T=1.61 min. The measurements of the retention were done with a reversed phase column (C18). Shimadzu LCMS 2020; 50*3.0 Agilent Poroshell HPH-C18, 2.7 um; Eluent A: water (0.05% ammonia water); Eluent B: Acetonitrile; linear gradient from 5% acetonitrile to 95% acetonitrile in 7.0 minutes; Oven temperature 40° C.; flow: 1.5 mL/min. $^1$H NMR (300 MHz, CDCL3, ppm) δ 11.43 (ds, 1H), 9.99 (ds, 1H), 8.72 (s, 1H), 8.40 (ds, 1H), 7.93-7.85 (m, 2H), 7.37-7.35 (m, 2H), 7.26 (s, 1H), 7.02-6.93 (m, 3H), 6.71-6.64 (m, 3H), 6.27 (s, 1H), 4.58 (s, 1H), 4.05-3.15 (m, 23H), 2.70-2.35 (m, 7H), 2.03 (s, 3H), 1.92-1.90 (m, 1H), 1.89-1.87 (m, 2H), 1.71-1.67 (m, 2H), 1.53-1.45 (m, 3H), 1.00 (s, 6H).

Example 63

Preparation of 4-(4-[[2-(4-chlorophenyl)-4,4-dimethylcyclohex-1-en-1-yl]methyl]piperazin-1-yl)-2-[13,13-difluoro-14-oxa-2,4,10-triazatricyclo[7.5.0.0^[3,7]]tetradeca-1(9),2,5,7-tetraen-10-yl]-N-(4-[[(2R)-1,4-dioxan-2-ylmethyl]amino]-2-nitrobenzenesulfonyl)benzamide hydrochloride Synthesis of 1-bromo-3,3-diethoxy-1,1-difluoropropane: Into a 250-mL sealed tube, was placed ethoxyethene (14.40 g, 199.703 mmol, 1.00 equiv), EtOH (80.00 mL), dibromodifluoromethane (62.85 g, 0.300 mmol, 1.5 equiv), $Na_2S_2O_4$ (52.15 g, 0.300 mmol, 1.5 equiv), $NaHCO_3$ (50.33 g, 0.599 mmol, 3 equiv). The resulting solution was stirred for 4 h at 60 degrees C. in an oil bath. The reaction was then quenched by the addition of 200 mL of water/ice. The resulting solution was extracted with 3×200 mL of petroleum ether. The resulting mixture was washed with 2×100 ml of water. The mixture was dried over anhydrous sodium sulfate. The solids were filtered out. The resulting mixture was concentrated under vacuum. This resulted in 12 g (24.32%) of 1-bromo-3,3-diethoxy-1,1-difluoropropane as yellow oil. $^1$H NMR (300 MHz, DMSO-$d_6$): δ 4.82 (t, J=5.2 Hz, 1H), 3.7-3.55 (m, 2H), 3.54-3.43 (m, 2H), 2.83 (td, J=14.7, 5.1 Hz, 2H), 1.13 (t, J=7.2 Hz, 6H).

Synthesis of ethyl 3-bromo-3,3-difluoropropanoate: Into a 250-mL round-bottom flask, was placed 1-bromo-3,3-diethoxy-1,1-difluoropropane (12.00 g, 48.567 mmol, 1.00 equiv), DCM (120.00 mL), m-CPBA (11.73 g, 0.068 mmol, 1.4 equiv), $H_2SO_4$ (0.10 g, 0.001 mmol, 0.02 equiv). The resulting solution was stirred for overnight at 55 degrees C. in an oil bath. The solids were filtered out. The pH value of the solution was adjusted to 8 with $NaHCO_3$ (5 mol/L). The resulting solution was extracted with 2×120 mL of dichloromethane. The solution was concentrated under vacuum. This resulted in 8 g (75.90%) of ethyl 3-bromo-3,3-difluoropropanoate as light yellow oil.

Synthesis of 5-bromo-1-[[2-(trimethylsilyl)ethoxy]methyl]-1H-pyrrolo[2,3-b]pyridin-6-ol: Into a 100-mL round-bottom flask, was placed 5-bromo-6-fluoro-[[2-(trimethylsilyl)ethoxy]methyl]-1H-pyrrolo[2,3-b]pyridine (3.00 g, 8.688 mmol, 1.00 equiv), NMP (50.00 mL), $H_2O$ (5.00 mL), KOH (1.46 g, 0.026 mmol, 3 equiv). The resulting solution was stirred for 3 h at 135 degrees C. in an oil bath. The reaction was then quenched by the addition of 50 mL of water. The resulting solution was extracted with 4×50 mL of ethyl acetate and concentrated under vacuum. The residue was applied onto a silica gel column and eluted with ethyl acetate/petroleum ether (1:5). The collected fractions were combined and concentrated. This resulted in 1.5 g (50.29%) of 5-bromo-[[2-(trimethylsilyl)ethoxy]methyl]-1H-pyrrolo[2,3-b]pyridin-6-ol as a white solid. LCMS (ES, m/z): M+1: 343/345.

Synthesis of ethyl 3-[(5-bromo-1-[[2-(trimethylsilyl)ethoxy]methyl]-1H-pyrrolo[2,3-b]pyridin-6-yl)oxy]-3,3-difluoropropanoate: Into a 50-mL round-bottom flask, was placed 5-bromo-1-[[2-(trimethylsilyl)ethoxy]methyl]-1H-pyrrolo[2,3-b]pyridin-6-ol (1.02 g, 2.971 mmol, 1.00 equiv), DMF (10.00 mL), TEA (0.75 g, 0.007 mmol, 2.5 equiv), ethyl 3-bromo-3,3-difluoropropanoate (0.64 g, 0.003 mmol, 1 equiv). The resulting solution was stirred for overnight at 0 degrees C. to room temperature. The reaction was then quenched by the addition of 20 mL of water. The resulting solution was extracted with 3×20 mL of ethyl acetate and concentrated. The residue was applied onto a silica gel column and eluted with ethyl acetate/petroleum ether (1:10).

The collected fractions were combined and concentrated. This resulted in 1.6 g (112.33%) of ethyl 3-[(5-bromo-1-[[2-(trimethylsilyl)ethoxy]methyl]-1H-pyrrolo[2,3-b]pyridin-6-yl)oxy]-3,3-difluoropropanoate as yellow oil. LC-MS: (ES, m/z): M+1:479/481.

Synthesis of 3-[(5-bromo-1-[[2-(trimethylsilyl)ethoxy] methyl]-1H-pyrrolo[2,3-b]pyridin-6-yl)oxy]-3,3-difluoropropan-1-01: Into a 100-mL 3-necked round-bottom flask purged and maintained with an inert atmosphere of nitrogen, was placed ethyl 3-[(5-bromo-1-[[2-(trimethylsilyl)ethoxy] methyl]-1H-pyrrolo[2,3-b]pyridin-6-yl)oxy]-3,3-difluoropropanoate (1.60 g, 3.338 mmol, 1.00 equiv), THF (20.00 mL), LiAlH$_4$ (0.51 g, 0.013 mmol, 4 equiv). The resulting solution was stirred for 2 h at −78- to −30 degrees C. The reaction was then quenched by the addition of 20 mL of water. The solids were filtered out. The resulting solution was extracted with 3×20 mL of ethyl acetate and concentrated. The residue was applied onto a silica gel column and eluted with ethyl acetate/petroleum ether (1:4). The collected fractions were combined and concentrated under vacuum. This resulted in 900 mg (61.66%) of 3-[(5-bromo-1-[[2-(trimethylsilyl)ethoxy]methyl]-1H-pyrrolo[2,3-b] pyridin-6-yl)oxy]-3,3-difluoropropan-1-ol as light yellow oil. LC-MS: (ES, m/z): M+1:437/439.

Synthesis of 3-[(5-bromo-1-[[2-(trimethylsilyl)ethoxy] methyl]-1H-pyrrolo[2,3-b]pyridin-6-yl)oxy]-3,3-difluoropropyl methanesulfonate: Into a 100-mL round-bottom flask, was placed 3-[(5-bromo-1-[[2-(trimethylsilyl)ethoxy] methyl]-1H-pyrrolo[2,3-b]pyridin-6-yl)oxy]-3,3-difluoropropan-1-ol (900.00 mg, 2.058 mmol, 1.00 equiv), DCM (20.00 mL), TEA (624.69 mg, 6.173 mmol, 3 equiv), methanesulfonyl chloride (259.27 mg, 2.26 mmol, 1.10 equiv). The resulting solution was stirred for 3 h at 0 degrees C. to room temperature. The reaction was then quenched by the addition of 20 mL of water. The resulting solution was extracted with 3×20 mL of ethyl acetate and concentrated. The residue was applied onto a silica gel column and eluted with ethyl acetate/petroleum ether (1:5). The collected fractions were combined and concentrated under vacuum. This resulted in 1 g (94.28%) of 3-[(5-bromo-1-[[2-(trimethylsilyl)ethoxy]methyl]-1H-pyrrolo[2,3-b]pyridin-6-yl)oxy]-3, 3-difluoropropyl methanesulfonate as light yellow oil. LC-MS: (ES, m/z): M+1:515/517.

Synthesis of 3-[(5-bromo-1-[[2-(trimethylsilyl)ethoxy] methyl]-1H-pyrrolo[2,3-b]pyridin-6-yl)oxy]-3,3-difluoropropan-1-amine: Into a 50-mL sealed tube, was placed 3-[(5-bromo-1-[[2-(trimethylsilyl)ethoxy]methyl]-1H-pyrrolo[2,3-b]pyridin-6-yl)oxy]-3,3-difluoropropyl methanesulfonate (1.00 g, 1.94 mmol, 1.00 equiv). NH$_3$/MeOH (7M) (20.00 mL). The resulting solution was stirred for overnight at 70 degrees C. in an oil bath. The resulting mixture was concentrated under vacuum. This resulted in 600 mg (70.87%) of 3-[(5-bromo-1-[[2-(trimethylsilyl)ethoxy] methyl]-1H-pyrrolo[2,3-b]pyridin-6-yl)oxy]-3,3-difluoropropan-1-amine as yellow oil. LC-MS: (ES, m/z): M+1:436/438.

Synthesis of 13,13-difluoro-4-[[2-(trimethylsilyl)ethoxy] methyl]-14-oxa-2,4,10-triazatricyclo[7.5.0.0ˆ[3,7]]tetradeca-1(9),2,5,7-tetraene: Into a 40-mL vial purged and maintained with an inert atmosphere of nitrogen, was placed 3-[(5-bromo-1-[[2-(trimethylsilyl)ethoxy]methyl]-1H-pyrrolo[2,3-b]pyridin-6-yl)oxy]-3,3-difluoropropan-1-amine (600.00 mg, 1.375 mmol, 1.00 equiv), toluene (10.00 mL), t-BuONa (396.42 mg, 4.125 mmol, 3 equiv), XPhos Pd G3 Precatalyst (116.38 mg, 0.137 mmol, 0.10 equiv). The resulting solution was stirred for 2 h at 80 degrees C. in an oil bath. The resulting mixture was concentrated under vacuum. The residue was applied onto a silica gel column and eluted with ethyl acetate/petroleum ether (1:3). The collected fractions were combined and concentrated. This resulted in 400 mg (81.84%) of 13,13-difluoro-4-[[2-(trimethylsilyl)ethoxy]methyl]-14-oxa-2,4,10-triazatricyclo [7.5.0.0ˆ[3,7]]tetradeca-1(9),2,5,7-tetraene as light yellow oil. LC-MS: (ES, m/z): M+1:356.

Synthesis of methyl 4-(4-[[2-(4-chlorophenyl)-4,4-dimethylcyclohex-1-en-1-yl]methyl]piperazin-1-yl)-2-(13,13-difluoro-4-[[2-(trimethylsilyl)ethoxy]methyl]-14-oxa-2,4, 10-triazatricyclo[7.5.0.0ˆ[3,7]]tetradeca-1(9),2,5,7-tetraen-10-yl)benzoate: Into a 100-mL round-bottom flask purged and maintained with an inert atmosphere of nitrogen, was placed 13,13-difluoro-4-[[2-(trimethylsilyl)ethoxy]methyl]-14-oxa-2,4,10-triazatricyclo[7.5.0.0ˆ[3,7]]tetradeca-1(9),2, 5,7-tetraene (400.00 mg, 1.125 mmol, 1.00 equiv), toluene (30.00 mL), methyl 2-bromo-4-(4-[[2-(4-chlorophenyl)-4,4-dimethylcyclohex-1-en-1-yl]methyl]piperazin-1-yl)benzoate (838.00 mg, 1.575 mmol, 1.40 equiv), Cs$_2$CO$_3$ (1099.93 mg, 3.376 mmol, 3 equiv), XantPhos Pd G2 Precatalyst (65.11 mg, 0.113 mmol, 0.1 equiv). The resulting solution was stirred for overnight at 110 degrees C. in an oil bath. The solids were filtered out. The resulting mixture was concentrated. The residue was applied onto a silica gel column and eluted with ethyl acetate/petroleum ether (1:3). The collected fractions were combined and concentrated. This resulted in 400 mg (44.08%) of methyl 4-(4-[[2-(4-chlorophenyl)-4,4-dimethylcyclohex-1-en-1-yl]methyl]piperazin-1-yl)-2-(13,13-difluoro-4-[[2-(trimethylsilyl)ethoxy] methyl]-14-oxa-2,4,10-triazatricyclo[7.5.0.0ˆ[3,7]] tetradeca-1(9),2,5,7-tetraen-10-yl)benzoate as yellow oil. LC-MS: (ES, m/z): M+1:806.

Synthesis of 4-(4-[[2-(4-chlorophenyl)-4,4-dimethylcyclohex-1-en-1-yl]methyl]piperazin-1-yl)-2-(13,13-difluoro-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl) benzoic acid: Into a 40-mL vial, was placed methyl 4-(4-[[2-(4-chlorophenyl)-4,4-dimethylcyclohex-1-en-1-yl] methyl]piperazin-1-yl)-2-(13,13-difluoro-4-[[2-(trimethylsilyl)ethoxy]methyl]-14-oxa-2,4,10-triazatricyclo [7.5.0.0ˆ[3,7]]tetradeca-1(9),2,5,7-tetraen-10-yl)benzoate (200.00 mg, 0.248 mmol, 1.00 equiv), dioxane (2.00 mL), MeOH (2.00 mL), NaOH (4M) (0.40 mL, 1.600 mmol, 6.45 equiv). The resulting solution was stirred for overnight at 70 degrees C. in an oil bath. The resulting mixture was concentrated. The pH value of the solution was adjusted to 6 with HCl (2 mol/L). The resulting solution was extracted with 3×20 mL of ethyl acetate concentrated under vacuum. The residue was applied onto a silica gel column and eluted with dichloromethane/methanol (10:1). The collected fractions were combined and concentrated. This resulted in 100 mg (508.85%) of 4-(4-[[2-(4-chlorophenyl)-4,4-dimethylcyclohex-1-en-1-yl]methyl]piperazin-1-yl)-2-(13,13-difluoro-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl) benzoic acid as a white solid. LC-MS: (ES, m/z): M+1:792.

Synthesis of 4-(4-[[2-(4-chlorophenyl)-4,4-dimethylcyclohex-1-en-1-yl]methyl]piperazin-1-yl)-2-(13,13-difluoro-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl)-N-(4-[[(2S)-1,4-dioxan-2-ylmethyl]amino]-3-nitrobenzenesulfonyl)benzamide: Into a 50-mL round-bottom flask, was placed 4-(4-[[2-(4-chlorophenyl)-4,4-dimethylcyclohex-1-en-1-yl]methyl]piperazin-1-yl)-2-(13, 13-difluoro-4-[[2-(trimethylsilyl)ethoxy]methyl]-14-oxa-2, 4,10-triazatricyclo[7.5.0.0ˆ[3,7]]tetradeca-1(9),2,5,7-tetraen-10-yl)benzoic acid (100.00 mg, 0.126 mmol, 1.00 equiv), 4-[[(2S)-1,4-dioxan-2-ylmethyl]amino]-3-nitrobenzenesulfonamide (40.04 mg, 0.126 mmol, 1.00 equiv), DCM (20.00 mL), EDCI (48.38 mg, 0.25 mmol, 2.00 equiv), DMAP (61.67 mg, 0.505 mmol, 4.00 equiv). The resulting solution was stirred for overnight at room temperature. The resulting mixture was concentrated. The residue was applied onto a silica gel column and eluted with ethyl acetate/petroleum ether (1:1). The collected fractions were combined and concentrated under vacuum. This resulted in 80 mg (58.07%) of 4-(4-[[2-(4-chlorophenyl)-4,4-dimethylcyclohex-1-en-1-yl]methyl]piperazin-1-yl)-2-(13,13-difluoro-4-[[2-(trimethylsilyl)ethoxy]methyl]-14-oxa-2,4,10-triazatricycloo[7.5.0.0[3,7]]tetradeca-1(9),2,5,7-tetraen-10-yl)-N-(4-[[(2S)-1,4-dioxan-2-ylmethyl]amino]-3-nitrobenzenesulfonyl)benzamide as a yellow solid. LC-MS: (ES, m/z): M+1:1091.

Synthesis of 4-(4-[[2-(4-chlorophenyl)-4,4-dimethylcyclohex-1-en-1-yl]methyl]piperazin-1-yl)-2-[13,13-difluoro-14-oxa-2,4,10-triazatricyclo[7.5.0.0^[3,7]]tetradeca-1(9),2,5,7-tetraen-10-yl]-N-(4-[[(2R)-1,4-dioxan-2-ylmethyl]amino]-2-nitrobenzenesulfonyl)benzamide hydrochloride: Into a 8-mL vial, was placed 4-(4-[[2-(4-chlorophenyl)-4,4-dimethylcyclohex-1-en-1-yl]methyl]piperazin-1-yl)-2-(13,13-difluoro-4-[[2-(trimethylsilyl)ethoxy]methyl]-14-oxa-2,4,10-triazatricyclo[7.5.0.0^[3,7]]tetradeca-1(9),2,5,7-tetraen-10-yl)-N-(4-[[(2S)-1,4-dioxan-2-ylmethyl]amino]-3-nitrobenzenesulfonyl)benzamide (50.00 mg, 0.046 mmol, 1.00 equiv), THF (5.00 mL), TBAF (119.75 mg, 0.458 mmol, 10.00 equiv), ethylene diamine (27.52 mg, 0.458 mmol, 10.00 equiv). The resulting solution was stirred for overnight at 70 degrees C. in an oil bath. The resulting mixture was concentrated. The crude product was purified by Prep-HPLC with the following conditions: Column, X-bridge RP18; mobile phase, 0.05% HCl in water and CH$_3$CN (45% CH$_3$CN up to 60% in 5 min); Detector, UV 254 nm. This resulted in 15.1 mg (33.04%) of 4-(4-[[2-(4-chlorophenyl)-4,4-dimethylcyclohex-1-en-1-yl]methyl]piperazin-1-yl)-2-[13,13-difluoro-14-oxa-2,4,10-triazatricyclo[7.5.0.0^[3,7]]tetradeca-1(9),2,5,7-tetraen-10-yl]-N-(4-[[(2R)-1,4-dioxan-2-ylmethyl]amino]-2-nitrobenzenesulfonyl)benzamide hydrochloride as a yellow solid. LC-MS: (ES, m/z): M+1-HCl: 961. $^1$H NMR (300 MHz, DMSO-d$_6$) δ 11.68 (s, 1H), 11.43 (s, 1H), 9.73 (s, 1H), 8.60 (t, J=5.7 Hz, 1H), 8.40 (d, J=2.4 Hz, 1H), 7.62 (dd, J=9.3, 2.4 Hz, 1H), 7.48-7.28 (m, 4H), 7.24-7.07 (m, 3H), 7.02 (d, J=9.3 Hz, 1H), 6.70-6.56 (m, 2H), 6.22 (dd, J=3.3, 1.8 Hz, 1H), 3.94-3.74 (m, 5H), 3.71-3.58 (m, 4H), 3.56-3.39 (m, 5H), 3.31 (s, 2H), 3.22 (d, J=12.3 Hz, 2H), 2.89-2.67 (m, 2H), 2.35 (d, J=36.3 Hz, 4H), 2.06 (s, 2H), 1.50 (d, J=7.5 Hz, 2H), 0.97 (s, 6H).

Example 64

Synthesis of 4-(4-[[2-(4-chlorophenyl)-4,4-dimethylcyclohex-1-en-1-yl]methyl]piperazin-1-yl)-N-[4-([[(2R)-1,4-dioxan-2-ylmethyl]amino]-3-nitrobenzenesulfonyl]-2-[(13R)-13-methyl-14-oxa-2,4,10-triazatricyclo[7.5.0.0^[3,7]]tetradeca-1(9),2,5,7-tetraen-10-yl]benzamide (Assumed Synthesis of methyl 2-bromo-4-(4-[[2-(4-chlorophenyl)-4,4-dimethylcyclohex-1-en-1-yl]methyl]piperazin-1-yl)benzoate: Into a 250-mL round-bottom flask, was placed a solution of 1-[[2-(4-chlorophenyl)-4,4-dimethylcyclohex-1-en-1-yl]methyl]piperazine (15.09 g, 47.32 mmol, 1.00 equiv) in DMA (150 mL), DIEA (12.9 g, 99.81 mmol, 2.00 equiv), methyl 2-bromo-4-fluorobenzoate (11.6 g, 49.78 mmol, 1.00 equiv). The resulting solution was stirred for 12 h at 100 degree. The reaction mixture was cooled to room temperature. The reaction was then quenched by the addition of 50 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 7 g (crude) of methyl 2-bromo-4-(4-[[2-(4-chlorophenyl)-4,4-dimethylcyclohex-1-en-1-yl]methyl]piperazin-1-yl)benzoate as yellow oil. LC-MS: (ES, m/z): M+1=533, 531.

Synthesis of 4-([[(2R)-1,4-dioxan-2-yl]methyl]amino)-3-nitrobenzene-1-sulfonamide: Into a 100-mL round-bottom flask, was placed 4-fluoro-3-nitrobenzene-1-sulfonamide (1.43 g, 0.007 mmol, 1 equiv), 1-[(2R)-1,4-dioxan-2-yl]methanamine hydrochloride (1 g, 6.510 mmol, 1 equiv), THF (30 mL), CS$_2$CO$_3$ (8.48 g, 0.026 mmol, 4 equiv). The resulting solution was stirred overnight at 50° C. in an oil bath. The solids were collected by filtration. The solid was dried in an oven under reduced pressure. This resulted in 1.8 g (87.14%) of 4-([[(2R)-1,4-dioxan-2-yl]methyl]amino)-3-nitrobenzene-1-sulfonamide as a yellow solid. LC-MS: (ES, m/z): M+1=318, R,T=0.740 min.

Synthesis of N-(3-hydroxybutyl)-4-methylbenzene-1-sulfonamide: Into a 250-mL round-bottom flask purged and maintained with an inert atmosphere of nitrogen, was placed 4-aminobutan-2-ol hydrochloride (4 g, 31.847 mmol, 1 equiv), DCM (40 mL), TEA (3.56 g, 35.181 mmol, 1.10 equiv). This was followed by the addition of 4-methylbenzene-1-sulfonyl chloride (6.08 g, 31.893 mmol, 1.00 equiv) in portions at 0 degrees C. The resulting solution was stirred for 2 h at 25 degrees C. The resulting mixture was concentrated under vacuum. The residue was applied onto a silica gel column with ethyl acetate/petroleum ether (1:1). This resulted in 4.4 g (56.78%) of N-(3-hydroxybutyl)-4-methylbenzene-1-sulfonamide as colorless oil. $^1$H NMR (300 MHz, CDCl$_3$-d, ppm) δ 7.82-7.73 (d, J=9.0 Hz, 2H), 7.39-7.30 (d, J=9.0 Hz, 2H), 4.06-3.82 (m, 1H), 3.24-3.16 (m, 1H), 3.06-3.00 (m, 1H), 2.45 (s, 3H), 1.70-1.55 (m, 2H), 1.20 (d, J=6.2 Hz, 3H).

Synthesis of N-[3-[(5-bromo-1-[[2-(trimethylsilyl)ethoxy]methyl]-1H-pyrrolo[2,3-b]pyridin-6-yl)oxy]butyl]-4-methylbenzene-1-sulfonamide: Into a 250-mL 3-necked round-bottom flask purged and maintained with an inert atmosphere of nitrogen, was placed N-(3-hydroxybutyl)-4-methylbenzene-1-sulfonamide (4.4 g, 18.083 mmol, 1.10 equiv), THF (60 mL). This was followed by the addition of NaH (1.97 g, 49.255 mmol, 3.00 equiv, 60%), in portions at 0 degrees C. The resulting solution was stirred for 0.5 h at 0 degrees C. To this was added 5-bromo-6-fluoro-1-[[2-(trimethylsilyl)ethoxy]methyl]-1H-pyrrolo[2,3-b]pyridine (5.66 g, 16.392 mmol, 1 equiv). The resulting solution was stirred overnight at 50 degrees C. in an oil bath. The reaction mixture was cooled to 25 degree C. The reaction was then quenched by the addition of 500 mL of NH$_4$Cl. The resulting solution was extracted with 2×200 mL of ethyl acetate and the organic layers combined. The resulting mixture was washed with 1×500 ml of brine. The mixture was dried over anhydrous sodium sulfate and concentrated under vacuum. The residue was applied onto a silica gel column with ethyl acetate/petroleum ether (1:3). This resulted in 6 g (64.37%) of N-[3-[(5-bromo-[[2-(trimethylsilyl)ethoxy]methyl]-1H-pyrrolo[2,3-b]pyridin-6-yl)oxy]butyl]-4-methylbenzene-1-sulfonamide as colorless oil. $^1$H NMR (300 MHz, CDCl$_3$-d, ppm) δ 8.04 (s, 1H), 7.74-7.63 (m, 2H), 7.23-7.11 (m, 3H), 6.41 (d, J=3.6 Hz, 1H), 5.56 (d, J=3.3 Hz, 2H), 5.89-5.33 (m, 1H), 3.59-3.46 (m, 2H), 3.17 (t, J=6.0 Hz, 2H), 2.37 (s, 3H), 2.08-1.78 (m, 2H), 1.37 (d, J=6.2 Hz, 3H), 0.94-0.85 (m, 2H), −0.06 (s, 9H).

Synthesis of 13-methyl-10-(4-methylbenzenesulfonyl)-4-[[2-(trimethylsilyl)ethoxy]methyl]-14-oxa-2,4,10-triazatricyclo[7.5.0.0ˆ[3,7]]tetradeca-1(9),2,5,7-tetraene: Into a 250-mL round-bottom flask purged and maintained with an inert atmosphere of nitrogen, was placed N-[3-[(5-bromo-1-[[2-(trimethylsilyl)ethoxy]methyl]-1H-pyrrolo[2,3-b]pyridin-6-yl)oxy]butyl]-4-methylbenzene-1-sulfonamide (6 g, 10.552 mmol, 1 equiv), DMSO (60 mL), pyridine-2-carboxylic acid (1.04 g, 8.448 mmol, 0.80 equiv), CuI (2.41 g, 12.654 mmol, 1.20 equiv), $K_2CO_3$ (4.38 g, 31.692 mmol, 3.00 equiv). The resulting solution was stirred for 2 days at 125 degrees C. in an oil bath. The reaction mixture was cooled to 25 degree C. The resulting solution was diluted with 500 mL of water. The resulting solution was extracted with 3×200 mL of ethyl acetate and the organic layers combined. The resulting mixture was washed with 2×1000 ml of brine. The mixture was dried over anhydrous sodium sulfate and concentrated under vacuum. The residue was applied onto a silica gel column with ethyl acetate/petroleum ether (1:3). This resulted in 2.8 g (54.41%) of 13-methyl-10-(4-methylbenzenesulfonyl)-4-[[2-(trimethylsilyl)ethoxy]methyl]-14-oxa-2,4,10-triazatricyclo[7.5.0.0ˆ[3,7]]tetradeca-1(9),2,5,7-tetraene as yellow oil. $^1$H NMR (300 MHz, $CDCl_3$-d, ppm) δ 8.10 (s, 1H), 7.53-7.40 (m, 2H), 7.30 (d, J=3.6 Hz, 1H), 7.24-7.12 (m, 2H), 6.50 (d, J=3.6 Hz, 1H), 5.65 (d, J=10.7 Hz, 1H), 5.49 (d, J=10.7 Hz, 1H), 4.37-4.23 (m, 1H), 3.94-3.80 (m, 1H), 3.62-3.36 (m, 3H), 2.37 (s, 3H), 1.89-1.64 (m, 2H), 1.23 (d, J=6.3 Hz, 3H), 1.01-0.76 (m, 2H), −0.07 (s, 9H).

Synthesis of 13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene: Into a 250-mL round-bottom flask purged and maintained with an inert atmosphere of nitrogen, was placed Na (793.5 mg, 34.51 mmol, 6.01 equiv), naphthalene (4.42 g, 34.48 mmol, 6.01 equiv), DME (20 mL). The mixture was stirred at room temperature for 40 min until the formation of Na/naphthalene was complete. Another 250-mL round-bottom flask purged and maintained with an inert atmosphere of nitrogen, was placed 13-methyl-10-(4-methylbenzenesulfonyl)-4-[[2-(trimethylsilyl)ethoxy]methyl]-14-oxa-2,4,10-triazatricyclo[7.5.0.0ˆ[3,7]]tetradeca-1(9),2,5,7-tetraene (2.8 g, 5.741 mmol, 1 equiv), THF (20 mL). This was followed by the addition of above solution at −78 degrees C. The resulting solution was stirred for 2 hr at room temperature. The reaction was then quenched by the addition of 500 mL of $NH_4Cl$. The resulting solution was extracted with 3×200 mL of ethyl acetate and the organic layers combined. The resulting mixture was washed with 1×500 ml of brine. The mixture was dried over anhydrous sodium sulfate and concentrated under vacuum. The residue was applied onto a silica gel column with ethyl acetate/petroleum ether (1:3). This resulted in 1.2 g (62.67%) of 13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene as yellow oil. $^1$H NMR (300 MHz, DMSO-$d_6$, ppm) δ 7.43-7.26 (m, 2H), 6.27 (d, J=3.5 Hz, 1H), 5.43 (d, J=3.4 Hz, 2H), 5.13 (s, 1H), 4.14-4.04 (m, 1H), 3.58-3.39 (m, 3H), 3.28-3.10 (m, 1H), 2.95-2.77 (m, 1H), 2.09-1.85 (m, 1H), 1.85-1.64 (m, 1H), 1.37 (d, J=6.3 Hz, 3H), 0.88-078 (m, 2H), −0.09 (s, 9H).

Synthesis of 13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene: The crude product (0.5 g) was purified by Chiral-Prep-HPLC with the following conditions: Instrument Name: SHIMADZU LC-20AD, LC parameters: Pump Mode: Binary gradient, Start Conc. of Pump B: 50.0%, Total Flow: 15 mL/min, Phase A: n-Hexane (0.1% DEA), Phase B: ethanol, Column Name: CHIRALpak IA-3, Length: 50 mm, Internal Diameter: 4.6 mm, Particle Size: 3.0 um, Column Temp: 25° C., PDA Model: SPD-M20A, Wavelength: from 190 nm to 500 nm. This resulted in 220 mg (peak 1 Assumed R) [a]=−6.78° (C=0.129 g/100 mL in $CH_2Cl_2$, T=27° C.) of (13R or S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene as a yellow oil and 230 mg (peak 2 Assumed S) [a]=+11.84° (C=0.106 g/100 mL in $CH_2Cl_2$, T=27° C.) of (13S or R)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene as a yellow oil.

Synthesis of methyl 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoate: Into a 40-mL vial purged and maintained with an inert atmosphere of nitrogen, was placed (13 S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene (210.00 mg, 0.630 mmol, 1.00 equiv), toluene (5.00 mL), methyl 2-bromo-4-(4-[[2-(4-chlorophenyl)-4,4-dimethylcyclohex-1-en-1-yl]methyl]piperazin-1-yl)benzoate (669.87 mg, 1.259 mmol, 2.00 equiv), $Cs_2CO_3$ (1025.80 mg, 3.148 mmol, 5.00 equiv), Xantphos Pd 2G Precatalyst (111.70 mg, 0.126 mmol, 0.20 equiv). The resulting solution was stirred overnight at 110 degrees C. in an oil bath. The reaction mixture was cooled to room temperature. The resulting mixture was concentrated under vacuum. The residue was applied onto a silica gel column with ethyl acetate/petroleum ether (1:1). This resulted in 240 mg (31.09%) of methyl 4-(4-[[2-(4-chlorophenyl)-4,4-dimethylcycloohex-1-en-1-yl]ethyl]piperazin-1-yl)-2-[(13S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoate as yellow oil. LC-MS: (ES, m/z): M+1=784.

Synthesis of 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoic acid: Into a 8-mL round-bottom flask, was placed methyl 4-(4-[[2-(4-chlorophenyl)-4,4-dimethylcyclohex-1-en-1-yl]methyl]piperazin-1-yl)-2-[(13 S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoate (200 mg, 0.255 mmol, 1.00 equiv), $H_2O$ (1.00 mL), MeOH (2.00 mL), dioxane (2.00 mL), NaOH (61.18 mg, 1.530 mmol, 6.00 equiv). The resulting solution was stirred for 12 h at 70 degrees C. The resulting mixture was concentrated. The pH value of the solution was adjusted to 5 with HCl (1 mol/L). The solids were collected by filtration. This resulted in 180 mg (91.64%) of 4-(4-[[2-(4-chlorophenyl)-4,4-dimethylcyclohex-1-en-1-yl]ethyl]piperazin-1-yl)-2-[(13 S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoic acid as a white solid. H-NMR (CDCl3, 300 ppm): δ 8.17 (s, 1H), 7.28 (s, 1H), 7.00-6.79 (m, 4H), 6.35 (s, 1H), 5.70-5.67 (d, J=9 Hz, 1H), 5.56-5.52 (d, J=12 Hz, 1H), 4.38-4.35 (m, 1H), 3.81 (s, 1H), 3.58-3.56 (m, 4H), 3.26 (s, 3H), 2.84 (s, 1H), 2.35 (s, 3H), 2.24 (s, 2H), 2.12 (s, 2H), 2.04 (s, 2H), 1.60 (s, 6H), 1.28 (s, 1H), 1.01 (s, 7H), 0.98-0.95 (m, 3H), 0.00 (s, 9H).

Synthesis of 4-(4-[[2-(4-chlorophenyl)-4,4-dimethylcyclohex-1-en1-yl]methyl]piperazin-1-yl)-N-[4-([[(2R)-1,4-dioxan-2-yl]methyl]amino)-3-nitrobenzenesulfonyl]-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzamide: Into a 8-mL round-bottom flask, was placed 4-([[(2R)-1,4-dioxan-2-yl]methyl]amino)-3-nitrobenzene-1-sulfonamide (41.18 mg, 0.130 mmol, 1 equiv), 4-(4-[[2-(4-chlorophenyl) 4,4-dimethylcyclohex-1-en-1-yl]methyl]piperazin-1-yl)-2-[(13 S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoic acid (100.00 mg, 0.130 mmol, 1.00 equiv), DCM (3 mL), DMAP (63.42 mg, 0.519 mmol, 4.00 equiv), EDCI (49.76 mg, 0.260 mmol, 2 equiv). The resulting solution was stirred for 12 h at room temperature. The resulting mixture was concentrated. The residue was applied onto a silica gel column with ethyl acetate/petroleum ether (0:1-1:0). This resulted in 80 mg (57.62%) of 4-(4-[[2-(4-chlorophenyl)-4,4-dimethylcyclohex-1-en1-yl]ethyl]piperazin-1-yl)-N-[4-([[(2R)-1,4-dioxan-2-yl]methyl]amino)-3-nitrobenzene sulfonyl]-2-[(13 S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzamide as a yellow solid.

Synthesis of 4-(4-[[2-(4-chlorophenyl)-4,4-dimethylcyclohex-1-en-1-yl]methyl]piperazin-1-yl)-N-[4-([[(2R)-1,4-dioxan-2-yl]methyl]amino)-3-nitrobenzenesulfonyl]-2-[(13R)-13-methyl-14-oxa-2,4,10-triazatricyclo[7.5.0.0^[3,7]]tetradeca-1(9),2,5,7-tetraen-10-yl]benzamide: Into a 8-mL round-bottom flask, was placed 4-4-[[2-(4-chlorophenyl)4,4-dimethylcyclohex1-en-1-yl]methyl]piperazin-1-yl)-N-[4-([[(2R)-1,4-dioxan-2-yl]methyl]amino)-3-nitrobenzenesulfonyl]-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzamide (80.00 mg, 0.075 mmol, 1.00 equiv), THF (5.00 mL), ethane-1,2-diamine (89.89 mg, 1.496 mmol, 20 equiv), TBAF (391.05 mg, 1.496 mmol, 20 equiv). The resulting solution was stirred for 48 h at 70 degrees C. The resulting mixture was concentrated. The crude product was purified by Prep-HPLC with the following conditions (Waters-2767): Column, X-bridge RP18, 5 um, 19*100 mm; mobile phase, 0.03% ammonia in water (0.03% $NH_4HCO_3$ & $NH_4OH$) and $CH_3CN$ (32% $CH_3CN$ up to 52% in 6 min); Detector, UV 254 nm. This resulted in 25 mg (35.58%) of 4-(4-[[2-(4-chlorophenyl)-4,4-dimethylcyclohex-1-en-1-yl]methyl]piperazin-1-yl)-N-[4-([[(2R)-1,4-dioxan-2-yl]methyl]amino)-3-nitrobenzenesulfonyl]-2-[(13R)-13-methyl-14-oxa-2,4,10-triazatricyclo[7.5.0.0^[3,7]]tetradeca-1(9),2,5,7-tetraen-10-yl]benzamide as a yellow solid. H-NMR: (d-DMSO, 300M Hz, ppm): δ 8.87-8.86 (m, 1H), 8.69 (s, 1H), 8.47 (s, 1H), 8.00-7.92 (m, 2H), 7.13 (s, 1H), 7.00-6.93 (m, 2H), 6.75-6.72 (m, 2H), 6.60-6.50 (s, 1H), 6.19 (s, 1H), 3.92-3.67 (m, 7H), 3.45-3.31 (m, 8H), 2.85 (s, 2H), 2.38-2.25 (m, 6H), 2.09-2.03 (m, 3H), 1.71-1.69 (m, 3H), 1.50-1.46 (m, 2H), 1.06-0.99 (m, 6H).

Example 65

Synthesis of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(13S)-13-methyl-14-oxa-2,4,10-triazatricyclo[7.5.0.0^[3,7]]tetradeca-1(9),2,5,7-tetraen-10-yl]benzamide Synthesis of methyl 2-bromo-4-(4-[[2-(4-chlorophenyl)-4,4-dimethylcyclohex-1-en-1-yl]methyl]piperazin-1-yl) benzoate: Into a 250-mL round-bottom flask, was placed a solution of 1-[[2-(4-chlorophenyl)-4,4-dimethylcyclohex-1-en-1-yl]methyl]piperazine (15.09 g, 47.32 mmol, 1.00 equiv) in DMA (150 mL), DIEA (12.9 g, 99.81 mmol, 2.00 equiv), methyl 2-bromo-4-fluorobenzoate (11.6 g, 49.78 mmol, 1.00 equiv). The resulting solution was stirred for 12 h at 100 degree. The reaction mixture was cooled to room temperature. The reaction was then quenched by the addition of 50 mL of water. The resulting solution was extracted with 3×100 mL of ethyl acetate and the organic layers combined. The resulting mixture was washed with 3×100 mL of brine. The mixture was dried over anhydrous sodium sulfate, then filtered and concentrated under vacuum. The residue was applied onto a silica gel column with ethyl acetate/petroleum ether (0:1-1:5). This resulted in 7 g (crude) of methyl 2-bromo-4-(4-[[2-(4-chlorophenyl)-4,4-dimethylcyclohex-1-en-1-yl]methyl]piperazin-1-yl)benzoate as yellow oil. LC-MS: (ES, m/z): M+1=533, 531.

Synthesis of 1,6-dioxaspiro[2.5]octane-2-carbonitrile: Into a 3000-mL round-bottom flask, was placed oxan-4-one (204.2 g, 2039.74 mmol, 1.1 equiv), 2-chloroacetonitrile (140 g, 1854.30 mmol, 1 equiv), t-BuOH (200 mL). The resulting solution was stirred for 30 min at 25 degrees C. This was followed by the addition of a solution of t-BuOK (249.7 g, 2225.25 mmol, 1.20 equiv) in tert-Butanol (2000 mL) dropwise with stirring at 25 degrees C. in 40 min. The resulting solution was stirred for overnight at 25 degrees C. The resulting solution was diluted with 400 mL of water and quenched with 80 mL of 10% hydrogen chloride. The resulting mixture was concentrated to one-third of its volume. The resulting solution was extracted with 3×800 mL of ether and the organic layers combined. The resulting mixture was washed with 3000 mL of brine. The mixture was dried over anhydrous sodium sulfate and concentrated under vacuum. This resulted in 162 g (62.78%) of 1,6-dioxaspiro[2.5]octane-2-carbonitrile as brown oil. $^1$H NMR (300 MHz, $CDCl_3$-d, ppm) δ 3.95-3.81 (m, 4H), 2.17-2.02 (m, 1H), 1.99-1.77 (m, 2H), 1.66-1.54 (m, 1H).

Synthesis of 2-(4-fluorooxan-4-yl)-2-hydroxyacetonitrile: Into a 2000-mL round-bottom flask, was placed 1,6-dioxaspiro[2.5]octane-2-carbonitrile (162 g, 1164.18 mmol, 1 equiv), DCM (800 mL). This was followed by the addition of 70% HF/Py (150 mL, 0.95 equiv) dropwise with stirring at 0 degrees C. The resulting solution was stirred for overnight at 40 degrees C. in an oil bath. The resulting solution was diluted with 1500 mL of ethyl acetate and poured into Sat. aqueous $NaHCO_3$. Additional solid $NaHCO_3$ was used to neutralize the mixture carefully until bubbling ceased. The resulting solution was extracted with 2×1000 mL of ethyl acetate and the organic layers combined. The resulting mixture was washed with 1×3000 mL of 1% hydrogen chloride and 1×3000 mL of brine. The mixture was dried over anhydrous sodium sulfate and concentrated under vacuum. The residue was applied onto a silica gel column with ethyl acetate/petroleum ether (1:2). This resulted in 95 g (51.27%) of 2-(4-fluorooxan-4-yl)-2-hydroxyacetonitrile as a yellow solid. $^1$H NMR (300 MHz, $CDCl_3$-d, ppm) δ 4.39 (d, J=15.6 Hz, 1H), 4.05-3.90 (m, 2H), 3.83-3.70 (m, 2H), 2.08-1.77 (m, 4H).

Synthesis of (4-fluorooxan-4-yl)methanol: Into a 2000-mL round-bottom flask, was placed 2-(4-fluorooxan-4-yl)-2-hydroxyacetonitrile (95 g, 596.88 mmol, 1 equiv), i-PrOH (1500 mL), $H_2O$ (375 mL). This was followed by the addition of $NaBH_4$ (35 g, 925.12 mmol, 1.55 equiv), in portions at 0 degrees C. The resulting solution was stirred for 2 hr at 25 degrees C. The reaction was then quenched by the addition of 100 mL of acetone and stirred for another 1 h.

The solids were filtered out. EtOAc (200 mL) was used to wash the solid. The filtration was concentrated under vacuum. The residue was applied onto a silica gel column with ethyl acetate/petroleum ether (1:1). This resulted in 66 g (82.43%) of (4-fluorooxan-4-yl)methanol as yellow oil. $^1$H NMR (300 MHz, CDCl$_3$-d, ppm) δ 3.90-3.70 (m, 2H), 3.62 (d, J=20.6 Hz, 1H), 1.88-1.61 (m, 2H).

Synthesis of (4-fluorooxan-4-yl)methyl methanesulfonate: Into a 2000-mL round-bottom flask, was placed (4-fluorooxan-4-yl)methanol (66 g, 491.99 mmol, 1 equiv), DCM (600 mL), TEA (74.7 g, 737.98 mmol, 1.5 equiv). This was followed by the addition of MsCl (84.5 g, 737.66 mmol, 1.50 equiv) dropwise with stirring at 0 degrees C. The resulting solution was stirred for 2 hr at 25 degrees C. The resulting solution was diluted with 2000 mL of water. The resulting solution was extracted with 2×500 mL of dichloromethane. The combined organic layer was dried over anhydrous sodium sulfate and concentrated under vacuum. This resulted in 100 g (95.77%) of (4-fluorooxan-4-yl) methyl methanesulfonate as yellow oil. $^1$H NMR (300 MHz, DMSO) δ 4.32 (d, J=21.6 Hz, 1H), 3.83-3.49 (m, 2H), 1.92-1.62 (m, 2H).

Synthesis of 4-(azidomethyl)-4-fluorooxane: Into a 2000-mL 4-necked round-bottom flask, was placed (4-fluorooxan-4-yl)methyl methanesulfonate (100 g, 471.16 mmol, 1 equiv), DMF (1000 mL), NaHCO$_3$ (93.0 g, 1107.06 mmol, 2.35 equiv), NaN$_3$ (90 g, 1384.40 mmol, 2.94 equiv). The resulting solution was stirred for overnight at 120 degrees C. in an oil bath. The reaction mixture was cooled to room temperature. The reaction was then quenched by the addition of 3000 mL of water. The resulting solution was extracted with 3×500 mL of ethyl acetate and the organic layers combined. The resulting mixture was washed with 3×3000 mL of brine. The mixture was dried over anhydrous sodium sulfate and concentrated under vacuum. This resulted in 70 g (93.34%) of 4-(azidomethyl)-4-fluorooxane as yellow oil without any further purification.

Synthesis of 1-(4-fluorooxan-4-yl)methanamine: Into a 2000-mL pressure tank reactor, was placed 4-(azidomethyl)-4-fluorooxane (70 g, 439.80 mmol, 1 equiv), EtOAc (700 mL), 10% Pd/C (7 g, 3472.43 mmol). The flask was evacuated and flushed three times with nitrogen, followed by flushing with hydrogen (2-5 atm pressure). The resulting solution was stirred for overnight at 25 degrees C. The solids were filtered out. The resulting mixture was concentrated under vacuum. This resulted in 52 g (crude) of 1-(4-fluorooxan-4-yl)methanamine as yellow oil. $^1$H NMR (300 MHz, MeOD d$_4$, ppm) δ 3.88-3.69 (m, 2H), 2.76 (d, J=20.5 Hz, 1H), 1.85-1.68 (m, 2H).

Synthesis of 4-[[(4-fluorooxan-4-yl)methyl]amino]-3-nitrobenzene-1-sulfonamide: Into a 2000-mL round-bottom flask, was placed 1-(4-fluorooxan-4-yl)methanamine (52.0 g, 390.49 mmol, 1.00 equiv), THF (1000 mL), 4-fluoro-3-nitrobenzene-1-sulfonamide (86 g, 390.61 mmol, 1 equiv), Cs$_2$CO$_3$ (254.5 g, 781.21 mmol, 2 equiv). The resulting solution was stirred for 4 hr at 50 degrees C. in an oil bath. The resulting solution was diluted with 3000 mL of water. The solids were collected by filtration. This resulted in 50.6 g (38.86%) of 4-[[(4-fluorooxan-4-yl)methyl]amino]-3-nitrobenzene-1-sulfonamide as a yellow solid, and some crude product from aqueous phase. $^1$H NMR (300 MHz, DMSO d$_6$, ppm) δ 8.58 (t, J=6.4 Hz, 1H), 8.48 (d, J=2.2 Hz, 1H), 7.83 (dd, J=9.1, 2.0 Hz, 1H), 7.41 (d, J=9.2 Hz, 1H), 7.34 (s, 2H), 3.84-3.70 (m, 4H), 3.59-3.45 (m, 2H), 1.87-1.66 (m, 4H).

Synthesis of N-(3-hydroxybutyl)-4-methylbenzene-1-sulfonamide: Into a 250-mL round-bottom flask purged and maintained with an inert atmosphere of nitrogen, was placed 4-aminobutan-2-ol hydrochloride (4 g, 31.847 mmol, 1 equiv), DCM (40 mL), TEA (3.56 g, 35.181 mmol, 1.10 equiv). This was followed by the addition of 4-methylbenzene-1-sulfonyl chloride (6.08 g, 31.893 mmol, 1.00 equiv) in portions at 0 degrees C. The resulting solution was stirred for 2 h at 25 degrees C. The resulting mixture was concentrated under vacuum. The residue was applied onto a silica gel column with ethyl acetate/petroleum ether (1:1). This resulted in 4.4 g (56.78%) of N-(3-hydroxybutyl)-4-methylbenzene-1-sulfonamide as colorless oil. $^1$H NMR (300 MHz, CDCl$_3$-d, ppm) δ 7.82-7.73 (d, J=9.0 Hz, 2H), 7.39-7.30 (d, J=9.0 Hz, 2H), 4.06-3.82 (m, 1H), 3.24-3.16 (m, 1H), 3.06-3.00 (m, 1H), 2.45 (s, 3H), 1.70-1.55 (m, 2H), 1.20 (d, J=6.2 Hz, 3H).

Synthesis of N-[3-[(5-bromo-1-[[2-(trimethylsilyl)ethoxy]methyl]-1H-pyrrolo[2,3-b]pyridin-6-yl)oxy]butyl]-4-methylbenzene-1-sulfonamide: Into a 250-mL 3-necked round-bottom flask purged and maintained with an inert atmosphere of nitrogen, was placed N-(3-hydroxybutyl)-4-methylbenzene-1-sulfonamide (4.4 g, 18.083 mmol, 1.10 equiv), THF (60 mL). This was followed by the addition of NaH (1.97 g, 49.255 mmol, 3.00 equiv, 60%), in portions at 0 degrees C. The resulting solution was stirred for 0.5 h at 0 degrees C. To this was added 5-bromo-6-fluoro-1-[[2-(trimethylsilyl)ethoxy]methyl]-1H-pyrrolo[2,3-b]pyridine (5.66 g, 16.392 mmol, 1 equiv). The resulting solution was stirred overnight at 50 degrees C. in an oil bath. The reaction mixture was cooled to 25 degree C. The reaction was then quenched by the addition of 500 mL of NH$_4$Cl. The resulting solution was extracted with 2×200 mL of ethyl acetate and the organic layers combined. The resulting mixture was washed with 1×500 ml of brine. The mixture was dried over anhydrous sodium sulfate and concentrated under vacuum. The residue was applied onto a silica gel column with ethyl acetate/petroleum ether (1:3). This resulted in 6 g (64.37%) of N-[3-[(5-bromo-[[2-(trimethylsilyl)ethoxy]methyl]-1H-pyrrolo[2,3-b]pyridin-6-yl)oxy]butyl]-4-methylbenzene-1-sulfonamide as colorless oil. $^1$H NMR (300 MHz, CDCl$_3$-d, ppm) δ 8.04 (s, 1H), 7.74-7.63 (m, 2H), 7.23-7.11 (m, 3H), 6.41 (d, J=3.6 Hz, 1H), 5.56 (d, J=3.3 Hz, 2H), 5.89-5.33 (m, 1H), 3.59-3.46 (m, 2H), 3.17 (t, J=6.0 Hz, 2H), 2.37 (s, 3H), 2.08-1.78 (m, 2H), 1.37 (d, J=6.2 Hz, 3H), 0.94-0.85 (m, 2H), −0.06 (s, 9H).

Synthesis of 13-methyl-10-(4-methylbenzenesulfonyl)-4-[[2-(trimethylsilyl)ethoxy]methyl]-14-oxa-2,4,10-triazatricyclo[7.5.0.0^[3,7]]tetradeca-1(9),2,5,7-tetraene: Into a 250-mL round-bottom flask purged and maintained with an inert atmosphere of nitrogen, was placed N-[3-[(5-bromo-1-[[2-(trimethylsilyl)ethoxy]methyl]-1H-pyrrolo[2,3-b]pyridin-6-yl)oxy]butyl]-4-methylbenzene-1-sulfonamide (6 g, 10.552 mmol, 1 equiv), DMSO (60 mL), pyridine-2-carboxylic acid (1.04 g, 8.448 mmol, 0.80 equiv), CuI (2.41 g, 12.654 mmol, 1.20 equiv), K$_2$CO$_3$ (4.38 g, 31.692 mmol, 3.00 equiv). The resulting solution was stirred for 2 days at 125 degrees C. in an oil bath. The reaction mixture was cooled to 25 degree C. The resulting solution was diluted with 500 mL of water. The resulting solution was extracted with 3×200 mL of ethyl acetate and the organic layers combined. The resulting mixture was washed with 2×1000 ml of brine. The mixture was dried over anhydrous sodium sulfate and concentrated under vacuum. The residue was applied onto a silica gel column with ethyl acetate/petroleum ether (1:3). This resulted in 2.8 g (54.41%) of 13-methyl-10-(4-methylbenzenesulfonyl)-4-[[2-(trimethylsilyl) ethoxy]methyl]-14-oxa-2,4,10-triazatricyclo[7.5.0.0^[3,7]]tetradeca-1(9),2,5,7-tetraene as yellow oil. $^1$H NMR (300 MHz, CDCl$_3$-d, ppm) δ

8.10 (s, 1H), 7.53-7.40 (m, 2H), 7.30 (d, J=3.6 Hz, 1H), 7.24-7.12 (m, 2H), 6.50 (d, J=3.6 Hz, 1H), 5.65 (d, J=10.7 Hz, 1H), 5.49 (d, J=10.7 Hz, 1H), 4.37-4.23 (m, 1H), 3.94-3.80 (m, 1H), 3.62-3.36 (m, 3H), 2.37 (s, 3H), 1.89-1.64 (m, 2H), 1.23 (d, J=6.3 Hz, 3H), 1.01-0.76 (m, 2H), −0.07 (s, 9H).

Synthesis of 13-methyl-4-[[2-(trimethylsilyl)ethoxy]methyl]-14-oxa-2,4,10-triazatricyclo[7.5.0.0^[3,7]]tetradeca-1(9),2,5,7-tetraene: Into a 250-mL round-bottom flask purged and maintained with an inert atmosphere of nitrogen, was placed Na (793.5 mg, 34.51 mmol, 6.01 equiv), naphthalene (4.42 g, 34.48 mmol, 6.01 equiv), DME (20 mL). The mixture was stirred at room temperature for 40 min until the formation of Na/naphthalene was complete. Another 250-mL round-bottom flask purged and maintained with an inert atmosphere of nitrogen, was placed 13-methyl-10-(4-methylbenzenesulfonyl)-4-[[2-(trimethylsilyl)ethoxy]methyl]-14-oxa-2,4,10-triazatricyclo[7.5.0.0^[3,7]]tetradeca-1(9),2,5,7-tetraene (2.8 g, 5.741 mmol, 1 equiv), THF (20 mL). This was followed by the addition of above solution at −78 degrees C. The resulting solution was stirred for 2 hr at room temperature. The reaction was then quenched by the addition of 500 mL of NH$_4$Cl. The resulting solution was extracted with 3×200 mL of ethyl acetate and the organic layers combined. The resulting mixture was washed with 1×500 ml of brine. The mixture was dried over anhydrous sodium sulfate and concentrated under vacuum. The residue was applied onto a silica gel column with ethyl acetate/petroleum ether (1:3). This resulted in 1.2 g (62.67%) of 13-methyl-4-[[2-(trimethylsilyl)ethoxy]methyl]-14-oxa-2,4,10-triazatricyclo[7.5.0.0^[3,7]]tetradeca-1(9),2,5,7-tetraene as yellow oil. $^1$H NMR (300 MHz, DMSO-d$_6$, ppm) δ 7.43-7.26 (m, 2H), 6.27 (d, J=3.5 Hz, 1H), 5.43 (d, J=3.4 Hz, 2H), 5.13 (s, 1H), 4.14-4.04 (m, 1H), 3.58-3.39 (m, 3H), 3.28-3.10 (m, 1H), 2.95-2.77 (m, 1H), 2.09-1.85 (m, 1H), 1.85-1.64 (m, 1H), 1.37 (d, J=6.3 Hz, 3H), 0.88-078 (m, 2H), −0.09 (s, 9H).

Synthesis of 13-methyl-4-[[2-(trimethylsilyl)ethoxy]methyl]-14-oxa-2,4,10-triazatricyclo[7.5.0.0^[3,7]]tetradeca-1(9),2,5,7-tetraene: The crude product (0.5 g) was purified by Chiral-Prep-HPLC with the following conditions: Instrument Name: SHIMADZU LC-20AD, LC parameters: Pump Mode: Binary gradient, Start Conc. of Pump B: 50.0%, Total Flow: 15 mL/min, Phase A: n-Hexane (0.1% DEA), Phase B: Ethanol, Column Name: CHIRAL-pak IA-3, Length: 50 mm, Internal Diameter: 4.6 mm, Particle Size: 3.0 um, Column Temp: 25° C., PDA Model: SPD-M20A, Wavelength: from 190 nm to 500 nm. This resulted in 220 mg (peak 1 Assumed R) [a]=−6.78° (C=0.129 g/100 mL in CH$_2$Cl$_2$, T=27° C.) of (13R or S)-13-methyl-4-[[2-(trimethylsilyl)ethoxy]methyl]-14-oxa-2,4,10-triazatricyclo[7.5.0.0^[3,7]]tetradeca-1(9),2,5,7-tetraene as a yellow oil and 230 mg (peak 2 Assumed S) [a]=+11.84° (C=0.106 g/100 mL in CH$_2$Cl$_2$, T=27° C.) of (13S or R)-13-methyl-4-[[2-(trimethylsilyl)ethoxy]methyl]-14-oxa-2,4,10-triazatricyclo[7.5.0.0^[3,7]]tetradeca-1(9),2,5,7-tetraene as a yellow oil.

Synthesis of methyl 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoate: Into a 40-mL vial purged and maintained with an inert atmosphere of nitrogen, was placed (13 S)-13-methyl-4-[[2-(trimethylsilyl)ethoxy]ethyl]-14-oxa-2,4,10-triazatricyclo[7.5.0.0^[3,7]]tetradeca-1(9),2,5,7-tetraene (210.00 mg, 0.630 mmol, 1.00 equiv), toluene (5.00 mL), methyl 2-bromo-4-(4-[[2-(4-chlorophenyl)-4,4-dimethylcyclohex-1-en-1-yl]methyl]piperazin-1-yl)benzoate (669.87 mg, 1.259 mmol, 2.00 equiv), Cs$_2$CO$_3$ (1025.80 mg, 3.148 mmol, 5.00 equiv), Xantphos Pd 2G Precatalyst (111.70 mg, 0.126 mmol, 0.20 equiv). The resulting solution was stirred overnight at 110 degrees C. in an oil bath. The reaction mixture was cooled to room temperature. The resulting mixture was concentrated under vacuum. The residue was applied onto a silica gel column with ethyl acetate/petroleum ether (1:1). This resulted in 240 mg (31.09%) of methyl 4-(4-[[2-(4-chlorophenyl)-4,4-dimethylcycloohex-1-en-1-yl]ethyl]piperazin-1-yl)-2-[(13 S)-13-methyl-4-[[2-(trimethylsilyl)ethoxy]ethyl]-14-oxa-2,4,10-triazatricycloo[7.5.0.0[3,7]]tetradeca-1(9),2,5,7-tetraen-10-yl]benzoate as yellow oil. LC-MS: (ES, m/z): M+1=784.

Synthesis of 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoic acid: Into a 8-mL round-bottom flask, was placed methyl 4-(4-[[2-(4-chlorophenyl)-4,4-dimethylcyclohex-1-en-1-yl]methyl]piperazin-1-yl)-2-[(13 S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoate (200 mg, 0.255 mmol, 1.00 equiv), H$_2$O (1.00 mL), MeOH (2.00 mL), dioxane (2.00 mL), NaOH (61.18 mg, 1.530 mmol, 6.00 equiv). The resulting solution was stirred for 12 h at 70 degrees C. The resulting mixture was concentrated. The pH value of the solution was adjusted to 5 with HCl (1 mol/L). The solids were collected by filtration. This resulted in 180 mg (91.64%) of 4-(4-[[2-(4-chlorophenyl)-4,4-dimethylcyclohex-1-en-1-yl]ethyl]piperazin-1-yl)-2-[(13 S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoic acid as a white solid. H-NMR: (CDCl3, 300 ppm): δ 8.17 (s, 1H), 7.28 (s, 1H), 7.00-6.79 (m, 4H), 6.35 (s, 1H), 5.70-5.67 (d, J=9 Hz, 1H), 5.56-5.52 (d, J=12 Hz, 1H), 4.38-4.35 (m, 1H), 3.81 (s, 1H), 3.58-3.56 (m, 4H), 3.26 (s, 3H), 2.84 (s, 1H), 2.35 (s, 3H), 2.24 (s, 2H), 2.12 (s, 2H), 2.04 (s, 2H), 1.60 (s, 6H), 1.28 (s, 1H), 1.01 (s, 7H), 0.98-0.95 (m, 3H), 0.00 (s, 9H).

Synthesis of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzamide: Into a 8-mL round-bottom flask, was placed 4-(4-[[2-(4-chlorophenyl)-4,4-dimethylcyclohex-1-en-1-yl]ethyl]piperazin-1-yl)-2-[(13 S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoic acid (100.00 mg, 0.130 mmol, 1.00 equiv), 4-[[(4-fluorooxan-4-yl)methyl]amino]-3-nitrobenzene-1-sulfonamide (43.26 mg, 0.130 mmol, 1.00 equiv), DCM (3 mL), DMAP (63.42 mg, 0.519 mmol, 4.00 equiv), EDCI (49.76 mg, 0.260 mmol, 2.00 equiv). The resulting solution was stirred for 12 h at room temperature. The resulting mixture was concentrated. The residue was applied onto a silica gel column with ethyl acetate/petroleum ether (0:1-1:0). This resulted in 80 mg (56.77%) of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzene sulfonyl)-2-[(13 S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzamide as a yellow solid.

Synthesis of 4-(4-[[2-(4-chlorophenyl)-4,4-dimethylcyclohex-1-en-1-yl]methy]piperazin-1-yl)-N-(4-[[[(4-fluorooxan-4-yl)methyl]amino]-3-nitrobenzenesulfonyl)-2-[(13S)-13-methyl-14-oxa-2,4,10-triazatricyclo[7.5.0.0^[3,7]]tetradeca-1(9),2,5,7-tetraen-10-yl]benzamide: Into a 8-mL round-bottom flask, was placed 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzamide (80.00 mg, 0.074 mmol, 1.00 equiv), THF (5 mL), TBAF (385.28 mg, 1.474 mmol, 20 equiv), ethane-1,2-diamine (88.56 mg, 1.474 mmol, 20.00 equiv). The resulting solution was stirred for 48 h at 70 degrees C. The resulting mixture was concentrated. The crude product was purified by Prep-HPLC with the following conditions (Waters-2767): Column, X-bridge RP18, 5 um, 19*100 mm; mobile phase, 0.03% ammonia in water (0.03% NH4HCO3 & NH4OH) and CH3CN (32% CH3CN up to 52% in 6 min); Detector, UV 254 nm. This resulted in 25 mg (35.51%) of 4-(4-[[2-(4-chlorophenyl)-4,4-dimethylcyclohex-1-en-1-yl]methyl]piperazin-1-yl)-N-(4-[[(4-fluorooxan-4-yl)methyl]amino]-3-nitrobenzenesulfonyl)-2-[(13S)-13-methyl-14-oxa-2,4,10-triazatricyclo[7.5.0.0^[3,7]]tetradeca-1(9),2,5,7-tetraen-10-yl]benzamide as a yellow solid. H-NMR: (d-DMSO, 300M Hz, ppm): δ 8.59-8.67 (m, 1H), 8.69 (s, 1H), 8.48 (s, 1H), 8.03-7.94 (m, 2H), 7.15-7.14 (m, 2H), 6.97-6.93 (m, 3H), 6.76-6.73 (m, 3H), 6.20 (s, 1H), 3.96-3.69 (m, 5H), 3.49-3.25 (m, 7H), 2.85 (s, 2H), 2.37-2.25 (m, 6H), 2.15-2.04 (m, 3H), 1.89-1.83 (m, 3H), 1.71-1.69 (m, 4H), 1.50-1.46 (m, 2H), 1.06-0.99 (m, 6H).

Example 66

Synthesis of 4-(4-[[2-(4-chlorophenyl)-4,4-dimethylcyclohex-1-en-1-yl]methyl]piperazin-1-yl)-2-[12-cyano-12-methyl-14-oxa-2,4,10-triazatricyclo [7.5.0.0^[3,7]]tetradeca-1(9),2,5,7-tetraen-10-yl]-N-[3-nitro-4-[(oxan-4-ylmethyl)amino] benzenesulfonyl]benzamide Synthesis of ethyl 2-cyano-3-hydroxy-2-methylpropanoate: Into a 500-mL round-bottom flask, was placed ethyl 2-cyanopropionate (20.00 g, 157.303 mmol, 1.00 equiv), CH₃CN (200.00 mL), formaldehyde (32.00 g, 394.325 mmol, 2.51 equiv, 37%), TEA (800.00 mg, 7.906 mmol, 0.05 equiv). The resulting solution was stirred overnight at 50 degrees C. in an oil bath. The reaction mixture was cooled to room temperature. The resulting mixture was concentrated under vacuum. The residue was applied onto a silica gel column and eluted with ethyl acetate/petroleum ether (1:4). This resulted in 20 g (80.90%) of ethyl 2-cyano-3-hydroxy-2-methylpropanoate as colorless oil. $^1$H NMR (300 MHz, CDCl₃-d, ppm) δ 5.01-4.72 (m, 1H), 4.38-4.23 (m, 2H), 4.04-3.82 (m, 2H), 1.60 (d, J=2.6 Hz, 3H), 1.35 (td, J=7.1, 2.7 Hz, 3H).

Synthesis of 3-hydroxy-2-(hydroxymethyl)-2-methylpropanenitrile: Into a 250-mL round-bottom flask, was placed ethyl 2-cyano-3-hydroxy-2-methylpropanoate (12.00 g, 76.351 mmol, 1.00 equiv), MeOH (120.00 mL). This was followed by the addition of NaBH₄ (4.40 g, 116.301 mmol, 1.52 equiv), in portions at 0 degrees C. The resulting solution was stirred for 1.5 hr at 25 degrees C. The reaction was then quenched by the addition of 20 mL of water. The resulting mixture was concentrated under vacuum. The residue was applied onto a silica gel column and eluted with dichloromethane/methanol (10:1). This resulted in 8 g (91.01%) of 3-hydroxy-2-(hydroxymethyl)-2-methylpropanenitrile as light yellow oil. $^1$H NMR (300 MHz, MeOD d₄, ppm) δ 3.74-3.50 (m, 4H), 1.29 (s, 3H).

Synthesis of 2-[[(5-bromo-1-[[2-(trimethylsilyl)ethoxy]methyl]pyrrolo[2,3-b]pyridin-6-yl)oxy]methyl]-3-hydroxy-2-methylpropanenitrile: Into a 500-mL round-bottom flask, was placed 5-bromo-6-fluoro-1-[[2-(trimethylsilyl)ethoxy]methyl]pyrrolo[2,3-b]pyridine (12.00 g, 34.754 mmol, 1.00 equiv), CH₃CN (200.00 mL), 3-hydroxy-2-(hydroxymethyl)-2-methylpropanenitrile (8.00 g, 69.485 mmol, 2.00 equiv), CS₂CO₃ (28.34 g, 86.981 mmol, 2.50 equiv). The resulting solution was stirred for 12 hr at 80 degrees C. in an oil bath. The reaction mixture was cooled to room temperature. The resulting solution was diluted with 500 mL of H₂O. The resulting solution was extracted with 2×300 mL of ethyl acetate and the organic layers combined. The resulting mixture was washed with 1×1000 ml of brine. The mixture was dried over anhydrous sodium sulfate. The solids were filtered out. The resulting mixture was concentrated under vacuum. The residue was applied onto a silica gel column and eluted with ethyl acetate/petroleum ether (1:5). This resulted in 6 g (39.20%) of 2-[[(5-bromo-1-[[2-(trimethylsilyl)ethoxy]methyl]pyrrolo[2,3-b]pyridin-6-yl)oxy]methyl]-3-hydroxy-2-methylpropanenitrile as light yellow oil. $^1$H NMR (300 MHz, CDCl₃-d, ppm) δ 8.08 (s, 1H), 7.18 (d, J=3.6 Hz, 1H), 6.42 (d, J=3.6 Hz, 1H), 5.55 (s, 2H), 4.70 (d, J=10.8 Hz, 1H), 4.53 (d, J=10.9 Hz, 1H), 3.85 (d, J=4.0 Hz, 2H), 3.62-3.46 (m, 2H), 1.53 (s, 3H), 1.05-0.85 (m, 2H), −0.03 (s, 8H).

Synthesis of N-[6-[2-cyano-2-(hydroxymethyl)-2-methylethoxy]-1-[[2-(trimethylsilyl)ethoxy]methyl]pyrrolo[2,3-b]pyridin-5-yl]-4-methylbenzenesulfonamide: Into a 250-mL round-bottom flask purged and maintained with an inert atmosphere of nitrogen, was placed 2-[[(5-bromo-1-[[2-(trimethylsilyl)ethoxy]methyl]pyrrolo[2,3-b]pyridin-6-yl)oxy]methyl]-3-hydroxy-2-methylpropanenitrile (6.00 g, 13.624 mmol, 1.00 equiv), DMSO (50.00 mL), p-toluenesulfonamide (4.67 g, 27.276 mmol, 2.00 equiv), picolinic acid (1.35 g, 10.966 mmol, 0.80 equiv), CuI (3.12 g, 16.382 mmol, 1.20 equiv), K₂CO₃ (5.66 g, 40.954 mmol, 3.01 equiv). The resulting solution was stirred for 2 days at 120 degrees C. in an oil bath. The reaction mixture was cooled to room temperature. The resulting solution was diluted with 500 mL of H₂O. The resulting solution was extracted with 3×200 mL of ethyl acetate and the organic layers combined. The resulting mixture was washed with 2×1000 ml of brine. The mixture was dried over anhydrous sodium sulfate and concentrated under vacuum. The residue was applied onto a silica gel column and eluted with ethyl acetate/petroleum ether (1:1). This resulted in 2.45 g (33.89%) of N4642-cyano-2-(hydroxymethyl)-2-methylethoxy]-1-[[2-(trimethylsilyl)ethoxy]methyl]pyrrolo[2,3-b]pyridin-5-yl]-4-methylbenzenesulfonamide as a white solid. $^1$H NMR (300 MHz, CDCl₃-d, ppm) δ 8.14 (s, 1H), 7.68-7.58 (m, 2H), 7.25-7.13 (m, 3H), 6.76 (s, 1H), 6.48 (d, J=3.6 Hz, 1H), 5.47 (d, J=4.4 Hz, 2H), 4.41 (d, J=11.2 Hz, 1H), 4.29 (d, J=11.3 Hz, 1H), 3.61 (dd, J=7.9, 6.3 Hz, 1H), 3.56-3.43 (m, 4H), 2.38 (s, 3H), 1.34 (s, 3H), 0.97-0.84 (m, 2H), −0.05 (s, 9H).

Synthesis of 12-methyl-10-(4-methylbenzenesulfonyl)-4-[[2-(trimethylsilyl)ethoxy]methyl]-14-oxa-2,4,10-triazatricyclo[7.5.0.0^[3,7]]tetradeca-1(9),2,5,7-tetraene-12-carbonitrile: Into a 250-mL round-bottom flask purged and maintained with an inert atmosphere of nitrogen, was placed N4642-cyano-2-(hydroxymethyl)-2-methylethoxy]-1-[[2-(trimethylsilyl)ethoxy]methyl]pyrrolo[2,3-b]pyridin-5-yl]-4-methylbenzenesulfonamide (2.45 g, 4.616 mmol, 1.00 equiv), THF (30 mL), PPh₃ (2.42 g, 9.227 mmol, 2.00 equiv). This was followed by the addition of DEAD (1.61 g, 9.245 mmol, 2.00 equiv) dropwise with stirring at 0 degrees C. The resulting solution was stirred for 1 hr at 25 degrees C. The resulting solution was diluted with 500 mL of H₂O. The resulting solution was extracted with 2×200 mL of ethyl acetate and the organic layers combined. The resulting mixture was washed with 1×500 ml of brine. The mixture was dried over anhydrous sodium sulfate and concentrated under vacuum. The residue was applied onto a silica gel column and eluted with ethyl acetate/petroleum ether (1:3). This resulted in 2 g (84.50%) of 12-methyl-10-(4-methylbenzenesulfonyl)-4-[[2-(trimethylsilyl)ethoxy]methyl]-14-oxa-2,4,10-triazatricyclo[7.5.0.0^[3,7]]tetradeca-1(9),2,5,7-tetraene-12-carbonitrile as a yellow solid.

Synthesis of 12-methyl-4-[[2-(trimethylsilyl)ethoxy]methyl]-14-oxa-2,4,10-triazatricyclo[7.5.0.0^[3,7]]tetradeca-1(9),2,5,7-tetraene-12-carbonitrile: Into a 40-mL vial purged and maintained with an inert atmosphere of nitrogen, was placed Na (539.00 mg, 23.445 mmol, 6.01 equiv), Naphthalene (3.00 g, 23.406 mmol, 6.00 equiv), DME (10.00 mL). The mixture was stirred at room temperature for 40 min until the formation of Na/naphthalene was complete. This was followed by the addition of above solution to the 12-methyl-10-(4-methylbenzenesulfonyl)-4-[[2-(trimethylsilyl)ethoxy]methyl]-14-oxa-2,4,10-triazatricyclo[7.5.0.0^[3,7]]tetradeca-1(9),2,5,7-tetraene-12-carbonitrile (2.00 g, 3.901 mmol, 1.00 equiv) in THF (10.00 mL) at −78 degrees C. The resulting solution was stirred for 2 hr at 25 degrees C. The reaction was then quenched by the addition of 500 mL of aqueous NH₄Cl. The resulting solution was extracted with 3×200 mL of ethyl acetate and the organic layer was combined. The resulting mixture was washed with 1×500 ml of brine. The mixture was dried over anhydrous sodium sulfate and concentrated under vacuum. The residue was applied onto a silica gel column and eluted with ethyl acetate/petroleum ether (1:3). This resulted in 1 g (71.50%) of 12-methyl-4-[[2-(trimethylsilyl)ethoxy]methyl]-14-oxa-2,4,10-triazatricyclo[7.5.0.0^[3,7]]tetradeca-1(9),2,5,7-tetraene-12-carbonitrile as yellow oil. ¹H NMR (300 MHz, DMSO-d₆, ppm) δ 7.44 (s, 1H), 7.40 (d, J=3.5 Hz, 1H), 6.34 (d, J=3.5 Hz, 1H), 5.65-5.52 (m, 1H), 5.44 (s, 2H), 4.51-4.36 (m, 1H), 3.86 (d, J=12.2 Hz, 1H), 3.56-3.42 (m, 3H), 2.94 (dd, J=13.2, 2.3 Hz, 1H), 1.31 (s, 3H), 0.89-0.71 (m, 2H), −0.08 (s, 9H).

Synthesis of methyl 4-(4-[[2-(4-chlorophenyl)-4,4-dimethylcyclohex-1-en-1-yl]methyl]piperazin-1-yl)-2-(12-cyano-12-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate: Into a 100-mL round-bottom flask purged and maintained with an inert atmosphere of nitrogen, was placed methyl 2-bromo-4-(4-[[2-(4-chlorophenyl)-4,4-dimethylcyclohex-1-en-1-yl]methyl]piperazin-1-yl)benzoate (1.18 g, 2.218 mmol, 1.99 equiv), toluene (10.00 mL), 12-methyl-4-[[2-(trimethylsilyl)ethoxy]methyl]-14-oxa-2,4,10-triazatricyclo[7.5.0.0^[3,7]]tetradeca-1(9),2,5,7-tetraene-12-carbonitrile (400.00 mg, 1.116 mmol, 1.00 equiv), Cs₂CO₃ (1.82 g, 5.586 mmol, 5.01 equiv), Xantphos Pd 2G Precatalyst (149.00 mg, 0.168 mmol, 0.15 equiv). The resulting solution was stirred 2 days at 110 degrees C. in an oil bath. The reaction mixture was cooled to room temperature. The resulting mixture was concentrated under vacuum. The residue was applied onto a silica gel column and eluted with ethyl acetate/petroleum ether (1:1). This resulted in 330 mg (36.54%) of methyl 4-(4-[[2-(4-chlorophenyl)-4,4-dimethylcyclohex-1-en-1-yl]methyl]piperazin-1-yl)-2-(12-cyano-12-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate as yellow oil. LC-MS: (ES, m/z): M+1=809.

Synthesis of methyl 4-(4-[[2-(4-chlorophenyl)-4,4-dimethylcyclohex-1-en-1-yl]methyl]piperazin-1-yl)-2-[12-cyano-12-methyl-14-oxa-2,4,10-triazatricyclo[7.5.0.0^[3,7]]tetradeca-1(9),2,5,7-tetraen-10-yl)benzoate: Into a 100-mL round-bottom flask, was placed methyl 4-(4-[[2-(4-chlorophenyl)-4,4-dimethylcyclohex-1-en-1-yl]methyl]piperazin-1-yl)-2-(12-cyano-12-methyl-4-[[2-(trimethylsilyl)ethoxy]methyl]-14-oxa-2,4,10-triazatricycloo[7.5.0.0^[3,7]]tetradeca-1(9),2,5,7-tetraen-10-yl)benzoate (330.00 mg, 0.408 mmol, 1.00 equiv), THF (20.00 mL), TBAF.3H₂O (5.00 g), ethylenediamine (2.50 g, 41.597 mmol, 102.04 equiv). The resulting solution was stirred for 2 days at 70 degrees C. in an oil bath. The reaction mixture was cooled to room temperature. The resulting mixture was concentrated under vacuum. The residue was applied onto a silica gel column with ethyl acetate/petroleum ether (2:1). This resulted in 220 mg (79.45%) of methyl 4-(4-[[2-(4-chlorophenyl)-4,4-dimethylcyclohex-1-en-1-yl]methyl]piperazin-1-yl)-2-[12-cyano-12-methyl-14-oxa-2,4,10-triazatricyclo[7.5.0.0^[3,7]]tetradeca-1(9),2,5,7-tetraen-10-yl]benzoate as a light yellow solid. LC-MS: (ES, m/z): M+1=679.

Synthesis of 4-(4-[[2-(4-chlorophenyl)-4,4-dimethylcyclohex-1-en-1-yl]methyl]piperazin-1-yl)-2-[12-cyano-12-methyl-14-oxa-2,4,10-triazatricyclo[7.5.0.0^[3,7]]tetradeca-1(9),2,5,7-tetraen-10-yl]benzoic acid Into a 40-mL vial, was placed methyl 4-(4-[[2-(4-chlorophenyl)-4,4-dimethylcyclohex-1-en-1-yl]methyl]piperazin-1-yl)-2-[12-cyano-12-methyl-14-oxa-2,4,10-triazatricyclo[7.5.0.0^[3,7]]tetradeca-1(9),2,5,7-tetraen-10-yl]benzoate (190.00 mg, 0.280 mmol, 1.00 equiv), MeOH (12.00 mL), dioxane (12.00 mL), H₂O (4.00 mL), LiOH·H₂O (353.00 mg, 8.412 mmol, 30.07 equiv). The resulting solution was stirred overnight at 60 degrees C. in an oil bath. The reaction mixture was cooled to room temperature. The resulting mixture was concentrated under vacuum. The pH value of the solution was adjusted to 6-7 with HCl (2 mol/L). The resulting solution was extracted with 2×100 mL of ethyl acetate and the organic layers combined. The resulting mixture was washed with 1×500 ml of brine. The mixture was dried over anhydrous sodium sulfate and concentrated under vacuum. The residue was purified by Prep-TLC with ethyl acetate. This resulted in 80 mg (42.99%) of 4-(4-[[2-(4-chlorophenyl)-4,4-dimethylcyclohex-1-en-1-yl]methyl]piperazin-1-yl)-2-[12-cyano-12-methyl-14-oxa-2,4,10-triazatricyclo[7.5.0.0^[3,7]]tetradeca-1(9),2,5,7-tetraen-10-yl]benzoic acid as a light yellow solid. LC-MS: (ES, m/z): M+1=665

Synthesis of 4-(4-[[2-(4-chlorophenyl)-4,4-dimethylcyclohex-1-en-1-yl]methyl]piperazin-1-yl)-2-[12-cyano-12-methyl-14-oxa-2,4,10-triazatricyclo[7.5.0.0^[3,7]]tetradeca-1(9),2,5,7-tetraen-10-yl]-N-[3-nitro-4-[(oxan-4-ylmethyl)amino]benzenesulfonyl]benzamide: Into a 40-mL vial, was placed 4-(4-[[2-(4-chlorophenyl)-4,4-dimethylcyclohex-1-en-1-yl]methyl]piperazin-1-yl)-2-[12-cyano-12-methyl-14-oxa-2,4,10-triazatricyclo[7.5.0.0^[3,7]]tetradeca-1(9),2,5,7-tetraen-10-yl]benzoic acid (40.00 mg, 0.060 mmol, 1.00 equiv), DCM (2.00 mL), 3-nitro-4-[(oxan-4-ylmethyl)amino]benzenesulfonamide (19.00 mg, 0.060 mmol, 1.00 equiv), EDCI (23.00 mg, 0.120 mmol, 2.00 equiv), DMAP (29.00 mg, 0.237 mmol, 3.95 equiv). The resulting solution was stirred overnight at 25 degrees C. The resulting mixture was concentrated under vacuum. The crude product was purified by Prep-HPLC with the following conditions (2 #SHIMADZU (HPLC-01)): Column, XBridge Prep C18

OBD Column 5 um, 19*150 mm; mobile phase, ACN and Water (0.05% $NH_3 \cdot H_2O$) (20% Phase B up to 75% in 1 min, up to 95% in 7 min, hold 95% in 1 min, down to 20% in 1 min); Detector, 254/220 nm. This resulted in 18.8 mg (32.48%) of 4-(4-[[2-(4-chlorophenyl)-4,4-dimethylcyclohex-1-en-1-yl]methyl]piperazin-1-yl)-2-[12-cyano-12-methyl-14-oxa-2,4,10-triazatricyclo[7.5.0.0ˆ[3,7]]tetradeca-1(9),2,5,7-tetraen-10-yl]-N-[3-nitro-4-[(oxan-4-ylmethyl) amino]benzenesulfonyl]benzamide as a yellow solid. LC-MS: (ES, m/z): M+1=962, R.T=1.461 min. The measurements of the retention were done with a reversed phase column (C18). Shimadzu LCMS 2020; SUPELCO Ascentis Express C18, 50*3.0 mm, 2.7 microm; Eluent A: water (0.05% TFA); Eluent B: Acetonitrile; linear gradient from 5% acetonitrile to 100% acetonitrile in 3.0 minutes; Oven temperature 40° C.; flow: 1.5 mL/min. $^1$H NMR (300 MHz, DMSO-$d_{6, ppm}$) δ 8.55 (s, 1H), 8.34 (s, 1H), 7.60-7.31 (m, 4H), 7.23-7.00 (m, 3H), 6.76 (d, J=26.1 Hz, 4H), 6.04 (s, 1H), 3.88 (dd, J=11.7, 4.0 Hz, 2H), 3.38-3.12 (m, 7H), 2.77 (d, J=19.8 Hz, 2H), 2.24 (d, J=20.9 Hz, 6H), 1.99 (s, 4H), 1.66 (d, J=12.4 Hz, 2H), 1.42 (t, J=6.3 Hz, 2H), 1.36-1.03 (m, 8H), 0.96 (s, 6H).

Example 67

Synthesis of 4-(4-[[2-(4-chlorophenyl)-4,4-dimethylcyclohex-1-en-1-yl]methyl]piperazin-1-yl)-2-[(13S)-13-methyl-14-oxa-2,4,10-triazatricyclo [7.5.0.0ˆ[3,7]]tetradeca-1(9),2,5,7-tetraen-10-yl]-N-(3-nitro-4-[[(oxan-4-yl)methyl]amino] benzenesulfonyl)benzamide Synthesis of N-(3-hydroxybutyl)-4-methylbenzene-1-sulfonamide: Into a 250-mL round-bottom flask purged and maintained with an inert atmosphere of nitrogen, was placed 4-aminobutan-2-ol hydrochloride (4 g, 31.847 mmol, 1 equiv), DCM (40 mL), TEA (3.56 g, 35.181 mmol, 1.10 equiv). This was followed by the addition of 4-methylbenzene-1-sulfonyl chloride (6.08 g, 31.893 mmol, 1.00 equiv) in portions at 0 degrees C. The resulting solution was stirred for 2 h at 25 degrees C. The resulting mixture was concentrated under vacuum. The residue was applied onto a silica gel column with ethyl acetate/petroleum ether (1:1). This resulted in 4.4 g (56.78%) of N-(3-hydroxybutyl)-4-methylbenzene-1-sulfonamide as colorless oil. $^1$H NMR (300 MHz, CDCl$_3$-d, ppm) δ 7.82-7.73 (d, J=9.0 Hz, 2H), 7.39-7.30 (d, J=9.0 Hz, 2H), 4.06-3.82 (m, 1H), 3.24-3.16 (m, 1H), 3.06-3.00 (m, 1H), 2.45 (s, 3H), 1.70-1.55 (m, 2H), 1.20 (d, J=6.2 Hz, 3H).

Synthesis of N-[3-[(5-bromo-1-[[2-(trimethylsilyl) ethoxy]methyl]-1H-pyrrolo[2,3-b]pyridin-6-yl)oxy]butyl]-4-methylbenzene-1-sulfonamide: Into a 250-mL 3-necked round-bottom flask purged and maintained with an inert atmosphere of nitrogen, was placed N-(3-hydroxybutyl)-4-methylbenzene-1-sulfonamide (4.4 g, 18.083 mmol, 1.10 equiv), THF (60 mL). This was followed by the addition of NaH (1.97 g, 49.255 mmol, 3.00 equiv, 60%), in portions at 0 degrees C. The resulting solution was stirred for 0.5 h at 0 degrees C. To this was added 5-bromo-6-fluoro-1-[[2-(trimethylsilyl)ethoxy]methyl]-1H-pyrrolo[2,3-b]pyridine (5.66 g, 16.392 mmol, 1 equiv). The resulting solution was stirred overnight at 50 degrees C. in an oil bath. The reaction mixture was cooled to 25 degree C. The reaction was then quenched by the addition of 500 mL of NH$_4$Cl. The resulting solution was extracted with 2×200 mL of ethyl acetate and the organic layers combined. The resulting mixture was washed with 1×500 ml of brine. The mixture was dried over anhydrous sodium sulfate and concentrated under vacuum. The residue was applied onto a silica gel column with ethyl acetate/petroleum ether (1:3). This resulted in 6 g (64.37%) of N-[3-[(5-bromo-1-[[2-(trimethylsilyl)ethoxy]methyl]-1H-pyrrolo[2,3-b]pyridin-6-yl)oxy]butyl]-4-methylbenzene-1-sulfonamide as colorless oil. $^1$H NMR (300 MHz, CDCl$_3$-d, ppm) δ 8.04 (s, 1H), 7.74-7.63 (m, 2H), 7.23-7.11 (m, 3H), 6.41 (d, J=3.6 Hz, 1H), 5.56 (d, J=3.3 Hz, 2H), 5.89-5.33 (m, 1H), 3.59-3.46 (m, 2H), 3.17 (t, J=6.0 Hz, 2H), 2.37 (s, 3H), 2.08-1.78 (m, 2H), 1.37 (d, J=6.2 Hz, 3H), 0.94-0.85 (m, 2H), −0.06 (s, 9H).

Synthesis of 13-methyl-10-(4-methylbenzenesulfonyl)-4-[[2-(trimethylsilyl)ethoxy]methyl]-14-oxa-2,4,10-triazatricyclo[7.5.0.0ˆ[3,7]]tetradeca-1(9),2,5,7-tetraene. Into a 250-mL round-bottom flask purged and maintained with an inert atmosphere of nitrogen, was placed N-[3-[(5-bromo-1-[[2-(trimethylsilyl)ethoxy]methyl]-1H-pyrrolo[2,3-b]pyridin-6-yl)oxy]butyl]-4-methylbenzene-1-sulfonamide (6 g, 10.552 mmol, 1 equiv), DMSO (60 mL), pyridine-2-carboxylic acid (1.04 g, 8.448 mmol, 0.80 equiv), CuI (2.41 g, 12.654 mmol, 1.20 equiv), K$_2$CO$_3$ (4.38 g, 31.692 mmol, 3.00 equiv). The resulting solution was stirred for 2 days at 125 degrees C. in an oil bath. The reaction mixture was cooled to 25 degree C. The resulting solution was diluted with 500 mL of water. The resulting solution was extracted with 3×200 mL of ethyl acetate and the organic layers combined. The resulting mixture was washed with 2×1000 ml of brine. The mixture was dried over anhydrous sodium sulfate and concentrated under vacuum. The residue was applied onto a silica gel column with ethyl acetate/petroleum ether (1:3). This resulted in 2.8 g (54.41%) of 13-methyl-10-(4-methylbenzenesulfonyl)-4-[[2-(trimethylsilyl) ethoxy]methyl]-14-oxa-2,4,10-triazatricyclo[7.5.0.0ˆ[3,7]]tetradeca-1(9),2,5,7-tetraene as yellow oil. $^1$H NMR (300 MHz, CDCl$_3$-d, ppm) δ 8.10 (s, 1H), 7.53-7.40 (m, 2H), 7.30 (d, J=3.6 Hz, 1H), 7.24-7.12 (m, 2H), 6.50 (d, J=3.6 Hz, 1H), 5.65 (d, J=10.7 Hz, 1H), 5.49 (d, J=10.7 Hz, 1H), 4.37-4.23 (m, 1H), 3.94-3.80 (m, 1H), 3.62-3.36 (m, 3H), 2.37 (s, 3H), 1.89-1.64 (m, 2H), 1.23 (d, J=6.3 Hz, 3H), 1.01-0.76 (m, 2H), −0.07 (s, 9H).

Synthesis of 13-methyl-4-[[2-(trimethylsilyl)ethoxy] methyl]-14-oxa-2,4,10-triazatricyclo[7.5.0.0ˆ[3,7]]tetradeca-1(9),2,5,7-tetraene; Into a 250-mL round-bottom flask purged and maintained with an inert atmosphere of nitrogen, was placed Na (793.5 mg, 34.51 mmol, 6.01 equiv), naphthalene (4.42 g, 34.48 mmol, 6.01 equiv), DME (20 mL). The mixture was stirred at room temperature for 40 min until the formation of Na/naphthalene was complete. Another 250-mL round-bottom flask purged and maintained with an inert atmosphere of nitrogen, was placed 13-methyl-10-(4-methylbenzenesulfonyl)-4-[[2-(trimethylsilyl)ethoxy] methyl]-14-oxa-2,4,10-triazatricyclo[7.5.0.0ˆ[3,7]]tetradeca-1(9),2,5,7-tetraene (2.8 g, 5.741 mmol, 1 equiv), THF (20 mL). This was followed by the addition of above solution at −78 degrees C. The resulting solution was stirred for 2 hr at room temperature. The reaction was then quenched by the addition of 500 mL of NH$_4$Cl. The resulting solution was extracted with 3×200 mL of ethyl acetate and the organic layers combined. The resulting mixture was washed with 1×500 ml of brine. The mixture was dried over anhydrous sodium sulfate and concentrated under vacuum. The residue was applied onto a silica gel column with ethyl acetate/petroleum ether (1:3). This resulted in 1.2 g (62.67%) of 13-methyl-4-[[2-(trimethylsilyl)ethoxy] methyl]-14-oxa-2,4,10-triazatricyclo[7.5.0.0ˆ[3,7]]tetradeca-1(9),2,5,7-tetraene as yellow oil. $^1$H NMR (300 MHz, DMSO-$d_6$, ppm) δ 7.43-7.26 (m, 2H), 6.27 (d, J=3.5 Hz, 1H), 5.43 (d, J=3.4 Hz, 2H), 5.13 (s, 1H), 4.14-4.04 (m, 1H), 3.58-3.39 (m, 3H), 3.28-3.10 (m, 1H), 2.95-2.77 (m, 1H), 2.09-1.85 (m, 1H), 1.85-1.64 (m, 1H), 1.37 (d, J=6.3 Hz, 3H), 0.88-078 (m, 2H), −0.09 (s, 9H).

Synthesis of 13-methyl-4-[[2-(trimethylsilyl)ethoxy] methyl]-14-oxa-2,4,10-triazatricyclo[7.5.0.0^[3,7]]tetradeca-1(9),2,5,7-tetraene: The crude product (0.5 g) was purified by Chiral-Prep-HPLC with the following conditions: Instrument Name: SHIMADZU LC-20AD, LC parameters: Pump Mode: Binary gradient, Start Conc. of Pump B: 50.0%, Total Flow: 15 mL/min, Phase A: n-Hexane (0.1% DEA), Phase B: Ethanol, Column Name: CHIRALpak IA-3, Length: 50 mm, Internal Diameter: 4.6 mm, Particle Size: 3.0 um, Column Temp: 25° C., PDA Model: SPD-M20A, Wavelength: from 190 nm to 500 nm. This resulted in 220 mg (peak 1 Assumed R) [a]=−6.78° (C=0.129 g/100 mL in $CH_2Cl_2$, T=27° C.) of (13R or S)-13-methyl-4-[[2-(trimethylsilyl)ethoxy]methyl]-14-oxa-2,4,10-triazatricyclo[7.5.0.0^[3,7]]tetradeca-1(9),2,5,7-tetraene as a yellow oil and 230 mg (peak 2 Assumed S) [a]=+11.84° (C=0.106 g/100 mL in $CH_2Cl_2$, T=27° C.) of (13S or R)-13-methyl-4-[[2-(trimethylsilyl)ethoxy]methyl]-14-oxa-2,4,10-triazatricyclo[7.5.0.0^[3,7]]tetradeca-1(9),2,5,7-tetraene as a yellow oil.

Synthesis of methyl 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoate: Into a 40-mL vial purged and maintained with an inert atmosphere of nitrogen, was placed (13 S)-13-methyl-4-[[2-(trimethylsilyl)ethoxy]ethyl]-14-oxa-2,4,10-triazatricyclo[7.5.0.0^[3,7]]tetradeca-1(9),2,5,7-tetraene (210.00 mg, 0.630 mmol, 1.00 equiv), toluene (5.00 mL), methyl 2-bromo-4-(4-[[2-(4-chlorophenyl)-4,4-dimethylcyclohex-1-en-1-yl]methyl]piperazin-1-yl)benzoate (669.87 mg, 1.259 mmol, 2.00 equiv), $Cs_2CO_3$ (1025.80 mg, 3.148 mmol, 5.00 equiv), Xantphos Pd 2G Precatalyst (111.70 mg, 0.126 mmol, 0.20 equiv). The resulting solution was stirred overnight at 110 degrees C. in an oil bath. The reaction mixture was cooled to room temperature. The resulting mixture was concentrated under vacuum. The residue was applied onto a silica gel column with ethyl acetate/petroleum ether (1:1). This resulted in 240 mg (31.09%) of methyl 4-(4-[[2-(4-chlorophenyl)-4,4-dimethylcycloohex-1-en-1-yl]ethyl]piperazin-1-yl)-2-[(13 S)-13-methyl-4-[[2-(trimethylsilyl)ethoxy]ethyl]-14-oxa-2,4,10-triazatricycloo[7.5.0.0^[3,7]]tetradeca-1(9),2,5,7-tetraen-10-yl]benzoate as yellow oil. LC-MS: (ES, m/z): M+1=784.

Synthesis of 4-(4-[[2-(4-chlorophenyl)-4,4-dimethylcyclohex-1-en-1-yl]methyl]piperazin-1-yl) -2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoic acid: Into a 8-mL round-bottom flask, was placed methyl 4-(4-[[2-(4-chlorophenyl)-4,4 dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoate (200 mg, 0.255 mmol, 1.00 equiv), $H_2O$ (1.00 mL), MeOH (2.00 mL), dioxane (2.00 mL), NaOH (61.18 mg, 1.530 mmol, 6.00 equiv). The resulting solution was stirred for 12 h at 70 degrees C. The resulting mixture was concentrated. The pH value of the solution was adjusted to 5 with HCl (1 mol/L). The solids were collected by filtration. This resulted in 180 mg (91.64%) of 4-(4-[[2-(4-chlorophenyl)-4,4-dimethylcycloohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoic acid as a white solid. H-NMR-PH-PHNW-4-82-1: (CDCl3, 300 ppm): δ 8.17 (s, 1H), 7.28 (s, 1H), 7.00-6.79 (m, 4H), 6.35 (s, 1H), 5.70-5.67 (d, J=9 Hz, 1H), 5.56-5.52 (d, J=12 Hz, 1H), 4.38-4.35 (m, 1H), 3.81 (s, 1H), 3.58-3.56 (m, 4H), 3.26 (s, 3H), 2.84 (s, 1H), 2.35 (s, 3H), 2.24 (s, 2H), 2.12 (s, 2H), 2.04 (s, 2H), 1.60 (s, 6H), 1.28 (s, 1H), 1.01 (s, 7H), 0.98-0.95 (m, 3H), 0.00 (s, 9H).

Synthesis of 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]-N-(3-nitro-4-[[(oxan-4-yl)methyl]amino] benzenesulfonyl)benzamide: Into a 8-mL round-bottom flask, was placed 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]benzoic acid (100.00 mg, 0.130 mmol, 1.00 equiv), 3-nitro-4-[[(oxan-4-yl)methyl]amino]benzene-1-sulfonamide (40.93 mg, 0.130 mmol, 1 equiv), DCM (3 mL), DMAP (63.42 mg, 0.519 mmol, 4 equiv), EDCI (49.76 mg, 0.260 mmol, 2.00 equiv). The resulting solution was stirred for 12 hr at room temperature. The resulting mixture was concentrated. The residue was applied onto a silica gel column with ethyl acetate/petroleum ether (0:1-1:0). This resulted in 80 mg (57.72%) of 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0^[3,7]]tetradeca-1(9),2,5,7-tetraen-10-yl]-N-(3-nitro-4-[[(oxan-4-yl)methyl]amino] benzenesulfonyl)benzamide as a yellow solid. LC-MS: (ES, m/z): M+1=1066.46.

Synthesis of 4-(4-[[2-(4-chlorophenyl)-4,4-dimethylcyclohex-1-en-1-yl]methyl]piperazin-1-yl)-2-[(13S)-13-methyl-14-oxa-2,4,10-triazatricyclo[7.5.0.0^[3,7]]tetradeca-1(9),2,5,7-tetraen-10-yl]-N-(3-nitro-4-[[(oxan-4-yl)methyl] amino]benzenesulfonyl)benzamide: Into a 8-mL round-bottom flask, was placed 4-(4-[[2-(4-chlorophenyl)-4,4-dimethylcyclohex-1-en-1-yl]methyl]piperazin-1-yl)-2-[(13 S)-13-methyl-4-[[2-(trimethylsilyl)ethoxy]ethyl]-14-oxa-2,4,10-triazatricyclo[7.5.0.0^[3,7]]tetradeca-1(9),2,5,7-tetraen-10-yl]-N-(3-nitro-4-[[(oxan-4-yl)methyl]amino]benzenesulfonyl)benzamide (80.00 mg, 0.075 mmol, 1.00 equiv), THF (5 mL), TBAF (391.77 mg, 1.498 mmol, 20.00 equiv), ethane-1,2-diamine (90.05 mg, 1.498 mmol, 20 equiv). The resulting solution was stirred for 48 hr at 70 degrees C. The resulting mixture was concentrated. The crude product was purified by Prep-HPLC with the following conditions (Waters-2767): Column, X-bridge RP18, 5 um, 19*100 mm; mobile phase, 0.03% ammonia in water (0.03% $NH_4HCO_3$ & $NH_4OH$) and $CH_3CN$ (32% $CH_3CN$ up to 52% in 6 min); Detector, UV 254 nm. This resulted in 25 mg (35.59%) of 4-(4-[[2-(4-chlorophenyl)-4,4-dimethylcyclohex-1-en-1-yl] ethyl]piperazin-1-yl)-2-[(13S)-13-methyl-14-oxa-2,4,10-triazatricyclo[7.5.0.0^[3,7]]tetradeca-1(9),2,5,7-tetraen-10-yl]-N-(3-nitro-4-[[(oxan-4-yl)methyl]amino] benzenesulfonyl)benzamide as a yellow solid. LC-MS-PH-PHNW-4-77-0B: (ES, m/z): M+1=937.54 The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient. H-NMR-PH-PHNW-4-77-0B: (300 MHz, Chloroform-d) δ 8.84-8.78 (m, 2H), 8.34 (s, 1H), 7.98-7.96 (d, J=6.0 Hz, 2H), 7.28-7.27 (m, 1H), 7.17-7.15 (m, 1H), 7.04-6.94 (m, 3H), 6.76-6.73 (m, 2H), 6.64 (s, 1H), 6.22 (s, 1H), 4.02-3.93 (m, 3H), 3.46-3.30 (m, 7H), 3.10 (s, 2H), 2.85 (s, 2H), 2.37 (s, 4H), 2.25 (s, 2H), 2.15-2.03 (m, 3H), 185-1.80 (m, 1H), 1.70 (s, 4H), 1.60 (s, 2H), 1.50-1.46 (m, 4H), 1.00 (s, 6H).

Example 68

Synthesis of 4-(4-[[2-(4-chlorophenyl)-4,4-dimethylcyclohex-1-en-1-yl]methyl]piperazin-1-yl)-N-[4-([[(2S)-1,4-dioxan-2-yl]methyl]amino]-3-nitrobenzene sulfonyl]-2-[(13 S)-13-methyl-4-[[2-(trimethylsilyl ethoxy]methyl]-14-oxa-2,4,10-triazatricycloo[7.5.0.0ˆ[3,7]]tetradeca-1(9),2,5,7-tetraen-10-yl]benzamide, and Synthesis of 4-(4-[[2-(4-chlorophenyl)-4,4-dimethylcycloohex-1-en-1-yl] methyl]piperazin-1-yl)-N-(4-[[(1,4-dioxan-2-yl) methyl]amino]-3-nitrobenzene sulfonyl)-2-[(13 S)-13-methyl-14-oxa-2,4,10-triazatricyclo[7.5.0.0[3,7]]tetradeca-1(9),2,5,7-tetraen-10-yl]benzamide Synthesis of N-(3-hydroxybutyl)-4-methylbenzene-1-sulfonamide: Into a 250-mL round-bottom flask purged and maintained with an inert atmosphere of nitrogen, was placed 4-aminobutan-2-ol hydrochloride (4 g, 31.847 mmol, 1 equiv), DCM (40 mL), TEA (3.56 g, 35.181 mmol, 1.10 equiv). This was followed by the addition of 4-methylbenzene-1-sulfonyl chloride (6.08 g, 31.893 mmol, 1.00 equiv) in portions at 0 degrees C. The resulting solution was stirred for 2 h at 25 degrees C. The resulting mixture was concentrated under vacuum. The residue was applied onto a silica gel column and eluted with ethyl acetate/petroleum ether (1:1). This resulted in 4.4 g (56.78%) of N-(3-hydroxybutyl)-4-methylbenzene-1-sulfonamide as colorless oil. $^1$H NMR (300 MHz, CDCl$_3$-d, ppm) δ 7.82 7.73 (d, J=9.0 Hz, 2H), 7.39-7.30 (d, J=9.0 Hz, 2H), 4.06-3.82 (m, 1H), 3.24-3.16 (m, 1H), 3.06-3.00 (m, 1H), 2.45 (s, 3H), 1.70-1.55 (m, 2H), 1.20 (d, J=6.2 Hz, 3H). The measurements of the NMR spectra were done with Bruker AvanceIII HD 300 MHz with a probe head of BBOF.

Synthesis of N-[3-[(5-bromo-1-[[2-(trimethylsilyl)ethoxy]methyl]-1H-pyrrolo[2,3-b]pyridin-6-yl)oxy]butyl]-4-methylbenzene-1-sulfonamide: Into a 250-mL 3-necked round-bottom flask purged and maintained with an inert atmosphere of nitrogen, was placed N-(3-hydroxybutyl)-4-methylbenzene-1-sulfonamide (4.4 g, 18.083 mmol, 1.10 equiv), THF (60 mL). This was followed by the addition of NaH (1.97 g, 49.255 mmol, 3.00 equiv, 60%), in portions at 0 degrees C. The resulting solution was stirred for 0.5 h at 0 degrees C. To this was added 5-bromo-6-fluoro-1-[[2-(trimethylsilyl)ethoxy]methyl]-1H-pyrrolo[2,3-b]pyridine (5.66 g, 16.392 mmol, 1 equiv). The resulting solution was stirred overnight at 50 degrees C. in an oil bath. The reaction mixture was cooled to 25 degree C. The reaction was then quenched by the addition of 500 mL of aq. NH$_4$Cl. The resulting solution was extracted with 2×200 mL of ethyl acetate and the organic layers combined. The resulting mixture was washed with 1×500 ml of brine. The mixture was dried over anhydrous sodium sulfate and concentrated under vacuum. The residue was applied onto a silica gel column and eluted with ethyl acetate/petroleum ether (1:3). This resulted in 6 g (64.37%) of N-[3-[(5-bromo-1-[[2-(trimethylsilyl)ethoxy]methyl]-1H-pyrrolo[2,3-b]pyridin-6-yl)oxy]butyl]-4-methylbenzene-1-sulfonamide as colorless oil. $^1$H NMR (300 MHz, CDCl$_3$-d, ppm) δ 8.04 (s, 1H), 7.74-7.63 (m, 2H), 7.23-7.11 (m, 3H), 6.41 (d, J=3.6 Hz, 1H), 5.56 (d, J=3.3 Hz, 2H), 5.89-5.33 (m, 1H), 3.59-3.46 (m, 2H), 3.17 (t, J=6.0 Hz, 2H), 2.37 (s, 3H), 2.08-1.78 (m, 2H), 1.37 (d, J=6.2 Hz, 3H), 0.94-0.85 (m, 2H), −0.06 (s, 9H). The measurements of the NMR spectra were done with Bruker AvanceIII HD 300 MHz with a probe head of BBOF.

Synthesis of 13-methyl-10-(4-methylbenzenesulfonyl)-4-[[2-(trimethylsilyl)ethoxy]methyl]-14-oxa-2,4,10-triazatricyclo[7.5.0.0ˆ[3,7]]tetradeca-1(9),2,5,7-tetraene: Into a 250-mL round-bottom flask purged and maintained with an inert atmosphere of nitrogen, was placed N-[3-[(5-bromo-1-[[2-(trimethylsilyl)ethoxy]methyl]-1H-pyrrolo[2,3-b]pyridin-6-yl)oxy]butyl]-4-methylbenzene-1-sulfonamide (6 g, 10.552 mmol, 1 equiv), DMSO (60 mL), pyridine-2-carboxylic acid (1.04 g, 8.448 mmol, 0.80 equiv), CuI (2.41 g, 12.654 mmol, 1.20 equiv), K$_2$CO$_3$ (4.38 g, 31.692 mmol, 3.00 equiv). The resulting solution was stirred for 2 days at 125 degrees C. in an oil bath. The reaction mixture was cooled to 25 degree C. The resulting solution was diluted with 500 mL of water. The resulting solution was extracted with 3×200 mL of ethyl acetate and the organic layers combined. The resulting mixture was washed with 2×1000 ml of brine. The mixture was dried over anhydrous sodium sulfate and concentrated under vacuum. The residue was applied onto a silica gel column and eluted with ethyl acetate/petroleum ether (1:3). This resulted in 2.8 g (54.41%) of 13-methyl-10-(4-methylbenzenesulfonyl)-4-[[2-(trimethylsilyl)ethoxy]methyl]-14-oxa-2,4,10-triazatricyclo[7.5.0.0ˆ[3,7]]tetradeca-1(9),2,5,7-tetraene as yellow oil. $^1$H NMR (300 MHz, CDCl$_3$-d, ppm) δ 8.10 (s, 1H), 7.53-7.40 (m, 2H), 7.30 (d, J=3.6 Hz, 1H), 7.24-7.12 (m, 2H), 6.50 (d, J=3.6 Hz, 1H), 5.65 (d, J=10.7 Hz, 1H), 5.49 (d, J=10.7 Hz, 1H), 4.37-4.23 (m, 1H), 3.94-3.80 (m, 1H), 3.62-3.36 (m, 3H), 2.37 (s, 3H), 1.89-1.64 (m, 2H), 1.23 (d, J=6.3 Hz, 3H), 1.01-0.76 (m, 2H), −0.07 (s, 9H). The measurements of the NMR spectra were done with Bruker AvanceIII HD 300 MHz with a probe head of BBOF.

Synthesis of 13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene: Into a 250-mL round-bottom flask purged and maintained with an inert atmosphere of nitrogen, was placed Na (793.5 mg, 34.51 mmol, 6.01 equiv), naphthalene (4.42 g, 34.48 mmol, 6.01 equiv), DME (20 mL). The mixture was stirred at room temperature for 40 min until the formation of Na/naphthalene was complete. Another 250-mL round-bottom flask purged and maintained with an inert atmosphere of nitrogen, was placed 13-methyl-10-(4-methylbenzenesulfonyl)-4-[[2-(trimethylsilyl)ethoxy]methyl]-14-oxa-2,4,10-triazatricyclo[7.5.0.0ˆ[3,7]]tetradeca-1(9),2,5,7-tetraene (2.8 g, 5.741 mmol, 1 equiv), THF (20 mL). This was followed by the addition of above Na/naphthalene solution at −78 degrees C. The resulting solution was stirred for 3 hr at room temperature. The reaction was then quenched by the addition of 500 mL of NH$_4$Cl. The resulting solution was extracted with 3×200 mL of ethyl acetate and the organic layers combined. The resulting mixture was washed with 1×500 ml of brine. The mixture was dried over anhydrous sodium sulfate and concentrated under vacuum. The residue was applied onto a silica gel column with ethyl acetate/petroleum ether (1:3). This resulted in 1.2 g (62.67%) of 13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene as yellow oil. $^1$H NMR (300 MHz, DMSO-d$_6$, ppm) δ 7.43-7.26 (m, 2H), 6.27 (d, J=3.5 Hz, 1H), 5.43 (d, J=3.4 Hz, 2H), 5.13 (s, 1H), 4.14-4.04 (m, 1H), 3.58-3.39 (m, 3H), 3.28-3.10 (m, 1H), 2.95-2.77 (m, 1H), 2.09-1.85 (m, 1H), 1.85-1.64 (m, 1H), 1.37 (d, J=6.3 Hz, 3H), 0.88-078 (m, 2H), −0.09 (s, 9H). The measurements of the NMR spectra were done with Bruker AvanceIII HD 300 MHz with a probe head of BBOF.

Synthesis of 13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene The crude product (0.5 g) was purified by Chiral-Prep-HPLC with the following conditions: Instrument Name: SHIMADZU LC-20AD, LC parameters: Pump Mode: Binary gradient, Start Conc. of Pump B: 50.0%, Total Flow: 15 mL/min, Phase A: n-Hexane (0.1% DEA), Phase B: Ethanol, Column Name: CHIRALpak IA-3, Length: 50 mm, Internal Diameter: 4.6 mm, Particle Size: 3.0 um, Column Temp: 25° C., PDA Model: SPD-M20A, Wavelength: from 190 nm to 500 nm. This resulted in 220 mg (peak 1, assumed as R) [a]=−6.78° (C=0.129 g/100 mL in $CH_2Cl_2$, T=27° C.) of (13R or S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene as a yellow oil and 230 mg (peak 2, assumed as S) [a]=+11.84°(C=0.106 g/100 mL in $CH_2Cl_2$, T=27° C.) of (13S or R)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene as a yellow oil.

Synthesis of methyl 4-(4-[[2-(4-chlorophenyl)-4,4-dimethylcyclohex-1-en-1-yl]methyl]piperazin-1-yl)-2-[(13R)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoate Into a 40-mL vial purged and maintained with an inert atmosphere of nitrogen, was placed (13R)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene (210.00 mg, 0.630 mmol, 1.00 equiv), toluene (5.00 mL), methyl 2-bromo-4-(4-[[2-(4-chlorophenyl)-4,4-dimethylcyclohex-1-en-1-yl]methyl]piperazin-1-yl)benzoate (669.87 mg, 1.259 mmol, 2.00 equiv), $Cs_2CO_3$ (1025.80 mg, 3.148 mmol, 5.00 equiv), Xantphos Pd 2G Precatalyst (111.70 mg, 0.126 mmol, 0.20 equiv). The resulting solution was stirred overnight at 110 degrees C. in an oil bath. The reaction mixture was cooled to room temperature. The resulting mixture was concentrated under vacuum. The residue was applied onto a silica gel column and eluted with ethyl acetate/petroleum ether (1:1). This resulted in 240 mg (31.09%) of methyl 4-(4-[[2-(4-chlorophenyl)-4,4-dimethylcyclohex-1-en-1-yl]methyl]piperazin-1-yl)-2-[(13R)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoate as yellow oil. LC-MS: (ES, m/z): M+1=784.

Synthesis of methyl 4-(4-[[2-(4-chlorophenyl)-4,4-dimethylcyclohex-1-en-1-yl]methyl]piperazin-1-yl)-2-[(13R)-13-methyl-14-oxa-2,4,10-triazatricyclo[7.5.0.0ˆ[3,7]]tetradeca-1(9),2,5,7-tetraen-10-yl]benzoate: Into a 40-mL vial, was placed methyl 4-(4-[[2-(4-chlorophenyl)-4,4-dimethylcyclohex-1-en-1-yl]methyl]piperazin-1-yl)-2-[(13R)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoate (240.00 mg, 64%), THF (10.00 mL), $TBAF.3H_2O$ (3.00 g), ethylenediamine (1.50 g). The resulting solution was stirred for 3 days at 70 degrees C. in an oil bath. The reaction mixture was cooled to room temperature. The resulting mixture was concentrated under vacuum. The residue was applied onto a silica gel column with ethyl acetate/petroleum ether (2:1). This resulted in 80 mg (37.47%) of methyl 4-(4-[[2-(4-chlorophenyl)-4,4-dimethylcyclohex-1-en-1-yl]methyl]piperazin-1-yl)-2-[(13R)-13-methyl-14-oxa-2,4,10-triazatricyclo[7.5.0.0ˆ[3,7]]tetradeca-1(9),2,5,7-tetraen-10-yl]benzoate as a white solid. LC-MS: (ES, m/z): M+1=654.

Synthesis of 4-(4-[[2-(4-chlorophenyl)-4,4-dimethylcyclohex-1-en-1-yl]methyl]piperazin-1-yl)-2-[(13R)-13-methyl-14-oxa-2,4,10-triazatricyclo[7.5.0.0ˆ[3,7]]tetradeca-1(9),2,5,7-tetraen-10-yl]benzoic acid: Into a 40-mL vial, was placed methyl 4-(4-[[2-(4-chlorophenyl)-4,4-dimethylcyclohex-1-en-1-yl]methyl]piperazin-1-yl)-2-[(13R)-13-methyl-14-oxa-2,4,10-triazatricyclo[7.5.0.0ˆ[3,7]]tetradeca-1(9),2,5,7-tetraen-10-yl]benzoate (80.00 mg, 0.073 mmol, 1.00 equiv, 60%), MeOH (3.00 mL), dioxane (3.00 mL), 4M NaOH (0.60 mL, 2.400 mmol, 32.71 equiv). The resulting solution was stirred overnight at 70 degrees C. in an oil bath. The reaction mixture was cooled to room temperature. The resulting mixture was concentrated under vacuum. The pH value of the solution was adjusted to 6-7 with HCl (2 mol/L). The resulting solution was extracted with 2×30 mL of ethyl acetate and the organic layers combined. The resulting mixture was washed with 1×200 mL of brine. The mixture was dried over anhydrous sodium sulfate and concentrated under vacuum. The residue was purified by Prep-TLC with ethyl acetate. This resulted in 45 mg (47.90%) of 4-(4-[[2-(4-chlorophenyl)-4,4-dimethylcyclohex-1-en-1-yl]methyl]piperazin-1-yl)-2-[(13R)-13-methyl-14-oxa-2,4,10-triazatricyclo[7.5.0.0ˆ[3,7]]tetradeca-1(9),2,5,7-tetraen-10-yl]benzoic acid as a white solid. LC-MS: (ES, m/z): M+1=640.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(13R)-13-methyl-14-oxa-2,4,10-triazatricyclo[7.5.0.0ˆ[3,7]]tetradeca-1(9),2,5,7-tetraen-10-yl]benzamide Into a 40-mL vial, was placed 4-(4-[[2-(4-chlorophenyl)-4,4-dimethylcyclohex-1-en-1-yl]methyl]piperazin-1-yl)-2-[(13R)-13-methyl-14-oxa-2,4,10-triazatricyclo[7.5.0.0ˆ[3,7]]tetradeca-1(9),2,5,7-tetraen-10-yl]benzoic acid (40.00 mg, 0.062 mmol, 1.00 equiv), DCM (10.00 mL), 4-[[(2S)-1,4-dioxan-2-ylmethyl]amino]-3-nitrobenzenesulfonamide (20.00 mg, 0.063 mmol, 1.01 equiv), EDCI (24.00 mg, 0.125 mmol, 2.00 equiv), DMAP (31.00 mg, 0.254 mmol, 4.06 equiv). The resulting solution was stirred overnight at 25 degrees C. The resulting mixture was concentrated under vacuum. The crude product was purified by Prep-HPLC with the following conditions (2 #SHIMADZU (HPLC-01)): Column, XBridge Prep C18 OBD Column 5 um, 19*150 mm; mobile phase, ACN and Water (0.05% $NH_3·H_2O$) (20% Phase B up to 75% in 1 min, up to 95% in 7 min, hold 95% in 1 min, down to 20% in 1 min); Detector, 254/220 nm. This resulted in 12.6 mg (21.47%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[(13R)-13-methyl-14-oxa-2,4,10-triazatricyclo[7.5.0.0ˆ[3,7]]tetradeca-1(9),2,5,7-tetraen-10-yl]benzamide as a yellow solid. LC-MS: (ES, m/z): M+1=939, R.T=3.510 min. The measurements of the retention were done with a reversed phase column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 40° C.; flow: 1.5 mL/min. $^1$H NMR (300 MHz, DMSO-$d_6$, ppm) δ 11.17 (s, 1H), 8.47 (d, J=2.2 Hz, 2H), 7.63 (dd, J=9.2, 2.3 Hz, 1H), 7.49 (d, J=8.6 Hz, 1H), 7.42-7.31 (m, 2H), 7.21 (t, J=2.9 Hz, 1H), 7.13-7.02 (m, 2H), 6.96-6.79 (m, 2H), 6.70 (s, 2H), 6.12 (dd, J=3.4, 1.8 Hz, 1H), 4.25 (s, 1H), 3.92-3.42 (m, 11H), 3.30-3.10 (m, 4H), 2.78 (s, 2H), 2.22 (d, J=18.1 Hz, 6H), 1.95 (d, J=20.3 Hz, 4H), 1.41 (d, J=6.1 Hz, 5H), 0.95 (s, 6H). The measurements of the NMR spectra were done with Bruker AvanceIII HD 300 MHz with a probe head of BBOF.

Synthesis of methyl 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen- 10-yl]benzoate Into a 40-mL vial purged and maintained with an inert atmosphere of nitrogen, was placed (13S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraene (210.00 mg, 0.630 mmol, 1.00 equiv), toluene (5.00 mL), methyl 2-bromo-4-(4-[[2-(4-chlorophenyl)-4,4-dimethylcyclohex-1-en-1-yl]methyl]piperazin-1-yl)benzoate (669.87 mg, 1.259 mmol, 2.00 equiv), Cs$_2$CO$_3$ (1025.80 mg, 3.148 mmol, 5.00 equiv), Xantphos Pd 2G Precatalyst (111.70 mg, 0.126 mmol, 0.20 equiv). The resulting solution was stirred overnight at 110 degrees C. in an oil bath. The reaction mixture was cooled to room temperature. The resulting mixture was concentrated under vacuum. The residue was applied onto a silica gel column with ethyl acetate/petroleum ether (1:1). This resulted in 240 mg (31.09%) of methyl 4-(4-[[2-(4-chlorophenyl)-4,4-dimethylcycloohex-1-en-1-yl]methyl]piperazin-1-yl)-2-[(13 S)-13-methyl-4-[[2-(trimethylsilyl)ethoxy]ethyl]-14-oxa-2,4,10-triazatricycloo [7.5.0.0[3,7]]tetradeca-1(9),2,5,7-tetraen-10-yl]benzoate as yellow oil. LC-MS: (ES, m/z): M+1=784.

Synthesis of 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoic acid: Into a 8-mL round-bottom flask, was placed methyl 4-(4-[[2-(4-chlorophenyl)-4,4 dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoate (200 mg, 0.255 mmol, 1.00 equiv), H$_2$O (1.00 mL), MeOH (2.00 mL), dioxane (2.00 mL), NaOH (61.18 mg, 1.530 mmol, 6.00 equiv). The resulting solution was stirred for 12 h at 70 degrees C. The resulting mixture was concentrated. The pH value of the solution was adjusted to 5 with HCl (1 mol/L). The solids were collected by filtration. This resulted in 180 mg (91.64%) of 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl]benzoic acid as a white solid. H-NMR-PH-PHNW-4-82-1: (CDCl3, 300 ppm): δ 8.17 (s, 1H), 7.28 (s, 1H), 7.00-6.79 (m, 4H), 6.35 (s, 1H), 5.70-5.67 (d, J=9 Hz, 1H), 5.56-5.52 (d, J=12 Hz, 1H), 4.38-4.35 (m, 1H), 3.81 (s, 1H), 3.58-3.56 (m, 4H), 3.26 (s, 3H), 2.84 (s, 1H), 2.35 (s, 3H), 2.24 (s, 2H), 2.12 (s, 2H), 2.04 (s, 2H), 1.60 (s, 6H), 1.28 (s, 1H), 1.01 (s, 7H), 0.98-0.95 (m, 3H), 0.00 (s, 9H). The measurements of the NMR spectra were done with Bruker AvanceIII HD 300 MHz with a probe head of BBOF.

Synthesis of 4-(4-[[2-(4-chlorophenyl)-4,4-dimethylcyclohex-1-en-1-yl]methyl]piperazin-1-yl)-N-[4-([[(2S)-1,4-dioxan-2-yl]methyl]amino)-3-nitrobenzenesulfonyl]-2-[(13S)-13-methyl-4-[[2-(trimethylsilyl ethoxy]methyl]-14-oxa-2,4,10-triazatricyclo[7.5.0.0ˆ[3,7]]tetradeca-1(9),2,5,7-tetraen-10-yl]benzamide: Into a 40-mL round-bottom flask, was placed 4-(4-[[2-(4-chlorophenyl)-4,4-dimethylcyclohex-1-en-1-yl]methyl]piperazin-1-yl)-2-[(13S)-13-methyl-4-[[2-(trimethylsilyl)ethoxy]methyl]-14-oxa-2,4,10-triazatricyclo[7.5.0.0ˆ[3,7]]tetradeca-1(9),2,5,7-tetraen-10-yl] benzoic acid (180.00 mg, 0.234 mmol, 1.00 equiv), 4-[[(1,4-dioxan-2-yl)methyl]amino]-3-nitrobenzene-1-sulfonamide (88.96 mg, 0.280 mmol, 1.20 equiv), DCM (20.00 mL), DMAP (114.16 mg, 0.934 mmol, 4 equiv), EDC.HCl (89.57 mg, 0.467 mmol, 2 equiv). The resulting solution was stirred for 12 h at room temperature. The resulting mixture was concentrated. The residue was applied onto a silica gel column with ethyl acetate/petroleum ether (0:1-1:1). This resulted in 180 mg (72.02%) of 4-(4-[[2-(4-chlorophenyl)-4,4-dimethylcyclohex-1-en-1-yl]ethyl]piperazin-1-yl)-N-[4-([[(2S)-1,4-dioxan-2-yl]methyl]amino)-3-nitrobenzenesulfonyl]-2-[(13S)-13-methyl-4-[[2-(trimethylsilyl ethoxy]methyl]-14-oxa-2,4,10-triazatricyclo[7.5.0.0ˆ[3,7]]tetradeca-1(9),2,5,7-tetraen-10-yl]benzamide as a yellow solid. LC-MS-PH-PHNW-4-82-2: (ES, m/z): M+1=1069.6. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient.

Synthesis of 4-(4-[[2-(4-chlorophenyl)-4,4-dimethylcyclohex-1-en-1-yl]methyl]piperazin-1-yl)-N-(4-[[(1,4-dioxan-2-yl)methyl]amino]-3-nitrobenzenesulfonyl)-2-[(13S)-13-methyl-14-oxa-2,4,10-triazatricyclo[7.5.0.0ˆ[3,7]]tetradeca-1(9),2,5,7-tetraen-10-yl]benzamide: Into a 40-mL round-bottom flask, was placed 4-(4-[[2-(4-chlorophenyl)-4,4-dimethylcyclohex-1-en-1-yl]methyl]piperazin-1-yl)-2-[(13 S)-13-methyl-4-[[2-(trimethylsilyl)ethoxy]methyl]-14-oxa-2,4,10-triazatricyclo[7.5.0.0[3,7]]tetradeca-1(9),2,5,7-tetraen-10-yl]-N-(3-nitro-4-[[(oxan-3-yl)methyl]amino]benzenesulfonyl)benzamide (180.00 mg, 0.169 mmol, 1.00 equiv), THF (10.00 mL), ethane-1,2-diamine (202.61 mg, 3.371 mmol, 20.00 equiv), TBAF (881.48 mg, 3.371 mmol, 20 equiv). The resulting solution was stirred for 12 h at 70 degrees C. The resulting mixture was concentrated. The crude product was purified by Prep-HPLC with the following conditions (Waters-2767): Column, X-bridge RP18, 5 um, 19*100 mm; mobile phase, 0.03% ammonia in water (0.03% NH$_4$HCO$_3$ & NH$_4$OH) and CH$_3$CN (32% CH$_3$CN up to 52% in 6 min); Detector, UV 254 nm. This resulted in 30 mg (18.94%) of 4-(4-[[2-(4-chlorophenyl)-4,4-dimethylcyclohex-1-en-1-yl]methyl]piperazin-1-yl)-N-(4-[[(1,4-dioxan-2-yl)methyl]amino]-3-nitrobenzene sulfonyl)-2-[(13 S)-13-methyl-14-oxa-2,4,10-triazatricyclo[7.5.0.0ˆ[3,7]]tetradeca-1(9),2,5,7-tetraen-10-yl]benzamide as a yellow solid. LC-MS-PH-PHNW-4-82-0B: (ES, m/z): M+1=939.52. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient H-NMR-PH-PHNW-4-82-0B: (CDCl3, 300 ppm): δ 8.84-8.83 (m, 2H), 8.45 (s, 1H), 7.99-7.94 (m, 2H), 7.15 (s, 1H), 6.97-6.93 (m, 2H), 6.75-6.62 (m, 3H), 6.20 (s, 1H), 3.94-3.62 (m, 7H), 3.49-3.42 (m, 2H), 3.30 (s, 5H), 2.85 (s, 2H), 2.37 (s, 3H), 2.26 (s, 2H), 2.11-2.03 (m, 3H), 1.68-1.48 (m, 4H), 1.28 (s, 1H), 1.00 (s, 6H).

Example 69

Preparation of 4-(4-[[2-(4-chlorophenyl)-4,4-dimethylcyclohex-1-en-1-yl]methyl]piperazin-1-yl)-N-(3-nitro-4-[[(oxan-4-yl)methyl]amino]benzene sulfonyl)-2-[15-oxa-2,4,10-triazatricyclo[7.6.0.0ˆ[3,7]]pentadeca-1(9),2,5,7-tetraen-10-yl]benzamide Synthesis of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-15-oxa-2,4,10-triazatricyclo[7.6.0.0ˆ[3,7]]pentadeca-1(9),2,5,7-tetraen-10-yl)benzoate: Into a 40-mL vial purged and maintained with an inert atmosphere of nitrogen, was placed 4-[[2-(trimethylsilyl)ethoxy]methyl]-15-oxa-2,4,10-triazatricyclo[7.6.0.0ˆ[3,7]]pentadeca-1(9),2,5,7-tetraene (125 mg, 0.375 mmol, 1 equiv), toluene (5 mL), methyl 2-bromo-4-(4-[[2-(4-chlorophenyl)-4,4-dimethylcyclohex-1-en-1-yl]ethyl]piperazin-1-yl)benzoate (359 mg, 0.675 mmol, 1.80 equiv), Cs$_2$CO$_3$ (610 mg, 1.874 mmol, 5 equiv), XantPhos Pd 2G (266 mg, 0.300 mmol, 0.8 equiv). The resulting solution was stirred overnight at 110° C. in an oil bath. The reaction mixture was cooled to room temperature. The resulting mixture was concentrated under vacuum. The residue was applied onto a silica gel column with ethyl acetate/petroleum ether (1:1). This resulted in 140 mg (47.61%) of methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-15-oxa-2,4,10-triazatricyclo[7.6.0.0^[3,7]]pentadeca-1(9),2,5,7-tetraen-10-yl)benzoate as a yellow solid. LC-MS: (ES, m/z): M+H=784, R.T=1.236 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile; linear gradient from 5% acetonitrile to 100% acetonitrile in 2.0 minutes; Oven temperature 40° C.; flow: 1.5 mL/min.

Synthesis of methyl 4-(4-[[2-(4-chlorophenyl)-4,4-dimethylcyclohex-1-en-1-yl]methyl]piperazin-1-yl)-2-[15-oxa-2,4,10-triazatricyclo[7.6.0.0[3,7]]pentadeca-1(9),2,5,7-tetraen-10-yl]benzoate. Into a 40-mL vial, was placed methyl 4-(4-[[2-(4-chlorophenyl)-4,4-dimethylcyclohex-1-en-1-yl]methyl]piperazin-1-yl)-2-(4-[[2-(trimethylsilyl)ethoxy]methyl]-15-oxa-2,4,10-triazatricyclo[7.6.0.0^[3,7]]pentadeca-1(9),2,5,7-tetraen-10-yl)benzoate (140 mg, 0.178 mmol, 1 equiv), THF (10 mL), ethane-1,2-diamine (500 mg, 8.319 mmol, 46.62 equiv), TBAF.3H$_2$O (1 g). The resulting solution was stirred overnight at 70° C. in an oil bath. The reaction mixture was cooled to room temperature. The resulting solution was diluted with 100 mL of water. The resulting solution was extracted with 2×50 mL of ethyl acetate and the organic layers combined. The resulting mixture was washed with 1×200 mL of brine. The mixture was dried over anhydrous sodium sulfate and concentrated under vacuum. The residue was purified by Prep-TLC with ethyl acetate/petroleum ether (2:1). This resulted in 60 mg (51.39%) of methyl 4-(4-[[2-(4-chlorophenyl)-4,4-dimethylcyclohex-1-en-1-yl]methyl]piperazin-1-yl)-2-[15-oxa-2,4,10-triazatricyclo[7.6.0.0^[3,7]]pentadeca-1(9),2,5,7-tetraen-10-yl]benzoate as a yellow solid. LC-MS: (ES, m/z): M+H=654, R.T=1.099 min. The measurements of the retention were done with a reversed phase column (C18). Shimadzu LCMS 2020; 50*3.0 Kinetex 2.6u XB-C18, 2.6 microm; Eluent A: water (0.05% TFA); Eluent B: Acetonitrile (0.05% TFA); linear gradient from 5% acetonitrile to 100% acetonitrile in 2.0 minutes; Oven temperature 40° C.; flow: 1.5 mL/min.

Synthesis of 4-(4-[[2-(4-chlorophenyl)-4,4-dimethylcyclohex-1-en-1-yl]methyl]piperazin-1-yl)-2-[15-oxa-2,4,10-triazatricyclo[7.6.0.0[3,7]]pentadeca-1(9),2,5,7-tetraen-10-yl]benzoic acid: Into a 40-mL vial, was placed methyl 4-(4-[[2-(4-chlorophenyl)-4,4-dimethylcyclohex-1-en-1-yl]ethyl]piperazin-1-yl)-2-[15-oxa-2,4,10-triazatricyclo[7.6.0.0^[3,7]]pentadeca-1(9),2,5,7-tetraen-10-yl]benzoate (60 mg, 0.092 mmol, 1 equiv), MeOH (3 mL), THF (1 mL), H$_2$O (1 mL), NaOH (37 mg, 0.917 mmol, 10.00 equiv). The resulting solution was stirred overnight at 60° C. in an oil bath. The reaction mixture was cooled to room temperature. The resulting mixture was concentrated under vacuum. The pH value of the solution was adjusted to 4-5 with HCl (2 mol/L). The resulting solution was extracted with 2×30 mL of ethyl acetate and the organic layers combined. The resulting mixture was washed with 1×100 mL of brine. The mixture was dried over anhydrous sodium sulfate and concentrated under vacuum. The residue was purified by Prep-TLC with ethyl acetate. This resulted in 16 mg (27.25%) of 4-(4-[[2-(4-chlorophenyl)-4,4-dimethylcyclohex-1-en-1-yl] methyl]piperazin-1-yl)-2-[15-oxa-2,4,10-triazatricyclo [7.6.0.0^[3,7]]pentadeca-1(9),2,5,7-tetraen-10-yl]benzoic acid as a white solid. LC-MS: (ES, m/z): M+H=640, R.T=1.396 min. The measurements of the retention were done with a reversed phase column (C18). Shimadzu LCMS 2020; 50*3.0, Shimadzu shim-pack XR-ODS, 2.2 microm; Eluent A: water (0.05% TFA); Eluent B: Acetonitrile; linear gradient from 5% acetonitrile to 100% acetonitrile in 2.6 minutes; Oven temperature 40° C.; flow: 1.0 mL/min.

Synthesis of 4-(4-[[2-(4-chlorophenyl)-4,4-dimethylcyclohex-1-en-1-yl]methyl]piperazin-1-yl)-N-(3-nitro-4-[[(oxan-4-yl)methyl]amino]benzene sulfonyl)-2-[15-oxa-2,4,10-triazatricyclo[7.6.0.0^[3,7]]pentadeca-1(9),2,5,7-tetraen-10-yl]benzamide. Into a 8-mL vial, was placed 4-(4-[[2-(4-chlorophenyl)-4,4-dimethylcyclohex-1-en-1-yl] methyl]piperazin-1-yl)-2-[15-oxa-2,4,10-triazatricyclo [7.6.0.0^[3,7]]pentadeca-1(9),2,5,7-tetraen-10-yl]benzoic acid (16 mg, 0.025 mmol, 1 equiv), DCM (3 mL), 3-nitro-4-[[(oxan-4-yl)methyl]amino]benzene-1-sulfonamide (7.9 mg, 0.025 mmol, 1 equiv), EDCI (9.6 mg, 0.050 mmol, 2 equiv), DMAP (12.2 mg, 0.100 mmol, 4 equiv). The resulting solution was stirred overnight at room temperature. The resulting mixture was concentrated under vacuum. The crude product was purified by Prep-HPLC with the following conditions (2 #SHIMADZU (HPLC-01)): Column, X Bridge Prep C18 OBD Column, 5 um, 19*150 mm; mobile phase, ACN and Water (0.05% NH$_3$·H$_2$O) (20% Phase B up to 75% in 1 min, up to 95% in 7 min, hold 95% in 1 min, down to 20% in 1 min); Detector, 254 and 220 nm. This resulted in 4.5 mg (19.21%) of 4-(4-[[2-(4-chlorophenyl)-4,4-dimethylcyclohex-1-en-1-yl]methyl]piperazin-1-yl)-N-(3-nitro-4-[[(oxan-4-yl)methyl]amino]benzene sulfonyl)-2-[15-oxa-2,4,10-triazatricyclo[7.6.0.0^[3,7]]pentadeca-1(9),2,5,7-tetraen-10-yl]benzamide as a yellow solid. LC-MS: (ES, m/z): M+1=937, R.T=2.522 min. The measurements of the retention were done with a reversed phase column (C18). Shimadzu LCMS 2020; SUPELCO Ascentis Express C18, 50*3.0 mm, 2.7 microm; Eluent A: water (0.05% TFA); Eluent B: Acetonitrile; linear gradient from 5% acetonitrile to 100% acetonitrile in 5 minutes; Oven temperature 40° C.; flow: 1.5 mL/min.

Example 70

Preparation of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[11-methyl-12-oxo-2,4,10,11-tetraazatricyclo[7.3.0.0^[3,7]]dodeca-1,3(7),5,8-tetraen-10-yl]benzamide Synthesis of methyl 6-amino-3-bromo-5-iodopyridine-2-carboxylate: Into a 500-mL round-bottom flask, was placed methyl 6-amino-3-bromopyridine-2-carboxylate (20.00 g, 86.562 mmol, 1.00 equiv), HOAc (200.00 mL), TFA (10.00 mL). This was followed by the addition of NIS (29.35 g, 130.453 mmol, 1.51 equiv), in portions at 25 degrees C. The resulting solution was stirred overnight at 25 degrees C. The resulting solution was diluted with 2000 mL of water. The resulting solution was extracted with 3×500 mL of ethyl acetate and the organic layers combined. The resulting mixture was washed with 2×2000 mL of brine. The mixture was dried over anhydrous sodium sulfate and concentrated under vacuum.

The crude product was re-crystallized from PE:EA in the ratio of 1:1. The solids were collected by filtration. This resulted in 25.8 g (83.50%) of methyl 6-amino-3-bromo-5- iodopyridine-2-carboxylate as a red solid. $^1$H-NMR (300 MHz, Chloroform-d, ppm) δ 8.14 (s, 1H), 5.21 (br, 2H), 3.99 (s, 3H).

Synthesis of methyl 6-amino-3-bromo-5-(2-ethoxyethenyl)pyridine-2-carboxylate: Into a 500-mL round-bottom flask purged and maintained with an inert atmosphere of nitrogen, was placed methyl 6-amino-3-bromo-5-iodopyridine-2-carboxylate (24.00 g, 67.237 mmol, 1.00 equiv), 2-(2-ethoxyethenyl)-4,4,5,5-tetramethyl-1,3,2-dioxaborolane (26.50 g, 133.791 mmol, 1.99 equiv), i-PrOH (300 mL), K$_3$PO$_4$ (42.60 g, 200.691 mmol, 2.98 equiv), Pd(OAc)$_2$ (1.50 g, 6.681 mmol, 0.10 equiv), Ruphos (3.13 g, 6.708 mmol, 0.10 equiv). The resulting solution was stirred overnight at 30 degrees C. in an oil bath. The reaction mixture was cooled to room temperature. The solids were filtered out. The resulting mixture was concentrated. The residue was applied onto a silica gel column with ethyl acetate/petroleum ether (1:1). This resulted in 10.7 g (52.85%) of methyl 6-amino-3-bromo-5-(2-ethoxyethenyl)pyridine-2-carboxylate as brown oil. $^1$H NMR (300 MHz, Chloroform-d, ppm) δ 8.10 (s, 0.5H), 7.57 (s, 0.5H), 6.90 (d, J=12.6 Hz, 0.5H), 6.41 (d, J=7.1 Hz, 0.5H), 3.97 (s, 3H).

Synthesis of methyl 5-bromo-1H-pyrrolo[2,3-b]pyridine-6-carboxylate: Into a 250-mL round-bottom flask, was placed methyl 6-amino-3-bromo-5-(2-ethoxyethenyl)pyridine-2-carboxylate (10.70 g, 35.532 mmol, 1.00 equiv), MeOH (100.00 mL), Conc. HCl (20.00 mL, 12 N). The resulting solution was stirred overnight at 25 degrees C. The resulting mixture was concentrated under vacuum. The pH value of the solution was adjusted to 7 with NaOH (2 mol/L). The solids were collected by filtration. This resulted in 9 g (99.30%) of methyl 5-bromo-1H-pyrrolo[2,3-b]pyridine-6-carboxylate as a brown solid. $^1$H NMR (300 MHz, Chloroform-d, ppm) δ 11.60 (s, 1H), 8.29 (s, 1H), 7.69 (t, J=3.0 Hz, 1H), 6.54 (dd, J=3.4, 1.7 Hz, 1H), 4.10 (s, 3H).

Synthesis of methyl 5-bromo-1-[[2-(trimethylsilyl)ethoxy]methyl]pyrrolo[2,3-b]pyridine-6-carboxylate: Into a 250-mL round-bottom flask purged and maintained with an inert atmosphere of nitrogen, was placed methyl 5-bromo-1H-pyrrolo[2,3-b]pyridine-6-carboxylate (9.00 g, 35.284 mmol, 1.00 equiv), DMF (100.00 mL). This was followed by the addition of NaH (2.83 g, 70.757 mmol, 2.01 equiv, 60%), in portions at 0 degrees C. The resulting solution was stirred for 30 min at 0 degrees C. To this was added SEM-Cl (8.82 g, 52.903 mmol, 1.50 equiv) at 0 degrees C. The resulting solution was stirred for 2 hr at 25 degrees C. The reaction was then quenched by the addition of 500 mL of water. The resulting solution was extracted with 2×200 mL of ethyl acetate and the organic layers combined. The resulting mixture was washed with 1×500 mL of brine. The mixture was dried over anhydrous sodium sulfate and concentrated under vacuum. The residue was applied onto a silica gel column with ethyl acetate/petroleum ether (1:3). This resulted in 8.2 g (60.31%) of methyl 5-bromo-1-[[2-(trimethylsilyl)ethoxy]methyl]pyrrolo[2,3-b]pyridine-6-carboxylate as yellow oil. $^1$H NMR (300 MHz, Chloroform-d, ppm) δ 8.17 (s, 1H), 7.50 (d, J=3.7 Hz, 1H), 6.53 (d, J=3.6 Hz, 1H), 5.68 (s, 2H), 4.02 (s, 3H), 3.60-3.45 (m, 2H), 0.99-0.88 (m, 2H), −0.05 (s, 9H).

Synthesis of methyl 5-([[(benzyloxy)carbonyl](methyl)amino]amino)-1-[[2-(trimethylsilyl)ethoxy]methyl]pyrrolo[2,3-b]pyridine-6-carboxylate: Into a 40-mL vial purged and maintained with an inert atmosphere of nitrogen, was placed methyl 5-bromo-1-[[2-(trimethylsilyl)ethoxy]methyl]pyrrolo[2,3-b]pyridine-6-carboxylate (1.64 g, 4.256 mmol, 1.00 equiv), N-methylbenzyloxycarbohydrazide (975.00 mg, 5.410 mmol, 1.27 equiv), dioxane (20.00 mL), methyl[2-(methylamino)ethyl]amine (113.00 mg, 1.282 mmol, 0.30 equiv), CuI (487.00 mg, 2.557 mmol, 0.60 equiv), K$_3$PO$_4$ (1.24 g, 5.842 mmol, 1.37 equiv). The resulting solution was stirred for 7 hr at 80 degrees C. in an oil bath. The reaction mixture was cooled to room temperature. The resulting mixture was concentrated under vacuum. The residue was applied onto a silica gel column with ethyl acetate/petroleum ether (1:1). This resulted in 700 mg (33.94%) of methyl 5-([[(benzyloxy)carbonyl](methyl)amino]amino)-1-[[2-(trimethylsilyl)ethoxy]methyl]pyrrolo[2,3-b]pyridine-6-carboxylate as yellow oil. LC-MS (ES, m/z): M+1=485, R,T=1.403 min.

Synthesis of 11-methyl-4-[[2-(trimethylsilyl)ethoxy]methyl]-2,4,10,11-tetraazatricyclo[7.3.0.0^[3,7]]dodeca-1(9),2,5,7-tetraen-12-one: Into a 100-mL round-bottom flask, was placed methyl 5-([[(benzyloxy)carbonyl](methyl)amino]amino)-1-[[2-(trimethylsilyl)ethoxy]methyl]pyrrolo[2,3-b]pyridine-6-carboxylate (500.00 mg, 1.032 mmol, 1.00 equiv), MeOH (10.00 mL), Pd/C (50.00 mg, 0.047 mmol, 0.05 equiv, 10%). To the above H$_2$ (balloon, 1 atm) was introduced in. The resulting solution was stirred for 6.5 hr at 0 degrees C. The solids were filtered out. The resulting mixture was concentrated under vacuum. The crude product was purified by Prep-HPLC with the following conditions: (Prep-HPLC-006): Column, X Bridge Shield RP18 OBD Column, 5 um, 19*150 mm; mobile phase, Water (0.05% NH$_3$·H$_2$O) and ACN (40% Phase B up to 70% in 7 min); Detector, UV 254/220 nm. This resulted in 20 mg (6.09%) of 11-methyl-4-[[2-(trimethylsilyl)ethoxy]methyl]-2,4,10,11-tetraazatricyclo[7.3.0.0^[3,7]]dodeca-1(9),2,5,7-tetraen-12-one as a white solid. $^1$H NMR (300 MHz, Chloroform-d, ppm) δ 7.71 (s, 1H), 7.53 (d, J=3.7 Hz, 1H), 6.52 (d, J=3.7 Hz, 1H), 5.71 (s, 2H), 3.65 (s, 3H), 3.59 (t, J=8.2 Hz, 2H), 1.00-0.86 (m, 2H), −0.04 (s, 9H).

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(11-methyl-12-oxo-4-[[2-(trimethylsilyl)ethoxy]methyl]-2,4,10,11-tetraazatricyclo[7.3.0.0^[3,7]]dodeca-1,3(7),5,8-tetraen-10-yl)benzamide: Into a 40-mL vial purged and maintained with an atmosphere of nitrogen, was placed 11-methyl-4-[[2-(trimethylsilyl)ethoxy]methyl]-2,4,10,11-tetraazatricyclo[7.3.0.0^[3,7]]dodeca-1(9),2,5,7-tetraen-12-one (20.00 mg, 0.063 mmol, 1.00 equiv), 2-bromo-4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)benzamide (51.00 mg, 0.062 mmol, 0.99 equiv), DME (5.00 mL), 1,10-phenanthroline (11.30 mg, 0.063 mmol, 1.00 equiv), CuI (12.00 mg, 0.063 mmol, 1.00 equiv), K$_2$CO$_3$ (26.00 mg, 0.188 mmol, 3.00 equiv). The resulting solution was stirred for 3 hr at 90 degrees C. in an oil bath. The reaction mixture was cooled to room temperature. The resulting mixture was concentrated under vacuum. The residue was purified by Prep-TLC with dichloromethane/methanol (10:1). This resulted in 30 mg (45.29%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(11-methyl-12-oxo-4-[[2-(trimethylsilyl)ethoxy]ethyl]-2,4,10,11-tetraazatricycloo[7.3.0.0^[3,7]]dodeca-1,3(7),5,8-tetraen-10-yl)benzamide as a yellow solid. LC-MS (ES, m/z): M+1=1055, R,T=1.269 min.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[11-methyl-12-oxo-2,4,10,11-tetraazatricyclo[7.3.0.0^[3,7]]dodeca-1,3(7),5,8-tetraen-10-yl]benzamide: Into a 40-mL vial, was placed 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(11-methyl-12-oxo-4-[[2-(trimethylsilyl)ethoxy]methyl]-2,4,10,11-tetraazatricycloo[7.3.0.0^[3,7]]dodeca-1,3(7),5,8-tetraen-10-yl)benzamide (30.00 mg, 0.028 mmol, 1.00 equiv), TBAF/THF (1.0M, 2.00 mL), ethylenediamine (50.00 mg). The resulting solution was stirred for 1.5 hr at 70 degrees C. in an oil bath. The reaction mixture was cooled to room temperature. The resulting solution was diluted with 100 mL of water. The resulting solution was extracted with 3×30 mL of dichloromethane and the organic layer combined. The resulting mixture was washed with 1×200 ml of brine. The mixture was dried over anhydrous sodium sulfate and concentrated under vacuum. The residue was purified by Prep-TLC with dichloromethane/methanol (10:1). The crude product was purified by Prep-HPLC with the following conditions (Prep-HPLC-006): Column, X Bridge Shield RP18 OBD Column, 5 um, 19*150 mm; mobile phase, Water (0.05% $NH_3 \cdot H_2O$) and ACN (40% Phase B up to 70% in 7 min); Detector, UV 254/220 nm. This resulted in 4 mg (15.21%) of 4-(4-[[2-(4-chlorophenyl)-4,4-dimethylcyclohex-1-en-1-yl]ethyl]piperazin-1-yl)-N-(4-[[(2S)-1,4-dioxan-2-ylmethyl]amino]-3-nitrobenzenesulfonyl)-2-[11-methyl-12-oxo-2,4,10,11-tetraazatricyclo[7.3.0.0^[3,7]]dodeca-1,3(7),5,8-tetraen-10-yl]benzamide as a yellow solid. LC-MS (ES, m/z): M+1=924, R,T=3.192 min. $^1H$ NMR (300 MHz, DMSO-$d_6$, ppm) δ 11.71 (s, 1H), 8.35 (t, J=2.0 Hz, 1H), 8.24 (t, J=15.6 Hz, 1H), 7.67 (tt, J=7.1, 3.1 Hz, 2H), 7.57 (dd, J=8.8, 4.2 Hz, 1H), 7.44-7.32 (m, 2H), 7.27 (d, J=5.2 Hz, 1H), 7.12-7.00 (m, 2H), 6.91 (d, J=8.7 Hz, 1H), 6.85-6.72 (m, 1H), 6.35 (s, 1H), 6.29 (ddd, J=6.5, 3.4, 1.8 Hz, 1H), 3.86-3.71 (m, 3H), 3.71-3.55 (m, 2H), 3.49 (t, J=10.2 Hz, 1H), 3.30-3.20 (m, 2H), 3.17 (d, J=4.8 Hz, 4H), 3.09 (s, 3H), 2.73 (d, J=1.8 Hz, 2H), 2.18 (d, J=16.9 Hz, 5H), 1.96 (s, 2H), 1.57 (s, 1H), 1.39 (t, J=6.3 Hz, 2H), 1.33-1.23 (m, 1H), 0.93 (d, J=2.5 Hz, 6H).

Example 71

Preparation of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[4,8,14,16-tetraazatetracyclo[7.7.0.0^[2,7].0[11,15]]hexadeca-1(16),2(7),3,5,9,11(15),12-heptaen-8-yl]benzamide Synthesis of 5-bromo-1H-pyrrolo[2,3-b]pyridin-7-ium-7-olate: Into a 2-L 3-necked round-bottom flask, was placed 5-bromo-1H-pyrrolo[2,3-b]pyridine (50.00 g, 253.762 mmol, 1.00 equiv), $Et_2O$ (500.00 mL, 6.746 mmol, 0.03 equiv). This was followed by the addition of m-CPBA (76.63 g, 444.084 mmol, 1.75 equiv), in portions at 0 degrees C. in 30 min. The resulting solution was stirred for 14 hr at room temperature. The solids were collected by filtration. This resulted in 30 g of 5-bromo-1H-pyrrolo[2,3-b]pyridin-7-ium-7-olate as a white solid. LC-MS-11: (ES, m/z): 213 [M+H].

Synthesis of benzyl 5-bromo-6-chloropyrrolo[2,3-b]pyridine-1-carboxylate: Into a 1-L 3-necked round-bottom flask purged and maintained with an inert atmosphere of nitrogen, was placed 5-bromo-1H-pyrrolo[2,3-b]pyridin-7-ium-7-olate (30.00 g, 140.823 mmol, 1.00 equiv), THF (300.00 mL), HMDS (25.00 g, 154.902 mmol, 1.10 equiv). This was followed by the addition of Cbz-Cl (60.06 g, 352.066 mmol, 2.50 equiv) dropwise with stirring at 0 degrees C. in 15 min. The resulting solution was stirred for 14 hr at room temperature. The reaction was then quenched by the addition of 20 mL of $H_2O$. The resulting mixture was concentrated. The resulting solution was diluted with 500 mL of DCM. The resulting mixture was washed with 2×100 ml of $H_2O$. The resulting mixture was washed with 1×100 mL of NaCl (aq.). The mixture was dried over anhydrous sodium sulfate. The residue was applied onto a silica gel column and eluted with ethyl acetate/petroleum ether (1:10). This resulted in 15 g (29.13%) of benzyl 5-bromo-6-chloropyrrolo[2,3-b]pyridine-1-carboxylate as a brown solid. LC-MS-12: (ES, m/z): 365 [M+H].

Synthesis of 5-bromo-6-chloro-1H-pyrrolo[2,3-b]pyridine: Into a 500-mL round-bottom flask, was placed benzyl 5-bromo-6-chloropyrrolo[2,3-b]pyridine-1-carboxylate (13.00 g, 35.557 mmol, 1.00 equiv), $CH_3CN$ (150.00 mL), $K_2CO_3$ (14.74 g, 106.653 mmol, 3.00 equiv). The resulting solution was stirred for 6 hr at 70 degrees C. in an oil bath. The resulting mixture was concentrated. The residue was applied onto a silica gel column and eluted with ethyl acetate/petroleum ether (1:3). This resulted in 6 g (61.96%) of 5-bromo-6-chloro-1H-pyrrolo[2,3-b]pyridine as a brown solid. LC-MS-13: (ES, m/z): 231 [M+H].

Synthesis of 5-bromo-6-chloro-1-[[2-(trimethylsilyl)ethoxy]methyl]pyrrolo[2,3-b]pyridine: Into a 250-mL 3-necked round-bottom flask purged and maintained with an inert atmosphere of nitrogen, was placed 5-bromo-6-chloro-1H-pyrrolo[2,3-b]pyridine (6.00 g, 25.920 mmol, 1.00 equiv), DMF (100.00 mL). This was followed by the addition of NaH (2.00 g, 60%, 2 equiv), in portions at 0 degrees C. in 10 min. To this was added SEM-Cl (6.48 g, 38.867 mmol, 1.50 equiv) at 0 degrees C. in 15 min. The resulting solution was stirred for 2 hr at room temperature. The reaction was then quenched by the addition of 10 mL of $H_2O$ at 0 degrees C. The resulting solution was diluted with 500 mL of $H_2O$. The resulting solution was extracted with 3×100 mL of ethyl acetate. The resulting mixture was washed with 2×100 ml of $H_2O$. The resulting mixture was washed with 1×100 mL of NaCl (aq.). The mixture was dried over anhydrous sodium sulfate. The residue was applied onto a silica gel column and eluted with ethyl acetate/petroleum ether (10:1). This resulted in 8 g (85.32%) of 5-bromo-6-chloro-1-[[2-(trimethylsilyl)ethoxy]ethyl]pyrrolo[2,3-b]pyridine as a light yellow solid. LC-MS-14: (ES, m/z): 361 [M+H].

Synthesis of N-(6-chloro-1-[[2-(trimethylsilyl)ethoxy]methyl]pyrrolo[2,3-b]pyridin-5-yl) pyridin-4-amine: Into a 50-mL round-bottom flask purged and maintained with an inert atmosphere of nitrogen, was placed 5-bromo-6-chloro-1-[[2-(trimethylsilyl)ethoxy]methyl]pyrrolo[2,3-b]pyridine (1.60 g, 4.423 mmol, 1.00 equiv), dioxane (20.00 mL), 4-aminopyridine (0.62 g, 6.635 mmol, 1.50 equiv), t-BuXPhos Pd 3G (350.75 mg, 0.442 mmol, 0.10 equiv), t-BuONa (1275.22 mg, 13.269 mmol, 3.00 equiv). The resulting solution was stirred for 16 hr at 110 degrees C. The resulting mixture was concentrated. The residue was applied onto a silica gel column and eluted with dichloromethane/methanol (10:1). This resulted in 500 mg (30.15%) of N-(6-chloro-1-[[2-(trimethylsilyl)ethoxy]methyl]pyrrolo[2,3-b]pyridin-5-yl)pyridin-4-amine as a brown solid. LC-MS-1: (ES, m/z): 375 [M+H].

Synthesis of 14-[[2-(trimethylsilyl)ethoxy]methyl]-4,8,14,16-tetraazatetracyclo[7.7.0.0^[2,7].0[11,15]]hexadeca-1(16),2(7),3,5,9,11(15),12-heptaene: Into a 50-mL round-bottom flask purged and maintained with an inert atmosphere of nitrogen, was placed N-(6-chloro-1-[[2-(trimethylsilyl)ethoxy]ethyl]pyrrolo[2,3-b]pyridin-5-yl)pyridin-4-amine (500.00 mg, 1.334 mmol, 1.00 equiv), DMA (10.00 mL), K$_2$CO$_3$ (0.55 g, 3.980 mmol, 2.98 equiv), Pd(AcO)$_2$ (59.88 mg, 0.267 mmol, 0.20 equiv), t-Bu$_3$P—HBF$_4$ (154.76 mg, 0.533 mmol, 0.40 equiv). The resulting solution was stirred for 16 hr at 130 degrees C. in an oil bath. The resulting mixture was concentrated. The residue was applied onto a silica gel column and eluted with dichloromethane/methanol (5:1). This resulted in 200 mg (26.58%) of 1-[4-[2-(trimethylsilyl)ethoxy]methyl]-4,8,14,16-tetraazatetracyclo [7.7.0.0^[2,7].0[11,15]]hexadeca-1(16),2(7),3,5,9,11(15), 12-heptaene as a solid as a red solid. LC-MS-2: (ES, m/z): 339 [M+H].

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(14-[[2-(trimethylsilyl)ethoxy]methyl]-4,8,14,16-tetraazatetracyclo[7.7.0.0^[2,7].0[11,15]]hexadeca-1(16),2(7),3,5,9,11(15),12-heptaen-8-yl)benzamide: Into a 8-mL vial purged and maintained with an inert atmosphere of nitrogen, was placed 14-[[2-(trimethylsilyl)ethoxy]methyl]-4,8,14,16-tetraazatetracyclo[7.7.0.0^[2,7].0[1 1,15]]hexadeca-1(16),2(7),3,5,9,11(15),12-heptaene (100.00 mg, 0.295 mmol, 1.00 equiv), 2-bromo-4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)benzamide (241.43 mg, 0.295 mmol, 1.00 equiv), N,N-diethyl-2-hydroxybenzamide (17.11 mg, 0.089 mmol, 0.30 equiv), CuI (33.76 mg, 0.177 mmol, 0.60 equiv), K$_2$CO$_3$ (122.49 mg, 0.886 mmol, 3.00 equiv), DMA (2.00 mL, Infinity equiv). The resulting solution was stirred for 14 hr at 110 degrees C. The resulting mixture was concentrated. The residue was applied onto a silica gel column and eluted with dichloromethane/methanol (10:1). This resulted in 120 mg (30.23%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(14-[[2-(trimethylsilyl)ethoxy]methyl]-4,8,14,16-tetraazatetracyclo[7.7.0.0^[2,7].0[11,15]]hexadeca-1(16),2(7),3,5,9,11(15),12-heptaen-8-yl)benzamide as brown a solid.

LC-MS (ES, m/z): 1074 [M+H].

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[4,8,14,16-tetraazatetracyclo[7.7.0.0^[2,7].0[11,15]]hexadeca-1 (16),2(7),3,5,9,11(15),12-heptaen-8-yl]benzamide, Into a 8-mL vial, was placed 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(14-[[2-(trimethylsilyl)ethoxy]methyl]-4,8,14,16-tetraazatetracyclo[7.7.0.0^[2,7].0[11,15]]hexadeca-1(16),2(7),3,5,9,11(15),12-heptaen-8-yl)benzamide (100.00 mg), ethane-1,2-diamine (0.20 mL), TBAF in THF (1 ml, 2M). The resulting solution was stirred for 24 hr at 70 degrees C. in an oil bath. The resulting mixture was concentrated. The residue was purified by Prep-HPLC with dichloromethane/methanol (10:1). LC-MS (ES, m/z): 944 [M+H], $^1$H NMR (300 MHz, DMSO, ppm): δ 11.55 (s, 1H), 9.24 (s, 1H), 8.27-8.15 (m, 2H), 8.09-7.97 (m, 1H), 7.90-7.80 (m, 1H), 7.57-7.47 (m, 2H), 7.41-7.30 (m, 2H), 7.15-6.94 (m, 5H), 6.87-6.74 (m, 1H), 6.46-6.27 (m, 1H), 3.93-3.49 (m, 6H), 3.45-3.32 (m, 4H), 3.30-3.10 (m, 5H), 2.88-2.74 (m, 2H), 2.34-2.26 (m, 4H), 2.21-2.11 (m, 2H), 2.03-1.90 (m, 2H), 0.98 (s, 6H).

Example 72

Preparation of 4-(4-[[4-(4-chlorophenyl)-6,6-dimethyl-2,5-dihydropyran-3-yl]methyl]piperazin-1-yl)-N-(4-[[(2S)-1,4-dioxan-2-ylmethyl]amino]-3-nitrobenzene sulfonyl)-2-[14-oxa-2,4,10-triazatricyclo [7.5.0.0^[3,7]]tetradeca-1(9),2,5,7-tetraen-10-yl] benzamide Synthesis of 4-bromo-6,6-dimethyl-2,5-dihydropyran-3-carbaldehyde: Into a 250-mL 3-necked round-bottom flask, was added CHCl$_3$ (80.00 mL), dimethylformamide (7.13 g, 97.5 mmol, 2.5 equiv). This was followed by the addition of phosphorus tribromide (24.28 g, 89.7 mmol, 2.30 equiv) dropwise with stirring at 0° C. The resulting solution was stirred for 1 h at Rt. To this was added 2,2-dimethyloxan-4-one (5.00 g, 39.01 mmol, 1.00 equiv) at RT. The resulting solution was allowed to react an additional 12 h at RT. The reaction was then quenched by the addition of 200 mL of water/ice. The pH value of the solution was adjusted to 5 with Na$_2$CO$_3$ (s). The resulting solution was extracted with 3×50 mL of dichloromethane and the organic layers combined and concentrated. The residue was dissolved in 100 mL of EA. The resulting mixture was washed with 2×50 mL of brine. The mixture was dried over anhydrous sodium sulfate and concentrated. This resulted in 5.6 g (65.53%) of 4-bromo-6,6-dimethyl-2,5-dihydropyran-3-carbaldehyde as light yellow oil. $^1$H NMR (300 MHz, DMSO-d$_6$, ppm) δ 9.84 (s, 1H), 4.23 (t, J=2.5 Hz, 2H), 2.73 (t, J=2.5 Hz, 2H), 1.20 (s, 6H).

Synthesis of 4-(4-chlorophenyl)-6,6-dimethyl-2,5-dihydropyran-3-carbaldehyde: Into a 100-mL round-bottom flask purged and maintained with an inert atmosphere of nitrogen, was added 4-bromo-6,6-dimethyl-2,5-dihydropyran-3-carbaldehyde (5.40 g, 24.6 mmol, 1.00 equiv), DCE (50.00 mL), p-chloro-benzeneboronic acid (4.63 g, 29.6 mmol, 1.2 equiv), sodium methaneperoxoate sodium (5.27 g, 49.2 mmol, 2 equiv), Pd(PPh$_3$)$_2$Cl$_2$ (1.73 g, 2.46 mmol, 0.1 equiv), water (5 mL). The resulting solution was stirred for 12 h at 60° C. The reaction mixture was cooled and diluted with 50 ml water. The resulting solution was extracted with 3×50 mL of ethyl acetate and the organic layers combined. The resulting mixture was washed with 50 mL of brine. The mixture was dried over anhydrous sodium sulfate and concentrated. The residue was applied onto a silica gel column with ethyl acetate/petroleum ether (1:10-2:5). This resulted in 5.2 g (84.14%) of 4-(4-chlorophenyl)-6,6-dimethyl-2,5-dihydropyran-3-carbaldehyde as light yellow oil. LC-MS: (ES, m/z): M+1: 251.

Synthesis of methyl 2-bromo-4-(4-[[4-(4-chlorophenyl)-6,6-dimethyl-2,5-dihydropyran-3-yl]methyl]piperazin-1-yl) benzoate: Into a 100-mL 3-necked round-bottom flask, was added 4-(4-chlorophenyl)-6,6-dimethyl-2,5-dihydropyran-3-carbaldehyde (2.00 g, 7.9 mmol, 1.00 equiv), DCE (20.00 mL), methyl 2-bromo-4-(piperazin-1-yl)benzoate (2.36 g, 7.9 mmol, 1 equiv), Ti(Oi-Pr)$_4$ (6.74 g, 23.7 mmol, 3 equiv). The resulting solution was stirred for 3 h at RT. This was followed by the addition of NaBH(OAc)$_3$ (3.35 g, 15.8 mmol, 2 equiv) in several batches at RT. The resulting solution was allowed to react for overnight at RT. The reaction was then quenched by the addition of 10 mL of. The resulting mixture was concentrated. The residue was applied onto a silica gel column with ethyl acetate/petroleum ether (1:10-2:5). This resulted in 3 g (70.44%) of methyl 2-bromo-4-(4-[[4-(4-chlorophenyl)-6,6-dimethyl-2,5-dihydropyran-3-yl]methyl]piperazin-1-yl)benzoate as light yellow oil. LC-MS: (ES, m/z): M+1: 533.

Synthesis of 2-[3-[(5-bromo-1-[[2-(trimethylsilyl)ethoxy]methyl]pyrrolo[2,3-b]pyridine-6-yl)oxy]propyl]isoindole-1,3-dione: Into a 1000-mL 3-necked round-bottom flask purged and maintained with an inert atmosphere of nitrogen, was placed 5-bromo-6-fluoro-1-[[2-(trimethylsilyl)ethoxy]methyl]pyrrolo[2,3-b]pyridine (53.50 g, 154.944 mmol, 1 equiv). This was followed by the addition of 2-(3-hydroxypropyl)isoindole-1,3-dione (31.80 g, 154.944 mmol, 1 equiv), in portions at RT. To this was added Dioxane (500.00 mL) at RT, NaH (9.30 g, 232.415 mmol, 1.50 equiv, 60%). The resulting solution was stirred for 4 h at 80° C. The reaction mixture was cooled with a water/ice bath. The reaction was then quenched by the addition of 500 mL AcOH/ice/water. The resulting solution was extracted with 2×500 mL of ethyl acetate. The resulting mixture was washed with 3×500 ml of Brine. The mixture was dried over anhydrous sodium sulfate and concentrated. The residue was applied onto a silica gel column with ethyl acetate/petroleum ether (0:1-1:10). This resulted in 58 g (70.56%) of 2-[3-[(5-bromo-1-[[2-(trimethylsilyl)ethoxy]methyl]pyrrolo[2,3-b]pyridin-6-yl)oxy]propyl]isoindole-1,3-dione as colorless oil. The measurements of the retention were done with a reversed phase column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 4° C.; flow: 1.5 mL/min. LC-MS: (ES, m/z): M+1:554.

Synthesis of 3-[(5-bromo-1-[[2-(trimethylsilyl)ethoxy]methyl]pyrrolo[2,3-b]pyridin-6-yl)oxy]propan-1-amine:
Into a 500-mL round-bottom flask, was placed ethoxy]methyl]propyl]isoindole-pyrrolo[2,3-b]pyridin-6-yl)oxy]2-[3-[(5-bromo-1-[[2-(trimethylsilyl)1,3-dione (58.00 g, 109.332 mmol, 1.00 equiv), EtOH (300.00 mL), NH₂NH₂·H₂O (68.42 g, 1093.32 mmol, 10 equiv, 80%). The resulting solution was stirred for 4 h at room temperature. The resulting mixture was concentrated. The reaction was then quenched by the addition of 200 mL of water. The resulting solution was extracted with 2×500 mL of ethyl acetate. The resulting mixture was washed with 2×300 ml of Brine. The mixture was dried over anhydrous sodium sulfate and concentrated. The residue was applied onto a silica gel column with ethyl acetate/petroleum ether (0:1-1:2). This resulted in 37.5 g (85.66%) of 3-[(5-bromo-1-[[2-(trimethylsilyl)ethoxy]methyl]pyrrolo[2,3-b]pyridin-6-yl)oxy]propan-1-amine as yellow oil.

Synthesis of 4-[[2-(trimethylsilyl)ethoxy]methyl]-14-oxa-2,4,10-triazatricyclo[7.5.0.0^[3,7]]tetradeca-1(9),2,5,7-tetraene: Into a 1000-mL round-bottom flask, was placed 3-[(5-bromo-1-[[2-(trimethylsilyl)ethoxy]methyl]pyrrolo[2,3-b]pyridin-6-yl)oxy]propan-1-amine (37.50 g, 93.658 mmol, 1.00 equiv), toluene (500.00 mL), t-BuONa (27.00 g, 280.947 mmol, 3.00 equiv), BrettPhos Pd G3 (4.25 g, 4.688 mmol, 0.05 equiv). The resulting solution was stirred for 4 h at 110° C. The solids were filtered out. The resulting mixture was concentrated. The residue was applied onto a silica gel column with ethyl acetate/petroleum ether (0:1-1:1). This resulted in 16.1 g (53.81%) of 4-[[2-(trimethylsilyl)ethoxy]methyl]-14-oxa-2,4,10-triazatricyclo[7.5.0.0^[3,7]]tetradeca-1(9),2,5,7-tetraene as a brown solid. The measurements of the retention were done with a reversed phase column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 4° C.; flow: 1.5 mL/min. LC-MS: (ES, m/z): M+1:320.

Synthesis of methyl4-(4-[[4-(4-chlorophenyl)-6,6-dimethyl-2,5-dihydropyran-3-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl) benzoate: Into a 40-mL vial purged and maintained with an inert atmosphere of nitrogen, was added methyl 2-bromo-4-(4-[[4-(4-chlorophenyl)-6,6-dimethyl-2,5-dihydropyran-3-yl]methyl]piperazin-1-yl)benzoate (500.00 mg, 0.939 mmol, 2.00 equiv), Toluene (5.00 mL), 4-[[2-(trimethylsilyl)ethoxy]methyl]-14-oxa-2,4,10-triazatricyclo[7.5.0.0^[3,7]]tetradeca-1(9),2,5,7-tetraene (150.00 mg, 0.47 mmol, 1.00 equiv), Cs₂CO₃ (306.00 mg, 0.94 mmol, 2.00 equiv), Chloro[9,9-dimethyl-4,5-bis(diphenylphosphino)xanthene][2-amino-1,1-biphenyl-2-yl]palladium(II) (41.65 mg, 0.047 mmol, 0.10 equiv). The resulting solution was stirred for overnight at 110° C. The reaction mixture was cooled to RT. The resulting solution was diluted with 10 mL of H₂O. The resulting solution was extracted with 4×10 mL of ethyl acetate and the organic layers combined. The resulting mixture was washed with 20 mL of brine. The mixture was dried over anhydrous sodium sulfate and concentrated. The residue was applied onto a silica gel column with ethyl acetate/petroleum ether (1:5-1:1). This resulted in 250 mg (68.93%) of methyl 4-(4-[[4-(4-chlorophenyl)-6,6-dimethyl-2,5-dihydropyran-3-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl) benzoate as yellow oil. LC-MS: (ES, m/z): M+1: 772.

Synthesis of 4-(4-[[4-(4-chlorophenyl)-6,6-dimethyl-2,5-dihydropyran-3-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid: Into a 40-mL vial, was added methyl 4-(4-[[4-(4-chlorophenyl)-6,6-dimethyl-2,5-dihydropyran-3-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate (250 mg crude, 0.324 mmol, 1.00 equiv), methanol (3 mL), Dioxane (3.00 mL), NaOH (0.48 mL, 1.940 mmol, 6 equiv). The resulting solution was stirred for 3 h at 70° C. The reaction mixture was cooled to RT. The resulting solution was diluted with 10 mL of H₂O. HOAc was employed to adjust the pH to 5. The resulting solution was extracted with 4×10 mL of ethyl acetate and the organic layers combined. The resulting mixture was washed with 20×20 mL of brine. The mixture was dried over anhydrous sodium sulfate and concentrated. The residue was applied onto a silica gel column with ethyl acetate/petroleum ether (1:2-2:1). This resulted in 125 mg (50.92%) of 4-(4-[[4-(4-chlorophenyl)-6,6-dimethyl-2,5-dihydropyran-3-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid as brown solid. LC-MS: (ES, m/z): M+1: 758.

Synthesis of 4-([[(2S)-1,4-dioxan-2-yl]methyl]amino)-3-nitrobenzene-1-sulfonamide: Into a 100-mL round-bottom flask, was placed 4-fluoro-3-nitrobenzene-1-sulfonamide (1.43 g, 0.007 mmol, 1 equiv), 1-[(2S)-1,4-dioxan-2-yl]methanamine hydrochloride (1 g, 6.510 mmol, 1 equiv), THF (30 mL), Cs₂CO₃ (8.48 g, 0.026 mmol, 4 equiv). The resulting solution was stirred overnight at 50° C. in an oil bath. The solids were collected by filtration. The solid was dried in an oven under reduced pressure. This resulted in 1.82 g (88.10%) of 4-([[(2S)-1,4-dioxan-2-yl]methyl]amino)-3-nitrobenzene-1-sulfonamide as yellow solid. LC-MS: (ES, m/z): M+1:318.

Synthesis of 4-(4-[[4-(4-chlorophenyl)-6,6-dimethyl-2,5-dihydropyran-3-yl]methyl]piperazin-1-yl)-N-(4-[[(2S)-1,4- dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide: Into a 40-mL vial, was added 4-(4-[[4-(4-chlorophenyl)-6,6-dimethyl-2,5-dihydropyran-3-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid (120.00 mg, 0.158 mmol, 1.00 equiv), DCM, 4-[[(2S)-1,4-dioxan-2-ylmethyl]amino]-3-nitrobenzenesulfonamide (60.00 mg, 0.189 mmol, 1.20 equiv), DMAP (38.66 mg, 0.316 mmol, 2.00 equiv), EDCI (36.40 mg, 0.189 mmol, 1.20 equiv). The resulting solution was stirred for 12 h at 30° C. The resulting solution was diluted with 10 mL of $H_2O$. The resulting solution was extracted with 4×10 mL of ethyl acetate and the organic layers combined. The resulting mixture was washed with 20 mL of brine. The mixture was dried over anhydrous sodium sulfate and concentrated. The residue was applied onto Pre-TLC with dichloromethane/methanol (5:95). This resulted in 100 mg (59.75%) of 4-(4-[[4-(4-chlorophenyl)-6,6-dimethyl-2,5-dihydropyran-3-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide as yellow solid. LC-MS: (ES, m/z): M+1: 1057.

Synthesis of 4-(4-[[4-(4-chlorophenyl)-6,6-dimethyl-2,5-dihydropyran-3-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide: Into a 40-mL vial, was added 4-(4-[[4-(4-chlorophenyl)-6,6-dimethyl-2,5-dihydropyran-3-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide (100 mg, 0.095 mmol, 1.00 equiv), tetrahydrofuran (4.00 mL), ethylenediamine (113.00 mg, 1.89 mmol, 20 equiv), TBAF (1.89 mL, 1.89 mmol, 20 equiv). The resulting solution was stirred for 8 h at 70° C. The reaction mixture was cooled. The resulting solution was diluted with 10 mL of $H_2O$. The resulting solution was extracted with 4×10 mL of ethyl acetate and the organic layers combined. The resulting mixture was washed with 20 mL of brine. The mixture was dried over anhydrous sodium sulfate and concentrated. The residue was applied onto Pre-TLC with dichloromethane/methanol (95:5). The residue was applied onto Pre-TLC with dichloromethane/methanol (95:5). The crude product (50 mg) was purified by Flash-Prep-HPLC with column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 4° C.; flow: 1.5 mL/min. This resulted in 15 mg of 4-(4-[[4-(4-chlorophenyl)-6,6-dimethyl-2,5-dihydropyran-3-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide as a yellow solid. LC-MS: (ES, m/z): M+1:927. $^1H$ NMR (300 MHz, DMSO-$d_6$, ppm) δ 11.84 (s, 1H), 8.88-8.71 (m, 2H), 8.47 (s, 1H), 7.97 (m, 2H), 7.38 (s, 3H), 7.14 (s, 1H), 7.06 (m, 2H), 6.97 (s, 1H), 6.80-6.63 (m, 3H), 6.22 (s, 1H), 4.58 (s, 4H), 4.04 3.75 (m, 7H), 3.75-3.55 (m, 5H), 3.47 (m, 2H), 3.31 (m, 4H), 2.43 (m, 7H), 1.33 (m, 7H).

Example 73

Preparation of 4-(4-[[2-(4-chlorophenyl)-5,5-dimethylcyclohex-1-en-1-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide Synthesis of 4-([[[(2S)-1,4-dioxan-2-yl]methyl]amino)-3-nitrobenzene-1-sulfonamide: Into a 100-mL round-bottom flask, was placed 4-fluoro-3-nitrobenzene-1-sulfonamide (1.43 g, 0.007 mmol, 1 equiv), 1-[(2S)-1,4-dioxan-2-yl]methanamine hydrochloride (1 g, 6.510 mmol, 1 equiv), THF (30 mL), $Cs_2CO_3$ (8.48 g, 0.026 mmol, 4 equiv). The resulting solution was stirred overnight at 50° C. in an oil bath. The solids were collected by filtration. The solid was dried in an oven under reduced pressure. This resulted in 1.82 g (88.10%) of 4-([[[(2S)-1,4-dioxan-2-yl]methyl]amino)-3-nitrobenzene-1-sulfonamide as a yellow solid. LC-MS: (ES, m/z): M+1=318.

Synthesis of 2-[3-[(5-bromo-1-[[2-(trimethylsilyl)ethoxy]methyl]pyrrolo[2,3-b]pyridin-6-yl)oxy]propyl]isoindole-1,3-dione: Into a 1000-mL 3-necked round-bottom flask purged and maintained with an inert atmosphere of nitrogen, was placed 5-bromo-6-fluoro-1-[[2-(trimethylsilyl)ethoxy]methyl]pyrrolo[2,3-b]pyridine (53.50 g, 154.944 mmol, 1 equiv). This was followed by the addition of 2-(3-hydroxypropyl)isoindole-1,3-dione (31.80 g, 154.944 mmol, 1 equiv), in portions at degrees C. To this was added Dioxane (500.00 mL) at degrees C., NaH (9.30 g, 232.415 mmol, 1.50 equiv, 60%). The resulting solution was stirred for 4 h at 80 degrees C. The reaction mixture was cooled with a water/ice bath. The reaction was then quenched by the addition of 500 mL AcOH/ice/water. The resulting solution was extracted with 2×500 mL of ethyl acetate. The resulting mixture was washed with 3×500 ml of Brine. The mixture was dried over anhydrous sodium sulfate and concentrated. The residue was applied onto a silica gel column with ethyl acetate/petroleum ether (0:1-1:10). This resulted in 58 g (70.56%) of 2-[3-[(5-bromo-1-[[2-(trimethylsilyl)ethoxy]methyl]pyrrolo[2,3-b]pyridin-6-yl)oxy]propyl]isoindole-1,3-dione as colorless oil. LC-MS: (ES, m/z): M+1=554.

Synthesis of 3-[(5-bromo-1-[[2-(trimethylsilyl)ethoxy]methyl]pyrrolo[2,3-b]pyridin-6-yl)oxy]propan-1-amine: Into a 500-mL round-bottom flask, was placed 2-[3-[(5-bromo-1-[[2-(trimethylsilyl)ethoxy]methyl]pyrrolo[2,3-b]pyridin-6-yl)oxy]propyl]isoindole-1,3-dione (58.00 g, 109.332 mmol, 1.00 equiv), EtOH (300.00 mL), $NH_2NH_2·H_2O$ (68.42 g, 1093.321 mmol, 10 equiv, 80%). The resulting solution was stirred for 4 h at room temperature. The resulting mixture was concentrated. The reaction was then quenched by the addition of 200 mL of water. The resulting solution was extracted with 2×500 mL of ethyl acetate The resulting mixture was washed with 2×300 ml of Brine. The mixture was dried over anhydrous sodium sulfate and concentrated. The residue was applied onto a silica gel column with ethyl acetate/petroleum ether (0:1-1:2). This resulted in 37.5 g (85.66%) of 3-[(5-bromo-1-[[2-(trimethylsilyl)ethoxy]methyl]pyrrolo[2,3-b]pyridin-6-yl)oxy]propan-1-amine as yellow oil.

Synthesis of 4-[[2-(trimethylsilyl)ethoxy]methyl]-14-oxa-2,4,10-triazatricyclo[7.5.0.0^[3,7]]tetradeca-1(9),2,5,7-tetraene: Into a 1000-mL round-bottom flask, was placed 3-[(5-bromo-1-[[2-(trimethylsilyl)ethoxy]methyl]pyrrolo[2,3-b]pyridin-6-yl)oxy]propan-1-amine (37.50 g, 93.658 mmol, 1.00 equiv), toluene (500.00 mL), t-BuONa (27.00 g, 280.947 mmol, 3.00 equiv), BrettPhos Pd G3 (4.25 g, 4.688 mmol, 0.05 equiv). The resulting solution was stirred for 4 h at 110 degrees C. The solids were filtered out. The resulting mixture was concentrated. The residue was applied onto a silica gel column with ethyl acetate/petroleum ether (0:1-1:1). This resulted in 16.1 g (53.81%) of 4-[[2-(trimethylsilyl)ethoxy]methyl]-14-oxa-2,4,10-triazatricyclo [7.5.0.0^[3,7]]tetradeca-1(9),2,5,7-tetraene as a brown solid. LC-MS: (ES, m/z): M+1=320.

Synthesis of 2-bromo-5,5-dimethylcyclohex-1-ene-1-carbaldehyde Into a 250-mL 3-necked round-bottom flask, was placed DMF (7.24 g, 99.050 mmol, 2.5 equiv), DCM (100 mL). This was followed by the addition of PBr3 (24.67 g, 91.139 mmol, 2.30 equiv) dropwise with stirring at 0 degrees C. The resulting solution was stirred for 1 h at 0 degrees C. To this was added 4,4-dimethylcyclohexan-1-one (5.00 g, 39.620 mmol, 1.00 equiv), in portions at 0 degrees C. The resulting solution was stirred for overnight at room temperature. The reaction was then quenched by the addition of 100 mL of water/ice. The pH value of the solution was adjusted to 5 with $Na_2CO_3$. The resulting solution was extracted with 3×100 mL of dichloromethane dried over anhydrous sodium sulfate and concentrated. This resulted in 5 g (58.13%) of 2-bromo-5,5-dimethylcyclohex-1-ene-1-carbaldehyde as yellow oil. LC-MS: (ES, m/z): M+1=217/219.

Synthesis of 2-(4-chlorophenyl)-5,5-dimethylcyclohex-1-ene-1-carbaldehyde Into a 100-mL round-bottom flask, was placed 2-bromo-5,5-dimethylcyclohex-1-ene-1-carbaldehyde (2.50 g, 11.515 mmol, 1.00 equiv), benzeneboronic acid, p-chloro- (1.80 g, 11.515 mmol, 1 equiv), DME (25 mL), $H_2O$ (25 mL), $Na_2CO_3$ (2.44 g, 23.030 mmol, 2 equiv), $Pd(dppf)Cl_2CH_2Cl_2$ (0.94 g, 1.151 mmol, 0.10 equiv). The resulting solution was stirred for 12 h at 60 degrees C. The reaction mixture was cooled to room temperature. The reaction was then quenched by the addition of 50 mL of water. The resulting solution was extracted with 3×50 mL of ethyl acetate dried over anhydrous sodium sulfate and concentrated. The residue was applied onto a silica gel column with ethyl acetate/petroleum ether (0:1-1:1). This resulted in 1.2 g (41.89%) of 2-(4-chlorophenyl)-5,5-dimethylcyclohex-1-ene-1-carbaldehyde as yellow oil. LC-MS: (ES, m/z): M+1=249.

Synthesis of methyl 2-bromo-4-(4-[[2-(4-chlorophenyl)-5,5-dimethylcyclohex-1-en-1-yl]methyl]piperazin-1-yl) benzoate: Into a 100-mL round-bottom flask, was placed 2-(4-chlorophenyl)-5,5-dimethylcyclohex-1-ene-1-carbaldehyde (1.20 g, 4.824 mmol, 1.00 equiv), methyl 2-bromo-4-(piperazin-1-yl)benzoate (1.44 g, 4.824 mmol, 1.00 equiv), DCE (50.00 mL), $Ti(Oi-Pr)_4$ (4.11 g, 14.472 mmol, 3.00 equiv). The resulting solution was stirred for 3 h at room temperature. This was followed by the addition of $NaBH(OAc)_3$ (2.04 g, 9.648 mmol, 2.00 equiv), in portions at room temperature. The resulting solution was stirred for overnight at room temperature. The reaction was then quenched by the addition of 10 mL of water. The resulting mixture was concentrated. The residue was applied onto a silica gel column with ethyl acetate/petroleum ether (0:1-1:1). This resulted in 600 mg (23.38%) of methyl 2-bromo-4-(4-[[2-(4-chlorophenyl)-5,5-dimethylcyclohex-1-en-1-yl]methyl]piperazin-1-yl)benzoate as off-white oil. LC-MS: (ES, m/z): M+1=531/533.

Synthesis of methyl 4-(4-[[2-(4-chlorophenyl)-5,5-dimethylcyclohex-1-en-1-yl]methyl]piperazin-1-yl)-2-(4-[[2-(trimethylsilyl)ethoxy]methyl]-14-oxa-2,4,10-triazatricyclo [7.5.0.0^[3,7]]tetradeca-1(9),2,5,7-tetraen-10-yl)benzoate: Into a 40-mL round-bottom flask, was placed 4-[[2-(trimethylsilyl) ethoxy]methyl]-14-oxa-2,4,10-triazatricyclo [7.5.0.0^[3,7]]tetradeca-1(9),2,5,7-tetraene (150.15 mg, 0.470 mmol, 1.00 equiv), methyl 2-bromo-4-(4-[[2-(4-chlorophenyl)-5,5-dimethylcyclohex-1-en-1-yl]methyl]piperazin-1-yl)benzoate (250.00 mg, 0.470 mmol, 1.00 equiv), $Cs_2CO_3$ (459.40 mg, 1.410 mmol, 3.00 equiv), Toluene (5.00 mL), xantphos Pd 2G (27.19 mg, 0.047 mmol, 0.10 equiv). The resulting solution was stirred for 12 h at 110 degrees C. The resulting mixture was concentrated. The residue was applied onto a silica gel column with ethyl acetate/petroleum ether (0:1-1:1). This resulted in 120 mg (33.14%) of methyl 4-(4-[[2-(4-chlorophenyl)-5,5-dimethylcyclohex-1-en-1-yl]methyl]piperazin-1-yl)-2-(4-[[2-(trimethylsilyl)ethoxy]ethyl]-14-oxa-2,4,10-triazatricyclo [7.5.0.0^[3,7]]tetradeca-1(9),2,5,7-tetraen-10-yl)benzoate as a white solid. LC-MS: (ES, m/z): M+1=770.

Synthesis of 4-(4-[[2-(4-chlorophenyl)-5,5-dimethylcyclohex-1-en-1-yl]methyl]piperazin-1-yl)-2-(4-[[2-(trimethylsilyl)ethoxy]methyl]-14-oxa-2,4,10-triazatricyclo[7.5.0.0^ [3,7]]tetradeca-1(9),2,5,7-tetraen-10-yl)benzoic acid: Into a 8-mL round-bottom flask, was placed methyl 4-(4-[[2-(4-chlorophenyl)-5,5-dimethylcyclohex-1-en-1-yl]methyl]piperazin-1-yl)-2-(4-[[2-(trimethylsilyl)ethoxy]ethyl]-14-oxa-2,4,10-triazatricyclo[7.5.0.0^[3,7]]tetradeca-1(9),2,5,7-tetraen-10-yl)benzoate (120.00 mg, 0.156 mmol, 1.00 equiv), MeOH (1.00 mL), Dioxane (1.00 mL), $H_2O$ (1.00 mL), NaOH (37.38 mg, 0.934 mmol, 6 equiv). The resulting solution was stirred for 12 h at 70 degrees C. The reaction was then quenched by the addition of 5 mL of water. The pH value of the solution was adjusted to 5 with HCl (1 mol/L). The solids were collected by filtration. This resulted in 100 mg (84.88%) of 4-(4-[[2-(4-chlorophenyl)-5,5-dimethylcyclohex-1-en-1-yl]methyl]piperazin-1-yl)-2-(4-[[2-(trimethylsilyl)ethoxy]ethyl]-14-oxa-2,4,10-triazatricyclo[7.5.0.0^ [3,7]]tetradeca-1(9),2,5,7-tetraen-10-yl)benzoic acid as a white crude solid. LC-MS: (ES, m/z): M+1=756, R.T=1.288 min.

Synthesis of 4-(4-[[2-(4-chlorophenyl)-5,5-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1 (9),2,5,7-tetraen-10-yl)benzoic acid (100.00 mg, 0.132 mmol, 1.00 equiv), DCM (5 mL), DMAP (64.60 mg, 0.529 mmol, 4 equiv), EDCI (50.68 mg, 0.264 mmol, 2 equiv), 4-[[(2S)-1,4-dioxan-2-ylmethyl]amino]-3-nitrobenzenesulfonamide (46.14 mg, 0.145 mmol, 1.10 equiv). The resulting solution was stirred for overnight at room temperature. The resulting mixture was concentrated. The residue was applied onto a silica gel column with dichloromethane/methanol (1:0-10:1). This resulted in 100 mg (71.65%) of 4-(4-[[2-(4-chlorophenyl)-5,5-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3, 7]]tetradeca-1(9),2,5,7-tetraen-10-yl)benzamide as a yellow solid. LC-MS: (ES, m/z): M+1=1056.

Synthesis of 4-(4-[[2-(4-chlorophenyl)-5,5-dimethylcyclohex-1-en-1-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide: Into a 40-mL round-bottom flask, was placed 4-(4-[[2-(4-chlorophenyl)-5,5-dimethylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide (100.00 mg, 0.095 mmol, 1.00 eq), ethylenediamine (113.85 mg, 1.894 mmol, 20.00 eq), TBAF (495.31 mg, 1.894 mmol, 20 eq), THF (10 ml). The resulting solution was stirred for 12 h at 70 degrees C. The reaction was then quenched by the addition of 10 mL of water. The resulting solution was extracted with 2×10 mL of ethyl acetate concentrated. The crude product was purified by Prep-HPLC with the following conditions (Waters-2767): Column, X-bridge RP18, 5 um, 19*100 mm; mobile phase, 0.03% ammonia in water (0.03% NH$_4$HCO$_3$ & NH$_4$OH) and CH$_3$CN (32% CH$_3$CN up to 52% in 6 min); Detector, UV 254 nm. This resulted in 25 mg (28.52%) of 4-(4-[[2-(4-chlorophenyl)-5,5-dimethylcyclohex-1-en-1-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide as a yellow solid. LC-MS: (ES, m/z): M+1=925. $^1$H-NMR: (DMSO-d$_6$, 300 ppm) δ: 11.91 (s, 1H), 11.22 (s, 1H), 8.52-8.48 (m, 2H), 7.68-7.63 (m, 1H), 7.47-7.45 (d, J=6 Hz, 1H), 7.38-7.35 (d, J=9 Hz, 2H), 7.20 (s, 1H), 7.12-7.09 (d, J=9 Hz, 2H), 6.92-6.89 (m, 2H), 6.72 (s, 1H), 6.13-6.11 (m, 1H), 4.21 (s, 2H),3.82-3.75 (m, 3H), 3.68-3.51 (m, 8H), 3.22-3.19 (m, 2H), 2.73 (s, 2H), 2.3-2.10 (m, 4H), 2.08-1.90 (m, 3H), 1.40 (m, 2H), 1.21 (m, 1H) 0.97 (s, 6H).

Example 74

Preparation of 4-(4-[[2-(4-chlorophenyl)cyclohex-1-en-1-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide Synthesis of 2-bromocyclohex-1-ene-1-carbaldehyde: Into a 250-mL 3-necked round-bottom flask, was added CHCl$_3$ (80.00 mL, 991.80 mmol, 19.47 equiv). This was followed by the addition of DMF (9.31 g, 0.12 mmol, 2.5 equiv) dropwise with stirring at 0° C. To this was added PBr$_3$ (31.72 g, 0.11 mmol, 2.3 equiv) dropwise with stirring at 0° C. The resulting solution was stirred for 1 h at 0° C. To the mixture was added cyclohexanone (5.00 g, 50.94 mmol, 1.00 equiv) dropwise with stirring at RT. The resulting solution was allowed to react for overnight at RT. The reaction was then quenched by the addition of 100 mL of water/ice. The pH value of the solution was adjusted to 5 with Na$_2$CO$_3$. The resulting solution was extracted with 3×100 mL of dichloromethane dried over anhydrous sodium sulfate and concentrated. This resulted in 5.2 g (53.99%) of 2-bromocyclohex-1-ene-1-carbaldehyde as light yellow oil. LC-MS: (ES, m/z): M+1: 189.

Synthesis of 2-(4-chlorophenyl)cyclohex-1-ene-1-carbaldehyde: Into a 100-mL round-bottom flask, was added 2-bromocyclohex-1-ene-1-carbaldehyde (5.00 g, 26.44 mmol, 1.00 equiv), DME (50.00 mL), p-chloro-benzeneboronic acid (4.14 g, 26.44 mmol, 1 equiv), Na$_2$CO$_3$ (5.66 g, 52.89 mmol, 2.0 equiv), Pd$_2$(dba)$_3$ (2.42 g, 2.64 mmol, 0.1 equiv), water (5 mL). The resulting solution was stirred for 12 h at 60° C. The reaction mixture was cooled to RT. The resulting solution was diluted with 50 mL of H$_2$O. The resulting solution was extracted with 3×50 mL of ethyl acetate. The resulting mixture was washed with 50 mL of brine. The mixture was dried over anhydrous sodium sulfate and concentrated. The residue was applied onto a silica gel column with ethyl acetate/petroleum ether (1:10-2:5). This resulted in 3.5 g (59.96%) of 2-(4-chlorophenyl)cyclohex-1-ene-1-carbaldehyde as light yellow oil. LC-MS: (ES, m/z): M+1: 221.

Synthesis of methyl 2-bromo-4-(4-[[2-(4-chlorophenyl)cyclohex-1-en-1-yl]methyl]piperazin-1-yl)benzoate: Into a 100-mL 3-necked round-bottom flask, was added 2-(4-chlorophenyl)cyclohex-1-ene-1-carbaldehyde (3.50 g, 15.85 mmol, 1.00 equiv), DCE (35.00 mL, 442.10 mmol, 27.88 equiv), methyl 2-bromo-4-(piperazin-1-yl)benzoate (4.74 g, 15.85 mmol, 1 equiv), Ti(Oi-Pr)$_4$ (13.52 g, 47.57 mmol, 3 equiv). The resulting solution was stirred for 3 h at RT. This was followed by the addition of NaBH(AcO)$_3$ (6.72 g, 31.71 mmol, 2 equiv) in several batches at RT. The resulting solution was allowed to react for an additional 16 h at RT. The reaction was then quenched by the addition of 10 mL of MeOH. The resulting mixture was concentrated. The residue was applied onto a silica gel column with ethyl acetate/petroleum ether (1:10-2:5). This resulted in 4.2 g (52.56%) of methyl 2-bromo-4-(4-[[2-(4-chlorophenyl)cyclohex-1-en-1-yl]methyl]piperazin-1-yl)benzoate as light yellow oil. LC-MS: (ES, m/z): M+1: 503.

Synthesis of 2-[3-[(5-bromo-1-[[2-(trimethylsilyl)ethoxy]methyl]pyrrolo[2,3-b]pyridine-6-yl)oxy]propyl]isoindole-1,3-dione: Into a 1000-mL 3-necked round-bottom flask purged and maintained with an inert atmosphere of nitrogen, was placed 5-bromo-6-fluoro-1-[[2-(trimethylsilyl)ethoxy]methyl]pyrrolo[2,3-b]pyridine (53.50 g, 154.944 mmol, 1 equiv). This was followed by the addition of 2-(3-hydroxypropyl) isoindole-1,3-dione (31.80 g, 154.944 mmol, 1 equiv), in portions at RT. To this was added Dioxane (500.00 mL) at RT, NaH (9.30 g, 232.415 mmol, 1.50 equiv, 60%). The resulting solution was stirred for 4 h at 80° C. The reaction mixture was cooled with a water/ice bath. The reaction was then quenched by the addition of 500 mL AcOH/ice/water. The resulting solution was extracted with 2×500 mL of ethyl acetate. The resulting mixture was washed with 3×500 ml of Brine. The mixture was dried over anhydrous sodium sulfate and concentrated. The residue was applied onto a silica gel column with ethyl acetate/petroleum ether (0:1-1:10). This resulted in 58 g (70.56%) of 2-[3-[(5-bromo-1-[[2-(trimethylsilyl)ethoxy]methyl]pyrrolo[2,3-b]pyridin-6-yl)oxy]propyl]isoindole-1,3-dione as colorless oil. The measurements of the retention were done with a reversed phase column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 4° C.; flow: 1.5 mL/min. LC-MS: (ES, m/z): M+1:554.

Synthesis of 3-[(5-bromo-1-[[2-(trimethylsilyl)ethoxy]methyl]pyrrolo[2,3-b]pyridin-6-yl)oxy]propan-1-amine: Into a 500-mL round-bottom flask, was placed ethoxy]methyl]propyl]isoindole-pyrrolo[2,3-b]pyridin-6-yl)oxy]2-[3-[(5-bromo-1-[[2-(trimethylsilyl)1,3-dione (58.00 g, 109.33 mmol, 1.0 equiv), EtOH (300.00 mL), NH$_2$NH$_2$·H$_2$O (68.42 g, 1093.32 mmol, 10 equiv, 80%). The resulting solution was stirred for 4 h at RT. The resulting mixture was concentrated. The reaction was then quenched by the addition of 200 mL of water. The resulting solution was extracted with 2×500 mL of ethyl acetate. The resulting mixture was washed with 2×300 ml of Brine. The mixture was dried over anhydrous sodium sulfate and concentrated. The residue was applied onto a silica gel column with ethyl acetate/petroleum ether (0:1-1:2). This resulted in 37.5 g (85.66%) of 3-[(5-bromo-1-[[2-(trimethylsilyl)ethoxy]methyl]pyrrolo[2,3-b]pyridin-6-yl)oxy]propan-1-amine as yellow oil.

Synthesis of 4-[[2-(trimethylsilyl)ethoxy]methyl]-14-oxa-2,4,10-triazatricyclo[7.5.0.0^[3,7]]tetradeca-1(9),2,5,7-tetraene: Into a 1000-mL round-bottom flask, was placed 3-[(5-bromo-1-[[2-(trimethylsilyl)ethoxy]methyl]pyrrolo[2,3-b]pyridin-6-yl)oxy]propan-1-amine (37.50 g, 93.658 mmol, 1.00 equiv), toluene (500.00 mL), t-BuONa (27.00 g, 280.947 mmol, 3.00 equiv), BrettPhos Pd G3 (4.25 g, 4.688 mmol, 0.05 equiv). The resulting solution was stirred for 4 h at 110 degrees C. The solids were filtered out. The resulting mixture was concentrated. The residue was applied onto a silica gel column with ethyl acetate/petroleum ether (0:1-1:1). This resulted in 16.1 g (53.81%) of 4-[[2-(trimethylsilyl)ethoxy]methyl]-14-oxa-2,4,10-triazatricyclo[7.5.0.0^[3,7]]tetradeca-1(9),2,5,7-tetraene as a brown solid. The measurements of the retention were done with a reversed phase column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 4° C.; flow: 1.5 mL/min. LC-MS: (ES, m/z): M+1:320.

Synthesis of methyl 4-(4-[[2-(4-chlorophenyl)cyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate: Into a 40-mL flask purged and maintained with an inert atmosphere of nitrogen, was added methyl 2-bromo-4-(4-[[2-(4-chlorophenyl)cyclohex-1-en-1-yl]methyl]piperazin-1-yl)benzoate (473.8 mg, 2 equiv), toluene (5 mL), 4-[[2-(trimethylsilyl)ethoxy]methyl]-14-oxa-2,4,10-triazatricyclo[7.5.0.0^[3,7]]tetradeca-1(9),2,5,7-tetraene (150 mg, 1.00 equiv), $Cs_2CO_3$ (306.4 mg, 2 equiv), X-antphos G2 (50 mg). The resulting solution was stirred for 12 h at 110° C. The resulting solution was diluted with 10 mL of $H_2O$. The resulting solution was extracted with 4×10 mL of ethyl acetate. The resulting mixture was washed with 20 mL of brine. The mixture was dried over anhydrous sodium sulfate and concentrated. The residue was applied onto a silica gel column with ethyl acetate/petroleum ether (1:5-1:1). This resulted in 280 mg (80.33%) of methyl 4-(4-[[2-(4-chlorophenyl)cyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate as light yellow oil. LC-MS: (ES, m/z): M+1: 742.

Synthesis of 4-(4-[[2-(4-chlorophenyl)cyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid: Into a 40-mL round-bottom flask, was added methyl 4-(4-[[2-(4-chlorophenyl)cyclohex-1-en-1-yl]methyl]piperazin-1-yl)-2-(4-[[2-(trimethylsilyl)ethoxy]ethyl]-14-oxa-2,4,10-triazatricyclo[7.5.0.0^[3,7]]tetradeca-1(9),2,5,7-tetraen-10-yl)benzoate (280.00 mg, 0.37 mmol, 1.00 equiv), methanol (3.00 mL, 0.094 mmol, 0.25 equiv), dioxane (3.00 mL, 35.41 mmol, 93.90 equiv), NaOH (0.57 mL, 2.262 mmol, 6.00 equiv). The resulting solution was stirred for 3 h at 70° C. The reaction mixture was cooled to RT. The resulting solution was diluted with 10 mL of $H_2O$. The pH value of the solution was adjusted to 5 with HOAc. The resulting solution was extracted with 4×10 mL of ethyl acetate. The resulting mixture was washed with 20 mL of brine. The mixture was dried over anhydrous sodium sulfate and concentrated. The residue was applied onto a silica gel column with ethyl acetate/petroleum ether (1:2-2:1). This resulted in 100 mg (36.40%) of 4-(4-[[2-(4-chlorophenyl)cyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid as a brown solid. LC-MS: (ES, m/z): M+1: 728.

Synthesis of 4-([[(2S)-1,4-dioxan-2-yl]methyl]amino)-3-nitrobenzene-1-sulfonamide: Into a 100-mL round-bottom flask, was placed 4-fluoro-3-nitrobenzene-1-sulfonamide (1.43 g, 0.007 mmol, 1 equiv), 1-[(2S)-1,4-dioxan-2-yl]methanamine hydrochloride (1 g, 6.510 mmol, 1 equiv), THF (30 mL), $Cs_2CO_3$ (8.48 g, 0.026 mmol, 4 equiv). The resulting solution was stirred overnight at 50° C. in an oil bath. The solids were collected by filtration. The solid was dried in an oven under reduced pressure. This resulted in 1.82 g (88.10%) of 4-([[(2S)-1,4-dioxan-2-yl]methyl]amino)-3-nitrobenzene-1-sulfonamide as yellow solid. LC-MS: (ES, m/z): M+1:318.

Synthesis of 4-(4-[[2-(4-chlorophenyl)cyclohex-1-en-1-yl]methyl]piperazin-1-yl)-N-(4-[[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide: Into a 40-mL round-bottom flask, was added 4-(4-[[2-(4-chlorophenyl)cyclohex-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid (95.00 mg, 0.130 mmol, 1.00 equiv), DCM (2.00 mL), DMAP (31.87 mg, 0.261 mmol, 2 equiv), 4-[[(2S)-1,4-dioxan-2-ylmethyl]amino]-3-nitrobenzenesulfonamide (49.60 mg, 0.156 mmol, 1.20 equiv), EDCI (30.00 mg, 0.15 mmol, 1.2 equiv). The resulting solution was stirred for 12 h at 30° C. The resulting solution was diluted with 10 mL of $H_2O$. The resulting solution was extracted with 4×10 mL of ethyl acetate and the organic layers combined. The resulting mixture was washed with 20 mL of brine. The mixture was dried over anhydrous sodium sulfate and concentrated. The residue was applied onto a silica gel column with dichloromethane/methanol (95:5). This resulted in 80 mg (59.69%) of 4-(4-[[2-(4-chlorophenyl)cyclohex-1-en-1-yl]methyl]piperazin-1-yl)-N-(4-[[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide as yellow solid. LC-MS: (ES, m/z): M+1: 1027.

Synthesis of 4-(4-[[2-(4-chlorophenyl)cyclohex-1-en-1-yl]methyl]piperazin-1-yl)-N-(4-[[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide: Into a 40-mL round-bottom flask, was added 4-(4-[[2-(4-chlorophenyl)cyclohex-1-en-1-yl]methyl]piperazin-1-yl)-N-(4-[[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide (80.00 mg, 0.078 mmol, 1.00 equiv), THF (4 mL), ethylenediamine (93.57 mg, 1.55 mmol, 20 equiv), TBAF (1.55 g, 5.92 mmol, 76.16 equiv). The resulting solution was stirred for 8 h at 70° C. The reaction mixture was cooled to RT. The resulting solution was diluted with 10 mL of $H_2O$. The resulting solution was extracted with 4×10 mL of ethyl acetate and the organic layers combined. The resulting mixture was washed with 20 mL of brine. The mixture was dried over anhydrous sodium sulfate and concentrated. The residue was applied onto a silica gel column with dichloromethane/methanol (95:5). The crude product (35 mg) was purified by Prep-HPLC with the following conditions: column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 4° C.; flow:

1.5 mL/min. This resulted in 19 mg (27.20%) of 4-(4-[[2-(4-chlorophenyl)cyclohex-1-en-1-yl]methyl]piperazin-1-yl)-N-(4-[[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl]benzamide as yellow solid. LC-MS: (ES, m/z): M+1: 897, $^1$H-NMR: (300 MHz, DMSO-$d_6$, ppm) δ 11.94 (s, 1H), 8.88 8.60 (m, 2H), 8.45 (s, 1H), 8.02 (m, 1H), 7.95 (m, 1H), 7.13 (m, 1H), 7.09-6.93 (m, 3H), 6.74 (s, 2H), 6.20 (s, 1H), 4.13-3.56 (m, 8H), 3.60-3.39 (m, 2H), 3.31 (s, 6H), 2.84 (s, 2H), 2.38 (s, 5H), 2.19 (d, J=30.5 Hz, 5H), 1.73 (s, 5H).

Example 75

Preparation of 4-(4-[[2-(4-chlorophenyl)cyclohept-1-en-1-yl]methyl]piperazin-1-yl)-N-(4-[[[(2S)-1,4-dioxan-2-ylmethyl]amino]-3-nitro benzenesulfonyl)-2-[14-oxa-2,4,10-triazatricyclo[7.5.0.0^[3,7]]tetradeca-1(9),2,5,7-tetraen-10-yl]benzamide Synthesis of 4-([[[(2S)-1,4-dioxan-2-yl]methyl]amino)-3-nitrobenzene-1-sulfonamide: Into a 100-mL round-bottom flask, was placed 4-fluoro-3-nitrobenzene-1-sulfonamide (1.43 g, 0.007 mmol, 1 equiv), 1-[(2S)-1,4-dioxan-2-yl]methanamine hydrochloride (1 g, 6.510 mmol, 1 equiv), THF (30 mL), $Cs_2CO_3$ (8.48 g, 0.026 mmol, 4 equiv). The resulting solution was stirred overnight at 50° C. in an oil bath. The solids were collected by filtration. The solid was dried in an oven under reduced pressure. This resulted in 1.82 g (88.10%) of 4-([[[(2S)-1,4-dioxan-2-yl]methyl]amino)-3-nitrobenzene-1-sulfonamide as a yellow solid. LC-MS: (ES, m/z): M+1=554.

Synthesis of 2-[3-[(5-bromo-1-[[2-(trimethylsilyl)ethoxy]methyl]pyrrolo[2,3-b]pyridin-6-yl)oxy]propyl]isoindole-1,3-dione: Into a 1000-mL 3-necked round-bottom flask purged and maintained with an inert atmosphere of nitrogen, was placed 5-bromo-6-fluoro-1-[[2-(trimethylsilyl)ethoxy]methyl]pyrrolo[2,3-b]pyridine (53.50 g, 154.944 mmol, 1 equiv). This was followed by the addition of 2-(3-hydroxypropyl)isoindole-1,3-dione (31.80 g, 154.944 mmol, 1 equiv), in portions at 0 degrees C. To this was added Dioxane (500.00 mL) at degrees C., NaH (9.30 g, 232.415 mmol, 1.50 equiv, 60%). The resulting solution was stirred for 4 h at 80 degrees C. The reaction mixture was cooled with a water/ice bath. The reaction was then quenched by the addition of 500 mL AcOH/ice/water. The resulting solution was extracted with 2×500 mL of ethyl acetate. The resulting mixture was washed with 3×500 ml of Brine. The mixture was dried over anhydrous sodium sulfate and concentrated. The residue was applied onto a silica gel column with ethyl acetate/petroleum ether (0:1-1:10). This resulted in 58 g (70.56%) of 2-[3-[(5-bromo-1-[[2-(trimethylsilyl)ethoxy]methyl]pyrrolo[2,3-b]pyridin-6-yl)oxy]propyl]isoindole-1,3-dione as colorless oil. LC-MS: (ES, m/z): M+1=554.

Synthesis of 3-[(5-bromo-1-[[2-(trimethylsilyl)ethoxy]methyl]pyrrolo[2,3-b]pyridin-6-yl)oxy]propan-1-amine Into a 500-mL round-bottom flask, was placed 2-[3-[(5-bromo-1-[[2-(trimethylsilyl)ethoxy]methyl]pyrrolo[2,3-b]pyridin-6-yl)oxy]propyl]isoindole-1,3-dione (58.00 g, 109.332 mmol, 1.00 equiv), EtOH (300.00 mL), $NH_2NH_2 \cdot H_2O$ (68.42 g, 1093.321 mmol, 10 equiv, 80%). The resulting solution was stirred for 4 h at room temperature. The resulting mixture was concentrated. The reaction was then quenched by the addition of 200 mL of water. The resulting solution was extracted with 2×500 mL of ethyl acetate. The resulting mixture was washed with 2×300 ml of Brine. The mixture was dried over anhydrous sodium sulfate and concentrated. The residue was applied onto a silica gel column with ethyl acetate/petroleum ether (0:1-1:2). This resulted in 37.5 g (85.66%) of 3-[(5-bromo-1-[[2-(trimethylsilyl)ethoxy]methyl]pyrrolo[2,3-b]pyridin-6-yl)oxy]propan-1-amine as yellow oil.

Synthesis of 4-[[2-(trimethylsilyl)ethoxy]methyl]-14-oxa-2,4,10-triazatricyclo[7.5.0.0^[3,7]]tetradeca-1(9),2,5,7-tetraene: Into a 1000-mL round-bottom flask, was placed 3-[(5-bromo-1-[[2-(trimethylsilyl)ethoxy]methyl]pyrrolo[2,3-b]pyridin-6-yl)oxy]propan-1-amine (37.50 g, 93.658 mmol, 1.00 equiv), toluene (500.00 mL), t-BuONa (27.00 g, 280.947 mmol, 3.00 equiv), BrettPhos Pd G3 (4.25 g, 4.688 mmol, 0.05 equiv). The resulting solution was stirred for 4 h at 110 degrees C. The solids were filtered out. The resulting mixture was concentrated. The residue was applied onto a silica gel column with ethyl acetate/petroleum ether (0:1-1:1). This resulted in 16.1 g (53.81%) of 4-[[2-(trimethylsilyl)ethoxy]methyl]-14-oxa-2,4,10-triazatricyclo[7.5.0.0^[3,7]]tetradeca-1(9),2,5,7-tetraene as a brown solid. LC-MS: (ES, m/z): M+1=320.

Synthesis of 2-bromocyclohept-1-ene-1-carbaldehyde: Into a 250-mL 3-necked round-bottom flask, was placed DMF (8.15 g, 111.436 mmol, 2.5 equiv), DCM (100.00 mL). This was followed by the addition of $PBr_3$ (27.75 g, 102.521 mmol, 2.3 equiv) dropwise with stirring at 0 degrees C. The resulting solution was stirred for 1 h at 0 degrees C. To this was added cycloheptanone (5.00 g, 44.574 mmol, 1.00 equiv), in portions at degrees C. The resulting solution was stirred for overnight at room temperature. The reaction was then quenched by the addition of 100 mL of water/ice. The pH value of the solution was adjusted to 5 with $Na_2CO_3$. The resulting solution was extracted with 3×100 mL of dichloromethane dried over anhydrous sodium sulfate and concentrated. This resulted in 5 g (55.24%) of 2-bromocyclohept-1-ene-1-carbaldehyde as yellow oil. LC-MS: (ES, m/z): M+1=203/205.

Synthesis of 2-(4-chlorophenyl)cyclohept-1-ene-1-carbaldehyde: Into a 100-mL round-bottom flask, was placed 2-bromocyclohept-1-ene-1-carbaldehyde (2.50 g, 12.310 mmol, 1.00 equiv), (4-chlorophenyl)boronic acid (1.92 g, 12.279 mmol, 1.00 equiv), DME (25.00 mL), $H_2O$ (25.00 mL), $Na_2CO_3$ (2.61 g, 24.621 mmol, 2 equiv), $Pd(pph_3)_2Cl_2$ (1.01 g, 1.231 mmol, 0.1 equiv). The resulting solution was stirred for 12 h at 60 degrees C. The reaction mixture was cooled to room temperature. The reaction was then quenched by the addition of 50 mL of water. The resulting solution was extracted with 3×50 mL of ethyl acetate. The resulting mixture was washed with 3×50 ml of Brine. The mixture was dried over anhydrous sodium sulfate and concentrated. The residue was applied onto a silica gel column with ethyl acetate/petroleum ether (0:1-1:1). This resulted in 0.6 g (20.76%) of 2-(4-chlorophenyl)cyclohept-1-ene-1-carbaldehyde as yellow oil. LC-MS: (ES, m/z): M+1=235.

Synthesis of methyl 2-bromo-4-(4-[[2-(4-chlorophenyl)cyclohept-1-en-1-yl]methyl]piperazin-1-yl)benzoate: Into a 100-mL round-bottom flask, was placed 2-(4-chlorophenyl)cyclohept-1-ene-1-carbaldehyde (0.60 g, 2.556 mmol, 1.00 equiv), methyl 2-bromo-4-(piperazin-1-yl)benzoate (0.76 g, 2.540 mmol, 0.99 equiv), DCM (30.00 mL, 471.901 mmol, 184.61 equiv), $Ti(Oi-Pr)_4$ (2.18 g, 7.669 mmol, 3.00 equiv). This was followed by the addition of $NaBH(OAc)_3$ (1.08 g, 5.112 mmol, 2.00 equiv), in portions at room temperature. The resulting solution was stirred for overnight at room temperature. The reaction was then quenched by the addition of 10 mL of water. The resulting mixture was concentrated. The residue was applied onto a silica gel column with ethyl acetate/petroleum ether (0:1-1:1). This resulted in 500 mg (37.77%) of methyl 2-bromo-4-(4-[[2-(4-chlorophenyl)cyclohept-1-en-1-yl]methyl]piperazin-1-yl)benzoate as off-white oil. LC-MS: (ES, m/z): M+1=517/519.

Synthesis of methyl 4-(4-[[2-(4-chlorophenyl)cyclohept-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate: Into a 40-mL round-bottom flask, was placed 4-[[2-(trimethylsilyl)ethoxy]methyl]-14-oxa-2,4,10-triazatricyclo[7.5.0.0^[3,7]]tetradeca-1(9),2,5,7-tetraene (154.22 mg, 0.483 mmol, 1.00 equiv), methyl 2-bromo-4-(4-[[2-(4-chlorophenyl)cyclohept-1-en-1-yl]methyl]piperazin-1-yl)benzoate (250.00 mg, 0.483 mmol, 1.00 equiv), Cs$_2$CO$_3$ (471.85 mg, 1.448 mmol, 3 equiv), Toluene (5.00 mL), Xantphos Pd 2G (46.00 mg, 0.1 equiv). The resulting solution was stirred for 11 h at 110 degrees C. The resulting mixture was concentrated. The residue was applied onto a silica gel column with ethyl acetate/petroleum ether (0:1-1:1). This resulted in 110 mg (30.12%) of methyl 4-(4-[[2-(4-chlorophenyl)cyclohept-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate as a solid. LC-MS: (ES, m/z): M+1=756.

Synthesis of 4-(4-[[2-(4-chlorophenyl)cyclohept-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid. Into a 8-mL round-bottom flask, was placed methyl 4-(4-[[2-(4-chlorophenyl)cyclohept-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoate (110.00 mg, 0.145 mmol, 1.00 equiv), MeOH (1.00 mL), Dioxane (1.00 mL), H$_2$O (1.00 mL, 55.508 mmol, 381.73 equiv), NaOH (34.90 mg, 0.873 mmol, 6.00 equiv). The resulting solution was stirred for 12 hr at 70 degrees C. The reaction was then quenched by the addition of 5 mL of water. The pH value of the solution was adjusted to 5 with HCl (1 mol/L). The solids were collected by filtration. This resulted in 100 mg (92.63%) of 4-(4-[[2-(4-chlorophenyl)cyclohept-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid as a white crude solid. LC-MS: (ES, m/z): M+1=742.

Synthesis of 4-(4-[[2-(4-chlorophenyl)cyclohept-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide. Into a 8-mL round-bottom flask, was placed 4-(4-[[2-(4-chlorophenyl)cyclohept-1-en-1-yl]methyl]piperazin-1-yl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzoic acid (100.00 mg, 0.135 mmol, 1.00 equiv), DCM (5.00 mL), DMAP (65.82 mg, 0.539 mmol, 4 equiv), EDCI (51.64 mg, 0.269 mmol, 2 equiv), 4-[[(2S)-1,4-dioxan-2-ylmethyl]amino]-3-nitrobenzenesulfonamide (47.01 mg, 0.148 mmol, 1.1 equiv). The resulting solution was stirred for overnight at room temperature. The resulting mixture was concentrated. The residue was applied onto a silica gel column with dichloromethane/methanol (1:0-10:1). This resulted in 120 mg (85.52%) of 4-(4-[[2-(4-chlorophenyl)cyclohept-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0^[3,7]]tetradeca-1(9),2,5,7-tetraen-10-yl)benzamide as a yellow crude solid. LC-MS: (ES, m/z): M+1=1041.

Synthesis of 4-(4-[[2-(4-chlorophenyl)cyclohept-1-en-1-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0^[3,7]]tetradeca-1(9),2,5,7-tetraen-10-yl] benzamide. Into a 40-mL round-bottom flask, was placed 4-(4-[[2-(4-chlorophenyl)cyclohept-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]ethyl]-14-oxa-2,4,10-triazatricyclo[7.5.0.0^[3,7]]tetradeca-1(9),2,5,7-tetraen-10-yl)benzamide (120.00 mg, 0.115 mmol, 1.00 equiv), ethylenediamine (138.46 mg, 2.304 mmol, 20.00 equiv), THF (10 mL), TBAF (602.37 mg, 2.304 mmol, 20 equiv). The resulting solution was stirred for 12 hr at 70 degrees C. The reaction was then quenched by the addition of 10 mL of water. The resulting solution was extracted with 2×10 mL of ethyl acetate concentrated. The crude product was purified by Prep-HPLC with the following conditions (Waters-2767): Column, X-bridge RP18, 5 um, 19*100 mm; mobile phase, 0.03% ammonia in water (0.03% NH$_4$HCO$_{3\&}$ NH$_4$OH) and CH$_3$CN (32% CH$_3$CN up to 52% in 6 min); Detector, UV 254 nm. This resulted in 26 mg (24.76%) of 4-(4-[[2-(4-chlorophenyl)cyclohept-1-en-1-yl]methyl]piperazin-1-yl)-N-(4-[[(2S)-1,4-dioxan-2-ylmethyl]amino]-3-nitro benzenesulfonyl)-2-[14-oxa-2,4,10-triazatricyclo[7.5.0.0^[3,7]]tetradeca-1(9),2,5,7-tetraen-10-yl] benzamide as a solid. LC-MS: (ES, m/z): M+1=911. $^1$H NMR (300 MHz, DMSO-d$_6$) δ 11.90 (s, 1H), 11.20 (s, 1H), 8.46 (s, 2H), 7.65 (dd, J=9.1, 1.8 Hz, 2H), 7.45 (s, 1H), 7.36 (d, J=8.3 Hz, 4H), 7.20 (s, 2H), 7.08 (d, J=8.4 Hz, 4H), 6.97-6.86 (m, 4H), 6.70 (s, 2H), 6.12 (d, J=2.5 Hz, 2H), 4.21 (s, 3H), 3.86-3.72 (m, 6H), 3.71-3.41 (m, 13H), 3.20 (s, 4H), 2.76 (s, 4H), 2.39 (s, 7H), 2.28 (s, 7H), 1.98 (s, 2H), 1.57 (s, 3H), 1.50 (s, 3H), 1.24 (s, 1H).

Example 76

Preparation of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[11-oxo-13-oxa-2,4,10-triazatricyclo[7.4.0.0[3,7]]trideca-1(9),2,5,7-tetraen-10-yl] benzamide Synthesis of 5-bromo-6-fluoropyridin-2-amine. Into a 5000-mL 3-necked round-bottom flask, was placed 6-fluoropyridin-2-amine (220 g, 2 mol, 1.00 equiv), CH$_3$CN (2.0 L), NBS (420 g, 2.2 mol, 1.20 equiv). The resulting solution was stirred for overnight at room temperature. The reaction was then quenched by the addition of 2 L of water. The resulting solution was extracted with 3×1 L of ethyl acetate and the organic layers combined. The resulting organic phase was washed with 3×1 L of brine. The mixture was dried over anhydrous sodium sulfate, then filtered and concentrated under vacuum. The residue was applied onto a silica gel column with ethyl acetate/petroleum ether (0:1-1:5). This resulted in 200 g (60%) of 5-bromo-6-fluoropyridin-2-amine as a white solid. LCMS: (ES, m/z): M+1: 191, 193.

Synthesis of 5-bromo-6-fluoro-3-iodopyridin-2-amine. Into a 2000-mL 4-necked round-bottom flask, was placed 5-bromo-6-fluoropyridin-2-amine (200 g, 1.05 mol, 1.00 equiv) in AcOH (1500 mL), iodo(sulfanyl)amine (NIS) (200 g, 1.15 mol, 1.10 equiv). The resulting solution was stirred for overnight at room temperature. The reaction was then quenched by the addition of 3000 mL of water. The solids were collected by filtration and wash by Et$_2$O. This resulted in 170 g (50%) of 5-bromo-6-fluoro-3-iodopyridin-2-amine as a white solid. The organic phase was concentrated under vacuum, result in 150 g crude product oil. ¹H-NMR: (CDCl₃, 300 MHz) δ: 7.98 (d, J=14.4 Hz, 1H), 4.94-5.00 (bs, 2H). Synthesis of 5-bromo-6-fluoro-3-[2-(trimethylsilyl)ethynyl]pyridin-2-amine. Into a 3000-mL 3-necked round-bottom flask, was placed a solution of 5-bromo-6-fluoro-3-iodopyridin-2-amine (170 g, 536.45 mmol, 1.00 equiv) in tetrahydrofuran (1500 mL), CuI (10.2 g, 53.56 mmol, 0.10 equiv), TEA (500 mL), dichloropalladium; bis(triphenylphosphane) (11.2 g, 15.96 mmol, 0.03 equiv), ethyl(ethynyl)dimethylsilane (63 g, 561.27 mmol, 1.20 equiv). The resulting solution was stirred for 16 hours at room temperature. The reaction was then quenched by the addition of 2000 mL of water. The resulting solution was extracted with 3×1000 mL of ethyl acetate and the organic layers combined. The resulting mixture was washed with 3×1000 mL of brine. The mixture was dried over anhydrous sodium sulfate, then filtered and concentrated under vacuum. The residue was applied onto a silica gel column with ethyl acetate/petroleum ether (0:1-1:1). This resulted in 120 g (78%) of 5-bromo-6-fluoro-3-[2-(trimethylsilyl)ethynyl]pyridin-2-amine as yellow oil. LC-MS (ES, m/z): M+1: 289, 287.

Synthesis of N-[5-bromo-6-fluoro-3-[2-(trimethylsilyl)ethynyl]pyridin-2-yl]acetamide. Into a 2000-mL 4-necked round-bottom flask, was placed a solution of 5-bromo-6-fluoro-3-[2-(trimethylsilyl)ethynyl]pyridin-2-amine (84 g, 292.48 mmol, 1.00 equiv) in dichloromethane (1000 mL), pyridine (57.8 g, 730.72 mmol, 2.50 equiv). This was followed by the addition of acetyl chloride (50.2 g, 639.51 mmol, 2.20 equiv) dropwise with stirring at 0 degree. The resulting solution was stirred for overnight at room temperature. The reaction was then quenched by the addition of 1000 mL of water. The resulting mixture was washed with 2×1000 mL of water. The mixture was dried over anhydrous sodium sulfate and concentrated under vacuum. The residue was applied onto a silica gel column with ethyl acetate/petroleum ether (0:1-1:10). This resulted in 80 g (83%) of N-[5-bromo-6-fluoro-3-[2-(trimethylsilyl)ethynyl]pyridin-2-yl]acetamide as a white solid. LC-MS: (ES, m/z): M+1=331.

Synthesis of 5-bromo-6-fluoro-1H-pyrrolo[2,3-b]pyridine. Into a 2000-mL round-bottom flask, was placed a solution of N-[5-bromo-6-fluoro-3-[2-(trimethylsilyl)ethynyl]pyridin-2-yl]acetamide (80 g, 242.98 mmol, 1.00 equiv) in tetrahydrofuran (300 mL), TBAF (1M in tetrahydrofuran) (729 mL, 3.00 equiv). The resulting solution was stirred for 12 h at 70 degree. The reaction mixture was cooled to room temperature. The resulting mixture was concentrated under vacuum. The reaction was then quenched by the addition of 500 mL of water. The resulting solution was extracted with 3×300 mL of ethyl acetate and the organic layers combined. The resulting mixture was washed with 3×300 mL of brine. The mixture was dried over anhydrous sodium sulfate and concentrated under vacuum. The residue was applied onto a silica gel column with ethyl acetate/petroleum ether (0:1-4:1). This resulted in 15 g (29%) of 5-bromo-6-fluoro-1H-pyrrolo[2,3-b]pyridine as a white solid. LC-MS: (ES, m/z): M+1=213.

Synthesis of 5-bromo-6-fluoro-1-[[2-(trimethylsilyl)ethoxy]methyl]-1H-pyrrolo[2,3-b]pyridine. Into a 250-mL 3-necked round-bottom flask purged and maintained with an inert atmosphere of nitrogen, was placed a solution of 5-bromo-6-fluoro-1H-pyrrolo[2,3-b]pyridine (15 g, 69.76 mmol, 1.00 equiv) in N,N-dimethylformamide (150 mL). This was followed by the addition of sodium hydride (4.2 g, 175.00 mmol, 1.50 equiv), in portions at 0 degree. After 0.5 h stirring, to this was added SEM-Cl (14 g, 84.34 mmol, 1.20 equiv) dropwise with stirring at 0 degree. The resulting solution was allowed to react, with stirring, for an additional 3 h at room temperature. The reaction was then quenched by the addition of 300 mL of water. The resulting solution was extracted with 3×200 mL of ethyl acetate and the organic layers combined. The resulting mixture was washed with 3×200 mL of brine. The mixture was dried over anhydrous sodium sulfate and concentrated under vacuum. The residue was applied onto a silica gel column with ethyl acetate/petroleum ether (0:1-1:10). This resulted in 15 g (62%) of 5-bromo-6-fluoro-1-[[2-(trimethylsilyl)ethoxy]methyl]-1H-pyrrolo[2,3-b]pyridine as yellow oil.

Synthesis of 6-(tert-butoxy)-N-(diphenylmethylidene)-1-[[2-(trimethylsilyl)ethoxy]methyl]-1H-pyrrolo[2,3-b]pyridin-5-amine. Into a 250-mL round-bottom flask, was placed a solution of 5-bromo-6-fluoro-1-[[2-(trimethylsilyl)ethoxy]methyl]-1H-pyrrolo[2,3-b]pyridine (20.7 g, 60 mmol, 1.00 equiv) in dioxane (300 mL), t-BuOK (20.5 g, 180 mmol, 3.00 equiv), xantphos (6.9 g, 12 mmol, 0.20 equiv), Pd₂(dba)₃·CHCl₃ (5.7 g, 0.10 equiv), diphenylmethanimine (14.04 g, 78 mmol, 1.20 equiv). The resulting solution was stirred for overnight at 100° C. The resulting mixture was concentrated under vacuum. The residue was applied onto a silica gel column with ethyl acetate/petroleum ether (0:1-1:20). This resulted in 15 g (crude) of 6-(tert-butoxy)-N-(diphenylmethylidene)-1-[[2-(trimethylsilyl)ethoxy]methyl]-1H-pyrrolo[2,3-b]pyridin-5-amine as white oil. LC-MS: (ES, m/z): M+1=500.

Synthesis of 5-amino-1-[[2-(trimethylsilyl)ethoxy]methyl]-1H-pyrrolo[2,3-b]pyridin-6-ol hydrogen chloride salt. Into a 500-mL round-bottom flask, was placed 6-(tert-butoxy)-N-(diphenylmethylidene)-1-[[2-(trimethylsilyl)ethoxy]methyl]-1H-pyrrolo[2,3-b]pyridin-5-amine (15 g, 30.02 mmol, 1.00 equiv) in dioxane (120 mL), HCl/dioxane (4M, 30 mL). The resulting solution was stirred for 5 h at room temperature. The resulting solution was diluted with 500 mL of ether. The solids were collected by filtration. This resulted in 5 g (crude) of 5-amino-1-[[2-(trimethylsilyl)ethoxy]methyl]-1H-pyrrolo[2,3-b]pyridin-6-ol hydrogen chloride salt as a red solid, Q-NMR show it might converted into 3 hydrogen chloride salt. LC-MS: (ES, m/z): M+1=280.

Synthesis of 4-[[2-(trimethylsilyl)ethoxy]methyl]-13-oxa-2,4,10-triazatricyclo[7.4.0.0ˆ[3,7]]trideca-1,3(7),5,8-tetraen-11-one. Into a 250-mL round-bottom flask, was placed 5-amino-1-[[2-(trimethylsilyl) ethoxy]methyl]-1H-pyrrolo[2,3-b]pyridin-6-ol hydrogen chloride salt (5 g, 17.89 mmol, 1.00 equiv) in N,N-dimethylformamide (100 mL), potassium carbonate (7.4 g, 53.54 mmol, 3.00 equiv), and add 2-chloroacetyl chloride (4 g, 35.42 mmol, 2.00 equiv) at 0 degree by dropwise. The resulting solution was stirred for overnight at 70° C. The reaction mixture was cooled to room temperature. The reaction was then quenched by the addition of 200 mL of water. The resulting solution was extracted with 3×100 mL of ethyl acetate and the organic layers combined. The resulting mixture was washed with 3×100 mL of brine. The mixture was dried over anhydrous sodium sulfate and concentrated under vacuum. The residue was applied onto a silica gel column with ethyl acetate/petroleum ether (0:1-1:1). This resulted in 2.5 g (44%) of 4-[[2-(trimethylsilyl)ethoxy]methyl]-13-oxa-2,4,10-triazatricyclo[7.4.0.0ˆ[3,7]]trideca-1,3(7),5,8-tetraen-11-one as a white solid. LC-MS: (ES, m/z): M+1=320.

Synthesis of methyl 2-bromo-4-(4-((2-(4-chlorophenyl)-4,4-dimethylcyclohex-1-enyl)methyl)piperazin-1-yl)benzoate. Into a 2000-mL round-bottom flask, was placed 1-((2-(4-chlorophenyl)-4,4-dimethylcyclohex-1-enyl)methyl)piperazine dihydrochloride (60 g, 0.153 mol, 1 equiv), methyl 2-bromo-4-fluorobenzoate (35.7 g, 0.153 mol, 1 equiv), DBU (31.9 g, 0.612 mol, 4 equiv) and DMSO (800 mL). The resulting solution was stirred for 20 h at 70 degrees C. LCMS showed material was completely consumed. The resulting mixture was cooled to R.T and poured into water (3 L). The mixture was filtrated, collection of filter cake and the filter cake was washed by water (300 mL×3) and dried by oven to give product 74 g (Y: 91%) methyl 2-bromo-4-(4-((2-(4-chlorophenyl)-4,4-dimethylcyclohex-1-enyl)methyl)piperazin-1-yl)benzoate as a white solid.

Synthesis of 2-bromo-4-(4-((2-(4-chlorophenyl)-4,4-dimethylcyclohex-1-enyl)methyl)piperazin-1-yl)benzoic acid. Into a 2000-mL round-bottom flask, was placed methyl 2-bromo-4-(4-((2-(4-chlorophenyl)-4,4-dimethylcyclohex-1-enyl)methyl)piperazin-1-yl)benzoate (73 g, 0.137 mol, 1 equiv), LiOH (13.15 g, 0.548 mol, 4 equiv) and MeOH/THF/water (450 mL/300 mL/100 mL). The resulting solution was stirred for 16 h at 70 degrees C. LCMS showed material was completely consumed. The resulting mixture was cooled to R.T and concentrated. The residue was diluted with water (500 mL) and the mixture was adjust PH to 3-5 with HCl (6 M), followed by filtrated, collection of filter cake and dried by oven to give product 65 g (Y: 93%)2-bromo-4-(4-((2-(4-chlorophenyl)-4,4-dimethylcyclohex-1-enyl)methyl)piperazin-1-yl)benzoic acid as a white solid.

Synthesis of 2-bromo-4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)benzamide. Into a 2000-mL round-bottom flask, was placed 2-bromo-4-(4-((2-(4-chlorophenyl)-4,4-dimethylcyclohex-1-enyl)methyl) piperazin-1-yl)benzoic acid (55 g, 0.107 mol, 1 equiv), DCM (1 L), (S)-4-(((1,4-dioxan-2-yl)methyl)amino)-3-nitrobenzenesulfonamide (32 g, 0.102 mol, 0.95 equiv), EDCI (30.8 g, 0.161 mol, 1.5 equiv), DMAP (52.2 g, 0.428 mol, 4 equiv). The resulting solution was stirred for overnight at 25 degrees C. LCMS showed material was completely consumed. The resulting mixture is followed by dilute hydrochloric acid (1.0 M) (100 mL×3), saturated sodium bicarbonate (100 mL×3) and brine (100 mL×1), and then the organic phase was dried by $Na_2SO_4$, filtrated. The filtrate was concentrated to give product 81 g (Y: 93%) as a light brown yellow solid 2-bromo-4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)benzamide as a brown yellow solid. LC-MS: (ES, m/z): M+1=816/819, R.T=2.01 min.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(11-oxo-4-[[2-(trimethylsilyl)ethoxy]ethyl]-13-oxa-2,4,10-triazatricyclo[7.4.0.0ˆ[3,7]]trideca-1(9),2,5,7-tetraen-10-yl)benzamide. Into a 40-mL round-bottom flask, was placed 2-bromo-4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)benzamide (214.89 mg, 0.263 mmol, 1.2 equiv), 4-[[2-(trimethylsilyl)ethoxy]methyl]-13-oxa-2,4,10-triazatricyclo[7.4.0.0ˆ[3,7]]trideca-1(9),2,5,7-tetraen-11-one (70.00 mg, 0.219 mmol, 1.00 equiv), 4,7-dimethoxy-1,10-phenanthroline (26.33 mg, 0.110 mmol, 0.5 equiv), $Cs_2CO_3$ (214.20 mg, 0.657 mmol, 3 equiv), Dioxane (10.00 mL), CuI (20.87 mg, 0.110 mmol, 0.5 equiv). The resulting solution was stirred for 3 h at 110 degrees C. The resulting mixture was concentrated. The residue was applied onto a silica gel column with ethyl acetate/petroleum ether (0:1-1:1). This resulted in 200 mg (86.45%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(11-oxo-4-[[2-(trimethylsilyl)ethoxy]methyl]-13-oxa-2,4,10-triazatricyclo[7.4.0.0ˆ[3,7]]trideca-1(9),2,5,7-tetraen-10-yl)benzamide as a yellow crude solid. LC-MS: (ES, m/z): M+1=1055.

Synthesis of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[11-oxo-13-oxa-2,4,10-triazatricyclo[7.4.0.0ˆ[3,7]]trideca-1(9),2,5,7-tetraen-10-yl]benzamide. Into a 40-mL round-bottom flask, was placed 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-(11-oxo-4-[[2-(trimethylsilyl)ethoxy]methyl]-13-oxa-2,4,10-triazatricyclo[7.4.0.0ˆ[3,7]]trideca-1(9),2,5,7-tetraen-10-yl)benzamide (200.00 mg, 0.189 mmol, 1.00 equiv), THF (10 mL), ethylenediamine (227.71 mg, 3.789 mmol, 20.00 equiv), TBAF (990.65 mg, 3.789 mmol, 20 equiv). The resulting solution was stirred for 12 h at 70 degrees C. The reaction was then quenched by the addition of 10 mL of water. The resulting solution was extracted with 2×10 mL of ethyl acetate concentrated. The crude product was purified by Prep-HPLC with the following conditions (Waters-2767): Column, X-bridge RP18, 5 um, 19*100 mm; mobile phase, 0.03% acerbity in water (0.03% HCl) and $CH_3CN$ (32% $CH_3CN$ up to 52% in 6 min); Detector, UV 254 nm. This resulted in 25 mg (14.26%) of 4-(4-[[2-(4-chlorophenyl)-4,4-dimethylcyclohex-1-en-1-yl]methyl]piperazin-1-yl)-N-(4-[[(2S)-1,4-dioxan-2-ylmethyl]amino]-3-nitrobenzenesulfonyl)-2-[11-oxo-13-oxa-2,4,10-triazatricyclo[7.4.0.0ˆ[3,7]]trideca-1(9),2,5,7-tetraen-10-yl]benzamide as a yellow solid. LC-MS: (ES, m/z): M+1=925. $^1H$ NMR (300 MHz, DMSO-$d_6$) δ 11.32 (d, J=7.2 Hz, 1H), 8.52 (s, 1H), 8.37 (dd, J=4.6, 2.3 Hz, 1H), 7.72 (d, J=8.5 Hz, 1H), 7.65 (s, 1H), 7.41 (d, J=8.1 Hz, 2H), 7.19 (d, J=5.8 Hz, 1H), 7.11 (d, J=8.3 Hz, 2H), 6.92 (d, J=9.7 Hz, 2H), 6.60 (d, J=1.8 Hz, 1H), 6.15-6.07 (m, 1H), 4.67 (d, J=15.0 Hz, 1H), 4.36 (s, 1H), 3.98-3.75 (m, 5H), 3.75-3.47 (m, 7H), 3.32 (s, 4H), 2.80 (s, 2H), 2.05 (s, 2H), 1.48 (s, 2H), 0.96 (s, 6H).

Example 77

Preparation of 4-(4-[[2-(4-chlorophenyl)-5-methoxy-5-methylcyclohex-1-en-1-yl]methyl]piperazin-1-yl)-N-(4-[[(2S)-1,4-dioxan-2-ylmethyl]amino]-3-nitrobenzene sulfonyl)-2-[14-oxa-2,4,10-triazatricyclo[7.5.0.0[3,7]]tetradeca-1(9),2,5,7-tetraen-10-yl]benzamide Synthesis of methyl 2-bromo-4-(4-[[2-(4-chlorophenyl)-5-methoxy-5-methylcyclohex-1-en-1-yl]methyl]piperazin-1-yl)benzoate: Into a 100-mL 3-necked round-bottom flask, was added methyl 2-bromo-4-(piperazin-1-yl)benzoate (2.00 g, 6.68 mmol, 1.00 equiv), DCE (20 mL), 2-(4-chlorophenyl)-5-methoxy-5-methylcyclohex-1-ene-1-carbaldehyde (1.77 g, 6.685 mmol, 1 equiv), Ti(Oi-Pr)$_4$ (5.70 g, 20.05 mmol, 3.00 equiv). The resulting solution was stirred for 3 h at RT. This was followed by the addition of NaBH(OAc)$_3$ (2.83 g, 13.37 mmol, 2.00 equiv) in several batches at RT. The resulting solution was allowed to react, for an additional 16 h at Rt. The reaction was then quenched by the addition of 10 mL of water. The resulting mixture was concentrated. The residue was applied onto a silica gel column with ethyl acetate/petroleum ether (1:10-2:5). This resulted in 3.0 g (81.90%) of methyl 2-bromo-4-(4-[[2-(4- chlorophenyl)-5-methoxy-5-methylcyclohex-1-en-1-yl]methyl]piperazin-1-yl)benzoate as light yellow oil. LC-MS: (ES, m/z): 547 [M+H]$^+$.

Synthesis of 2-[3-[(5-bromo-1-[[2-(trimethylsilyl)ethoxy]methyl]pyrrolo[2,3-b]pyridine-6-yl)oxy]propyl]isoindole-1,3-dione: Into a 1000-mL 3-necked round-bottom flask purged and maintained with an inert atmosphere of nitrogen, was placed 5-bromo-6-fluoro-1-[[2-(trimethylsilyl)ethoxy]methyl]pyrrolo[2,3-b]pyridine (53.50 g, 154.944 mmol, 1 equiv). This was followed by the addition of 2-(3-hydroxypropyl)isoindole-1,3-dione (31.80 g, 154.944 mmol, 1 equiv), in portions at RT. To this was added Dioxane (500.00 mL) at RT, NaH (9.30 g, 232.415 mmol, 1.50 equiv, 60%). The resulting solution was stirred for 4 h at 80° C. The reaction mixture was cooled with a water/ice bath. The reaction was then quenched by the addition of 500 mL AcOH/ice/water. The resulting solution was extracted with 2×500 mL of ethyl acetate. The resulting mixture was washed with 3×500 ml of Brine. The mixture was dried over anhydrous sodium sulfate and concentrated. The residue was applied onto a silica gel column with ethyl acetate/petroleum ether (0:1-1:10). This resulted in 58 g (70.56%) of 2-[3-[(5-bromo-1-[[2-(trimethylsilyl)ethoxy]methyl]pyrrolo[2,3-b]pyridin-6-yl)oxy]propyl]isoindole-1,3-dione as colorless oil. The measurements of the retention were done with a reversed phase column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 4° C.; flow: 1.5 mL/min. LC-MS: (ES, m/z): M+1:554.

Synthesis of 3-[(5-bromo-1-[[2-(trimethylsilyl)ethoxy]methyl]pyrrolo[2,3-[3]pyridin-6-yl)oxy]propan-1-amine: Into a 500-mL round-bottom flask, was placed ethoxy]methyl]propyl]isoindole-pyrrolo[2,3-b]pyridin-6-yl)oxy]2-[3-[(5-bromo-1-[[2-(trimethylsilyl)1,3-dione (58.00 g, 109.33 mmol, 1.0 equiv), EtOH (300.00 mL), NH$_2$NH$_2$·H$_2$O (68.42 g, 1093.32 mmol, 10 equiv, 80%). The resulting solution was stirred for 4 h at RT. The resulting mixture was concentrated. The reaction was then quenched by the addition of 200 mL of water. The resulting solution was extracted with 2×500 mL of ethyl acetate The resulting mixture was washed with 2×300 ml of Brine. The mixture was dried over anhydrous sodium sulfate and concentrated. The residue was applied onto a silica gel column with ethyl acetate/petroleum ether (0:1-1:2). This resulted in 37.5 g (85.66%) of 3-[(5-bromo-1-[[2-(trimethylsilyl)ethoxy]methyl]pyrrolo[2,3-b]pyridin-6-yl)oxy]propan-1-amine as yellow oil.

Synthesis of 4-[[2-(trimethylsilyl)ethoxy]methyl]-14-oxa-2,4,10-triazatricyclo[7.5.0.0ˆ[3,7]]tetradeca-1(9),2,5,7-tetraene: Into a 1000-mL round-bottom flask, was placed 3-[(5-bromo-1-[[2-(trimethylsilyl)ethoxy]methyl]pyrrolo[2,3-b]pyridin-6-yl)oxy]propan-1-amine (37.50 g, 93.658 mmol, 1.00 equiv), toluene (500.00 mL), t-BuONa (27.00 g, 280.947 mmol, 3.00 equiv), BrettPhos Pd G$_3$ (4.25 g, 4.688 mmol, 0.05 equiv). The resulting solution was stirred for 4 h at 110 degrees C. The solids were filtered out. The resulting mixture was concentrated. The residue was applied onto a silica gel column with ethyl acetate/petroleum ether (0:1-1:1). This resulted in 16.1 g (53.81%) of 4-[[2-(trimethylsilyl)ethoxy]methyl]-14-oxa-2,4,10-triazatricyclo[7.5.0.0ˆ[3,7]]tetradeca-1(9),2,5,7-tetraene as a brown solid. The measurements of the retention were done with a reversed phase column (C18). Shimadzu LCMS 2020; 50*3.0 SUPELCO Ascentis Express C18, 2.7 um; Eluent A: water (0.05% TFA); Eluent B: Acetonitrile; linear gradient from 5% acetonitrile to 95% acetonitrile in 7.0 minutes; Oven temperature 4° C.; flow: 1.5 mL/min. LC-MS: (ES, m/z): M+1:320.

Synthesis of methyl 4-(4-[[2-(4-chlorophenyl)-5-methoxy-5-methylcyclohex-1-en-1-yl]methyl]piperazin-1-yl)-2-(4-[[2-(trimethylsilyl)ethoxy]methyl]-14-oxa-2,4,10-triazatricyclo[7.5.0.0ˆ[3,7]]tetradeca-1(9),2,5,7-tetraen-10-yl)benzoate: Into a 40-mL round-bottom flask purged and maintained with an inert atmosphere of nitrogen, was added methyl 2-bromo-4-(4-[[2-(4-chlorophenyl)-5-methoxy-5-methylcyclohex-1-en-1-yl]methyl]piperazin-1-yl)benzoate (515 mg, 0.940 mmol, 1.00 equiv), Toluene (5 mg), 4-[[2-(trimethylsilyl)ethoxy]methyl]-14-oxa-2,4,10-triazatricyclo[7.5.0.0ˆ[3,7]]tetradeca-1(9),2,5,7-tetraene (150.14 mg, 0.47 mmol, 0.50 equiv), Cs$_2$CO$_3$ (306.24 mg, 0.94 mmol, 1.00 equiv), X-antphos Pd G3 (50.00 mg, 0.05 mmol, 0.06 equiv). The resulting solution was stirred for 12 h at 110° C. The resulting solution was diluted with 10 mL of H$_2$O. The resulting solution was extracted with 4×10 mL of ethyl acetate and the organic layers combined. The resulting mixture was washed with 20 mL of brine. The mixture was dried over anhydrous sodium sulfate and concentrated. The residue was applied onto a silica gel column with ethyl acetate/petroleum ether (1:5-1:1). This resulted in 230 mg (62.29%) of methyl 4-(4-[[2-(4-chlorophenyl)-5-methoxy-5-methylcyclohex-1-en-1-yl]methyl]piperazin-1-yl)-2-(4-[[2-(trimethylsilyl)ethoxy]methyl]-14-oxa-2,4,10-triazatricyclo[7.5.0.0ˆ[3,7]]tetradeca-1(9),2,5,7-tetraen-10-yl)benzoate as light yellow oil. LC-MS: (ES, m/z): 786 [M+H]$^+$.

Synthesis of 4-(4-[[2-(4-chlorophenyl)-5-methoxy-5-methylcyclohex-1-en-1-yl]methyl]piperazin-1-yl)-2-(4-[[2-(trimethylsilyl)ethoxy]methyl]-14-oxa-2,4,10-triazatricyclo[7.5.0.0ˆ[3,7]]tetradeca-1(9),2,5,7-tetraen-10-yl)benzoic acid: Into a 40-mL vial, was added methyl 4-(4-[[2-(4-chlorophenyl)-5-methoxy-5-methylcyclohex-1-en-1-yl]methyl]piperazin-1-yl)-2-(4-[[2-(trimethylsilyl)ethoxy]ethyl]-14-oxa-2,4,10-triazatricyclo[7.5.0.0ˆ[3,7]]tetradeca-1(9),2,5,7-tetraen-10-yl)benzoate (230 mg, 0.29 mmol, 1.00 equiv), methanol (3.00 mL), dioxane (3.00 mL), 4M NaOH (0.44 mL, 1.75 mmol, 6.0 equiv). The resulting solution was stirred for 3 h at 70° C. The reaction mixture was cooled to RT. The resulting solution was diluted with 10 mL of H$_2$O. The pH value of the solution was adjusted to 5 with HOAc. The resulting solution was extracted with 4×10 mL of ethyl acetate and the organic layers combined. The resulting mixture was washed with 20 mL of brine. The mixture was dried over anhydrous sodium sulfate. The residue was applied onto a silica gel column with ethyl acetate/petroleum ether (1:2-2:1). This resulted in 150 mg (66.40%) of 4-(4-[[2-(4-chlorophenyl)-5-methoxy-5-methylcyclohex-1-en-1-yl]methyl]piperazin-1-yl)-2-(4-[[2-(trimethylsilyl)ethoxy]ethyl]-14-oxa-2,4,10-triazatricyclo[7.5.0.0ˆ[3,7]]tetradeca-1(9),2,5,7-tetraen-10-yl)benzoic acid as brown solid. LC-MS: (ES, m/z): 772 [M+H]$^+$.

Synthesis of 4-([[(2S)-1,4-dioxan-2-yl]methyl]amino)-3-nitrobenzene-1-sulfonamide: Into a 100-mL round-bottom flask, was placed 4-fluoro-3-nitrobenzene-1-sulfonamide (1.43 g, 0.007 mmol, 1 equiv), 1-[(2S)-1,4-dioxan-2-yl]methanamine hydrochloride (1 g, 6.510 mmol, 1 equiv), THF (30 mL), Cs$_2$CO$_3$ (8.48 g, 0.026 mmol, 4 equiv). The resulting solution was stirred overnight at 50° C. in an oil bath. The solids were collected by filtration. The solid was dried in an oven under reduced pressure. This resulted in 1.82 g (88.10%) of 4-([[(2S)-1,4-dioxan-2-yl]methyl]amino)-3-nitrobenzene-1-sulfonamide as yellow solid. LC-MS: (ES, m/z): M+1:318.

Synthesis of 4-(4-[[2-(4-chlorophenyl)-5-methoxy-5-methylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0ˆ[3,7]]tetradeca-1(9),2,5,7-tetraen-10-yl)benzamide: Into a 40-mL vial, was added 4-(4-[[2-(4-chlorophenyl)-5-methoxy-5-methylcyclohex-1-en-1-yl]methyl]piperazin-1-yl)-2-(4-[[2-(trimethylsilyl)ethoxy]ethyl]-14-oxa-2,4,10-triazatricyclo[7.5.0.0ˆ[3,7]]tetradeca-1(9),2,5,7-tetraen-10-yl)benzoic acid (140.00 mg, 0.18 mmol, 1.00 equiv), DCM (2.00 mL), DMAP (44.28 mg, 0.36 mmol, 2 equiv), 4-[[(2S)-1,4-dioxan-2-ylmethyl]amino]-3-nitrobenzenesulfonamide (69.00 mg, 0.21 mmol, 1.20 equiv), EDCI (41.8 mg, 0.21 mmol, 1.20 equiv). The resulting solution was stirred for 12 h at 30° C. The resulting solution was diluted with 10 mL of $H_2O$. The resulting solution was extracted with 4×10 mL of ethyl acetate and the organic layers combined. The resulting mixture was washed with 1×20 mL of brine. The mixture was dried over anhydrous sodium sulfate and concentrated. The residue was applied onto Pre-TLC with dichloromethane/methanol (95:5). This resulted in 135 mg (69.50%) of 4-(4-[[2-(4-chlorophenyl)-5-methoxy-5-methylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0ˆ[3,7]]tetradeca-1(9),2,5,7-tetraen-10-yl)benzamide as yellow solid. LC-MS: (ES, m/z): 1071 $[M+H]^+$.

Synthesis of 4-(4-[[2-(4-chlorophenyl)-5-methoxy-5-methylcyclohex-1-en-1-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0ˆ[3,7]]tetradeca-1(9),2,5,7-tetraen-10-yl]benzamide: Into a 40-mL vial, was added 4-(4-[[2-(4-chlorophenyl)-5-methoxy-5-methylcyclohex-1-en-1-yl]methyl]piperazin-1-yl)-N-(4-[[(2S)-1,4-dioxan-2-ylmethyl]amino]-3-nitrobenzenesulfonyl)-2-(4-[[2-(trimethylsilyl)ethoxy]methyl]-14-oxa-2,4,10-triazatricyclo[7.5.0.0ˆ[3,7]]tetradeca-1(9),2,5,7-tetraen-10-yl)benzamide (135 mg, 0.125 mmol, 1.00 equiv), THF (4.00 mL), ethylenediamine (150.00 mg, 2.50 mmol, 20.0 equiv), TBAF 1M in THF (2.50 mL, 2.50 mmol, 20.0 equiv). The resulting solution was stirred for 8 h at 70° C. The reaction mixture was cooled to RT. The resulting solution was diluted with 10 mL of $H_2O$. The resulting solution was extracted with 4×10 mL of ethyl acetate and the organic layers combined. The resulting mixture was washed with 20 mL of brine. The mixture was dried over anhydrous sodium sulfate and concentrated. The residue was applied onto a silica gel column with dichloromethane/methanol (95:5). The crude product (50 mg) was purified by Flash-Prep-HPLC with the following conditions (IntelFlash-1): Column, C18 silica gel; mobile phase, $CH_3CN:H_2O$ (0.05$NH_3·H_2O$)=10% increasing to $CH_3CN:H_2O$ (0.05$NH_3·H_2O$)=50 within 6; Detector, 220. 23 mg product was obtained. This resulted in 23 mg (25.30%) of 4-(4-[[2-(4-chlorophenyl)-5-methoxy-5-methylcyclohex-1-en-1-yl]methyl]piperazin-1-yl)-N-(4-[[(2S)-1,4-dioxan-2-ylmethyl]amino]-3-nitrobenzenesulfonyl)-2-[14-oxa-2,4,10-triazatricyclo[7.5.0.0ˆ[3,7]]tetradeca-1(9),2,5,7-tetraen-10-yl]benzamide as yellow solid. LC-MS: (ES, m/z): 941 $[M+H]^{+1}$H NMR (300 MHz, DMSO, ppm): δ 11.93 (s, 1H), 8.81 (s, 1H), 8.70 (s, 1H), 8.45 (s, 1H), 7.98 (m, 2H), 7.31 (s, 1H), 7.13 (s, 1H), 7.08-6.94 (m, 3H), 6.74 (s, 2H), 6.66 (m, 1H), 6.20 (s, 1H), 4.08-3.54 (m, 8H), 3.47 (m, 2H), 3.29 (s, 8H), 2.84 (s, 2H), 2.61-2.04 (m, 10H), 1.89 (m, 1H), 1.80-1.63 (m, 2H), 1.28 (s, 3H).

The compounds below are prepared by methods substantially identical, similar, or analogous to those disclosed in above Schemes and Examples:

| Example | Chemical Name | m/z(MH$^+$) |
|---|---|---|
| Cpd-2 | (S)-N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(7,8-dihydro-1H-pyrrolo[2',3':5,6]pyrido[3,2-b][1,4]oxazepin-5(6H)-yl)benzamide | 925 |

Biological Example 1: BCL-2 Competition Binding (Fluorescence Polarization) Assay The fluorescence-labeled 23 amino acid peptide BH3 was purchased from CalBiochem (NLWAAQRYGRELRRMSDKFVD). An unbound Fluorescein labeled BH3 peptide emits random light with respect to the plane of polarization plane of excited light, resulting in a lower polarization degree (mP) value. When the peptide is bound to BCL-2, the complex tumble slower and the emitted light can have a higher level of polarization, resulting in a higher mP value. This binding assay was performed in 96-well plate and with each assay contained 15 and 30 nM of labeled peptide and purified BCL-2 protein (purchased from R&D Systems, Inc). The assay buffer contained 20 mM Hepes (pH 7.0), 50 mM KCl, 5 mM $MgCl_2$, 20 mM $Na_2MoO_4$, 0.1 mg/ml Bovine Gamma Globulin and 0.01% NP40. Compounds were diluted in DMSO and added to the final assay with concentration range from 20 μM to 2 nM. The polarization degree (mP) value was determined by BioTek Synergy II with background subtraction after 3 hours of incubation at room temperature. $IC_{50}$ was calculated using Prism software with sigmoidal dose-response curve fitting. ABT-737 was used as reference compound. Such assays, carried out with a range of doses of test compounds, allowed the determination of an approximate $IC_{50}$ value. Although the inhibitory properties of the compounds of the present invention vary with structural change as expected, the activity generally exhibited by these agents was in the range of $IC_{50}$=0.1-1000 nM.

The following table lists the $IC_{50}$ values of certain compounds of the invention.

| Compound | BCL2 IC50 (nM) |
|---|---|
| Example 27 | 0.3 |
| Example 32 | 1.2 |
| Example 33 | 42.6 |
| Example 34 | 122 |
| Example 35 | 27 |
| Example 37 | 0.3 |
| Example 37 | 0.5 |
| Example 38 | 47 |
| Example 39 | 1.5 |
| Example 41 | 0.1 |
| Example 42 | 4.1 |
| Example 43 | 1.5 |
| Example 43 | 0.8 |
| Example 44 | 1.3 |
| Example 44 | 0.8 |
| Example 45 | 1.0 |
| Example 45 | 1.6 |
| Example 46 | 0.6 |
| Example 46 | 0.5 |
| Example 47 | 0.5 |

| Compound | BCL2 IC50 (nM) |
|---|---|
| Example 47 | 0.7 |
| Example 50 | 0.6 |
| Example 51 | 0.9 |
| Example 53 | 1.2 |
| Example 54 | 0.6 |
| Example 55 | 1.1 |
| Example 56 | 0.4 |
| Example 57 | 0.5 |
| Example 58 | 0.3 |
| Example 59 | 1.1 |
| Example 60 | 0.4 |
| Example 69 | 0.6 |
| Example 70 | 0.1 |
| Example 71 | 0.6 |
| Example 72 | 0.01 |
| Example 73 | 0.9 |
| Example 74 | 0.3 |
| Example 75 | 0.6 |
| Example 76 | 0.3 |
| Example 77 | 0.08 |

Biological Example 2: In Vitro Anti-Proliferation Assay in BCL-2-Dependent Acute Lymphoblastic Leukemia (ALL) Cell Line RS4;11

Cell antiproliferation was assayed by PerkinElmer ATPlite™ Luminescence Assay System. Briefly, the various test cancer cell lines were plated at a density of about $1 \times 10^4$ cells per well in Costar 96-well plates, and were incubated with different concentrations of compounds for about 72 hours in medium supplemented with 5% FBS or 10% normal human serum (NHS). One lyophilized substrate solution vial was then reconstituted by adding 5 mL of substrate buffer solution, and was agitated gently until the solution was homogeneous. About 50 μL of mammalian cell lysis solution was added to 100 μL of cell suspension per well of a microplate, and the plate was shaken for about five minutes in an orbital shaker at 700 rpm. This procedure was used to lyse the cells and to stabilize the ATP. Next, 50 μL substrate solution was added to the wells and microplate was shaken for five minutes in an orbital shaker at 700 rpm. Finally, the luminescence was measured by a PerkinElmer TopCount® Microplate Scintillation Counter. Such assays, carried out with a range of doses of test compounds, allowed the determination of the cellular anti-antiproliferative $IC_{50}$ of the compounds of the present invention. The following table lists the $IC_{50}$ values of certain compounds of the invention.

The following table lists the $IC_{50}$ values of certain compounds of the invention.

| Compound | RS4; 11 IC50 (nM) |
|---|---|
| Example 27 | 21 |
| Example 32 | 6.9 |
| Example 36 | 0.95 |
| Example 37 | 25.6 |
| Example 37 | 21.4 |
| Example 39 | 544 |
| Example 40 | 5.6 |
| Example 41 | 1.1 |
| Example 42 | >1000 |
| Example 43 | 158 |
| Example 43 | 9.9 |
| Example 44 | 21 |
| Example 44 | 15 |
| Example 45 | 2.5 |
| Example 45 | 6.3 |
| Example 46 | 1.6 |
| Example 46 | 1.3 |
| Example 47 | 1.1 |
| Example 47 | 0.3 |
| Example 50 | 43 |
| Example 51 | 62 |
| Example 53 | 79 |
| Example 54 | 49.6 |
| Example 55 | 75 |
| Example 56 | 63.7 |
| Example 57 | 68 |
| Example 58 | 102 |
| Example 59 | 84 |
| Example 60 | 10 |
| Example 69 | 28.6 |
| Example 70 | 186 |
| Example 71 | 192 |
| Example 72 | 0.3 |
| Example 73 | 3.1 |
| Example 74 | 1.7 |
| Example 75 | 2.7 |
| Example 76 | 54 |
| Example 77 | 0.8 |

Biological Example 3: Mice PK Study

The pharmacokinetics of compounds were evaluated in CD-1 mouse via Intravenous and Oral Administration. The IV dose was administered as a slow bolus in the Jugular vein, and oral doses were administered by gavage. The formulation for IV dosing was 5% DMSO in 20% HPBCD in water, and the PO formulation was 2.5% DMSO, 10% EtOH, 20% Cremphor EL, 67.5% D5W. The PK time point for the IV arm was 5, 15, 30 min, 1, 2, 4, 6, 8, 12, 24 hours post dose, and for PO arm was 15, 30 min, 1, 2, 4, 6, 8, 12, 24 hours post dose. Approximately 0.03 mL blood was collected at each time point. Blood of each sample was transferred into plastic micro centrifuge tubes containing EDTA-K2 and collect plasma within 15 min by centrifugation at 4000 g for 5 minutes in a 4° C. centrifuge. Plasma samples were stored in polypropylene tubes. The samples were stored in a freezer at −75±15° C. prior to analysis. Concentrations of compounds in the plasma samples were analyzed using a LC-MS/MS method. WinNonlin (Phoenix™, version 6.1) or other similar software was used for pharmacokinetic calculations. The following pharmacokinetic parameters were calculated, whenever possible from the plasma concentration versus time data: IV administration: $C_0$, CL, $V_d$, $T_{1/2}$, $AUC_{inf}$, $AUC_{last}$, MRT, Number of Points for Regression; PO administration: $C_{max}$, $T_{max}$, $T_{1/2}$, $AUC_{inf}$, $AUC_{last}$, F %, Number of Points for Regression. The pharmacokinetic data was described using descriptive statistics such as mean, standard deviation. Additional pharmacokinetic or statistical analysis was performed at the discretion of the contributing scientist, and was documented in the data summary.

Biological Example 4: In Vivo Xenograft Studies

Compound of Example 3 is selected for in vivo studies in the BCL-2-dependent acute lymphoblastic leukemia (ALL) RS4;11 xenograft model. The CB.17 SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach 100-200 mm³, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/ΔC if ΔT>0. When tumor regression occurred (ΔT<0), however, the following formula is used: % T/T0=100×ΔT/T0. Values of <42% are considered significant.

What is claimed is:

1. A compound of Formula (A), or an N-oxide thereof, or a pharmaceutically acceptable salt, solvate, polymorph, tautomer, stereoisomer, an isotopic form, or a prodrug of said compound of Formula (A) or N-oxide thereof:

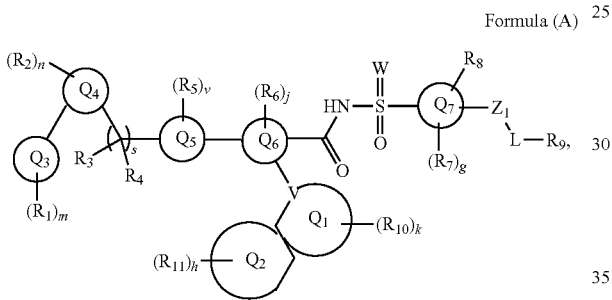

Formula (A)

wherein

V is N or P(O);

$Q_1$ is 7-9 membered heterocycloalkyl, 7-9 membered heterocycloalkenyl, or 7-9 membered heteroaryl;

$Q_2$ is 6-membered heterocycloalkyl, 6-membered heterocycloalkenyl, 6-membered aryl, or 6-membered heteroaryl;

$Q_3$ is cycloalkyl, cycloalkenyl, bridged cycloalkyl, heterocycloalkyl, heterocycloalkenyl, aryl or heteroaryl;

$Q_4$ is cycloalkyl, cycloalkenyl, heterocycloalkyl, heterocycloalkenyl, aryl, or heteroaryl;

$Q_5$ is 6-membered heterocycloalkyl, or 6-membered heterocycloalkenyl;

$Q_6$ is 6-membered aryl, or 5-6 membered heteroaryl;

$Q_7$ is 6-membered aryl or 5-6 membered heteroaryl, each of which is optionally fused with a benzene, heteroarene, cycloalkane, cycloalkene, heterocycloalkane, or heterocycloalkene;

each of $R_1$, $R_2$, $R_3$, $R_4$, $R_5$, $R_6$, $R_7$, $R_8$, $R_{10}$, and $R_{11}$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, —$P(O)R_bR_c$, -alkyl-$P(O)R_bR_c$, —$S(O)(=N(R_b))R_c$, —$N=S(O)R_bR_c$, =$NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_9$ is $R_{9A}$ or $R_{9B}$;

$R_{9A}$ is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $C(O)N(R_b)R_c$, $N(R_b)C(O)R_c$, —$P(O)R_bR_c$, -alkyl-$P(O)R_bR_c$, —$S(O)(=N(R_b))R_c$, —$N=S(O)R_bR_c$, —$NR_b$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$;

$R_{9B}$ is a small molecule E3 ubiquitin ligase binding moiety that binds an E3 ubiquitin ligase;

$R_d$, independently, is H, D, alkyl, spiroalkyl, alkenyl, alkynyl, halo, cyano, amine, nitro, hydroxy, =O, —$P(O)R_{bb}R_{cc}$, -alkyl-$P(O)R_{bb}R_{cc}$, —$S(O)(=N(R_{bb}))R_{cc}$, —$N=S(O)R_{bb}R_{cc}$, =$NR_{bb}$, $C(O)NHOH$, $C(O)OH$, $C(O)NH_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_a$, $R_b$, $R_c$, $R_{bb}$ and $R_{cc}$, independently, is H, D, alkyl, spiroalkyl, alkenyl, alkynyl, alkoxy, alkoxyalkyl, haloalkyl, hydroxyalkyl, aminoalkyl, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$, independently, is H, D, alkyl, spiroalkyl, alkenyl, alkynyl, halo, cyano, amine, nitro, hydroxy, =O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

$Z_1$ is a bond, $(CH_2)_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O$_2$)N(H), N(H)S(O$_2$), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, OC(O)N(H)(CH$_2$)$_{p+1}$N(H)(CH$_2$)$_q$, a bivalent alkenyl group, or a bivalent alkynyl group;

L is $L_1$ or $L_2$;

$L_1$ is bond, alkenyl, alkynyl, cycloalkyl, cycloalkenyl, heterocycloalkyl, heterocycloalkenyl, aryl, or heteroaryl, in which said alkenyl, alkynyl, cycloalkyl, cycloalkenyl, heterocycloalkyl, heterocycloalkenyl, aryl, or heteroaryl is optionally substituted with one or more $R_d$;

$L_2$ is an alkyl in which one or more -$L_i$- are optionally inserted between any two adjacent carbon atoms;

-$L_i$- is —N($R_a$)—, —O—, —S—, —C(O)—, —S(O$_2$)—, —OC(O)—, —C(O)O—, —OSO$_2$—, —S(O$_2$)O—, —C(O)S—, —SC(O)—, —C(O)C(O)—, —C(O)N($R_a$)—, —N($R_a$)C(O)—, —S(O$_2$)N($R_a$)—, —N($R_a$)S(O$_2$)—, —OC(O)O—, —OC(O)S—, —OC(O)N($R_a$)—, —N($R_a$)C(O)O—, —N($R_a$)C(O)S—, —N($R_a$)C(O)N($R_a$)—, a bivalent alkenyl group, a bivalent alkynyl group, a bivalent cycloalkyl group, a bivalent heterocycloalkyl group, a bivalent aryl group, a bivalent heteroaryl group;

W is O or $N(R_a)$;

two of $R_1$ group, taken together with the atoms to which they are attached, may optionally form a cycloalkyl or heterocycloalkyl, in which said cycloalkyl or heterocycloalkyl of $R_1$, is optionally substituted with one or more $R_d$;

two of $R_2$ group, taken together with the atom(s) to which they are attached, may optionally form a cycloalkyl or heterocycloalkyl, in which said cycloalkyl or heterocycloalkyl of $R_2$, is optionally substituted with one or more $R_d$;

$R_3$ and $R_4$ group, taken together with the atom to which they are attached, may optionally form a cycloalkyl or heterocycloalkyl, in which said cycloalkyl or heterocycloalkyl of $R_3$ and $R_4$, is optionally substituted with one or more $R_d$;

two of $R_5$ group, taken together with the atom(s) to which they are attached, may optionally form a cycloalkyl or heterocycloalkyl, in which said cycloalkyl or heterocycloalkyl of $R_5$, is optionally substituted with one or more $R_d$;

two of $R_6$ group, taken together with the atoms to which they are attached, may optionally form a cycloalkyl or heterocycloalkyl, in which said cycloalkyl or heterocycloalkyl of $R_6$, is optionally substituted with one or more $R_d$;

two of $R_7$ group, taken together with the atoms to which they are attached, may optionally form a cycloalkyl or heterocycloalkyl, in which said cycloalkyl or heterocycloalkyl of $R_7$, is optionally substituted with one or more $R_d$;

two of $R_{10}$ group, taken together with the atom(s) to which they are attached, may optionally form a cycloalkyl or heterocycloalkyl, in which said cycloalkyl or heterocycloalkyl of $R_{10}$, is optionally substituted with one or more $R_d$;

two of $R_{11}$ group, taken together with the atom(s) to which they are attached, may optionally form a cycloalkyl, heterocycloalkyl, aryl, or heteroaryl, in which said cycloalkyl, heterocycloalkyl, aryl, or heteroaryl of $R_{11}$, is optionally substituted with one or more $R_d$;

$R_2$ and $R_5$ group, taken together with the atoms to which they are attached, may optionally form a cycloalkyl or heterocycloalkyl, in which said cycloalkyl or heterocycloalkyl of $R_2$ and $R_5$, is optionally substituted with one or more $R_d$;

$R_3$ and $R_5$ group, taken together with the atoms to which they are attached, may optionally form a cycloalkyl or heterocycloalkyl, in which said cycloalkyl or heterocycloalkyl of $R_3$ and $R_5$, is optionally substituted with one or more $R_d$;

$R_b$ and $R_c$ group, taken together with the atom to which they are attached, may optionally form a cycloalkyl, or heterocycloalkyl, in which said cycloalkyl or heterocycloalkyl of $R_b$ and $R_c$, is optionally substituted with one or more $R_e$;

two of $R_d$ group, taken together with the atom(s) to which they are attached, may optionally form a cycloalkyl, or heterocycloalkyl, in which said cycloalkyl or heterocycloalkyl of $R_d$, is optionally substituted with one or more $R_e$;

two of $R_e$ group, taken together with the atom(s) to which they are attached, may optionally form a cycloalkyl or heterocycloalkyl, in which said cycloalkyl or heterocycloalkyl of $R_e$ is optionally substituted with one or more groups selected from H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

each of g and j is, independently, 0, 1, 2, or 3;

each of n, v and k is, independently, 0, 1, 2, 3, 4, 5, 6, 7, or 8;

s is 0 or 1; and each of h, m, p, and q is, independently, 0, 1, 2, 3, 4, or 5.

2. The compound according to claim 1, or an N-oxide thereof, or a pharmaceutically acceptable salt, solvate, polymorph, tautomer, stereoisomer, an isotopic form, or a prodrug thereof, wherein the compound is represented by Formula (A-1):

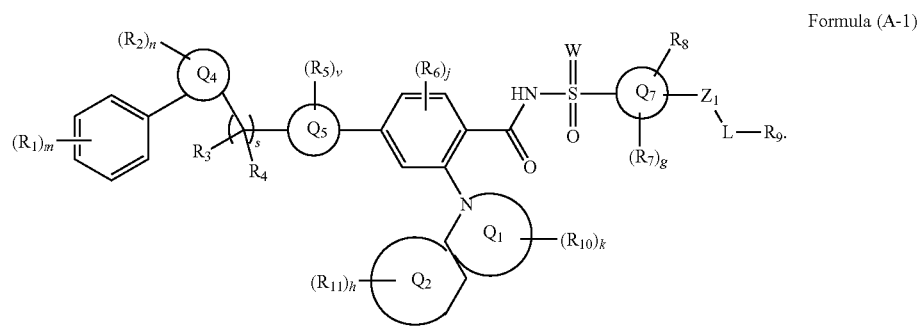

Formula (A-1)

3. The compound according to claim 2 or an N-oxide thereof, or a pharmaceutically acceptable salt, solvate, polymorph, tautomer, stereoisomer, an isotopic form, or a prodrug thereof, wherein the compound is represented by Formula (A-2):

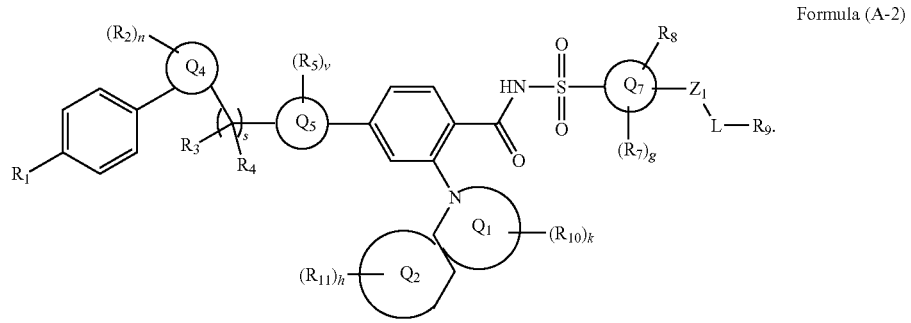

Formula (A-2)

4. The compound according to claim 3 or an N-oxide thereof, or a pharmaceutically acceptable salt, solvate, polymorph, tautomer, stereoisomer, an isotopic form, or a prodrug thereof, wherein the compound is represented by Formula (A-3):

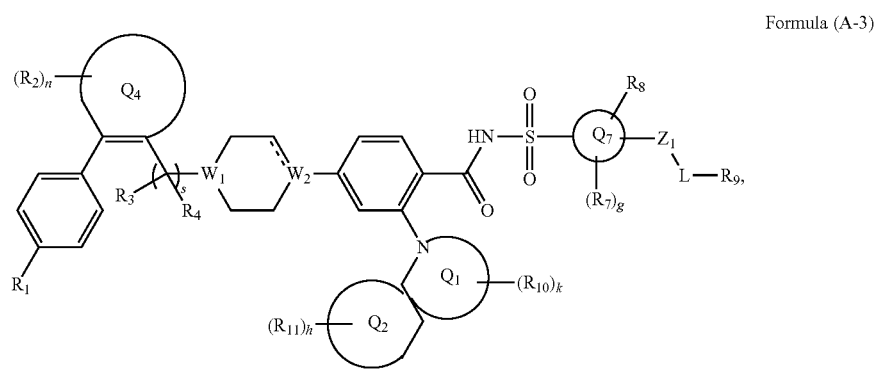

Formula (A-3)

wherein "—" is absent or a bond; $W_1$ is N or CH; and $W_2$ is N or C or CH.

5. The compound according to claim 4 or an N-oxide thereof, or a pharmaceutically acceptable salt, solvate, polymorph, tautomer, stereoisomer, an isotopic form, or a prodrug thereof, wherein the compound is represented by Formula (A-4):

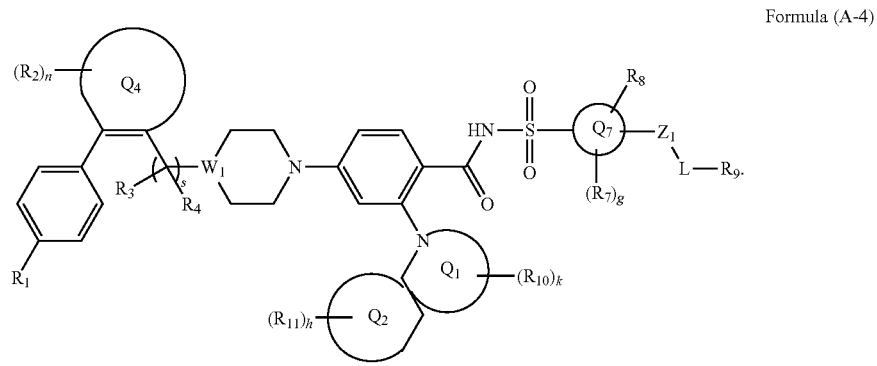

Formula (A-4)

6. The compound according to claim 5 or an N-oxide thereof, or a pharmaceutically acceptable salt, solvate, polymorph, tautomer, stereoisomer, an isotopic form, or a prodrug thereof, wherein the compound is represented by Formula (A-5):

Formula (A-5)

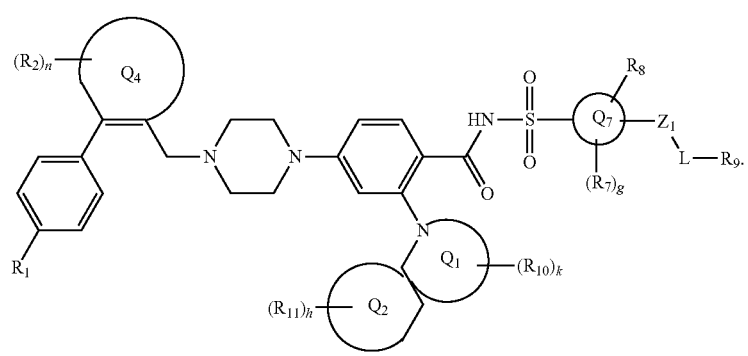

7. The compound according to claim 6, or an N-oxide thereof, or a pharmaceutically acceptable salt, solvate, polymorph, tautomer, stereoisomer, an isotopic form, or a prodrug thereof, wherein

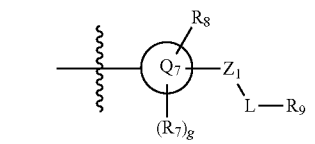

is

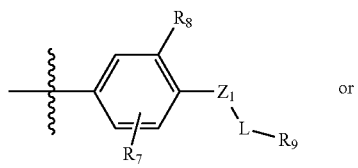

or

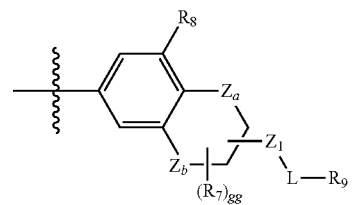

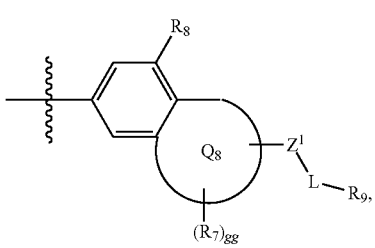

in which $Q_8$ is 5-7 membered heterocycloalkyl, 5-7 membered heterocycloalkenyl, phenyl, or 5-7 membered heteroaryl; and gg is 0, 1, 2, 3, or 4.

8. The compound according to claim 7, or an N-oxide thereof, or a pharmaceutically acceptable salt, solvate, polymorph, tautomer, stereoisomer, an isotopic form, or a prodrug thereof, wherein

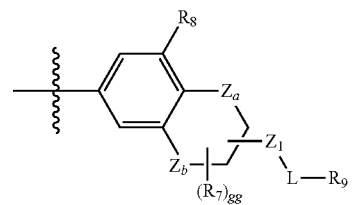

is

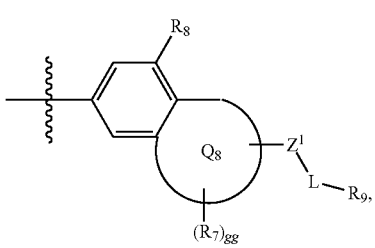

in which each $Z_a$ and $Z_b$ is independently —O—, —CH$_2$—, —C(O)—, —N(R$_a$)—, —S—, —S(O)—, —S(O$_2$)—, —S(O)(=N(R$_a$))—, —P(O)(R$_a$)—; wherein R$_a$ of $Z_a$ and $Z_b$, independently, is H, D, C$_1$-C$_6$alkyl, C$_2$-C$_6$alkenyl, C$_1$-C$_6$alkylcarbonyl, C$_1$-C$_6$alkoxycarbonyl, C$_3$-C$_6$cycloalkyl, 5-8 membered monocyclic heterocycloalkyl, C$_6$-C$_{14}$aryl, or 5-8 membered monocyclic heteroaryl, in which said C$_1$-C$_6$alkyl, C$_3$-C$_6$cycloalkyl, 5-8 membered monocyclic heterocycloalkyl, C$_6$-C$_{14}$aryl, 5-8 membered monocyclic heteroaryl is optionally substituted with one or more R$_e$.

9. The compound according to claim 8, or an N-oxide thereof, or a pharmaceutically acceptable salt, solvate, polymorph, tautomer, stereoisomer, an isotopic form, or a prodrug thereof, wherein

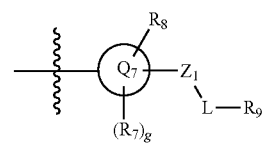

is

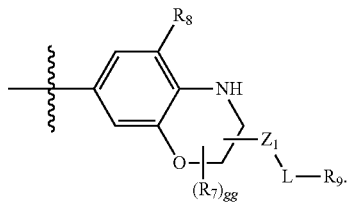

10. The compound according to claim 9, or an N-oxide thereof, or a pharmaceutically acceptable salt, solvate, polymorph, tautomer, stereoisomer, an isotopic form, or a prodrug thereof, wherein $Z_1$ is absent or $(CH_2)_p$;

L is $L_1$ and $L_1$ is bond, and $R_9$ is 5-7 membered heterocyclyl or 7-10 membered bridged heterocyclyl, each of which is optionally substituted with 1-3 groups selected from halo, —OH, —CN, —COOH, —NH$_2$, —N(CH$_3$)$_2$, —(C$_1$-C$_4$)alkyl, and —(C$_1$-C$_4$)alkoxy.

11. The compound according to claim 6, or an N-oxide thereof, or a pharmaceutically acceptable salt, solvate, polymorph, tautomer, stereoisomer, an isotopic form, or a prodrug thereof, wherein

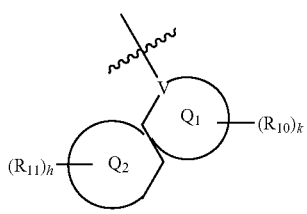

is

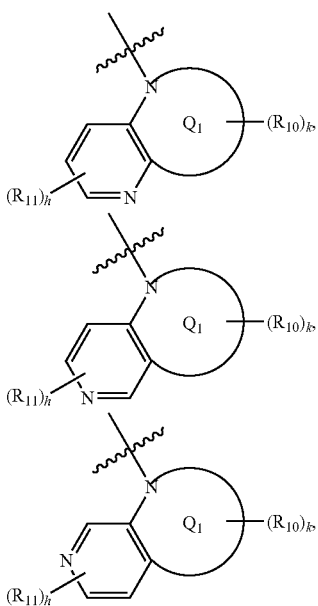

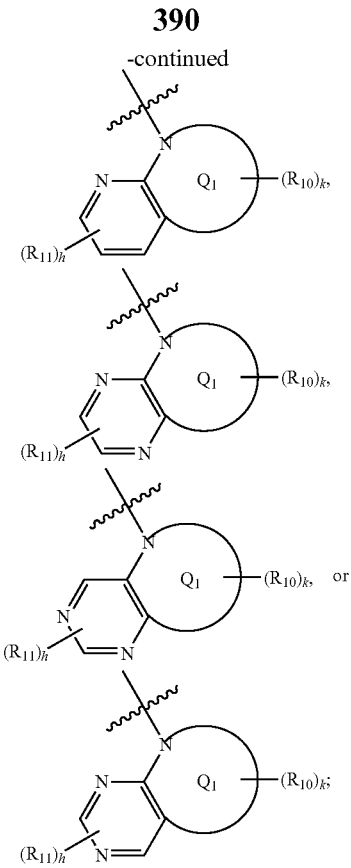

and h is 0, 1, or 2.

12. The compound according to claim 6, or an N-oxide thereof, or a pharmaceutically acceptable salt, solvate, polymorph, tautomer, stereoisomer, an isotopic form, or a prodrug thereof, wherein

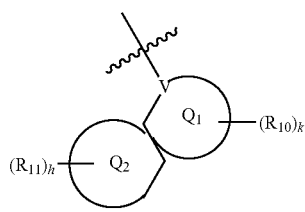

is

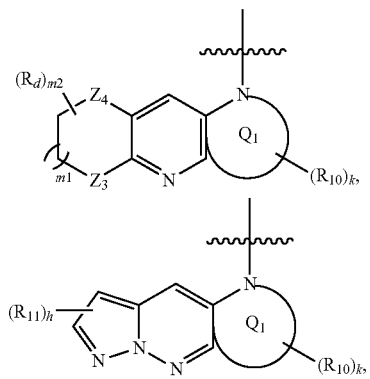

-continued

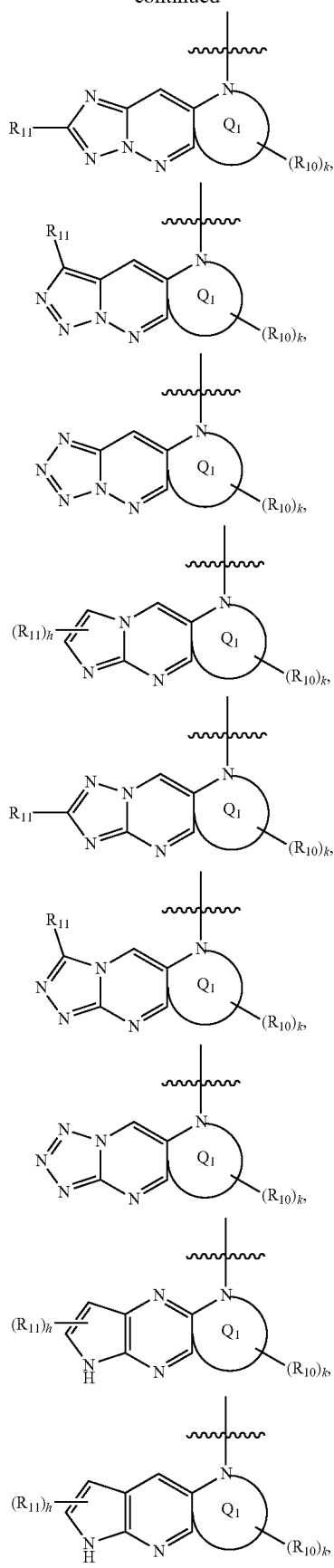

-continued

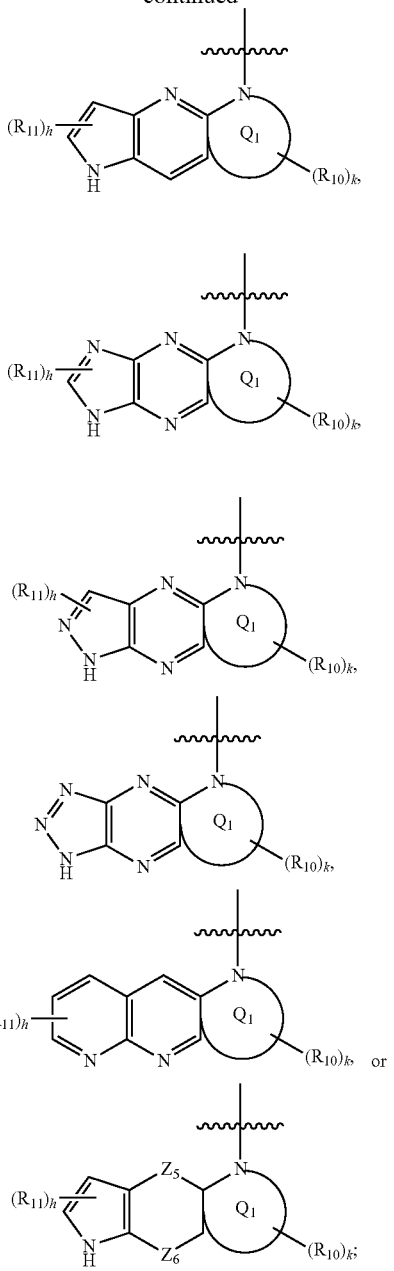

h is 0, 1, or 2;

each of $m_1$ and $m_2$, independently, is 0, 1, or 2; and each of $Z_3$, $Z_4$, $Z_5$ and $Z_6$, independently, is a bond, $(CH_2)_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O$_2$)N(H), N(H)S(O$_2$), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group.

13. The compound according to claim 12 or an N-oxide thereof, or a pharmaceutically acceptable salt, solvate, polymorph, tautomer, stereoisomer, an isotopic form, or a prodrug thereof, wherein is

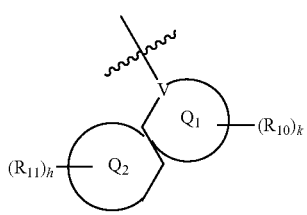

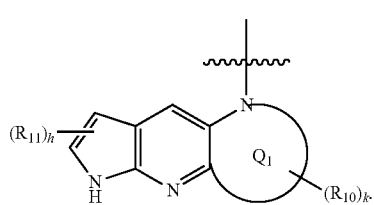

14. The compound according to claim 13 or an N-oxide thereof, or a pharmaceutically acceptable salt, solvate, polymorph, tautomer, stereoisomer, an isotopic form, or a prodrug thereof, wherein

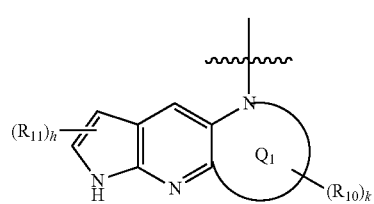

is

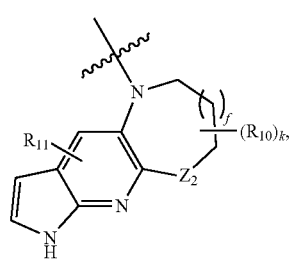

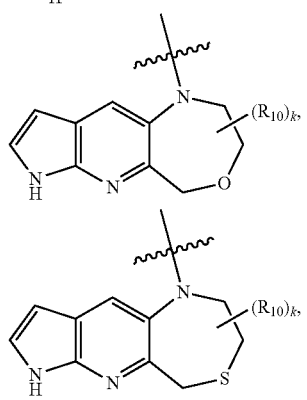

-continued

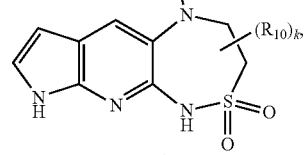

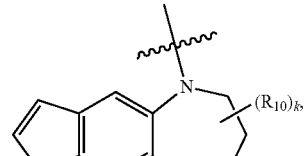

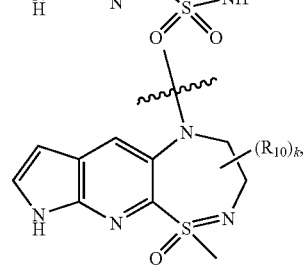

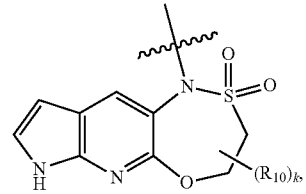

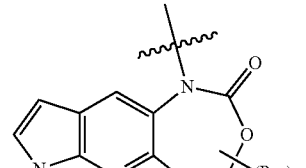

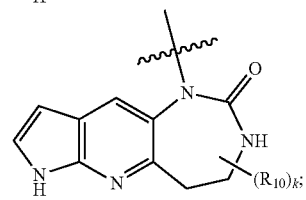

wherein $Z_2$ is —O—, —CH$_2$—, —C(O)—, —N(R$_a$)—, —S—, —S(O)—, —S(O$_2$)—, —S(O)(=N(R$_a$))—, —P(O)(R$_a$)—; wherein R$_a$ of $Z_2$, independently, is H, D, $C_1$-$C_6$alkyl, $C_2$-$C_6$alkenyl, $C_1$-$C_6$alkylcarbonyl, $C_1$-$C_6$alkoxycarbonyl, $C_3$-$C_6$cycloalkyl, 5-8 membered monocyclic heterocycloalkyl, $C_6$-$C_{14}$aryl, or 5-8 membered monocyclic heteroaryl, in which said $C_1$-$C_6$alkyl, $C_3$-$C_6$cycloalkyl, 5-8 membered monocyclic heterocycloalkyl, $C_6$-$C_{14}$aryl, 5-8 membered monocyclic heteroaryl is optionally substituted with one or more R$_e$;

k is 0, 1, 2, 3, or 4; and f is 1, 2, or 3.

15. The compound according to claim 14 or an N-oxide thereof, or a pharmaceutically acceptable salt, solvate, polymorph, tautomer, stereoisomer, an isotopic form, or a prodrug thereof, wherein

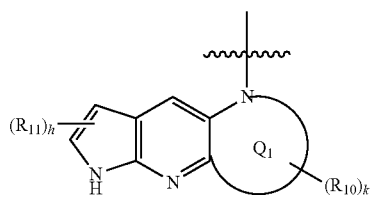

is

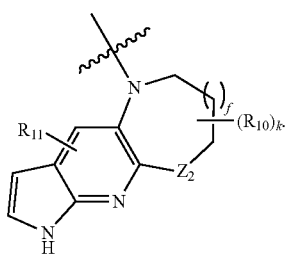

16. The compound according to claim 15, or an N-oxide thereof, or a pharmaceutically acceptable salt, solvate, polymorph, tautomer, stereoisomer, an isotopic form, or a prodrug thereof, wherein $R_{10}$ is aryl, heteroaryl, or

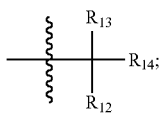

$R_{12}$ is H, D, alkyl, alkenyl, alkynyl, cycloalkyl, cycloalkenyl, heterocycloalkyl, heterocycloalkenyl, aryl, heteroaryl, halo, nitro, oxo, cyano, $OR_a$, $SR_a$, alkyl-$R_a$, $NH(CH_2)_pR_a$, $C(O)R_a$, $S(O)R_a$, $SO_2R_a$, $C(O)OR_a$, $OC(O)R_a$, $NR_bR_c$, $P(O)R_bR_c$, alkyl-$P(O)R_bR_c$, $C(O)N(R_b)R_c$, $N(R_b)C(O)R_c$, $S(O)(=N(R_b))R_c$, $-N=S(O)R_bR_c$, $SO_2N(R_b)R_c$, or $N(R_b)SO_2R_c$, in which said cycloalkyl, cycloalkenyl, heterocycloalkyl, heterocycloalkenyl, aryl, heteroaryl is optionally substituted with one or more $R_d$; and each of $R_{13}$, and $R_{14}$, independently, is H, D, alkyl, halo-alkyl, or $R_{13}$ and $R_{14}$, taken together with the atom to which they are attached, may optionally form a cycloalkyl or heterocycloalkyl, in which said cycloalkyl or heterocycloalkyl is optionally substituted with one or more $R_d$.

17. The compound according to claim 15, or an N-oxide thereof, or a pharmaceutically acceptable salt, solvate, polymorph, tautomer, stereoisomer, an isotopic form, or a prodrug thereof, wherein

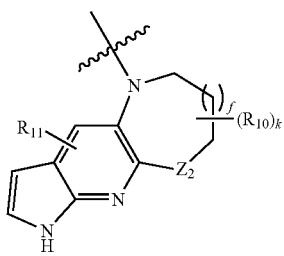

is

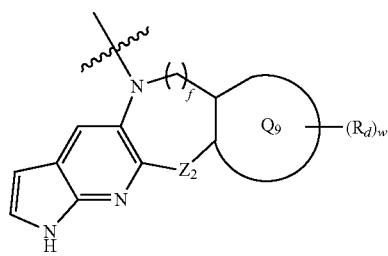

in which $Q_9$ is a $C_4$-$C_6$ cycloalkyl, 4-6 membered heterocycloalkyl, phenyl, or 5-6 membered heteroaryl; and w is 0, 1, 2, 3, or 4.

18. The compound according to claim 17, or an N-oxide thereof, or a pharmaceutically acceptable salt, solvate, polymorph, tautomer, stereoisomer, an isotopic form, or a prodrug thereof, wherein $Q_9$ is $C_5$-$C_6$ cycloalkyl, 5-6 membered heterocycloalkyl, or 5-6 membered heteroaryl; each of which is optionally substituted with 1 to 3 groups selected from halogen, $C_1$-$C_4$ alkyl, $C_1$-$C_4$ haloalkyl, $C_1$-$C_4$ alkoxy, —OH, CN, and $NH_2$.

19. The compound according to claim 1, or an N-oxide thereof, or a pharmaceutically acceptable salt, solvate, polymorph, tautomer, stereoisomer, an isotopic form, or a prodrug thereof, wherein $R_9$ is $R_{9B}$.

20. The compound according to claim 19 or an N-oxide thereof, or a pharmaceutically acceptable salt, solvate, polymorph, tautomer, stereoisomer, an isotopic form, or a prodrug thereof, wherein said E3 ubiquitin ligase is Von Hippel-Lindau (VLM), cereblon (CLM), mouse double-minute homolog2 (MLM), and IAP (ILM).

21. The compound according to claim 19, or an N-oxide thereof, or a pharmaceutically acceptable salt, solvate, polymorph, tautomer, stereoisomer, an isotopic form, or a prodrug thereof, wherein $R_9$ is

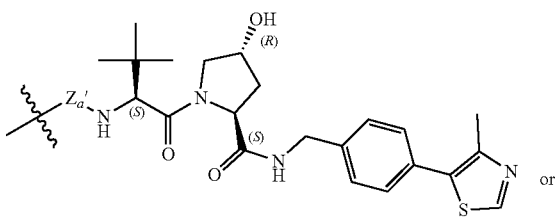

or

-continued

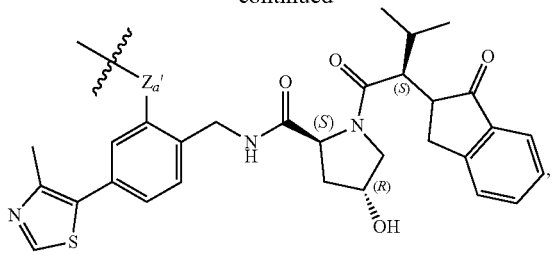

wherein
$Z_a'$ is a bond, $(CH_2)_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O$_2$)N(H), N(H)S(O$_2$), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, OC(O)N(H)$(CH_2)_{p+1}N(H)(CH_2)_q$, a bivalent alkenyl group, or a bivalent alkynyl group.

22. The compound according to claim 19, or an N-oxide thereof, or a pharmaceutically acceptable salt, solvate, polymorph, tautomer, stereoisomer, an isotopic form, or a prodrug thereof, wherein $R_9$ is

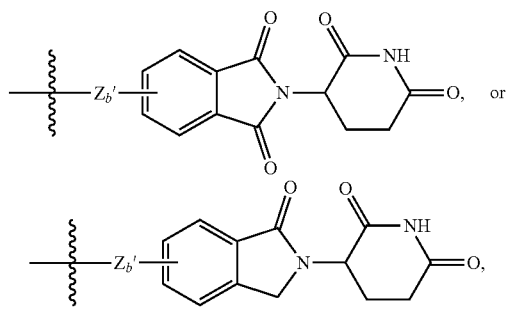

wherein
$Z_b'$ is a bond, $(CH_2)_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O$_2$)N(H), N(H)S(O$_2$), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, OC(O)N(H)$(CH_2)_{p+1}N(H)(CH_2)_q$, a bivalent alkenyl group, or a bivalent alkynyl group.

23. The compound according to claim 19, or an N-oxide thereof, or a pharmaceutically acceptable salt, solvate, polymorph, tautomer, stereoisomer, an isotopic form, or a prodrug thereof, wherein L is $L_2$, and $L_2$ is

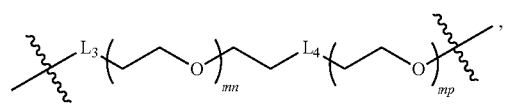

wherein
each of mn and mp is independently an integer of 0 to 12; and
each of $L_3$ and $L_4$ independently, is a bond, $(CH_2)_p$, N(H), O, S, C(O), S(O$_2$), OC(O), C(O)O, OSO$_2$, S(O$_2$)O, C(O)S, SC(O), C(O)C(O), C(O)N(H), N(H)C(O), S(O$_2$)N(H), N(H)S(O$_2$), OC(O)O, OC(O)S, OC(O)N(H), N(H)C(O)O, N(H)C(O)S, N(H)C(O)N(H), $(CH_2)_pN(H)(CH_2)_q$, $(CH_2)_pN(H)C(O)(CH_2)_q$, $(CH_2)_pC(O)N(H)(CH_2)_q$, OC(O)N(H)$(CH_2)_{p+1}N(H)(CH_2)_q$, a bivalent alkenyl group, or a bivalent alkynyl group.

24. The compound according to claim 23 or an N-oxide thereof, or a pharmaceutically acceptable salt, solvate, polymorph, tautomer, stereoisomer, an isotopic form, or a prodrug thereof, wherein said $L_2$ is

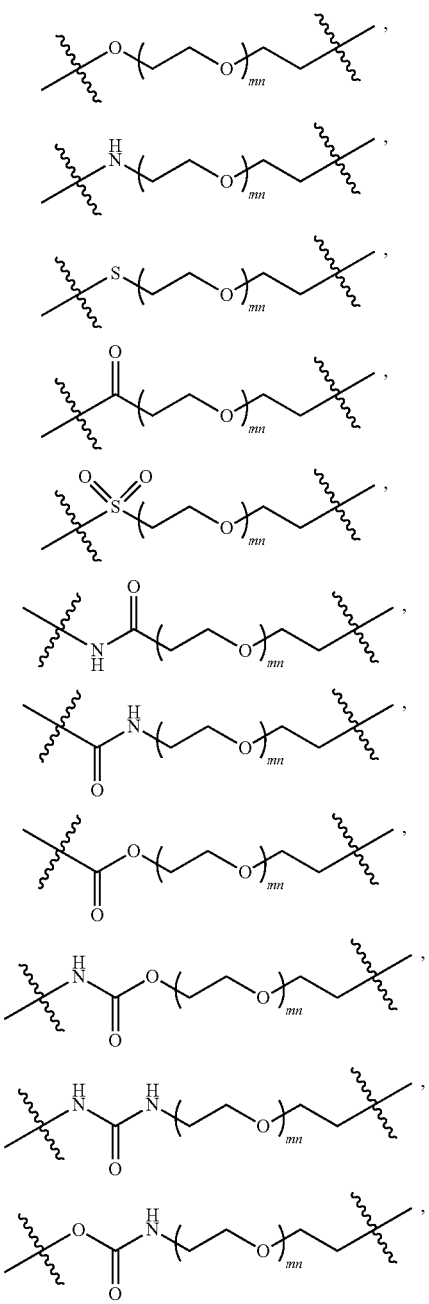

in which mn is 0 to 12.

25. The compound according to claim 1 or an N-oxide thereof, or a pharmaceutically acceptable salt, solvate, polymorph, tautomer, stereoisomer, an isotopic form, or a prodrug thereof, wherein

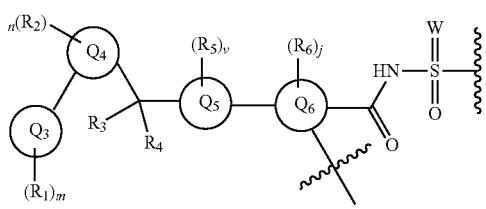

is

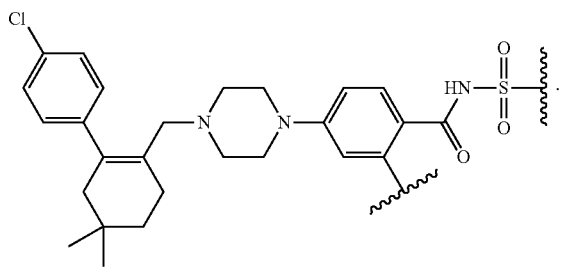 [SMILES: *c1cc(N2CCN(CC3=C(c4ccc(Cl)cc4)CC(C)(C)CC3)CC2)ccc1C(=O)NS(*)(=O)=O]

26. The compound according to claim 25 or an N-oxide thereof, or a pharmaceutically acceptable salt, solvate, polymorph, tautomer, stereoisomer, an isotopic form, or a prodrug thereof, wherein $R_8$ is $NO_2$.

27. The compound according to claim 1 or an N-oxide thereof, or a pharmaceutically acceptable salt, solvate, polymorph, tautomer, stereoisomer, an isotopic form, or a prodrug thereof, wherein the compound is N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-4-(trifluoromethyl)-3,4-dihydro-2H-pyrrolo[3',2' 5,6]pyrido[2,3-b][1,4]oxazepin-1(7H)-yl)benzamide, N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((R)-4-(trifluoromethyl)-3,4-dihydro-2H-pyrrolo[3',2':5,6]pyrido[2,3-b][1,4]oxazepin-1(7H)-yl)benzamide, N-((4-((((S)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-4-(trifluoromethyl)-3,4-dihydro-2H-pyrrolo[3',2':5,6]pyrido[2,3-b][1,4]oxazepin-1(7H)-yl)benzamide, N-((4-((((R)-1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-((S)-4-(trifluoromethyl)-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(6,7,8,9-tetrahydropyrrolo[3',2':5,6]pyrido[2,3-b][1,4]oxazocin-5(1H)-yl)benzamide, (R)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(pyridin-2-yl)-3,4-dihydro-2H-pyrrolo[3',2':5,6]pyrido[2,3-b][1,4]oxazepin-1(7H)-yl)benzamide, 2-(4-(2-aminopropan-2-yl)-3,4-dihydro-2H-pyrrolo[3',2':5,6]pyrido[2,3-b][1,4]oxazepin-1(7H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(4-(2-hydroxypropan-2-yl)-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(4-(1,1,1-trifluoro-2-methylpropan-2-yl)-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(3-(1,1,1-trifluoro-2-methylpropan-2-yl)-3,4-dihydro-2H-pyrrolo[3',2':5,6]pyrido[2,3-b][1,4]oxazepin-1(7H)-yl)benzamide, 4-(4-((4'-chloro-5,5-dimethyl-3,4,5,6-tetrahydro-[1,1'-biphenyl]-2-yl)methyl)piperazin-1-yl)-2-(4-(2-cyanopropan-2-yl)-3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, 4-(4-((4'-chloro-[1,1'-biphenyl]-2-yl)(hydroxy)methyl)piperidin-1-yl)-2-(3,4-dihydro-2H-pyrrolo[3',2':5,6]pyrido[2,3-b][1,4]oxazepin-1(7H)-yl)-N-((3-nitro-4-(((tetrahydro-2H-pyran-4-yl)methyl)amino)phenyl)sulfonyl)benzamide, N—(((S)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N—(((S)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N—(((R)-3-((S)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, N—(((R)-3-((R)-1,4-dioxan-2-yl)-5-nitro-3,4-dihydro-2H-benzo[b][1,4]oxazin-7-yl)sulfonyl)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzamide, (S)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((5-nitro-3-(tetrahydro-2H-pyran-4-yl)-3,4-dihydro-2H-benzo[b][1,4]oxazin-7-yl)sulfonyl)benzamide, (R)-4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((5-nitro-3-(tetrahydro-2H-pyran-4-yl)-3,4-dihydro-2H-benzo[b][1,4]oxazin-7-yl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2,3,5,7-tetrahydro-1H-pyrrolo[3',2':5,6]pyrido[3,2-e][1,4]oxazepin-1-yl)benzamide, (S)—N-((4-(((1,4-dioxan-2-yl)methyl)amino)-3-nitrophenyl)sulfonyl)-4-(4-((4'-chloro-5,5-dimethyl-3,4,5,6-tetrahydro-[1,1'-biphenyl]-2-yl)methyl)piperazin-1-yl)-2-(9,9-difluoro-6,7,8,9-tetrahydropyrrolo[3',2':5,6]pyrido[3,2-b]azepin-5(1H)-yl)benzamide, 4-(4-((4'-chloro-5,5-dimethyl-3,4,5,6-tetrahydro-[1,1'-biphenyl]-2-yl)methyl)piperazin-1-yl)-2-(1,1-dioxido-3,4-dihydro-2H-pyrrolo[3',2':5,6]pyrido[3,2-f][1,2,5]thiadiazepin-5(9H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-oxo-5,7-dihydro-2H-pyrrolo[3',2':5,6]pyrido[3,2-d][1,3]oxazepin-1(4H)-yl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2,3,5,7-tetrahydro-1H-pyrrolo[3',2':5,6]pyrido[3,2-e][1,4]thiazepin-1-yl)benzamide, 4-(4-((4'-chloro-5,5-dimethyl-3,4,5,6-tetrahydro-[1,1'-biphenyl]-2-yl)methyl)piperazin-1-yl)-2-(1-methyl-1-oxido-3,9-dihydro-1l4-pyrrolo[3',2':5,6]pyrido[3,2-f][1,2,5]thiadiazepin-5(4H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(2,2-dioxido-1,3,4,9-tetrahydro-5H-pyrrolo[3',2':5,6]pyrido[2,3-c][1,2,5]thiadiazepin-5-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-oxo-3,4,5,7-tetrahydropyrrolo[3',2':5,6]pyrido[3,2-d][1,3]diazepin-1(2H)-yl)benzamide, 4-(4-((4'-chloro-5,5-dimethyl-3,4,5,6-tetrahydro-[1,1'-biphenyl]-2-yl)methyl)piperazin-1-yl)-2-(2,2-dioxido-3,4-dihydropyrrolo[3',2':5,6]pyrido[3,2-f][1,4,5]oxathiazepin-1(7H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)-2-(2-oxo-3,4-dihydro-2H-pyrrolo[3',2':5,6]pyrido[2,3-b][1,4]oxazepin-1(7H)-yl)benzamide, 2-(7-amino-3,4-dihydropyrido[2,3-b][1,4]oxazepin-1(2H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7-(methylamino)-3,4-dihydropyrido[2,3-b][1,4]oxazepin-1(2H)-yl)-N-((3-nitro-4-(((tetrahydro-2H-pyran-4-yl)methyl)amino)phenyl)sulfonyl)benzamide, 2-(2-amino-7,8-dihydropyrimido[4,5-b][1,4]oxazepin-5(6H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, 2-(3-amino-7,8-dihydropyrazino[2,3-b][1,4]oxazepin-9(6H)-yl)-4-(4-((4'-chloro-5,5-dimethyl-3,4,5,6-tetrahydro-[1,1'-biphenyl]-2-yl)methyl)piperazin-1-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydro-1H-pyrrolo[3',2':5,6]pyrazino[2,3-b][1,4]oxazepin-5(6H)-yl)-N-((3-nitro-4-(((tetrahydro-2H-pyran-4-yl)methyl)amino)phenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(7,8-dihydro-3H-imidazo[4',5':5,6]pyrazino[2,3-b][1,4]oxazepin-9(6H)-yl)-N-((3-nitro-4-(((tetrahydro-2H-pyran-4-yl)methyl)amino)phenyl)sulfonyl)benzamide, (2S,4R)-1-((S)-14-(tert-butyl)-1-(4-(2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl) sulfamoyl)-2-nitrophenyl)amino)ethyl)piperazin-1-yl)-12-oxo-3,6,9-trioxa-13-azapentadecan-15-oyl)-4-hydroxy-N-(4-(4-methylthiazol-5-yl)benzyl) pyrrolidine-2-carboxamide, (2S,4R)-1-((S)-2-(3-(2-(2-(4-(2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo [3',2':5,6]pyrido[2,3-b][1,4]oxazepin-1(7H)-yl)benzoyl) sulfamoyl)-2-nitrophenyl)amino)ethyl)piperazin-1-yl) ethoxy)ethoxy)propanamido)-3,3-dimethylbutanoyl)-4-hydroxy-N-(4-(4-methylthiazol-5-yl)benzyl) pyrrolidine-2-carboxamide, (2S,4R)-1-((S)-2-(3-(2-(4-2-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl) sulfamoyl)-2-nitrophenyl)amino)ethyl)piperazin-1-yl) ethoxy)propanamido)-3,3-dimethylbutanoyl)-4-hydroxy-N-(4-(4-methylthiazol-5-yl)benzyl) pyrrolidine-2-carboxamide, (2S,4R)-1-((S)-20-(tert-butyl)-1-((4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl) sulfamoyl)-2-nitrophenyl)amino)-18-oxo-3,6,9,12,15-pentaoxa-19-azahenicosan-21-oyl)-4-hydroxy-N-(4-(4-methylthiazol-5-yl)benzyl) pyrrolidine-2-carboxamide, (2S,4R)-1-((S)-17-(tert-butyl)-1-(4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl) sulfamoyl)-2-nitrophenyl)amino)-15-oxo-3,6,9,12-tetraoxa-16-azaoctadecan-18-oyl)-4-hydroxy-N-(4-(4-methylthiazol-5-yl)benzyl) pyrrolidine-2-carboxamide, (2S,4R)-1-((S)-14-(tert-butyl)-1-(4-(N-(4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)benzoyl) sulfamoyl)-2-nitrophenyl)amino)-12-oxo-3,6,9-trioxa-13-azapentadecan-15-oyl)-4-hydroxy-N-(4-(4-methylthiazol-5-yl)benzyl) pyrrolidine-2-carboxamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1

(7H)-yl)-N-((4-((2-(4-(2-(2-(2-(2-((2-(2,6-dioxopiperidin-3-yl)-1,3-dioxoisoindolin-4-yl)amino)ethoxy)ethoxy)ethoxy)ethyl)piperazin-1-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(4-(2-(2-(2-((2-(2,6-dioxopiperidin-3-yl)-1,3-dioxoisoindolin-4-yl)amino)ethoxy)ethoxy)ethyl)piperazin-1-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(4-(2-(2-((2-(2,6-dioxopiperidin-3-yl)-1,3-dioxoisoindolin-4-yl)amino)ethoxy)ethyl)piperazin-1-yl)ethyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((17-((2-(2,6-dioxopiperidin-3-yl)-1,3-dioxoisoindolin-4-yl)amino)-3,6,9,12,15-pentaoxaheptadecyl)amino)-3-nitrophenyl)sulfonyl)benzamide, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((14-((2-(2,6-dioxopiperidin-3-yl)-1,3-dioxoisoindolin-4-yl)amino)-3,6,9,12-tetraoxatetradecyl)amino)-3-nitrophenyl)sulfonyl)benzamide, or, 4-(4-((4'-chloro-5,5-dimethyl-3,4,5,6-tetrahydro-[1,1'-biphenyl]-2-yl)methyl)piperazin-1-yl)-2-(3,4-dihydro-2H-pyrrolo[3',2':5,6]pyrido[2,3-b][1,4]oxazepin-1(7H)-yl)-N-((4-((2-(2-(2-(2-((2-(2,6-dioxopiperidin-3-yl)-1,3-dioxoisoindolin-4-yl)amino)ethoxy)ethoxy)ethoxy)ethyl)amino)-3-nitrophenyl)sulfonyl)benzamide.

28. A pharmaceutical composition comprising a compound of Formula (A) or an N-oxide thereof as defined in claim 1, or a pharmaceutically acceptable salt, solvate, polymorph, tautomer, stereoisomer, an isotopic form, or a prodrug of said compound of Formula (A) or an N-oxide thereof, and a pharmaceutically acceptable diluent or carrier.

29. A method of treating a neoplastic disease, an autoimmune disease, or a neorodegenerative disease, comprising administering to a subject in need thereof an effective amount of a compound of Formula (A) or an N-oxide thereof as defined in claim 1, or a pharmaceutically acceptable salt, solvate, polymorph, tautomer, stereoisomer, an isotopic form, or a prodrug of said compound of Formula (A) or an N-oxide thereof.

30. The compound according to claim 15 or an N-oxide thereof, or a pharmaceutically acceptable salt, solvate, polymorph, tautomer, stereoisomer, an isotopic form, or a prodrug thereof, wherein

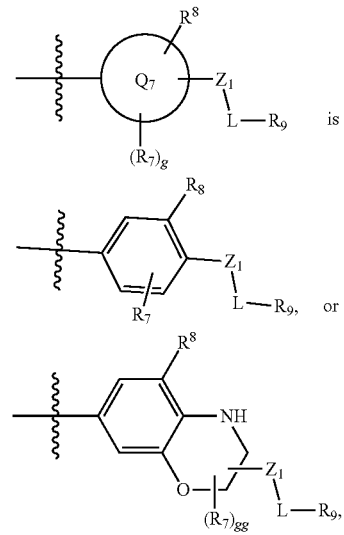

wherein gg is 0, 1, 2, 3, or 4.

* * * * *